(12) United States Patent
Uno

(10) Patent No.: US 12,378,259 B2
(45) Date of Patent: Aug. 5, 2025

(54) LIGHT EMITTING DEVICE AND POLYCYCLIC COMPOUND FOR THE SAME

(71) Applicant: Samsung Display Co., Ltd., Yongin-si (KR)

(72) Inventor: Takuya Uno, Yokohama (JP)

(73) Assignee: SAMSUNG DISPLAY CO., LTD., Yongin-si (KR)

( * ) Notice: Subject to any disclaimer, the term of this patent is extended or adjusted under 35 U.S.C. 154(b) by 902 days.

(21) Appl. No.: 17/486,049

(22) Filed: Sep. 27, 2021

(65) Prior Publication Data

US 2022/0199912 A1    Jun. 23, 2022

(30) Foreign Application Priority Data

Dec. 15, 2020 (KR) .................. 10-2020-0175327

(51) Int. Cl.
| | |
|---|---|
| H01L 51/00 | (2006.01) |
| C07D 498/06 | (2006.01) |
| C07D 513/06 | (2006.01) |
| C07D 519/00 | (2006.01) |
| H10K 85/60 | (2023.01) |
| H10K 50/11 | (2023.01) |

(Continued)

(52) U.S. Cl.
CPC ......... *C07D 513/06* (2013.01); *C07D 498/06* (2013.01); *C07D 519/00* (2013.01);

(Continued)

(58) Field of Classification Search
CPC ... H10K 85/657; C07D 498/06; C07D 513/06
See application file for complete search history.

(56) References Cited

U.S. PATENT DOCUMENTS 9,012,599 B2   4/2015  Stoessel et al.
9,133,119 B2   9/2015  Parham et al.

(Continued)

FOREIGN PATENT DOCUMENTS

CN   102203212   9/2011
CN   106469787   3/2017

(Continued)

OTHER PUBLICATIONS

Google_Translation_of_CN_111704624 (Year: 2024).*

*Primary Examiner* — Michael M Dollinger
(74) *Attorney, Agent, or Firm* — KILE PARK REED & HOUTTEMAN PLLC

(57) ABSTRACT

A light emitting device of an embodiment includes a first electrode, a second electrode disposed on the first electrode, and at least one functional layer disposed between the first electrode and the second electrode. The at least one functional layer includes a polycyclic compound represented by Formula 1, thereby showing high emission efficiency properties and improved life characteristics.

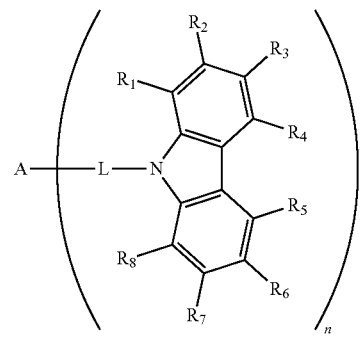

[Formula 1]

18 Claims, 6 Drawing Sheets

(51) Int. Cl.
*H10K 50/15* (2023.01)
*H10K 50/17* (2023.01)
*H10K 50/18* (2023.01)

(52) U.S. Cl.
CPC ....... *H10K 85/657* (2023.02); *H10K 85/6572* (2023.02); *H10K 85/6574* (2023.02); *H10K 85/6576* (2023.02); *H10K 50/11* (2023.02); *H10K 50/15* (2023.02); *H10K 50/17* (2023.02); *H10K 50/171* (2023.02); *H10K 50/18* (2023.02); *H10K 50/181* (2023.02)

(56) References Cited

U.S. PATENT DOCUMENTS

| 10,283,718 | B2 | 5/2019 | Watanabe et al. |
| 10,336,772 | B2 | 7/2019 | Ishii et al. |
| 10,797,246 | B2 | 10/2020 | Lee |
| 2017/0054083 | A1 | 2/2017 | Lee |
| 2020/0199154 | A1 | 6/2020 | Parham et al. |

FOREIGN PATENT DOCUMENTS

| CN | 111704624 A | * | 9/2020 | ........... C07D 498/06 |
| JP | 6782836 | | 9/2015 | |
| KR | 10-2017-0077781 | | 7/2017 | |
| KR | 10-1781235 | | 9/2017 | |
| KR | 10-1796227 | | 11/2017 | |
| KR | 10-1936221 | | 1/2019 | |
| KR | 10-2019-0080063 | | 7/2019 | |
| KR | 10-2019-0141220 | | 12/2019 | |
| KR | 10-2020-0136713 | | 12/2020 | |
| WO | 2010/050778 | | 5/2010 | |
| WO | 2011/088877 | | 7/2011 | |
| WO | 2018/197447 | | 11/2018 | |

* cited by examiner

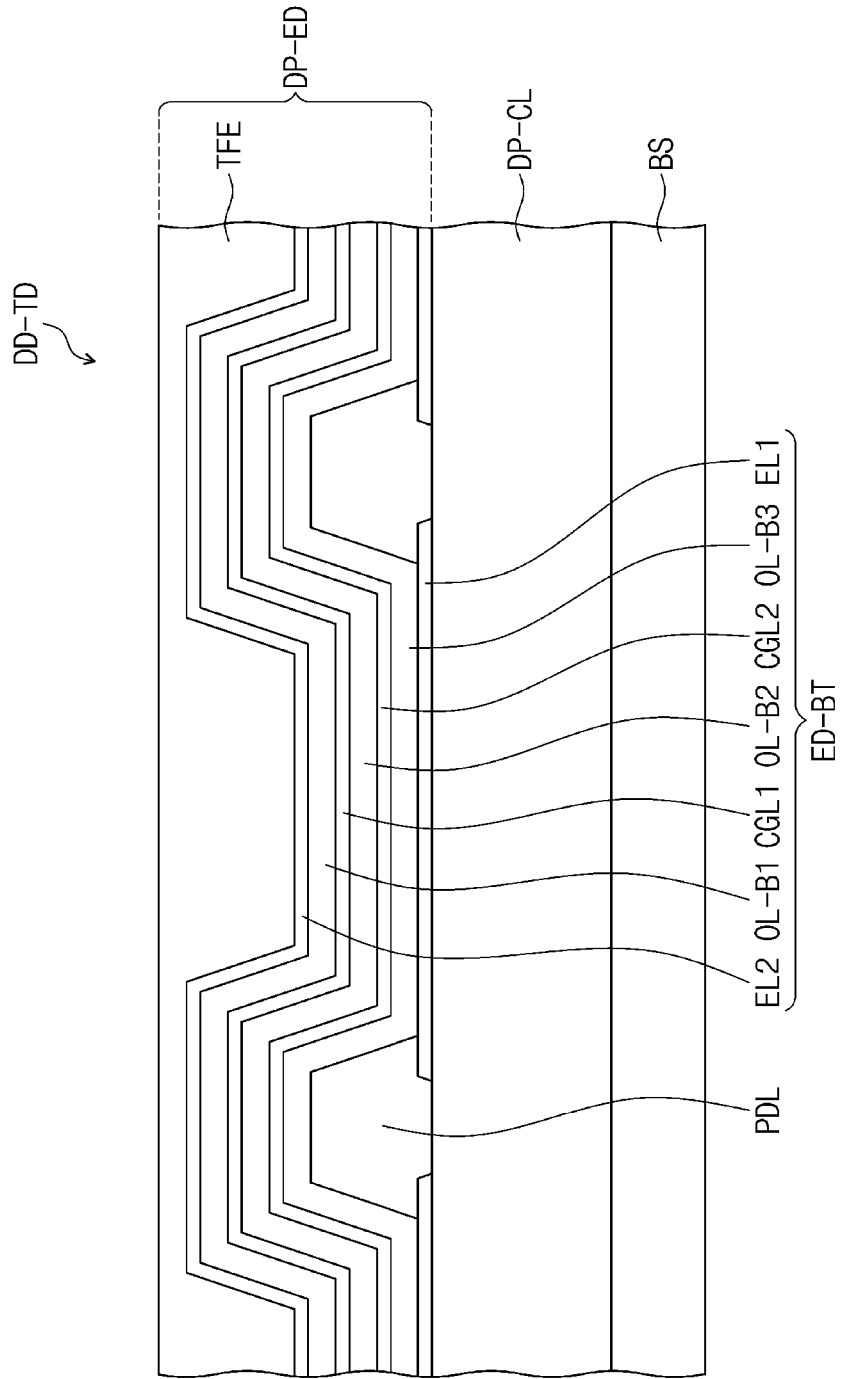

LIGHT EMITTING DEVICE AND POLYCYCLIC COMPOUND FOR THE SAME

CROSS-REFERENCE TO RELATED APPLICATION(S)

This application claims priority to and benefits of Korean Patent Application No. 10-2020-0175327 under 35 U.S.C. § 119, filed on Dec. 15, 2020 in the Korean Intellectual Property Office, the entire contents of which are incorporated herein by reference.

BACKGROUND

1. Technical Field

The disclosure relates to a polycyclic compound used in a hole transport region, and a light emitting device including the same.

2. Description of the Related Art

Active development continues for an organic electroluminescence display as an image display. The organic electroluminescence display includes a so-called self-luminescent light emitting device in which holes and electrons respectively injected from a first electrode and a second electrode recombine in an emission layer so that a light emitting material in the emission layer emits light to achieve display.

In the application of a light emitting device to an image display, there is a need for decreasing driving voltage, increasing emission efficiency, and increasing the life of the light emitting device, and continuous development is required for materials for a light emitting device which stably achieves such characteristics.

In order to implement a light emitting device with high efficiency, development is being conducted on a material for a hole transport region for restraining the diffusion of exciton energy of an emission layer.

SUMMARY

The disclosure provides a light emitting device showing excellent emission efficiency and long-life characteristics.

The disclosure also provides a polycyclic compound which is a material for a light emitting device having high efficiency and long-life characteristics.

An embodiment provides a light emitting device that may include a first electrode, a second electrode disposed on the first electrode, and at least one functional layer disposed between the first electrode and the second electrode, and including a polycyclic compound represented by Formula 1 below.

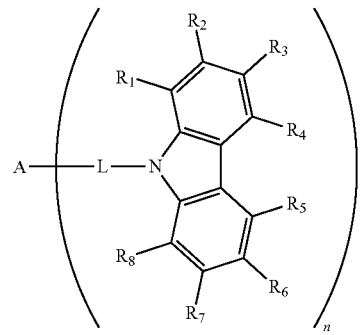

[Formula 1]

In Formula 1, L may be a substituted or unsubstituted arylene group of 6 to 30 ring-forming carbon atoms, $R_1$ to $R_8$ may each independently be a hydrogen atom, a deuterium atom, a halogen atom, a substituted or unsubstituted silyl group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring. In Formula 1, n may be 1 or 2, and A may be a group represented by Formula 2 below.

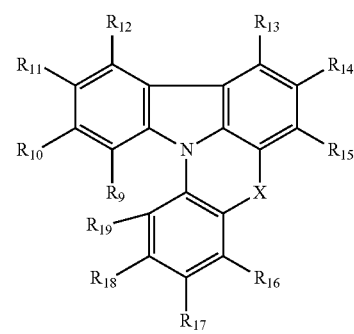

[Formula 2]

In Formula 2, X may be O or S, $R_9$ to $R_{19}$ may each independently be a hydrogen atom, a deuterium atom, a halogen atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring, and at least one of $R_9$ to $R_{19}$ may be bonded to L of Formula 1.

In an embodiment, the at least one functional layer may include an emission layer, a hole transport region disposed between the first electrode and the emission layer, and an electron transport region disposed between the emission layer and the second electrode, and the hole transport region may include the polycyclic compound.

In an embodiment, the hole transport region may include at least one of a hole injection layer, a hole transport layer, and an electron blocking layer, and at least one of the hole injection layer, the hole transport layer, and the electron blocking layer may include the polycyclic compound.

In an embodiment, the at least one functional layer may include an emission layer, a hole transport region disposed between the first electrode and the emission layer, and an electron transport region disposed between the emission layer and the second electrode, and the emission layer may include the polycyclic compound.

In an embodiment, L may be a substituted or unsubstituted phenylene group, a substituted or unsubstituted divalent biphenyl group, a substituted or unsubstituted divalent naphthyl group, a substituted or unsubstituted divalent fluorenyl group, or a substituted or unsubstituted divalent phenanthryl group.

In an embodiment, L may be a group selected from Compound Group L-1 below.

[Compound Group L-1]

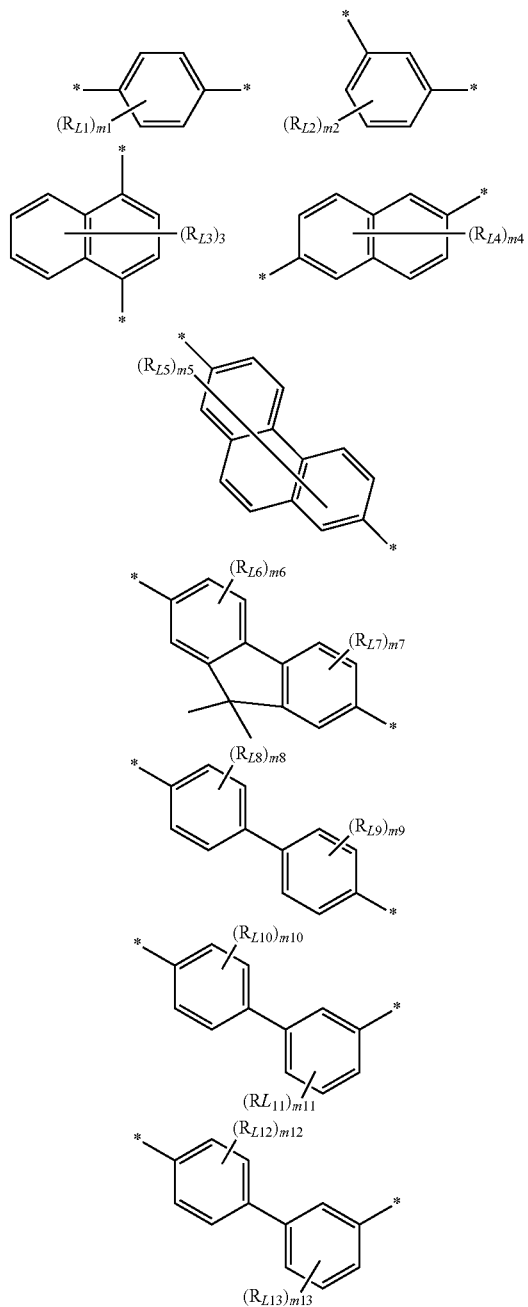

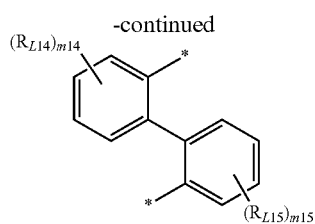

In Compound Group L-1, $R_{L1}$ to $R_{L15}$ may each independently be a hydrogen atom, a deuterium atom, a halogen atom, a substituted or unsubstituted silyl group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring. In Compound Group L-1, m1 and m2 may each independently be an integer from 0 to 4, m3 and m4 may each independently be an integer from 0 to 6, m5 may be an integer from 0 to 8, m6 and m7 may each independently be an integer from 0 to 3, m8 to m15 may each independently be an integer from 0 to 4, and -* represents a position bonded to A or N in Formula 1.

In an embodiment, $R_1$ to $R_8$ may each independently be a hydrogen atom, a deuterium atom, a halogen atom, a methyl group, a t-butyl group, a substituted or unsubstituted amine group, a substituted or unsubstituted silyl group, a substituted or unsubstituted phenyl group, a substituted or unsubstituted carbazole group, a substituted or unsubstituted dibenzofuran group, a substituted or unsubstituted dibenzothiophene group, a substituted or unsubstituted phenoxazine group, or a substituted or unsubstituted acridyl group.

In an embodiment, the polycyclic compound represented by Formula 1 may be represented by Formula 1-1 or Formula 1-2 below.

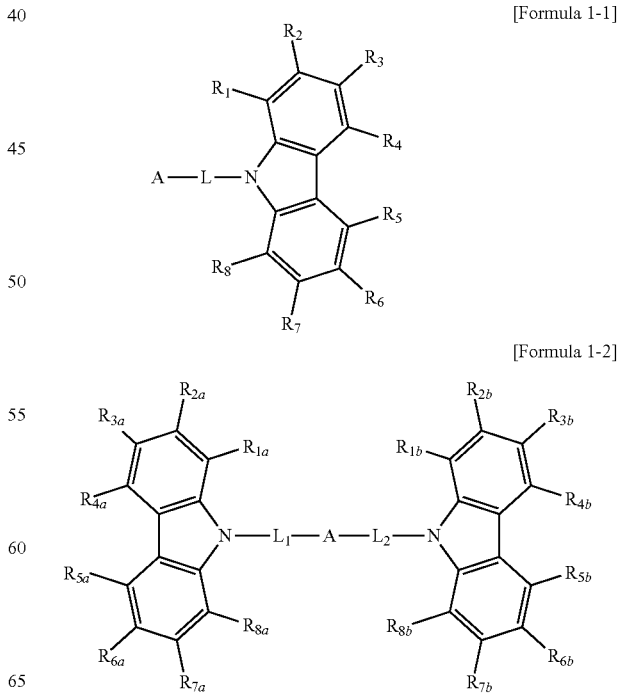

In Formula 1-1 and Formula 1-2, $L_1$ and $L_2$ may each independently be a substituted or unsubstituted arylene group of 6 to 30 ring-forming carbon atoms, $R_{1a}$ to $R_{8a}$, and $R_{1b}$ to $R_{8b}$ may each independently be a hydrogen atom, a deuterium atom, a halogen atom, a substituted or unsubstituted silyl group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring, and A, L, and $R_1$ to $R_8$ may be the same as defined in connection with Formula 1.

In an embodiment, the polycyclic compound represented by Formula 1 may be represented by any one among Formula 3-1 to Formula 3-6 below.

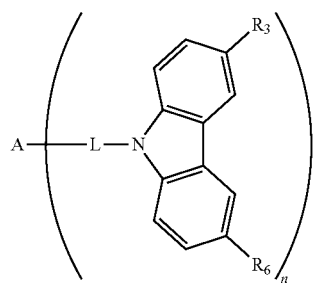

[Formula 3-1]

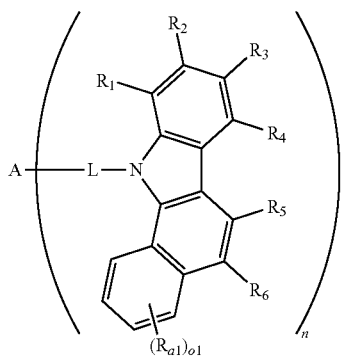

[Formula 3-2]

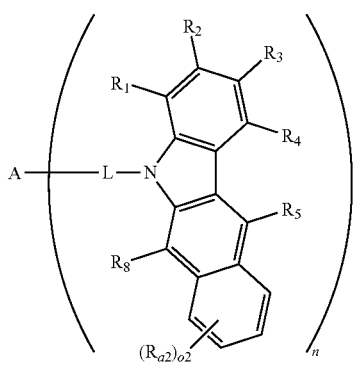

[Formula 3-3]

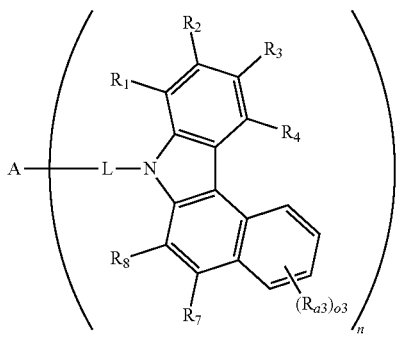

[Formula 3-4]

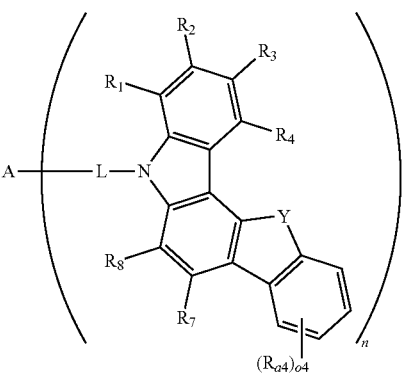

[Formula 3-5]

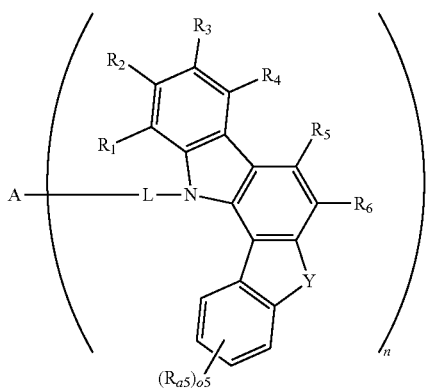

[Formula 3-6]

In Formula 3-1 to Formula 3-6, Y may be O or S, and $R_{a1}$ to $R_{a5}$ may each independently be a hydrogen atom, a deuterium atom, a halogen atom, a substituted or unsubstituted silyl group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring. In Formula 3-1 to Formula 3-6, o1 to o5 may each independently be an integer from 0 to 4, and A, L, n, and $R_1$ to $R_8$ may be the same as defined in connection with Formula 1.

In an embodiment, the polycyclic compound represented by Formula 1 may be represented by any one among Formula 4-1 to Formula 4-6 below.

[Formula 4-1]
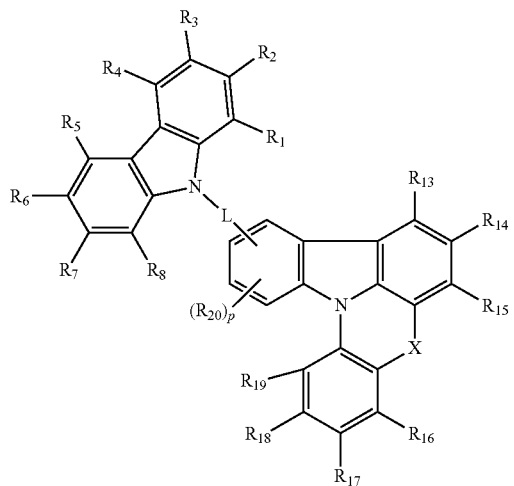
[Formula 4-2]
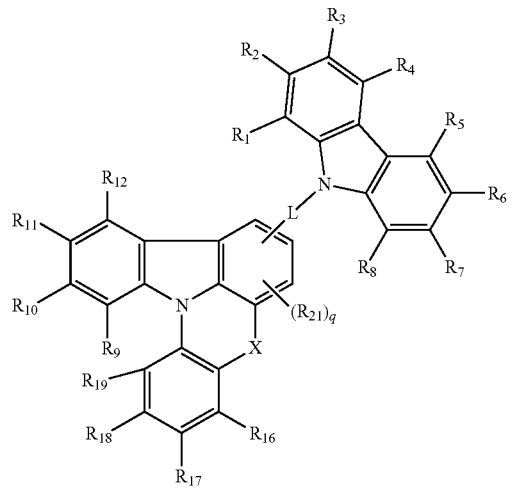
[Formula 4-3]
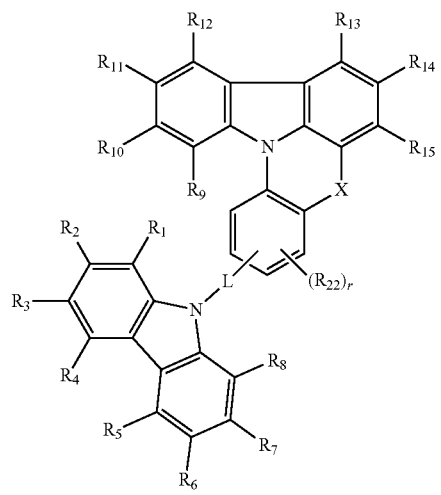
[Formula 4-4]
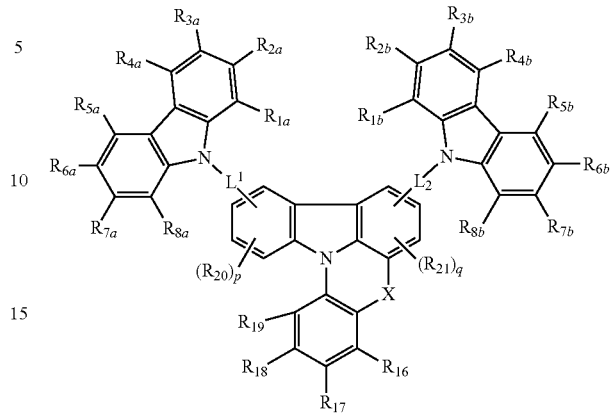
[Formula 4-5]
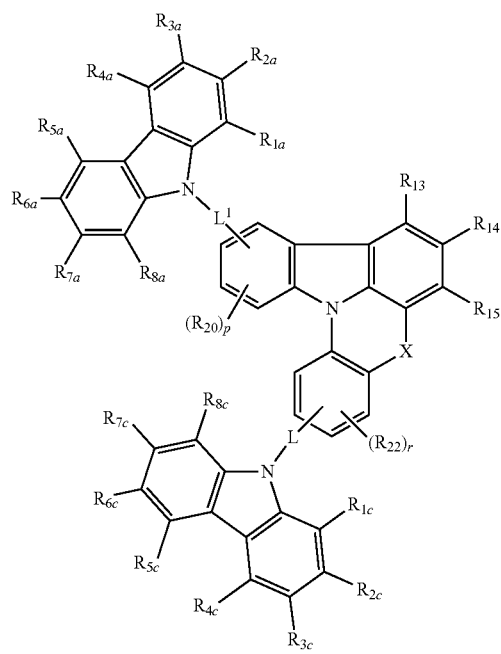

-continued

[Formula 4-6]

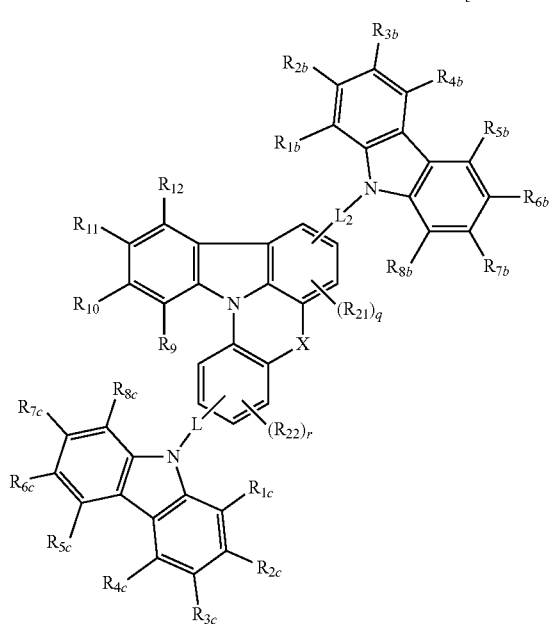

In Formula 4-1 to Formula 4-6, $R_{20}$, $R_{21}$, and $R_{22}$ may each independently be a hydrogen atom, a deuterium atom, a halogen atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring. In Formula 4-1 to Formula 4-6, p may be an integer from 0 to 3, q may be an integer from 0 to 2, r may be an integer from 0 to 3. In Formula 4-1 to Formula 4-6, $L_1$ to $L_3$ may each independently be a substituted or unsubstituted arylene group of 6 to 30 ring-forming carbon atoms, $R_{1a}$ to $R_{8a}$, $R_{1b}$ to $R_{8b}$, and $R_{1c}$ to $R_{8c}$ may each independently be a hydrogen atom, a deuterium atom, a halogen atom, a substituted or unsubstituted silyl group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring, and L, X, and $R_1$ to $R_{19}$ may be the same as defined in connection with Formula 1 and Formula 2.

In an embodiment, A in Formula 1 may be a group represented by Formula 2-1 or Formula 2-2 below.

[Formula 2-1]

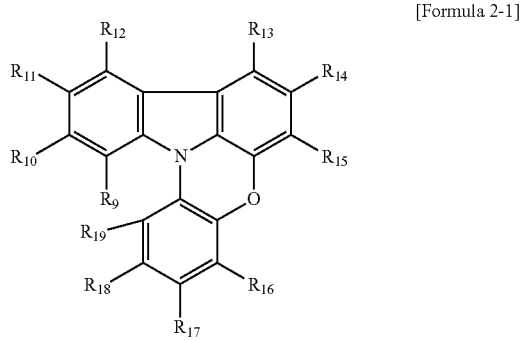

[Formula 2-2]

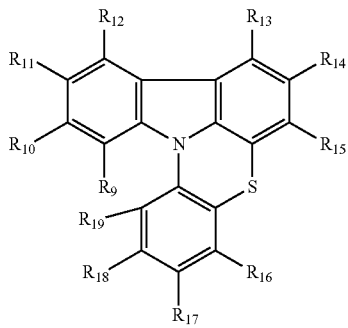

In Formula 2-1 and Formula 2-2, $R_9$ to $R_{19}$ may be the same as defined in connection with Formula 2.

A polycyclic compound according to an embodiment may be represented by Formula 1 above.

BRIEF DESCRIPTION OF THE DRAWINGS

The accompanying drawings are included to provide a further understanding of the embodiments and are incorporated in and constitute a part of this specification. The drawings illustrate embodiments of the disclosure and principles thereof. The above and other aspects and features of the disclosure will become more apparent by describing in detail embodiments thereof with reference to the attached drawings, in which:

FIG. 8 is a schematic cross-sectional view of a display apparatus according to an embodiment.

DETAILED DESCRIPTION OF THE EMBODIMENTS

Figure 1:
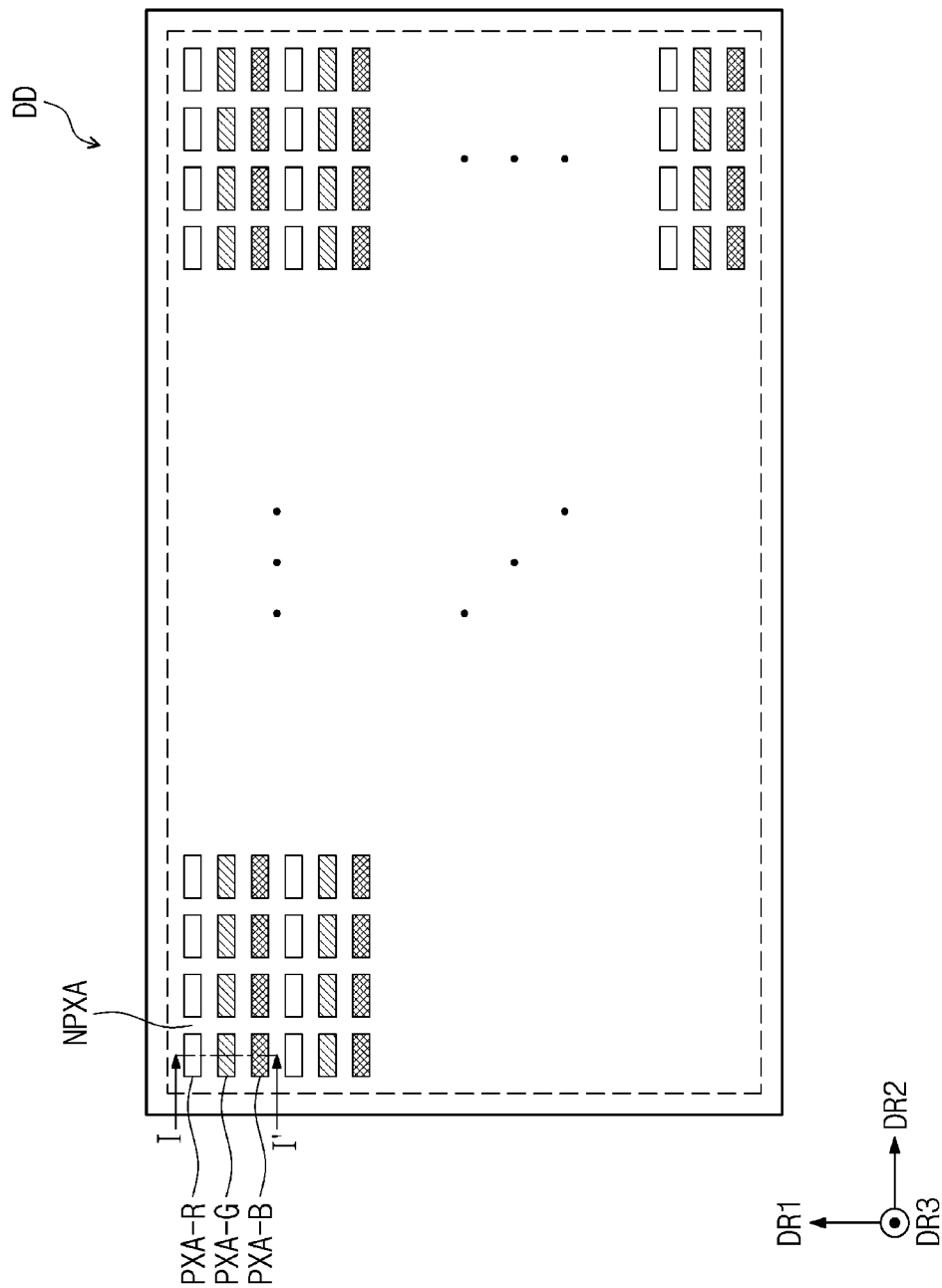
FIG. 1 is a plan view of a display apparatus according to an embodiment.

The disclosure will now be described more fully hereinafter with reference to the accompanying drawings, in which embodiments are shown. This disclosure may, however, be embodied in different forms and should not be construed as limited to the embodiments set forth herein. Rather, these embodiments are provided so that this disclosure will be thorough and complete, and will fully convey the scope of the disclosure to those skilled in the art.

In the drawings, the sizes, thicknesses, ratios, and dimensions of the elements may be exaggerated for ease of description and for clarity. Like numbers refer to like elements throughout.

In the description, it will be understood that when an element (or region, layer, part, etc.) is referred to as being "on", "connected to", or "coupled to" another element, it can be directly on, connected to, or coupled to the other element, or one or more intervening elements may be present therebetween. In a similar sense, when an element (or region, layer, part, etc.) is described as "covering" another element, it can directly cover the other element, or one or more intervening elements may be present therebetween.

In the description, when an element is "directly on," "directly connected to," or "directly coupled to" another element, there are no intervening elements present. For example, "directly on" may mean that two layers or two elements are disposed without an additional element such as an adhesion element therebetween.

As used herein, the expressions used in the singular such as "a," "an," and "the," are intended to include the plural forms as well, unless the context clearly indicates otherwise.

As used herein, the term "and/or" includes any and all combinations of one or more of the associated listed items. For example, "A and/or B" may be understood to mean "A, B, or A and B." The terms "and" and "or" may be used in the conjunctive or disjunctive sense and may be understood to be equivalent to "and/or".

The term "at least one of" is intended to include the meaning of "at least one selected from" for the purpose of its meaning and interpretation. For example, "at least one of A and B" may be understood to mean "A, B, or A and B." When preceding a list of elements, the term, "at least one of," modifies the entire list of elements and does not modify the individual elements of the list.

It will be understood that, although the terms first, second, etc. may be used herein to describe various elements, these elements should not be limited by these terms. These terms are only used to distinguish one element from another element. Thus, a first element could be termed a second element without departing from the teachings of the disclosure. Similarly, a second element could be termed a first element, without departing from the scope of the disclosure.

The spatially relative terms "below", "beneath", "lower", "above", "upper", or the like, may be used herein for ease of description to describe the relations between one element or component and another element or component as illustrated in the drawings. It will be understood that the spatially relative terms are intended to encompass different orientations of the device in use or operation, in addition to the orientation depicted in the drawings. For example, in the case where a device illustrated in the drawing is turned over, the device positioned "below" or "beneath" another device may be placed "above" another device. Accordingly, the illustrative term "below" may include both the lower and upper positions. The device may also be oriented in other directions and thus the spatially relative terms may be interpreted differently depending on the orientations.

The terms "about" or "approximately" as used herein is inclusive of the stated value and means within an acceptable range of deviation for the recited value as determined by one of ordinary skill in the art, considering the measurement in question and the error associated with measurement of the recited quantity (i.e., the limitations of the measurement system). For example, "about" may mean within one or more standard deviations, or within ±20%, 10%, or 5% of the stated value.

It should be understood that the terms "comprises," "comprising," "includes," "including," "have," "having," "contains," "containing," and the like are intended to specify the presence of stated features, integers, steps, operations, elements, components, or combinations thereof in the disclosure, but do not preclude the presence or addition of one or more other features, integers, steps, operations, elements, components, or combinations thereof.

Unless otherwise defined or implied herein, all terms (including technical and scientific terms) used have the same meaning as commonly understood by those skilled in the art to which this disclosure pertains. It will be further understood that terms, such as those defined in commonly used dictionaries, should be interpreted as having a meaning that is consistent with their meaning in the context of the relevant art and should not be interpreted in an ideal or excessively formal sense unless clearly defined in the specification.

In the description, the term "substituted or unsubstituted" may mean substituted or unsubstituted with at least one substituent selected from the group consisting of a deuterium atom, a halogen atom, a cyano group, a nitro group, an amine group, a silyl group, an oxy group, a thio group, a sulfinyl group, a sulfonyl group, a carbonyl group, a boron group, a phosphine oxide group, a phosphine sulfide group, an alkyl group, an alkenyl group, an alkynyl group, an alkoxy group, a hydrocarbon ring group, an aryl group, and a heterocyclic group. Each of the substituents listed above may themselves be substituted or unsubstituted. For example, a biphenyl group may be interpreted as an aryl group or as a phenyl group substituted with a phenyl group.

In the description, the term "combined with an adjacent group to form a ring" may mean a group that is bonded to an adjacent group to form a substituted or unsubstituted hydrocarbon ring, or a substituted or unsubstituted heterocycle. The hydrocarbon ring may include an aliphatic hydrocarbon ring and an aromatic hydrocarbon ring. The heterocycle may include an aliphatic heterocycle and an aromatic heterocycle. The hydrocarbon ring and the heterocycle may each be monocyclic or polycyclic. A ring formed by the combination of adjacent groups may be combined with another ring to form a spiro structure.

In the description, the term "adjacent group" may mean a substituent substituted for an atom which is directly bonded to an atom substituted with a corresponding substituent, another substituent substituted for an atom which is substituted with a corresponding substituent, or a substituent sterically positioned at the nearest position to a corresponding substituent. For example, in 1,2-dimethylbenzene, two methyl groups may be interpreted as "adjacent groups" to each other, and in 1,1-diethylcyclopentene, two ethyl groups may be interpreted as "adjacent groups" to each other. For example, in 4,5-dimethylphenanthrene, two methyl groups may be interpreted as "adjacent groups" to each other.

In the description, examples of a halogen atom may include a fluorine atom, a chlorine atom, a bromine atom, and an iodine atom.

In the description, an alkyl group may be a linear, a branched, or a cyclic type. The number of carbon atoms in the alkyl group may be 1 to 50, 1 to 30, 1 to 20, 1 to 10, or 1 to 6. Examples of the alkyl group may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldodecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

In the description, a hydrocarbon ring group may be an optional functional group or substituent derived from an aliphatic hydrocarbon ring. The hydrocarbon ring group may be a saturated hydrocarbon ring group having 5 to 20 ring-forming carbon atoms.

In the description, an aryl group may be an optional functional group or substituent derived from an aromatic hydrocarbon ring. The aryl group may be a monocyclic aryl group or a polycyclic aryl group. The number of ring-forming carbon atoms in the aryl group may be 6 to 30, 6 to 20, or 6 to 15. Examples of the aryl group may include phenyl, naphthyl, fluorenyl, anthracenyl, phenanthryl, biphenyl, terphenyl, quaterphenyl, quinqphenyl, sexiphenyl, triphenylenyl, pyrenyl, benzofluoranthenyl, chrysenyl, etc., without limitation.

In the description, a fluorenyl group may be substituted, and two substituents may be combined with each other to form a spiro structure. Examples of substituted fluorenyl groups are shown below, but embodiments are not limited thereto.

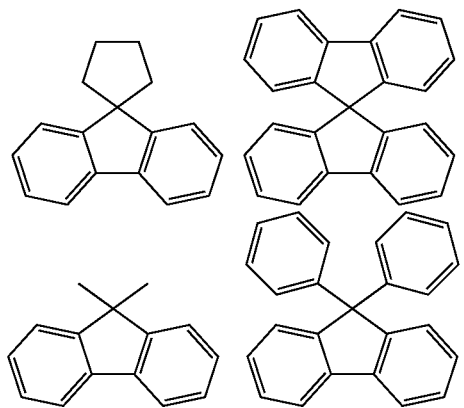

In the description, a heterocyclic group may be an optional functional group or substituent derived from a ring including at least one of B, O, N, P, Si, and S as heteroatoms. The heterocyclic group may include an aliphatic heterocyclic group and an aromatic heterocyclic group. The aromatic heterocyclic group may be a heteroaryl group. The aliphatic heterocyclic group and the aromatic heterocyclic group may each be monocyclic or polycyclic.

In the description, a heterocyclic group may include at least one of B, O, N, P, Si, and S as heteroatoms. If the heterocyclic group includes two or more heteroatoms, the two or more heteroatoms may be the same or different. The heterocyclic group may be a monocyclic heterocyclic group or a polycyclic heterocyclic group and may be a heteroaryl group. The number ring-forming carbon atoms in the heteroaryl group may be 2 to 30, 2 to 20, and 2 to 10.

In the description, an aliphatic heterocyclic group may include at least one of B, O, N, P, Si, and S as heteroatoms. The number of ring-forming carbon atoms of the aliphatic heterocyclic group may be 2 to 30, 2 to 20, or 2 to 10. Examples of the aliphatic heterocyclic group may include an oxirane group, a thiirane group, a pyrrolidine group, a piperidine group, a tetrahydrofuran group, a tetrahydrothiophene group, a thiane group, a tetrahydropyran group, a 1,4-dioxane group, etc., without limitation.

In the description, a heteroaryl group may include at least one of B, O, N, P, Si, and S as heteroatoms. If the heteroaryl group includes two or more heteroatoms, the two or more heteroatoms may be the same or different. The heteroaryl group may be a monocyclic heterocyclic group or polycyclic heterocyclic group. The number of ring-forming carbon atoms in the heteroaryl group may be 2 to 30, 2 to 20, or 2 to 10. Examples of the heteroaryl group may include thiophene, furan, pyrrole, imidazole, triazole, pyridine, bipyridine, pyrimidine, triazine, triazole, acridyl, pyridazine, pyrazinyl, quinoline, quinazoline, quinoxaline, phenoxazine, phthalazine, pyrido pyrimidine, pyrido pyrazine, pyrazino pyrazine, isoquinoline, indole, carbazole, N-arylcarbazole, N-heteroarylcarbazole, N-alkylcarbazole, benzoxazole, benzoimidazole, benzothiazole, benzocarbazole, benzothiophene, dibenzothiophene, thienothiophene, benzofuran, phenanthroline, thiazole, isooxazole, oxazole, oxadiazole, thiadiazole, phenothiazine, dibenzosilole, dibenzofuran, etc., without limitation.

In the description, the explanation with respect to the aryl group may be applied to an arylene group, except that the arylene group is a divalent group. The explanation with respect to the heteroaryl group may be applied to a heteroarylene group, except that the heteroarylene group is a divalent group.

In the description, a silyl group may include an alkyl silyl group and an aryl silyl group. Examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, etc., without limitation.

In the description, the number of carbon atoms in an amino group is not specifically limited, but may be 1 to 30. The amino group may include an alkyl amino group, an aryl amino group, or a heteroaryl amino group. Examples of the amino group may include a methylamino group, a dimethylamino group, a phenylamino group, a diphenylamino group, a naphthylamino group, a 9-methyl-anthracenylamino group, a triphenylamino group, etc., without limitation.

In the description, the number of carbon atoms in a carbonyl group is not specifically limited, but may be 1 to 40, 1 to 30, or 1 to 20. For example, a carbonyl group may have one of the structures below, but embodiments are not limited thereto.

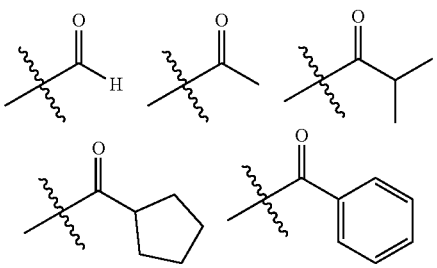

In the description, the number of carbon atoms in a sulfinyl group and a sulfonyl group is not specifically limited, but may be 1 to 30. The sulfinyl group may include an alkyl sulfinyl group and an aryl sulfinyl group. The sulfonyl group may include an alkyl sulfonyl group and an aryl sulfonyl group.

In the description, a thio group may include an alkyl thio group and an aryl thio group. The thio group may be a sulfur atom that is bonded to an alkyl group or an aryl group as defined above. Examples of the thio group include a methylthio group, an ethylthio group, a propylthio group, a pentylthio group, a hexylthio group, an octylthio group, a dodecylthio group, a cyclopentylthio group, a cyclohexylthio group, a phenylthio group, a naphthylthio group, etc., without limitation.

In the description, an oxy group may be an oxygen atom that is bonded to an alkyl group or an aryl group as defined above. The oxy group may include an alkoxy group and an aryl oxy group. The alkoxy group may be a linear, a branched, or a cyclic chain. The number of carbon atoms in the alkoxy group is not specifically limited but may be, for example, 1 to 20 or 1 to 10. Examples of the oxy group may include methoxy, ethoxy, n-propoxy, isopropoxy, butoxy, pentyloxy, hexyloxy, octyloxy, nonyloxy, decyloxy, benzyloxy, etc. However, embodiments are not limited thereto.

In the description, a boron group may be a boron atom that is bonded to an alkyl group or an aryl group as defined above. The boron group may include an alkyl boron group and an aryl boron group. Examples of the boron group may include a trimethylboron group, a triethylboron group, a t-butyldimethylboron group, a triphenylboron group, a diphenylboron group, a phenylboron group, etc., without limitation.

In the description, an alkenyl group may be a linear chain or a branched chain. The number of carbon atoms is not specifically limited but may be 2 to 30, 2 to 20, or 2 to 10. Examples of the alkenyl group may include a vinyl group, a 1-butenyl group, a 1-pentenyl group, a 1,3-butadienyl aryl group, a styrenyl group, a styrylvinyl group, etc., without limitation.

In the description, the number of carbon atoms in an amine group is not specifically limited, but may be 1 to 30. The amine group may include an alkyl amine group and an aryl amine group. Examples of the amine group may include a methylamine group, a dimethylamine group, a phenylamine group, a diphenylamine group, a naphthylamine group, a 9-methyl-anthracenylamine group, etc., without limitation.

In the description, an alkyl group in an alkylthio group, an alkylsulfoxy group, an alkylaryl group, an alkylamino group, an alkylboron group, an alkyl silyl group, and an alkyl amine group may be the same as the examples of the above-described alkyl group.

In the description, an aryl group in an aryloxy group, an arylthio group, an arylsulfoxy group, an aryl amino group, an arylboron group, and an aryl silyl group may be the same as the examples of the above-described aryl group.

In the description, a direct linkage may be a single bond.

In the description,

and -* each represent a binding site to a neighboring atom in a corresponding formula.

Hereinafter, embodiments will be explained with references to the drawings.

Figure 2:
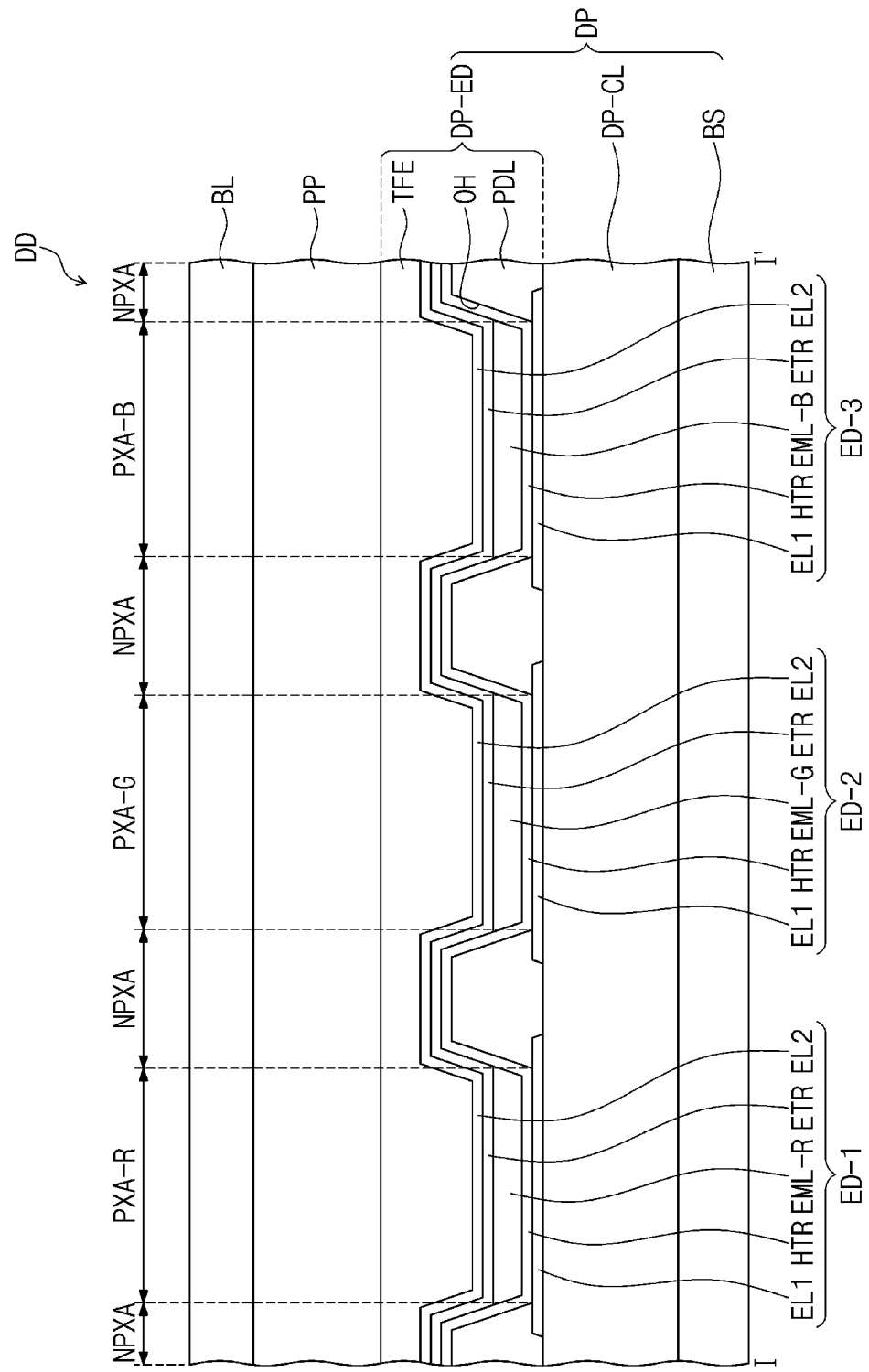
FIG. 2 is a schematic cross-sectional view of a display apparatus according to an embodiment.

FIG. 1 is a plan view showing an embodiment of a display apparatus DD. FIG. 2 is a schematic cross-sectional view of a display apparatus DD of an embodiment. FIG. 2 is a schematic cross-sectional view showing a part corresponding to line I-I' in FIG. 1.

The display apparatus DD may include a display panel DP and an optical layer PP disposed on the display panel DP. The display panel DP includes light emitting devices ED-1, ED-2, and ED-3. The display apparatus DD may include multiple light emitting devices ED-1, ED-2, and ED-3. The optical layer PP may be disposed on the display panel DP and may control light reflected from an external light at the display panel DP. The optical layer PP may include, for example, a polarization layer or a color filter layer. Although not shown in the drawings, in an embodiment, the optical layer PP may be omitted from the display apparatus DD.

A base substrate BL may be disposed on the optical layer PP. The base substrate BL may provide a base surface where the optical layer PP is disposed. The base substrate BL may be a glass substrate, a metal substrate, a plastic substrate, etc. However, embodiments are not limited thereto, and the base substrate BL may include an inorganic layer, an organic layer, or a composite material layer. Although not shown in the drawings, in an embodiment, the base substrate BL may be omitted.

The display apparatus DD according to an embodiment may further include a plugging layer (not shown). The plugging layer (not shown) may be disposed between a display device layer DP-ED and a base substrate BL. The plugging layer (not shown) may include an organic layer. The plugging layer (not shown) may include at least one of an acrylic resin, a silicon-based resin, and an epoxy-based resin.

The display panel DP may include a base layer BS, a circuit layer DP-CL provided on the base layer BS, and a display device layer DP-ED. The display device layer DP-ED may include a pixel definition layer PDL, light emitting devices ED-1, ED-2, and ED-3 disposed in the pixel definition layer PDL, and an encapsulating layer TFE disposed on the light emitting devices ED-1, ED-2, and ED-3.

The base layer BS may provide a base surface where the display device layer DP-ED is disposed. The base layer BS may be a glass substrate, a metal substrate, a plastic substrate, etc. However, embodiments are not limited thereto, and the base layer BS may include an inorganic layer, an organic layer, or a composite material layer.

In an embodiment, the circuit layer DP-CL is disposed on the base layer BS, and the circuit layer DP-CL may include multiple transistors (not shown). Each of the transistors (not shown) may include a control electrode, an input electrode, and an output electrode. For example, the circuit layer DP-CL may include switching transistors and driving transistors for driving the light emitting devices ED-1, ED-2, and ED-3 of the display device layer DP-ED.

Each of the light emitting devices ED-1, ED-2, and ED-3 may have a structure of light emitting devices ED of embodiments according to FIG. 3 to FIG. 6, which will be explained later. Each of the light emitting devices ED-1, ED-2, and ED-3 may include a first electrode EL1, a hole transport region HTR, emission layers EMLL-R, EMLL-G, and EMLL-B, an electron transport region ETR, and a second electrode EL2.

In FIG. 2, shown is an embodiment where the emission layers EML-R, EML-G, and EML-B of light emitting devices ED-1, ED-2, and ED-3 are disposed in opening portions OH defined in a pixel definition layer PDL, and a hole transport region HTR, an electron transport region ETR, and a second electrode EL2 are provided as common layers in all light emitting devices ED-1, ED-2, and ED-3.

However, embodiments are not limited thereto. Although not shown in FIG. 2, in an embodiment, the hole transport region HTR and the electron transport region ETR may be patterned and provided in the opening portions OH defined in the pixel definition layer PDL. For example, in an embodiment, the hole transport region HTR, the emission layers EMLL-R, EMLL-G, and EMLL-B, and the electron transport region ETR of the light emitting devices ED-1, ED-2, and ED-3 may each be patterned by an ink jet printing method and provided.

An encapsulating layer TFE may cover the light emitting devices ED-1, ED-2, and ED-3. The encapsulating layer TFE may encapsulate the display device layer DP-ED. The encapsulating layer TFE may be a thin film encapsulating layer. The encapsulating layer TFE may be one layer or a stack of multiple layers. The encapsulating layer TFE may include at least one insulating layer. The encapsulating layer TFE according to an embodiment may include at least one inorganic layer (hereinafter, encapsulating inorganic layer). In an embodiment, the encapsulating layer TFE may include at least one organic layer (hereinafter, encapsulating organic layer) and at least one encapsulating inorganic layer.

The encapsulating inorganic layer may protect the display device layer DP-ED from moisture and/or oxygen, and the encapsulating organic layer may protect the display device layer DP-ED from foreign materials such as dust particles. The encapsulating inorganic layer may include silicon nitride, silicon oxy nitride, silicon oxide, titanium oxide, or aluminum oxide, without specific limitation. The encapsulating organic layer may include an acrylic compound, an epoxy-based compound, etc. The encapsulating organic layer may include a photopolymerizable organic material, without specific limitation.

The encapsulating layer TFE may be disposed on the second electrode EL2 and may be disposed to fill the opening portions OH.

Referring to FIG. 1 and FIG. 2, the display apparatus DD may include a non-luminous area NPXA and luminous areas PXA-R, PXA-G, and PXA-B. The luminous areas PXA-R, PXA-G, and PXA-B may each be areas emitting light produced from the light emitting devices ED-1, ED-2, and ED-3, respectively. The luminous areas PXA-R, PXA-G, and PXA-B may be separated from each other on a plane.

The luminous areas PXA-R, PXA-G, and PXA-B may be areas separated by the pixel definition layer PDL. The non-luminous areas NPXA may be areas between neighboring luminous areas PXA-R, PXA-G, and PXA-B and may be areas corresponding to the pixel definition layer PDL. In the disclosure, each of the luminous areas PXA-R, PXA-G, and PXA-B may each correspond to a pixel. The pixel definition layer PDL may separate the light emitting devices ED-1, ED-2, and ED-3. The emission layers EML-R, EML-G, and EML-B of the light emitting devices ED-1, ED-2, and ED-3 may be disposed and divided in the opening portions OH defined in the pixel definition layer PDL.

The luminous areas PXA-R, PXA-G, and PXA-B may be divided into groups according to the color of light produced from the light emitting devices ED-1, ED-2, and ED-3. In the display apparatus DD of an embodiment, shown in FIG. 1 and FIG. 2, three luminous areas PXA-R, PXA-G, and PXA-B emitting red light, green light and blue light are illustrated as an embodiment. For example, the display apparatus DD of an embodiment may include a red luminous area PXA-R, a green luminous area PXA-G and a blue luminous area PXA-B, which are separated from each other.

In the display apparatus DD according to an embodiment, multiple light emitting devices ED-1, ED-2, and ED-3 may emit light having different wavelength regions. For example, in an embodiment, the display apparatus DD may include a first light emitting device ED-1 emitting red light, a second light emitting device ED-2 emitting green light, and a third light emitting device ED-3 emitting blue light. For example, each of the red luminous area PXA-R, the green luminous area PXA-G, and the blue luminous area PXA-B of the display apparatus DD may correspond to the first light emitting device ED-1, the second light emitting device ED-2, and the third light emitting device ED-3.

However, embodiments are not limited thereto, and the first to third light emitting devices ED-1, ED-2, and ED-3 may emit light in a same wavelength region, or at least one thereof may emit light in a different wavelength region. For example, the first to third light emitting devices ED-1, ED-2, and ED-3 may all emit blue light.

The luminous areas PXA-R, PXA-G, and PXA-B in the display apparatus DD according to an embodiment may be arranged in a stripe configuration. Referring to FIG. 1, multiple red luminous areas PXA-R, multiple green luminous areas PXA-G and multiple blue luminous areas PXA-B may be arranged along a second directional axis DR2. The red luminous area PXA-R, the green luminous area PXA-G, and the blue luminous area PXA-B may be arranged by turns along a first directional axis DR1.

In FIG. 1 and FIG. 2, the luminous areas PXA-R, PXA-G, and PXA-B are shown as having a similar area, but embodiments are not limited thereto. The areas of the luminous areas PXA-R, PXA-G, and PXA-B may be different from each other according to the wavelength region of light emitted. The areas of the luminous areas PXA-R, PXA-G, and PXA-B may be areas in a plan view that are defined by the first directional axis DR1 and the second directional axis DR2.

The arrangement type of the luminous areas PXA-R, PXA-G, and PXA-B is not limited to the configuration shown in FIG. 1, and the arrangement order of the red luminous areas PXA-R, the green luminous areas PXA-G, and the blue luminous areas PXA-B may be provided in various combinations according to the properties of display quality required for the display apparatus DD. For example, the arrangement type of the luminous areas PXA-R, PXA-G, and PXA-B may be a PenTile® arrangement type, or a diamond arrangement type.

The areas of the luminous areas PXA-R, PXA-G, and PXA-B may be different from each other. For example, in an embodiment, an area of the green luminous area PXA-G may be smaller than an area of the blue luminous area PXA-B, but embodiments are not limited thereto.

Hereinafter, FIG. 3 to FIG. 6 are each a schematic cross-sectional view showing light emitting devices according to embodiments. The light emitting device ED according to an embodiment may include a first electrode EL1, a second electrode EL2 disposed facing the first electrode EL1, and at least one functional layer disposed between the first electrode EL1 and the second electrode EL2. The at least one functional layer may include a hole transport region HTR, an emission layer EML, and an electron transport region ETR stacked in that order. For example, the light emitting device ED of an embodiment may include a first electrode EL1, a hole transport region HTR, an emission layer EML, an electron transport region ETR, and a second electrode EL2 stacked in order.

Figure 3:
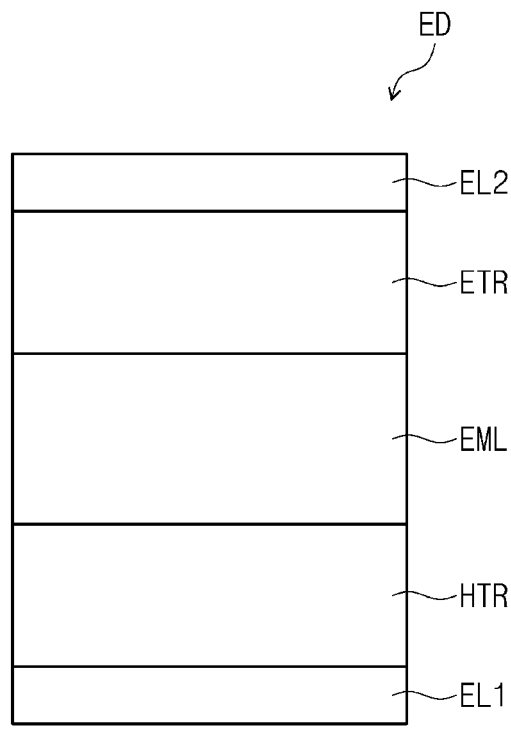
FIG. 3 is a schematic cross-sectional view showing a light emitting device according to an embodiment.
Figure 4:
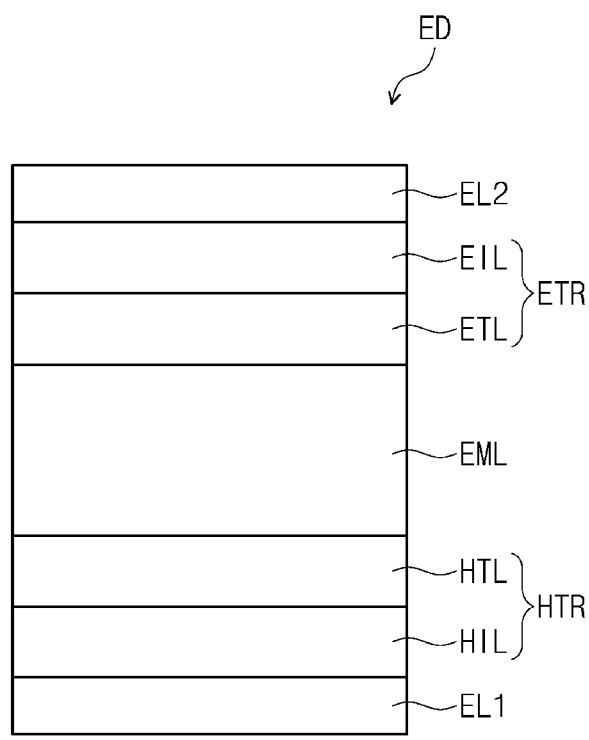
FIG. 4 is a schematic cross-sectional view showing a light emitting device according to an embodiment.
Figure 5:
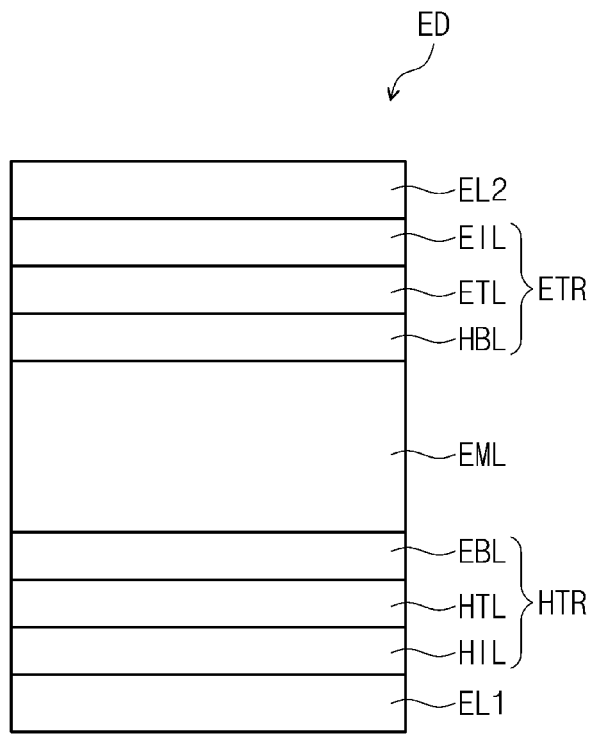
FIG. 5 is a schematic cross-sectional view showing a light emitting device according to an embodiment.
Figure 6:
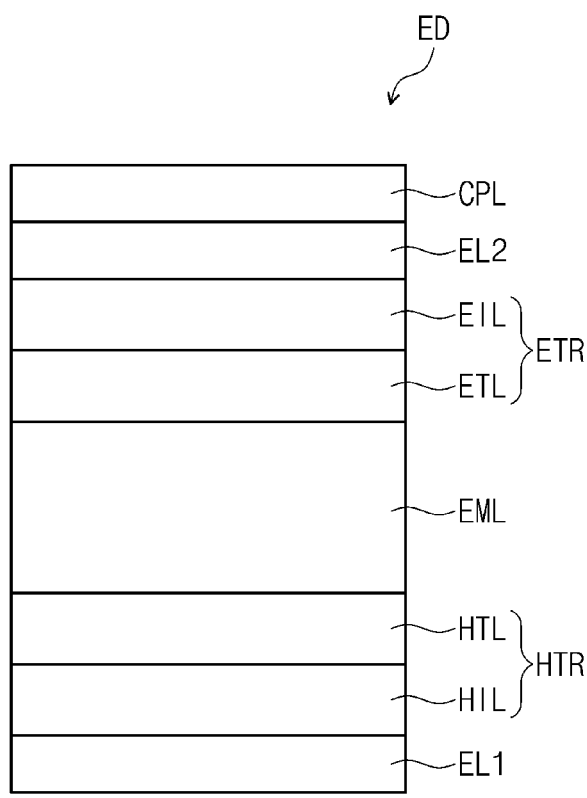
FIG. 6 is a schematic cross-sectional view showing a light emitting device according to an embodiment.

In comparison to FIG. 3, FIG. 4 shows a schematic cross-sectional view of a light emitting device ED of an embodiment, wherein a hole transport region HTR includes a hole injection layer HIL and a hole transport layer HTL, and an electron transport region ETR includes an electron injection layer EIL and an electron transport layer ETL. In comparison to FIG. 3, FIG. 5 shows a schematic cross-sectional view of a light emitting device ED of an embodiment, wherein a hole transport region HTR includes a hole injection layer HIL, a hole transport layer HTL, and an electron blocking layer EBL, and an electron transport region ETR includes an electron injection layer EIL, an electron transport layer ETL, and a hole blocking layer HBL. In comparison to FIG. 4, FIG. 6 shows a schematic cross-sectional view of a light emitting device ED of an embodiment, wherein a capping layer CPL is disposed on the second electrode EL2.

The light emitting device ED of an embodiment may include the polycyclic compound of an embodiment, which will be explained later, in at least one functional layer such as a hole transport region HTR, an emission layer EML, and an electron transport region ETR.

In the light emitting device ED according to an embodiment, the first electrode EL1 has conductivity. The first electrode EL1 may be formed of a metal material, a metal alloy, or a conductive compound. The first electrode EL1 may be an anode or a cathode. However, embodiments are not limited thereto. In an embodiment, the first electrode EL1 may be a pixel electrode. The first electrode EL1 may be a transmissive electrode, a transflective electrode, or a reflective electrode. If the first electrode EL1 is a transmissive electrode, the first electrode EL1 may include a transparent metal oxide such as indium tin oxide (ITO), indium zinc oxide (IZO), zinc oxide (ZnO), and indium tin zinc oxide (ITZO). If the first electrode EL1 is a transflective electrode or a reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, W, compounds thereof, or mixtures thereof (for example, a mixture of Ag and Mg). In an embodiment, the first electrode EL1 may have a structure including multiple layers including a reflective layer or a transflective layer formed using the above materials, and a transmissive conductive layer formed using ITO, IZO, ZnO, or ITZO. For example, the first electrode EL1 may include a three-layer structure of ITO/Ag/ITO. However, embodiments are not limited thereto. The first electrode EL1 may include the above-described metal materials, combinations of two or more metal materials selected from the above-described metal materials, or oxides of the above-described metal materials. A thickness of the first electrode EL1 may be in a range of about 700 Å to about 10,000 Å. For example, the thickness of the first electrode EL1 may be in a range of about 1,000 Å to about 3,000 Å.

The hole transport region HTR may be provided on the first electrode EL1. The hole transport region HTR may include at least one of a hole injection layer HIL, a hole transport layer HTL, a buffer layer (not shown), an emission auxiliary layer (not shown), and an electron blocking layer EBL. A thickness of the hole transport region HTR may be in a range of about 50 Å to about 15,000 Å.

The hole transport region HTR may have a layer formed using a single material, a layer formed using different materials, or a multilayer structure including layers formed using different materials.

For example, the hole transport region HTR may have a structure of a single layer of a hole injection layer HIL or a hole transport layer HTL, and may have a structure of a layer formed using a hole injection material and a hole transport material. In an embodiment, the hole transport region HTR may have a structure of a layer formed using different materials, or a structure stacked from the first electrode EL1 of a hole injection layer HIL/a hole transport layer HTL, a hole injection layer HIL/a hole transport layer HTL/a buffer layer (not shown), a hole injection layer HIL/a buffer layer (not shown), a hole transport layer HTL/a buffer layer (not shown), or a hole injection layer HIL/a hole transport layer HTL/a electron blocking layer EBL, without limitation.

The hole transport region HTR may be formed using various methods such as a vacuum deposition method, a spin coating method, a cast method, a Langmuir-Blodgett (LB) method, an inkjet printing method, a laser printing method, and a laser induced thermal imaging (LITI) method.

In the light emitting device ED of an embodiment, the hole transport region HTR may include a polycyclic compound represented by Formula 1 below. In the light emitting device ED of an embodiment, the hole transport region HTR may include at least one of a hole injection layer HIL, a hole transport layer HTL, and an electron blocking layer EBL, and at least one among the hole injection layer HIL, the hole transport layer HTL, and the electron blocking layer EBL may include the polycyclic compound of an embodiment, represented by Formula 1. For example, in the light emitting device ED of an embodiment, the hole transport layer HTL may include a polycyclic compound represented by Formula 1 below.

[Formula 1]

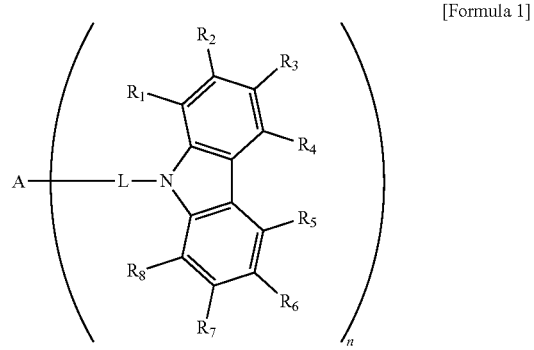

In Formula 1, L may be a substituted or unsubstituted arylene group of 6 to 30 ring-forming carbon atoms.

For example, in an embodiment, L may be a substituted or unsubstituted phenylene group, a substituted or unsubstituted divalent biphenyl group, a substituted or unsubstituted divalent naphthyl group, a substituted or unsubstituted divalent fluorenyl group, or a substituted or unsubstituted divalent phenanthryl group. However, embodiments are not limited thereto.

In an embodiment, L may be a group selected from any one among Compound Group L-1 below.

[Compound Group L-1]

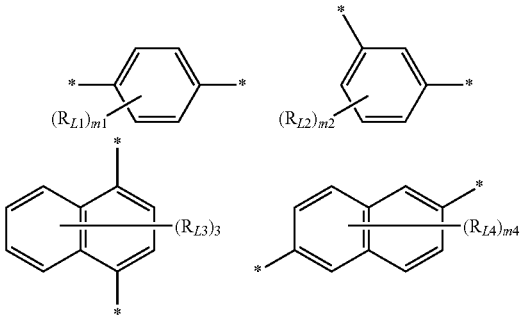

-continued

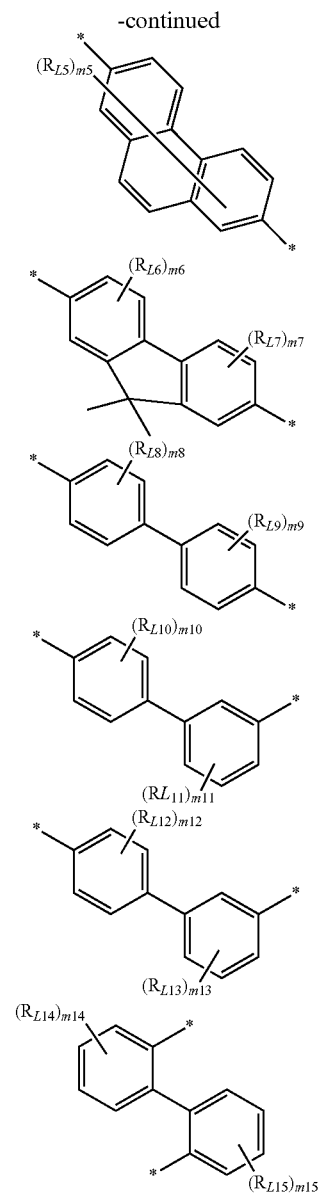

In Compound Group L-1, $R_{L1}$ to $R_{L15}$ may each independently be a hydrogen atom, a deuterium atom, a halogen atom, a substituted or unsubstituted silyl group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring. For example, $R_{L1}$ to $R_{L15}$ may each independently be a hydrogen atom or a deuterium atom.

In Compound Group L-1, m1 and m2 may each independently be an integer from 0 to 4. In Compound Group L-1, m3 and m4 may each independently be an integer from 0 to 6. In Compound Group L-1, m5 may be an integer from 0 to 8. In Compound Group L-1, m6 and m7 may each independently be an integer from 0 to 3. In Compound Group L-1, m8 to m15 may each independently be an integer from 0 to 4. For example, m1 to m15 may each be 0. A case where each of m1 to m15 is 0 may be the same as a case where each of m1 to m15 is 1 and each of $R_{L1}$ to $R_{L15}$ is a hydrogen atom. However, embodiments are not limited thereto.

In Compound Group L-1, -* represents a position bonded to A or N in Formula 1. For example, each of the compounds shown in Compound Group L-1 may include two -*, and the two -* may be bonded to A and N, respectively, in Formula 1.

In Formula 1, $R_1$ to $R_8$ may each independently be a hydrogen atom, a deuterium atom, a halogen atom, a substituted or unsubstituted silyl group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring.

For example, in an embodiment, $R_1$ to $R_8$ may each independently be a hydrogen atom, a deuterium atom, a halogen atom, a methyl group, a t-butyl group, a substituted or unsubstituted amine group, a substituted or unsubstituted silyl group, a substituted or unsubstituted phenyl group, a substituted or unsubstituted carbazole group, a substituted or unsubstituted dibenzofuran group, a substituted or unsubstituted dibenzothiophene group, a substituted or unsubstituted phenoxazine group, or a substituted or unsubstituted acridyl group.

However, embodiments are not limited thereto.

In case where $R_1$ to $R_8$ are combined with an adjacent group to form a ring, neighboring substituents may be combined with each other to form a fused ring with a carbazole group. For example, adjacent groups among $R_1$ to $R_8$ may be combined with each other to form a five-member ring or a six-member ring, and a heteroatom such as O, N, and S may be included in addition to a carbon atom as a ring-forming atom. A ring formed by the combination of adjacent groups among $R_1$ to $R_8$ may be monocyclic or may be polycyclic.

In Formula 1, n may be 1 or 2.
In Formula 1, A may be a group represented by Formula 2.

[Formula 2]

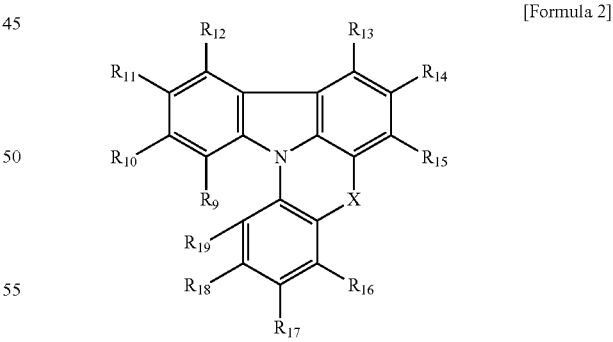

In Formula 2, X may be O or S. For example, in an embodiment, the polycyclic compound represented by Formula 1 may include an indolo phenoxazine skeleton or an indolo phenothiazine skeleton.

In Formula 2, $R_9$ to $R_{19}$ may each independently be a hydrogen atom, a deuterium atom, a halogen atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring.

In Formula 2, at least one of $R_9$ to $R_{19}$ may be bonded to L in Formula 1. For example, in Formula 1, if n is 1, any one among $R_9$ to $R_{19}$ may be bonded to L in Formula 1. For example, in Formula 1, if n is 2, any two among $R_9$ to $R_{19}$ may be respectively bonded to two L groups.

The substituents which are not bonded to L among $R_9$ to $R_{19}$ may each independently be a hydrogen atom or a deuterium atom.

The polycyclic compound represented by Formula 1 may be represented by Formula 1-1 or Formula 1-2 below.

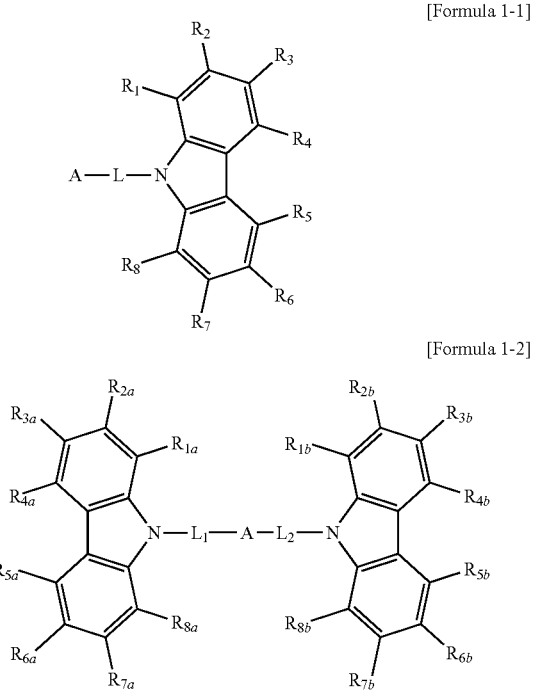

[Formula 1-1]

[Formula 1-2]

Formula 1-1 is an embodiment of Formula 1 where n is 1. Formula 1-2 is an embodiment of Formula 1 where n is 2.

Referring to Formula 1 and Formula 2, in an embodiment, if n is 1, any one among $R_9$ to $R_{19}$ may be bonded to L. In another embodiment, if n is 2, any two among $R_9$ to $R_{19}$ may be respectively bonded to $L_1$ and $L_2$. However, the value of n is not limited thereto.

In Formula 1-1 and Formula 1-2, $L_1$ and $L_2$ may each independently be a substituted or unsubstituted arylene group of 6 to 30 ring-forming carbon atoms.

For example, $L_1$ and $L_2$ may each independently be a substituted or unsubstituted phenylene group, a substituted or unsubstituted divalent biphenyl group, a substituted or unsubstituted divalent naphthyl group, a substituted or unsubstituted divalent fluorenyl group, or a substituted or unsubstituted divalent phenanthryl group. In an embodiment, $L_1$ and $L_2$ may each independently be a group selected from Compound Group L-1. However, embodiments are not limited thereto.

In Formula 1-1 and Formula 1-2, $R_{1a}$ to $R_{8a}$, and $R_{1b}$ to $R_{8b}$ may each independently be a hydrogen atom, a deuterium atom, a halogen atom, a substituted or unsubstituted silyl group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring.

For example, $R_{1a}$ to $R_{8a}$, and $R_{1b}$ to $R_{8b}$ may each independently be a hydrogen atom, a deuterium atom, a halogen atom, a methyl group, a t-butyl group, a substituted or unsubstituted amine group, a substituted or unsubstituted silyl group, a substituted or unsubstituted phenyl group, a substituted or unsubstituted carbazole group, a substituted or unsubstituted dibenzofuran group, a substituted or unsubstituted dibenzothiophene group, a substituted or unsubstituted phenoxazine group, or a substituted or unsubstituted acridyl group.

In case where $R_{1a}$ to $R_{8a}$, and $R_{1b}$ to $R_{8b}$ are combined with an adjacent group to form a ring, neighboring substituents may be combined with each other to form a fused ring with a carbazole group. For example, adjacent groups of $R_{1a}$ to $R_{8a}$, and $R_{1b}$ to $R_{8b}$ may be combined with each other to form a five-member ring or a six-member ring, and a heteroatom such as O, N, and S may be included as a ring-forming atom in addition to a carbon atom. The ring formed by the combination of adjacent groups among $R_{1a}$ to $R_{8a}$, and $R_{1b}$ to $R_{8b}$ may be monocyclic or polycyclic.

In Formula 1-1 and Formula 1-2, A, L, and $R_1$ to $R_8$ may be the same as defined in connection with Formula 1 and Formula 2.

In an embodiment, A in Formula 1 may be a group represented by Formula 2-1 or Formula 2-2 below.

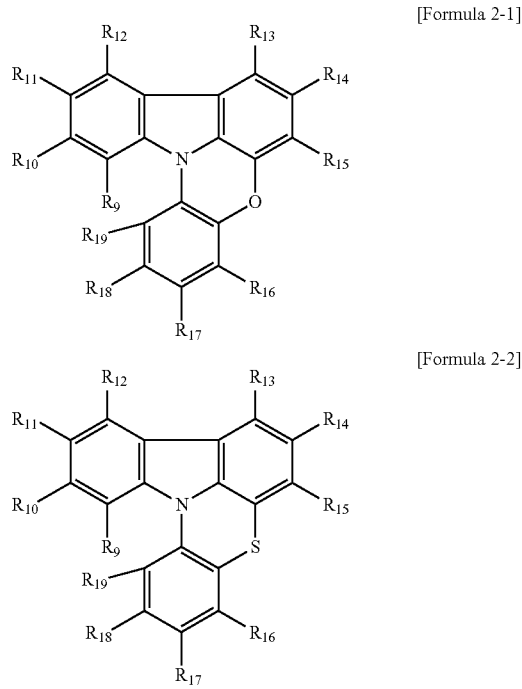

[Formula 2-1]

[Formula 2-2]

Formula 2-1 is an embodiment of Formula 2 where X is O. Formula 2-2 is an embodiment of Formula 2 where X is S. Formula 2 may include an indolo phenoxazine skeleton represented by Formula 2-1, or an indolo phenothiazine skeleton represented by Formula 2-2. For example, the polycyclic compound of an embodiment may include a crosslinked structure of 9-phenyl-9H-carbazole by O or S. By including the crosslinked structure by a heteroatom such as O and S, the polycyclic compound of an embodiment may show improved heat resistance and charge tolerance.

In Formula 2-1 and Formula 2-2, $R_9$ to $R_{19}$ may be the same as defined in connection with Formula 2.

In an embodiment, the polycyclic compound represented by Formula 1 may be represented by any one among Formula 3-1 to Formula 3-6 below.

[Formula 3-1]

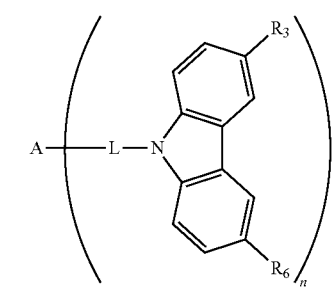

[Formula 3-2]

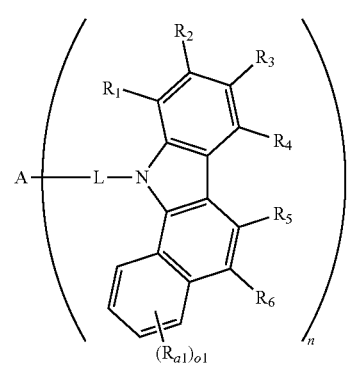

[Formula 3-3]

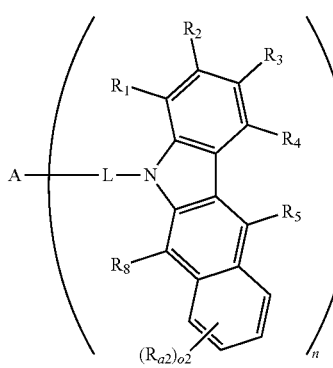

[Formula 3-4]

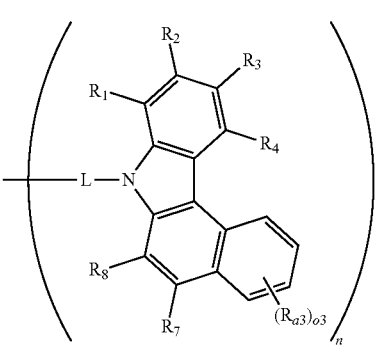

[Formula 3-5]

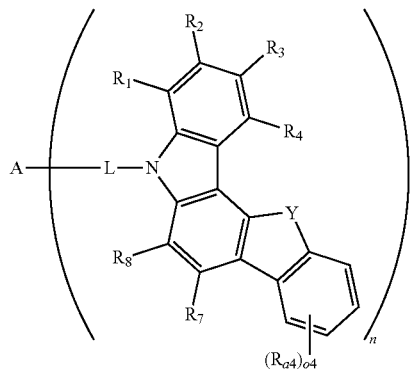

[Formula 3-6]

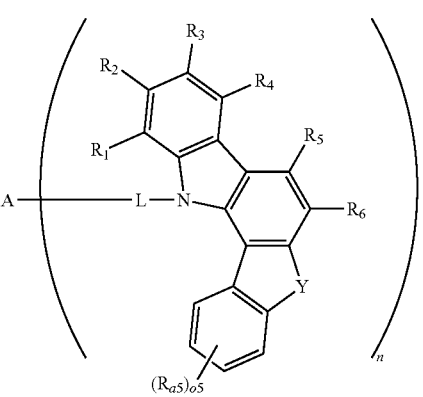

As embodied in Formula 3-1 to Formula 3-6, Formula 1 may include a substituted or unsubstituted carbazole group. For example, Formula 1 may include the skeleton of a carbazole group or a carbazole derivative.

In Formula 3-1 to Formula 3-6, Y may be O or S.

$R_{a1}$ to $R_{a5}$ may each independently be a hydrogen atom, a deuterium atom, a halogen atom, a substituted or unsubstituted silyl group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring. For example, $R_{a1}$ to $R_{a5}$ may each independently be a hydrogen atom or a deuterium atom.

In Formula 3-1 to Formula 3-6, o1 to o5 may each independently be an integer from 0 to 4. For example, each of o1 to o5 may be 0. A case where each of o1 to o5 is 0 may have the same structure as a case where each of o1 to o5 is 1 and each of $R_{a1}$ to $R_{a5}$ is a hydrogen atom. For example, each of o1 to o5 may be 1.

In Formula 3-1 to Formula 3-6, A, L, n, and $R_1$ to $R_8$ may be the same as defined in connection with Formula 1.

In an embodiment, the polycyclic compound represented by Formula 1 may be represented by any one among Formula 4-1 to Formula 4-6 below.

[Formula 4-1]
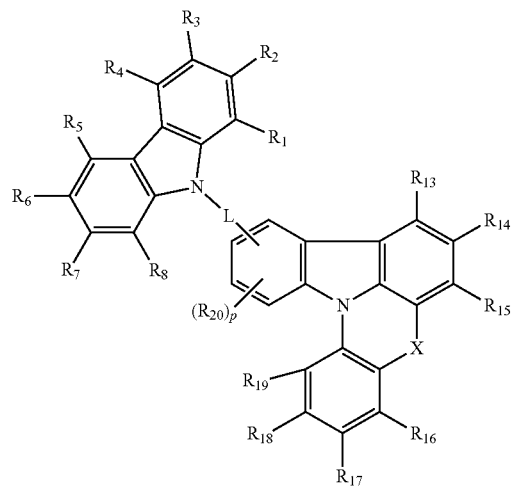
[Formula 4-2]
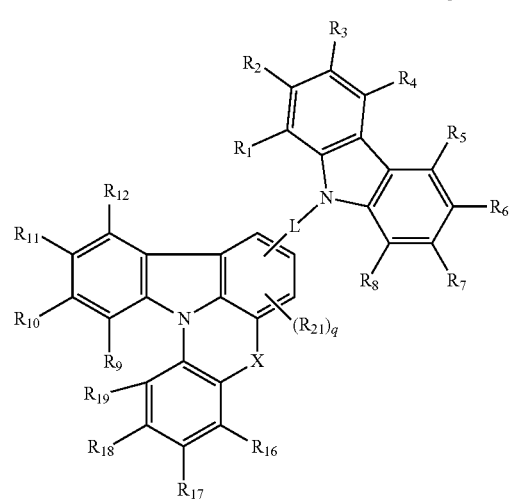
[Formula 4-3]
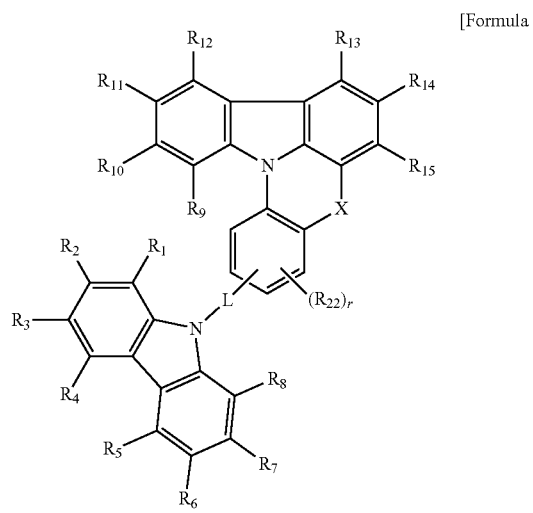
[Formula 4-4]
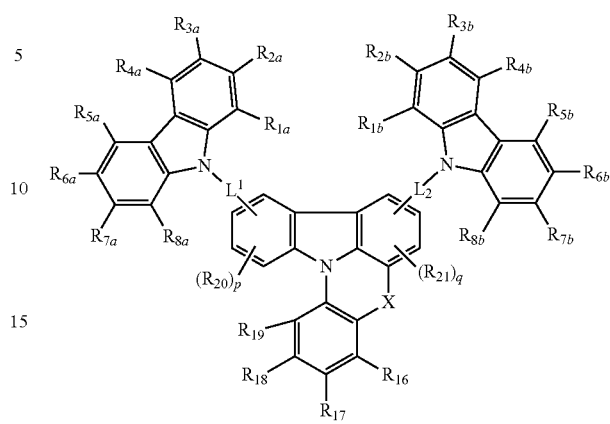
[Formula 4-5]
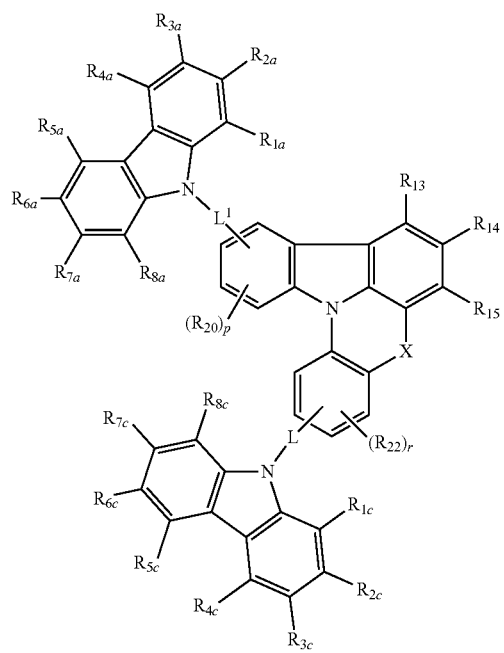

[Formula 4-6]

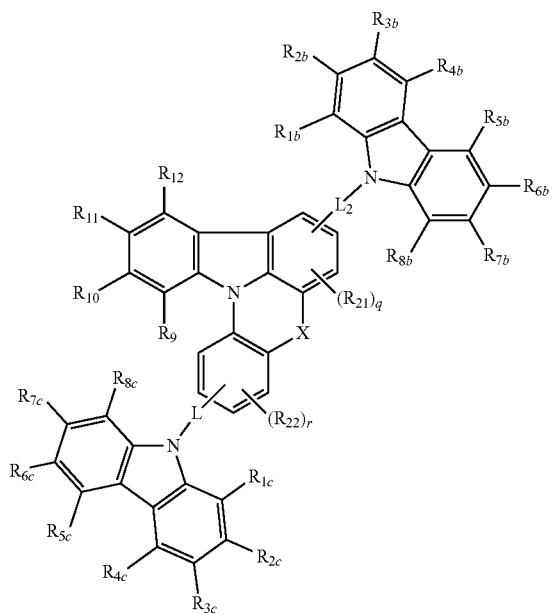

Formula 4-1 to Formula 4-3 are each embodiments of Formula 1 where n is 1, and Formula 4-4 to Formula 4-6 are each embodiments of Formula 1 where "n" is 2.

In Formula 4-1 to Formula 4-6, $R_{20}$, $R_{21}$, and $R_{22}$ may each independently be a hydrogen atom, a deuterium atom, a halogen atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring. For example, $R_{20}$, $R_{21}$ and $R_{22}$ may be each independently a hydrogen atom.

In Formula 4-1 to Formula 4-6, p may be an integer from 0 to 3, q may be an integer from 0 to 2, and r may be an integer from 0 to 3. For example, each of p, q, and r may be 0. A case where each of p, q, and r is 0 may have the same structure as a case where each of p, q, and r is 1 and each of $R_{20}$, $R_{21}$, and $R_{22}$ is a hydrogen atom.

In Formula 4-1 to Formula 4-6, $L_1$ to $L_3$ may each independently be a substituted or unsubstituted arylene group of 6 to 30 ring-forming carbon atoms. For example, $L_1$ to $L_3$ may each independently be a substituted or unsubstituted phenylene group, a substituted or unsubstituted divalent biphenyl group, a substituted or unsubstituted divalent naphthyl group, a substituted or unsubstituted divalent fluorenyl group, or a substituted or unsubstituted divalent phenanthryl group. In an embodiment, $L_1$ to $L_3$ may each independently be a group selected from Compound Group L-1. However, embodiments are not limited thereto.

In Formula 4-1 to Formula 4-6, $R_{1a}$ to $R_{8a}$, $R_{1b}$ to $R_{8b}$, and $R_{1c}$ to $R_{8c}$ may each independently be a hydrogen atom, a deuterium atom, a halogen atom, a substituted or unsubstituted silyl group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring.

For example, $R_{1a}$ to $R_{8a}$, $R_{1b}$ to $R_{8b}$, and $R_{1c}$ to $R_{8c}$ may each independently be a hydrogen atom, a deuterium atom, a halogen atom, a methyl group, a t-butyl group, a substituted or unsubstituted amine group, a substituted or unsubstituted silyl group, a substituted or unsubstituted phenyl group, a substituted or unsubstituted carbazole group, a substituted or unsubstituted dibenzofuran group, a substituted or unsubstituted dibenzothiophene group, a substituted or unsubstituted phenoxazine group, or a substituted or unsubstituted acridyl group.

In case where $R_{1a}$ to $R_{8a}$, $R_{1b}$ to $R_{8b}$, and $R_{1c}$ to $R_{8c}$ are combined with an adjacent group to form a ring, neighboring substituents may be combined with each other to form a fused ring with a carbazole group. For example, adjacent groups among $R_{1a}$ to $R_{8a}$, $R_{1b}$ to $R_{8b}$, and $R_{1c}$ to $R_{8c}$ may be combined with each other to form a five-member ring or a six-member ring, and a heteroatom such as O, N, and S may be included as a ring-forming atom in addition to a carbon atom. The ring formed by the combination of adjacent groups among $R_{1a}$ to $R_{8a}$, $R_{1b}$ to $R_{8b}$, and $R_{1c}$ to $R_{8c}$ may be monocyclic or polycyclic.

In Formula 4-1 to Formula 4-6, L, X, and $R_1$ to $R_{19}$ may be the same as defined in connection with Formula 1 and Formula 2.

The polycyclic compound of an embodiment represented by Formula 1 may be any one selected from Compound Group 1A to Compound Group 1D below. The hole transport region HTR of the light emitting device ED of an embodiment may include at least one among the compounds in Compound Group 1A to Compound Group 1D below.

[Compound Group 1A]

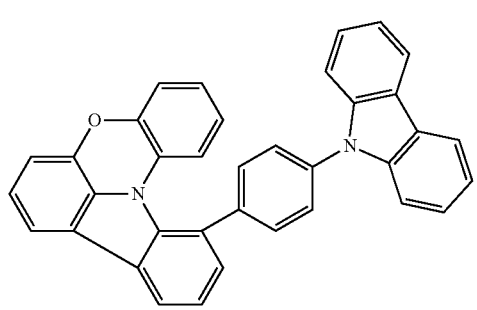

A1

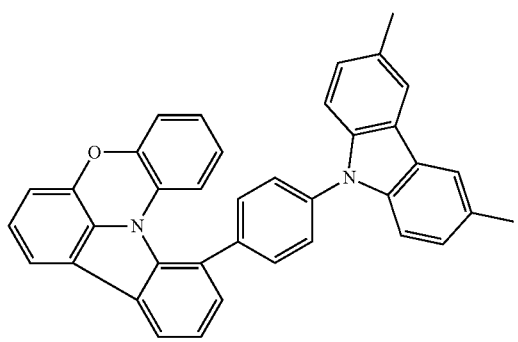

A2

-continued
A3
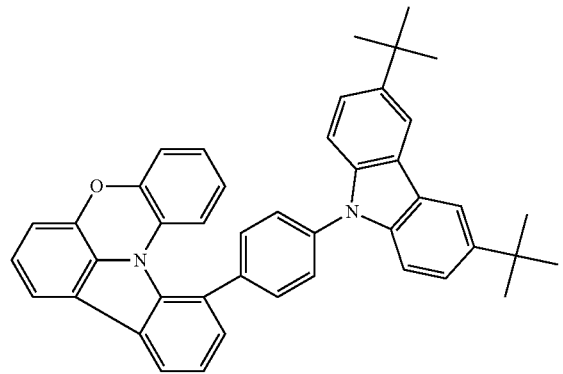
A4
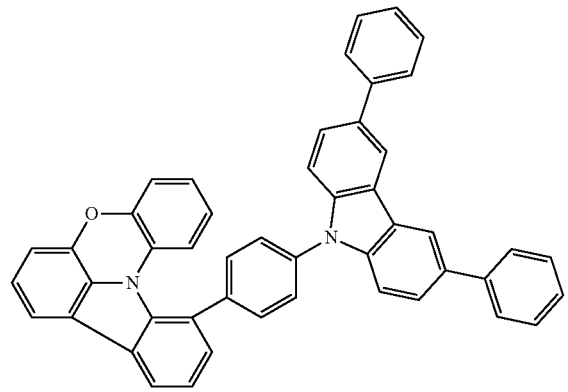
A5
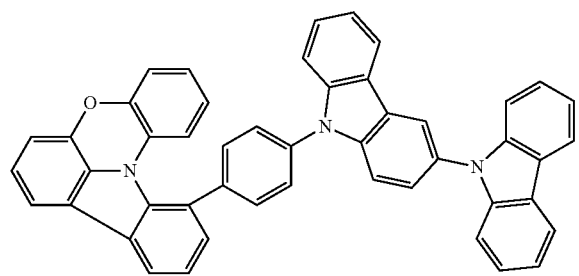
A6
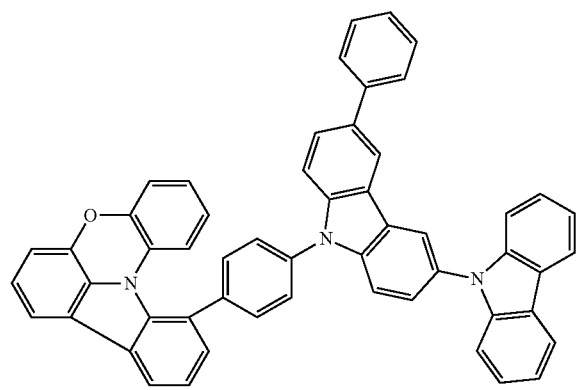
A7
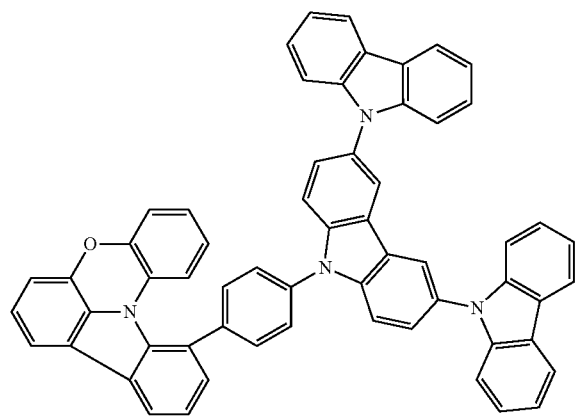
A8
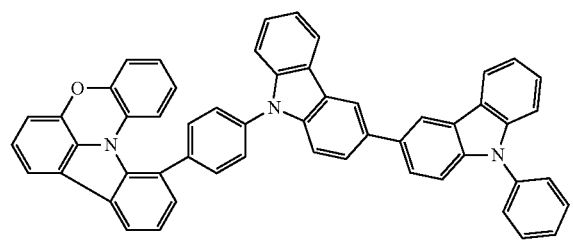

-continued
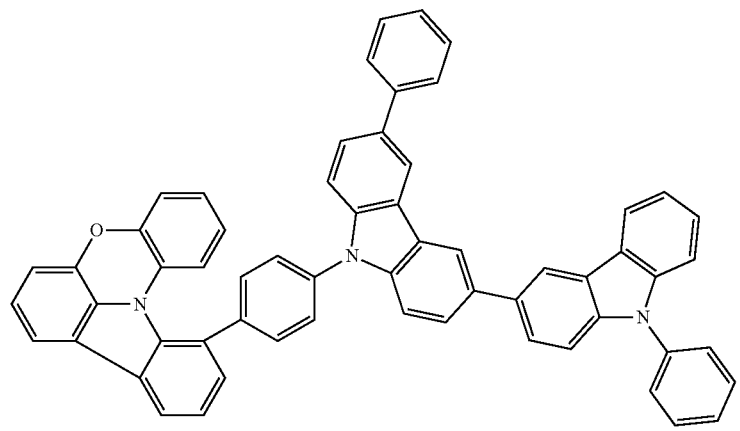
A9
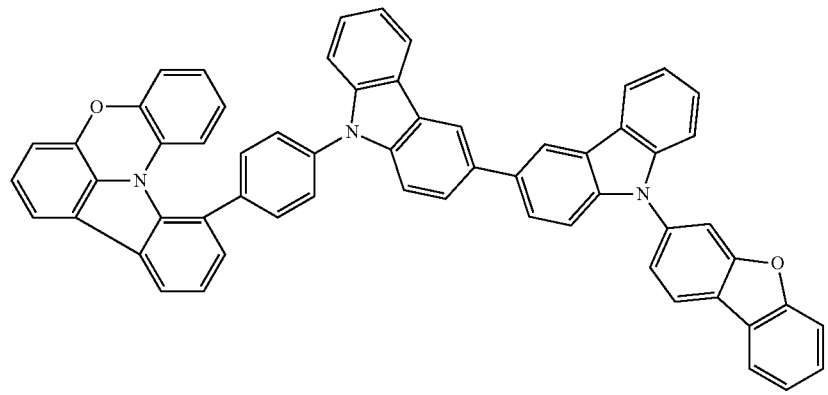
A10
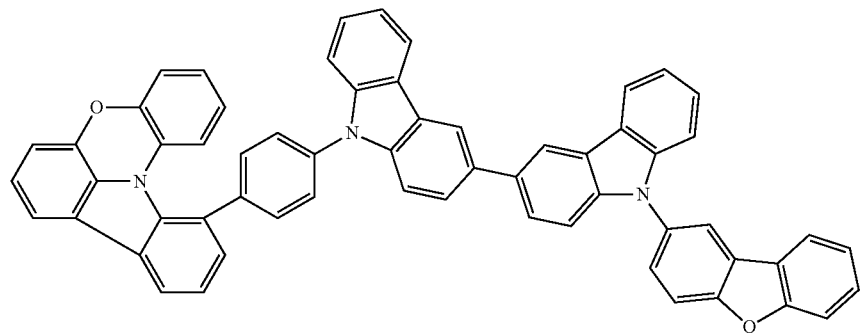
A11
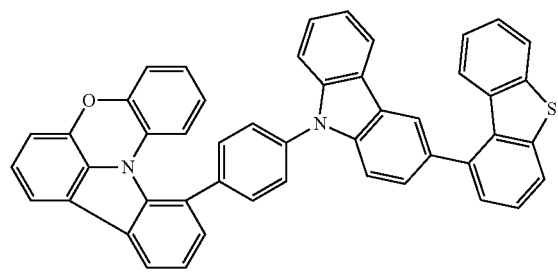
A12
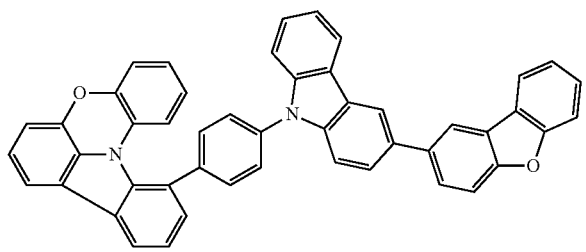
A13

-continued
| A14 | A15 |
|---|---|
| 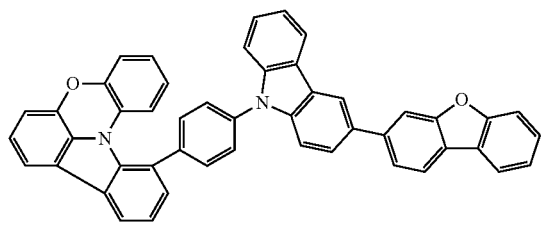 | 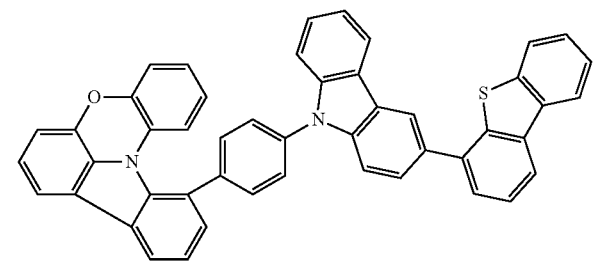 |
| A16 | A17 |
| 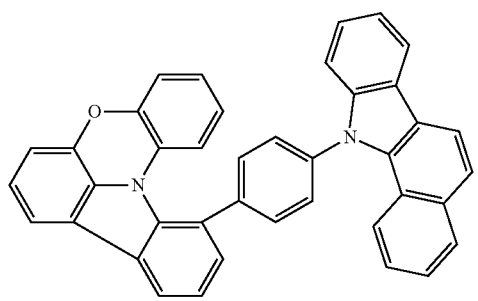 | 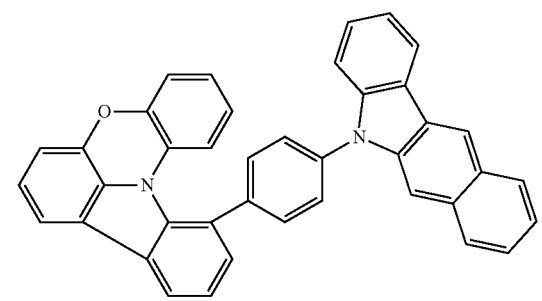 |
| A18 | A19 |
| 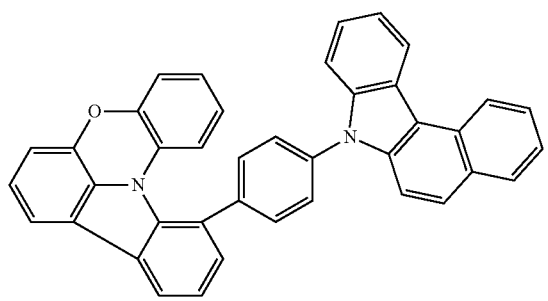 | 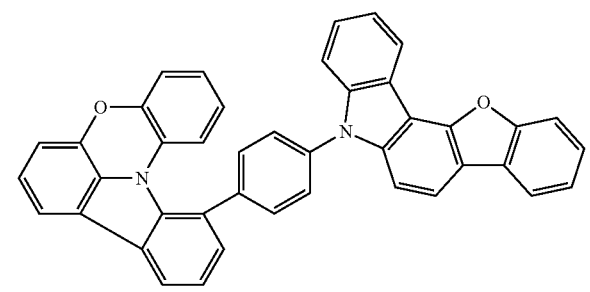 |
| A20 | A21 |
| 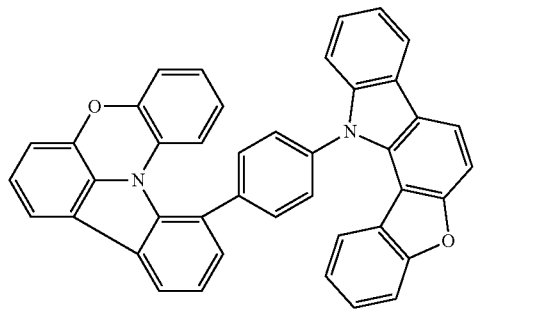 | 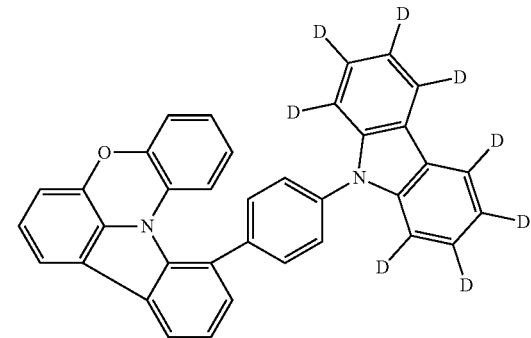 |
| A22 | A23 |
| 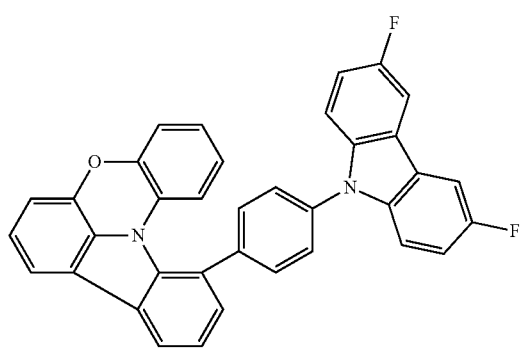 | 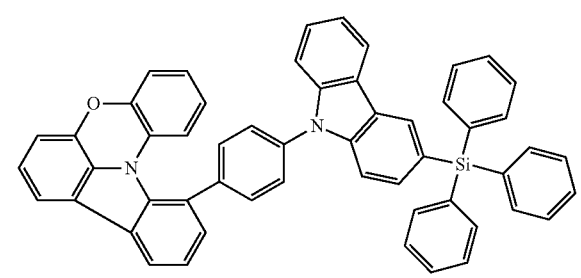 |

-continued
A24
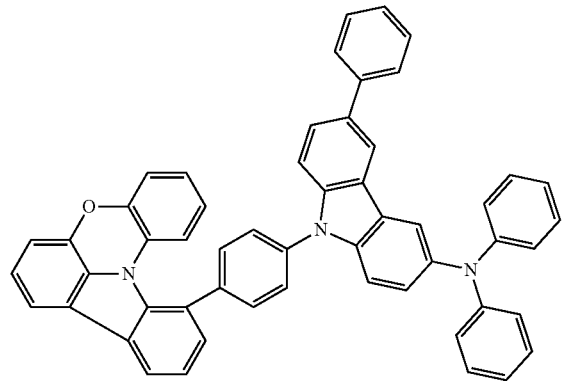
A25
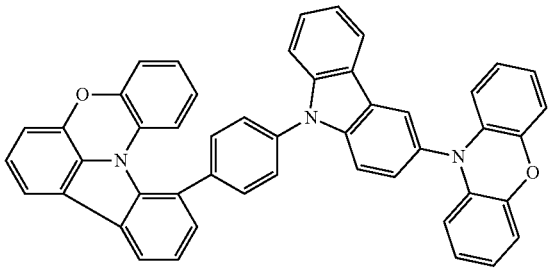
A26
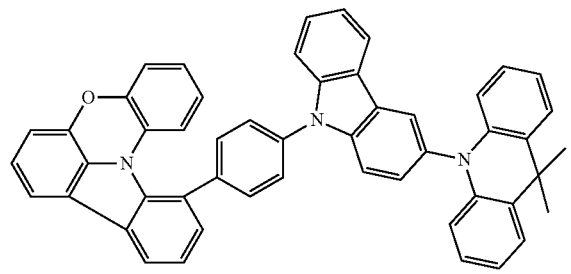
A27
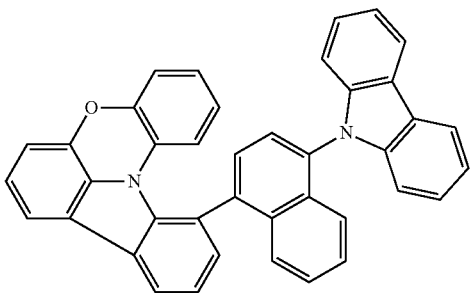
A28
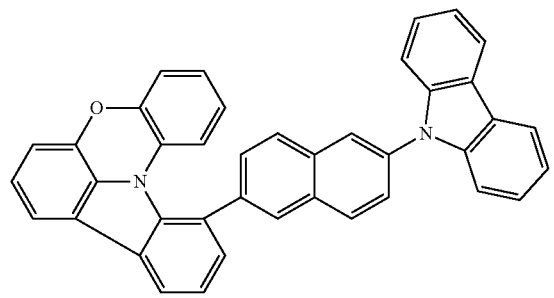
A29
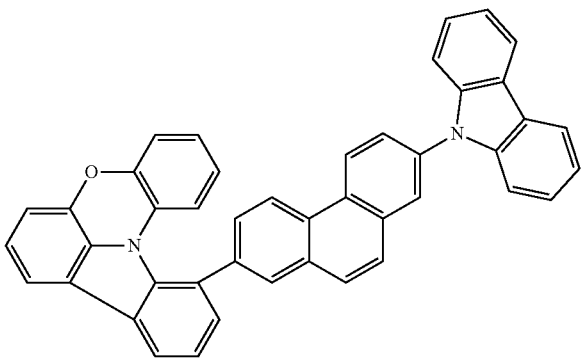
A30
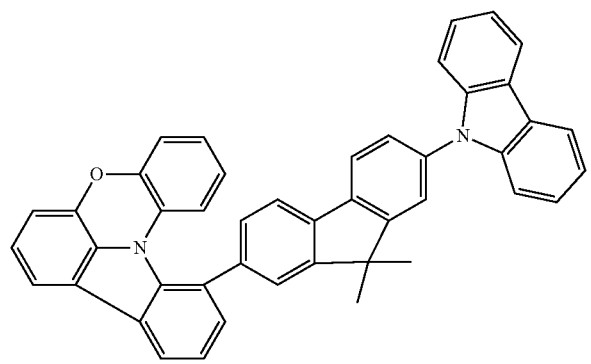
A31
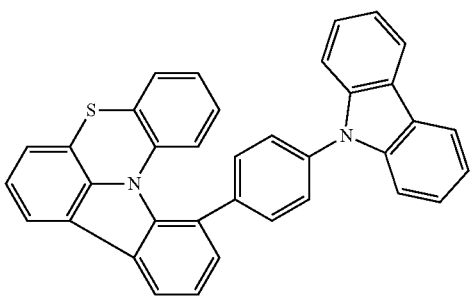

-continued
A32
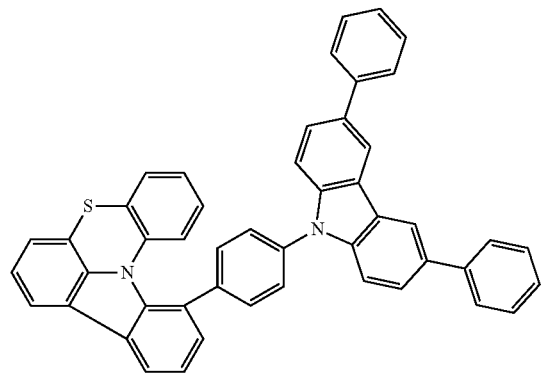
A33
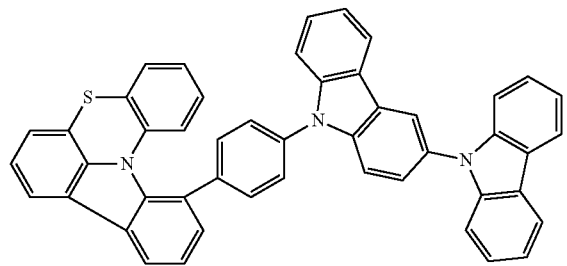
A34
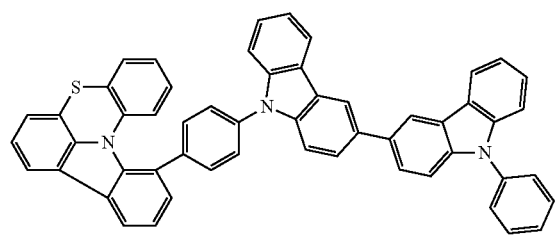
A35
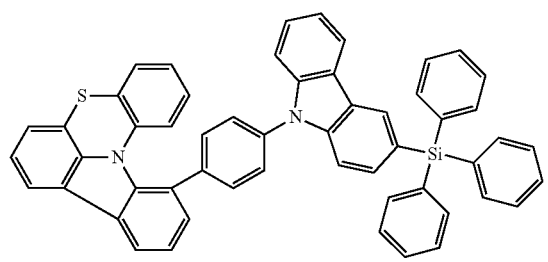
A36
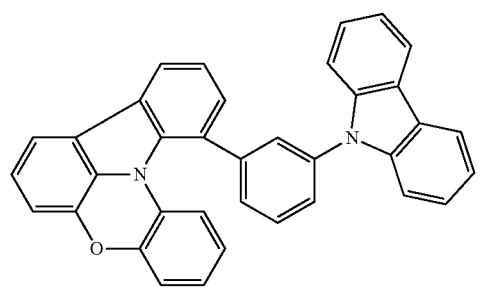
A37
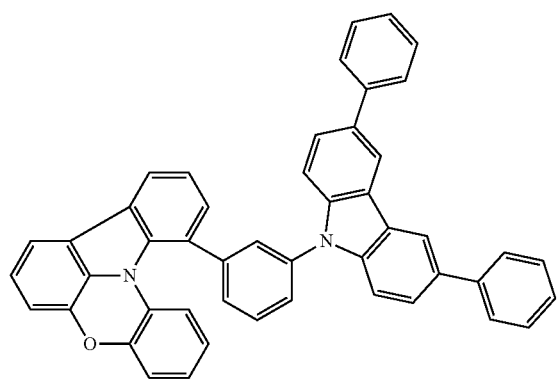
A38
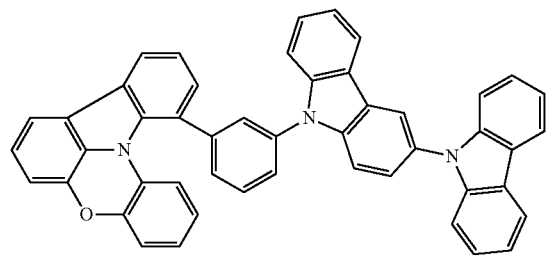
A39
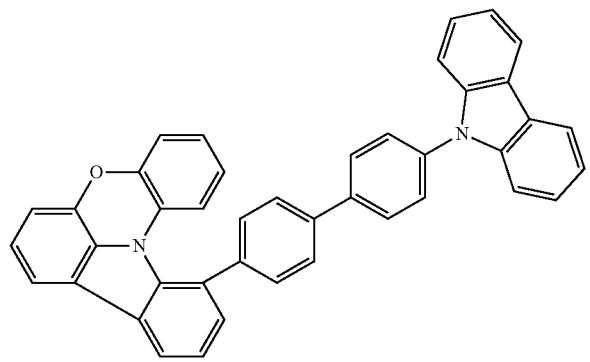

-continued
A40
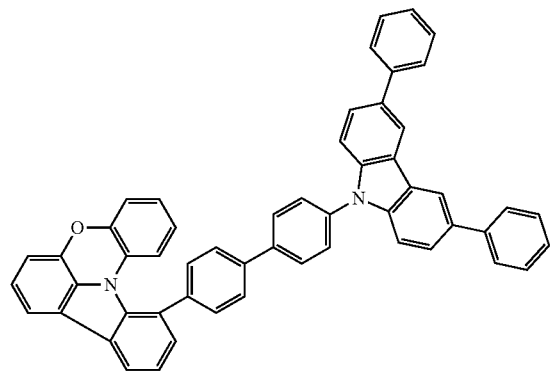
A41
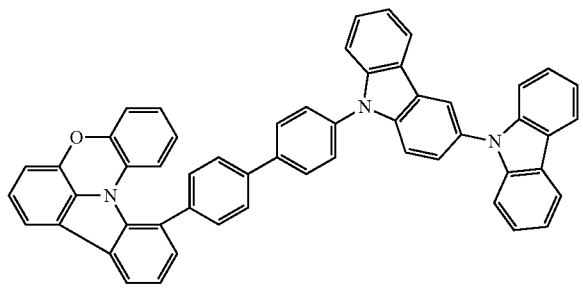
A42
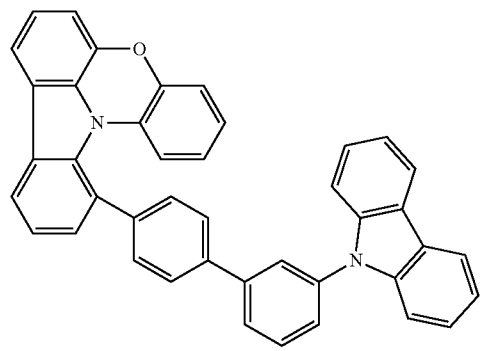
A43
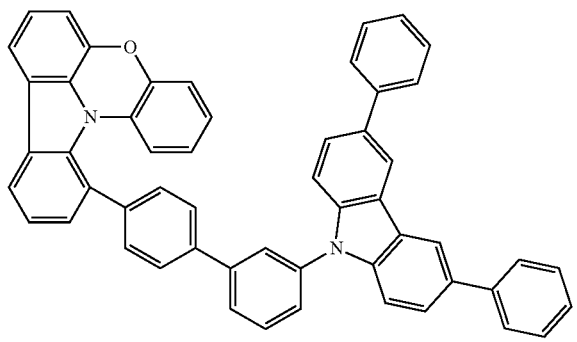
A44
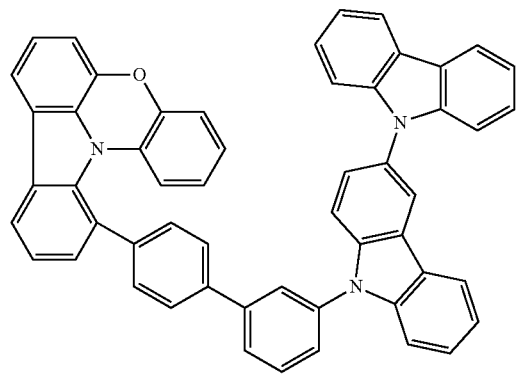
A45
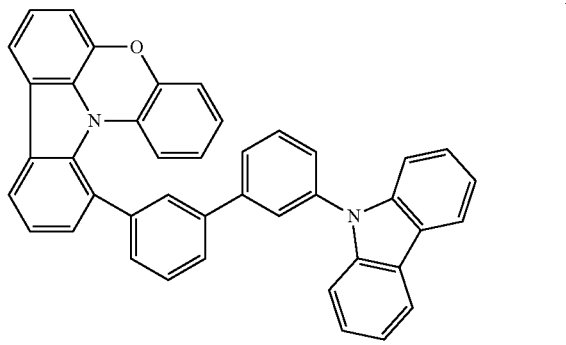
A46
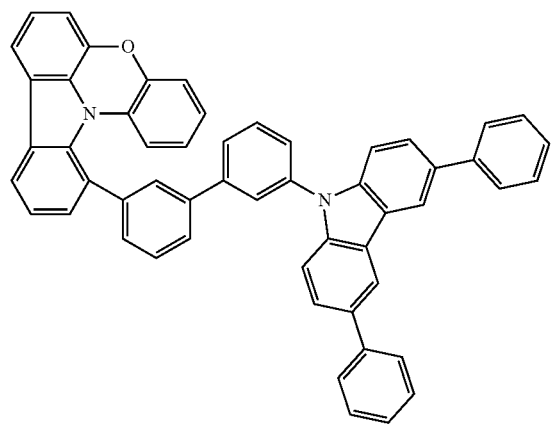
A47
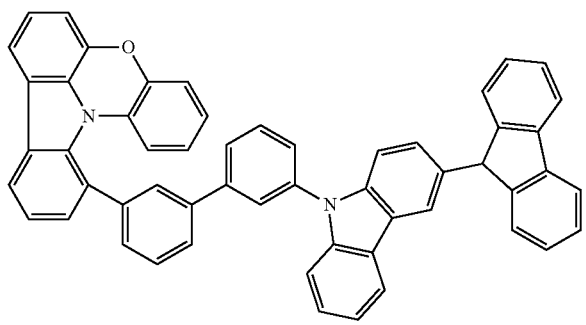

-continued
A48
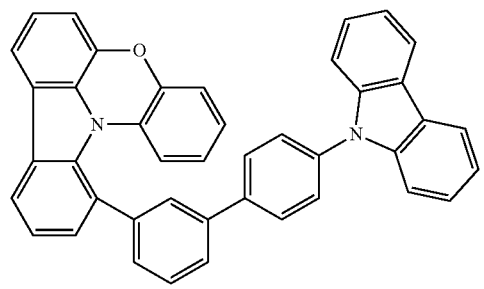
A49
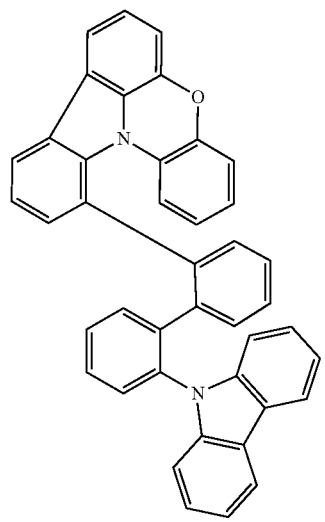
A50
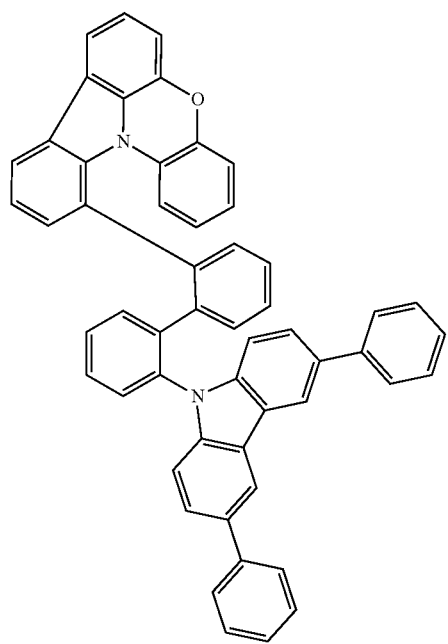
A51
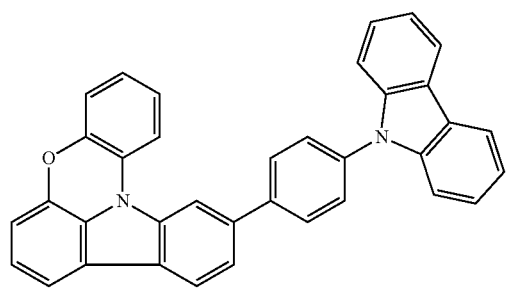
A52
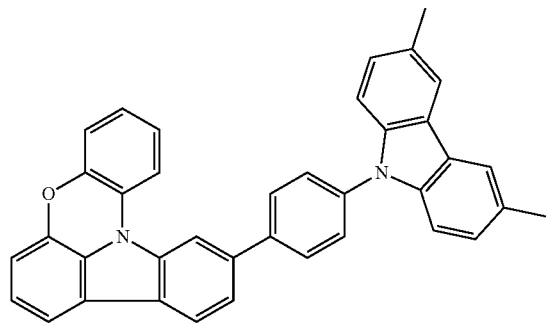
A53
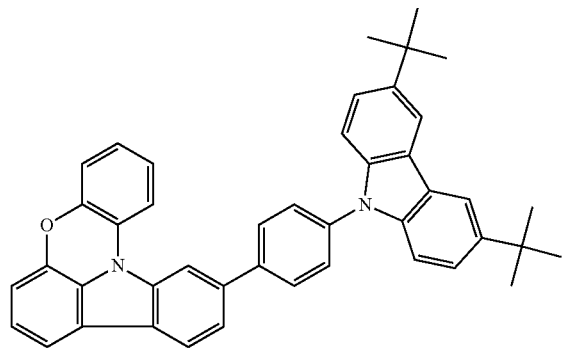

-continued
A54
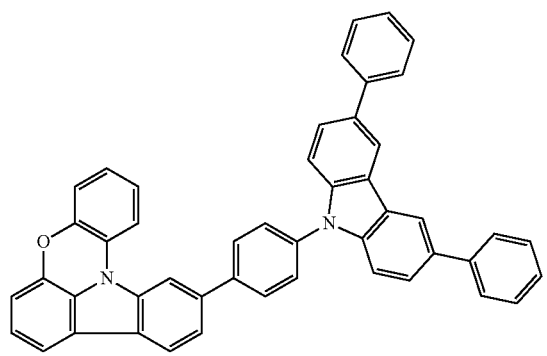
A55
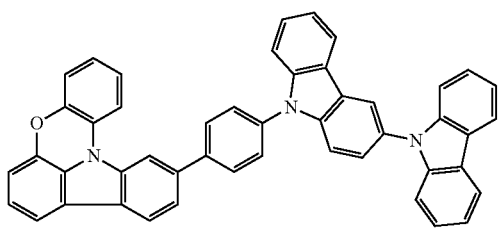
A56
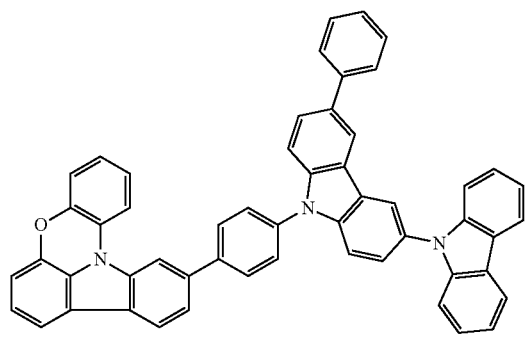
A57
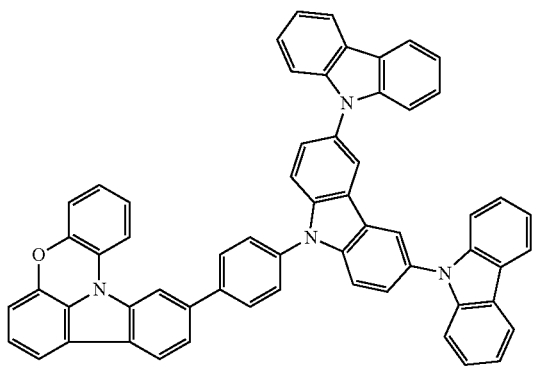
A58
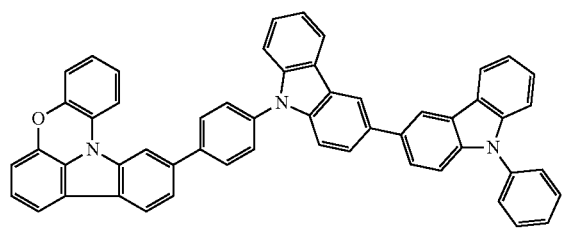
A59
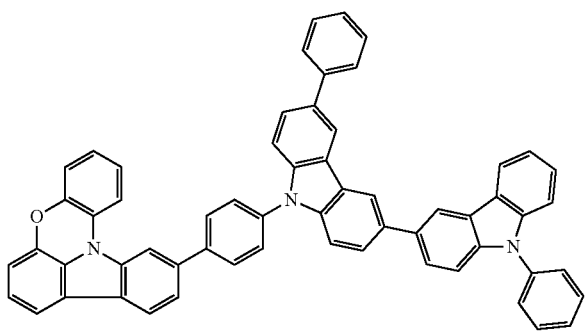
A60
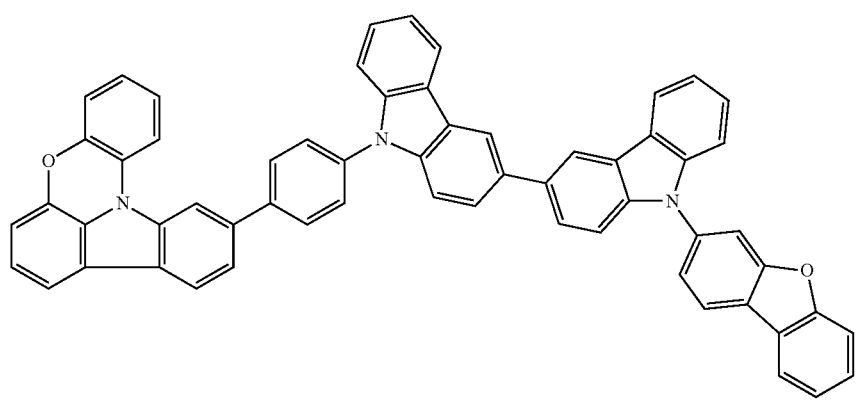

-continued
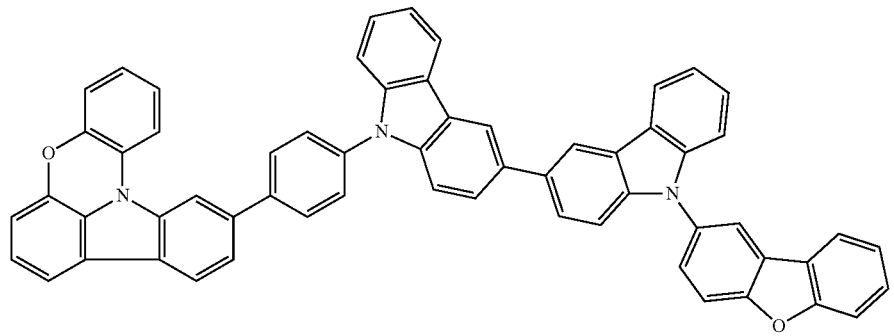
A61
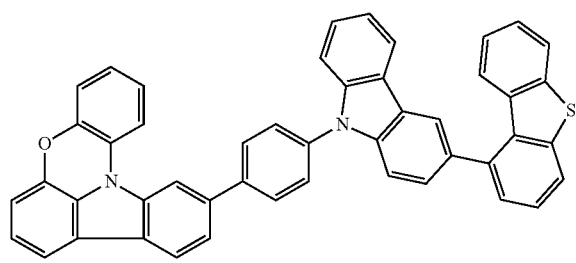
A62
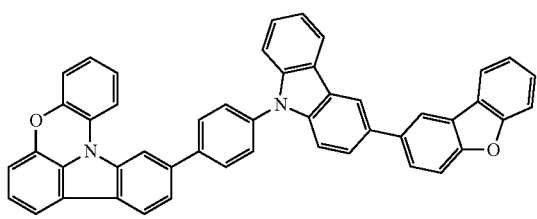
A63
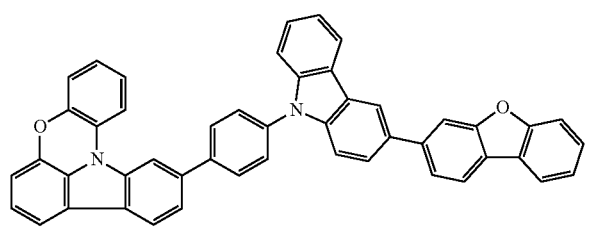
A64
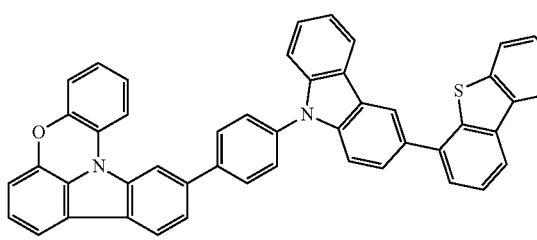
A65
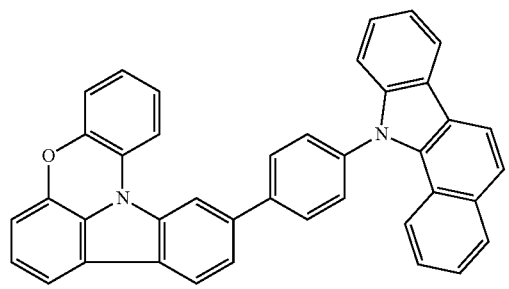
A66
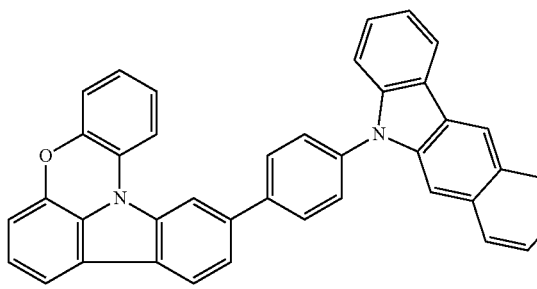
A67
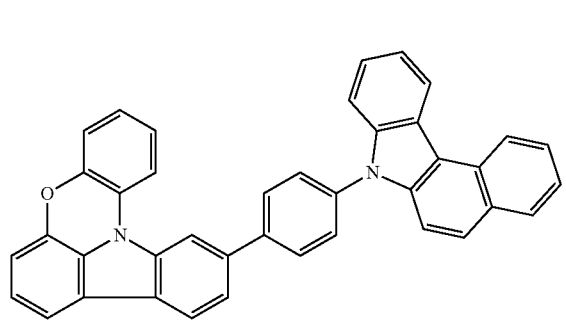
A68
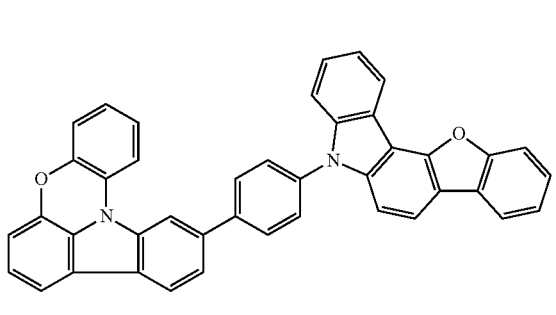
A69

-continued
A70
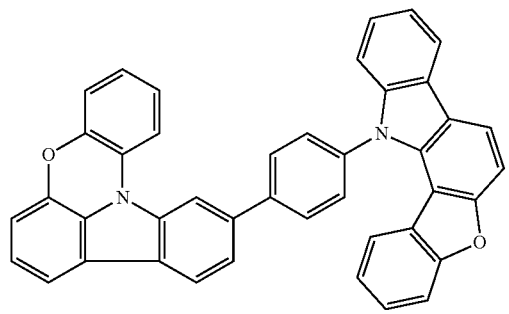
A71
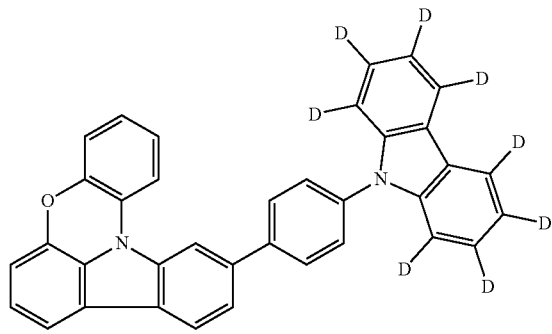
A72
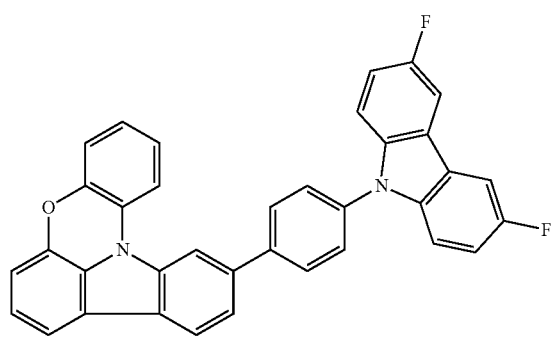
A73
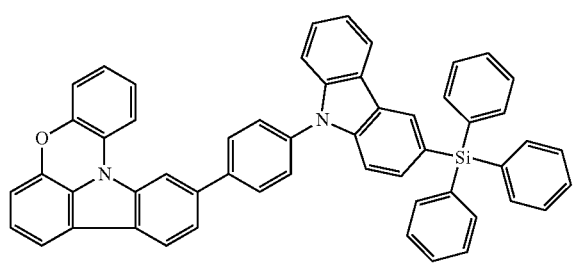
A74
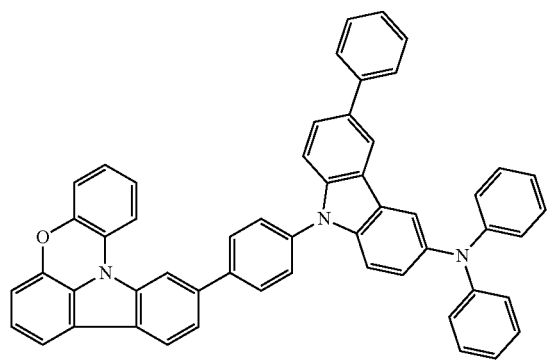
A75
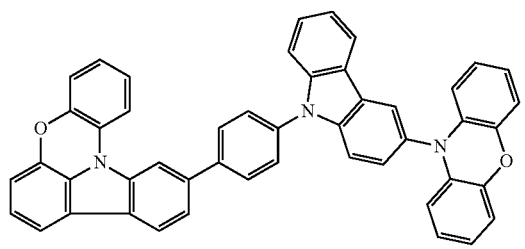
A76
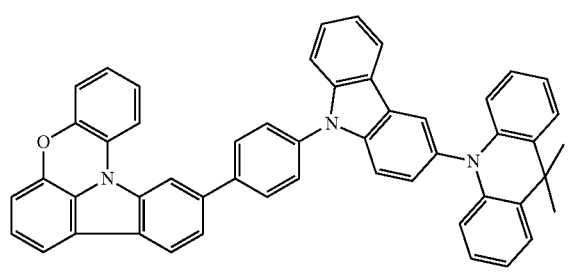
A77
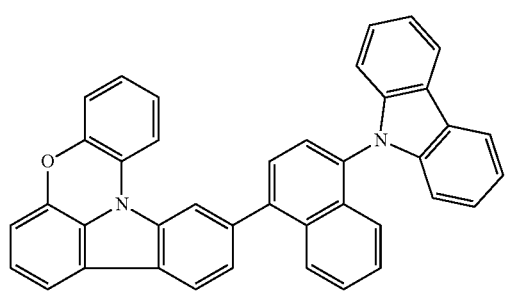

-continued
A78 A79
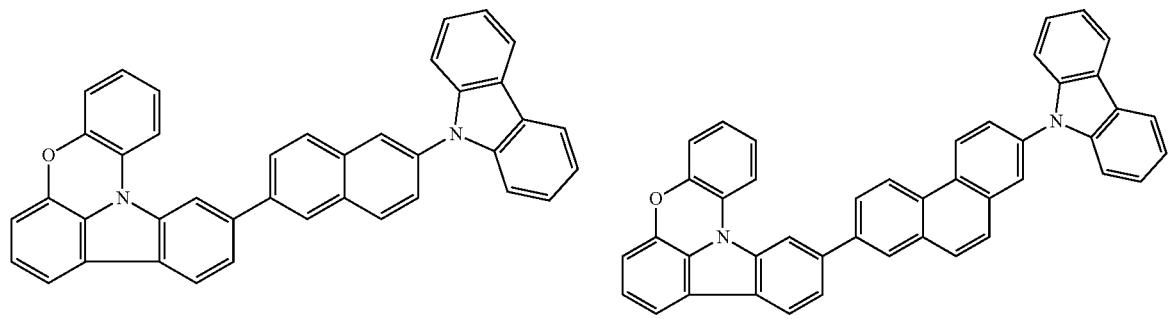
A80 A81
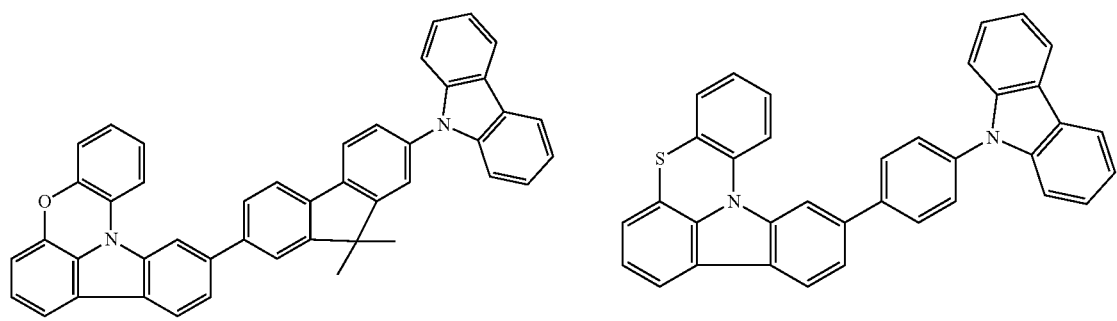
A82 A83
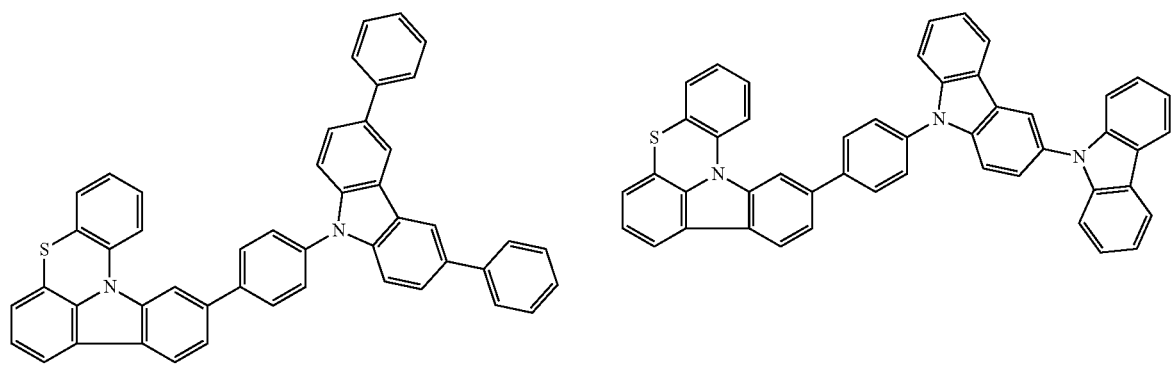
A84 A85
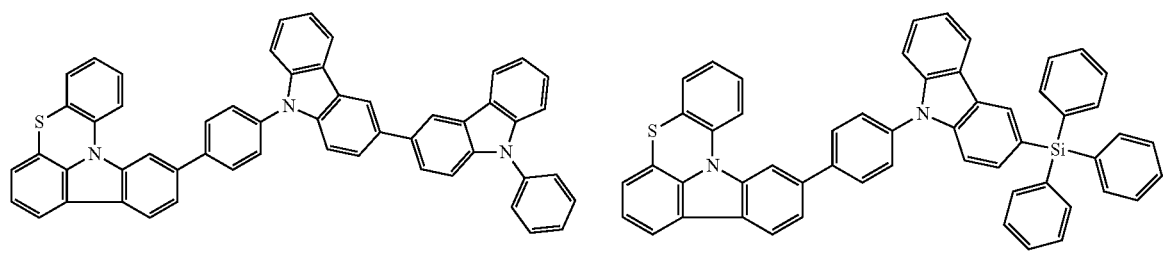

-continued
A86
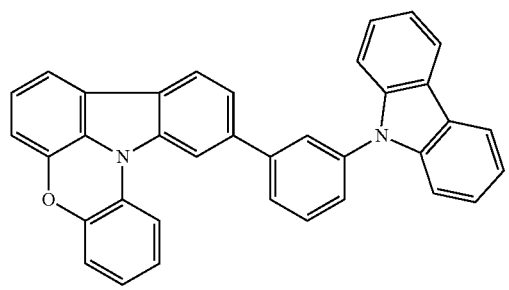
A87
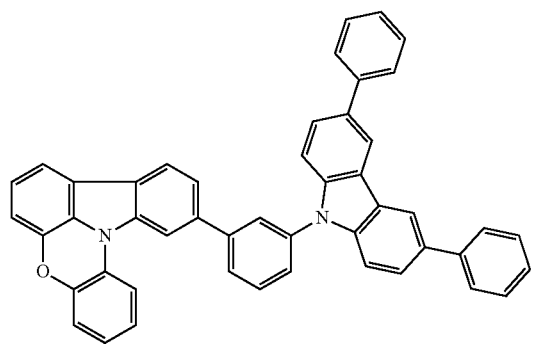
A88
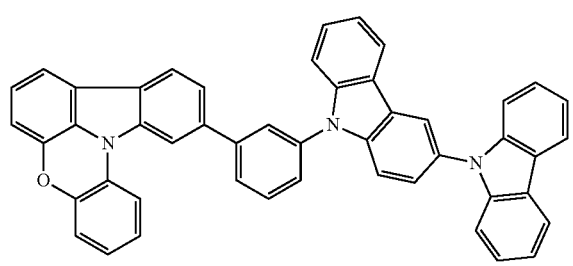
A89
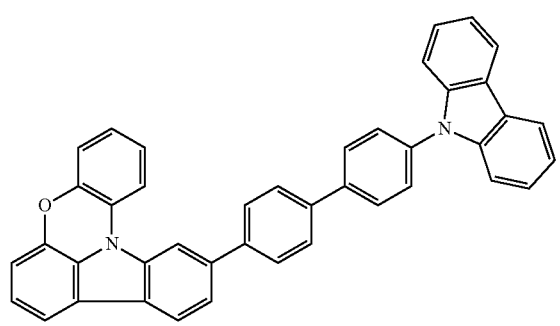
A90
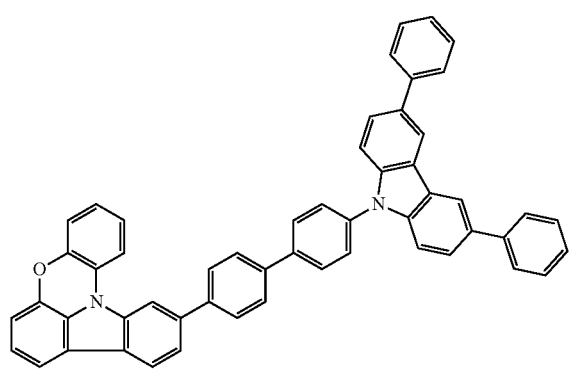
A91
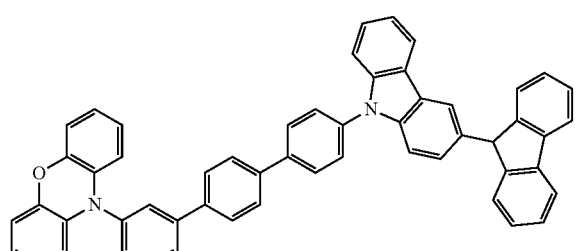
A92
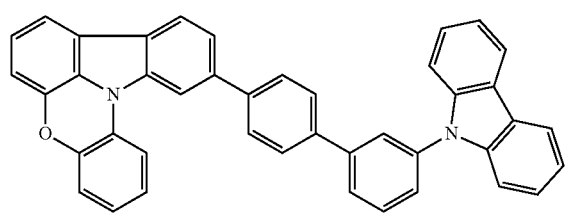
A93
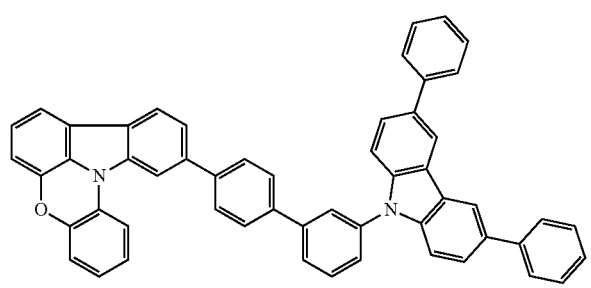

-continued
A93
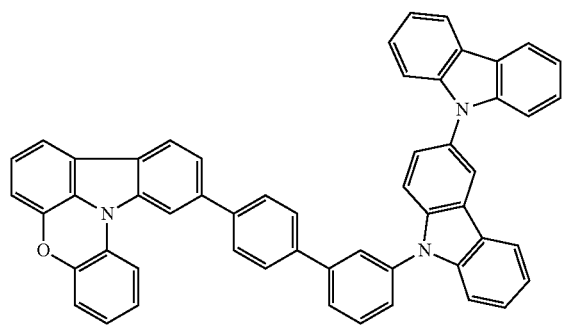
A95
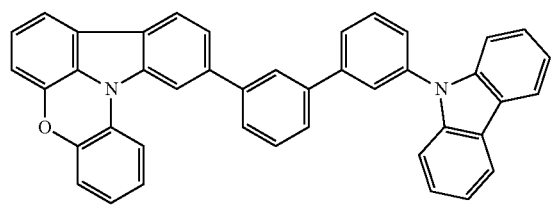
A96
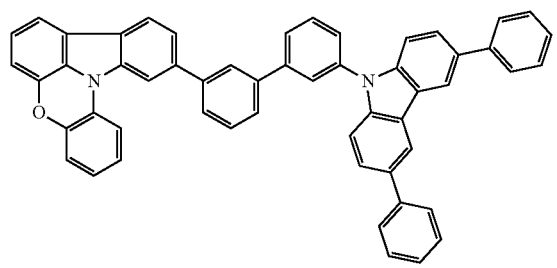
A97
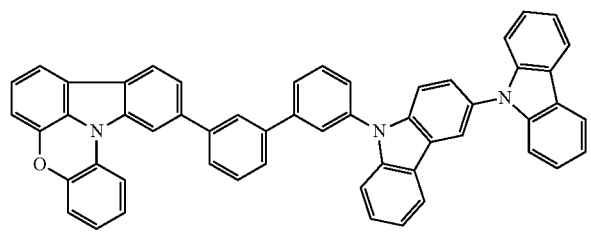
A98
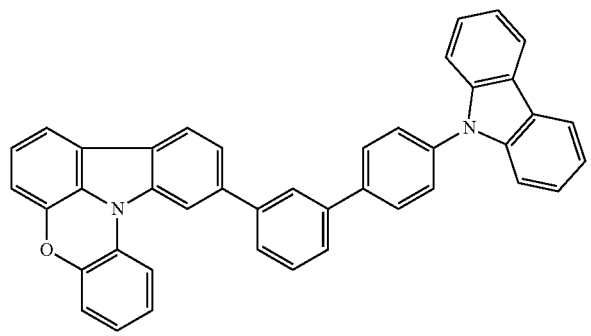
A99
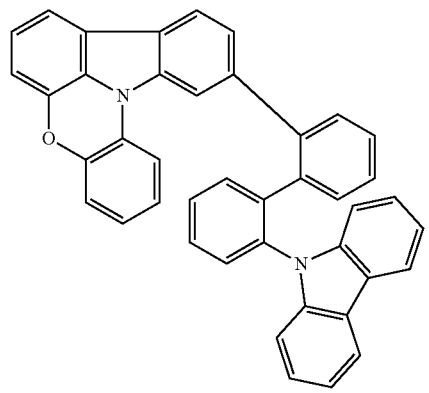
A100
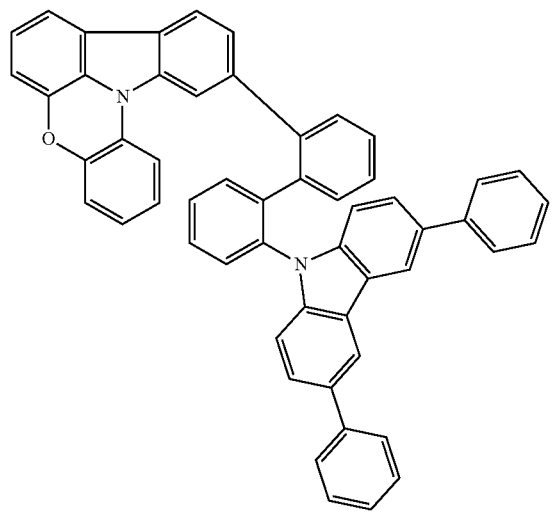
A101
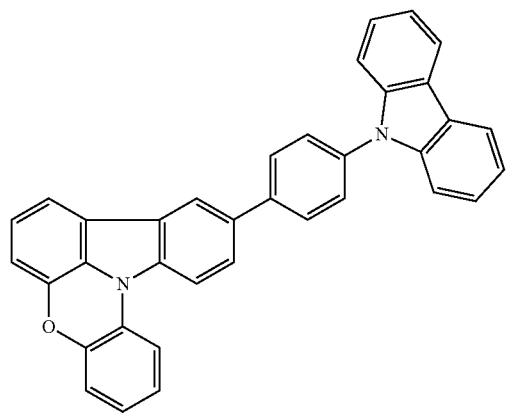

-continued
A102
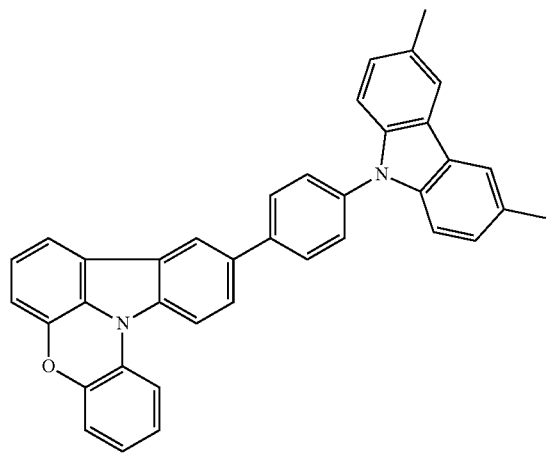
A103
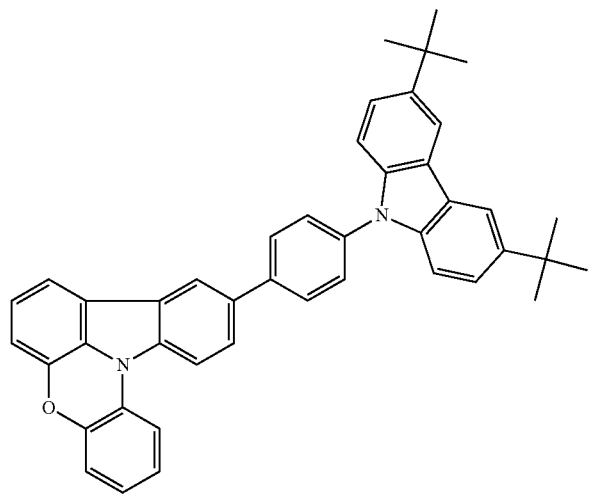
A104
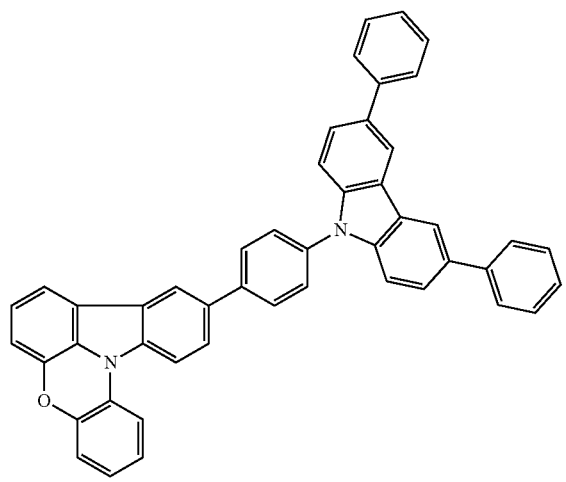
A105
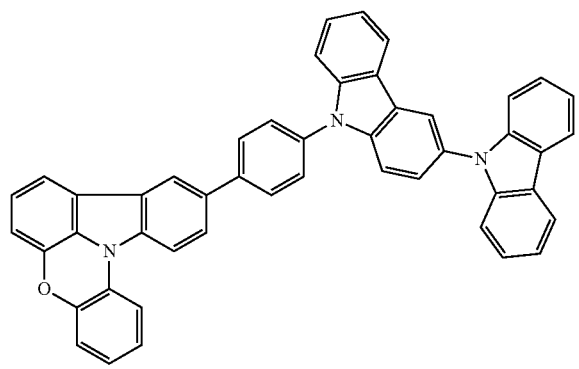
A106
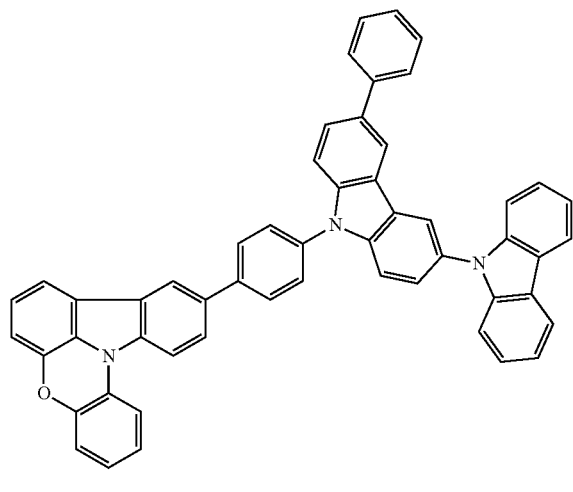
A107
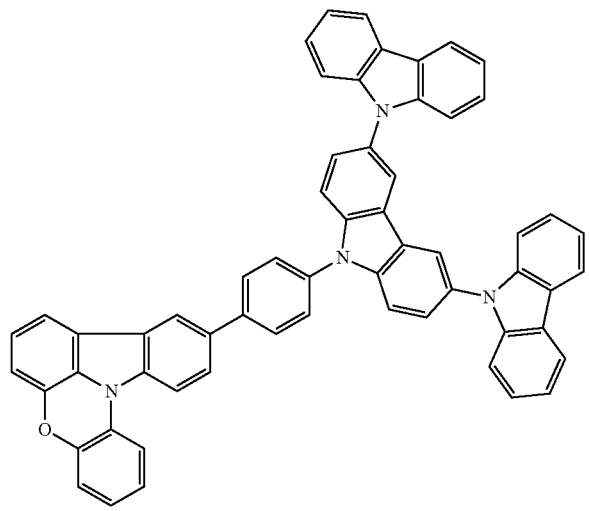

-continued
A108
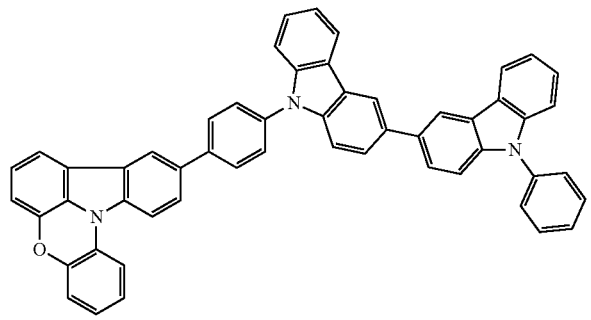
A109
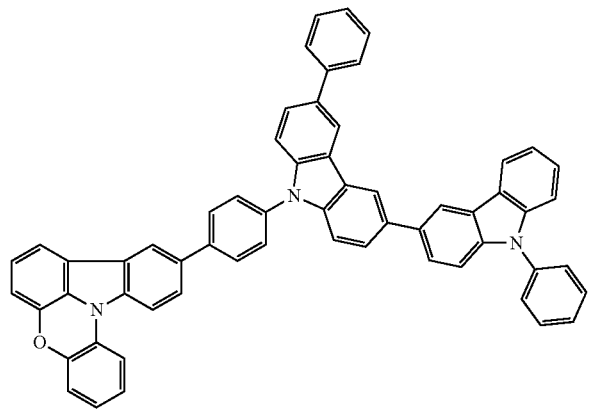
A110
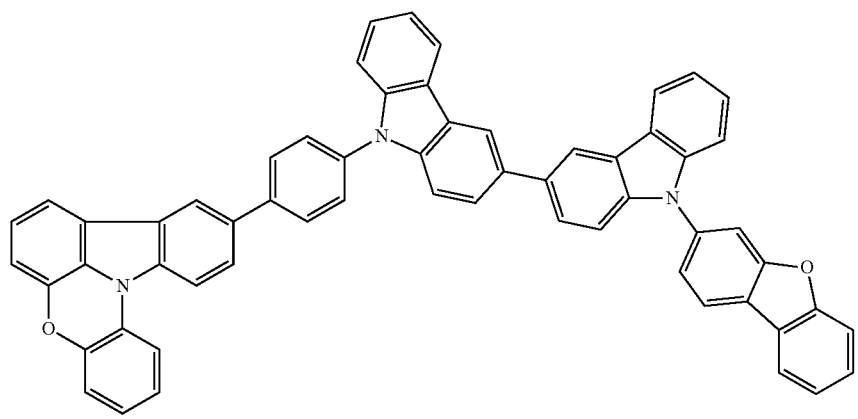
A111
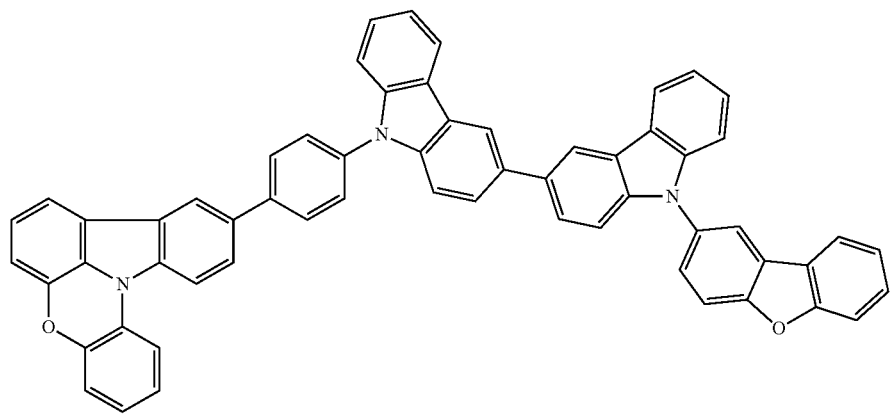
A112
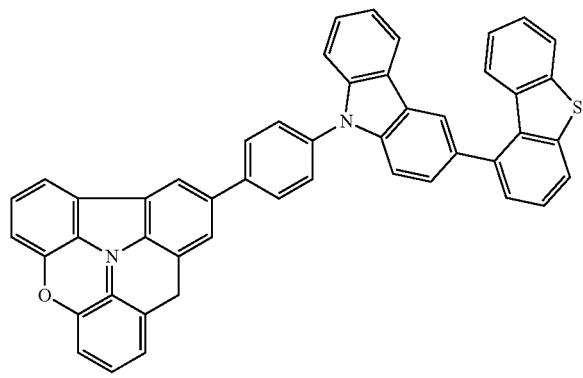
A113
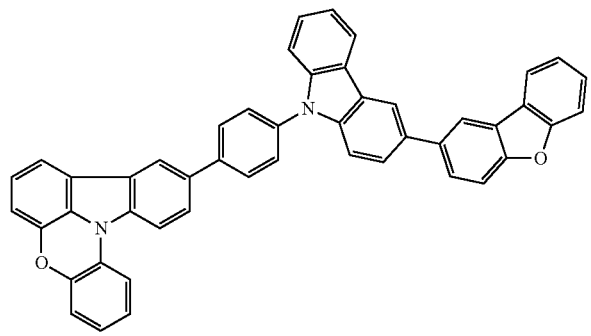

A114
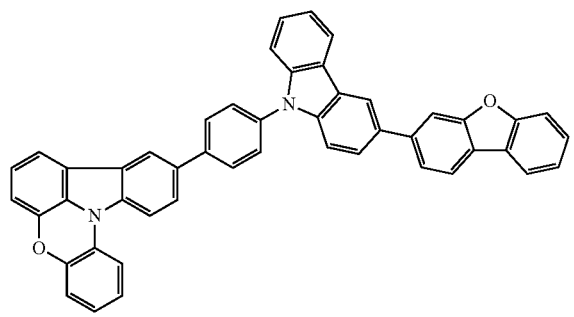
A115
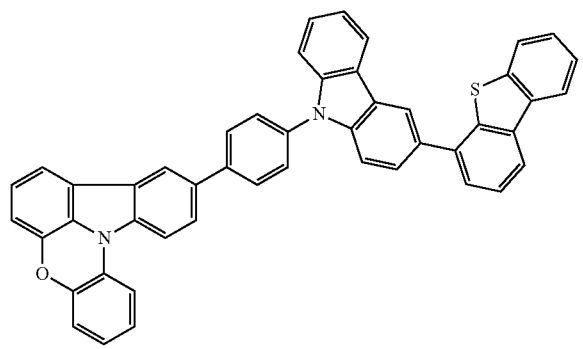
A116
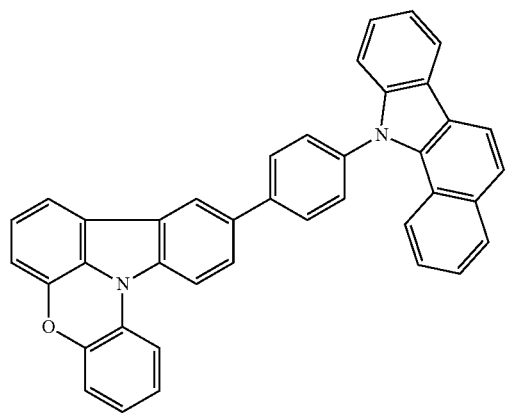
A117
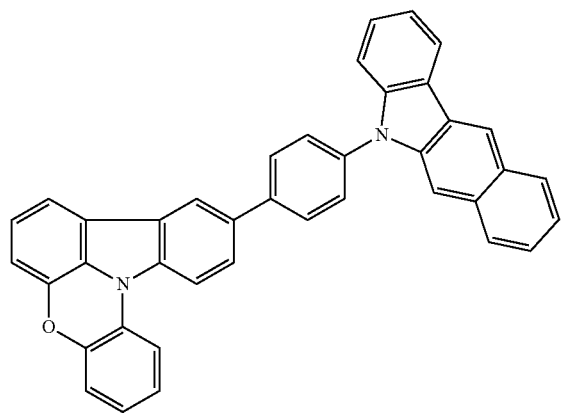
A118
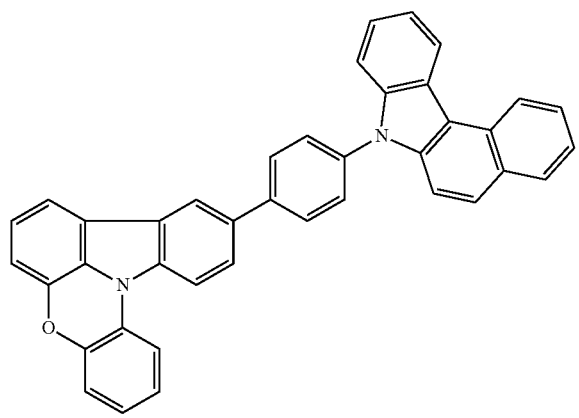
A119
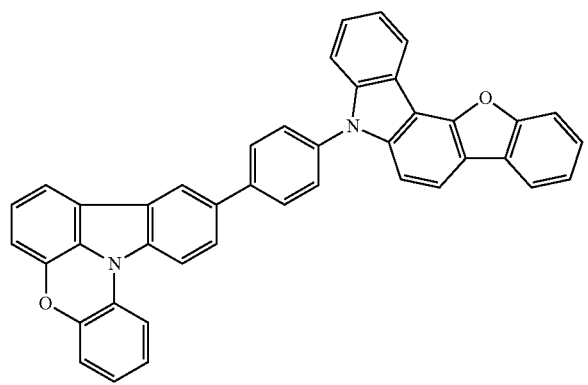

-continued
A120
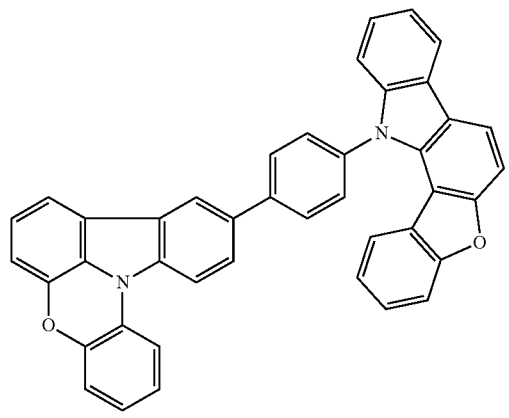
A121
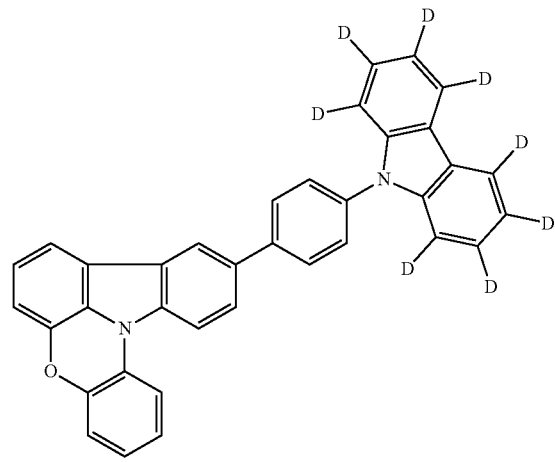
A122
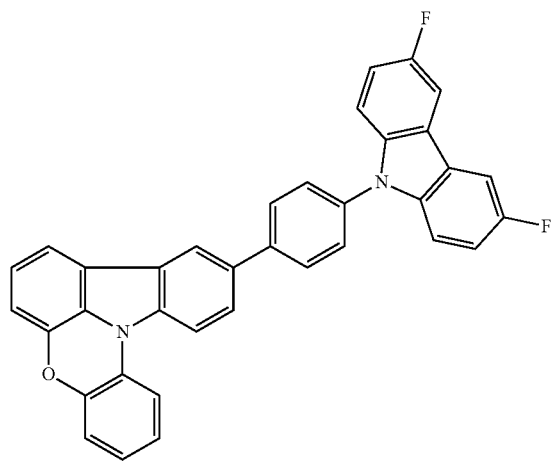
A123
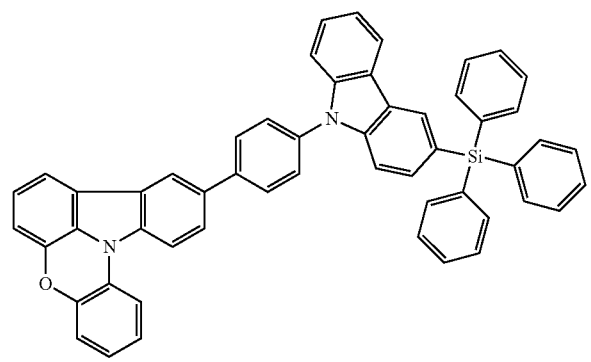
A124
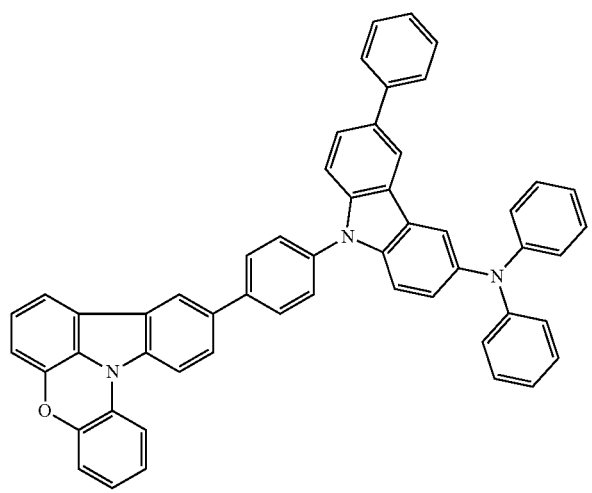
A125
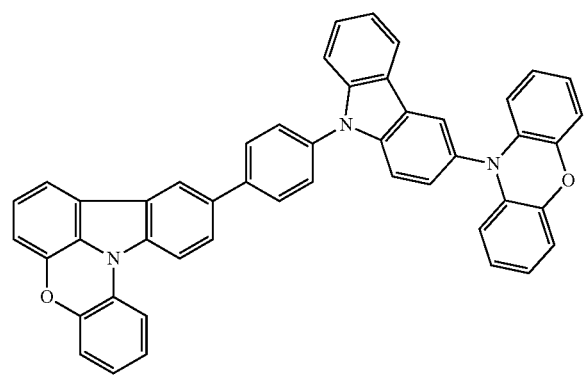

-continued
A126 A127
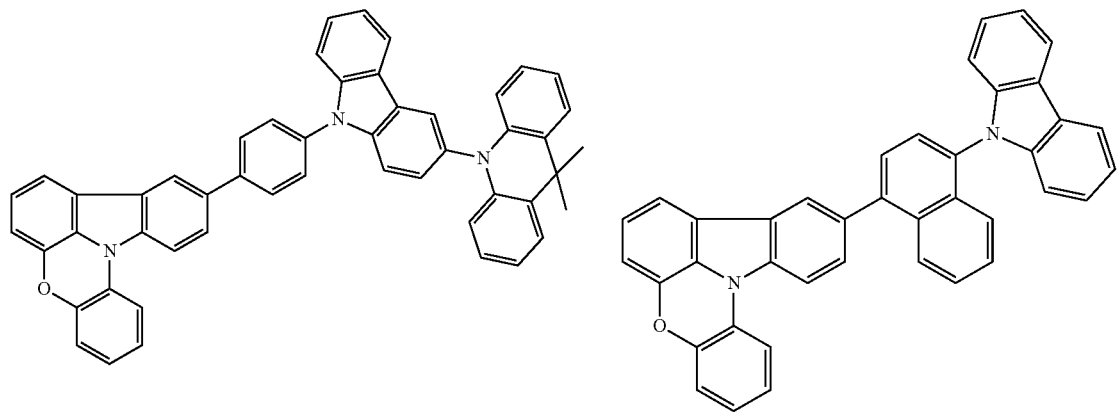
A128 A129
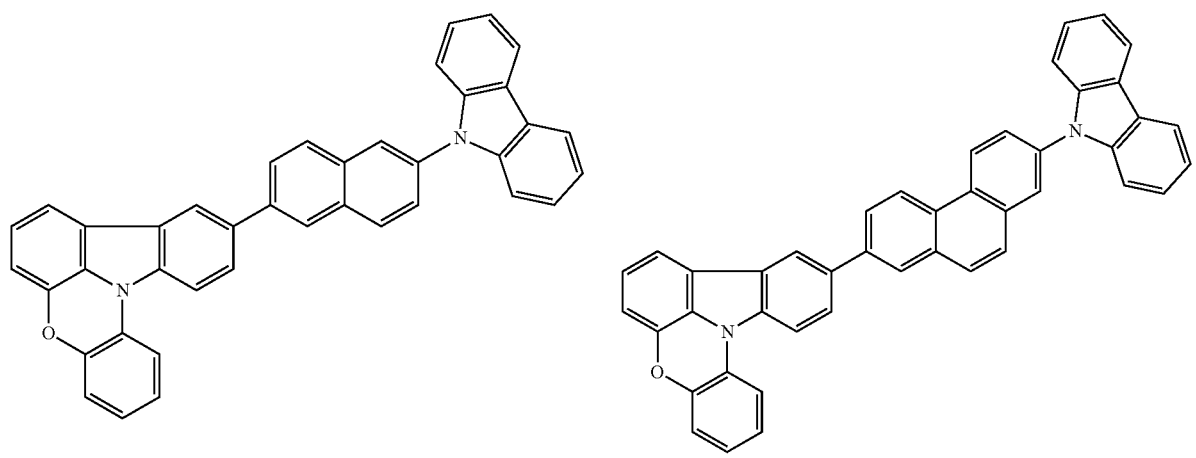
A130 A131
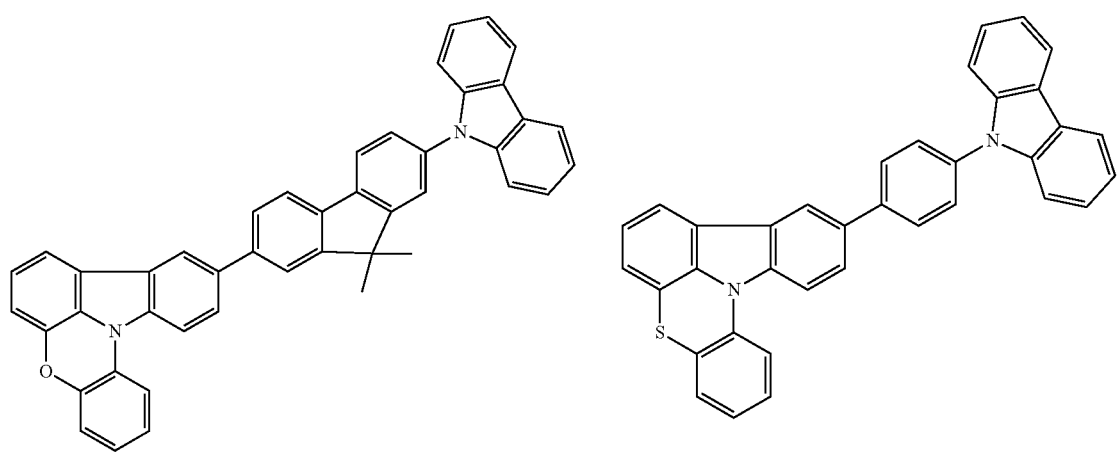

-continued
A132
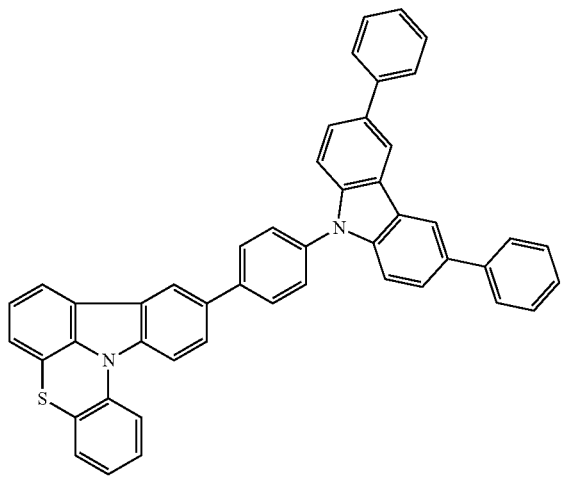
A133
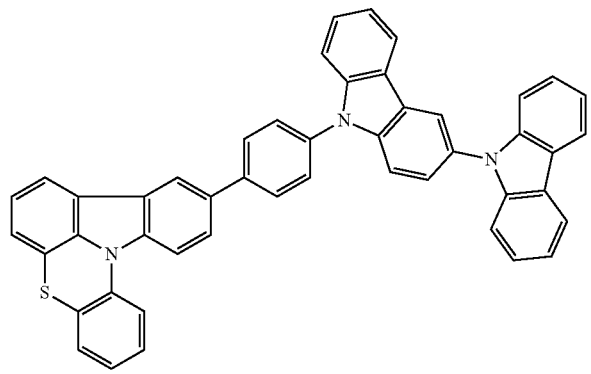
A134
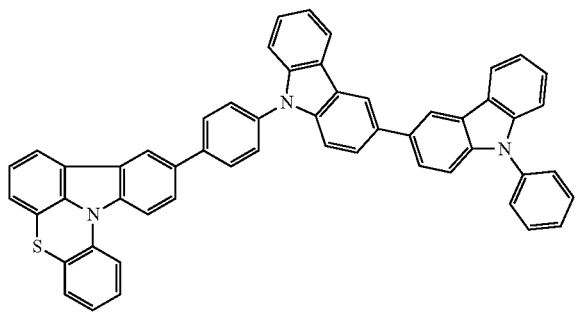
A135
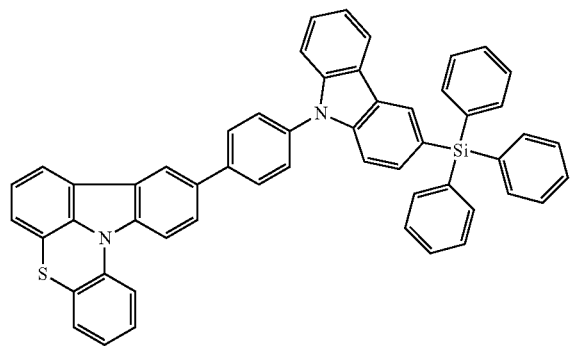
A136
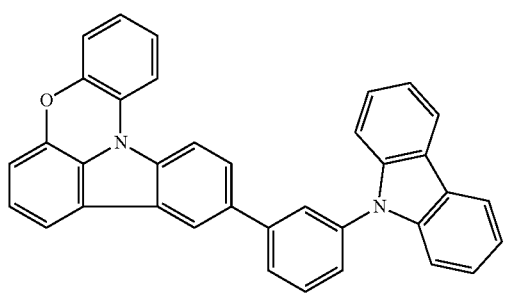
A137
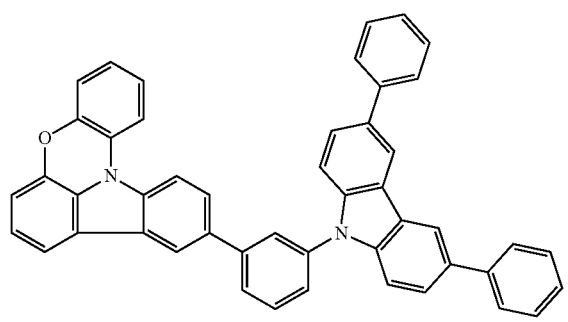
A138
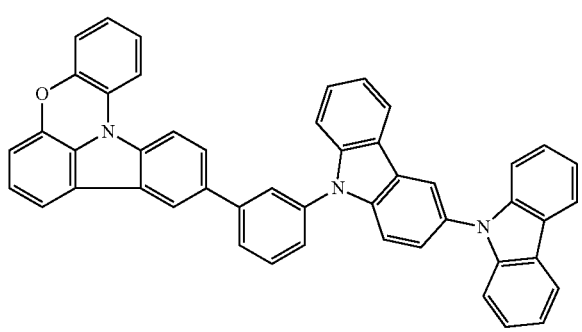
A139
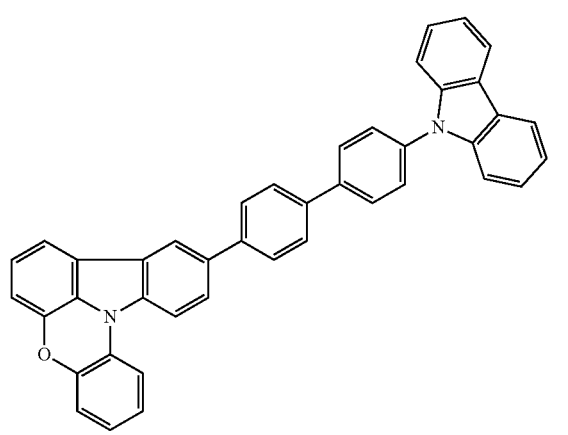

-continued
A140
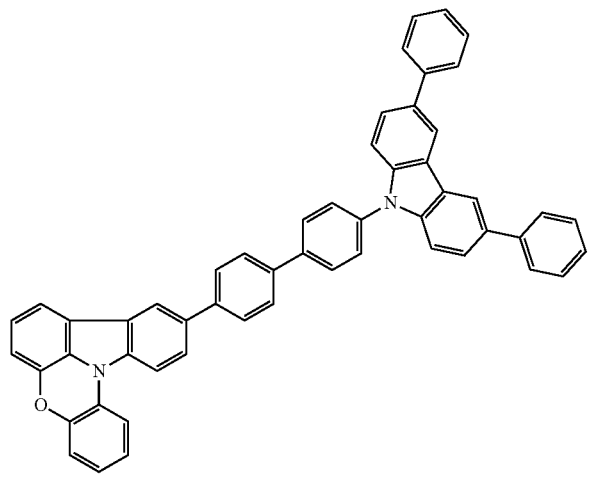
A141
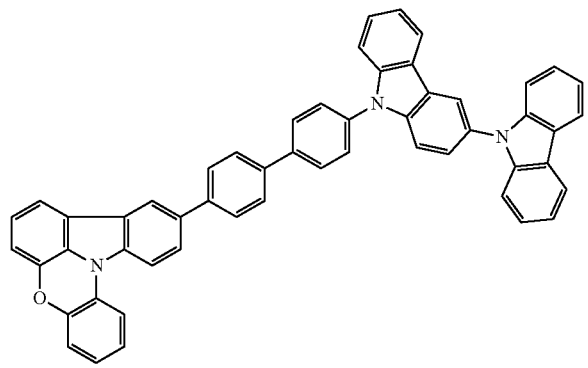
A142
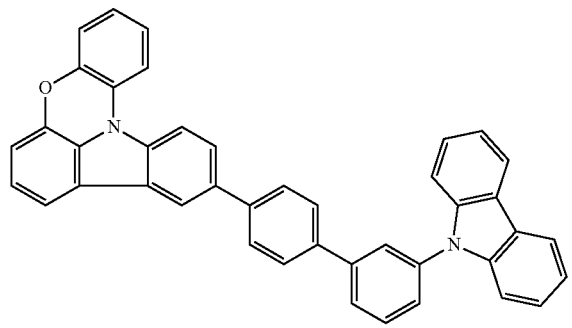
A143
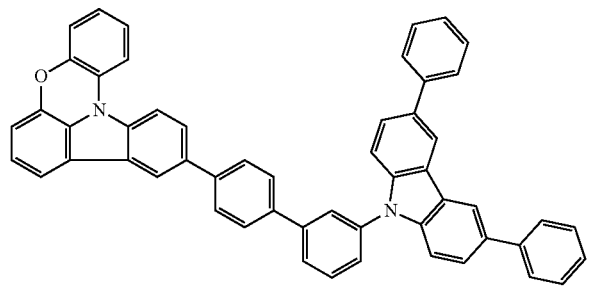
A144
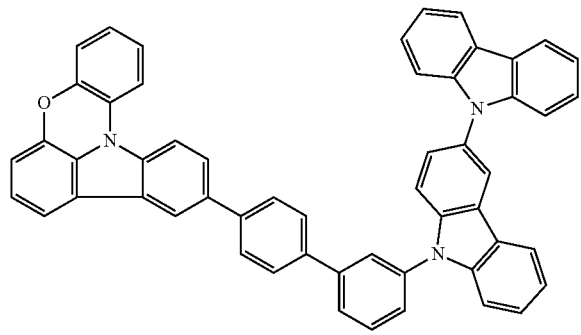
A145
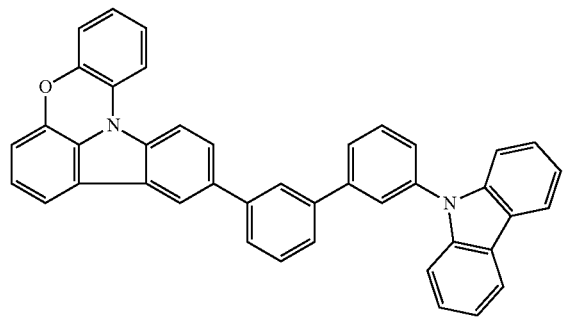
A146
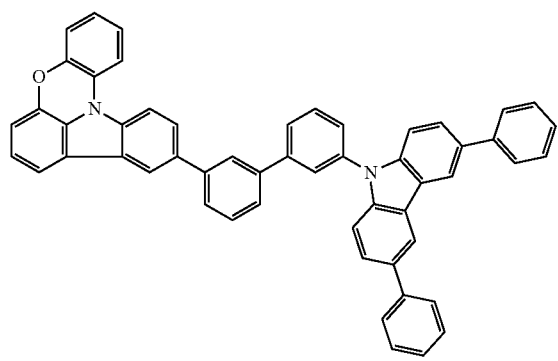
A147

A148
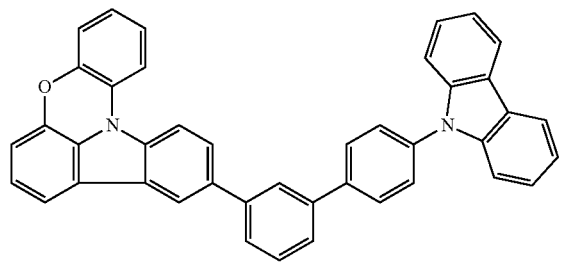
A149
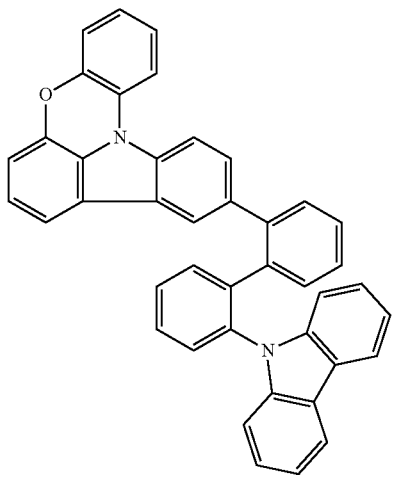
A150
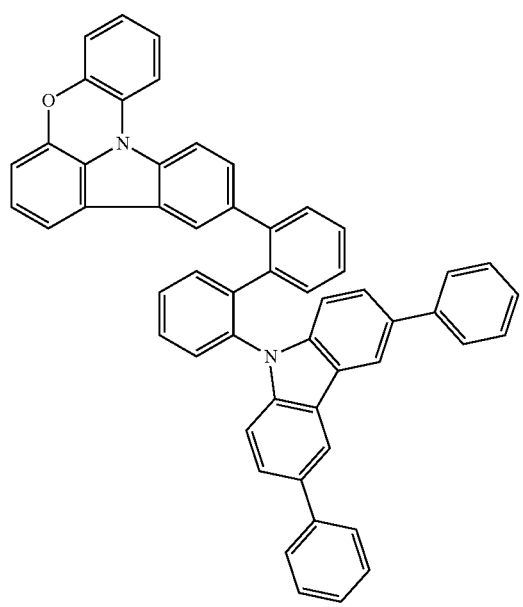
A151
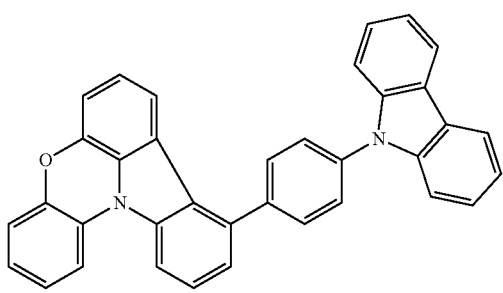
A152
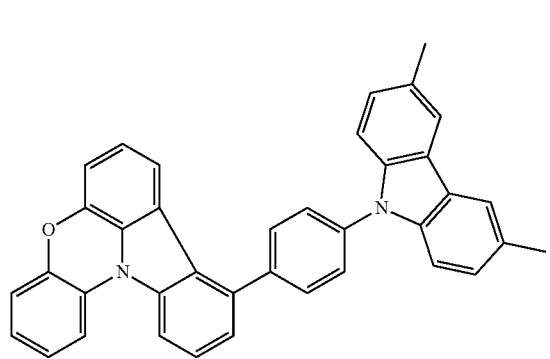
A153
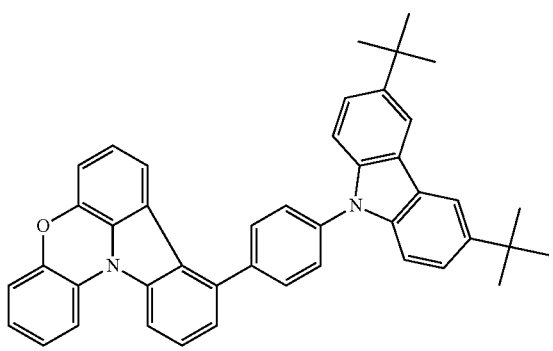

-continued
A154
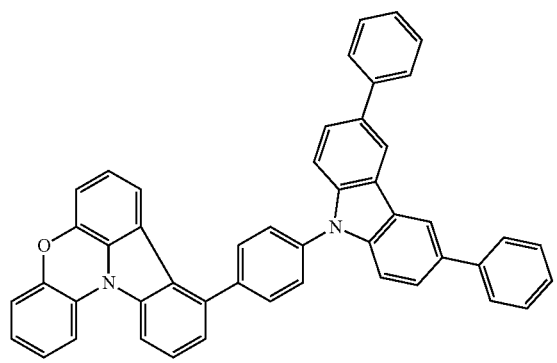
A155
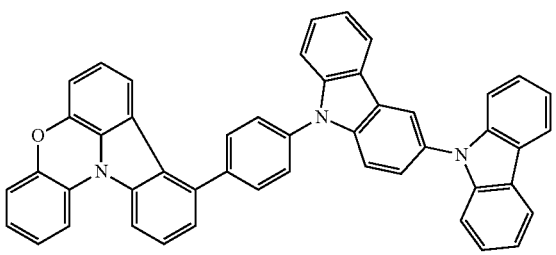
A156
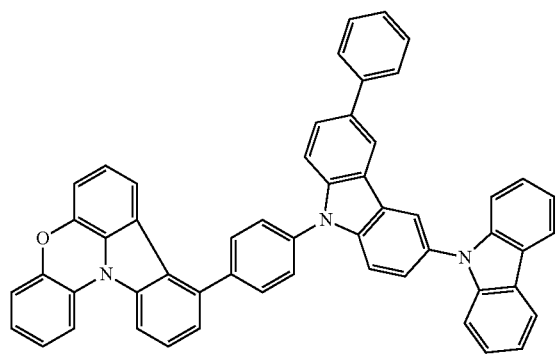
A157
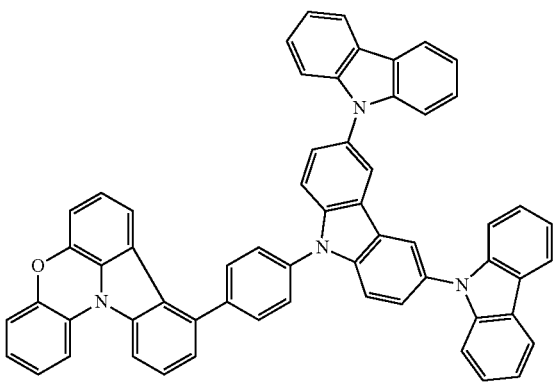
A158
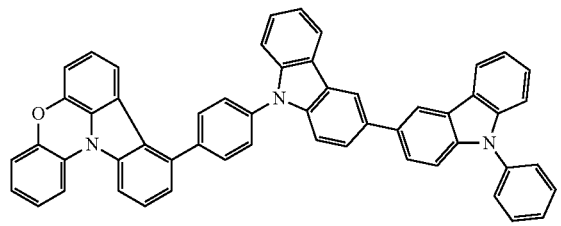
A159
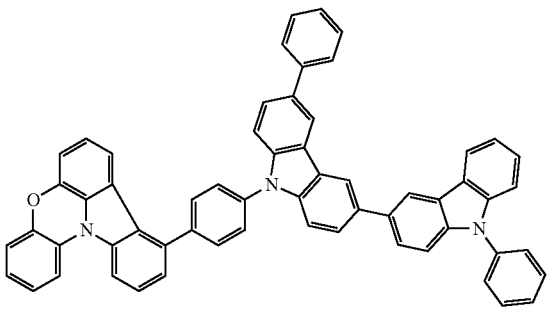
A160
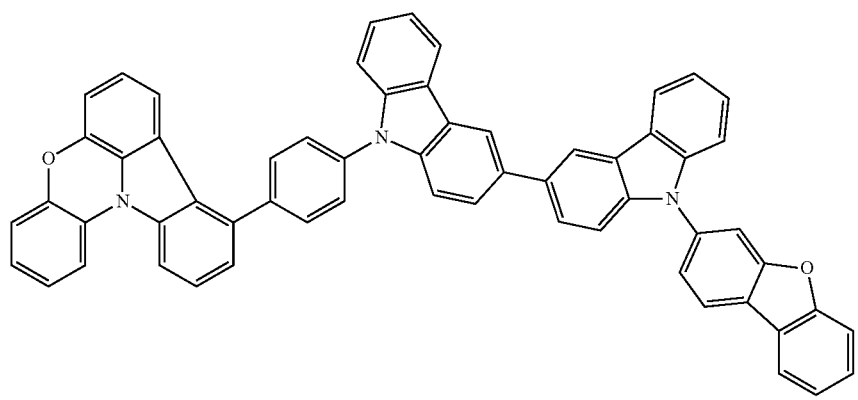

-continued
A161
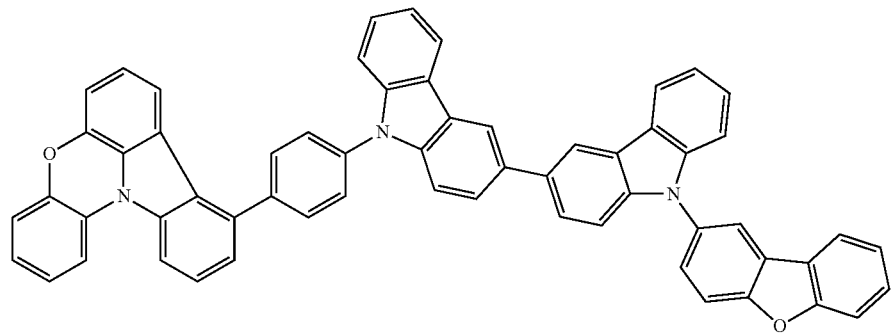
A162
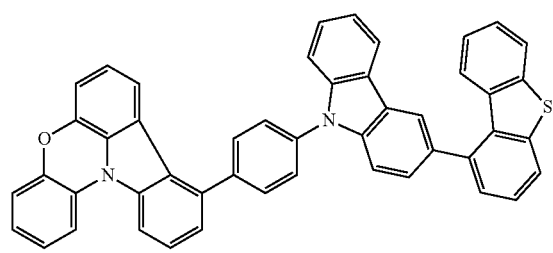
A163
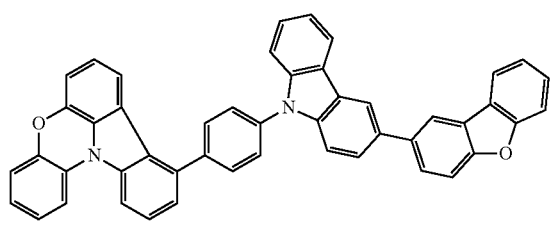
A164
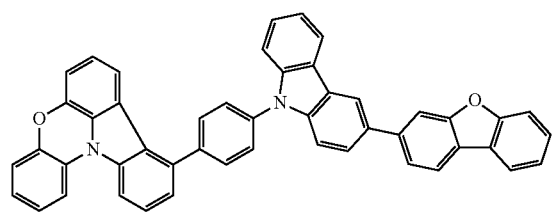
A165
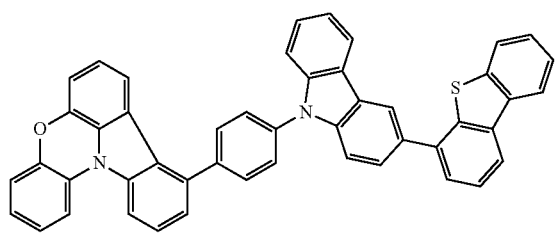
A166
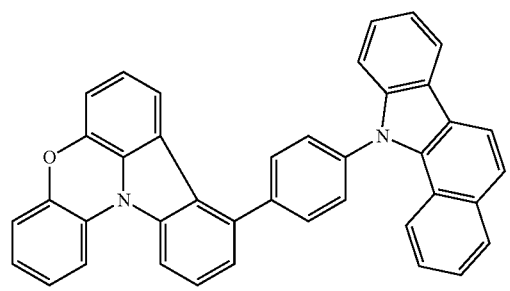
A167
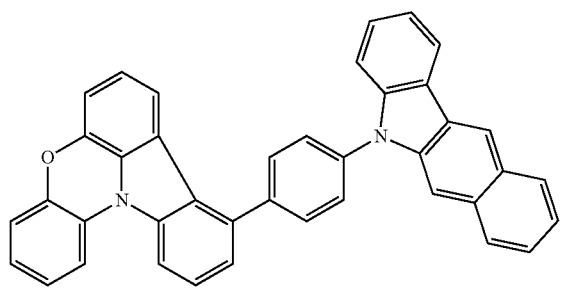
A168
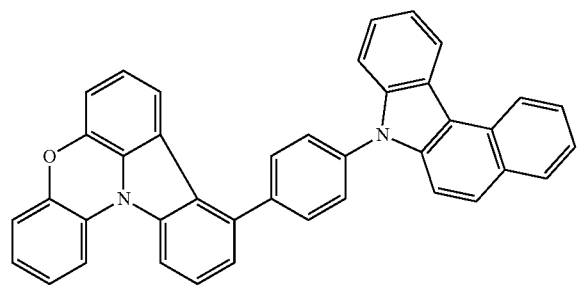
A169

-continued
A170
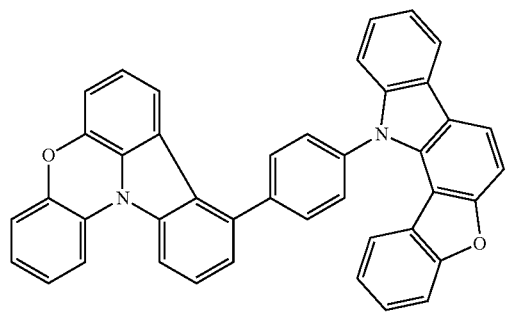
A171
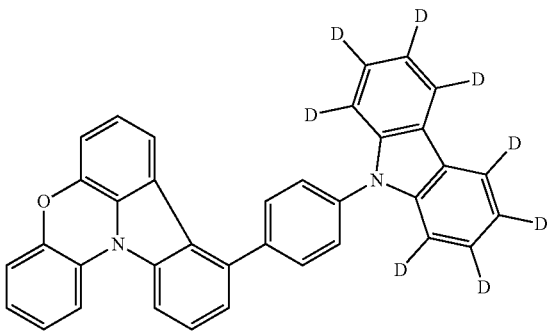
A172
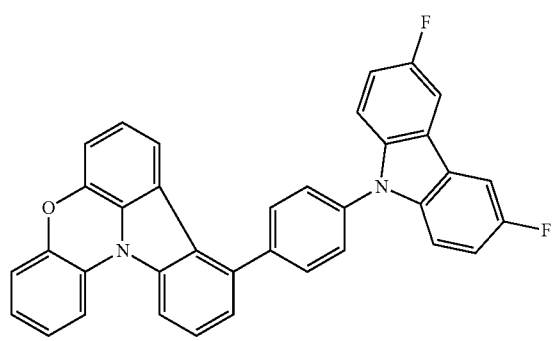
A173
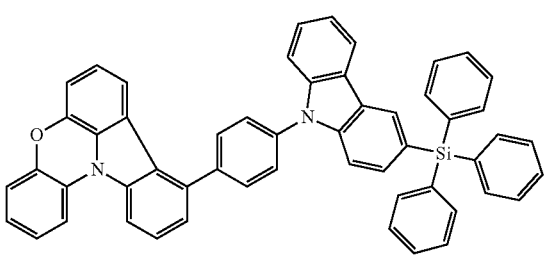
A174
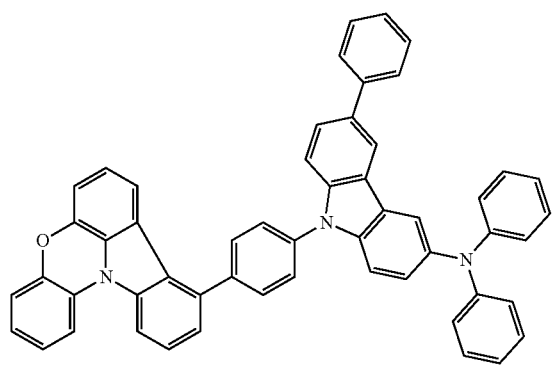
A175
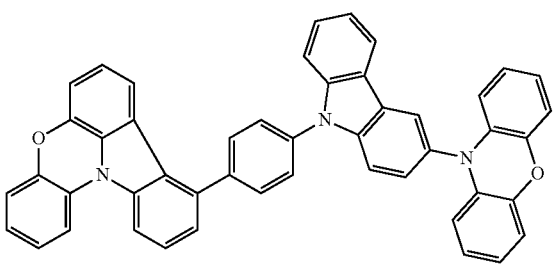
A176
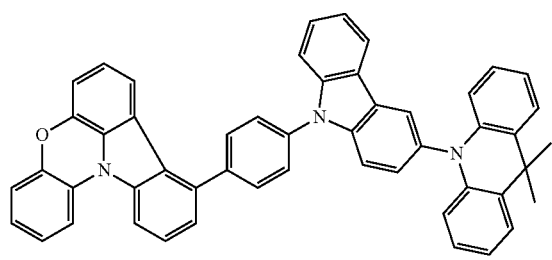
A177
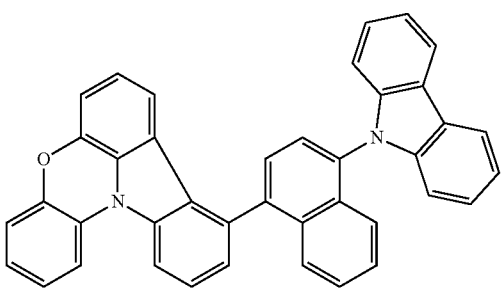

-continued
A178
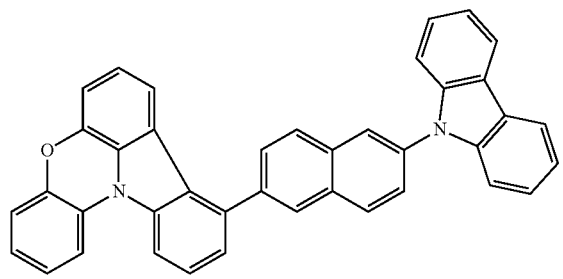
A179
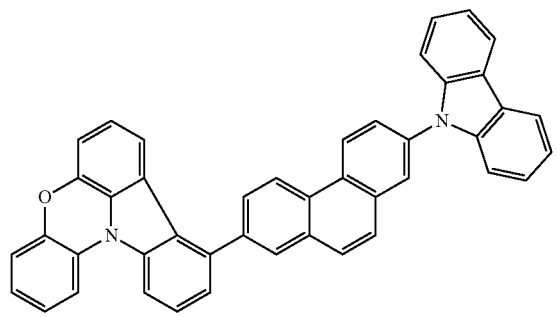
A180
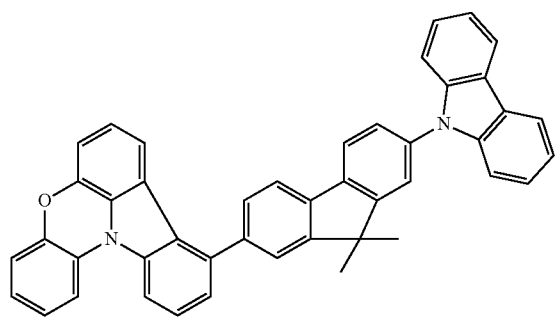
A181
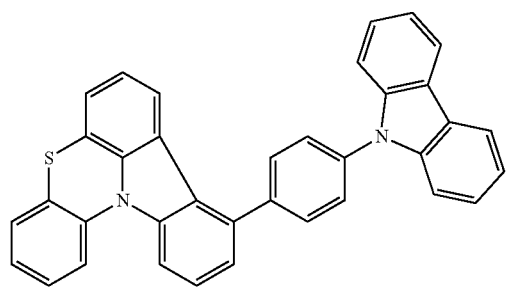
A182
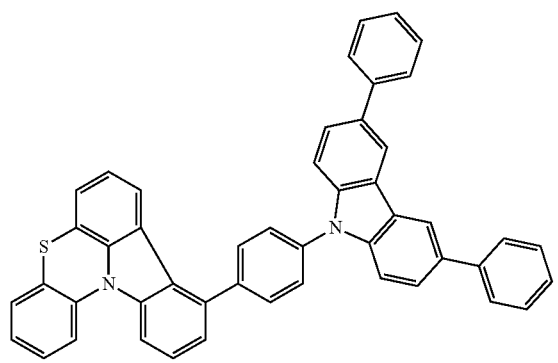
A183
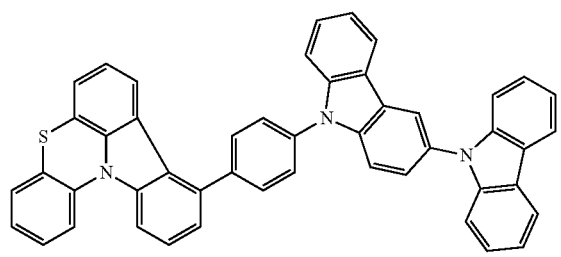
A184
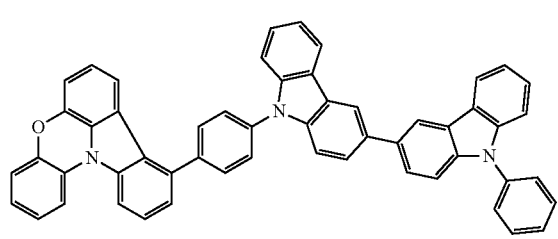
A185
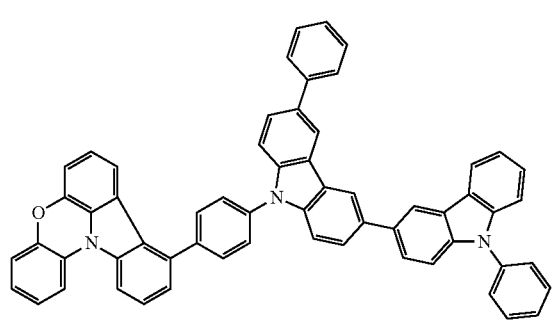

-continued
A186
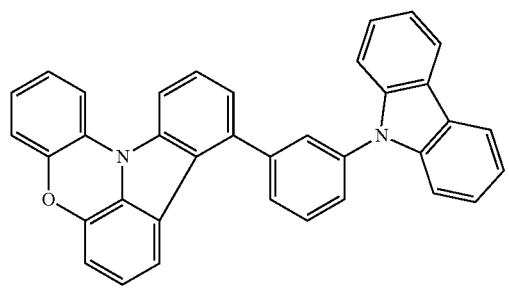
A187
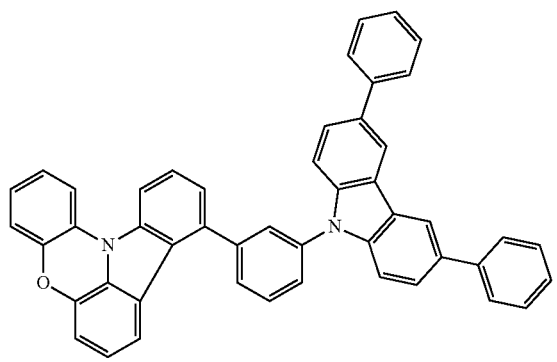
A188
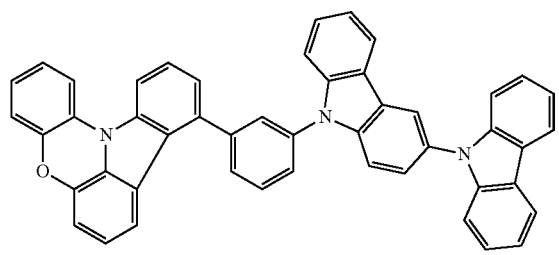
A189
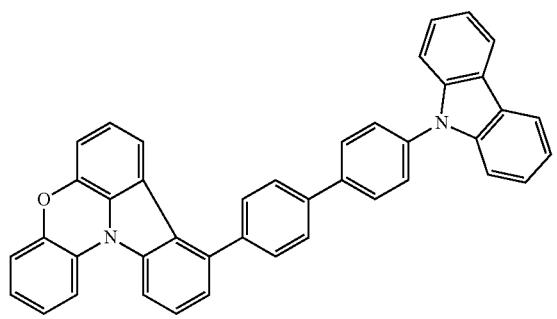
A190
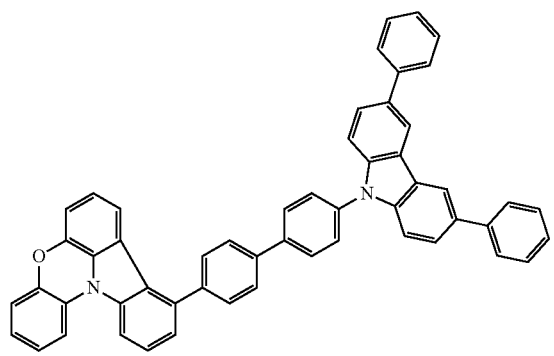
A191
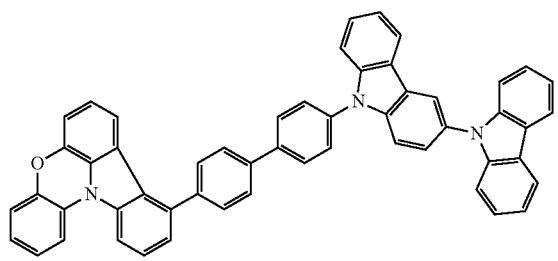
A192
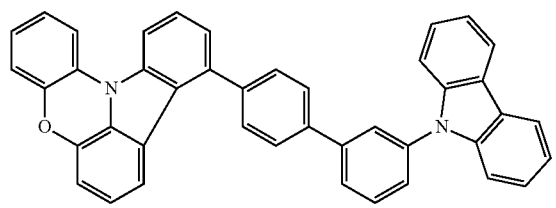
A193
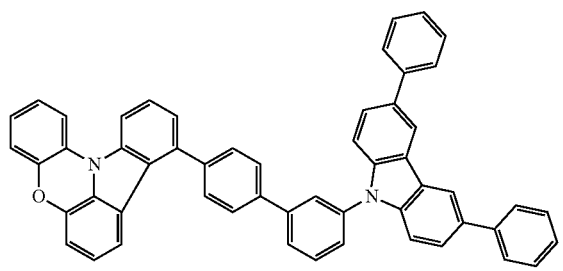

-continued
A194
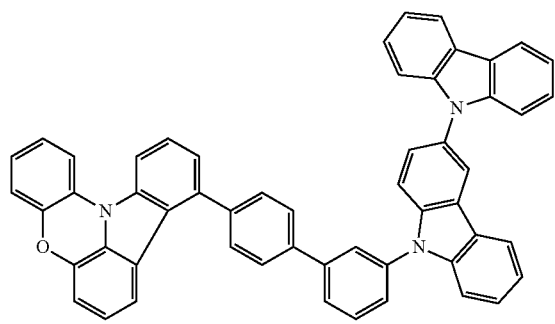
A195
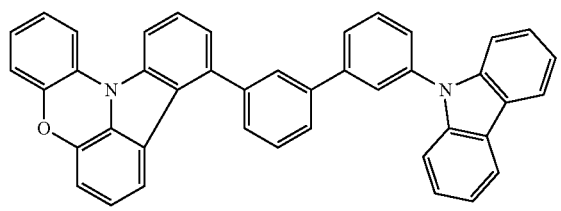
A196
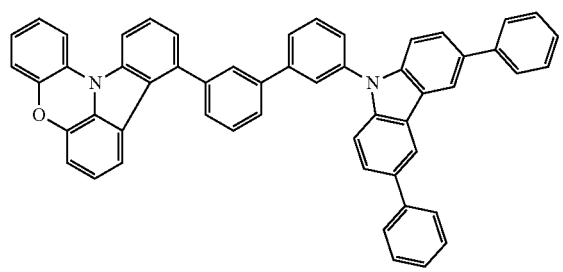
A197
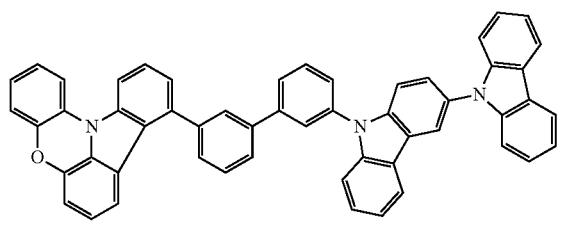
A198
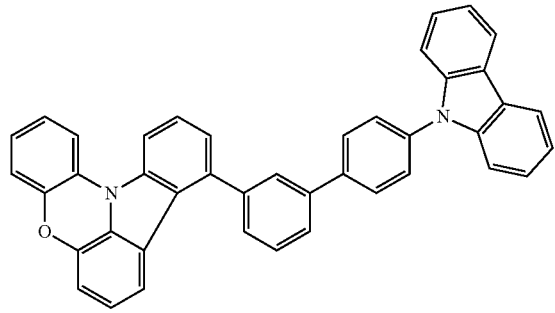
A199
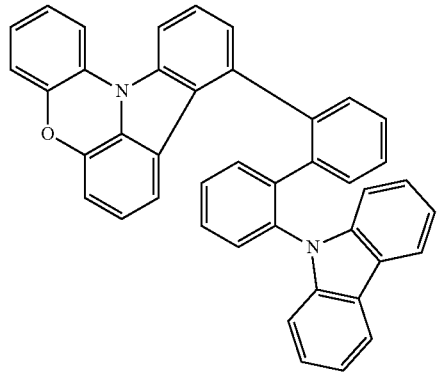
A200
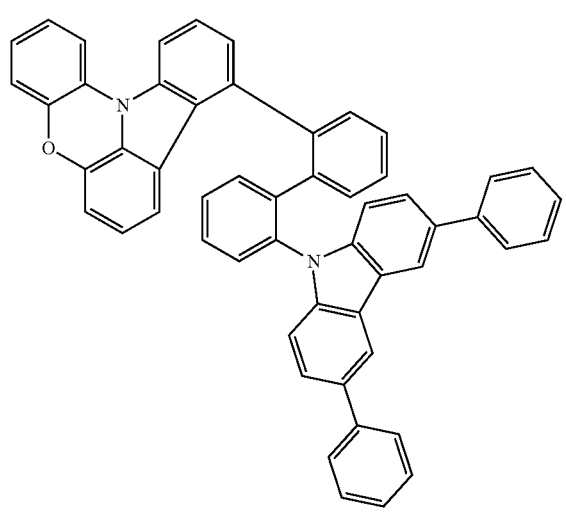

-continued
[Compound Group 1B]
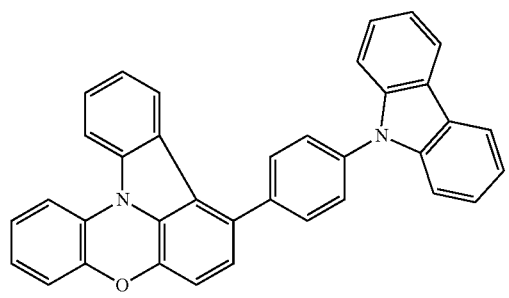
B1
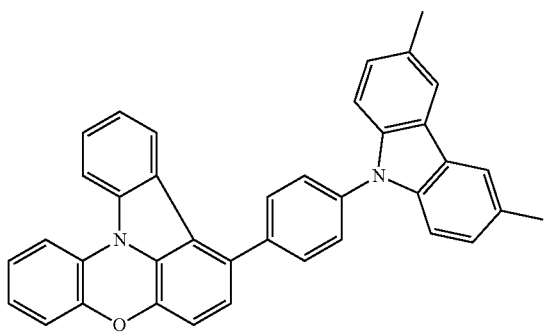
B2
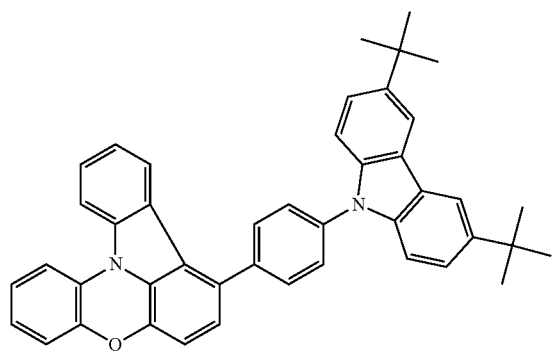
B3
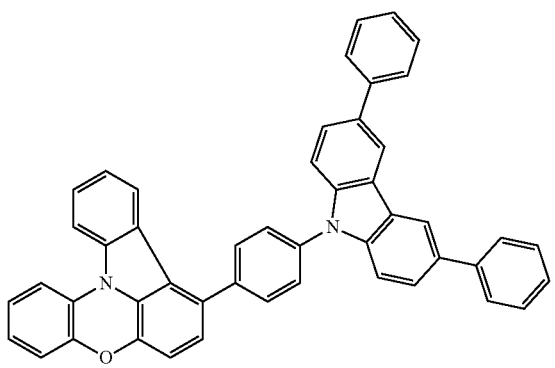
B4
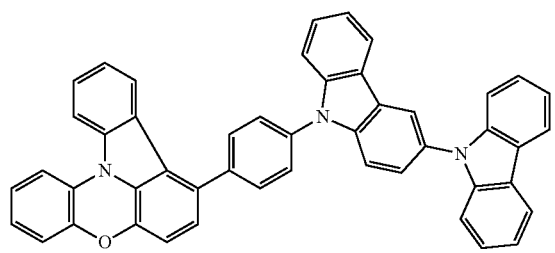
B5
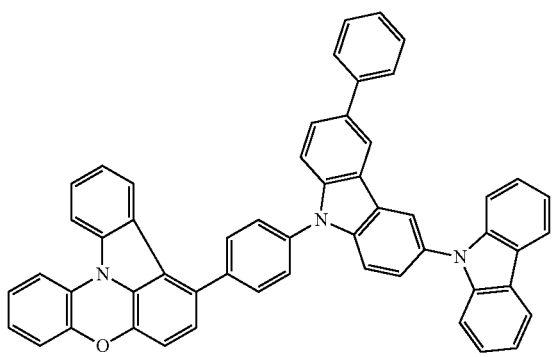
B6
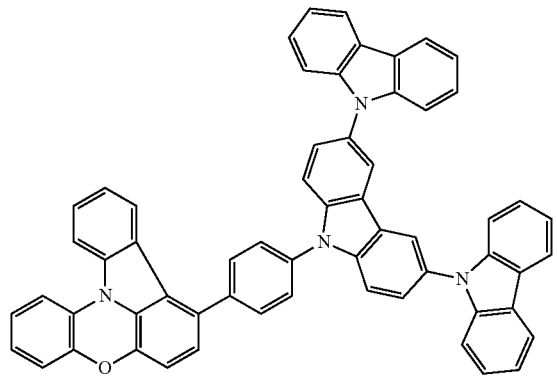
B7
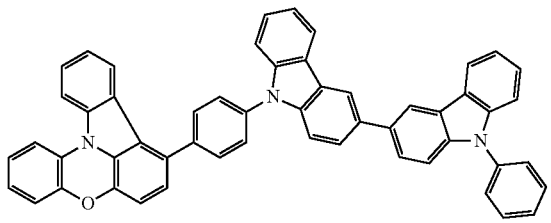
B8

B9
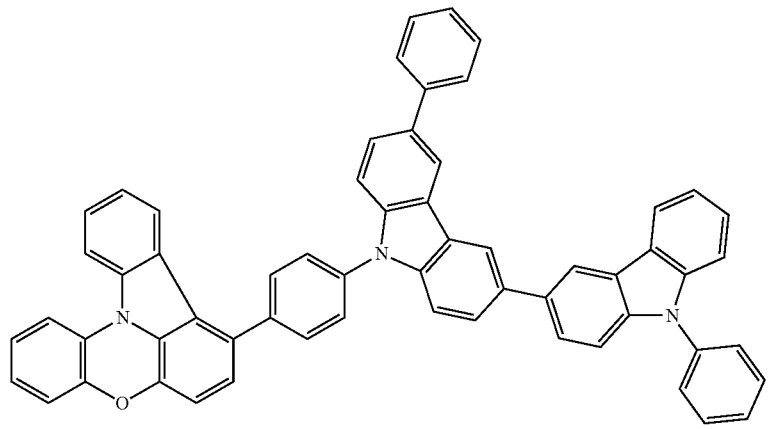
B10
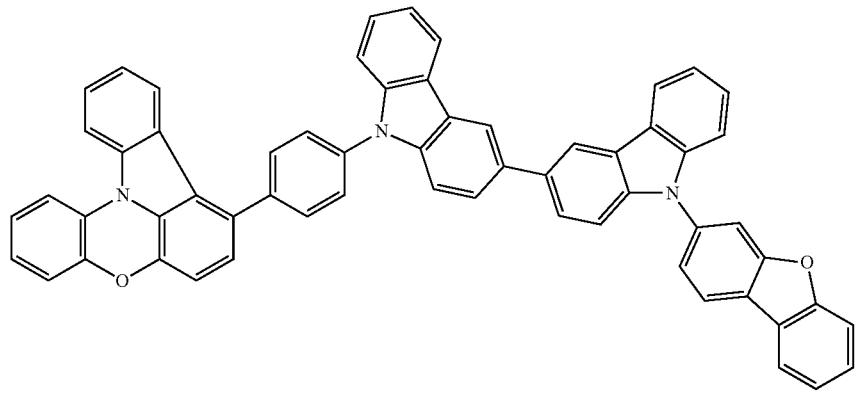
B11
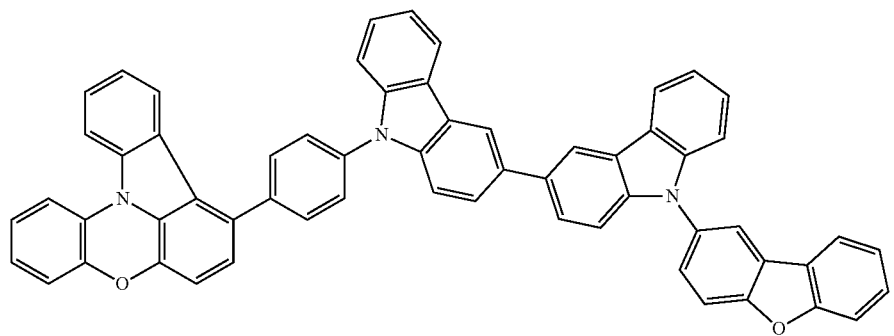
B12
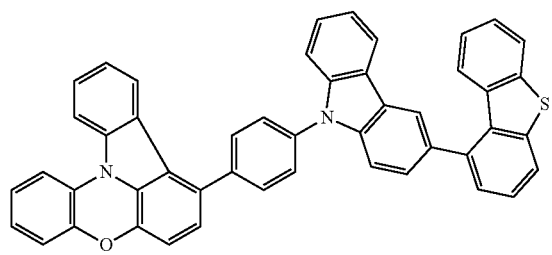
B13
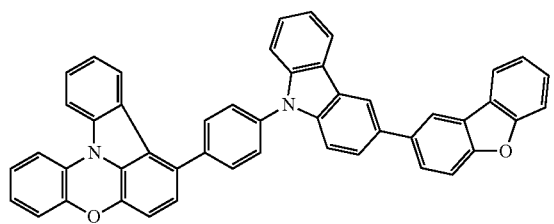

-continued
B14
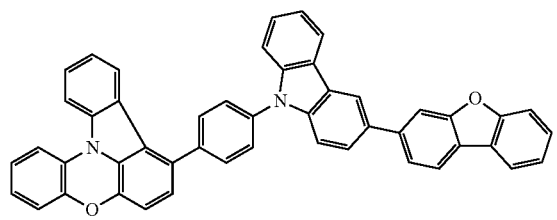
B15
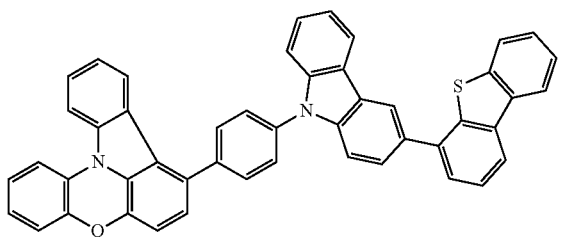
B16
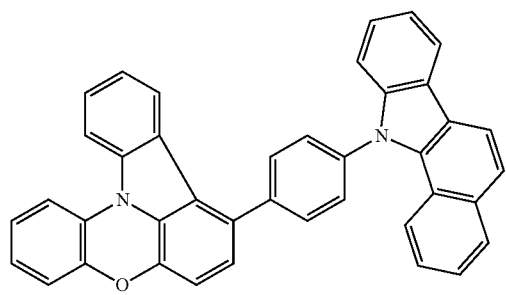
B17
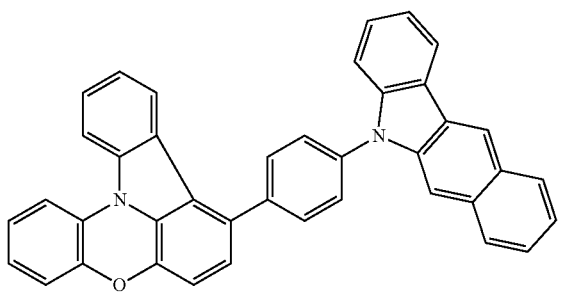
B18
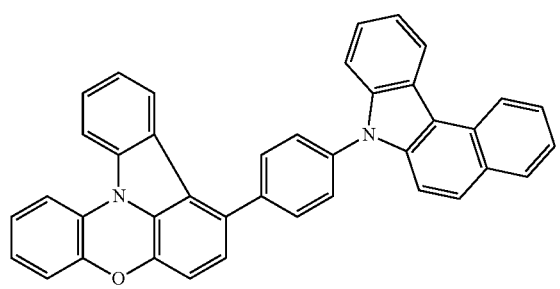
B19
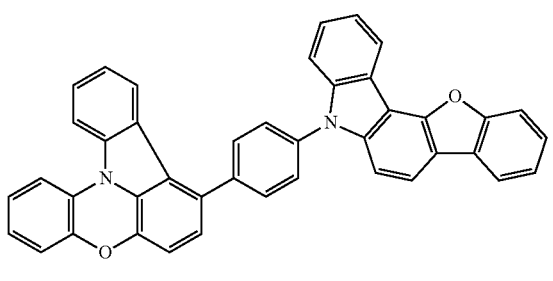
B20
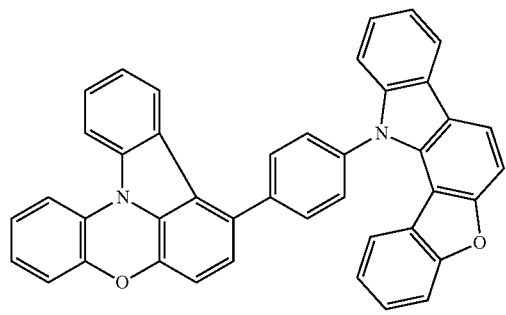
B21
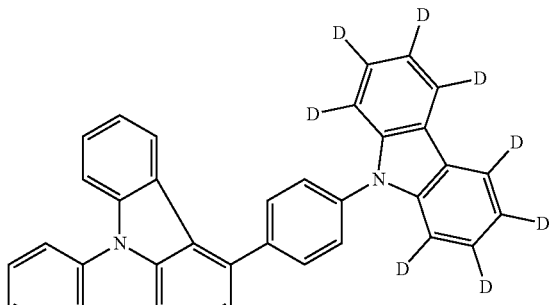
B22
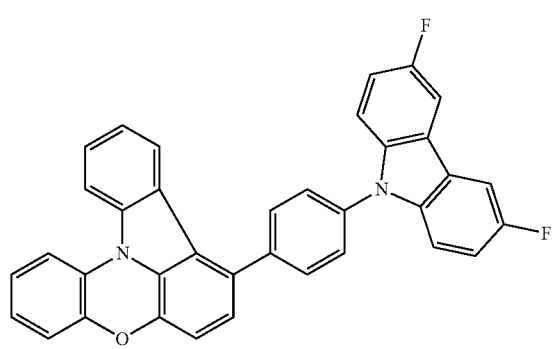
B23
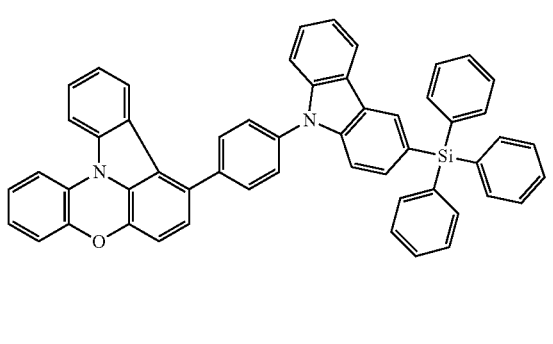

-continued
| B24 | B25 |
|---|---|
| 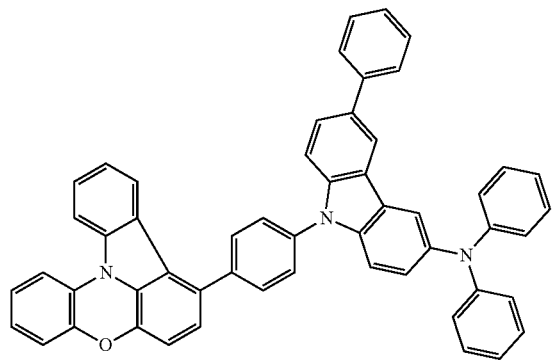 | 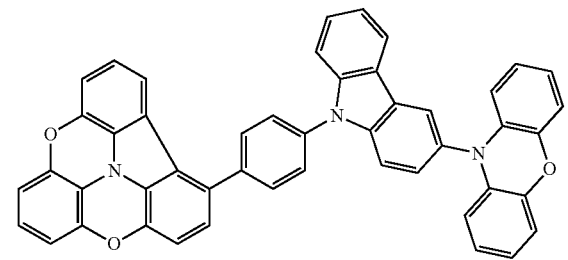 |
| B26 | B27 |
| 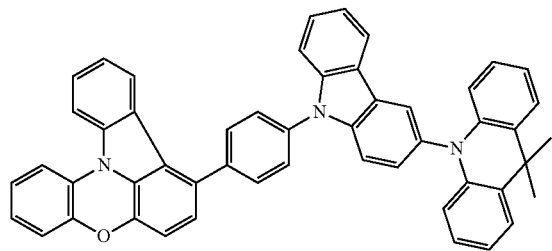 | 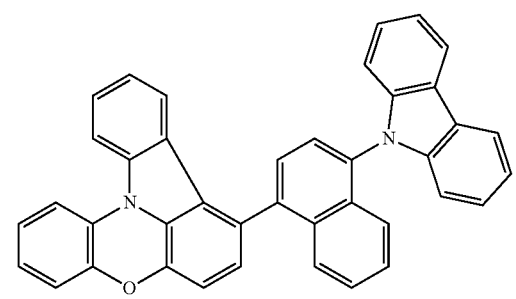 |
| B28 | B29 |
| 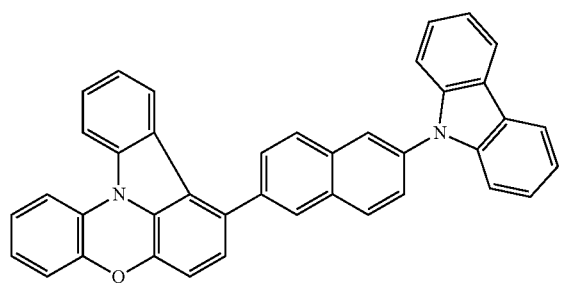 | 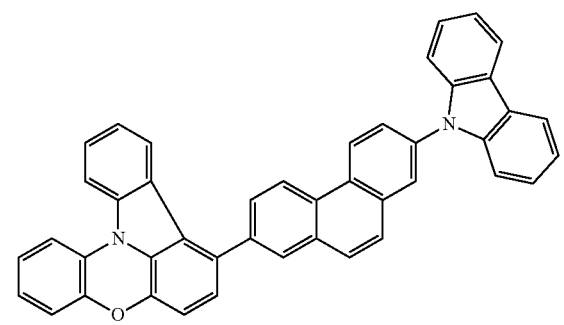 |
| B30 | B31 |
| 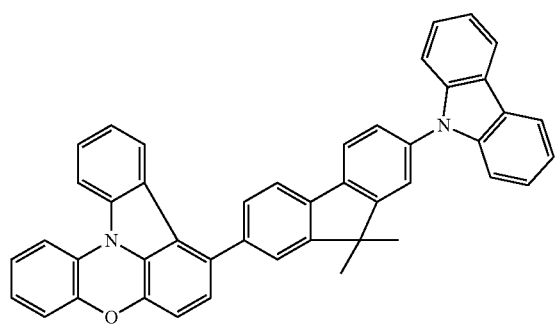 | 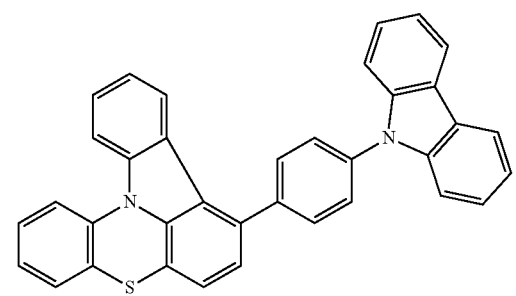 |

-continued
B32
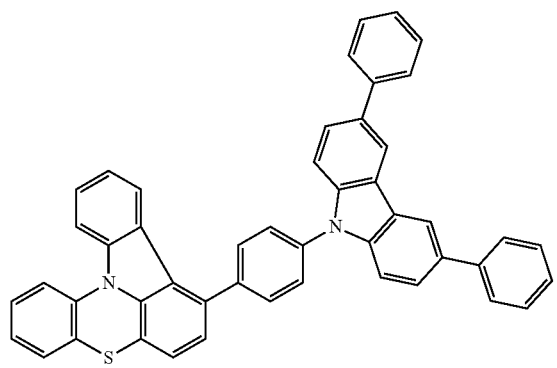
B33
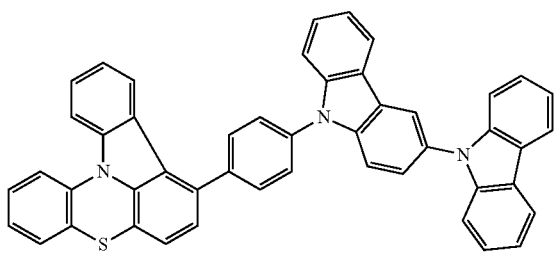
B34
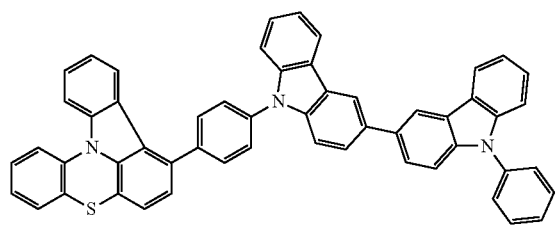
B35
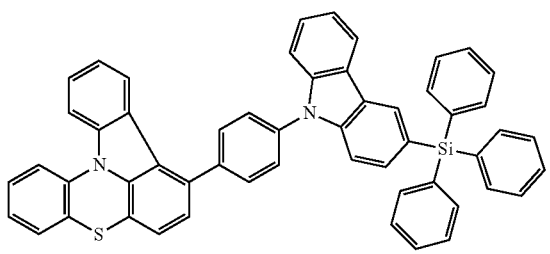
B36
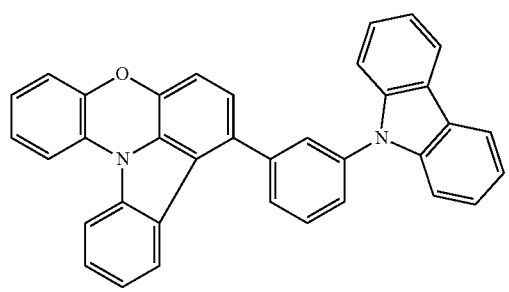
B37
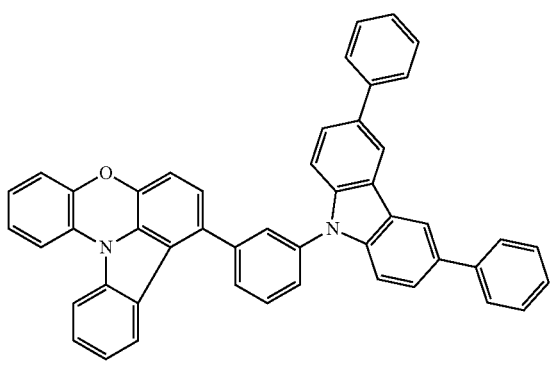
B38
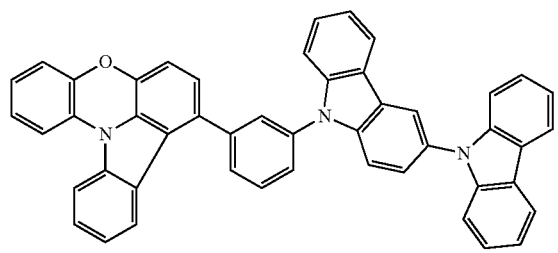
B39
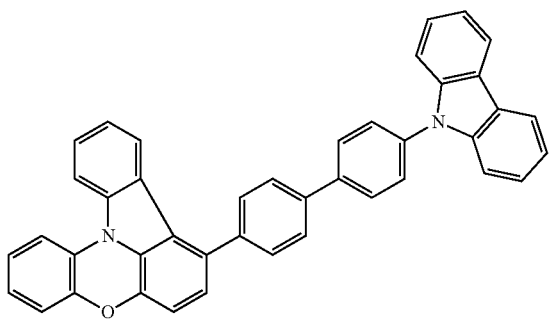

-continued
B40
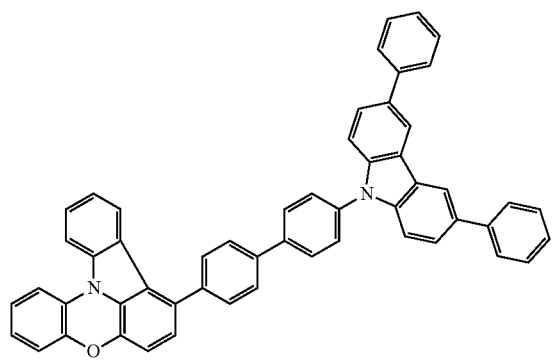
B41
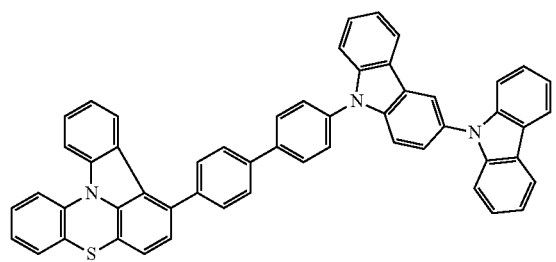
B42
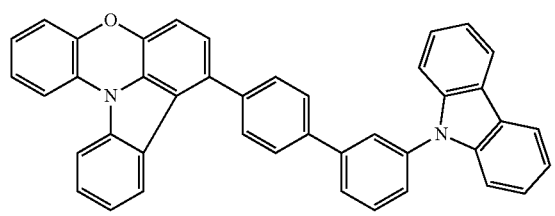
B43
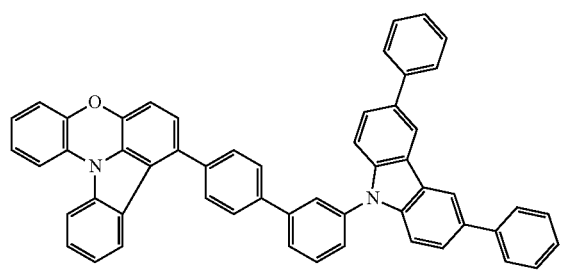
B44
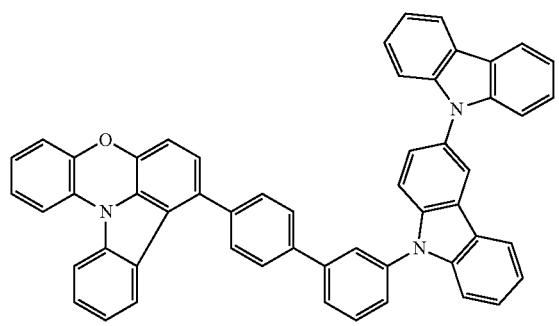
B45
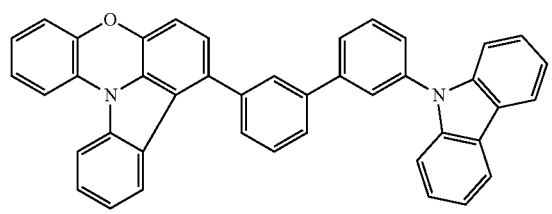
B46
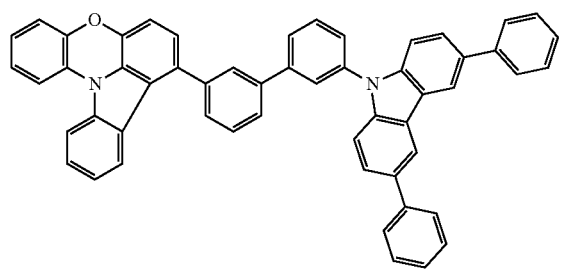
B47
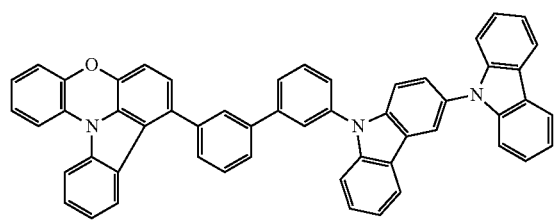

-continued
B48
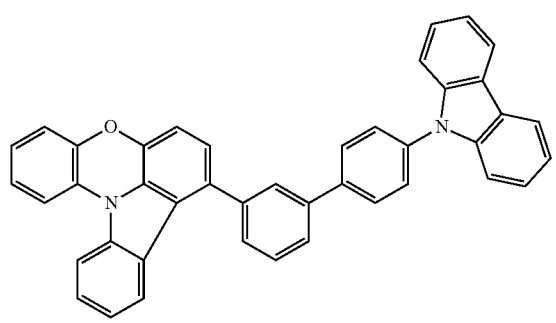
B49
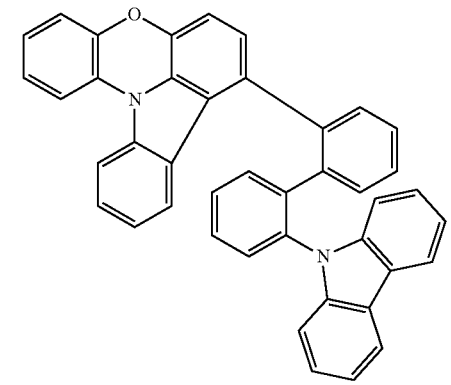
B50
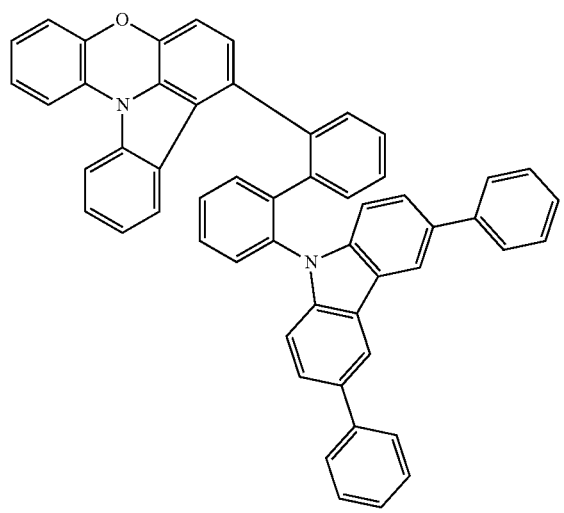
B51
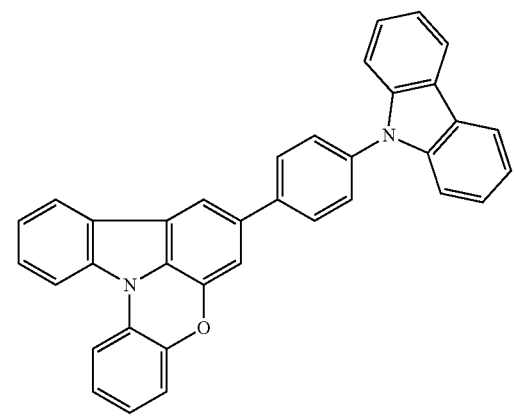
B52
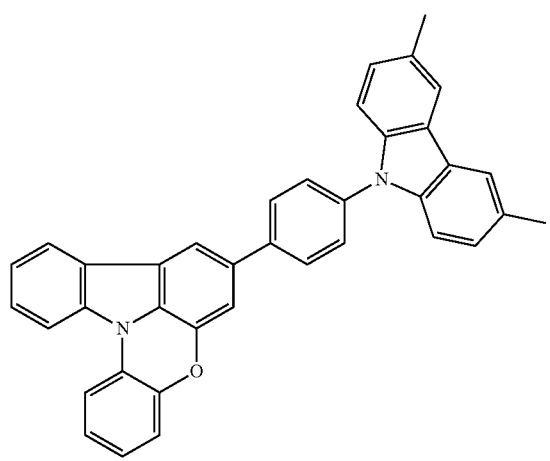
B53
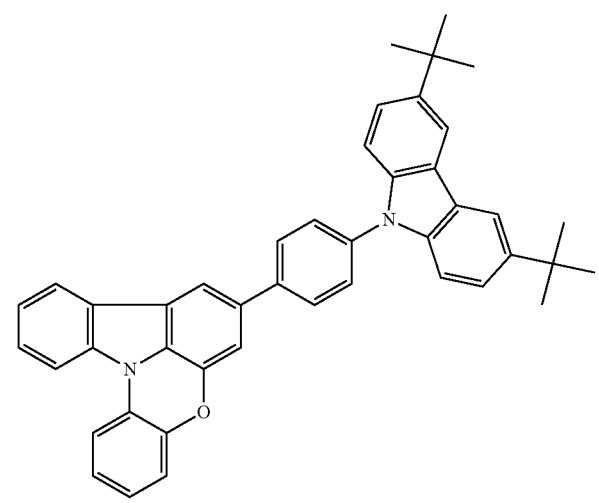

-continued
B54
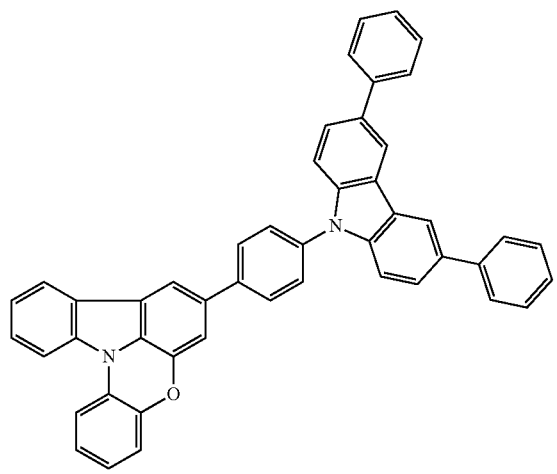
B55
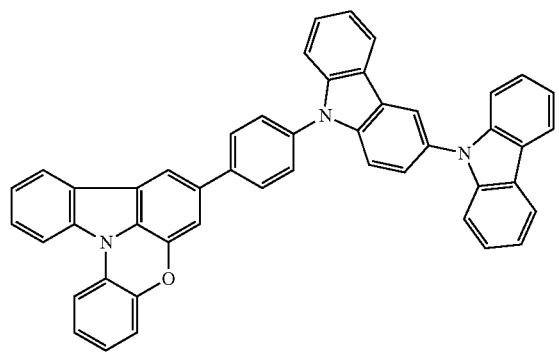
B56
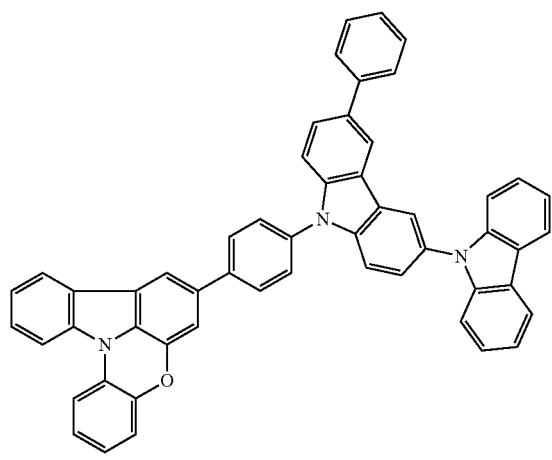
B57
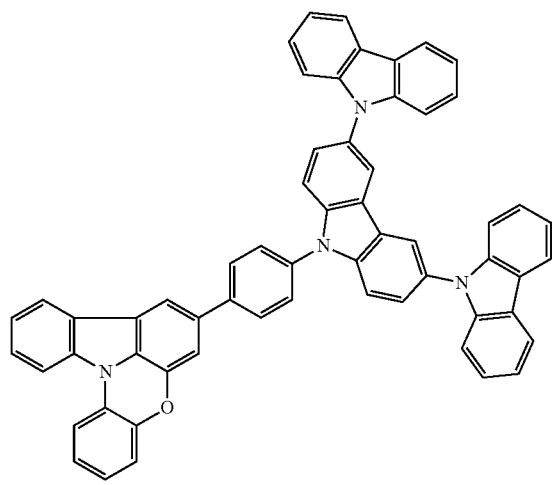
B58
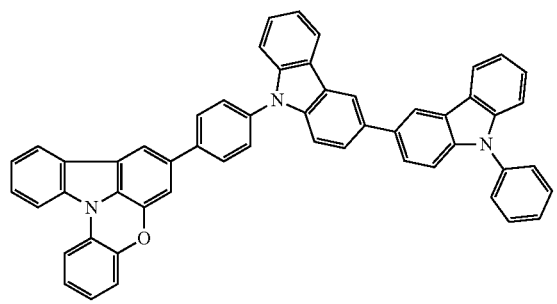
B59
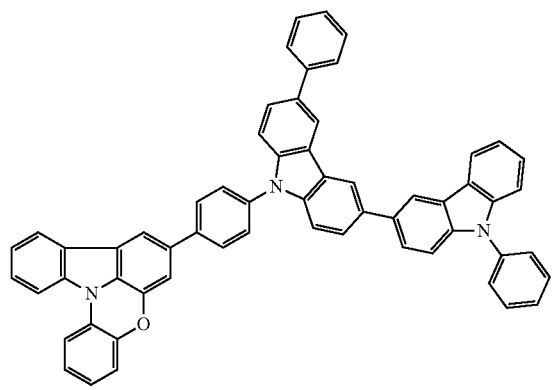

-continued
B60
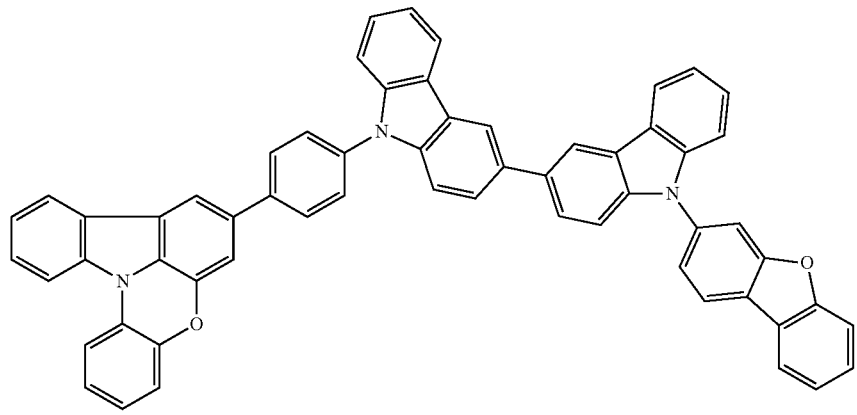
B61
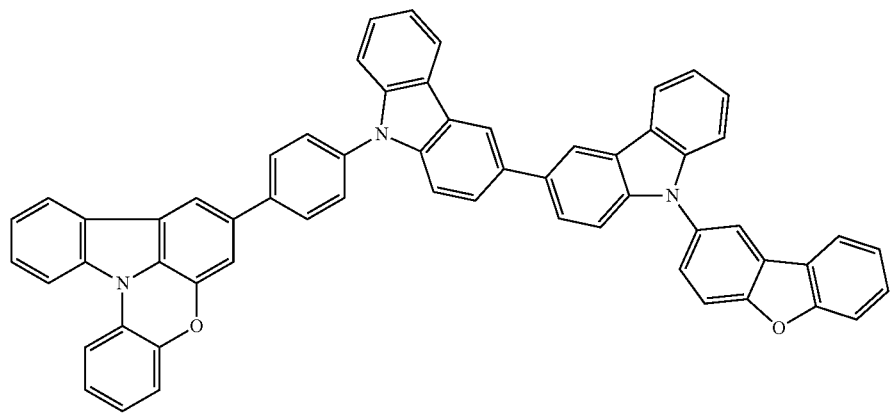
B62 B63
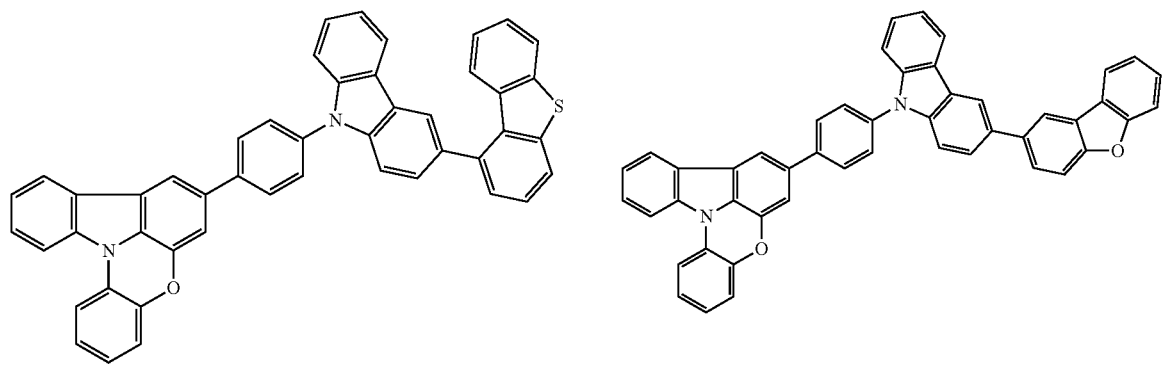
B64 B65
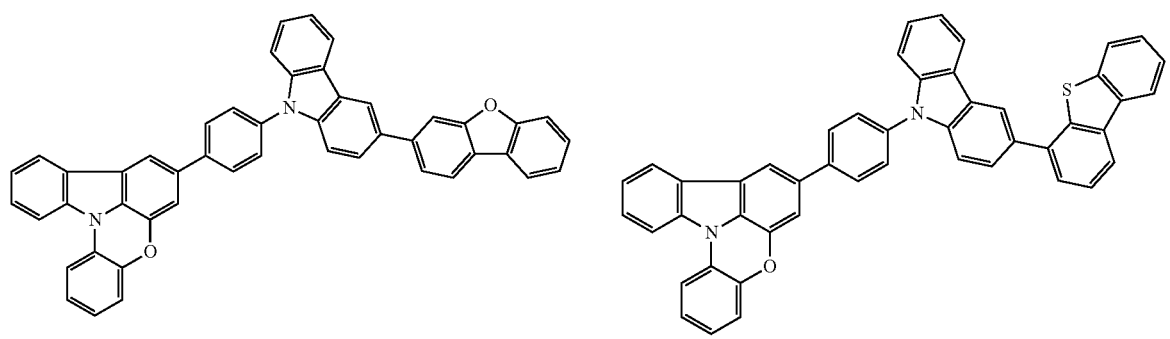

-continued
B66
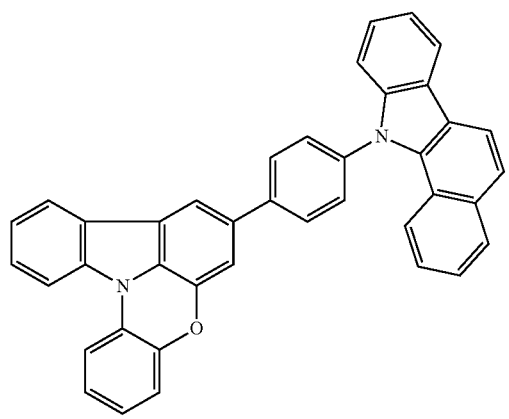
B67
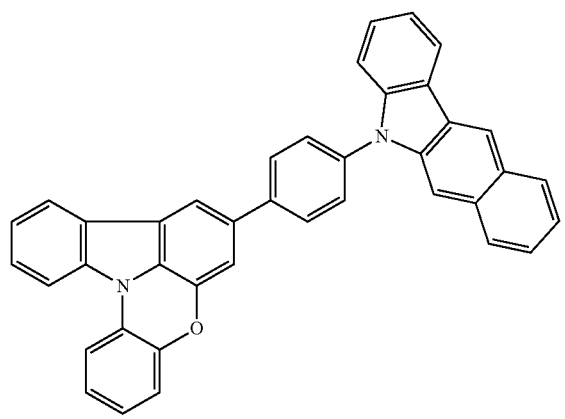
B68
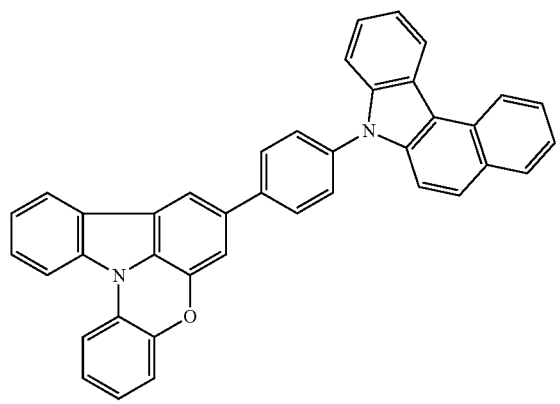
B69
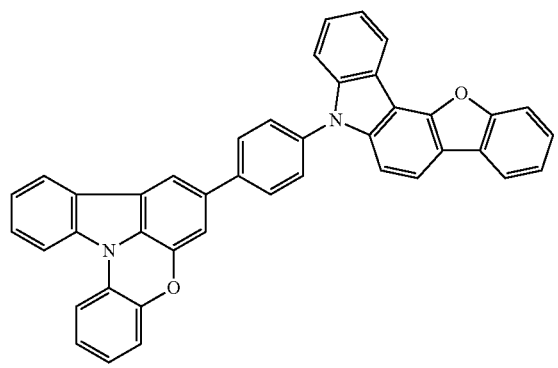
B71
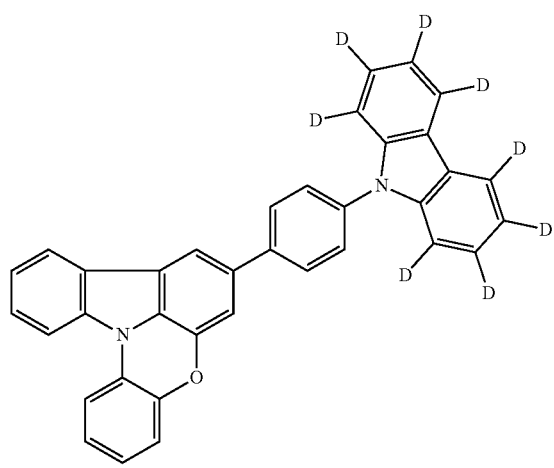
B72
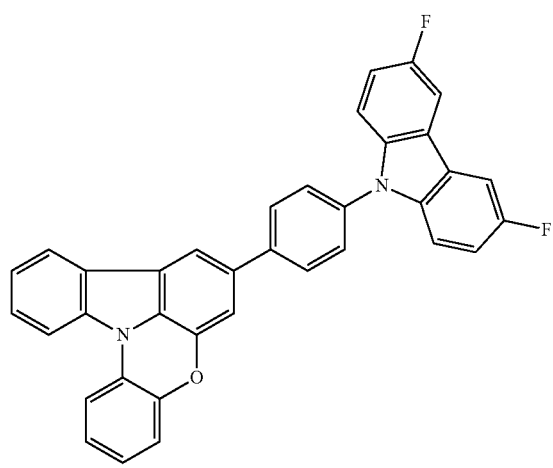

-continued
B70
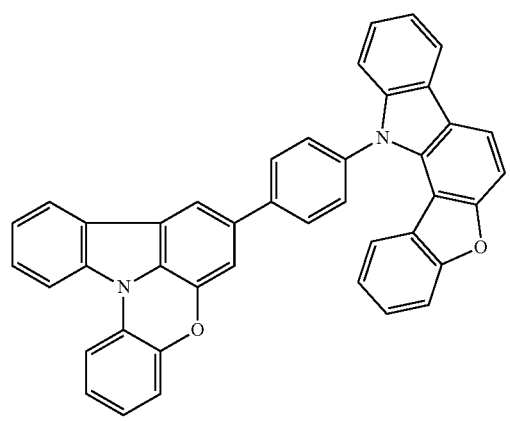
B73
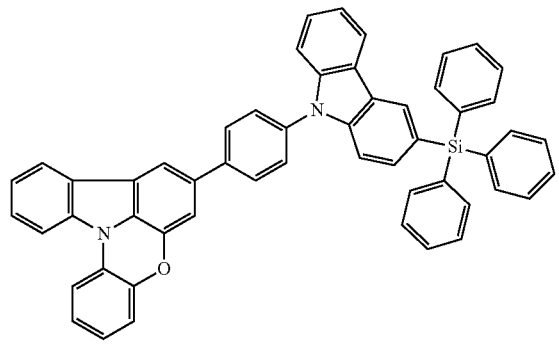
B74
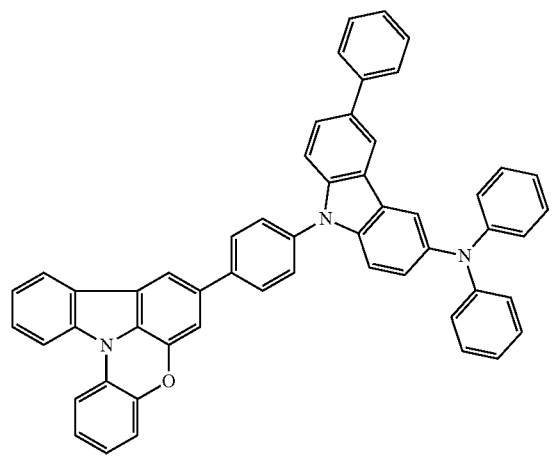
B75
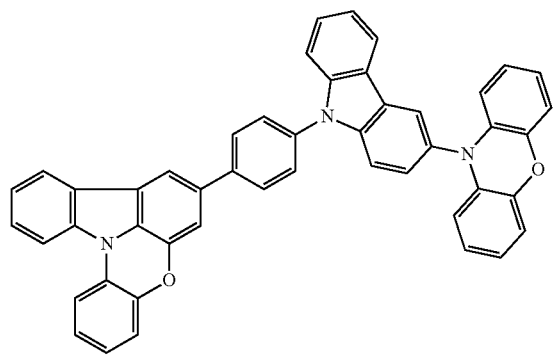
B76
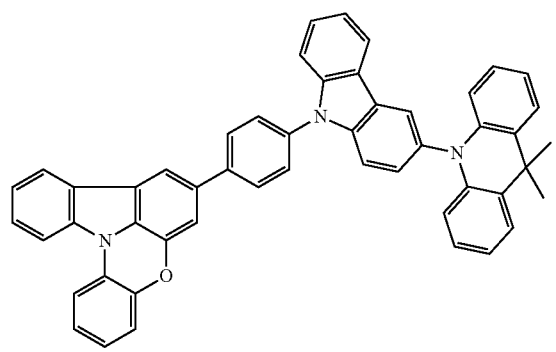
B77
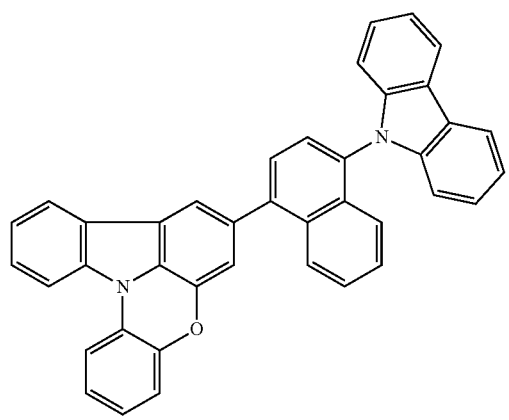

-continued
B78
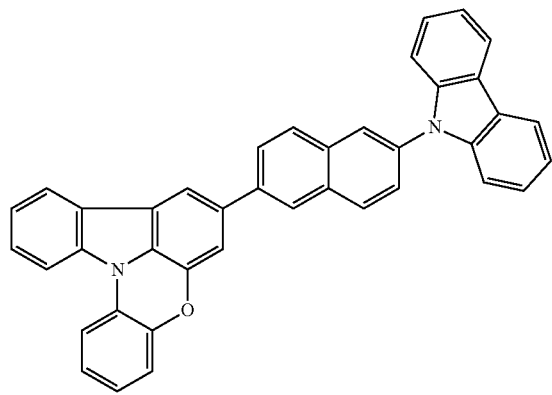
B79
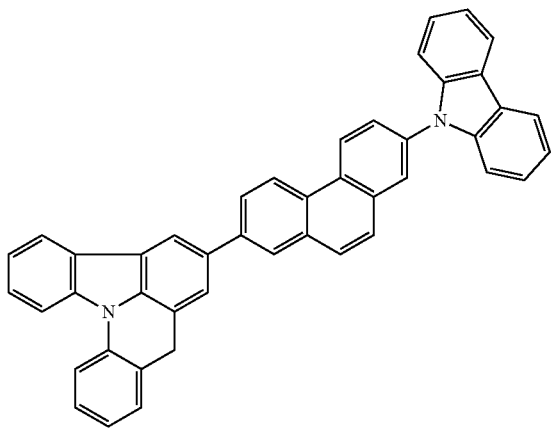
B80
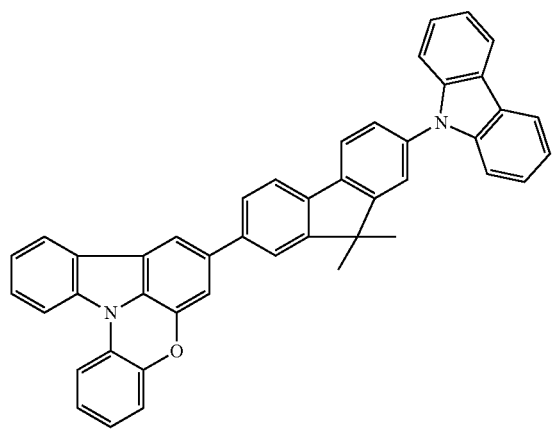
B81
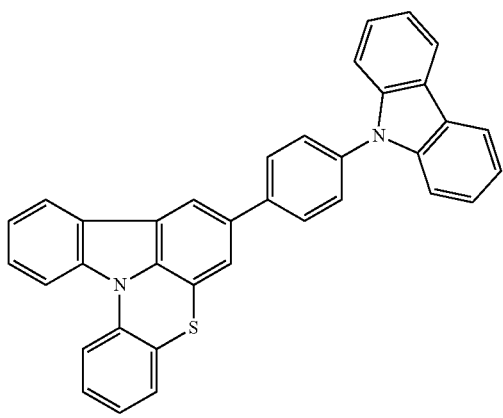
B82
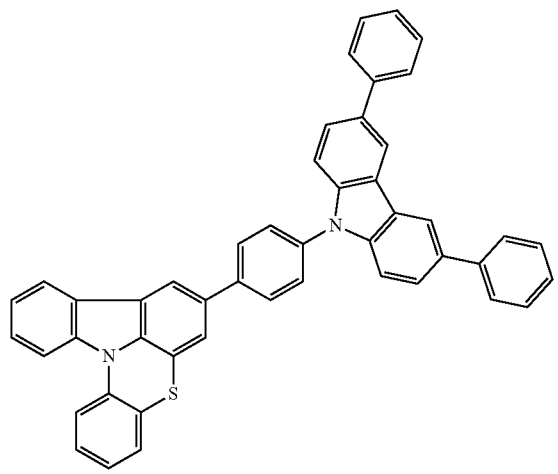
B83
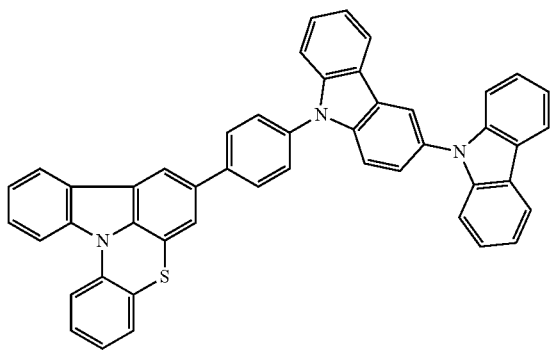

-continued
B84
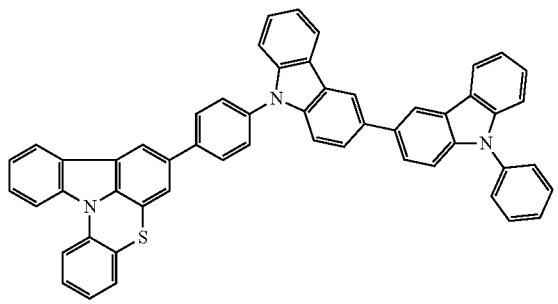
B85
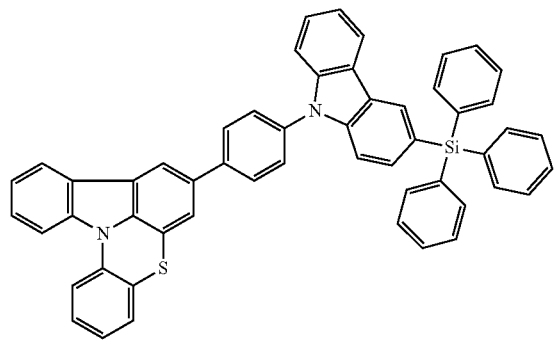
B86
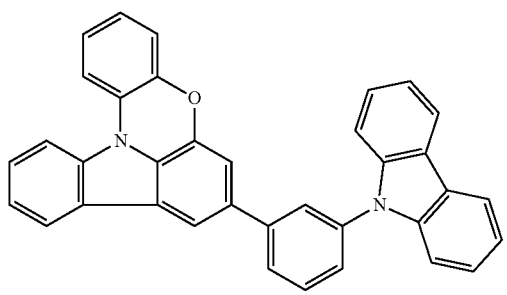
B87
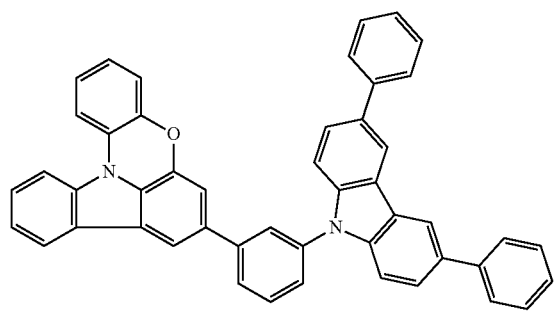
B88
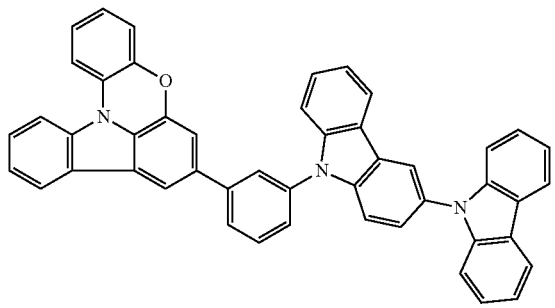
B89
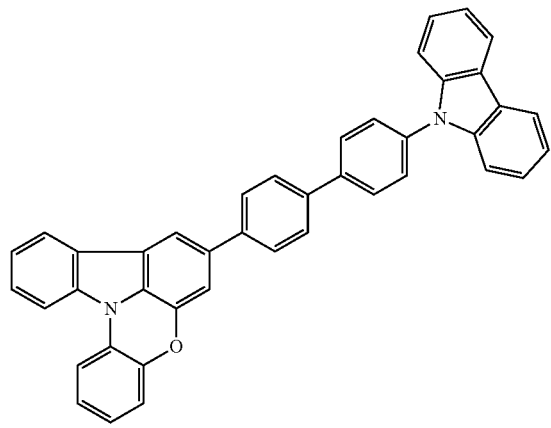
B90
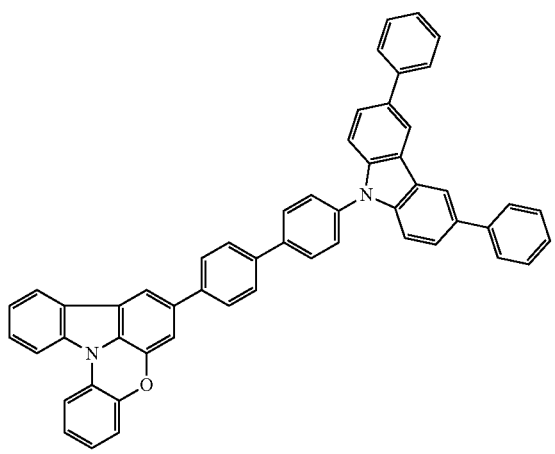
B91
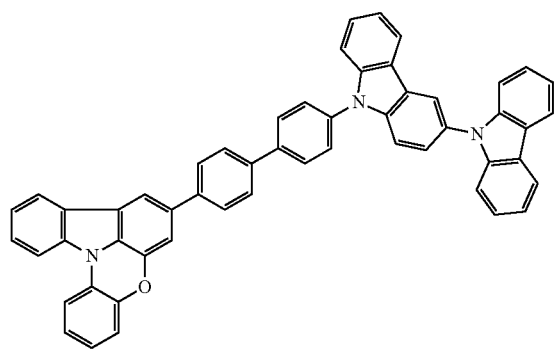

-continued
B92
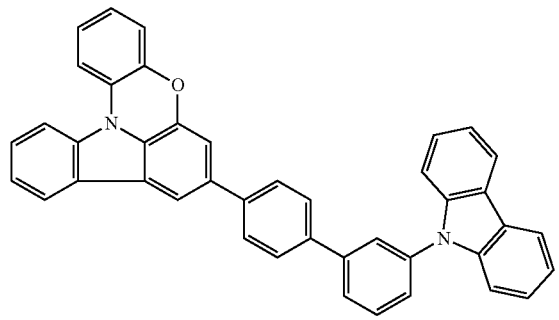
B93
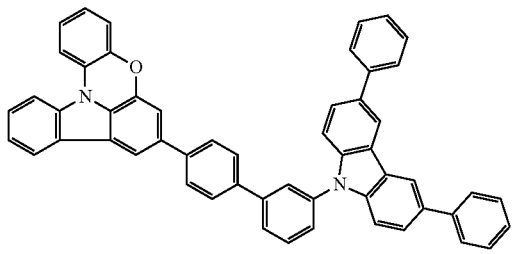
B94
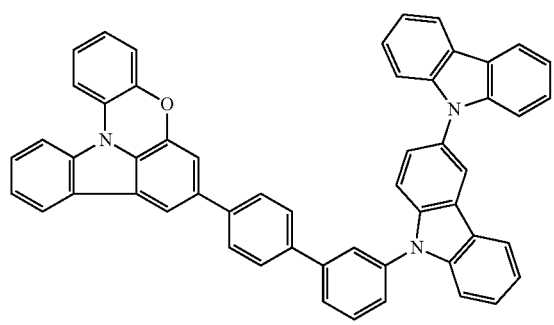
B95
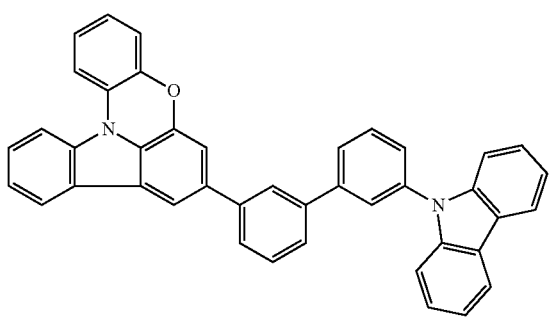
B96
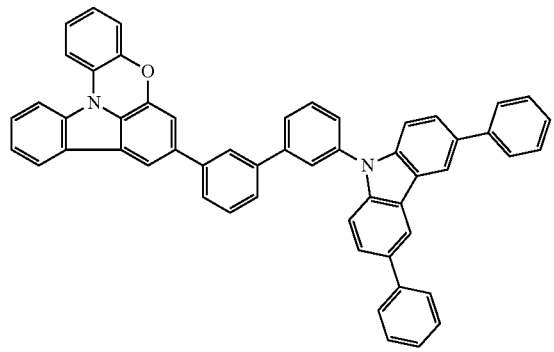
B97
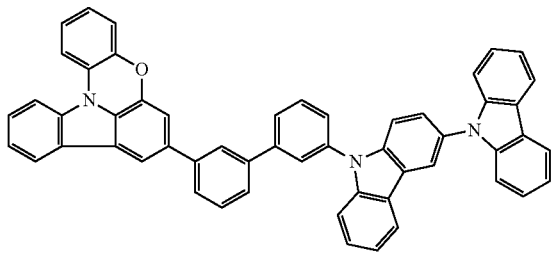
B98
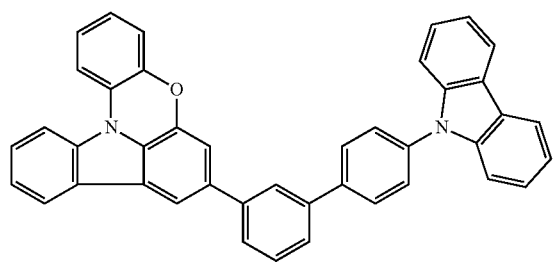
B99
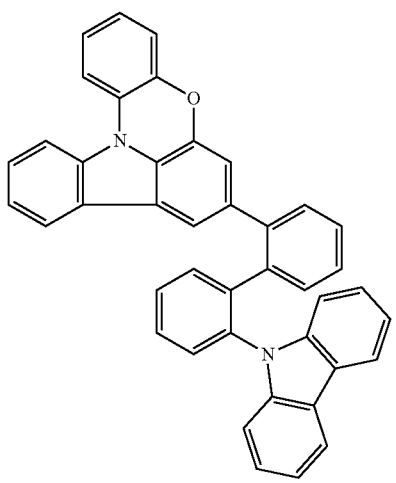

-continued
B100
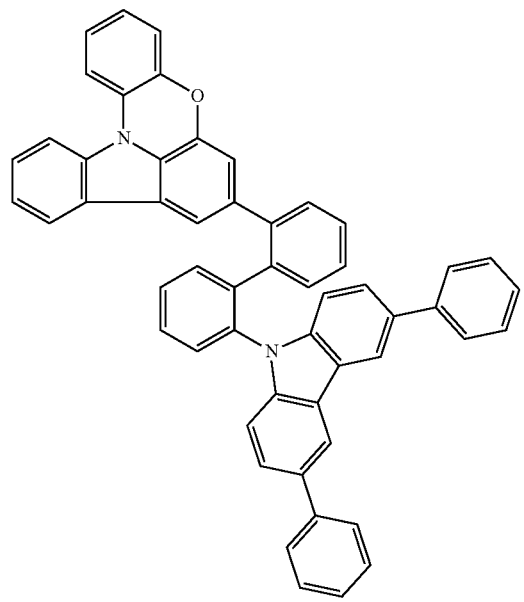
B101
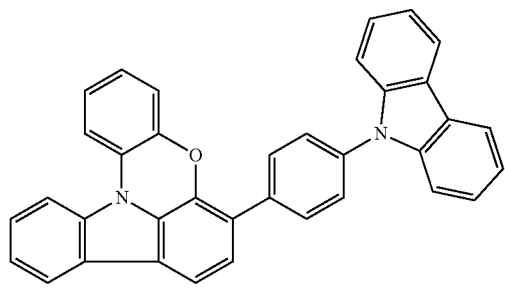
B102
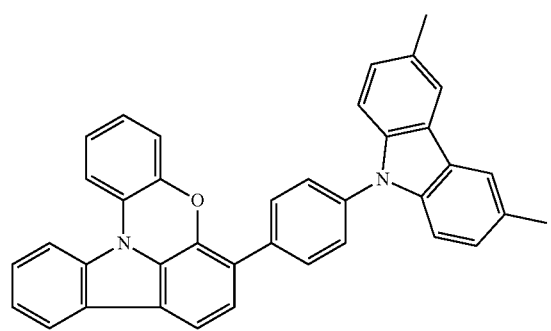
B103
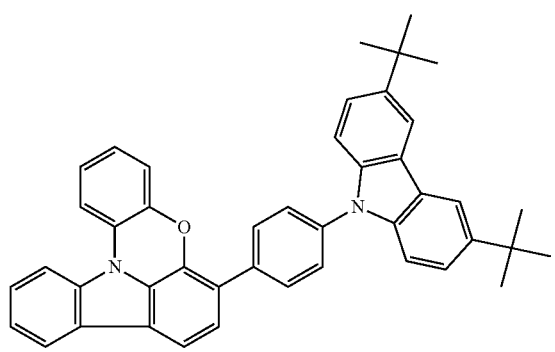
B104
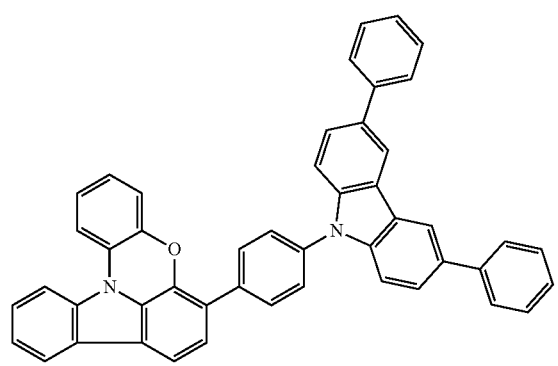
B105
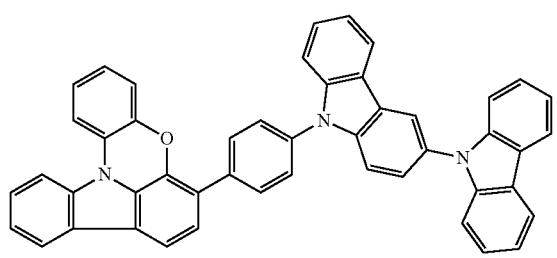

-continued
B106
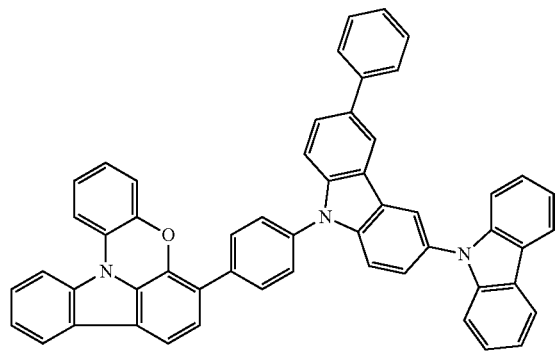
B107
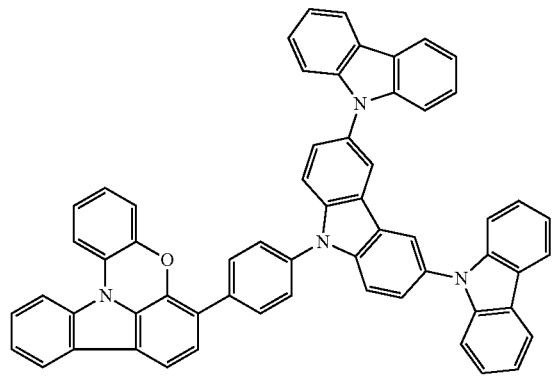
B108
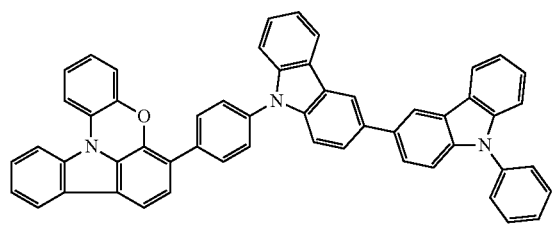
B109
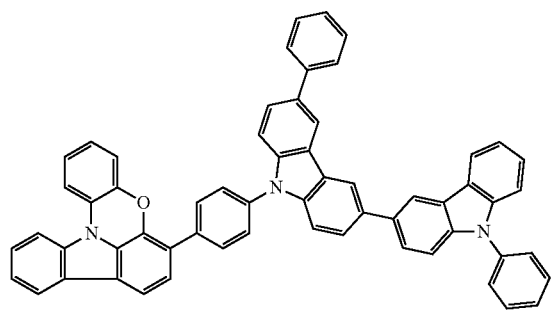
B110
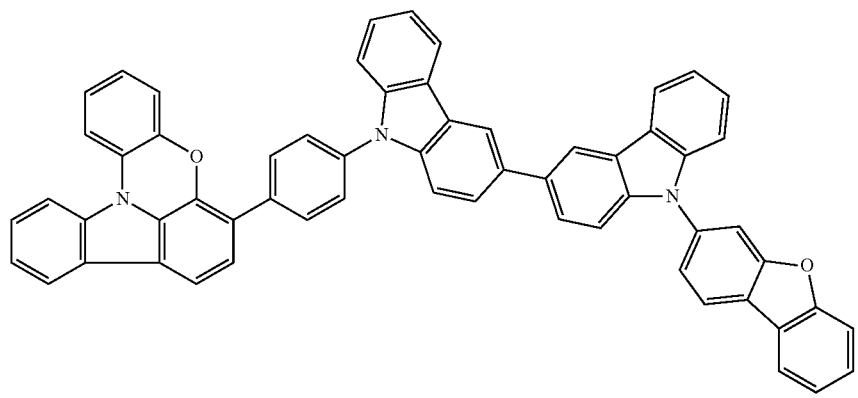
B111
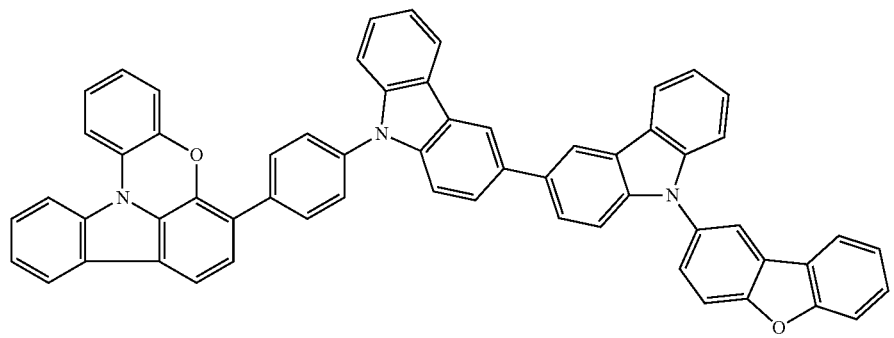

-continued
B112
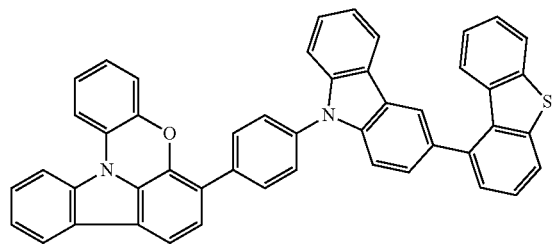
B113
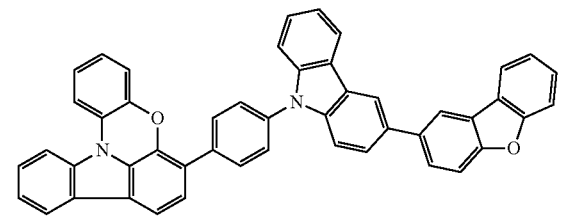
B114
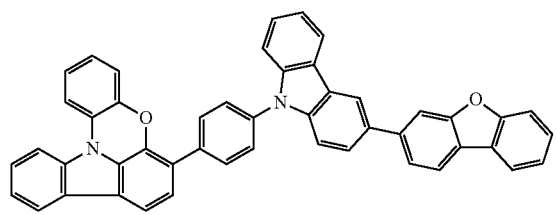
B115
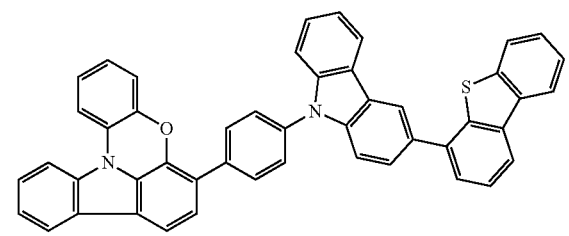
B116
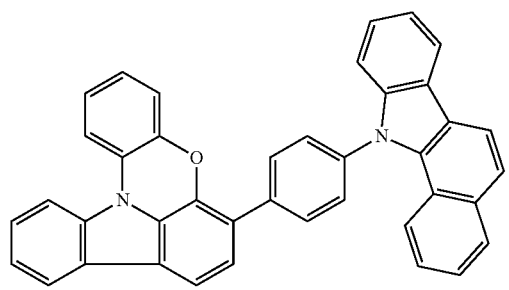
B117
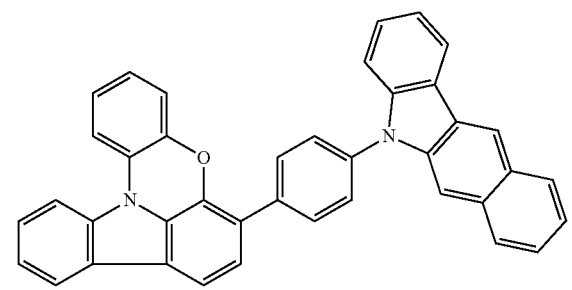
B118
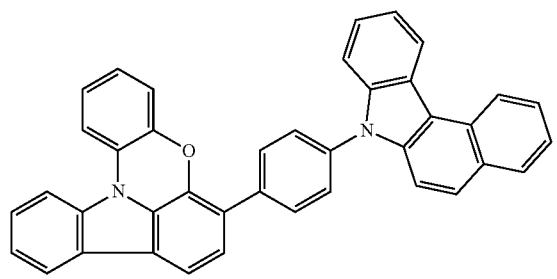
B119
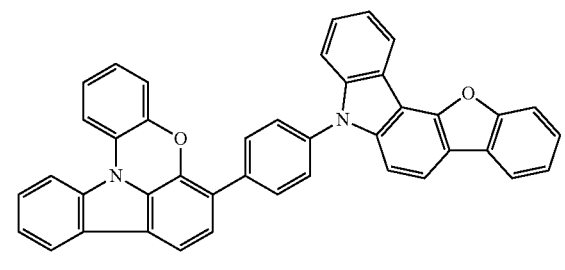
B120
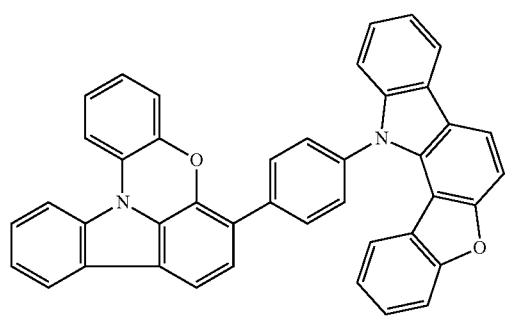
B121
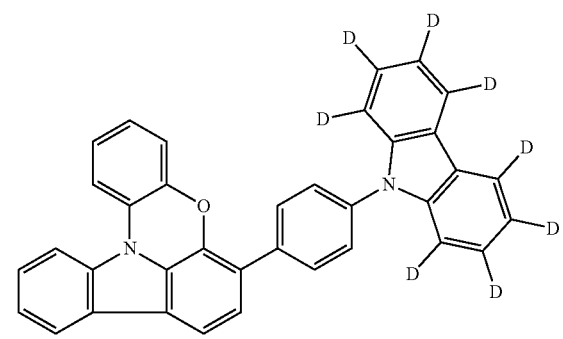

-continued
B122
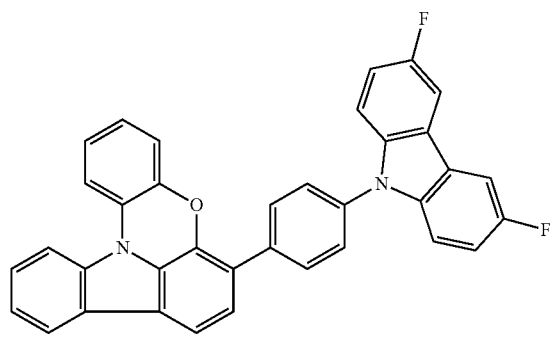
B123
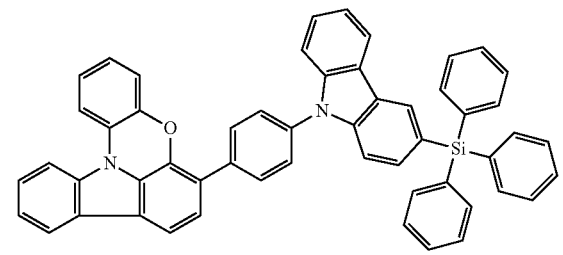
B124
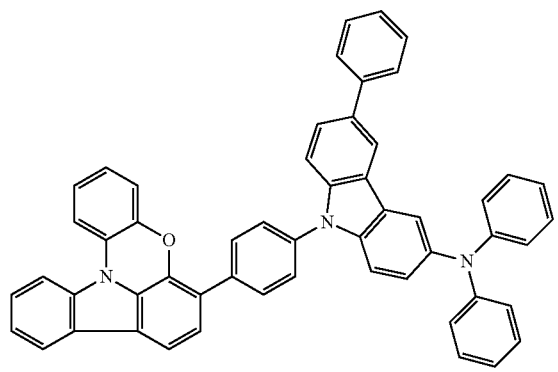
B125
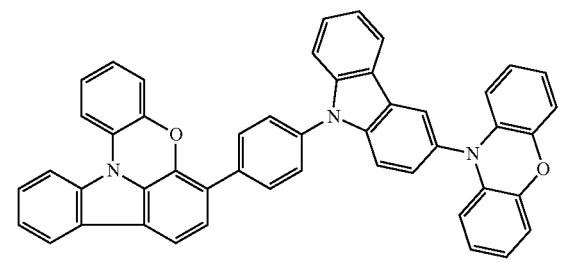
B126
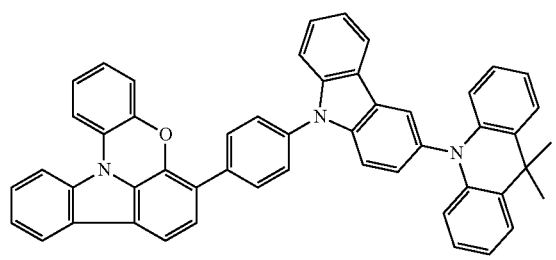
B127
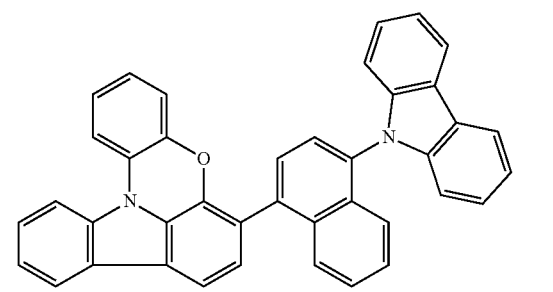
B128
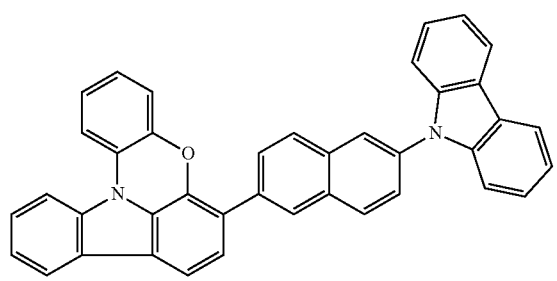
B129
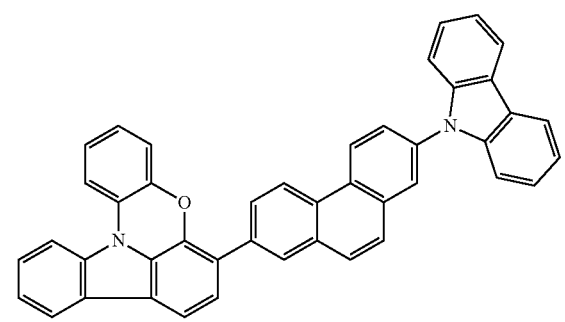

-continued
B130
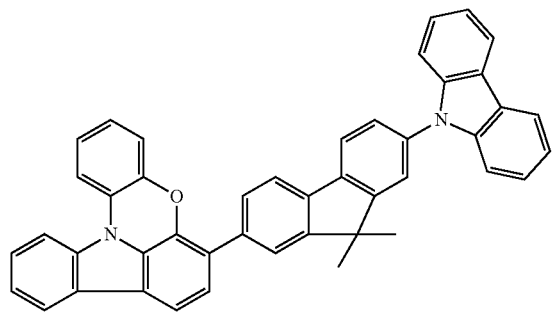
B131
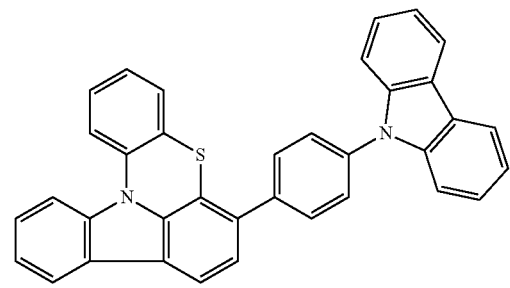
B132
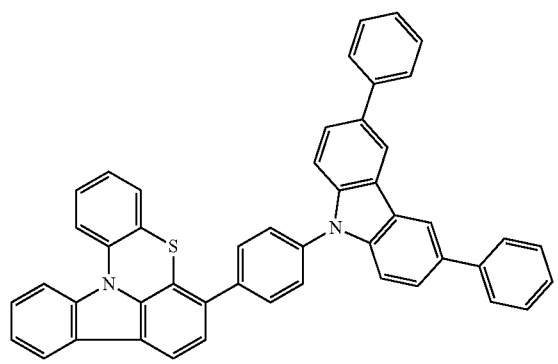
B133
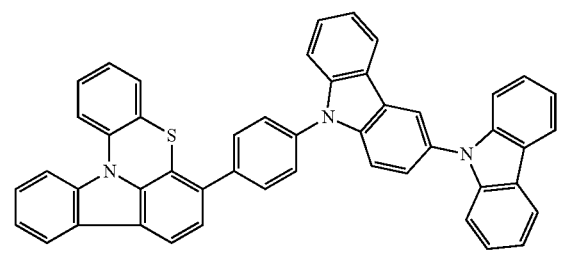
B134
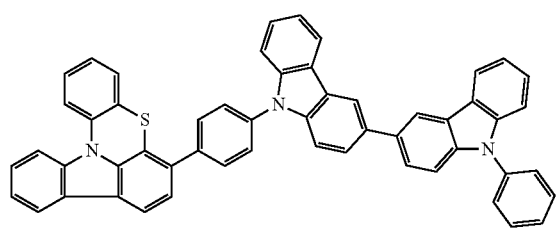
B135
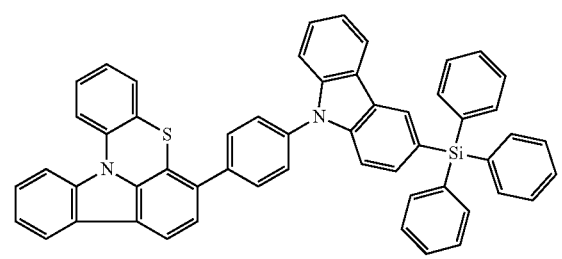
B136
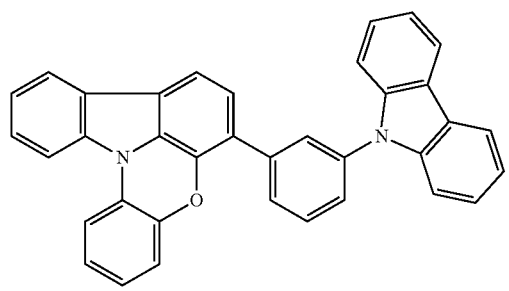
B137
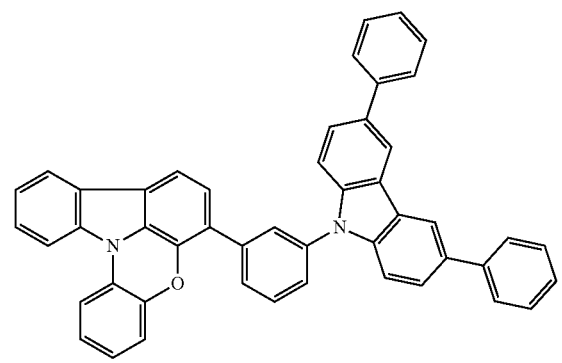

-continued
B138
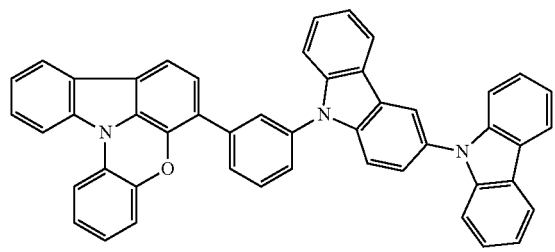
B139
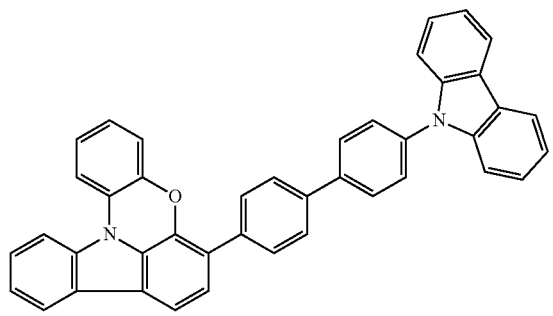
B140
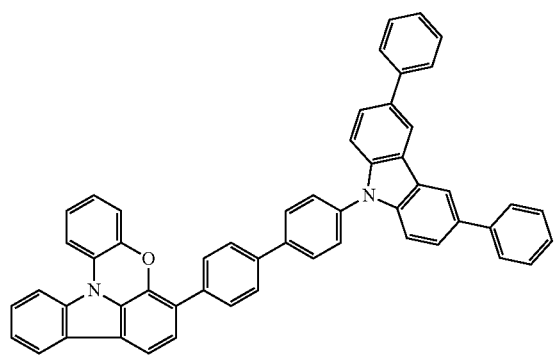
B141
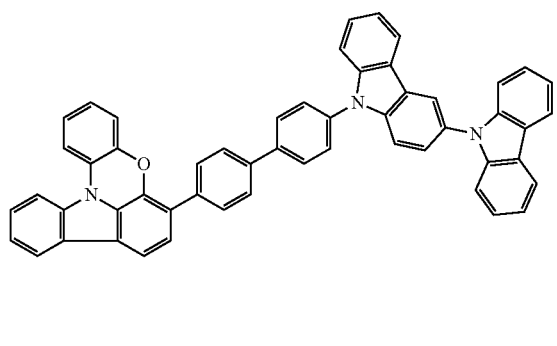
B142
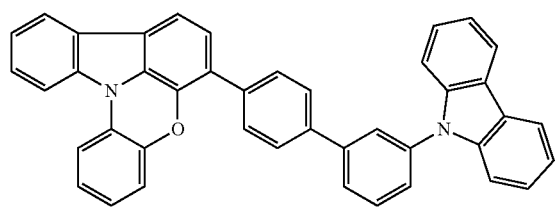
B143
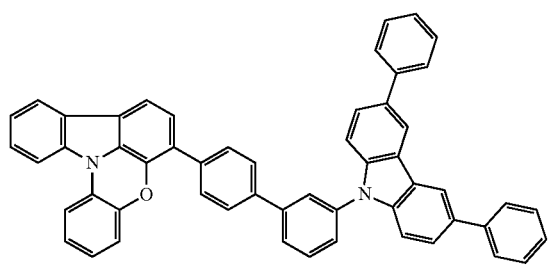
B144
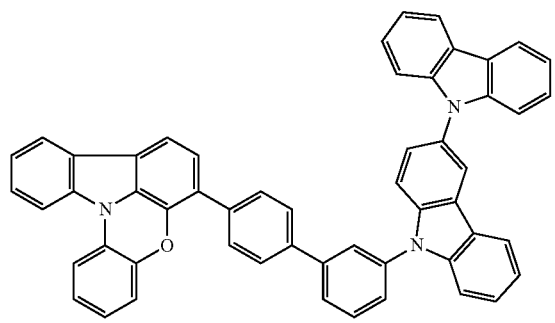
B145
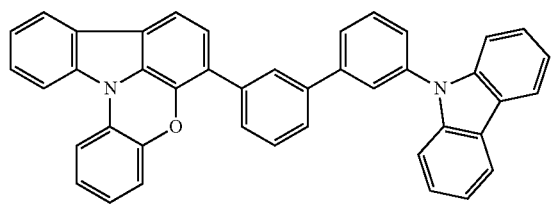
B146
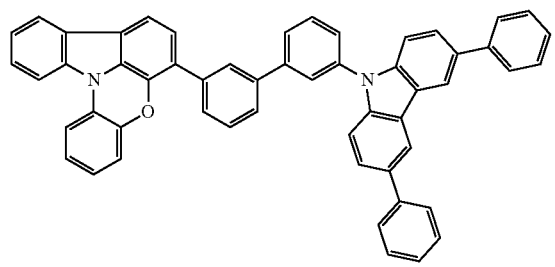
B147
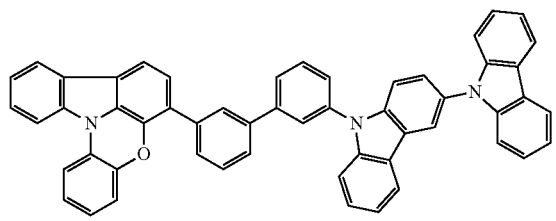

-continued
B148
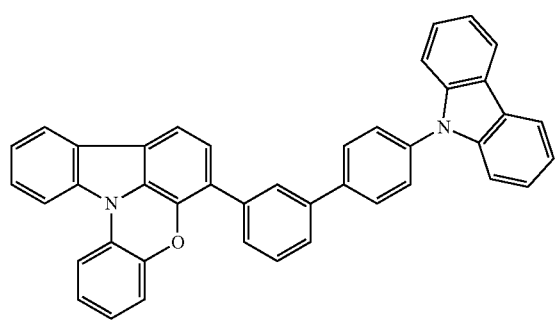
B149
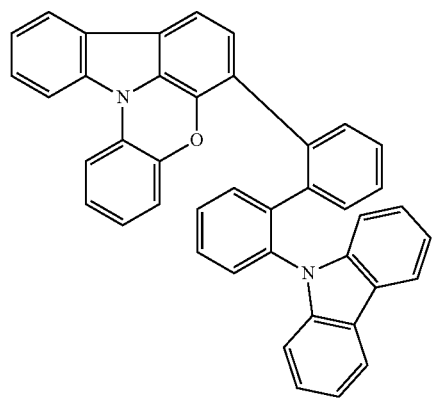
B150
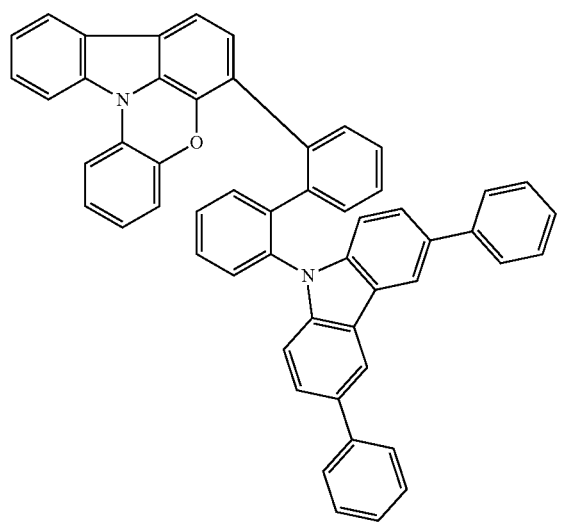
[Compound Group 1C]
C1
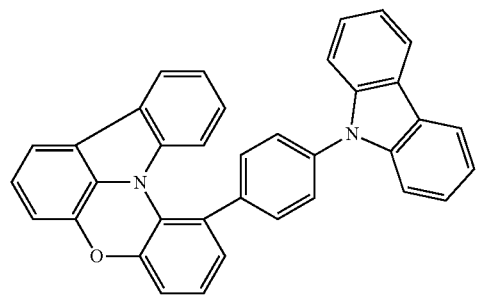
C2
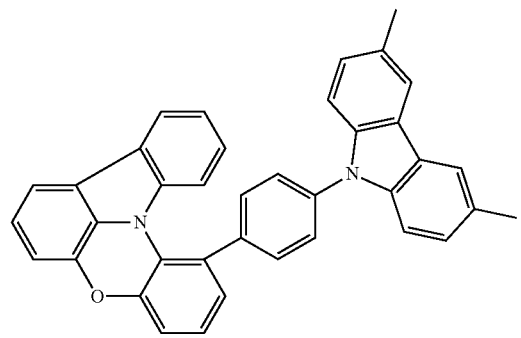

-continued
C3
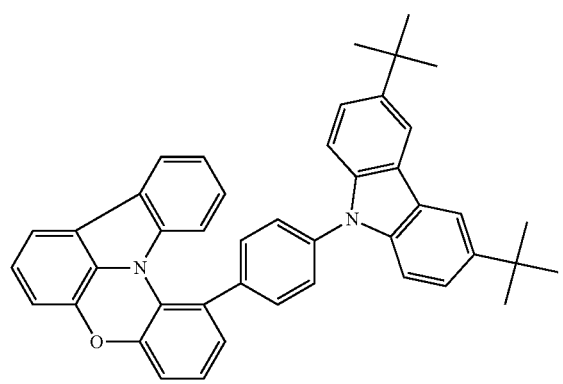
C4
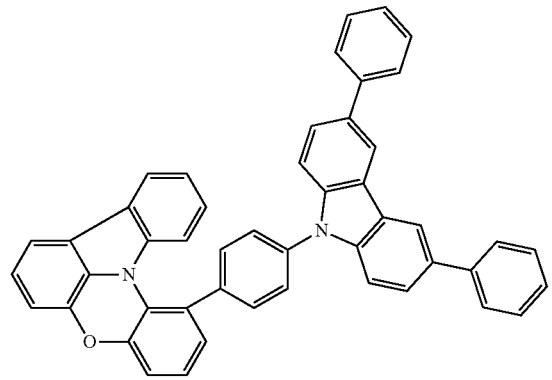
C5
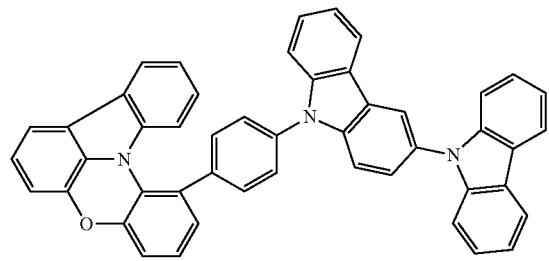
C6
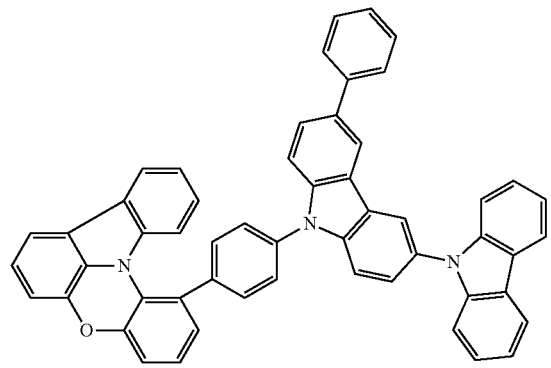
C7
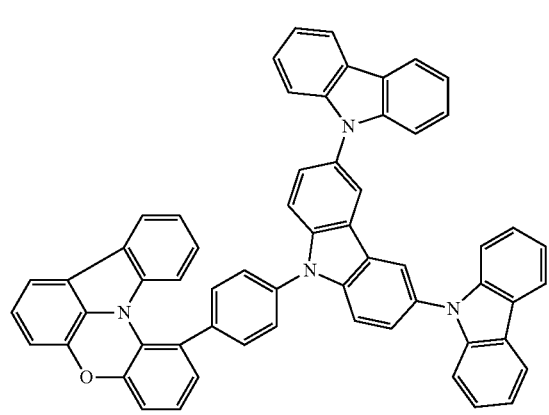
C8
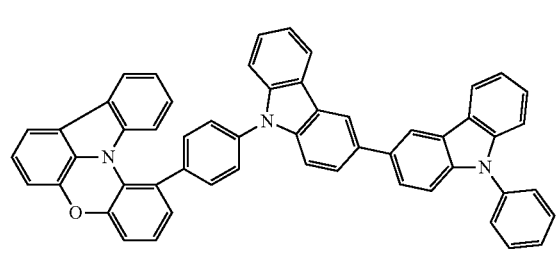
C9
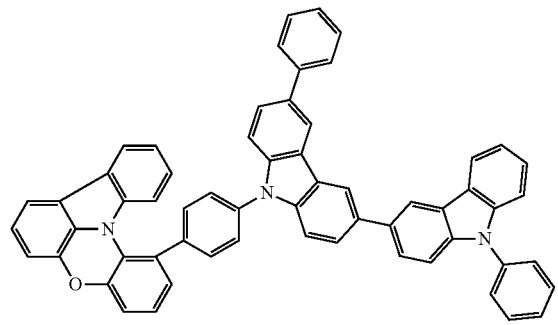
C10
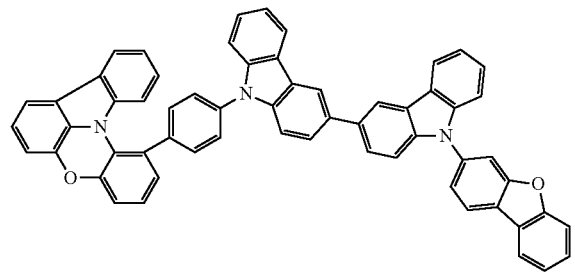

-continued
C11
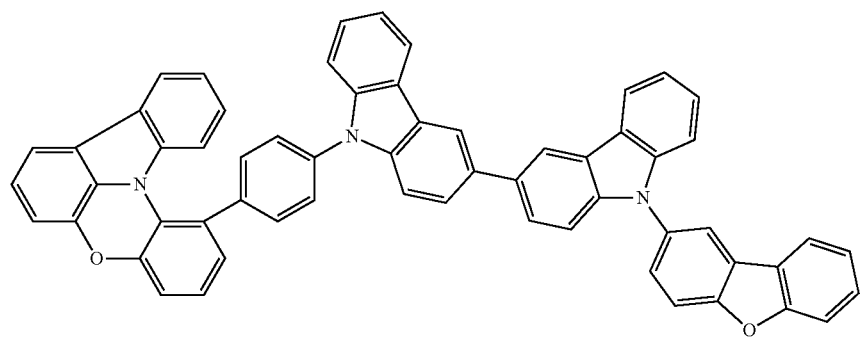
C12
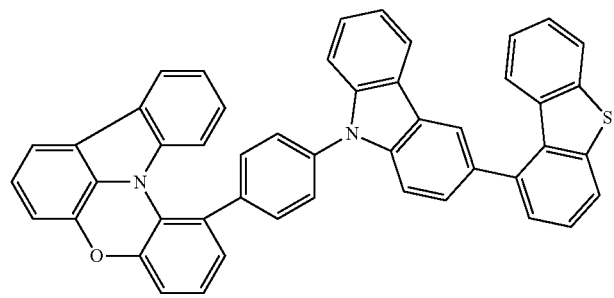
C13
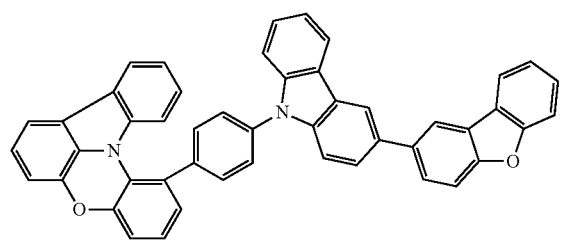
C14
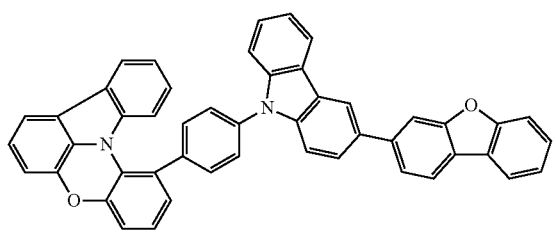
C15
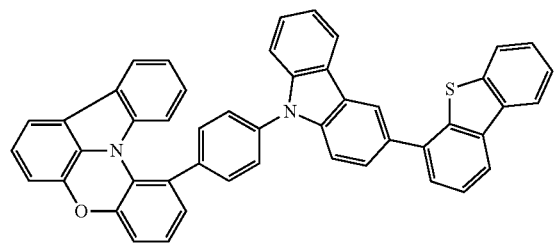
C16
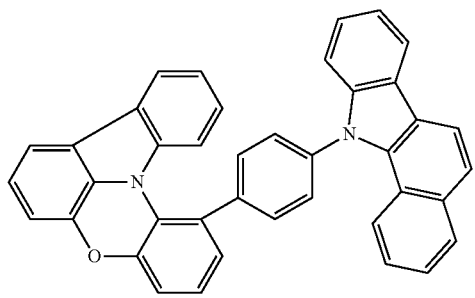
C17
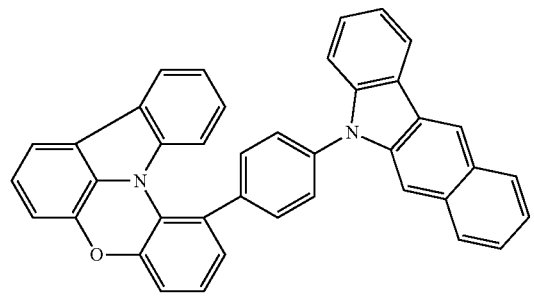
C18
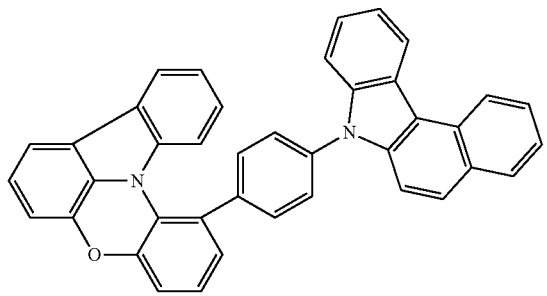

-continued
C19
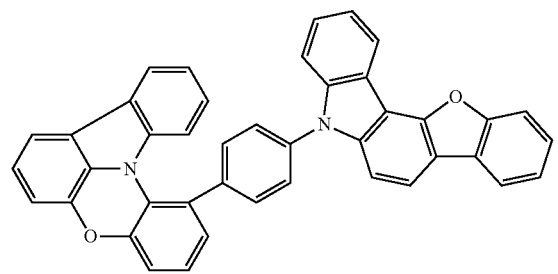
C20
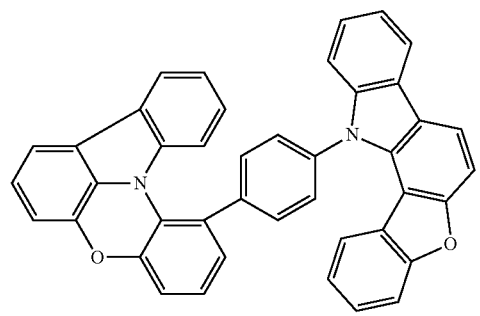
C21
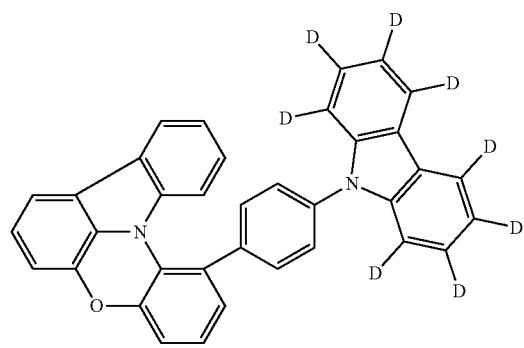
C22
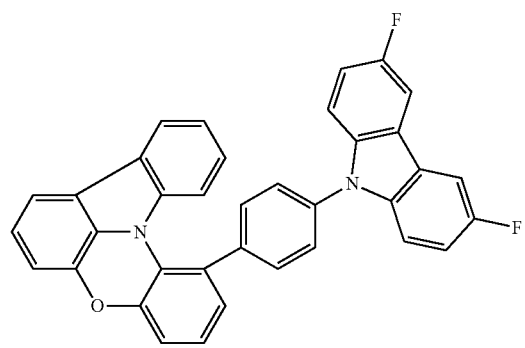
C23
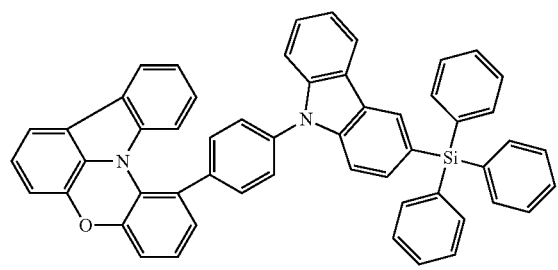
C24
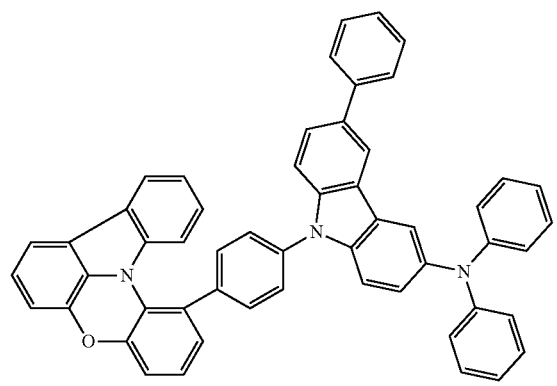
C25
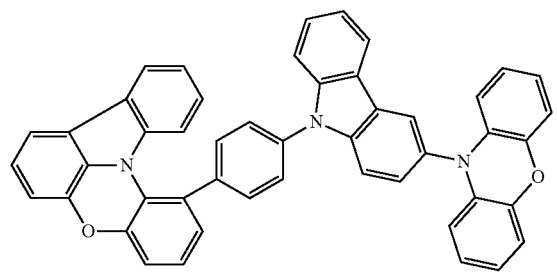
C26
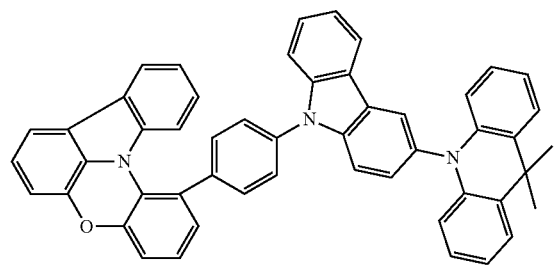

-continued
C27
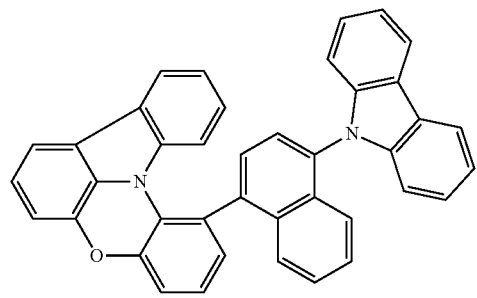
C28
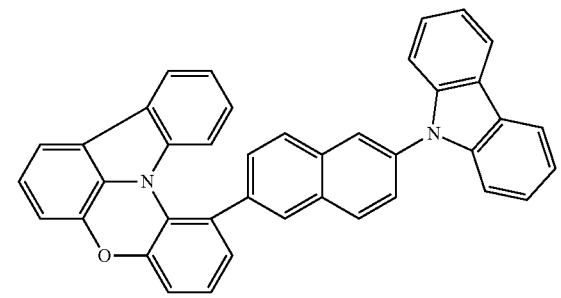
C29
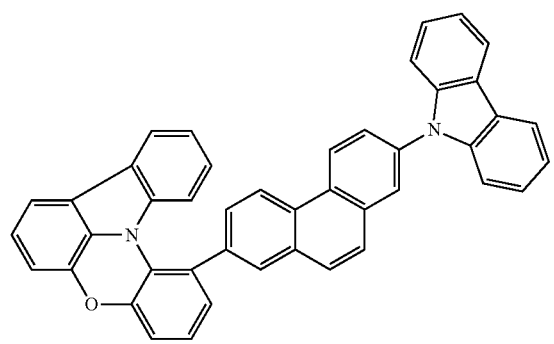
C30
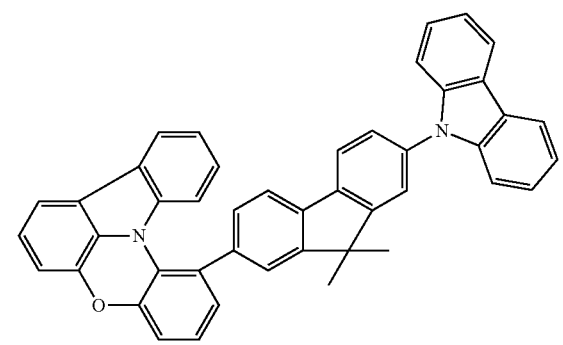
C31
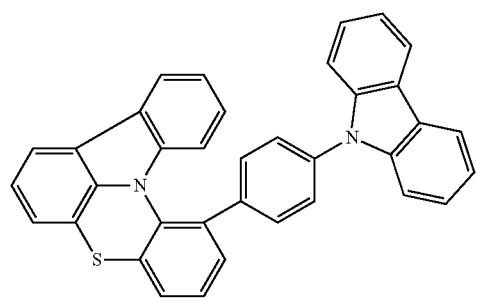
C32
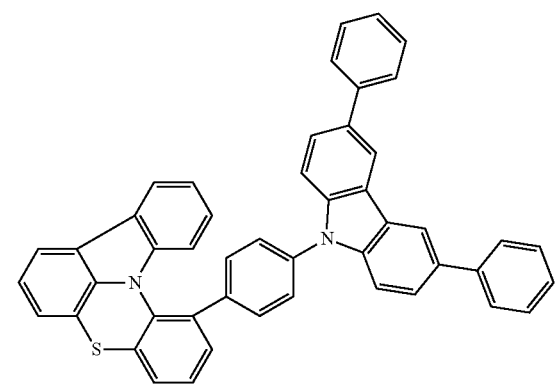
C33
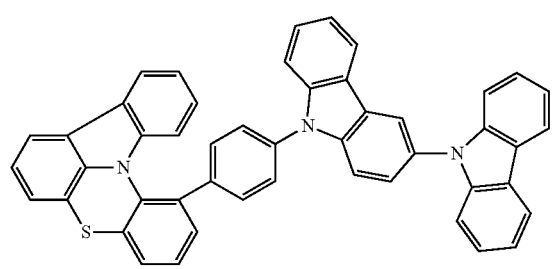
C34
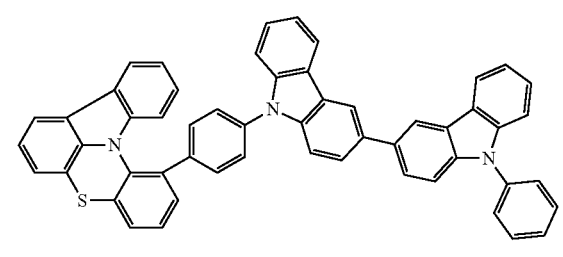
C35
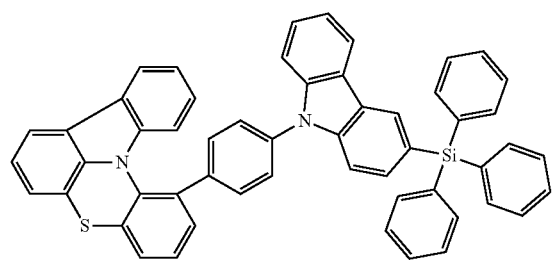
C36
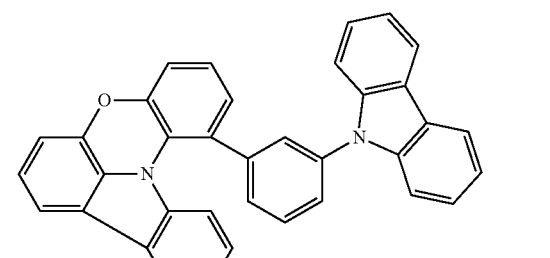

-continued
C37
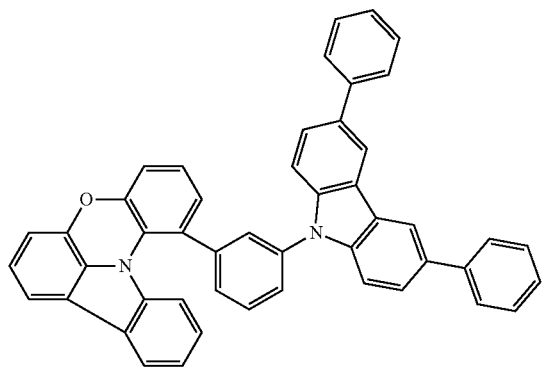
C38
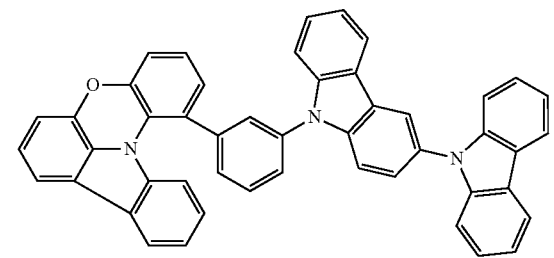
C39
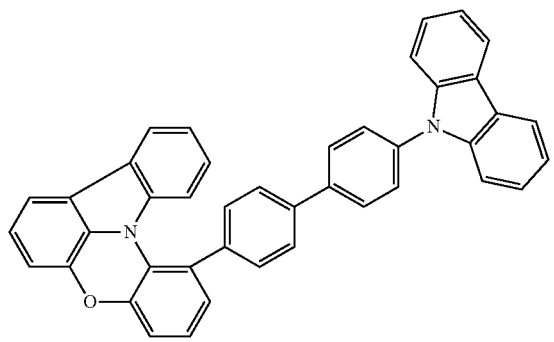
C40
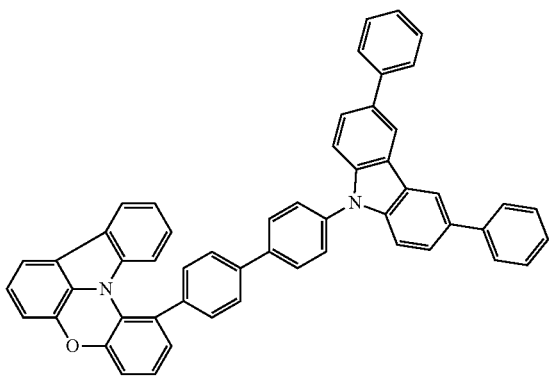
C41
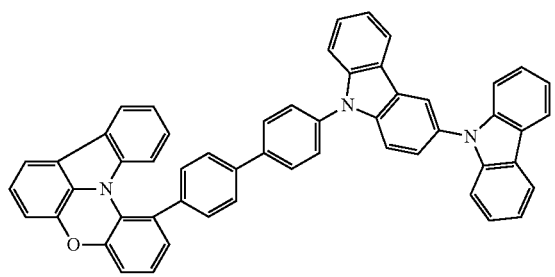
C42
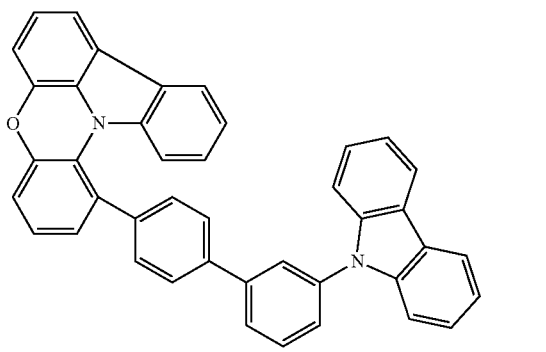
C43
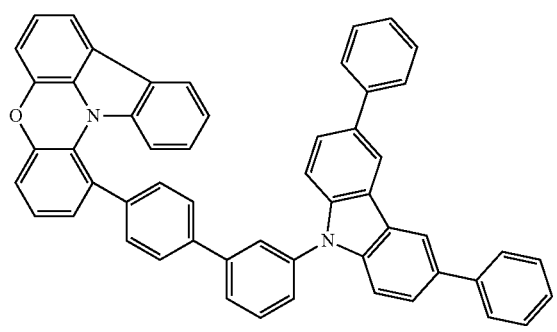
C44
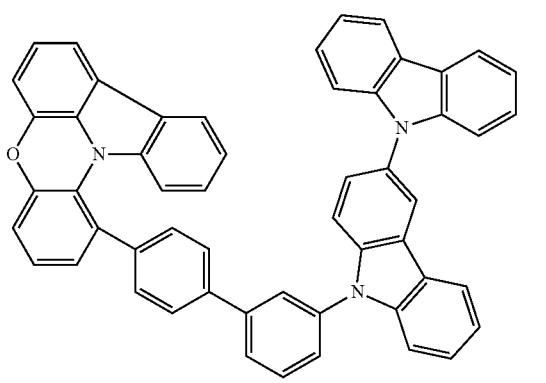

-continued
C45
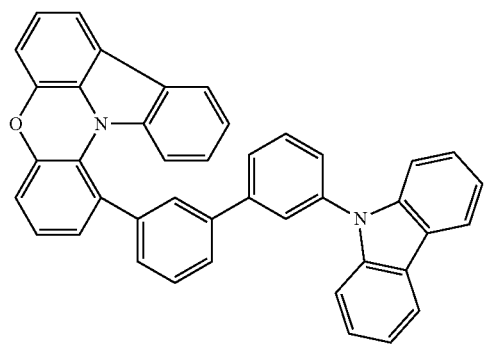
C46
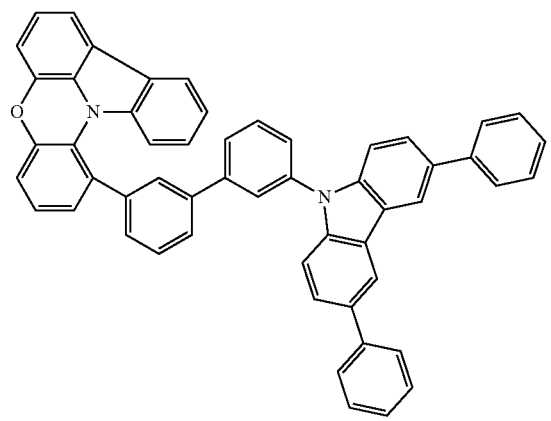
C47
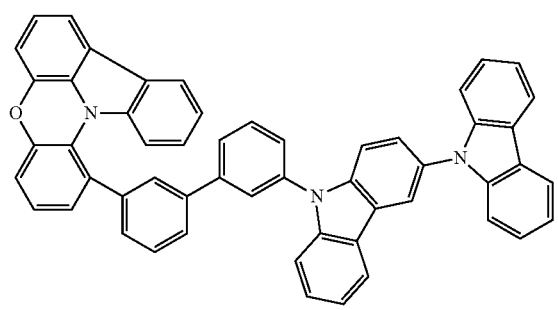
C48
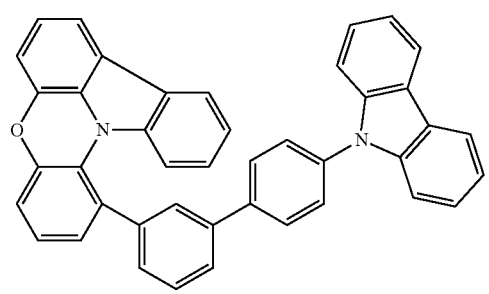
C49
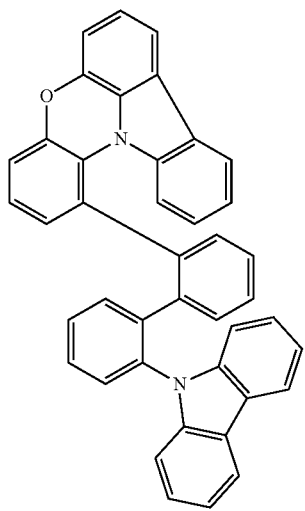
C50
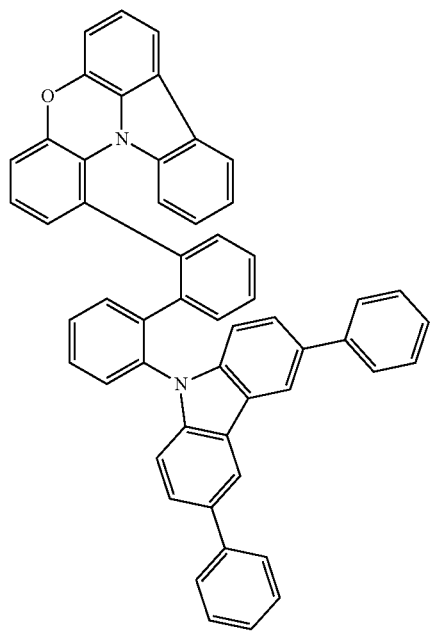

-continued
C51
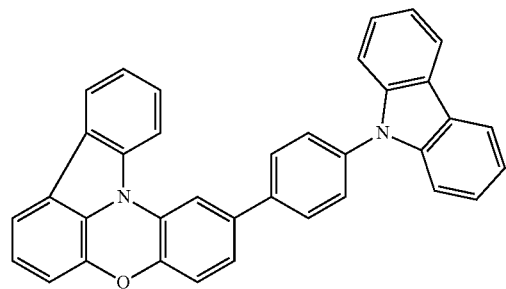
C52
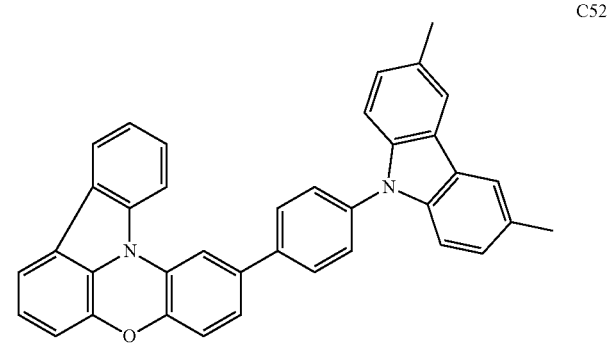
C53
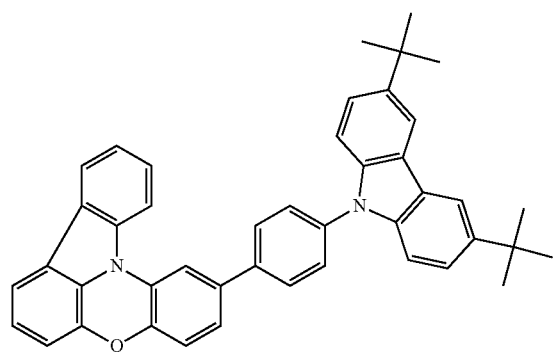
C54
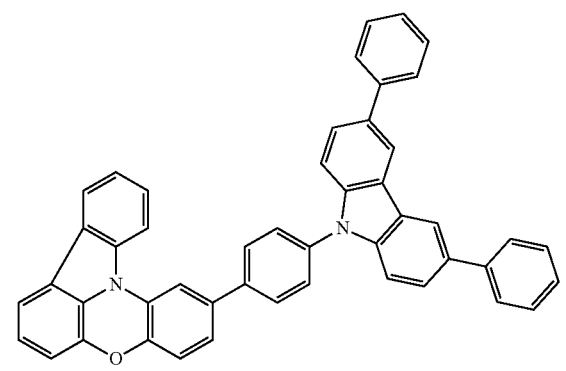
C55
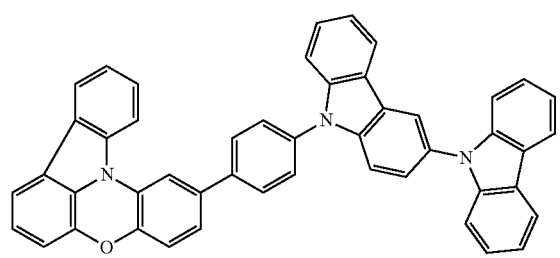
C56
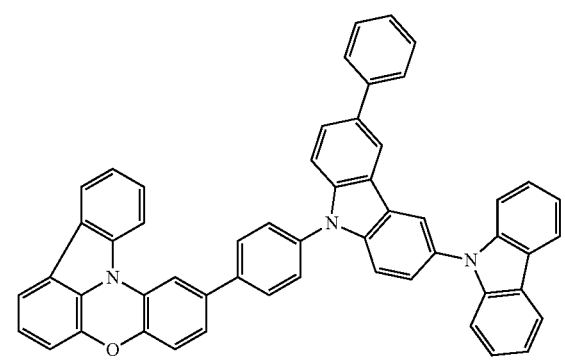
C57
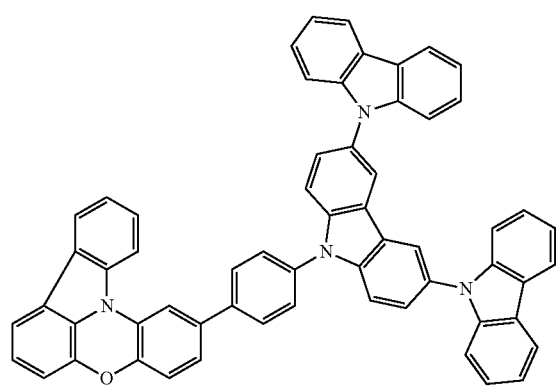
C58
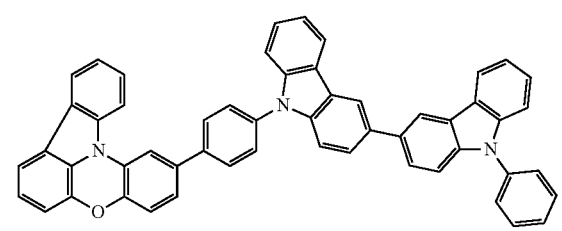

C59
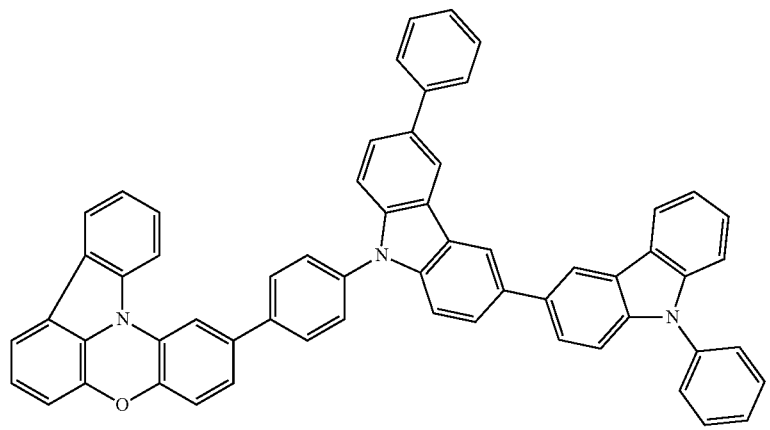
C60
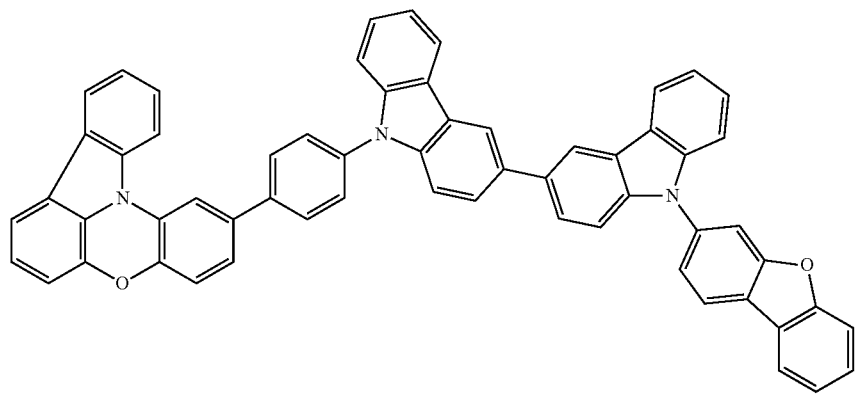
C61
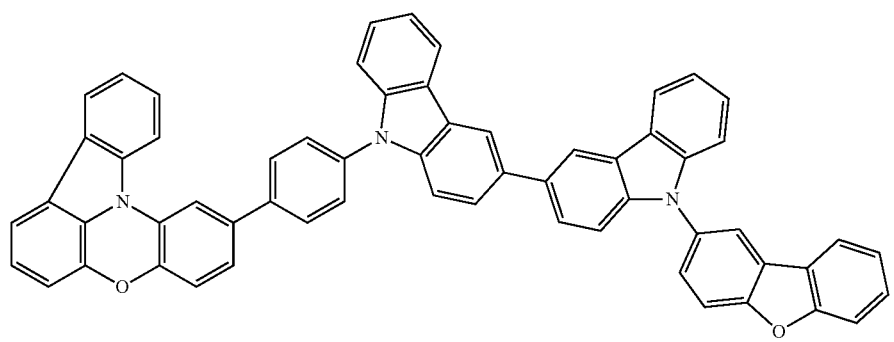
C62
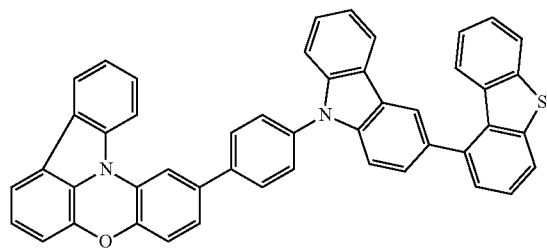
C63
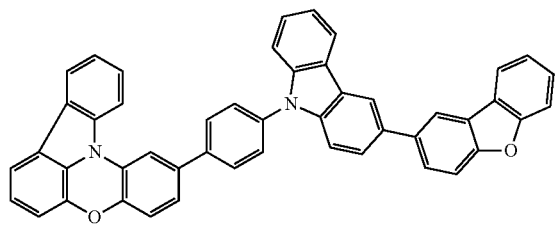

C64
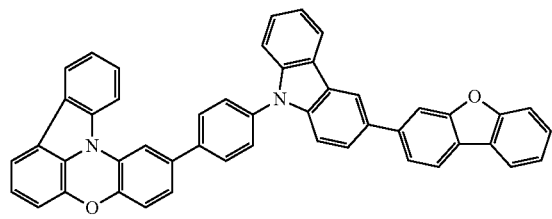
C65
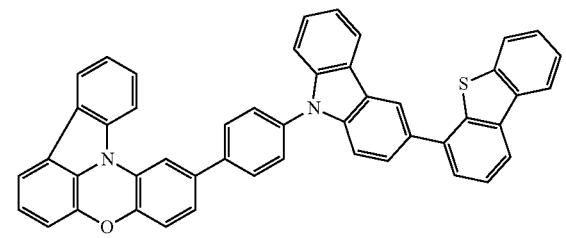
C66
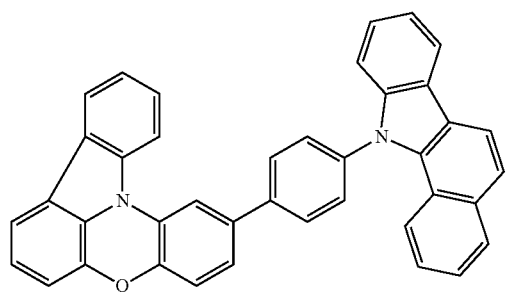
C64
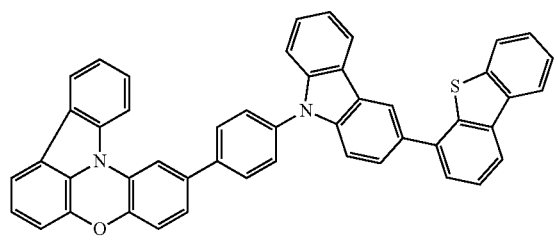
C65
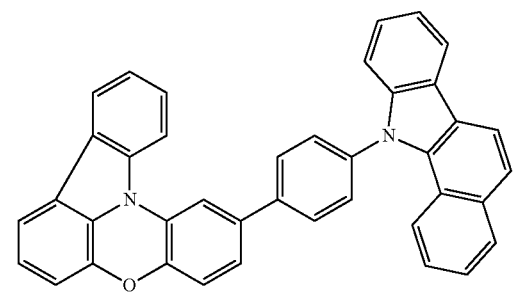
C66
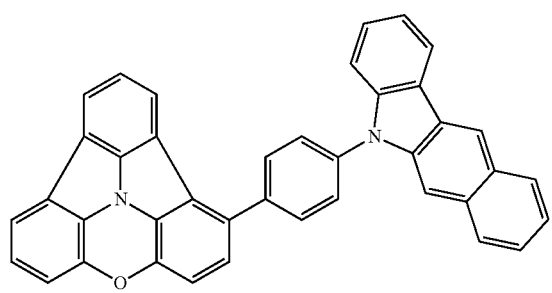
C67
C68
C69
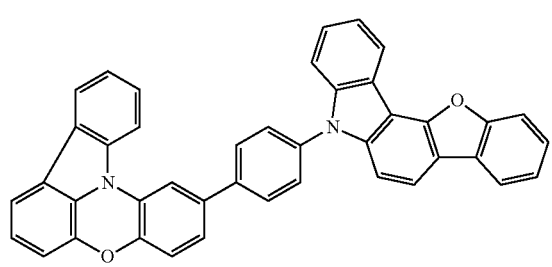
C70
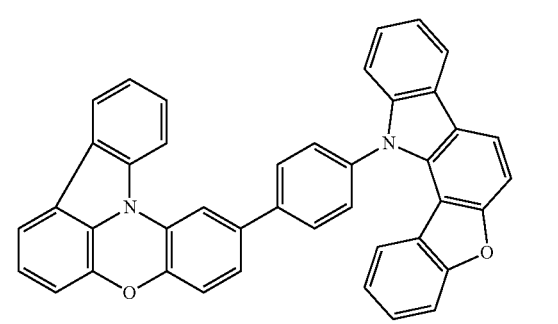

-continued
C71
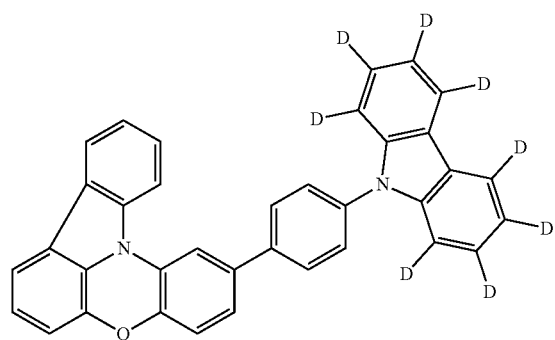
C72
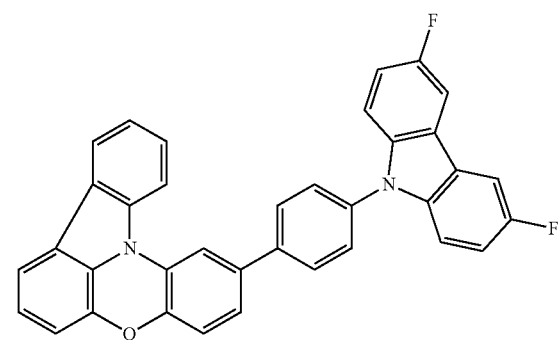
C73
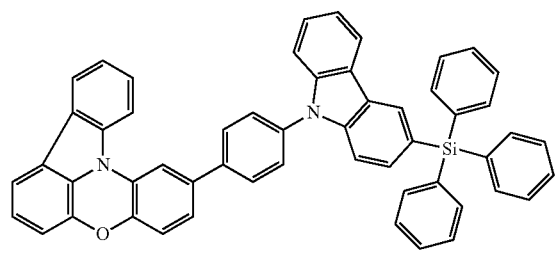
C74
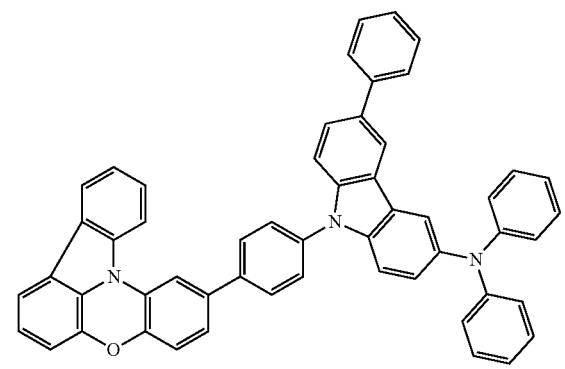
C75
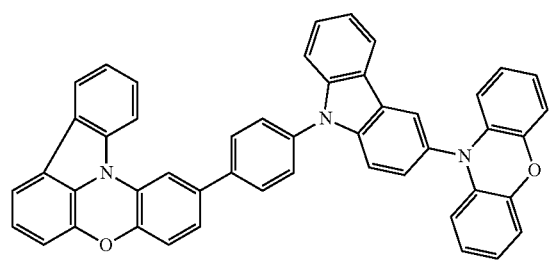
C76
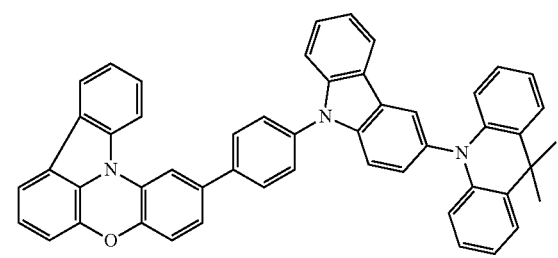
C77
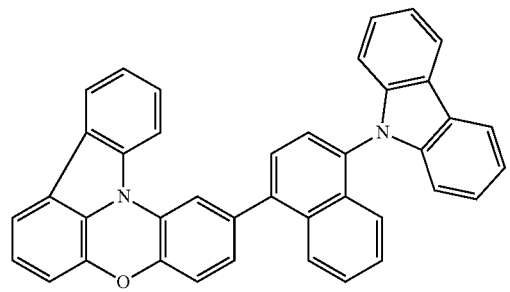
C78
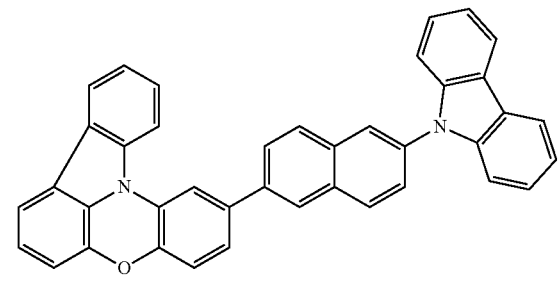

-continued
C79
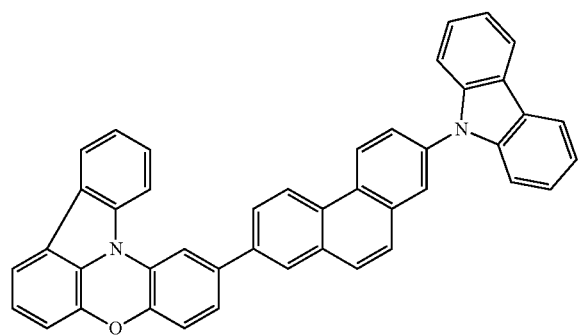
C80
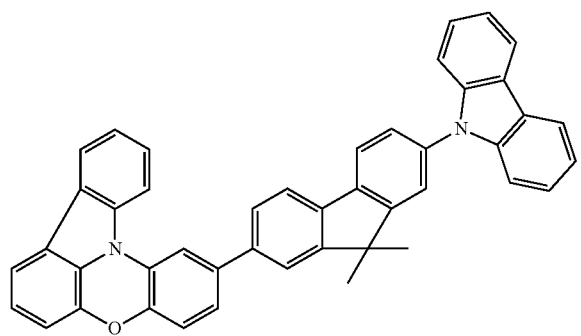
C81
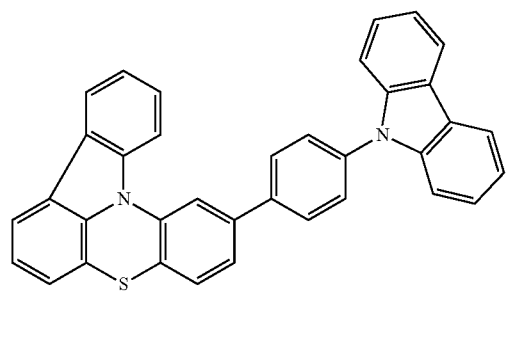
C82
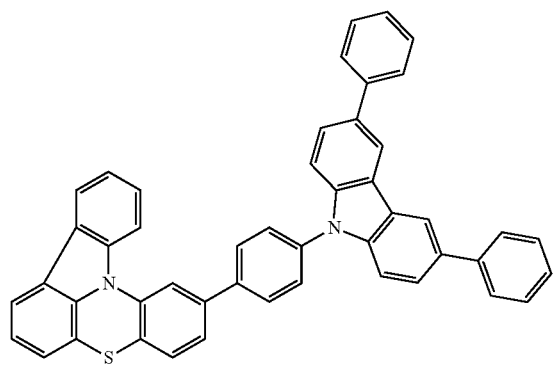
C83
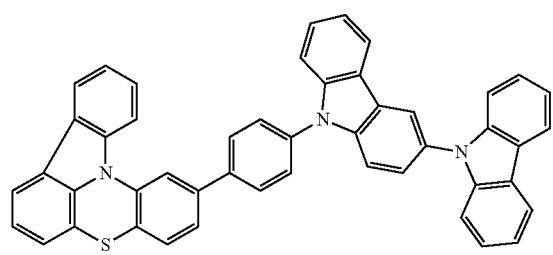
C84
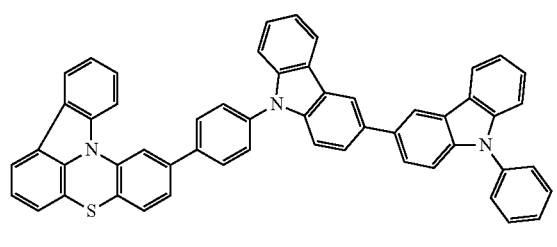
C85
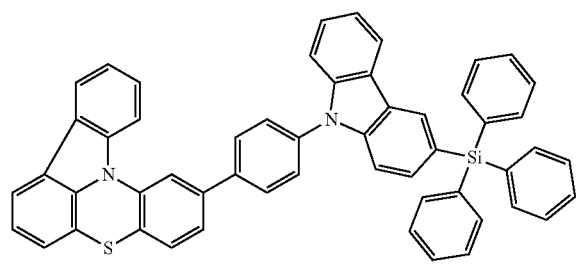
C86
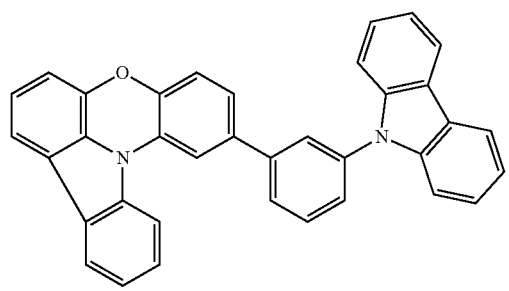

-continued
C87
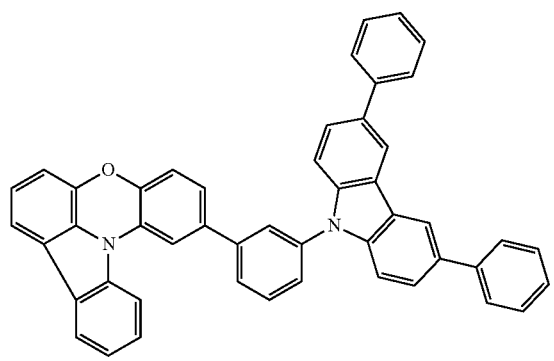
C88
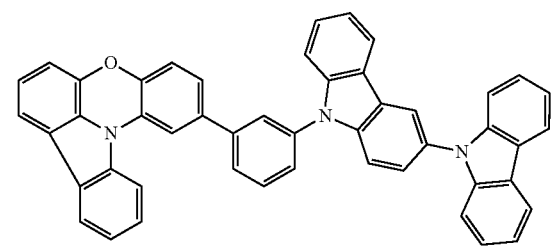
C89
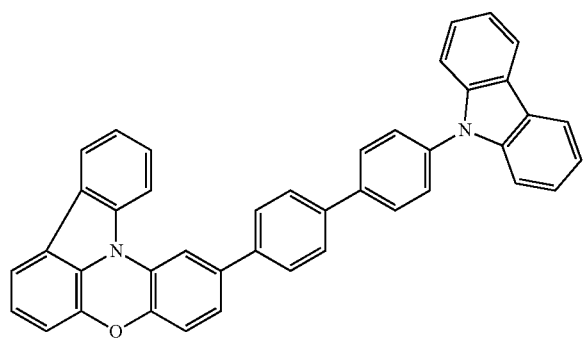
C90
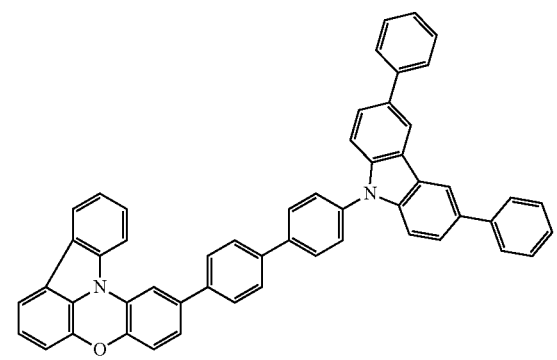
C91
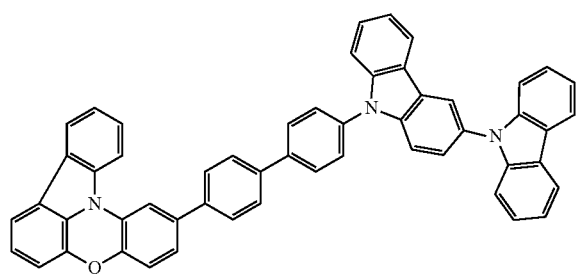
C92
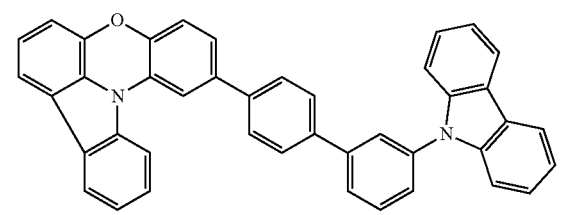
C93
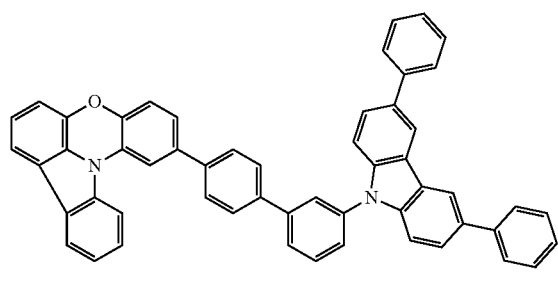
C94
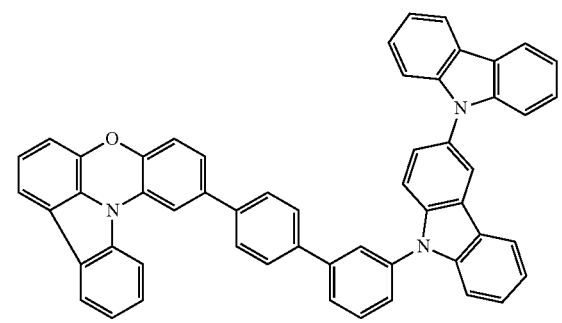

-continued
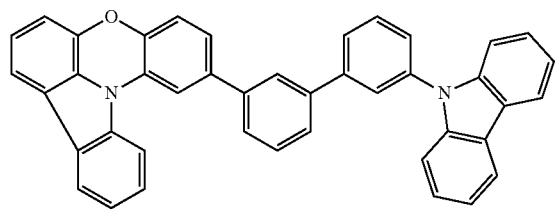
C95
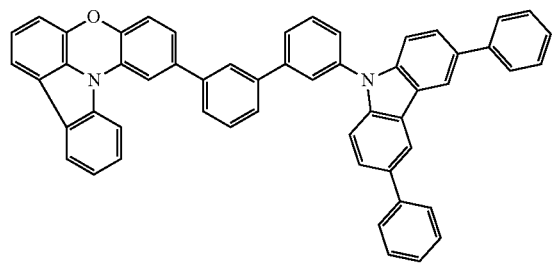
C96
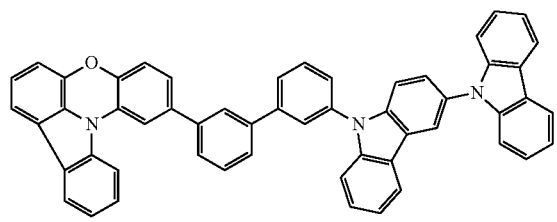
C97
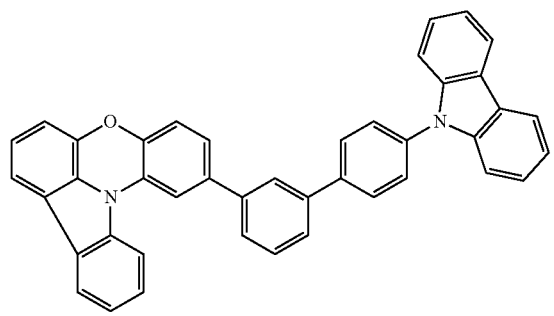
C98
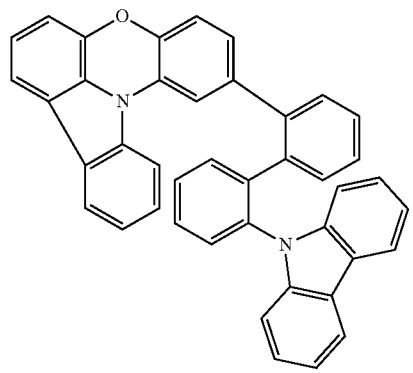
C99
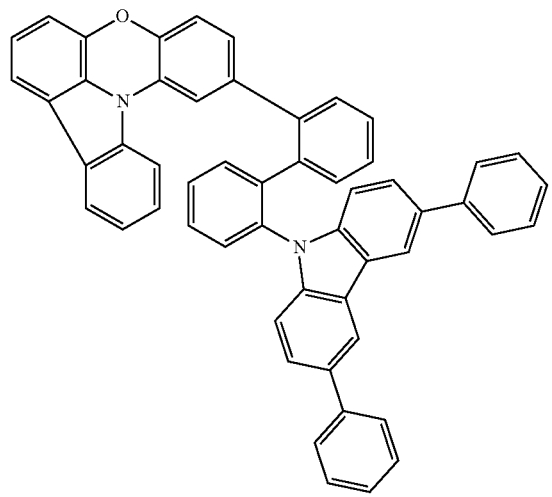
C100
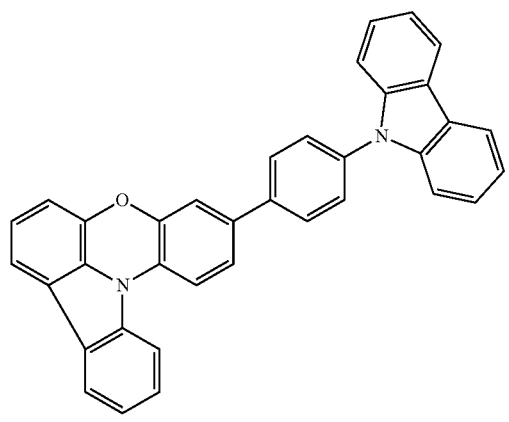
C101
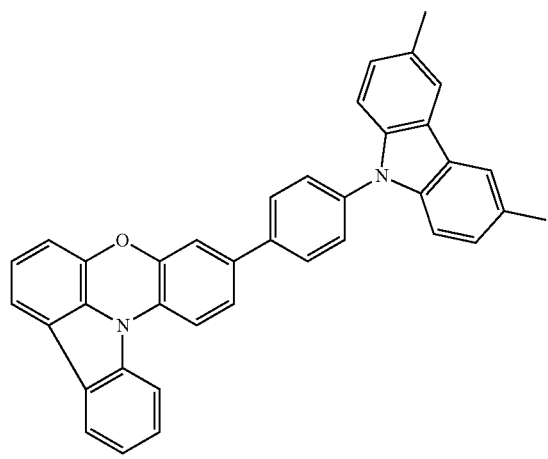
C102

-continued
C103
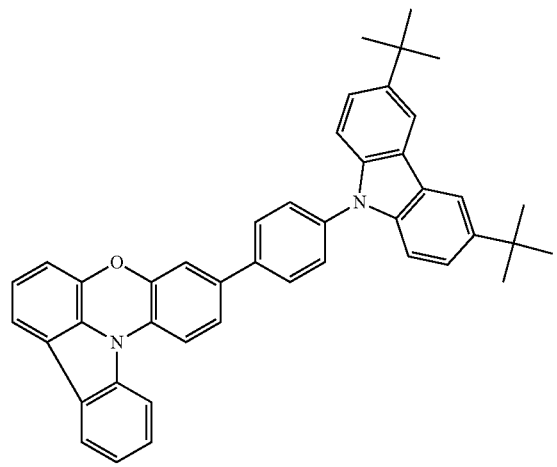
C104
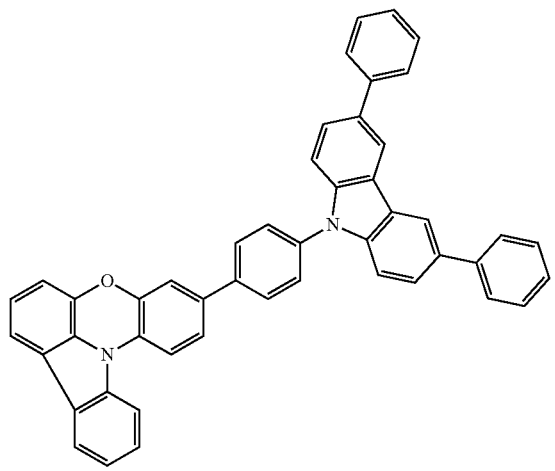
C105
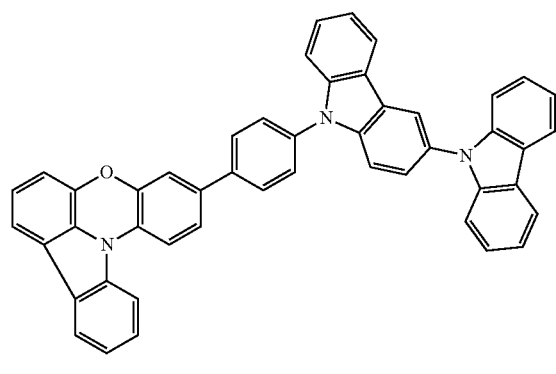
C106
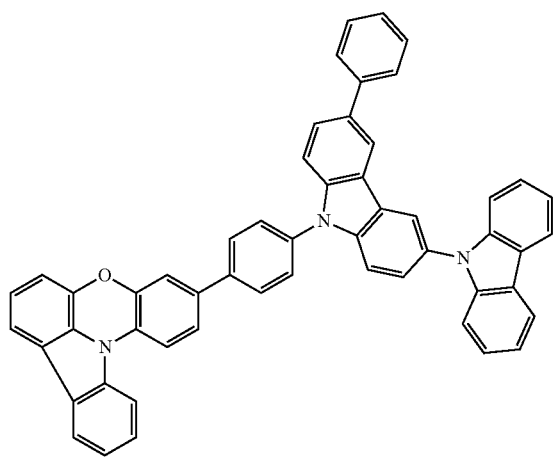
C107
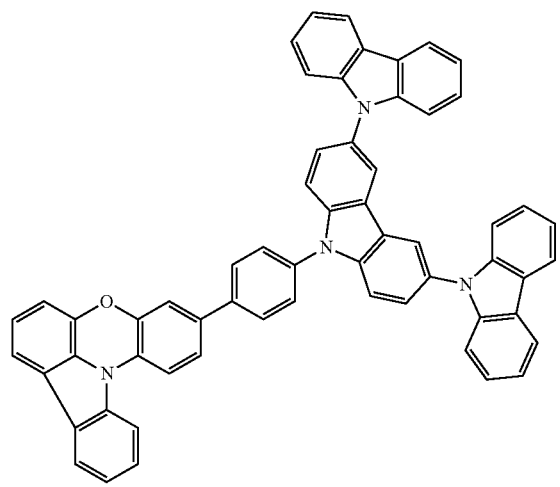
C108
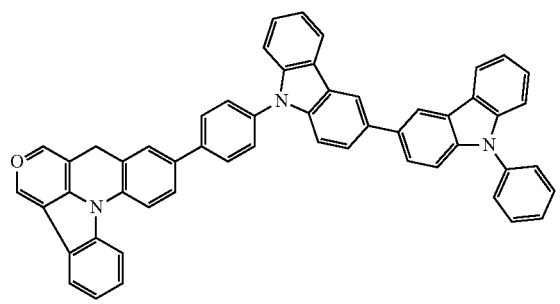

C109
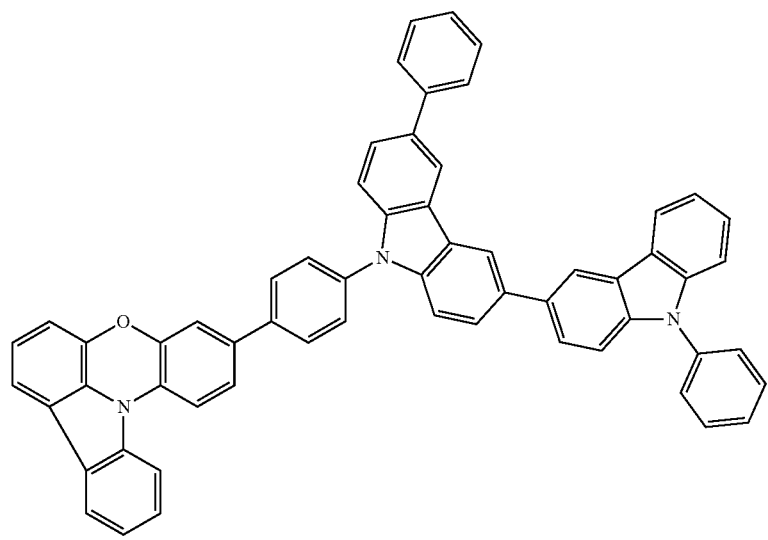
C110
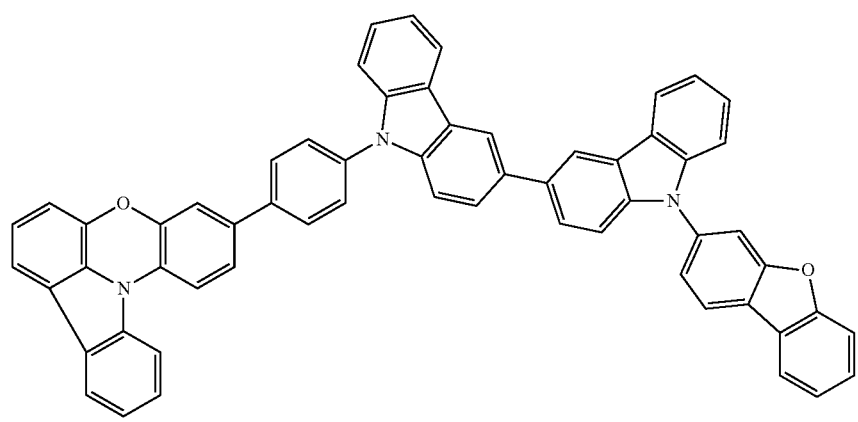
C111
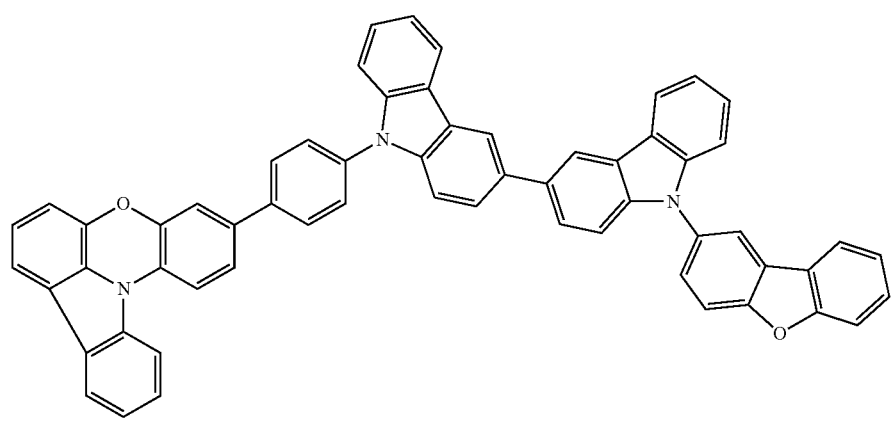

-continued
C112
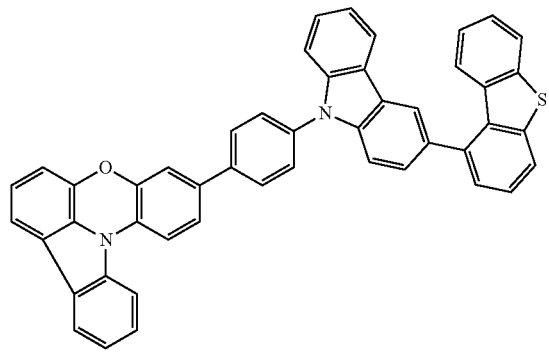
C113
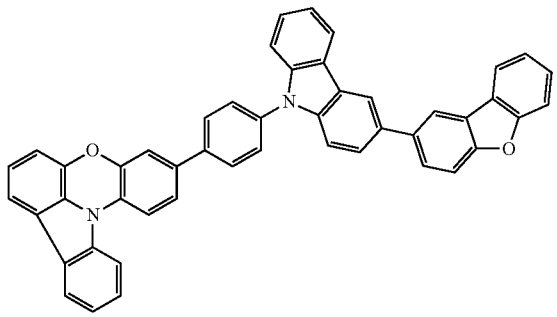
C114
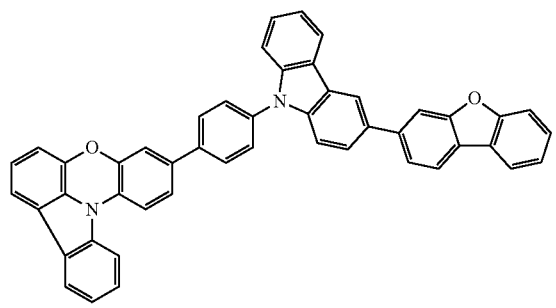
C115
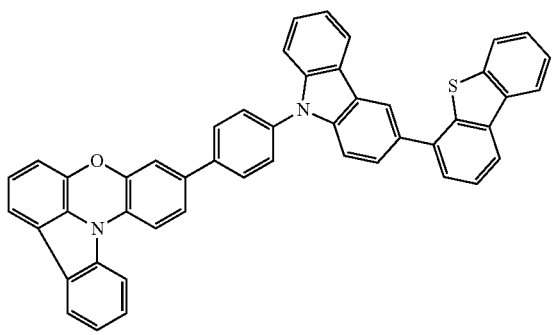
C116
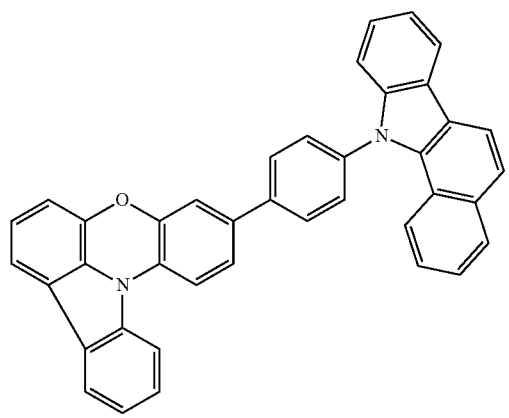
C117
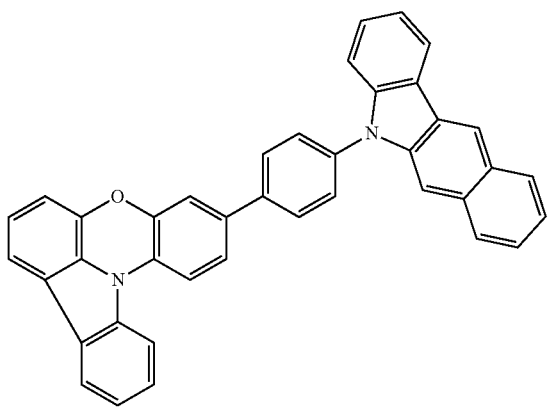
C118
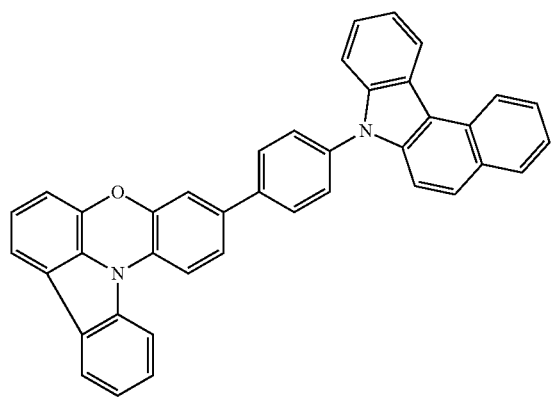
C119
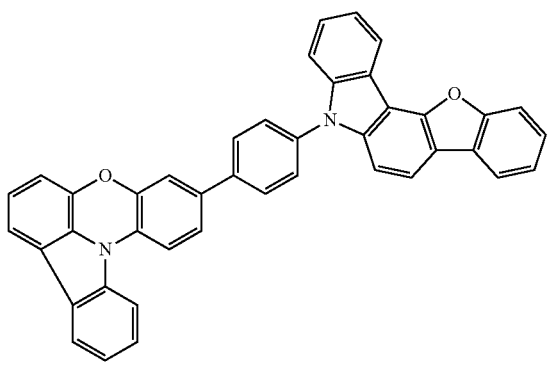

-continued
C120
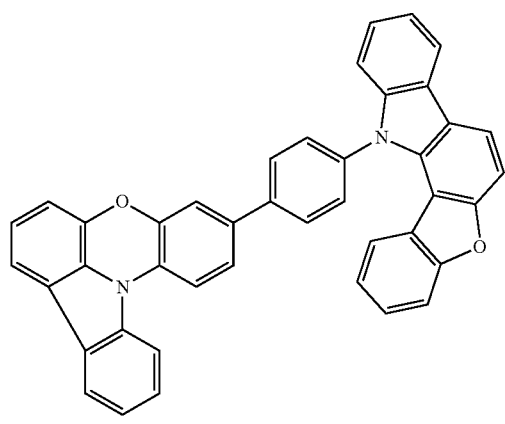
C121
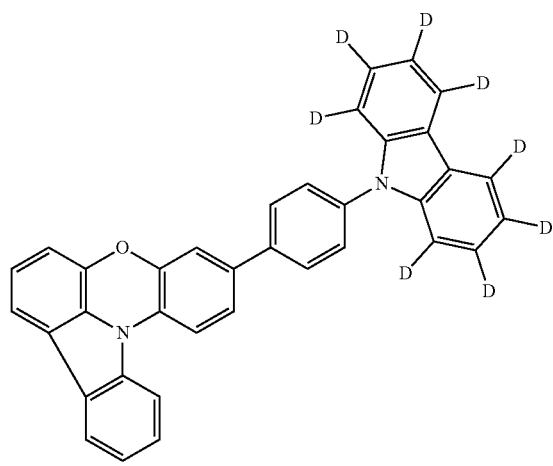
C122
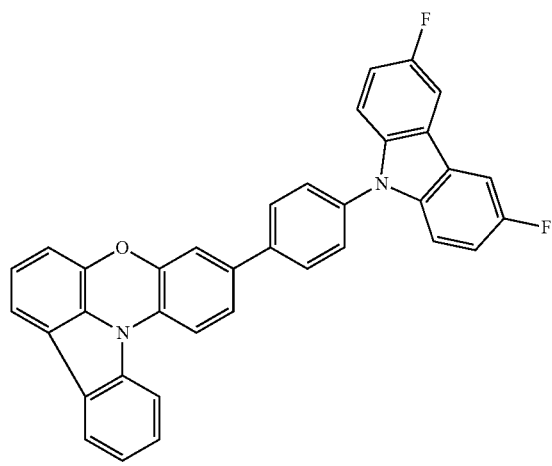
C123
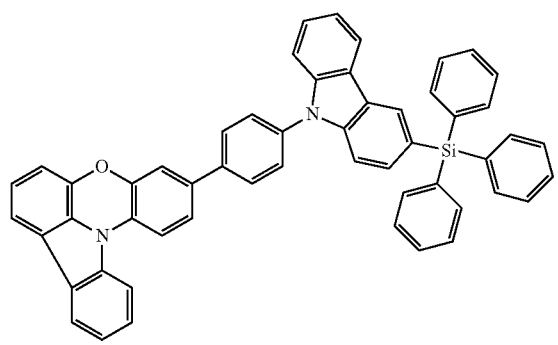
C124
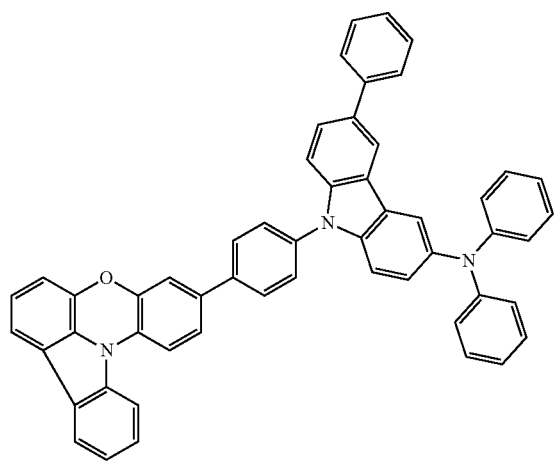
C125
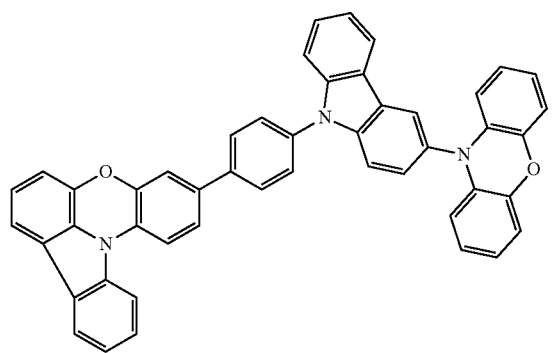

-continued
C126
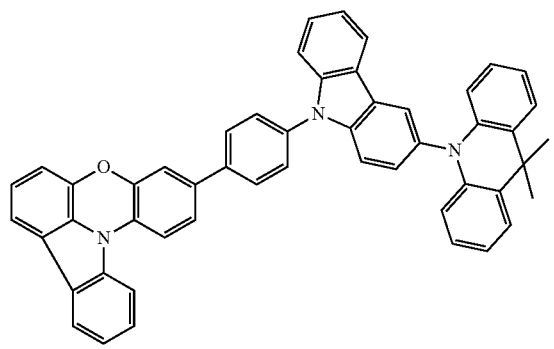
C127
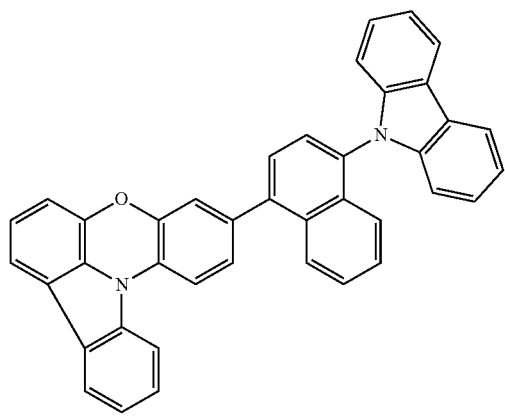
C128
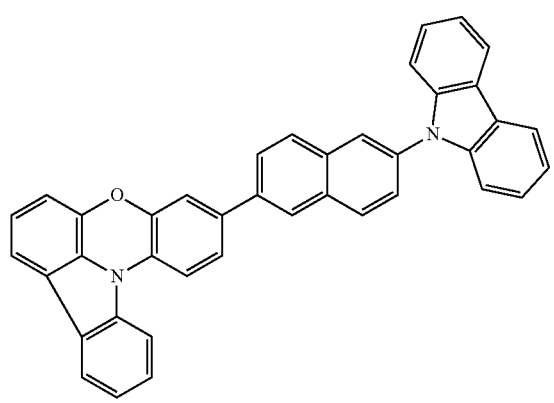
C129
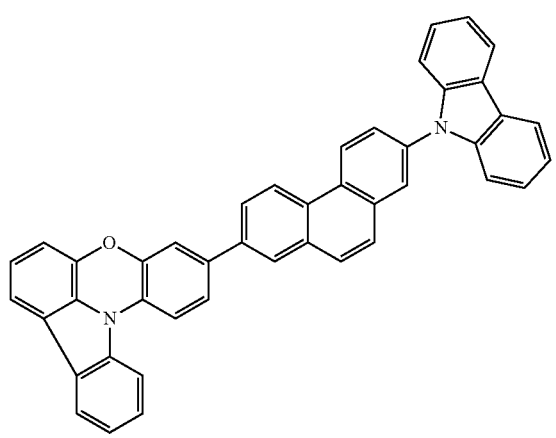
C130
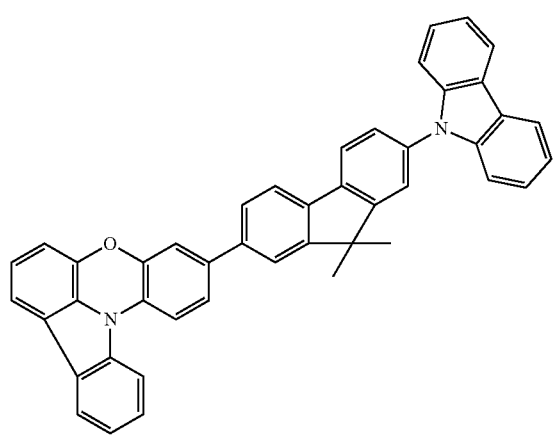
C131
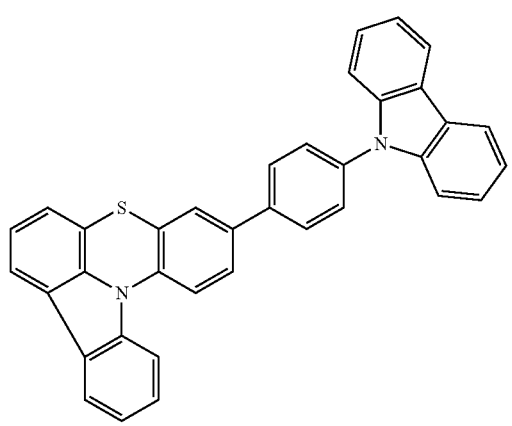

-continued
C132
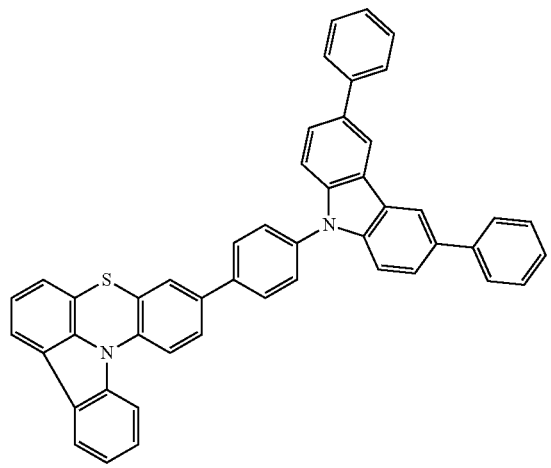
C133
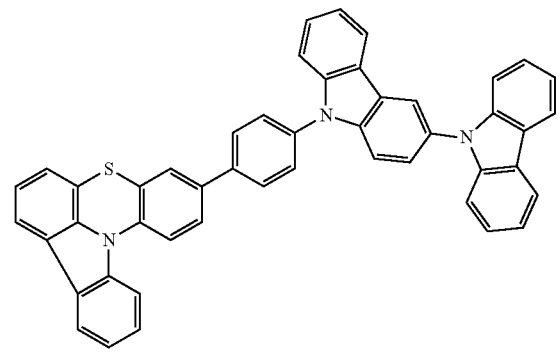
C134
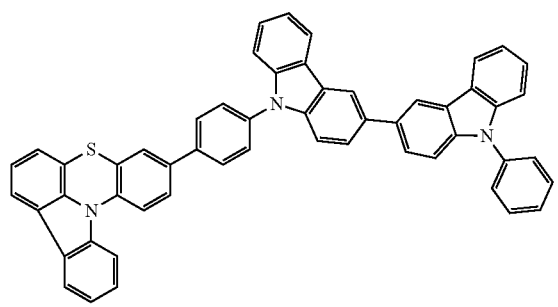
C135
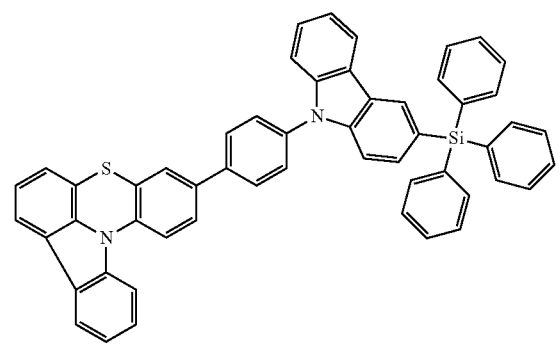
C136
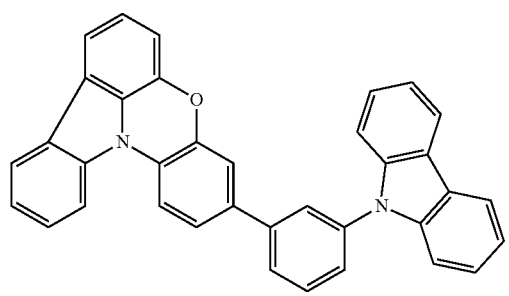
C137
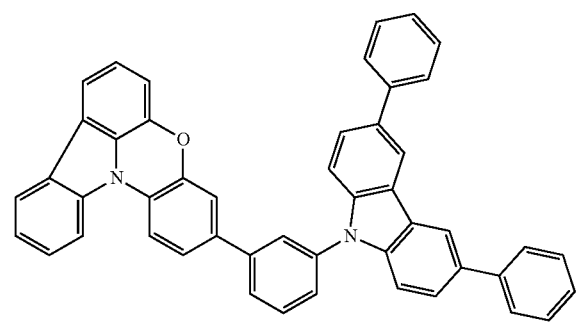

-continued
C138
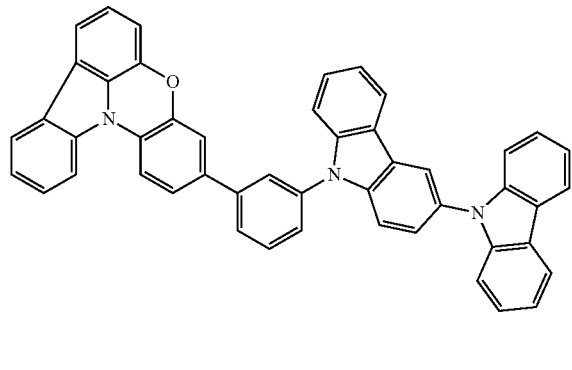
C139
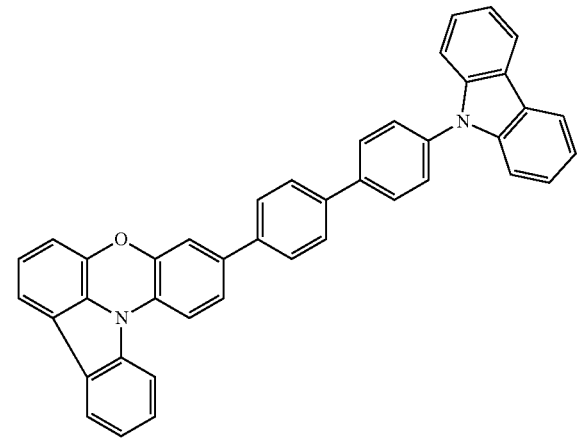
C140
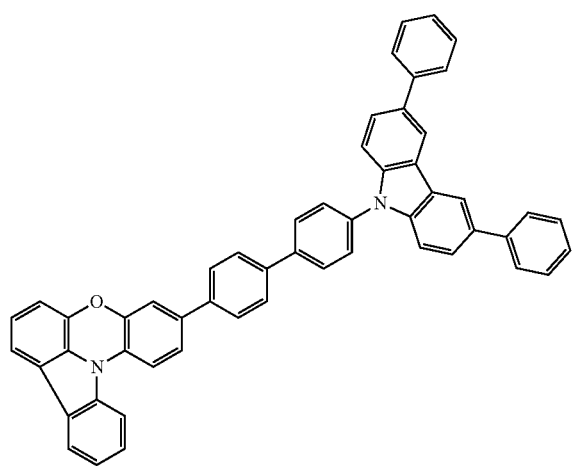
C141
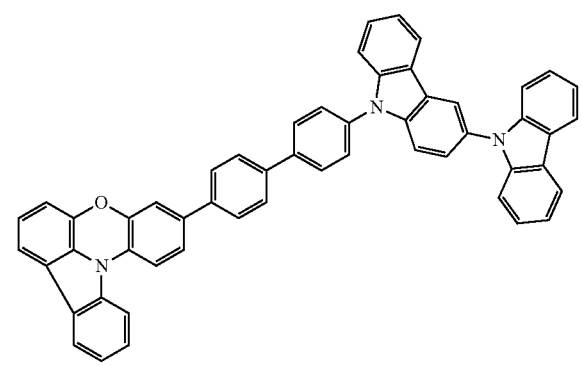
C142
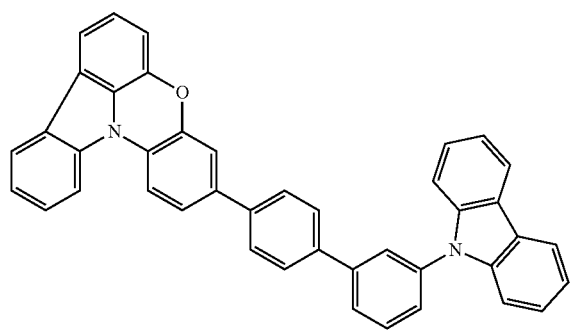
C143
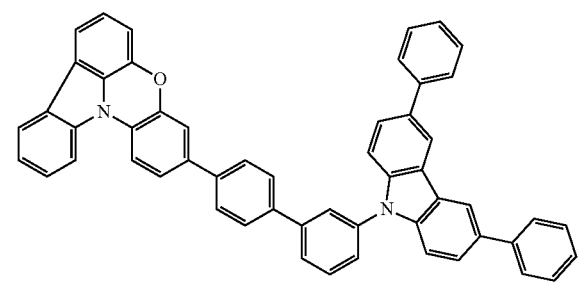
C144
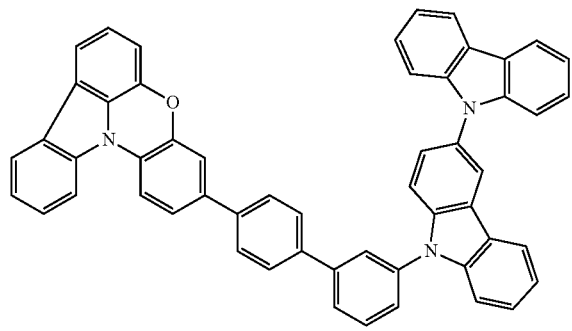
C145
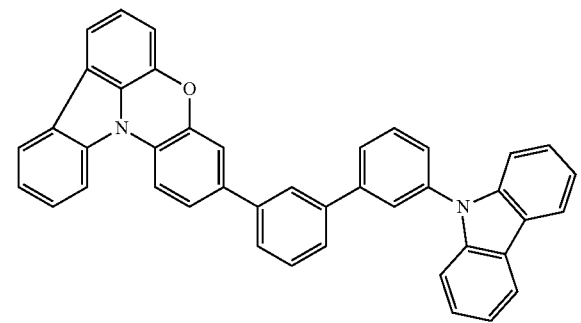

-continued
C146
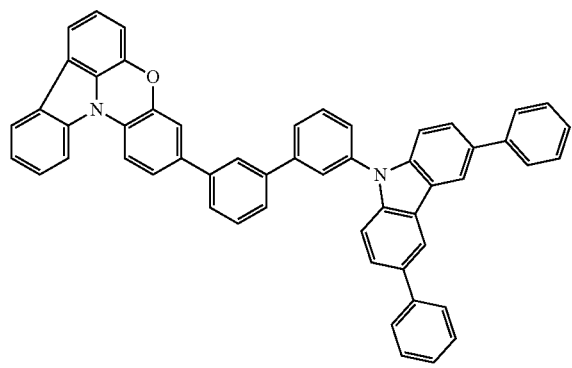
C147
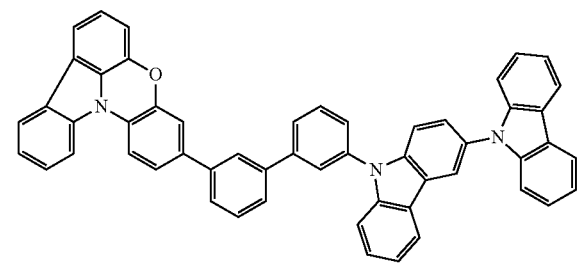
C148
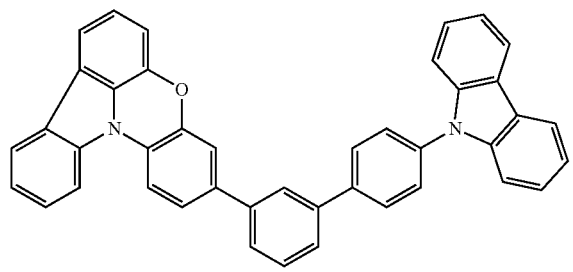
C149
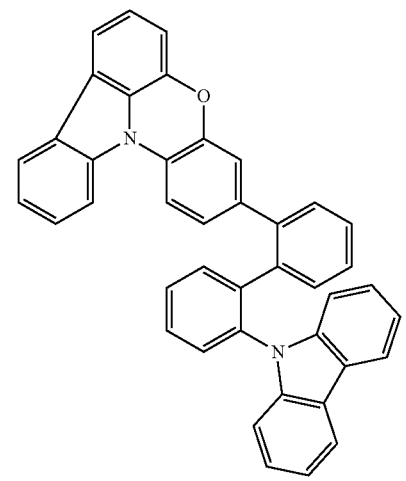
C150
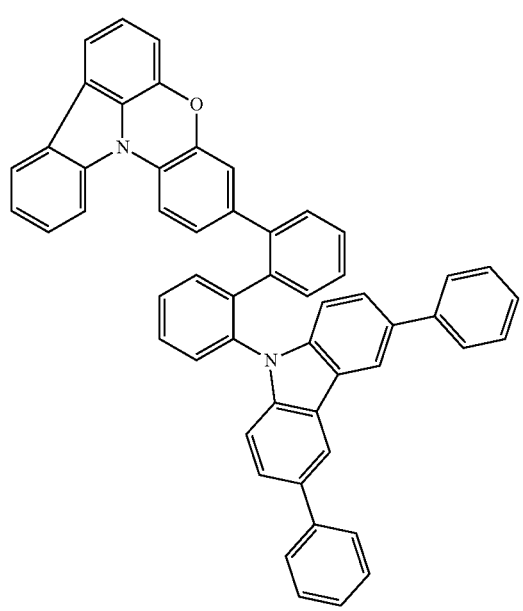
C151
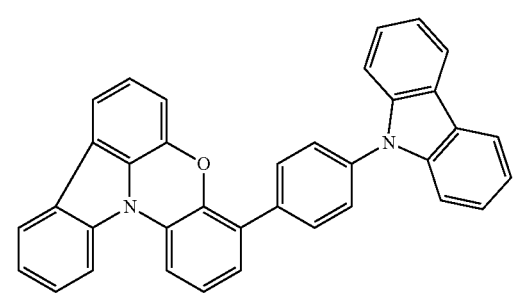

-continued
C152
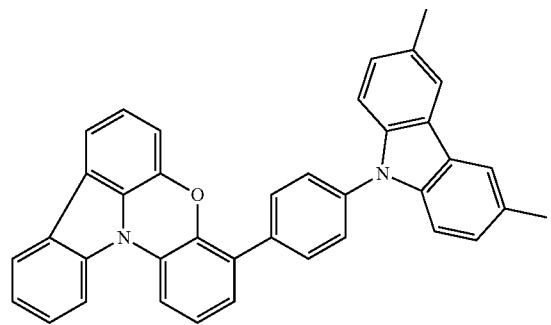
C153
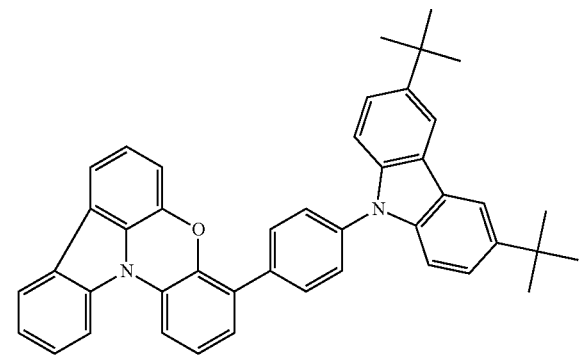
C154
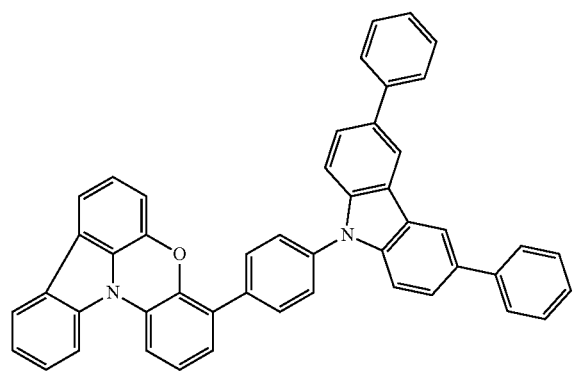
C155
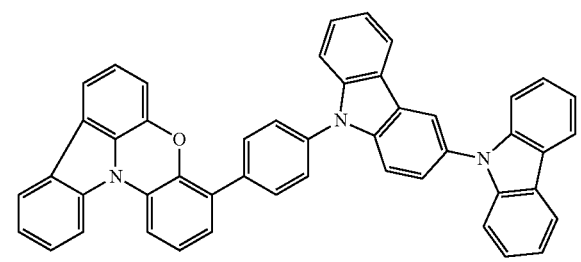
C156
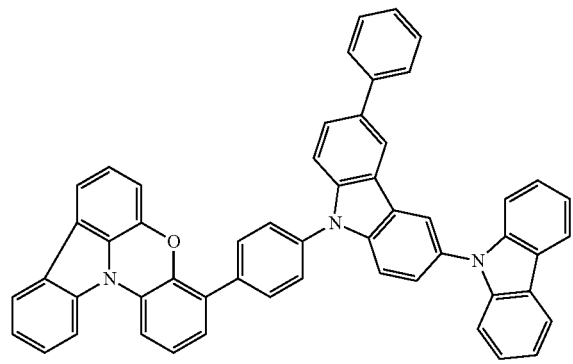
C157
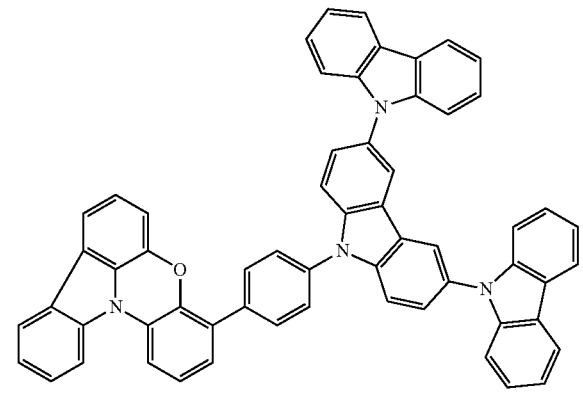
C158
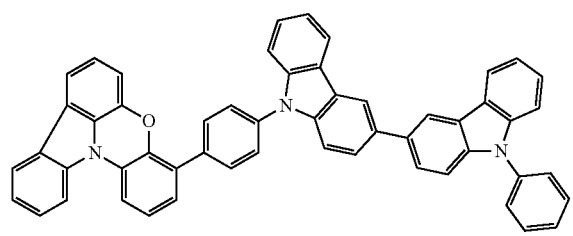
C159
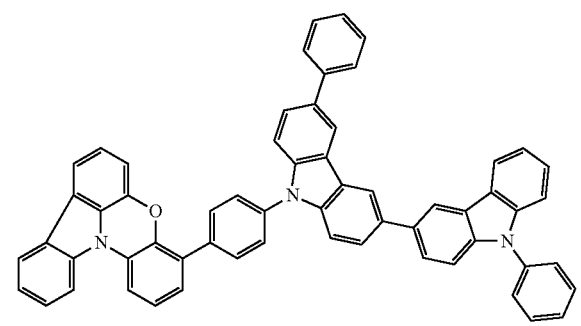

-continued
C160
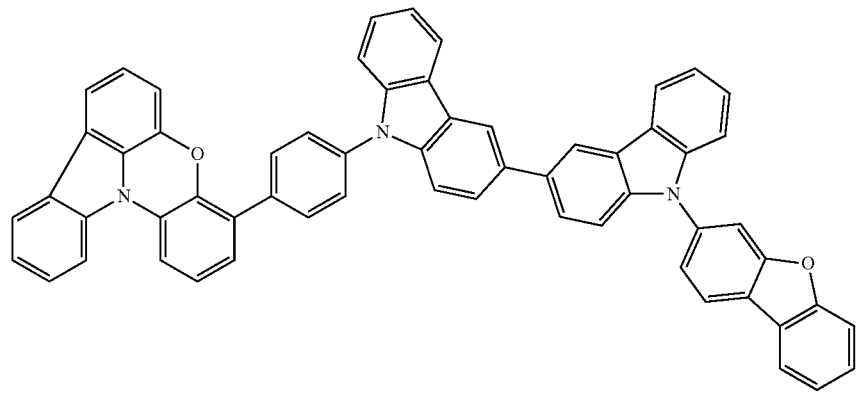
C161
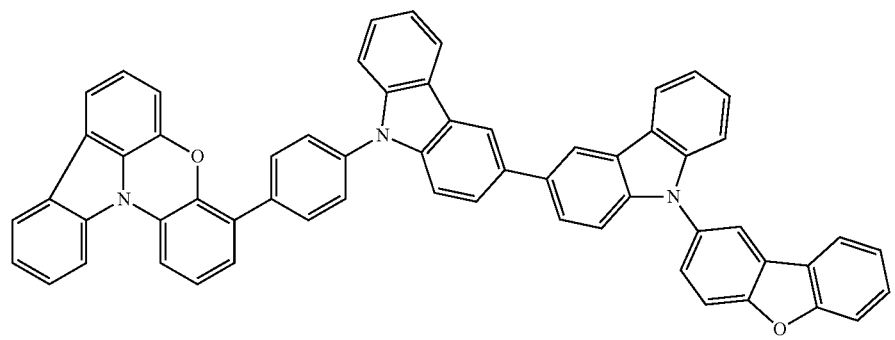
C162
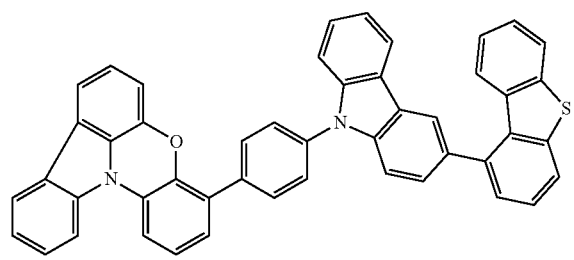
C163
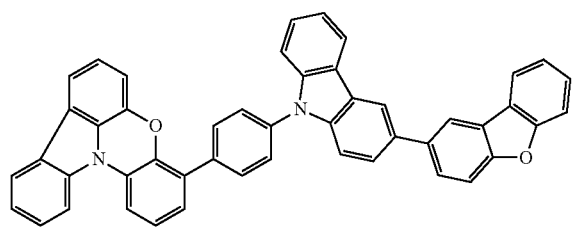
C164
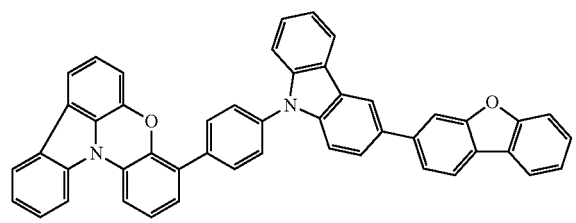
C165
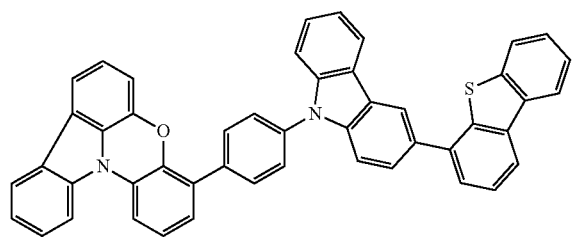
C166
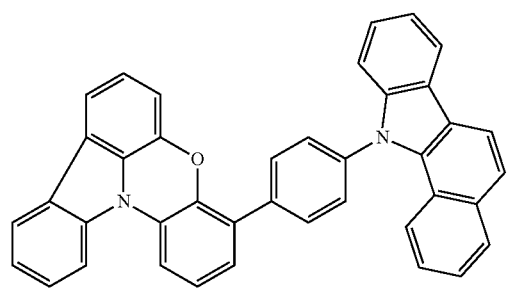
C167
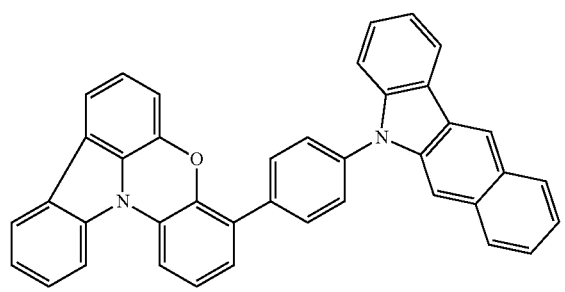

-continued
C168
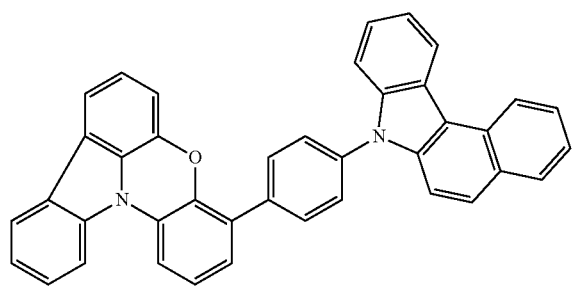
C169
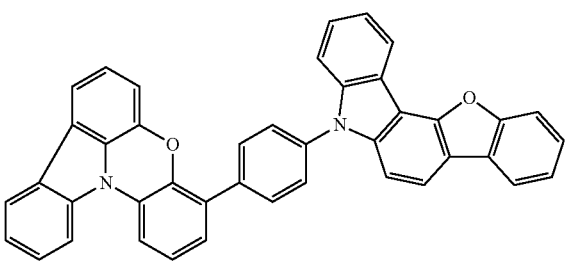
C170
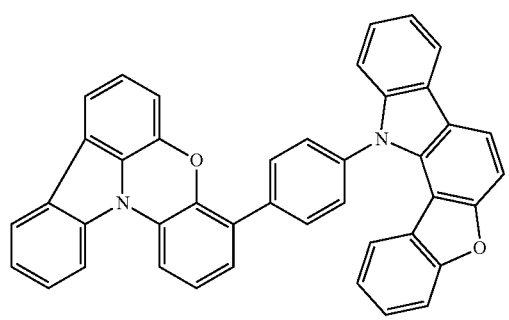
C171
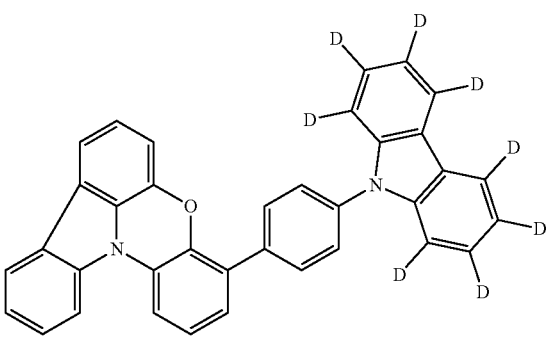
C172
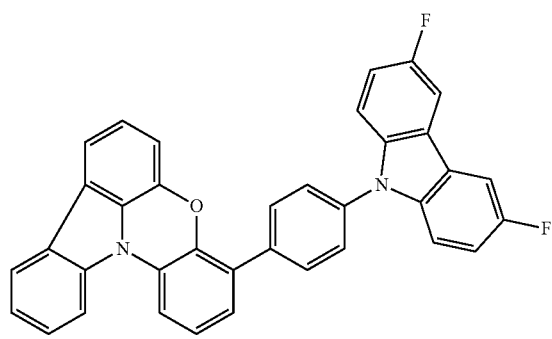
C173
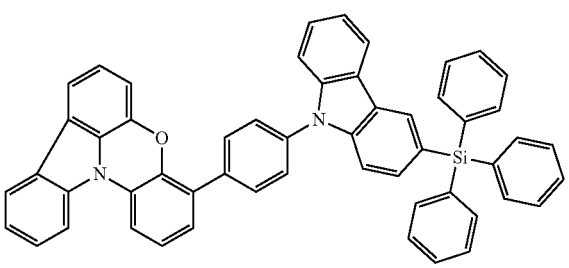
C174
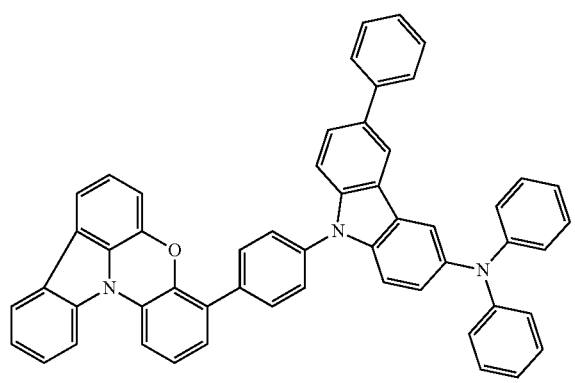
C175
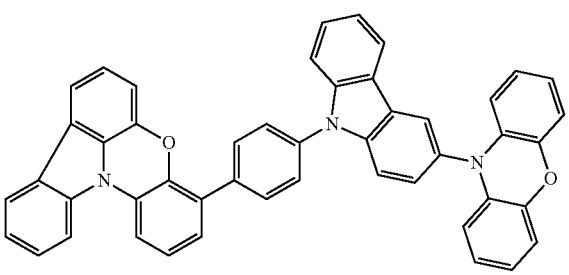

-continued
C176
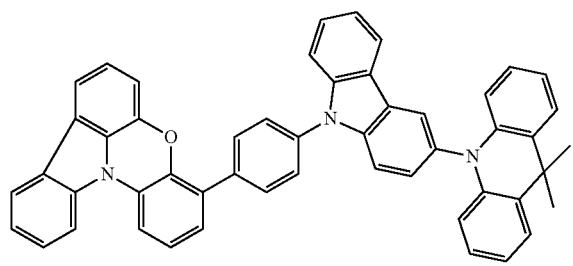
C177
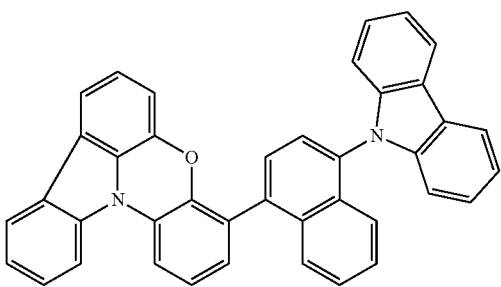
C178
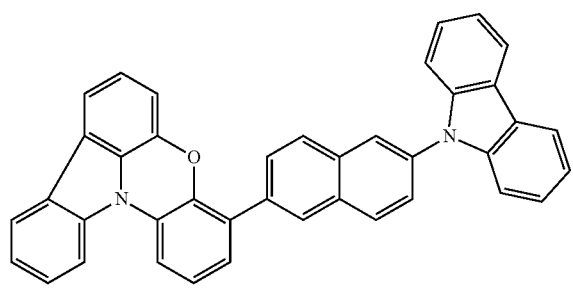
C179
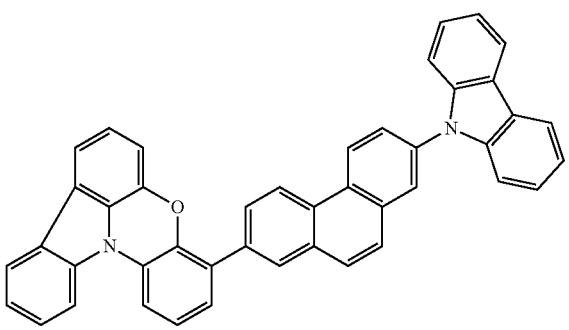
C180
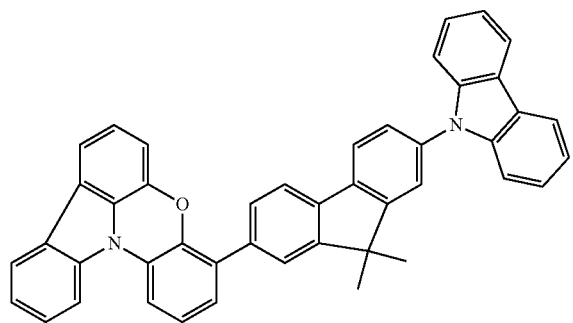
C181
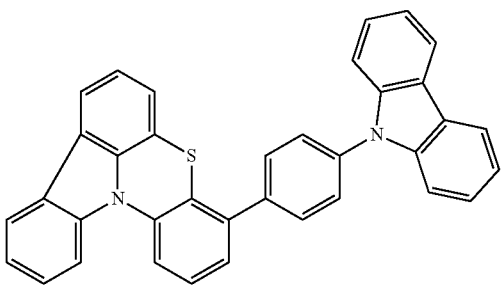
C182
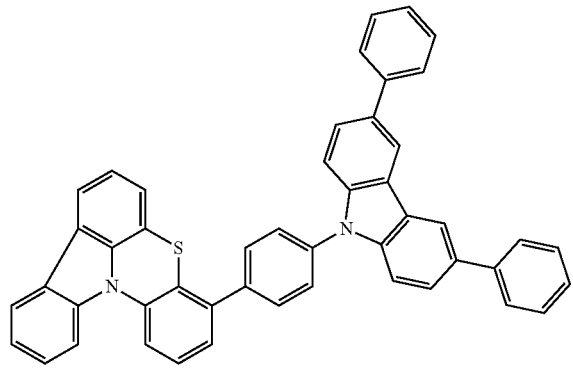
C183
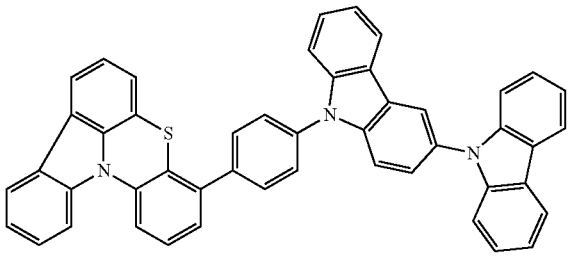

-continued
C184
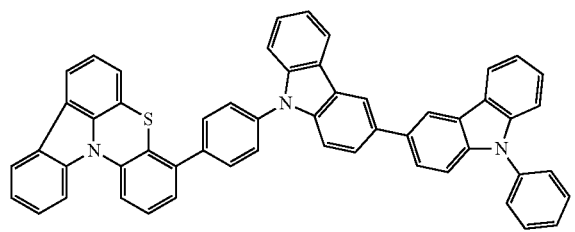
C185
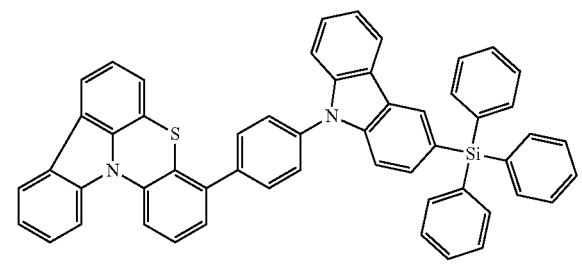
C186
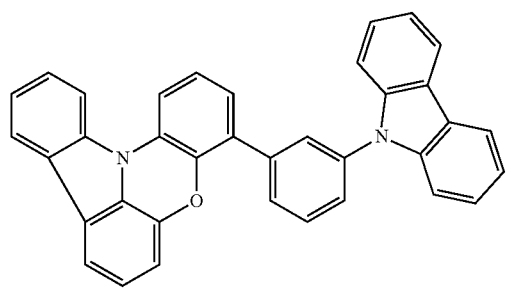
C187
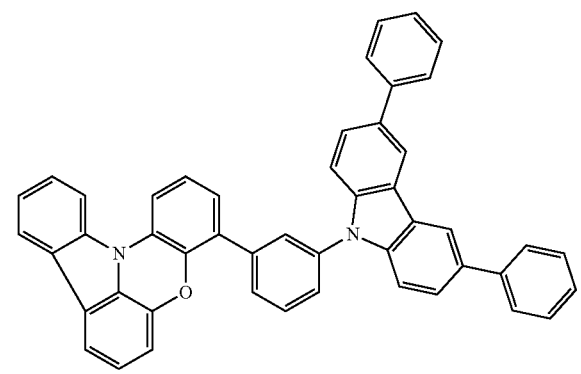
C188
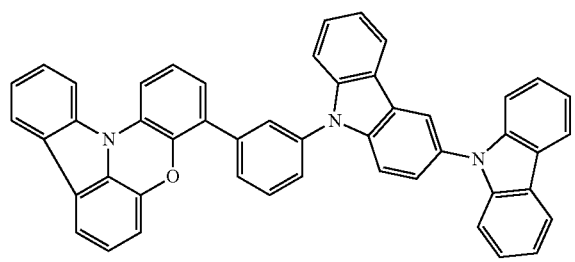
C189
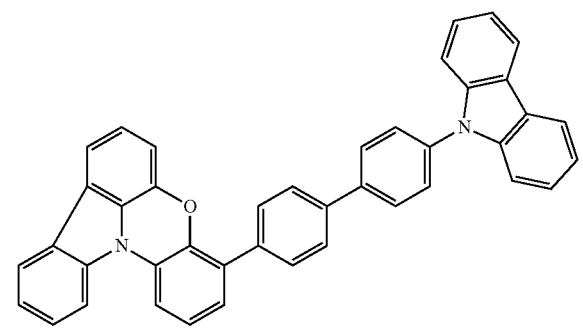
C190
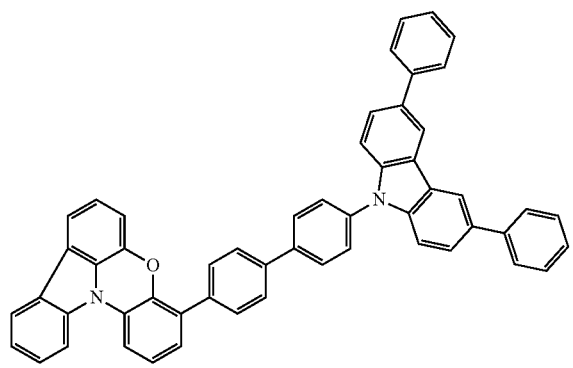
C191
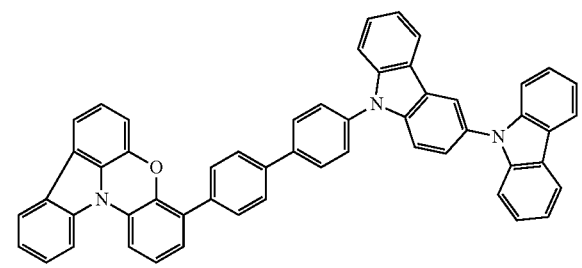

-continued
C192
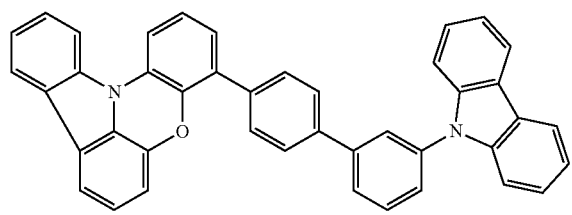
C193
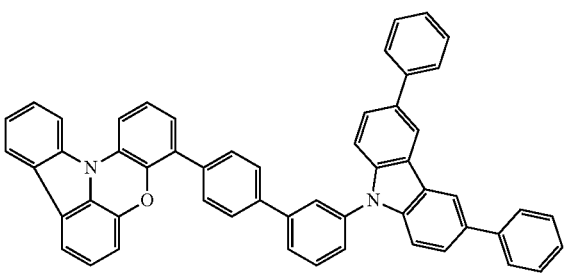
C194
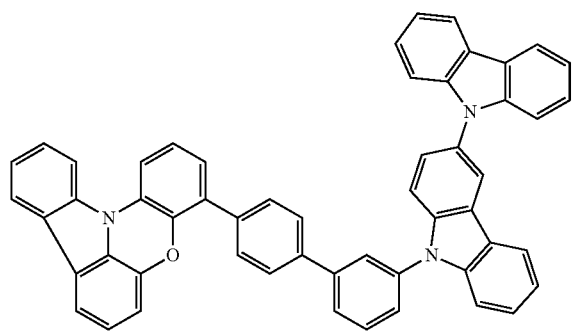
C195
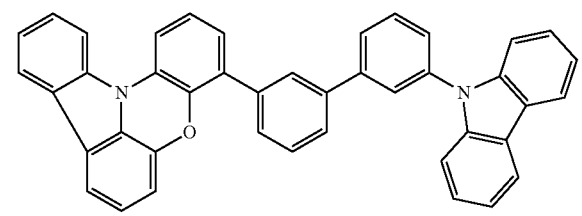
C196
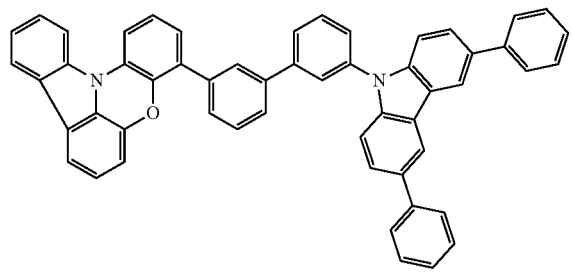
C197
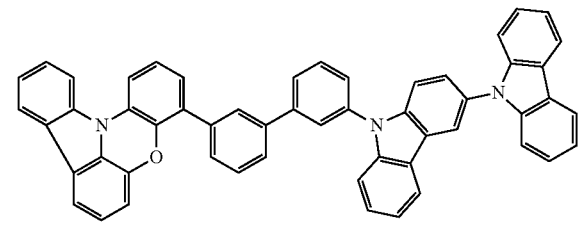
C198
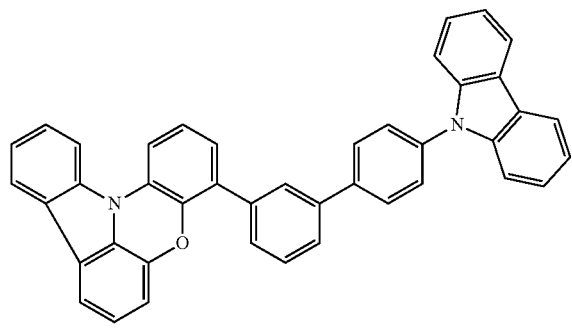
C199
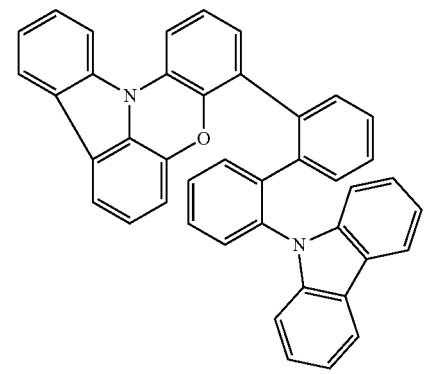

C200
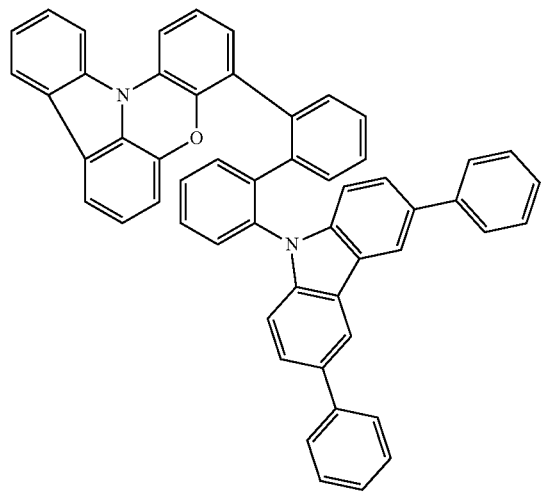
[Compound Group 1D]
D1
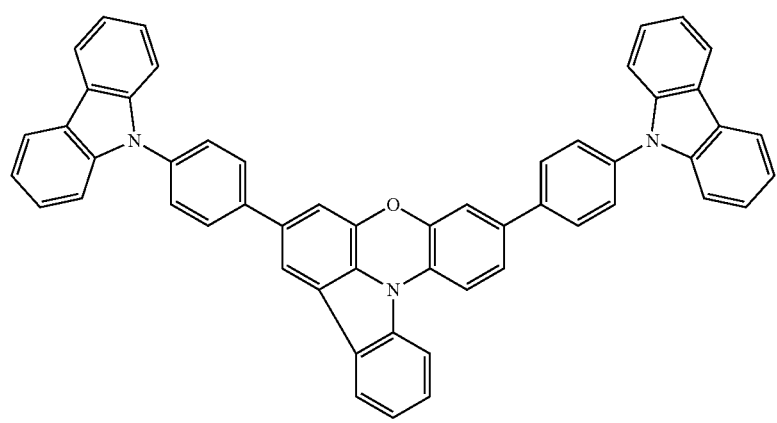
D2
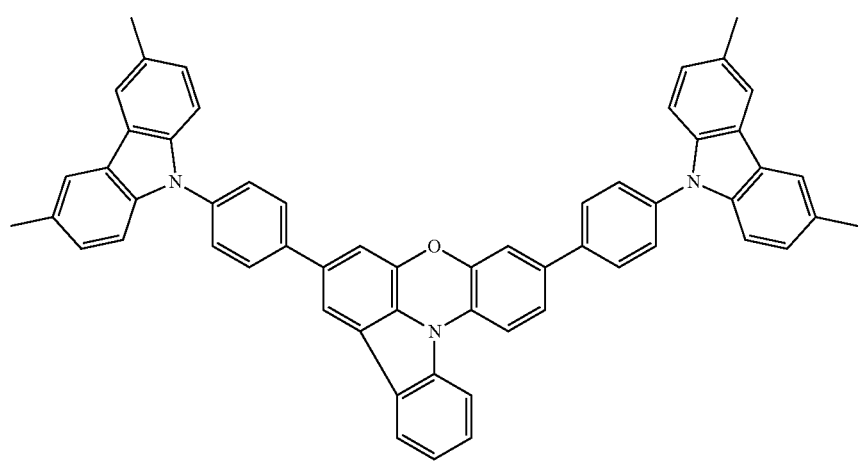

-continued
D3
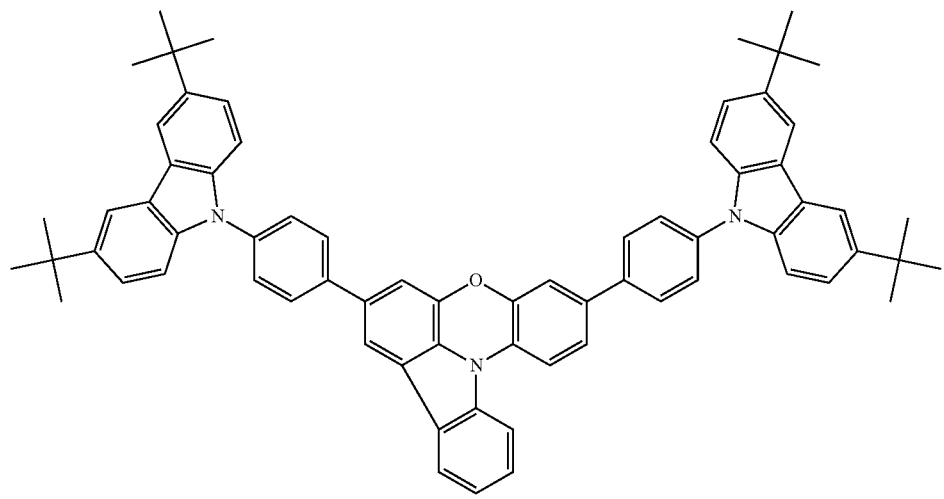
D4
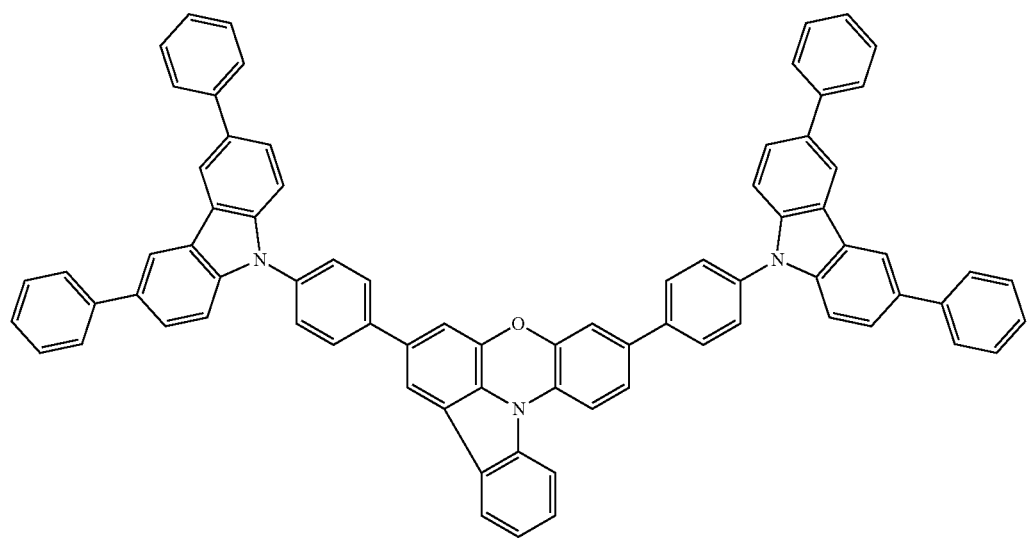
D5 D6
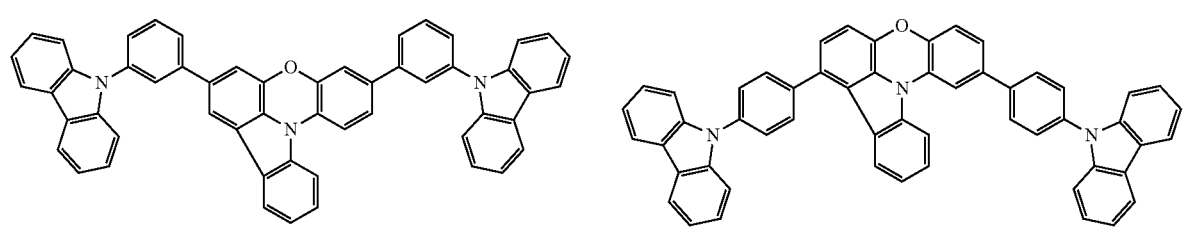
D7
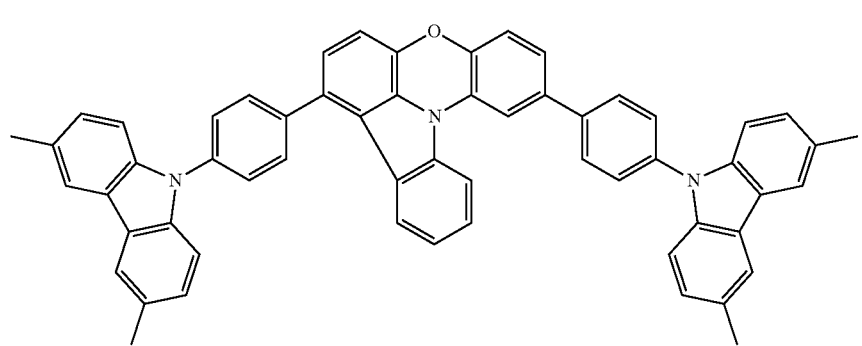

-continued
D8
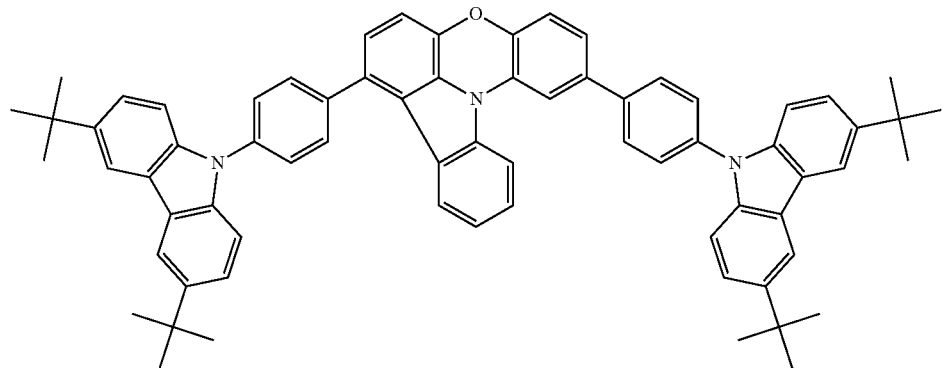
D9
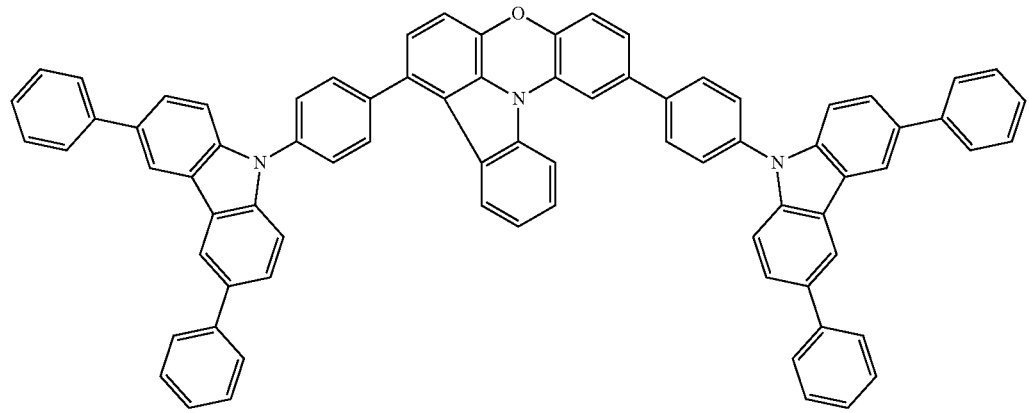
D10 D11
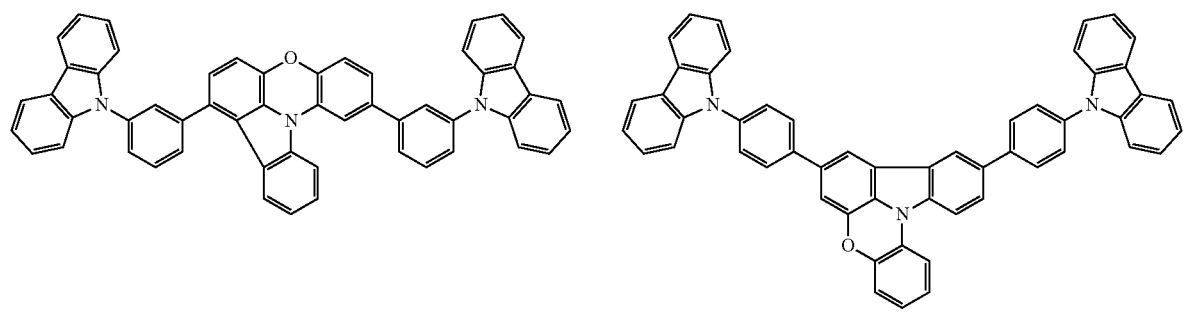
D12
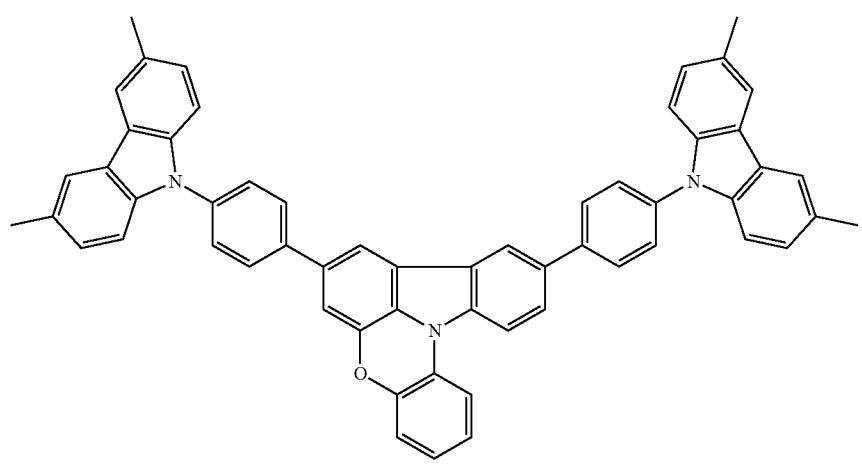

-continued
D13
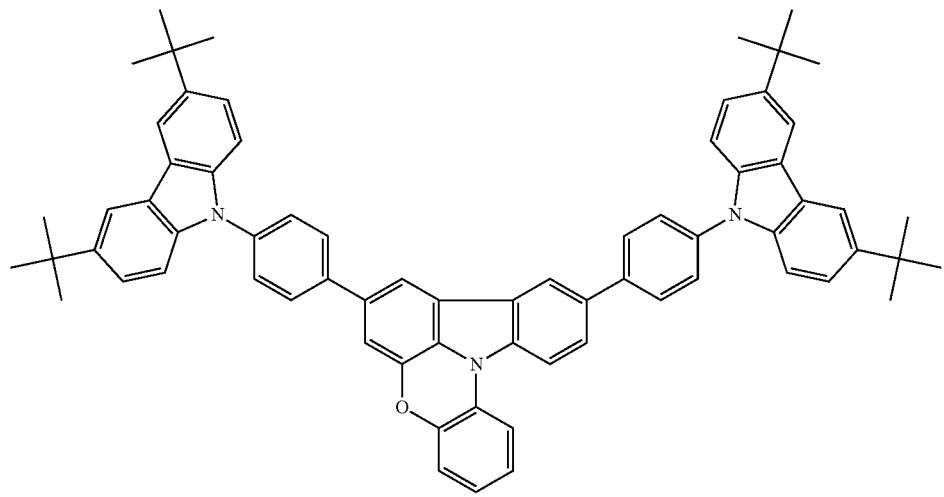
D14
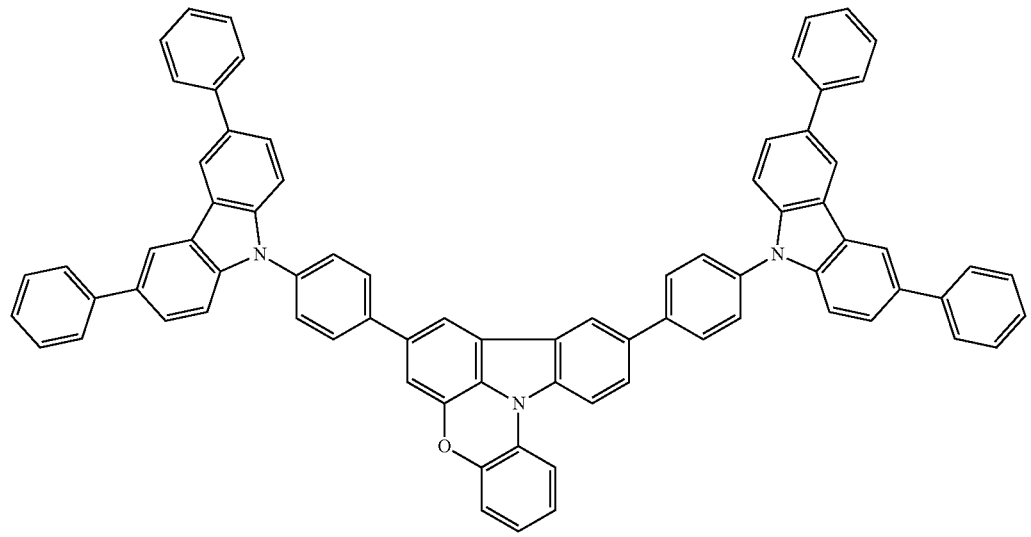
D15 D16
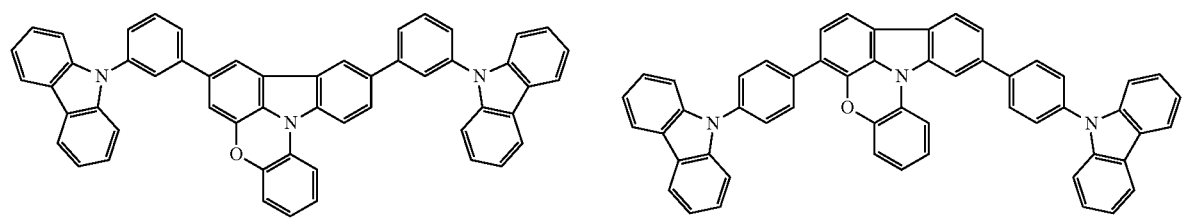
D17
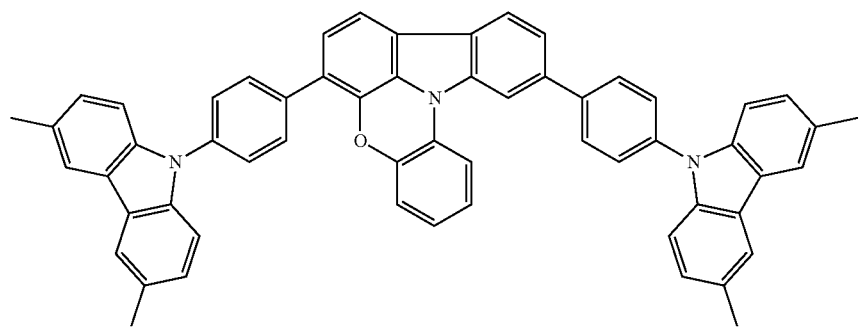

D18
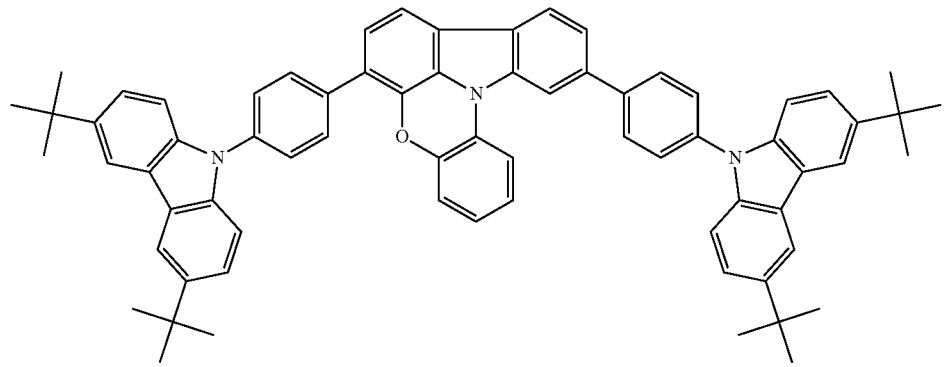
D19
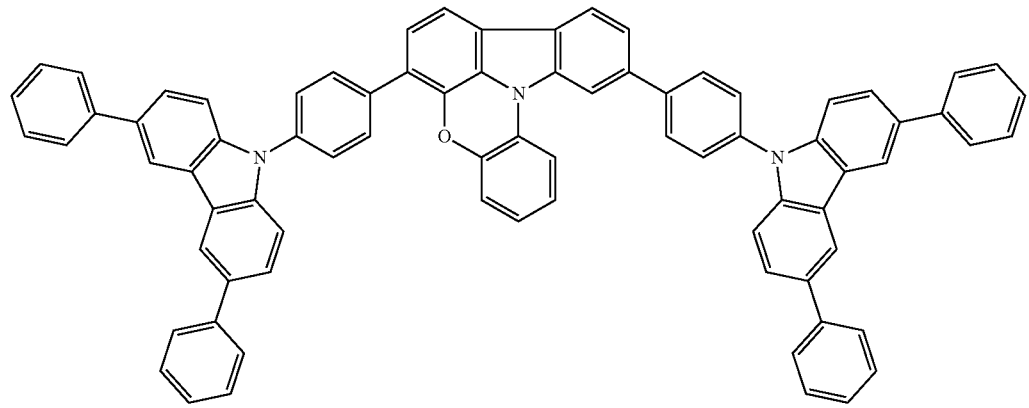
D20 D21
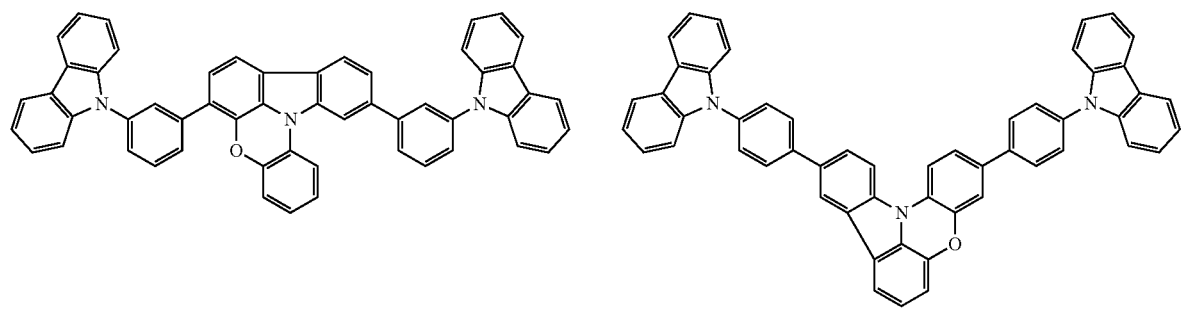
D22
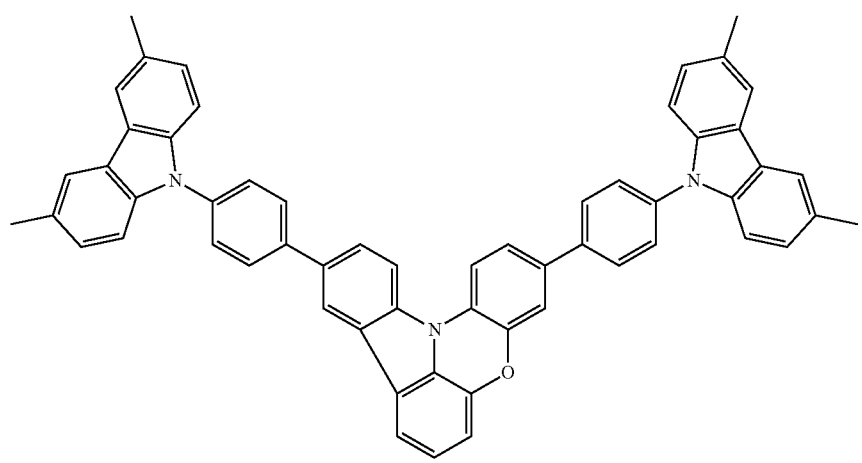

-continued
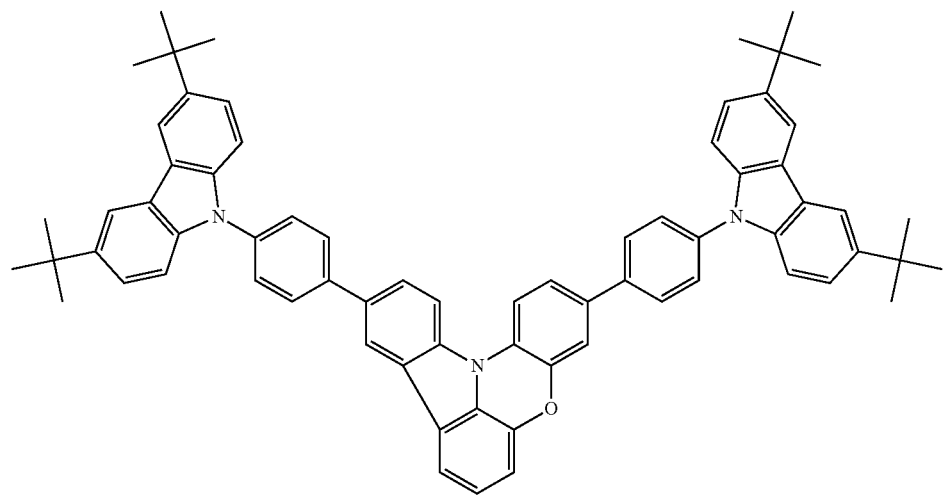
D23
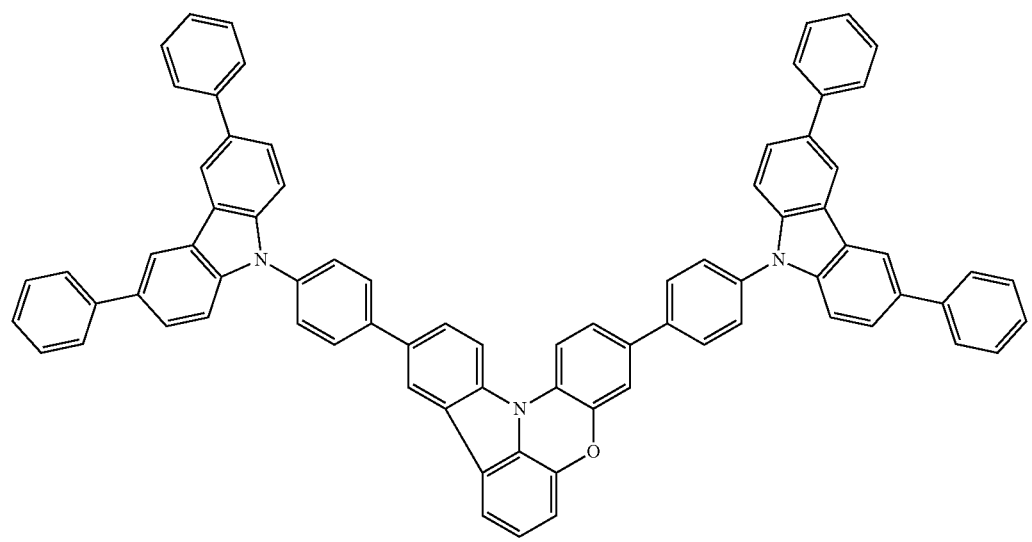
D24
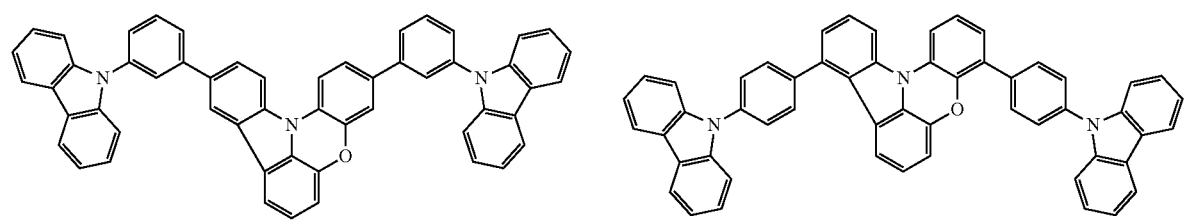
D25  D26
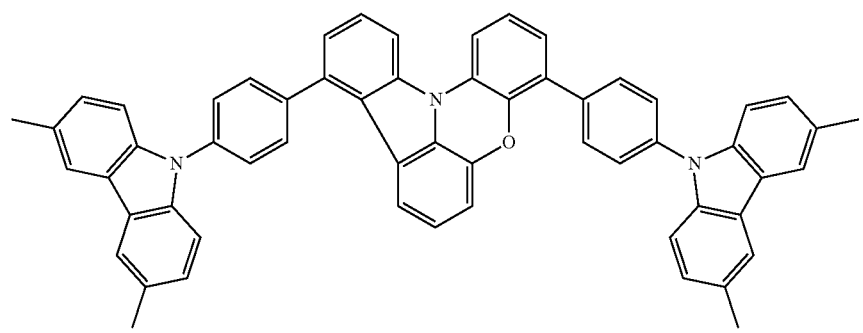
D27

-continued

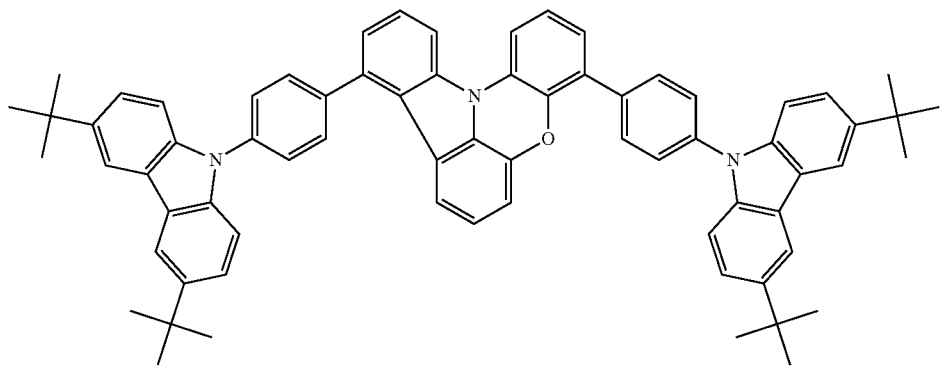
D28

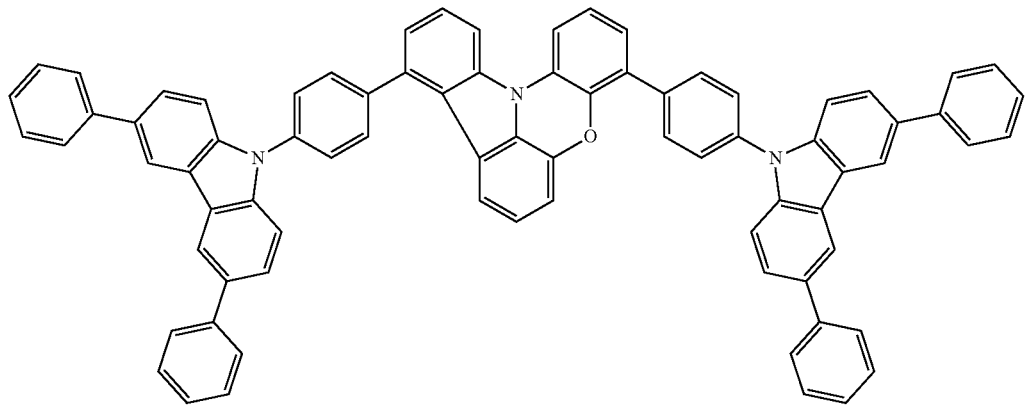
D29

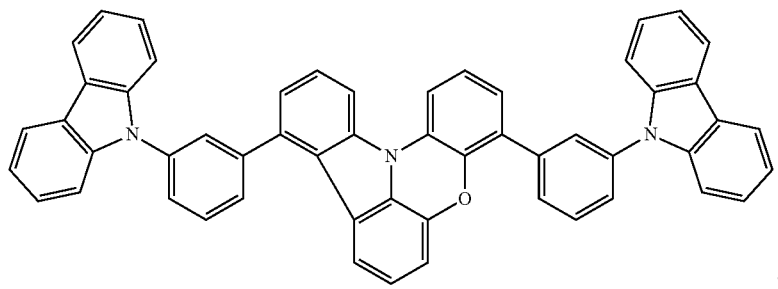
D30

The polycyclic compound of an embodiment represented by Formula 1 has a structure in which one or more substituted or unsubstituted carbazole groups are bonded to an indolo phenoxazine group or an indolo phenothiazine group. In an embodiment, the polycyclic compound represented by Formula 1 may have a structure in which one or more substituted or unsubstituted carbazole groups are bonded to an indolo phenoxazine group. In another embodiment, the polycyclic compound represented by Formula 1 may have a structure in which one or more substituted or unsubstituted carbazole groups are bonded to an indolo phenothiazine group.

By having a molecular structure in which a nitrogen atom at position 9 of a carbazole group is bonded to an indolo phenoxazine group or an indolo phenothiazine group, the polycyclic compound of an embodiment may improve the life and efficiency of a light emitting device.

The polycyclic compound according to an embodiment represented by Formula 1 has excellent hole transport capacity, and the molecular structure of the polycyclic compound may increase by including one or more substituted or unsubstituted carbazole groups. Accordingly, the deposition temperature of the polycyclic compound may be reduced, and the stability of the polycyclic compound material may be improved.

The light emitting device ED of an embodiment may further include a material of a hole transport region explained below in addition to the polycyclic compound of an embodiment.

The hole transport region HTR may include a compound represented by Formula H-1 below.

[Formula H-1]

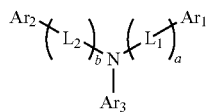

In Formula H-1 above, $L_1$ and $L_2$ may each independently be a direct linkage, a substituted or unsubstituted arylene group of 6 to 30 ring-forming carbon atoms, or a substituted or unsubstituted heteroarylene group of 2 to 30 ring-forming carbon atoms. In Formula H-1, a and b may each independently be an integer from 0 to 10. If a or b is 2 or more, multiple $L_1$ groups and multiple $L_2$ groups may each independently be a substituted or unsubstituted arylene group of 6 to 30 ring-forming carbon atoms, or a substituted or unsubstituted heteroarylene group of 2 to 30 ring-forming carbon atoms.

In Formula H-1, $Ar_1$ and $Ar_2$ may each independently be a substituted or unsubstituted aryl group of 6 to 30 ring-forming carbon atoms, or a substituted or unsubstituted heteroaryl group of 2 to 30 ring-forming carbon atoms. In Formula H-1, $Ar_3$ may be a substituted or unsubstituted aryl group of 6 to 30 ring-forming carbon atoms, or a substituted or unsubstituted heteroaryl group of 2 to 30 ring-forming carbon atoms.

In an embodiment, the compound represented by Formula H-1 may be a monoamine compound. In another embodiment, the compound represented by Formula H-1 may be a diamine compound in which at least one among $Ar_1$ to $Ar_3$ includes an amine group as a substituent. The compound represented by Formula H-1 may be a carbazole-based compound in which at least one of $Ar_1$ to $Ar_3$ includes a substituted or unsubstituted carbazole group, or a fluorene-based compound in which at least one among $Ar_1$ to $Ar_3$ includes a substituted or unsubstituted fluorene group.

The compound represented by Formula H-1 may be any one selected from Compound Group H below. However, the compounds shown in Compound Group H are only examples, and the compound represented by Formula H-1 is not limited to the compounds represented in Compound Group H below.

[Compound Group H]

H-1-1

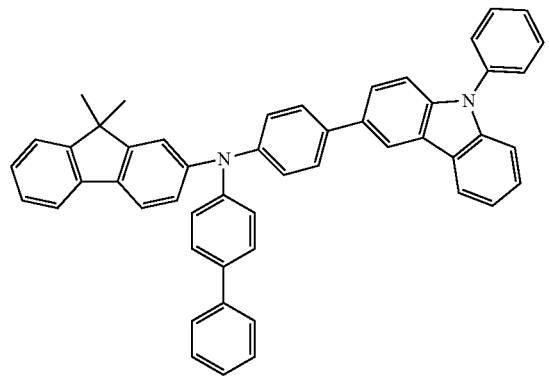

H-1-2

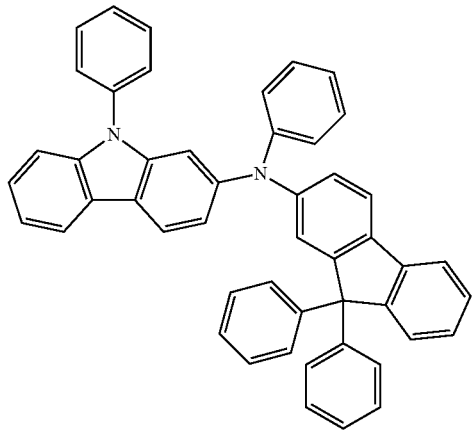

H-1-3

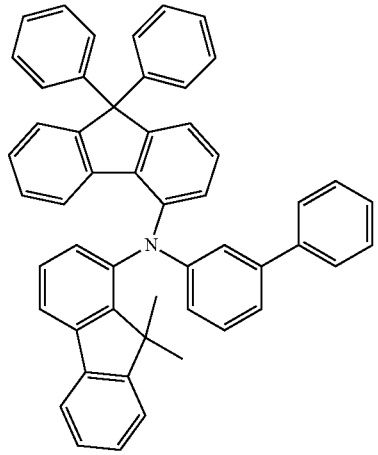

H-1-4

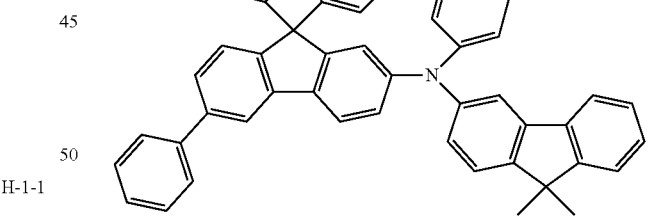

H-1-5

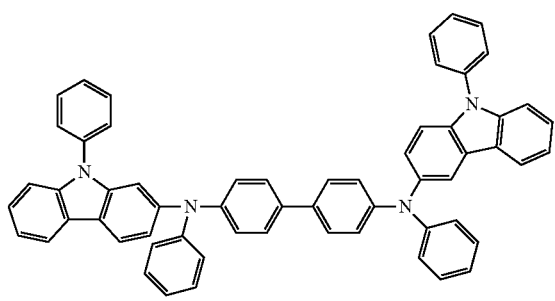

H-1-6
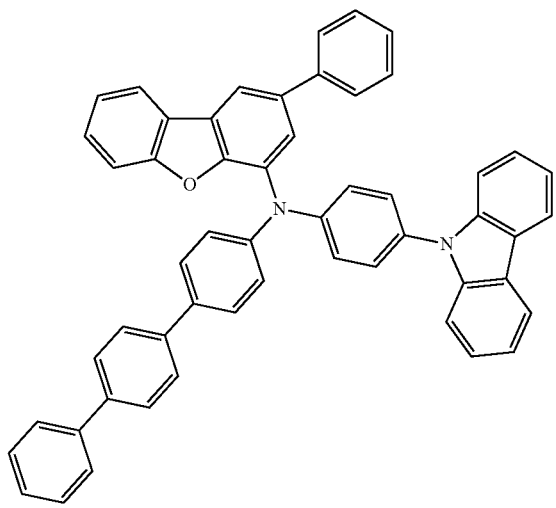
H-1-9
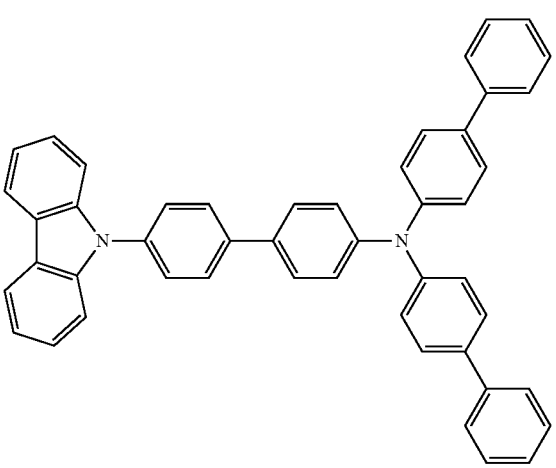
H-1-7
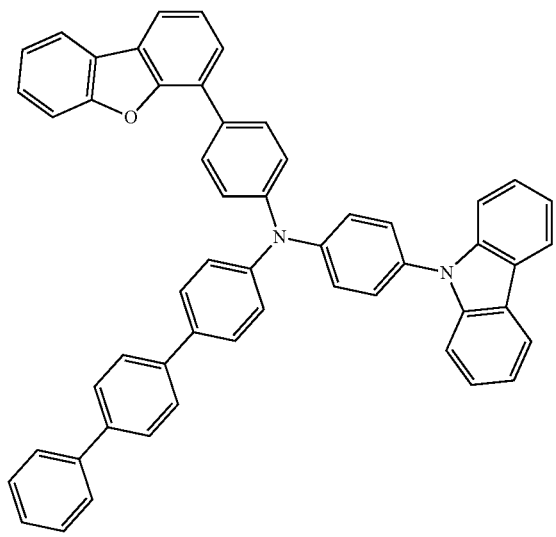
H-1-10
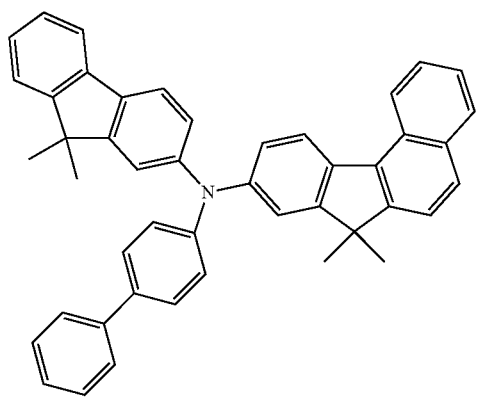
H-1-8
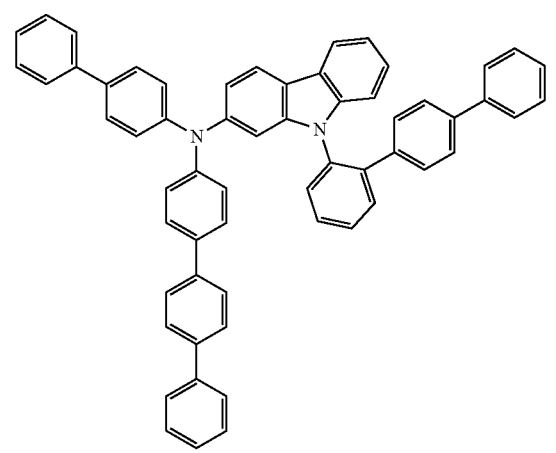
H-1-11
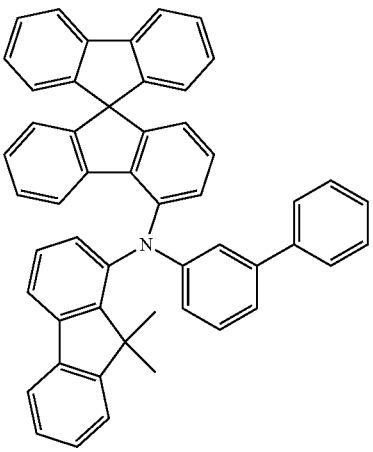

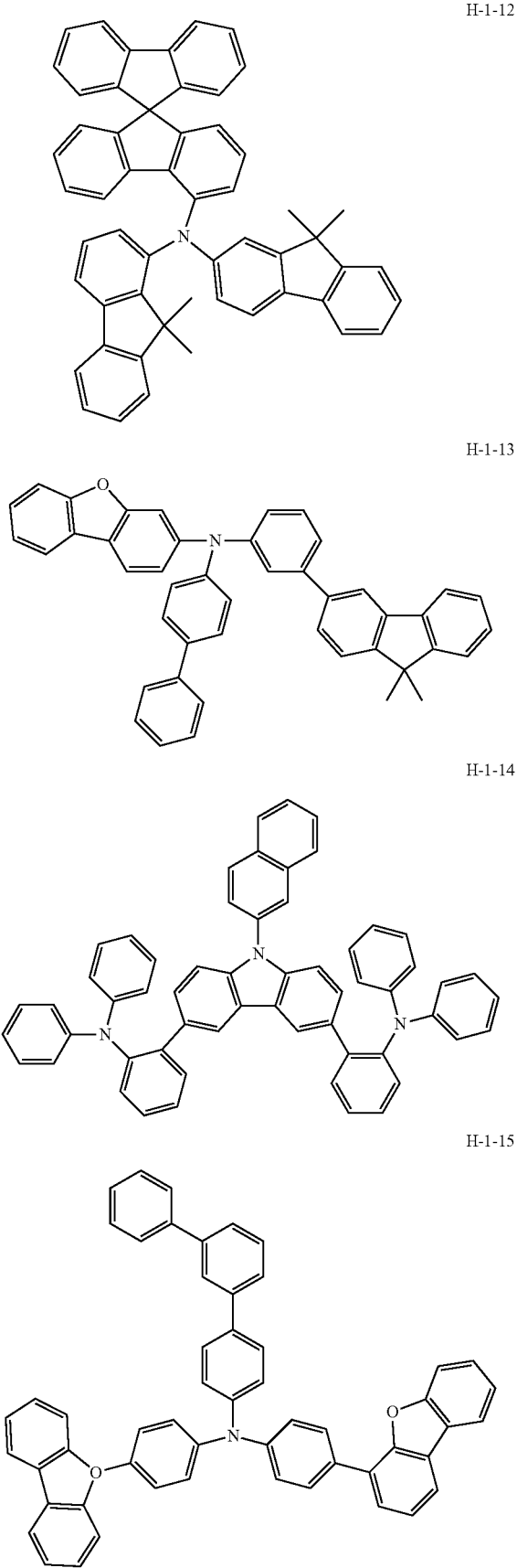
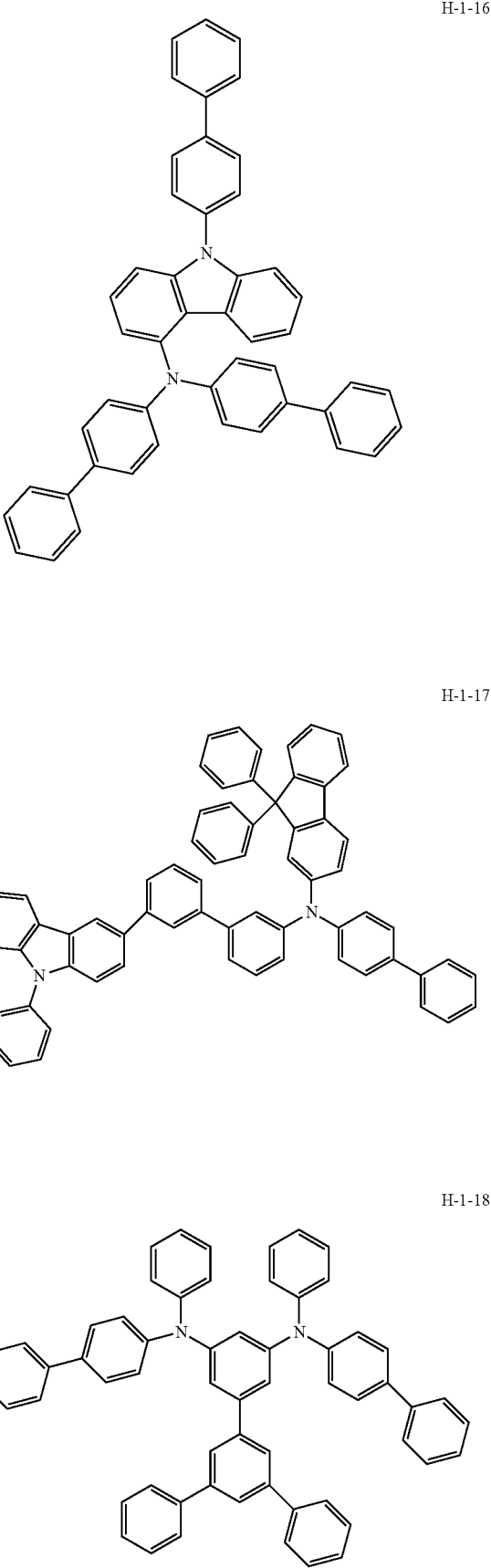

H-1-19

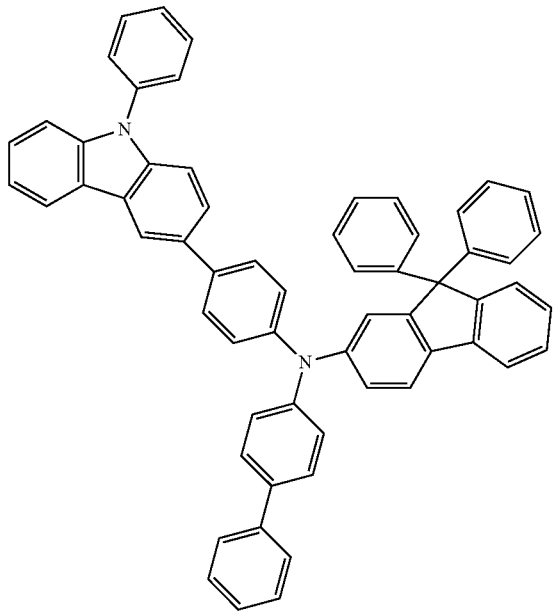

The hole transport region HTR may include a phthalocyanine compound such as copper phthalocyanine, $N^1,N^{1'}$-([1,1'-biphenyl]-4,4'-diyl)bis(N1-phenyl-$N^4,N^4$-di-m-tolyl-benzene-1,4-diamine) (DNTPD), 4,4',4''-[tris(3-methylphenyl)phenylamino] triphenylamine (m-MTDATA), 4,4',4''-tris(N,N-diphenylamino)triphenylamine (TDATA), 4,4',4''-tris[N(2-naphthyl)-N-phenylamino]-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(1-naphthalene-1-yl)-N,N'-diphenyl-benzidine (NPB), triphenylamine-containing polyetherketone (TPAPEK), 4-isopropyl-4'-methyldiphenyliodonium [tetrakis(pentafluorophenyl)borate], and dipyrazino[2,3-f:2',3'-h]quinoxaline-2,3,6,7,10,11-hexacarbonitrile (HAT-CN).

The hole transport region HTR may include carbazole derivatives such as N-phenyl carbazole and polyvinyl carbazole, fluorene-based derivatives, N,N'-bis(3-methylphenyl)-N,N'-diphenyl-[1,1'-biphenyl]-4,4'-diamine (TPD), triphenylamine-based derivatives such as 4,4',4''-tris(N-carbazolyl)triphenylamine (TCTA), N,N'-di(1-naphthalene-1-yl)-N,N'-diphenyl-benzidine (NPB), 4,4'-cyclohexylidene bis[N,N-bis(4-methylphenyl)benzeneamine](TAPC), 4,4'-bis[N,N'-(3-tolyl)amino]-3,3'-dimethylbiphenyl (HMTPD), 1,3-bis(N-carbazolyl)benzene (mCP), etc.

In an embodiment, the hole transport region HTR may include 9-(4-tert-butylphenyl)-3,6-bis(triphenylsilyl)-9H-carbazole (CzSi), 9-phenyl-9H-3,9'-bicarbazole (CCP), 1,3-bis(1,8-dimethyl-9H-carbazol-9-yl)benzene (mDCP), etc.

The hole transport region HTR may include the compounds of the hole transport region in at least one of a hole injection layer HIL, a hole transport layer HTL, and an electron blocking layer EBL.

A thickness of the hole transport region HTR may be in a range of about 100 Å to about 10,000 Å. For example, the thickness of the hole transport region HTR may be in a range of about 100 Å to about 5,000 Å. In case where the hole transport region HTR includes a hole injection layer HIL, a thickness of the hole injection region HIL may be, for example, in a range of about 30 Å to about 1,000 Å. In case where the hole transport region HTR includes a hole transport layer HTL, a thickness of the hole transport layer HTL may be in a range of about 30 Å to about 1,000 Å. For example, in case where the hole transport region HTR includes an electron blocking layer, a thickness of the electron blocking layer EBL may be in a range of about 10 Å to about 1,000 Å. If the thicknesses of the hole transport region HTR, the hole injection layer HIL, the hole transport layer HTL, and the electron blocking layer EBL satisfy the above-described ranges, satisfactory hole transport properties may be achieved without substantial increase of a driving voltage.

The hole transport region HTR may further include a charge generating material to increase conductivity in addition to the above-described materials. The charge generating material may be dispersed uniformly or non-uniformly in the hole transport region HTR. The charge generating material may be, for example, a p-dopant. The p-dopant may include at least one of metal halide compounds, quinone derivatives, metal oxides, and cyano group-containing compounds, without limitation. For example, the p-dopant may include metal halide compounds such as CuI and RbI, quinone derivatives such as tetracyanoquinodimethane (TCNQ) and 2,3,5,6-tetrafluoro-7,7',8,8-tetracyanoquinodimethane (F4-TCNQ), metal oxides such as tungsten oxide and molybdenum oxide, cyano group-containing compounds such as dipyrazino[2,3-f: 2',3'-h]quinoxaline-2,3,6,7,10,11-hexacarbonitrile (HATCN) and 4-[[2,3-bis[cyano-(4-cyano-2,3,5,6-tetrafluorophenyl)methylidene]cyclopropylidene]-cyanomethyl]-2,3,5,6-tetrafluorobenzonitrile, etc., without limitation.

As described above, the hole transport region HTR may further include at least one of a buffer layer (not shown) and an electron blocking layer EBL in addition to the hole injection layer HIL and the hole transport layer HTL. The buffer layer (not shown) may compensate for a resonance distance according to the wavelength of light emitted from an emission layer EML and may increase emission efficiency. Materials which may be included in the hole transport region HTR may be used as materials included in the buffer layer (not shown). The electron blocking layer EBL may block the injection of electrons from the electron transport region ETR into the hole transport region HTR.

The emission layer EML is provided on the hole transport region HTR. The emission layer EML may have a thickness in a range of about 100 Å to about 1,000 Å. For example, the emission layer EML may have a thickness in a range of about 100 Å to about 300 Å. The emission layer EML may have a layer formed using a single material, a layer formed using different materials, or a multilayer structure having layers formed using different materials.

In the light emitting device ED according to an embodiment, the emission layer EML may include a polycyclic compound of an embodiment.

The emission layer EML may include anthracene derivatives, pyrene derivatives, fluoranthene derivatives, chrysene derivatives, dihydrobenzanthracene derivatives, or triphenylene derivatives. In an embodiment, the emission layer EML may include anthracene derivatives or pyrene derivatives.

In the light emitting devices ED of embodiments, shown in FIG. 3 to FIG. 6, the emission layer EML may include a host and a dopant, and the emission layer EML may include a compound represented by Formula E-1 below. The compound represented by Formula E-1 below may be used as a fluorescence host material or a delayed fluorescence host material.

[Formula E-1]

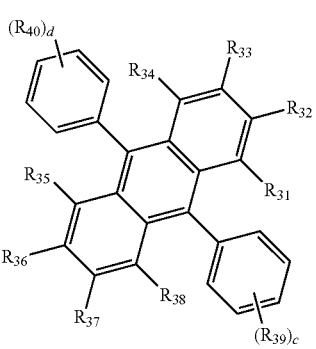

In Formula E-1, $R_{31}$ to $R_{40}$ may each independently be a hydrogen atom, a deuterium atom, a halogen atom, a substituted or unsubstituted silyl group, a substituted or unsubstituted thio group, a substituted or unsubstituted oxy group, a substituted or unsubstituted alkyl group of 1 to 20 carbon atoms, a substituted or unsubstituted alkenyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring. $R_{31}$ to $R_{40}$ may be combined with an adjacent group to form a saturated hydrocarbon ring or an unsaturated hydrocarbon ring. In an embodiment, $R_{31}$ to $R_{40}$ may be combined with an adjacent substituent or a benzene ring to form a fused ring.

In Formula E-1, c and d may each independently be an integer from 0 to 5.

The compound represented by Formula E-1 may be selected from any one among Compound E1 to Compound E19 below.

E1

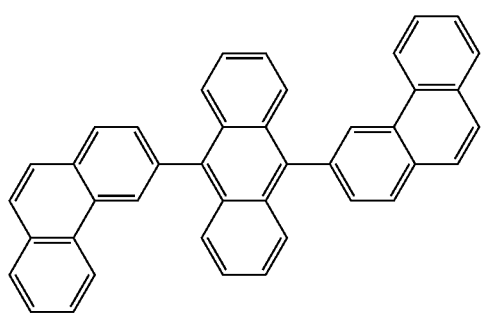

E2

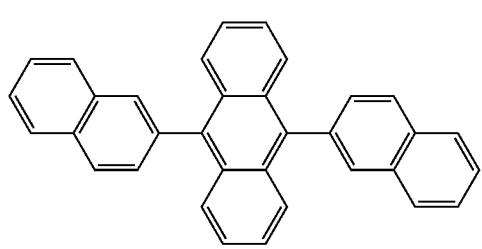

E3

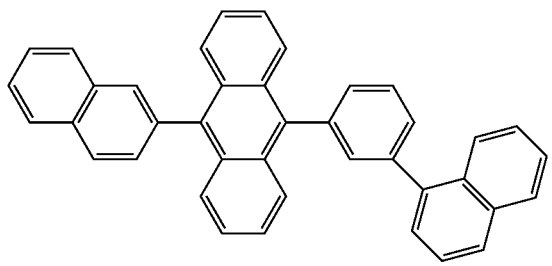

E4

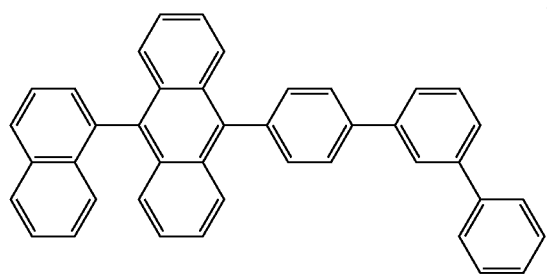

E5

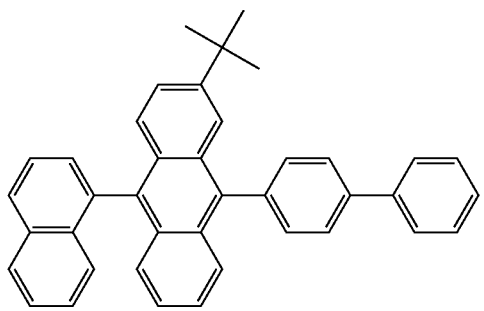

E6

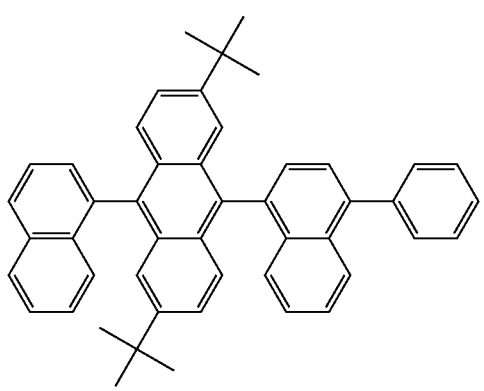

E7

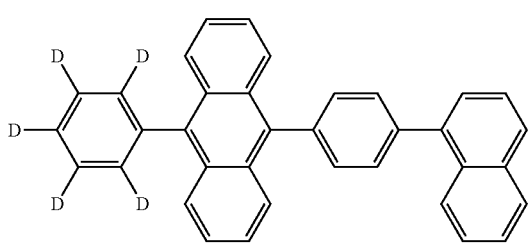

-continued
E8
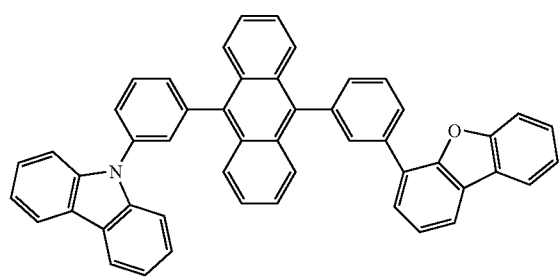
E9
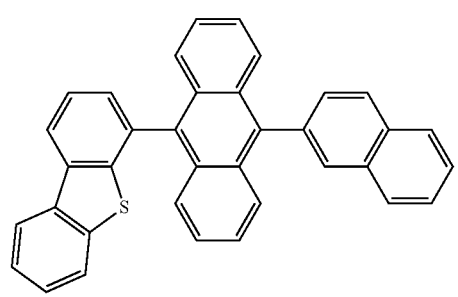
E10
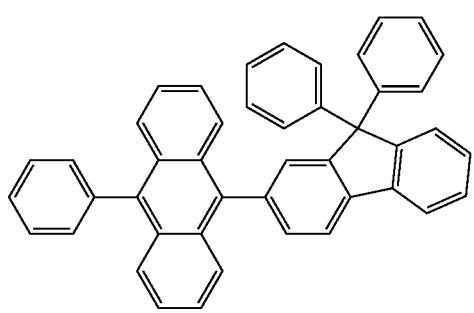
E11
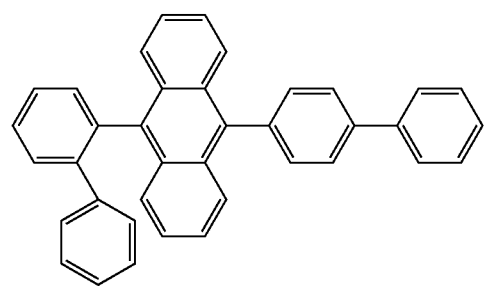
E12
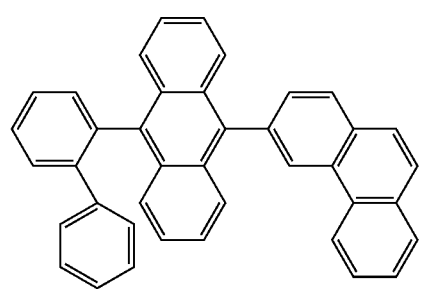
-continued
E13
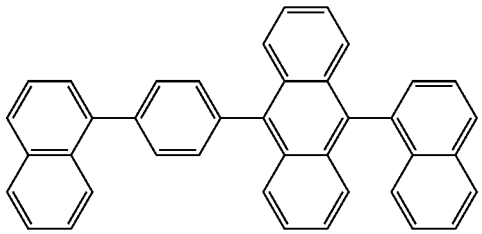
E14
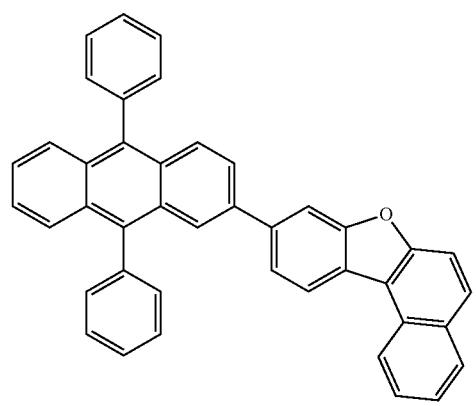
E15
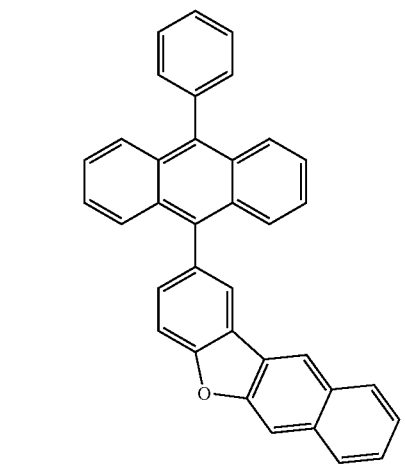
E16
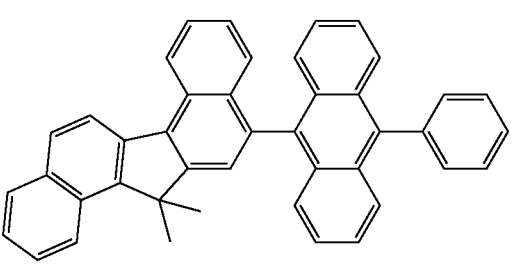

E17

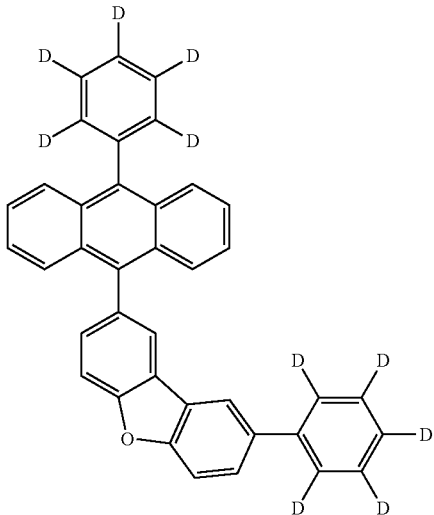

E18

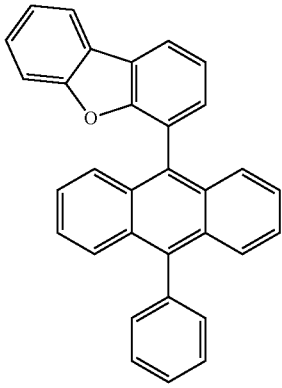

E19

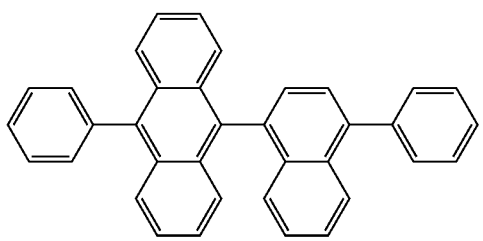

In an embodiment, the emission layer EML may include a compound represented by Formula E-2a or Formula E-2b below. The compound represented by Formula E-2a or Formula E-2b below may be used as a phosphorescence host material or a delayed fluorescence host material.

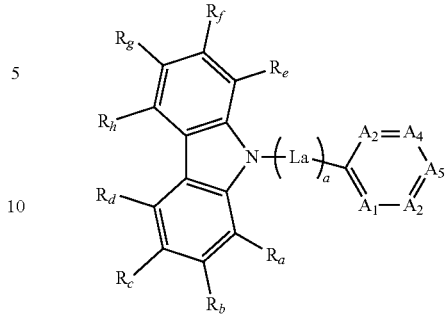

[Formula E-2a]

In Formula E-2b, a may be an integer from 0 to 10, and $L_a$ may be a direct linkage, a substituted or unsubstituted arylene group of 6 to 30 ring-forming carbon atoms, or a substituted or unsubstituted heteroarylene group of 2 to 30 ring-forming carbon atoms. In Formula E-2a, if a is 2 or more, multiple $L_a$ groups may each independently be a substituted or unsubstituted arylene group of 6 to 30 ring-forming carbon atoms, or a substituted or unsubstituted heteroarylene group of 2 to 30 ring-forming carbon atoms.

In Formula E-2a, $A_1$ to $A_5$ may each independently be N or C(Ri). $R_a$ to $R_i$ may each independently be a hydrogen atom, a deuterium atom, a substituted or unsubstituted amine group, a substituted or unsubstituted thio group, a substituted or unsubstituted oxy group, a substituted or unsubstituted alkyl group of 1 to 20 carbon atoms, a substituted or unsubstituted alkenyl group of 2 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring. In an embodiment, $R_a$ to $R_i$ may be combined with an adjacent group to form a hydrocarbon ring or a heterocycle including N, O, S, etc. as a ring-forming atom.

In Formula E-2a, two or three of $A_1$ to $A_5$ may be N, and the remainder of $A_1$ to $A_5$ may be $C(R_i)$.

[Formula E-2b]

$$(CBz1)\!\!-\!\!(L_b)_b\!\!-\!\!(CBz2)$$

In Formula E-2b, Cbz1 and Cbz2 may each independently be an unsubstituted carbazole group, or a carbazole group substituted with an aryl group of 6 to 30 ring-forming carbon atoms. In Formula E-2b, $L_b$ may be a direct linkage, a substituted or unsubstituted arylene group of 6 to 30 ring-forming carbon atoms, or a substituted or unsubstituted heteroarylene group of 2 to 30 ring-forming carbon atoms. In Formula E-2b, b may be an integer from 0 to 10. In an embodiment, if b is 2 or more, multiple $L_b$ groups may each independently be a substituted or unsubstituted arylene group of 6 to 30 ring-forming carbon atoms, or a substituted or unsubstituted heteroarylene group of 2 to 30 ring-forming carbon atoms.

The compound represented by Formula E-2a or Formula E-2b may be any one selected from Compound Group E-2 below. However, the compounds shown in Compound Group E-2 below are examples, and the compound represented by Formula E-2a or Formula E-2b is not limited to the compounds of Compound Group E-2 below.

[Compound Group E-2]
E-2-1
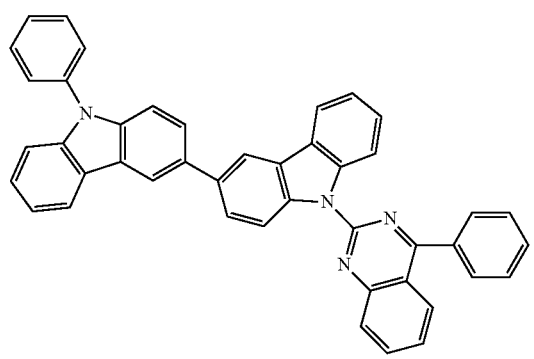
E-2-2
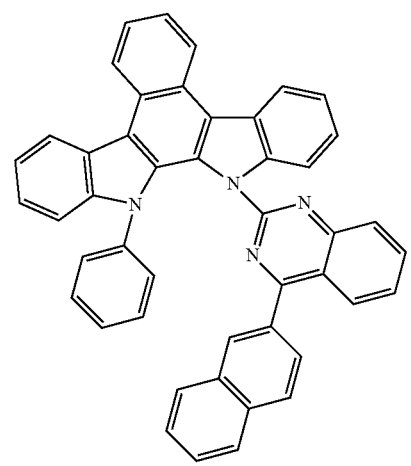
E-2-3
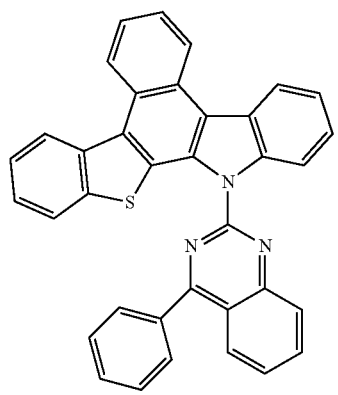
E-2-4
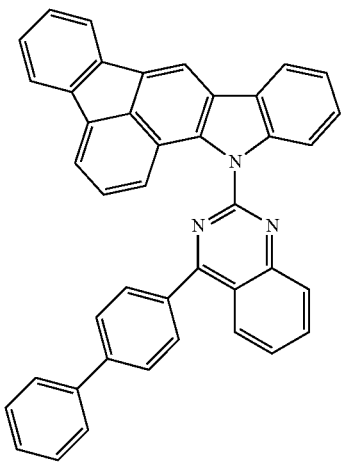
E-2-5
E-2-6

-continued
E-2-7
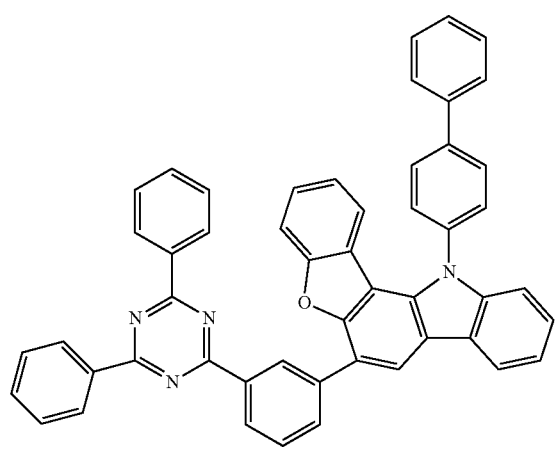
E-2-8
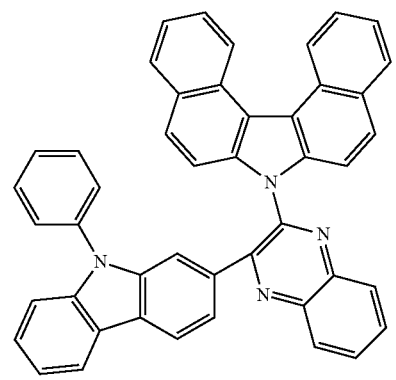
E-2-9
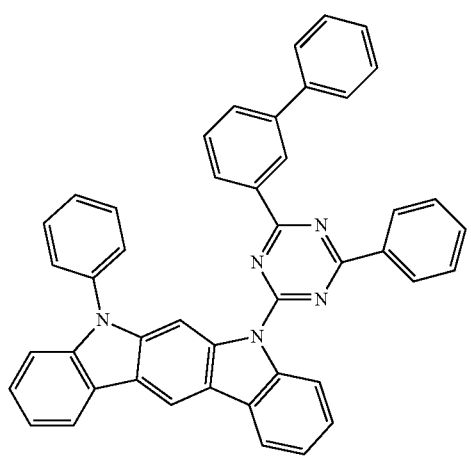
-continued
E-2-10
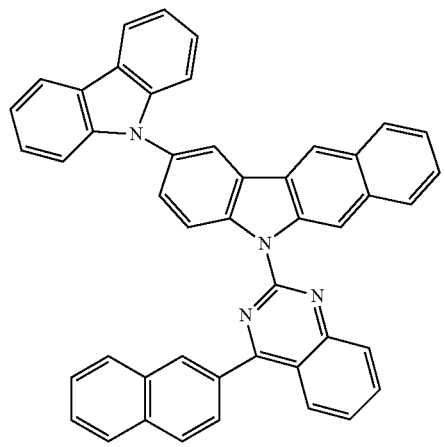
E-2-11
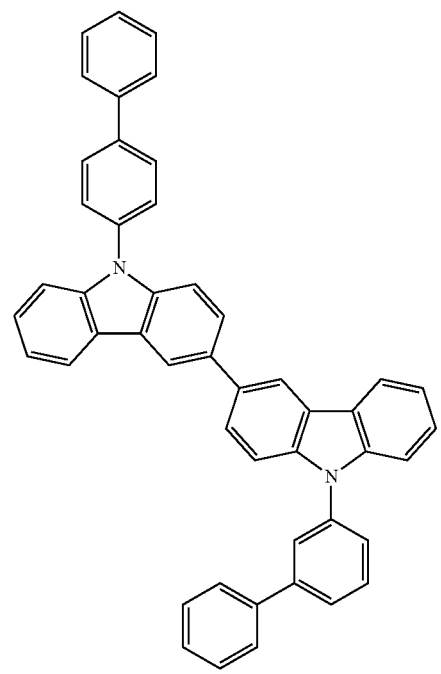
E-2-12
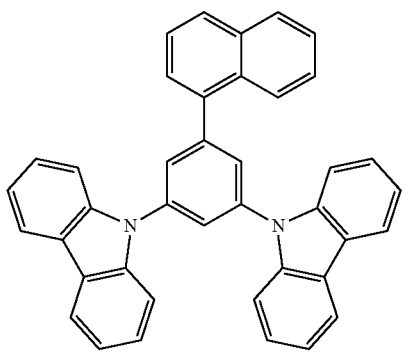

E-2-13
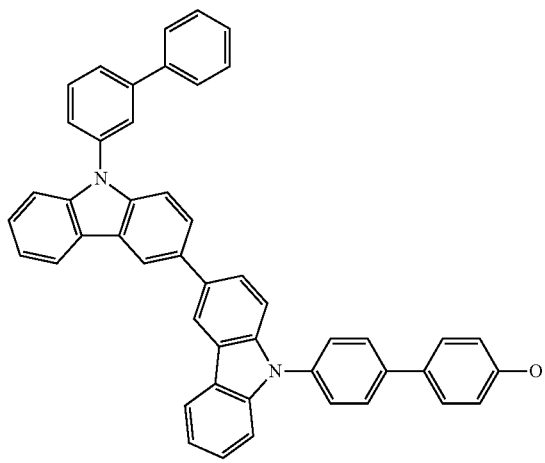
E-2-14
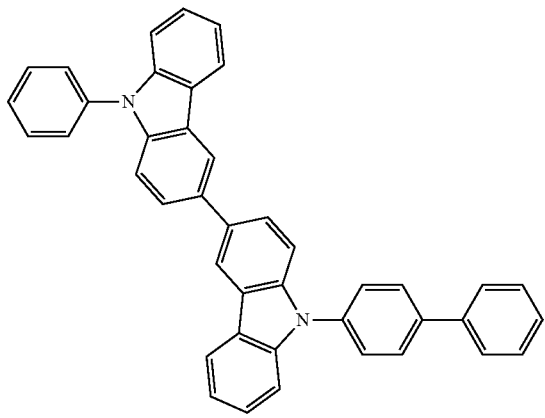
E-2-15
E-2-16
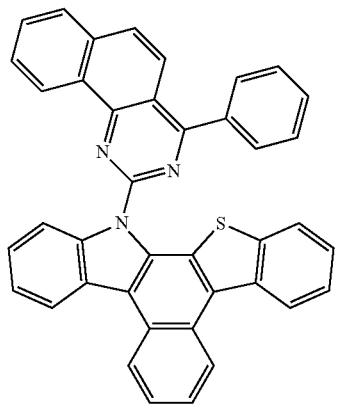
E-2-17
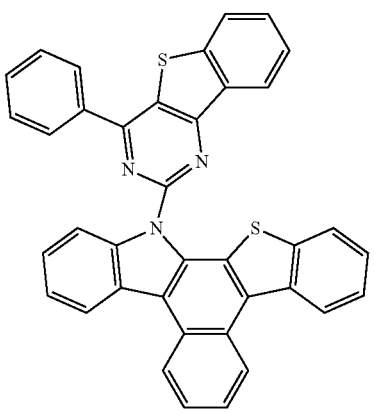
E-2-18
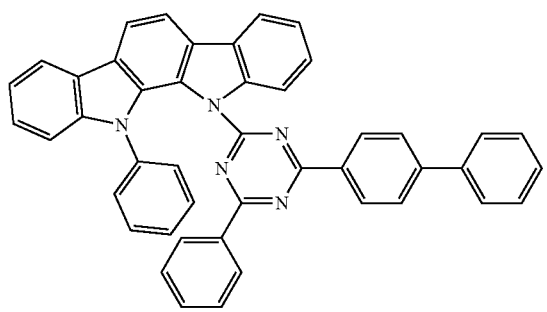
E-2-19
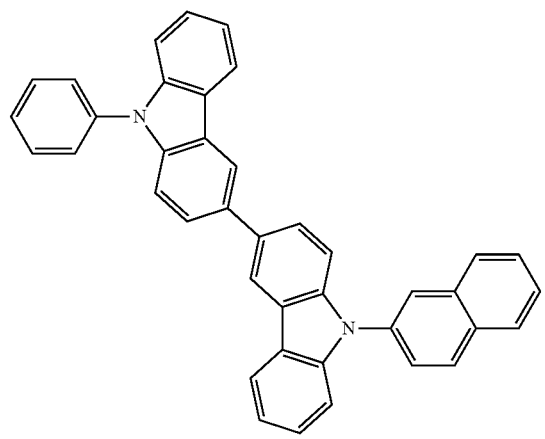

E-2-20

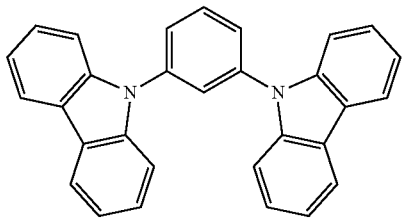

E-2-21

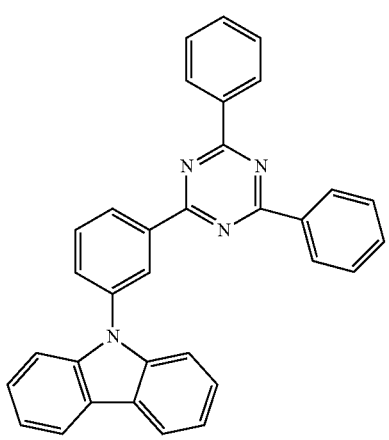

E-2-22

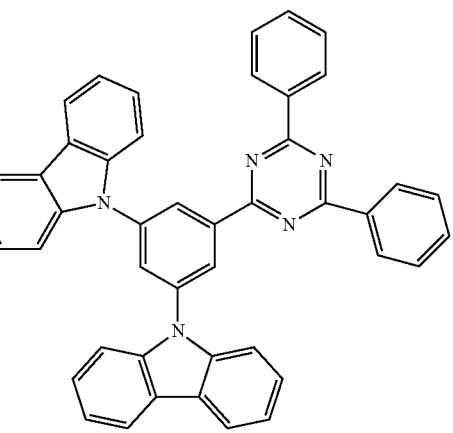

E-2-23

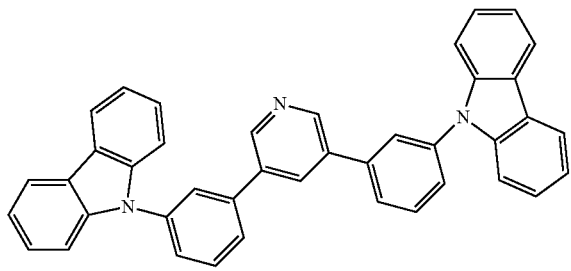

E-2-24

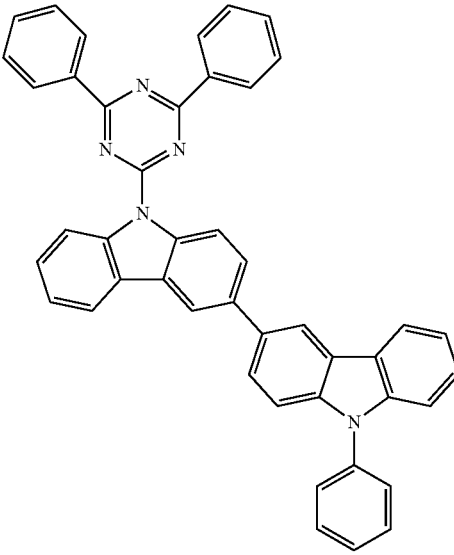

The emission layer EML may further include a common material in the art as a host material. For example, the emission layer EML may include as a host material, at least one of bis[2-(diphenylphosphino)phenyl]ether oxide (DPEPO), 4,4'-bis(carbazol-9-yl)biphenyl (CBP), 1,3-bis (carbazol-9-yl)benzene (mCP), 2,8-bis(diphenylphosphoryl) dibenzo[b,d]furan (PPF), 4,4',4"-tris(carbazol-9-yl)-triphenylamine (TCTA), and 1,3,5-tris(1-phenyl-1H-benzo[d] imidazol-2-yl)benzene (TPBi). However, embodiments are not limited thereto. For example, tris(8-hydroxyquinolino) aluminum (Alq$_3$), poly(N-vinylcarbazole) (PVK), 9,10-di (naphthalene-2-yl)anthracene (ADN), 2-tert-butyl-9,10-di (naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), hexaphenyl cyclotriphosphazene (CP1), 1,4-bis(triphenylsilyl)benzene (UGH2), hexaphenylcyclotrisiloxane (DPSiO$_3$), octaphenylcyclotetra siloxane (DPSiO$_4$), etc. may be used as the host material.

The emission layer EML may include a compound represented by Formula M-a or Formula M-b below. The compound represented by Formula M-a or Formula M-b may be used as a phosphorescence dopant material.

[Formula M-a]

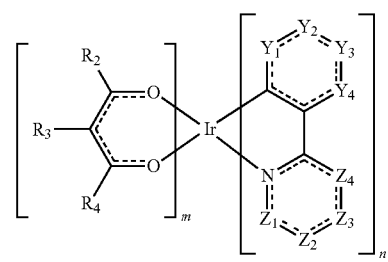

In Formula M-a, $Y_1$ to $Y_4$ and $Z_1$ to $Z_4$ may each independently be $C(R_1)$ or N, and $R_1$ to $R_4$ may each independently be a hydrogen atom, a deuterium atom, a substituted or unsubstituted amine group, a substituted or unsubstituted thio group, a substituted or unsubstituted oxy group, a substituted or unsubstituted alkyl group of 1 to 20 carbon atoms, a substituted or unsubstituted alkenyl group of 2 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring. In Formula M-a, m may be 0 or 1, and n may be 2 or 3. In Formula M-a, if m is 0, n may be 3, and if m is 1, n may be 2.

The compound represented by Formula M-a may be used as a red phosphorescence dopant or a green phosphorescence dopant.

The compound represented by Formula M-a may be any one selected from Compounds M-a1 to M-a21 below. However, Compounds M-a1 to M-a21 below are examples, and the compound represented by Formula M-a is not limited to the compounds of Compounds M-a1 to M-a21 below.

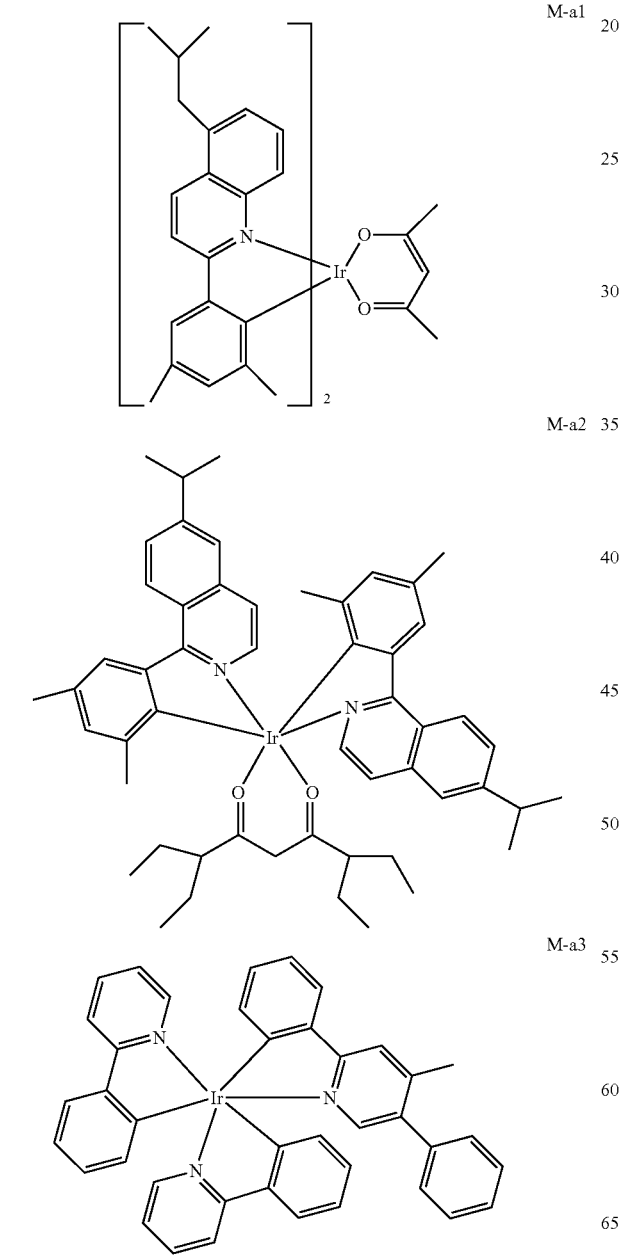

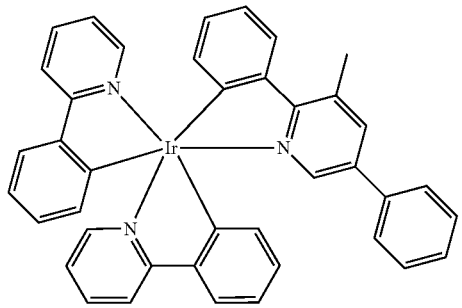

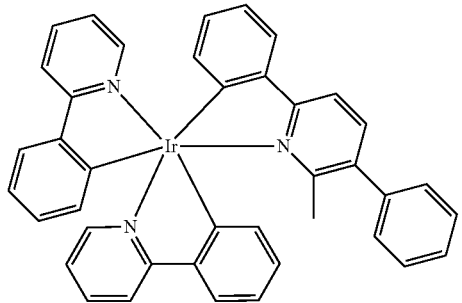

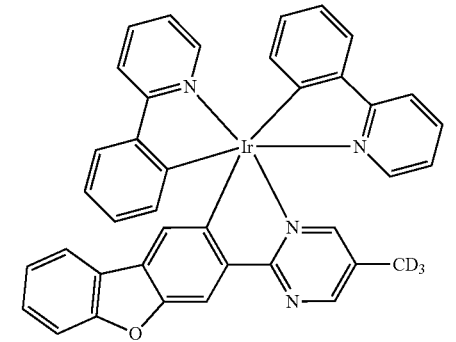

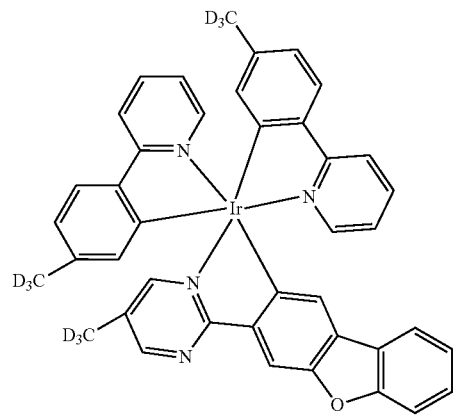

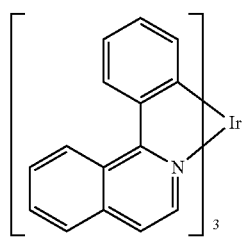

-continued
M-a9
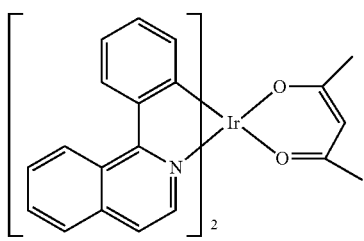
M-a10
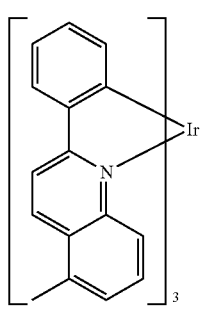
M-a11
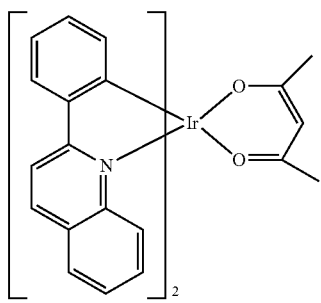
M-a12
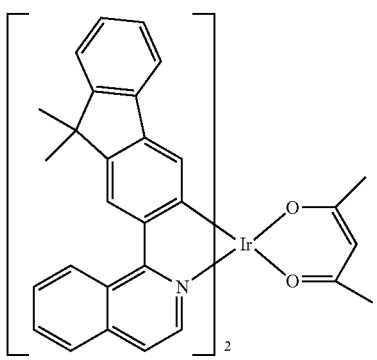
M-a13
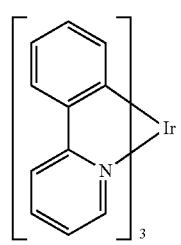
-continued
M-a14
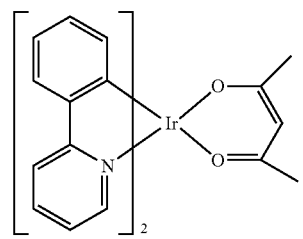
M-a15
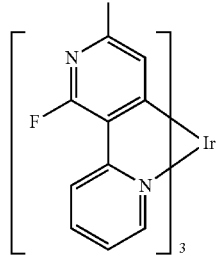
M-a16
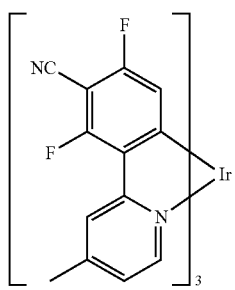
M-a17
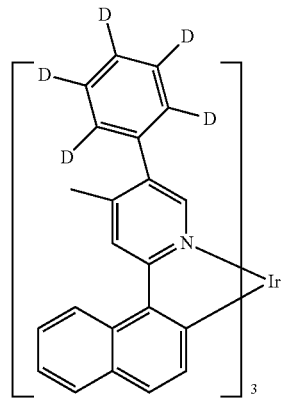
M-a18
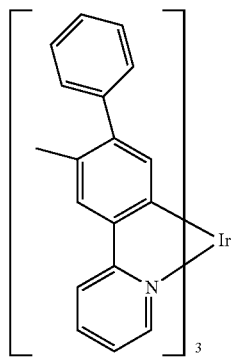

M-a19

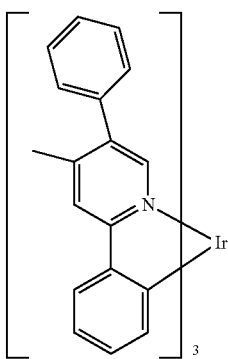

M-a20

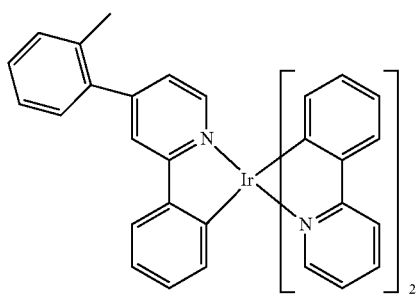

M-a21

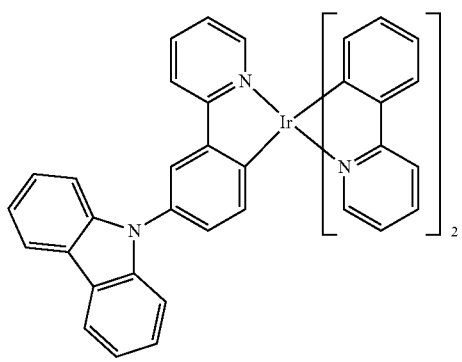

Compound M-a1 and Compound M-a2 may be used as red dopant materials, and Compound M-a3 to Compound M-a7 may be used as green dopant materials.

[Formula M-b]

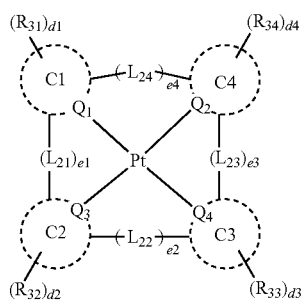

In Formula M-b, $Q_1$ to $Q_4$ may each independently be C or N, and $C_1$ to $C_4$ may each independently be a substituted or unsubstituted hydrocarbon ring of 5 to 30 ring-forming carbon atoms, or a substituted or unsubstituted heterocycle of 2 to 30 ring-forming carbon atoms. In Formula M-b, $L_{21}$ to $L_{24}$ may each independently be a direct linkage, *—O—*, *—S—*.

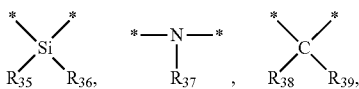

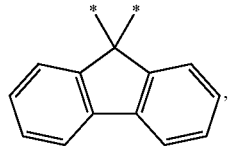

a substituted or unsubstituted divalent alkyl group of 1 to 20 carbon atoms, a substituted or unsubstituted arylene group of 6 to 30 ring-forming carbon atoms, or a substituted or unsubstituted heteroarylene group of 2 to 30 ring-forming carbon atoms, and e1 to e4 may each independently be 0 or 1. In Formula M-b, $R_{31}$ to $R_{39}$ may each independently be a hydrogen atom, a deuterium atom, a halogen atom, a cyano group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring, and d1 to d4 may each independently be an integer from 0 to 4.

The compound represented by Formula M-b may be used as a blue phosphorescence dopant or a green phosphorescence dopant.

The compound represented by Formula M-b may be any one selected from the compounds below. However, the compounds below are examples, and the compound represented by Formula M-b is not limited to the compounds represented below.

M-b-1

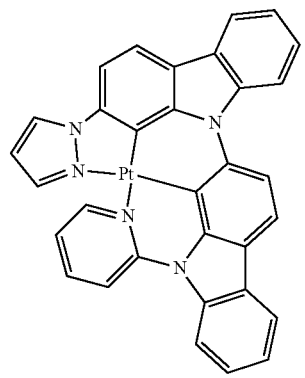

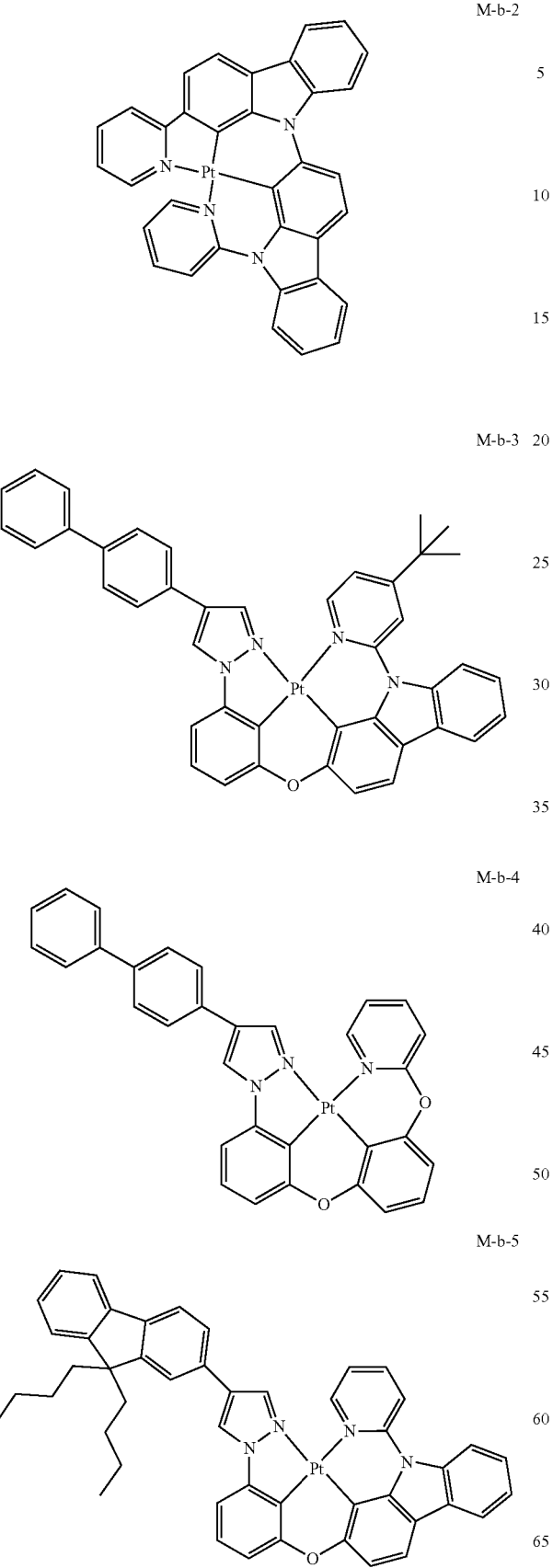
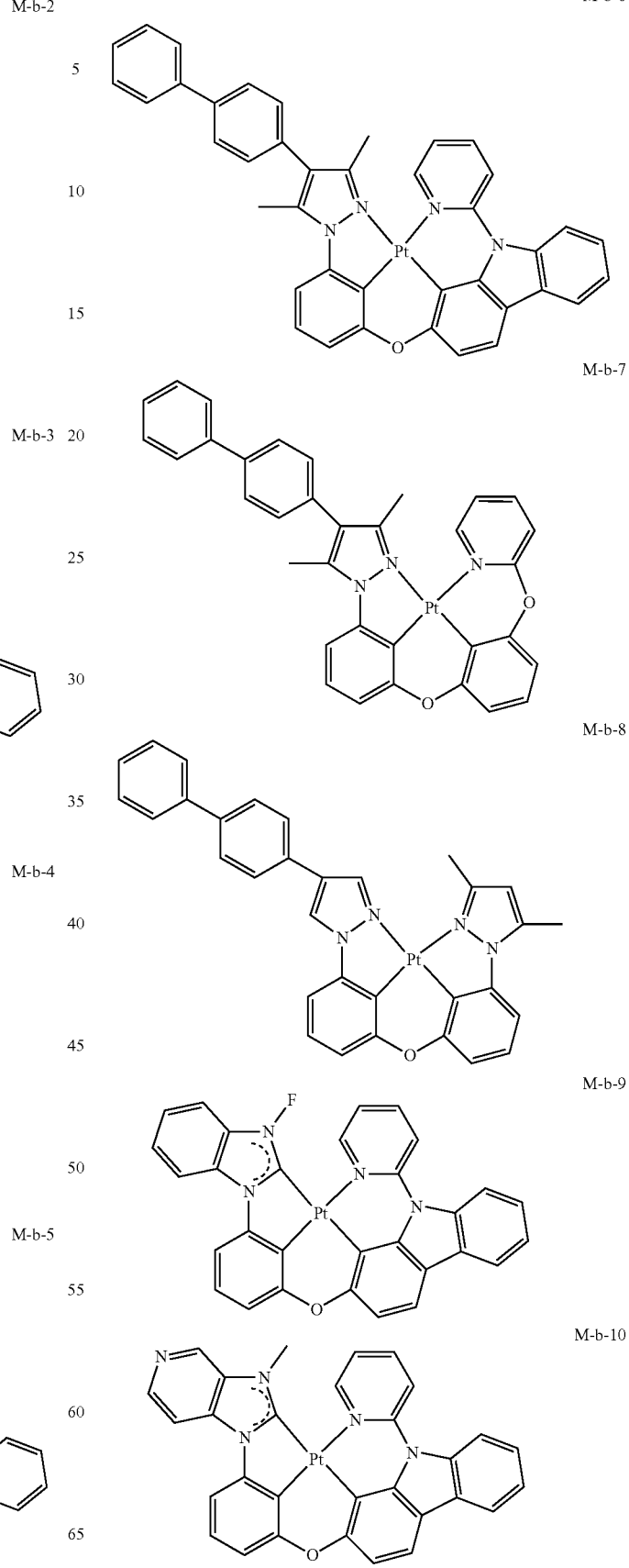

M-b-11

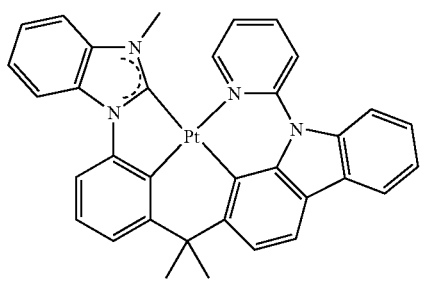

In the compounds above, R, $R_{38}$, and $R_{39}$ may each independently be a hydrogen atom, a deuterium atom, a halogen atom, a cyano group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms.

The emission layer EML may include a compound represented by any one among Formula F-a to Formula F-c below. The compounds represented by Formula F-a to Formula F-c below may be used as fluorescence dopant materials.

[Formula F-a]

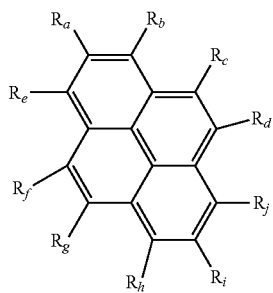

In Formula F-a, two selected from $R_a$ to $R_j$ may each independently be substituted with *—$NAr_1Ar_2$. The remainder of Ra to $R_j$ which are not substituted with *—$NAr_1Ar_2$ may each independently be a hydrogen atom, a deuterium atom, a halogen atom, a cyano group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms.

In Formula F-a, in the moiety represented by *—$NAr_1Ar_2$, $Ar_1$ and $Ar_2$ may each independently be a substituted or unsubstituted aryl group of 6 to 30 ring-forming carbon atoms, or a substituted or unsubstituted heteroaryl group of 2 to 30 ring-forming carbon atoms. For example, at least one of $Ar_1$ and $Ar_2$ may be a heteroaryl group including O or S as a ring-forming atom.

[Formula F-b]

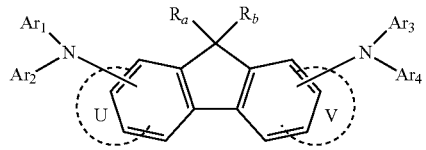

In Formula F-b, $R_a$ and $R_b$ may each independently be a hydrogen atom, a deuterium atom, a substituted or unsubstituted alkyl group of 1 to 20 carbon atoms, a substituted or unsubstituted alkenyl group of 2 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring.

In Formula F-b, U and V may each independently be a substituted or unsubstituted hydrocarbon ring of 5 to 30 ring-forming carbon atoms, or a substituted or unsubstituted heterocycle of 2 to 30 ring-forming carbon atoms.

In Formula F-b, the number of rings represented by U and V may each independently be 0 or 1. For example, in Formula F-b, if the number of U or V is 1, one ring may form a fused ring at the part designated by U or V, and if the number of U or V is 0, a ring may not be present at the part designated by U or V. If the number of U is 0 and the number of V is 1, or if the number of U is 1 and the number of V is 0, a fused ring having the fluorene core of Formula F-b may be a ring compound with four rings. If the number of both U and V is 0, the fused ring of Formula F-b may be a ring compound with three rings. If the number of both U and V is 1, a fused ring having the fluorene core of Formula F-b may be a ring compound with five rings.

[Formula F-c]

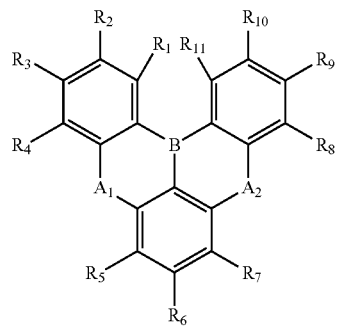

In Formula F-c, $A_1$ and $A_2$ may each independently be O, S, Se, or $N(R_m)$, and $R_m$ may be a hydrogen atom, a deuterium atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms. In Formula F-c, $R_1$ to $R_{11}$ may each independently be a hydrogen atom, a deuterium atom, a halogen atom, a cyano group, a substituted or unsubstituted amine group, a substituted or unsubstituted boryl group, a substituted or unsubstituted oxy group, a substituted or unsubstituted thio group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring.

In Formula F-c, $A_1$ and $A_2$ may each independently be combined with the substituents of an adjacent group to form a fused ring. For example, if $A_1$ and $A_2$ are each independently $N(R_m)$, $A_1$ may be combined with $R_4$ or $R_5$ to form a ring. In an embodiment, $A_2$ may be combined with $R_7$ or $R_8$ to form a ring.

In an embodiment, the emission layer EML may include as a dopant material, styryl derivatives (for example, 1,4-bis[2-(3-N-ethylcarbazoryl)vinyl]benzene (BCzVB), 4-(di-p-tolylamino)-4'-[(di-p-tolylamino)styryl]stilbene (DPAVB), N-(4-((E)-2-(6-((E)-4-(diphenylamino)styryl) naphthalen-2-yl)vinyl)phenyl)-N-phenylbenzenamine (N-BDAVBi), and 4,4'-bis[2-(4-(N,N-diphenylamino)phenyl)vinyl]biphenyl (DPAVBi)), perylene and the derivatives thereof (for example, 2,5,8,11-tetra-t-butylperylene (TBP)), pyrene and the derivatives thereof (for example, 1,1-dipyrene, 1,4-dipyrenylbenzene, and 1,4-bis(N,N-diphenylamino)pyrene), etc.

The emission layer EML may include a phosphorescence dopant material. For example, the phosphorescence dopant may use a metal complex including iridium (Ir), platinum (Pt), osmium (Os), gold (Au), titanium (Ti), zirconium (Zr), hafnium (Hf), europium (Eu), terbium (Tb), or thulium (Tm). In an embodiment, iridium(III) bis(4,6-difluorophenylpyridinato-N,C2')picolinate (FIrpic), bis(2,4-difluorophenylpyridinato)-tetrakis(1-pyrazolyl)borate iridium(III) (Fir6), or platinum octaethyl porphyrin (PtOEP) may be used as the phosphorescence dopant. However, embodiments are not limited thereto.

The emission layer EML may include a quantum dot material. The quantum dot may have a core selected from a II-VI group compound, a III-VI group compound, a I-III-VI group compound, a III-V group compound, a III-II-V group compound, a IV-VI group compound, a IV group element, a IV group compound, and combinations thereof.

The II-VI group compound may be selected from the group consisting of: a binary compound selected from the group consisting of CdSe, CdTe, CdS, ZnS, ZnSe, ZnTe, ZnO, HgS, HgSe, HgTe, MgSe, MgS, and mixtures thereof, a ternary compound selected from the group consisting of CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, and mixtures thereof, and a quaternary compound selected from the group consisting of HgZnTeS, CdZnSeS, CdZnSeTe, CdZnSTe, CdHgSeS, CdHgSeTe, CdHgSTe, HgZnSeS, HgZnSeTe, HgZnSTe, and mixtures thereof.

The III-VI group compound may include a binary compound such as $In_2S_3$, and $In_2Se_3$, a ternary compound such as $InGaS_3$, and $InGaSe_3$, or combinations thereof.

The 1-III-VI group compound may be selected from a ternary compound selected from the group consisting of $AgInS_2$, $AgInS_2$, $CuInS$, $CuInS_2$, $AgGaS_2$, $CuGaS_2$, $CuGaO_2$, $AgGaO_2$, $AgAlO_2$ and mixtures thereof, or a quaternary compound such as $AgInGaS_2$, and $CuInGaS_2$.

The III-V group compound may be selected from the group consisting of a binary compound selected from the group consisting of GaN, GaP, GaAs, GaSb, AlN, AlP, AlAs, AlSb, InN, InP, InAs, InSb, and mixtures thereof, a ternary compound selected from the group consisting of GaNP, GaNAs, GaNSb, GaPAs, GaPSb, AlNP, AlNAs, AlNSb, AlPAs, AlPSb, InGaP, InAlP, InNP, InNAs, InNSb, InPAs, InPSb, and mixtures thereof, and a quaternary compound selected from the group consisting of GaAlNP, GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, InAlPSb, and mixtures thereof. The III-V group compound may further include a II group metal. For example, InZnP, etc. may be selected as a III-II-V group compound.

The IV-VI group compound may be selected from the group consisting of a binary compound selected from the group consisting of SnS, SnSe, SnTe, PbS, PbSe, PbTe, and mixtures thereof, a ternary compound selected from the group consisting of SnSeS, SnSeTe, SnSTe, PbSeS, PbSeTe, PbSTe, SnPbS, SnPbSe, SnPbTe, and mixtures thereof, and a quaternary compound selected from the group consisting of SnPbSSe, SnPbSeTe, SnPbSTe, and mixtures thereof. The IV group element may be selected from the group consisting of Si, Ge, and a mixture thereof. The IV group compound may be a binary compound selected from the group consisting of SiC, SiGe, and a mixture thereof.

A binary compound, a ternary compound, or a quaternary compound may be present at a uniform concentration in a particle or may be present at a partially different concentration distribution in the same particle. The quantum for may have a core/shell structure in which one quantum dot surrounds another quantum dot. The interface of the core and the shell may have a concentration gradient in which the concentration of an element present in the shell may decrease toward the core.

In an embodiment, the quantum dot may have the above-described core-shell structure including a core including a nanocrystal and a shell surrounding the core. The shell of the quantum dot may function as a protection layer for preventing the chemical deformation of the core to maintain semiconductor properties and/or as a charging layer for imparting the quantum dot with electrophoretic properties. The shell may have a single layer or a multilayer. Examples of the shell of the quantum dot may include a metal or non-metal oxide, a semiconductor compound, or combinations thereof.

For example, the metal or non-metal oxide may include a binary compound such as $SiO_2$, $Al_2O_3$, $TiO_2$, ZnO, MnO, $Mn_2O_3$, $Mn_3O_4$, CuO, FeO, $Fe_2O_3$, $Fe_3O_4$, CoO, $Co_3O_4$ and NiO, or a ternary compound such as $MgAl_2O_4$, $CoFe_2O_4$, $NiFe_2O_4$ and $CoMn_2O_4$, but embodiments are not limited thereto.

For example, the semiconductor compound may include CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, AlSb, etc., but embodiments are not limited thereto.

The quantum dot may have a full width of half maximum (FWHM) of an emission wavelength spectrum equal to or less than about 45 nm. For example, the quantum dot may have a FWHM of an emission wavelength spectrum equal to or less than about 40 nm. For example, the quantum dot may have a FWHM of an emission wavelength spectrum equal to or less than about 30 nm. Within these ranges, color purity or color reproducibility may be improved. Light emitted through such a quantum dot may be emitted in all directions, and light viewing angle properties may be improved.

The quantum dot may have a shape used in the art, without specific limitation. For example, the quantum dot may have a spherical, a pyramidal, a multi-arm, or a cubic shape, or the quantum dot may be in the form of a nanoparticle, a nanotube, a nanowire, a nanofiber, or a nanoplate.

The quantum dot may control the color of light emitted according to the particle size, and accordingly, the quantum dot may have various emission colors such as blue, red, and green.

In the light emitting device ED of an embodiment, as shown in FIG. 3 to FIG. 6, the electron transport region ETR is provided on the emission layer EML. The electron transport region ETR may include at least one of an electron blocking layer HBL, an electron transport layer ETL, and an electron injection layer EIL. However, embodiments are not limited thereto.

The electron transport region ETR may have a layer formed of a single material, a layer formed of different materials, or a multilayer structure having layers formed of different materials.

For example, the electron transport region ETR may have a single layer structure of an electron injection layer EIL or an electron transport layer ETL, or a single layer structure formed using an electron injection material and an electron transport material. The electron transport region ETR may have a single layer structure formed using different materials, or a structure stacked from the emission layer EIL of an electron transport layer ETL/an electron injection layer EIL, or a hole blocking layer HBL/an electron transport layer ETL/an electron injection layer EIL, without limitation. A thickness of the electron transport region ETR may be, for example, in a range of about 1,000 Å to about 1,500 Å.

The electron transport region ETR may be formed using various methods such as a vacuum deposition method, a spin coating method, a cast method, a Langmuir-Blodgett (LB) method, an inkjet printing method, a laser printing method, and a laser induced thermal imaging (LITI) method.

The electron transport region ETR may include a compound represented by Formula ET-1 below.

[Formula ET-1]

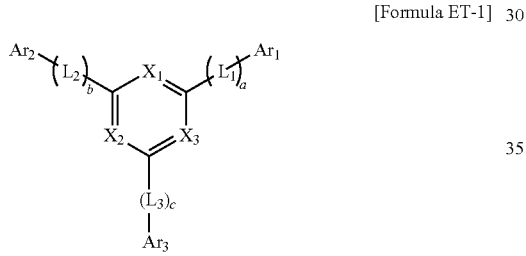

In Formula ET-1, at least one of $X_1$ to $X_3$ may be N, and the remainder of $X_1$ to $X_3$ may be $C(R_a)$. $R_a$ may be a hydrogen atom, a deuterium atom, a substituted or unsubstituted alkyl of 1 to 20 carbon atoms, a substituted or unsubstituted aryl group of 6 to 30 ring-forming carbon atoms, or a substituted or unsubstituted heteroaryl group of 2 to 30 ring-forming carbon atoms. In Formula ET-1, $Ar_1$ to $Ar_3$ may each independently be a hydrogen atom, a deuterium atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms.

In Formula ET-1, a to c may each independently be an integer from 0 to 10. In Formula ET-1, $L_1$ to $L_3$ may each independently be a direct linkage, a substituted or unsubstituted arylene group of 6 to 30 ring-forming carbon atoms, or a substituted or unsubstituted heteroarylene group of 2 to 30 ring-forming carbon atoms. In Formula ET-1, if a to c are 2 or more, $L_1$ to $L_3$ may each independently be a substituted or unsubstituted arylene group of 6 to 30 ring-forming carbon atoms, or a substituted or unsubstituted heteroarylene group of 2 to 30 ring-forming carbon atoms.

The electron transport region ETR may include an anthracene-based compound. However, embodiments are not limited thereto, and the electron transport region ETR may include, for example, tris(8-hydroxyquinolinato)aluminum (Alq$_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato)aluminum (BAlq), berylliumbis(benzoquinolin-10-olate (Bebg$_2$), 9,10-di(naphthalene-2-yl) anthracene (ADN), 1,3-bis[3,5-di(pyridin-3-yl)phenyl]benzene (BmPyPhB), and mixtures thereof, without limitation.

The electron transport region ETR may include at least one compound selected from Compounds ET1 to ET36 below.

ET1

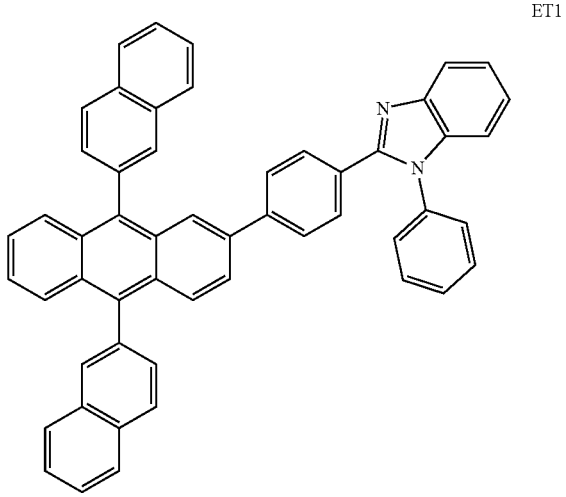

ET2

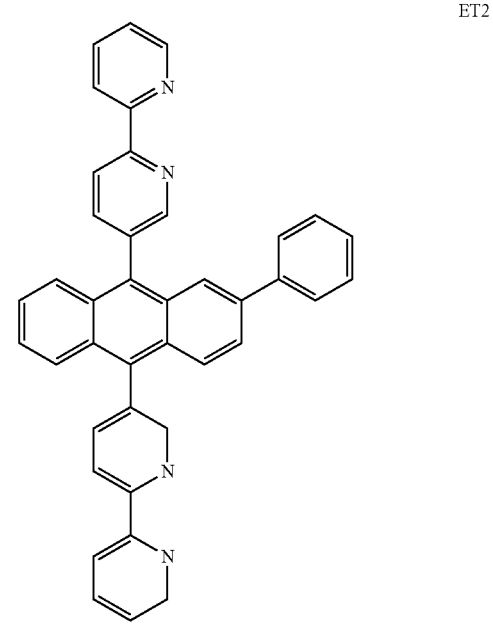

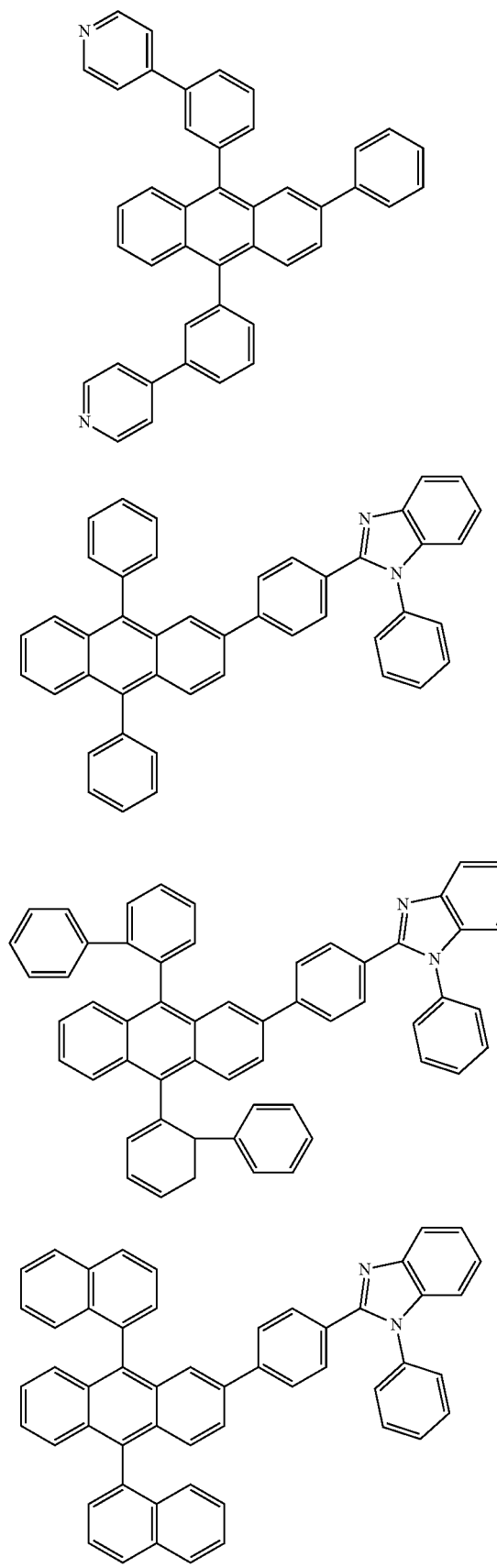
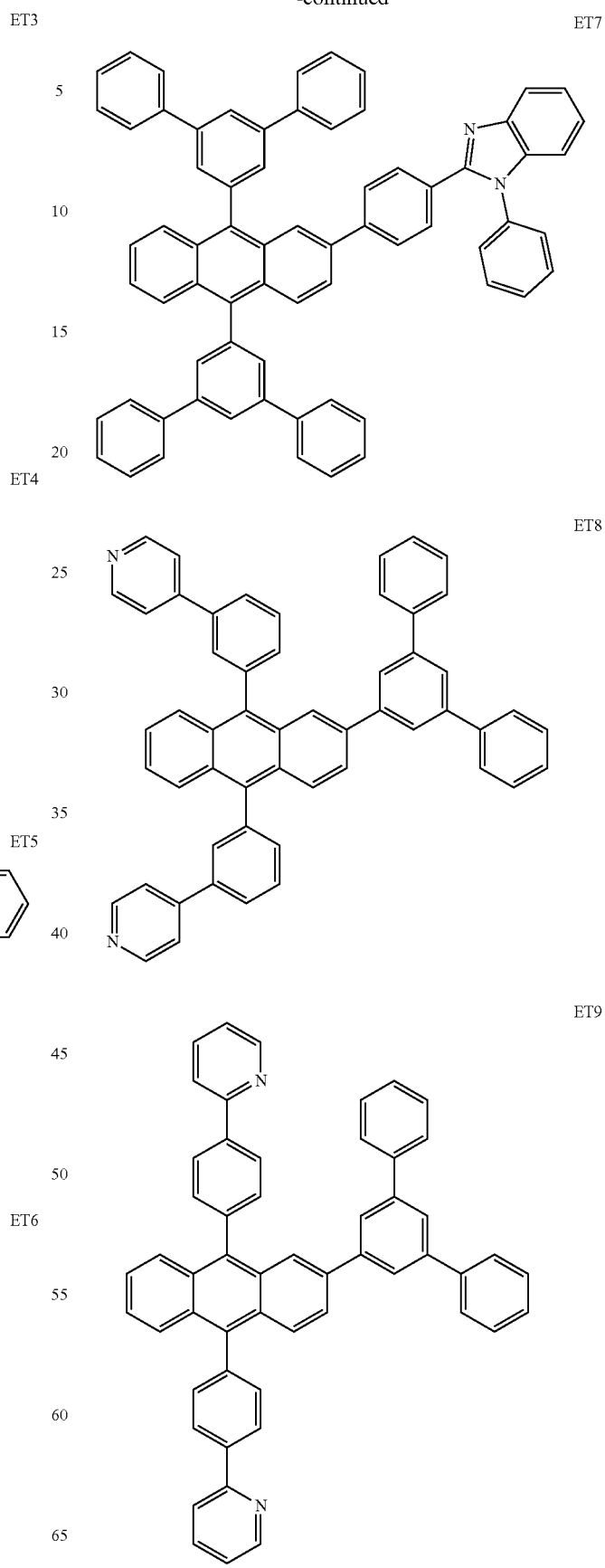

ET10
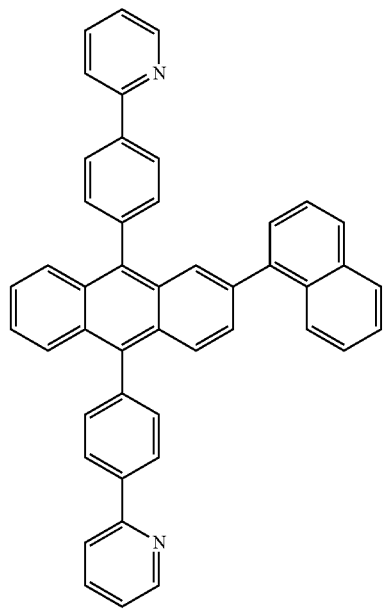
ET11
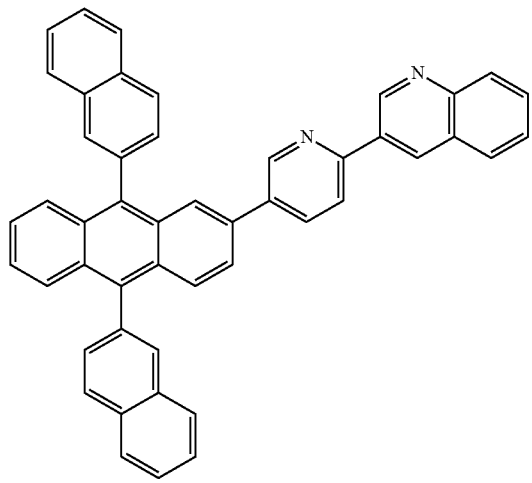
ET12
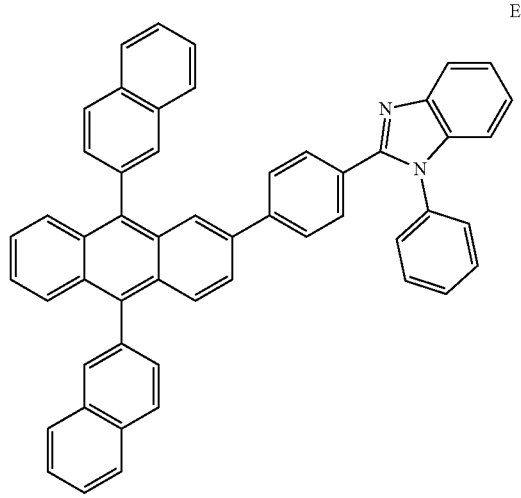
ET13
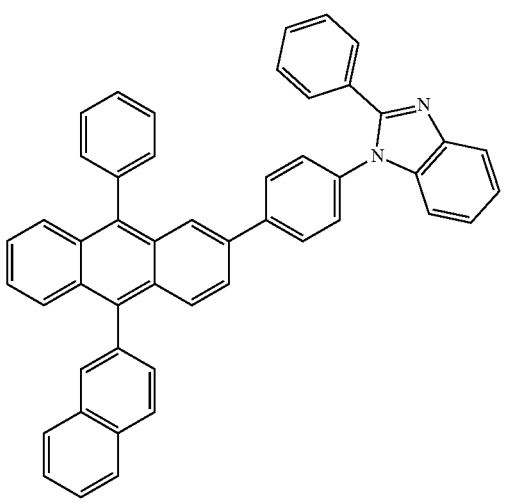
ET14
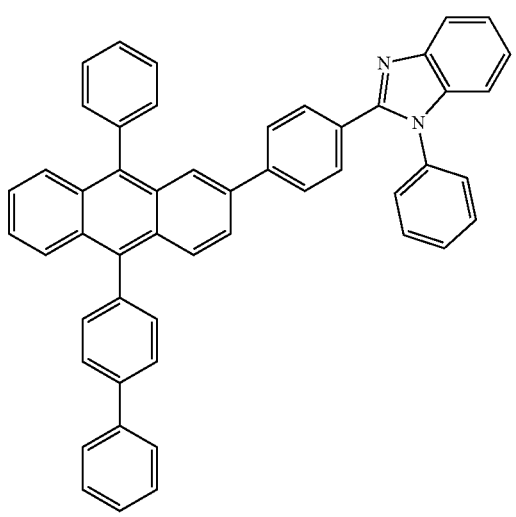
ET15
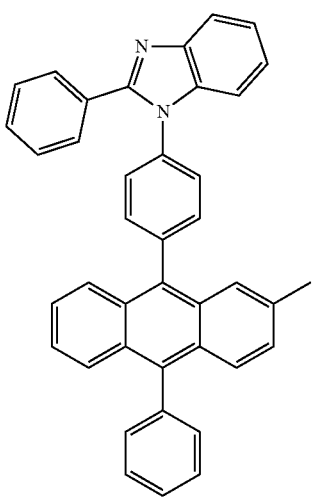

ET16
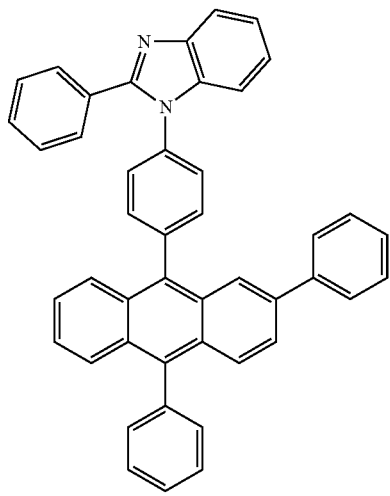
ET19
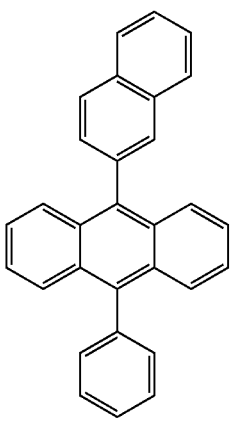
ET17
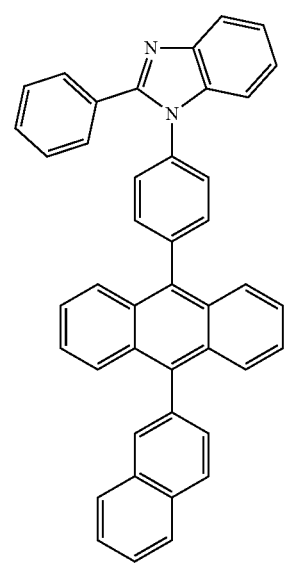
ET20
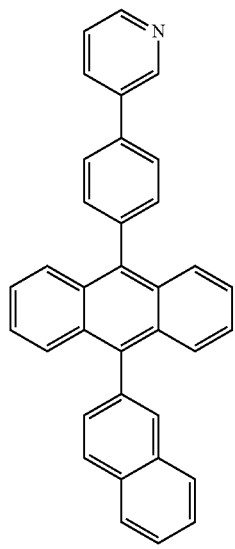
ET18
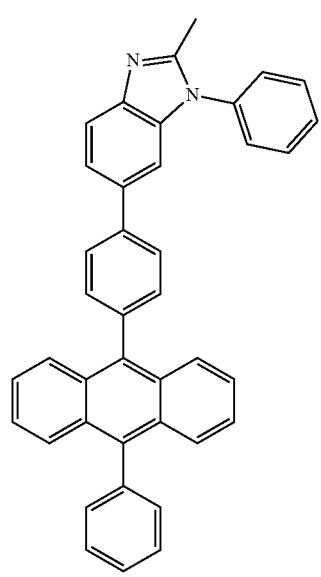
ET21
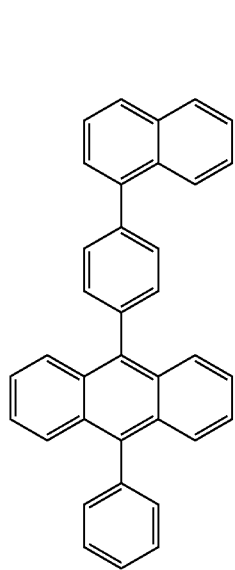

ET22
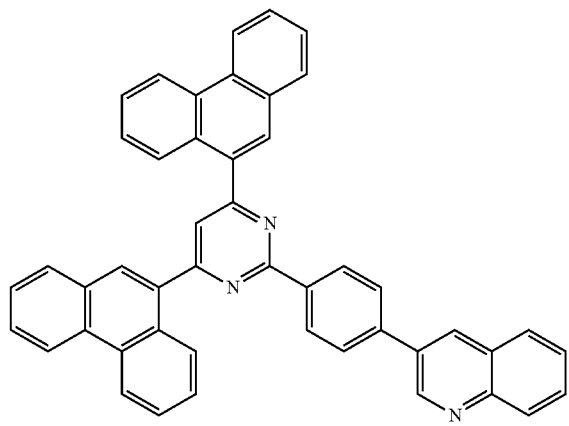
ET23
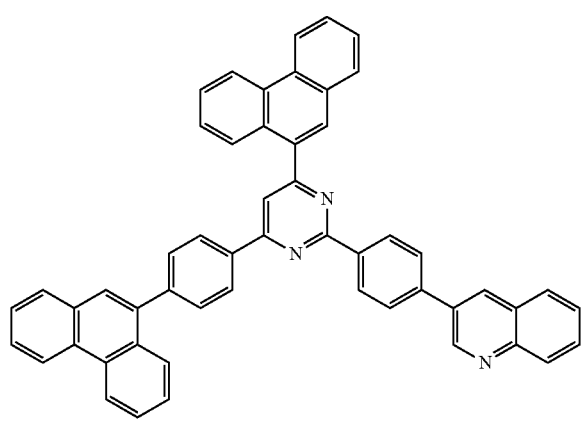
ET24
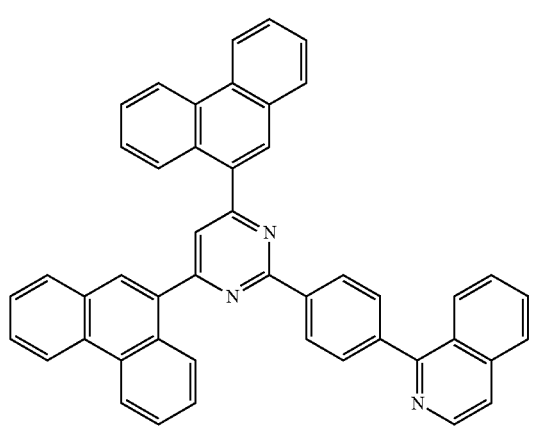
ET25
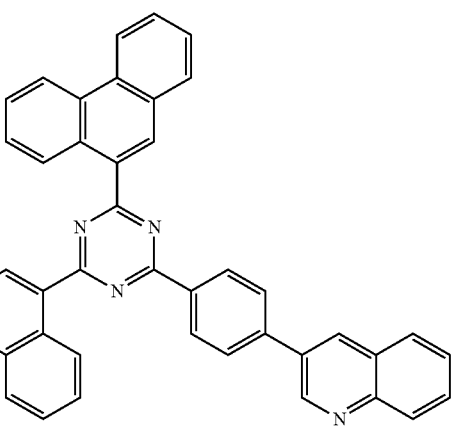
ET26
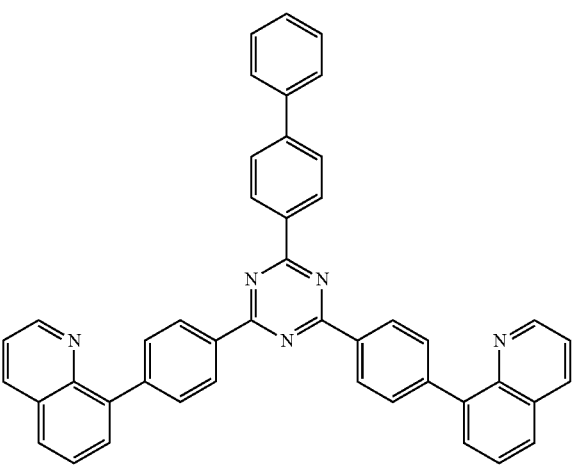
ET27
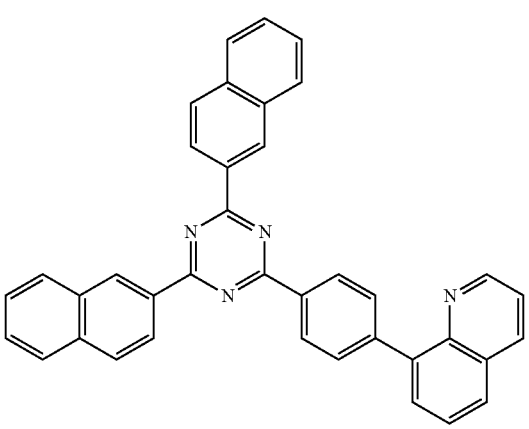

-continued
ET28
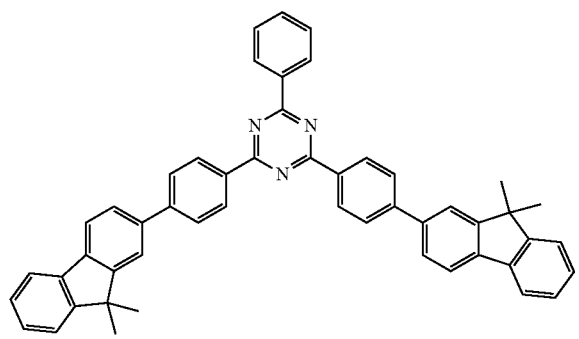
ET29
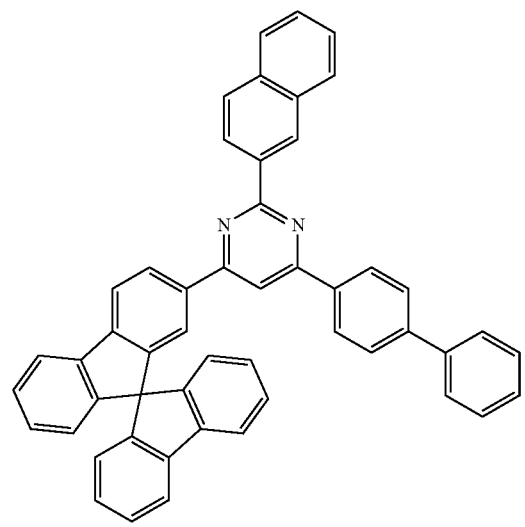
ET30
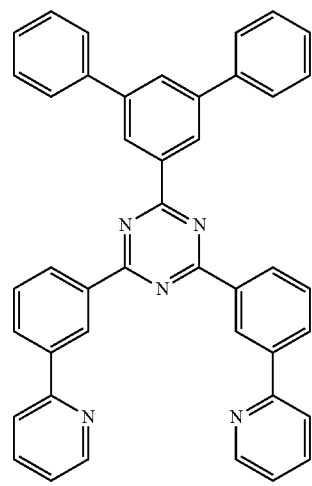
-continued
ET31
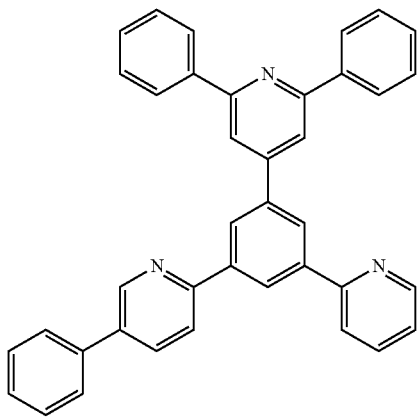
ET32
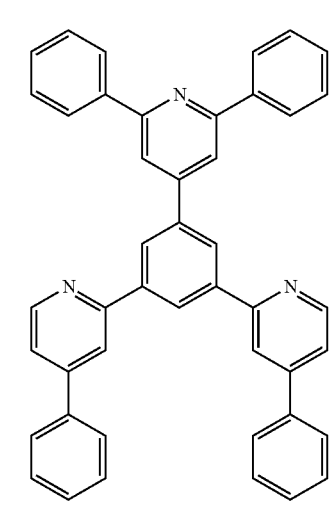
ET33
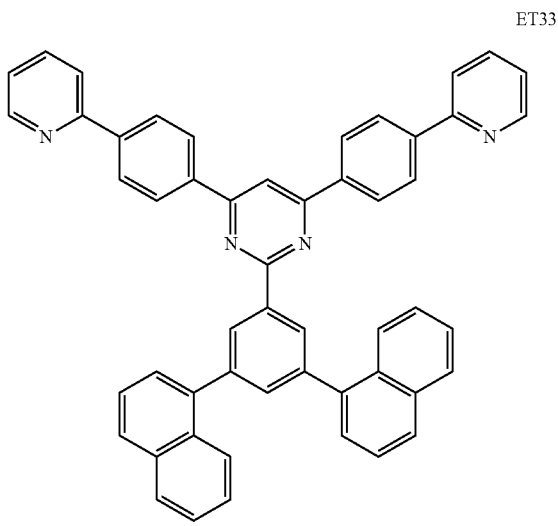

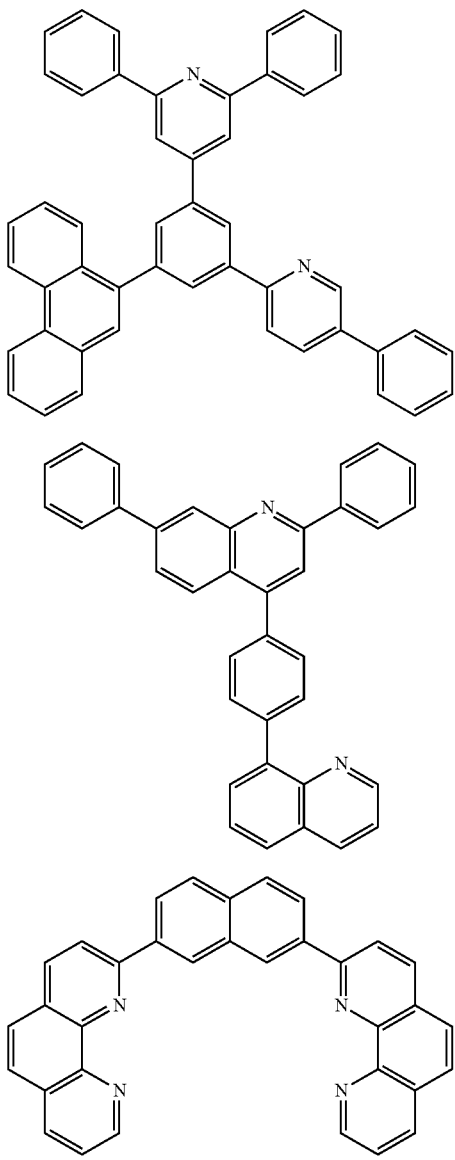

ET34

ET35

ET36

The electron transport region ETR may include a metal halide such as LiF, NaCl, CsF, RbCl, RbI, CuI and KI, a lanthanide such as Yb, or a co-depositing material of the metal halide and the lanthanide. For example, the electron transport region ETR may include KI:Yb, RbI:Yb, etc., as the co-depositing material. The electron transport region ETR may include a metal oxide such as $Li_2O$ and BaO, or 8-hydroxy-lithium quinolate (Liq). However, embodiments are not limited thereto. The electron transport region ETR may also include a mixture of an electron transport material and an insulating organo metal salt. The organo metal salt may be a material having an energy band gap equal to or greater than about 4 eV. In an embodiment, the organo metal salt may include, for example, metal acetates, metal benzoates, metal acetoacetates, metal acetylacetonates, or metal stearates.

The electron transport region ETR may include at least one of 2,9-dimethyl-4,7-diphenyl-1,10-phenanthroline (BCP), and 4,7-diphenyl-1,10-phenanthroline (Bphen) in addition to the aforementioned materials. However, embodiments are not limited thereto.

The electron transport region ETR may include the compounds of the electron transport region in at least one of an electron injection layer EIL, an electron transport layer ETL, and a hole blocking layer HBL.

If the electron transport region ETR includes an electron transport layer ETL, a thickness of the electron transport layer ETL may be in a range of about 100 Å to about 1,000 Å. For example, the thickness of the electron transport layer ETL may be in a range of about 150 Å to about 500 Å. If the thickness of the electron transport layer ETL satisfies the above-described range, satisfactory electron transport properties may be obtained without substantial increase of a driving voltage. If the electron transport region ETR includes an electron injection layer EIL, a thickness of the electron injection layer EIL may be in a range of about 1 Å to about 100 Å. For example, the thickness of the electron injection layer EIL may be in a range of about 3 Å to about 90 Å. If the thickness of the electron injection layer EIL satisfies the above described range, satisfactory electron injection properties may be obtained without inducing substantial increase of a driving voltage.

The second electrode EL2 is provided on the electron transport region ETR. The second electrode EL2 may be a common electrode. The second electrode EL2 may be a cathode or an anode, but embodiments are not limited thereto. For example, if the first electrode EL1 is an anode, the second cathode EL2 may be a cathode, and if the first electrode EL1 is a cathode, the second electrode EL2 may be an anode.

The second electrode EL2 may be a transmissive electrode, a transflective electrode, or a reflective electrode. If the second electrode EL2 is a transmissive electrode, the second electrode EL2 may include a transparent metal oxide, for example, ITO, IZO, ZnO, ITZO, etc.

If the second electrode EL2 is a transflective electrode or a reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, Yb, W, compounds thereof, or mixtures thereof (for example, AgMg, AgYb, or MgAg). In another embodiment, the second electrode EL2 may have a multi-layered structure including a reflective layer or a transflective layer formed using the above-described materials and a transparent conductive layer formed using ITO, IZO, ZnO, ITZO, etc. For example, the second electrode EL2 may include the aforementioned metal materials, combinations of two or more metal materials selected from the aforementioned metal materials, or oxides of the aforementioned metal materials.

Although not shown in the drawings, the second electrode EL2 may be electrically connected to an auxiliary electrode. If the second electrode EL2 is electrically connected to the auxiliary electrode, the resistance of the second electrode EL2 may decrease.

The light emitting device ED of an embodiment may further include a capping layer CPL disposed on the second electrode EL2. The capping layer CPL may include a multilayer or a single layer.

In an embodiment, the capping layer CPL may include an organic layer or an inorganic layer. For example, if the capping layer CPL includes an inorganic material, the inorganic material may include an alkali metal compound such as LiF, an alkaline earth metal compound such as $MgF_2$, SiON, SiNx, SiOy, etc.

For example, if the capping layer CPL includes an organic material, the organic material may include α-NPD, NPB, TPD, m-MTDATA, $Alq_3$, CuPc, N4,N4,N4',N4'-tetra(biphenyl-4-yl) biphenyl-4,4'-diamine (TPD15), 4,4',4"-tris(carbazol sol-9-yl) triphenylamine (TCTA), etc., or may include an epoxy resin, or acrylate such as methacrylate. In an embodiment, a capping layer CPL may include at least one of Compounds P1 to P5 below, but embodiments are not limited thereto.

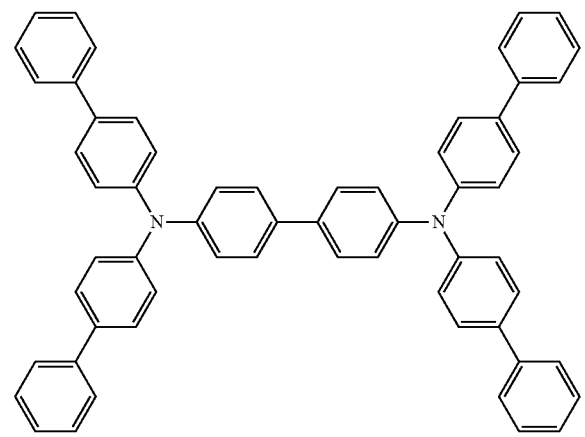

P1

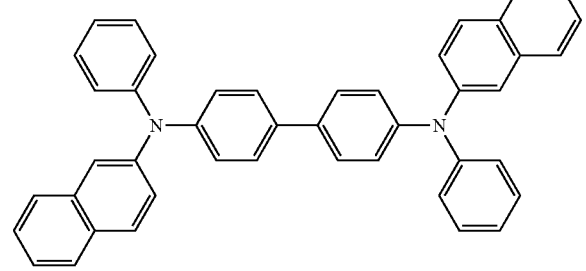

P2

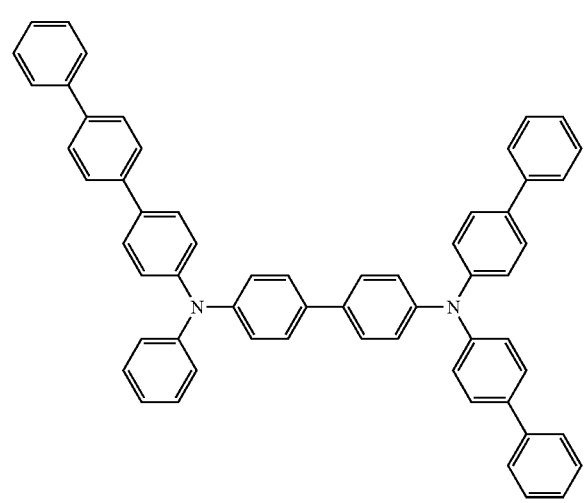

P3

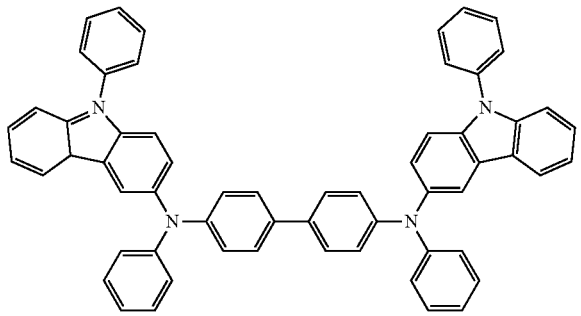

P4

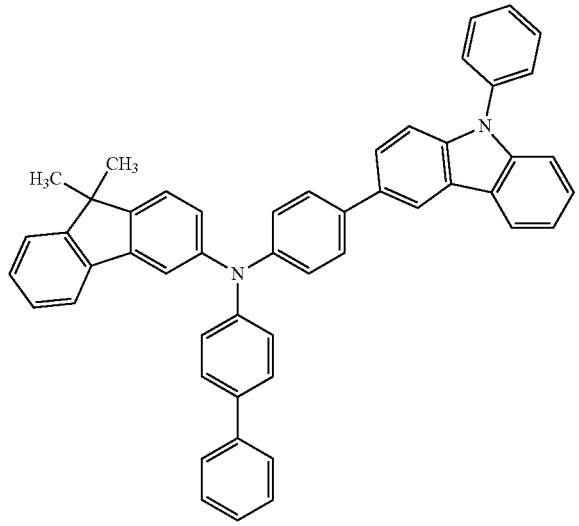

P5

A refractive index of the capping layer CPL may be equal to or greater than about 1.6. For example, the refractive index of the capping layer CPL with respect to light in a wavelength range of about 550 nm to about 660 nm may be equal to or greater than about 1.6.

Figure 7:
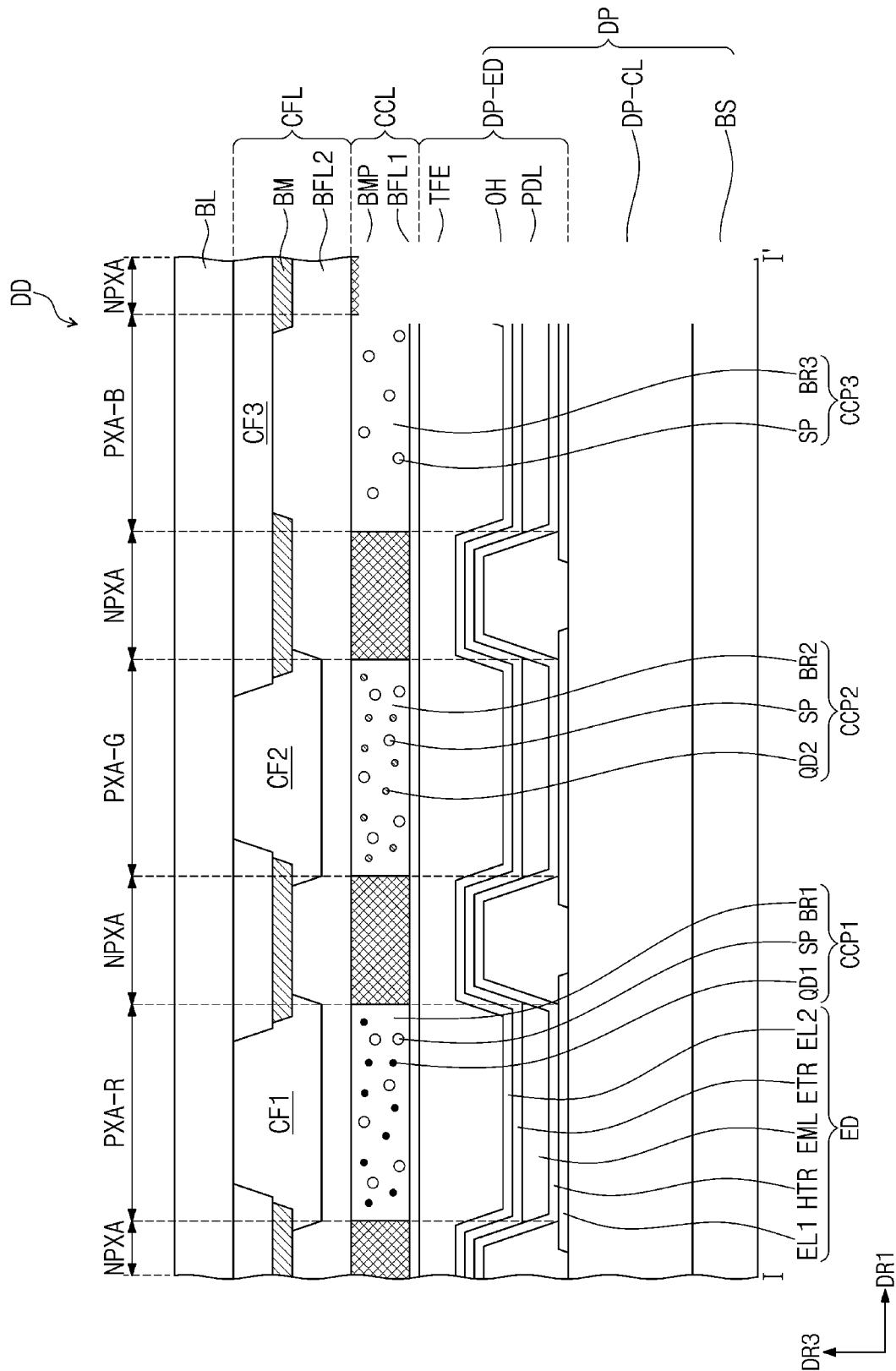
FIG. 7 is a schematic cross-sectional view of a display apparatus according to an embodiment.

FIG. 7 and FIG. 8 are each a schematic cross-sectional view of display apparatuses according to embodiments. In the explanation on the display apparatuses of embodiments with reference to FIG. 7 and FIG. 8, the overlapping features described in FIG. 1 to FIG. 6 will not be explained again, and the differing features will be explained.

Referring to FIG. 7, the display apparatus DD according to an embodiment may include a display panel DP including a display device layer DP-ED, a light controlling layer CCL disposed on the display panel DP, and a color filter layer CFL.

In an embodiment shown in FIG. 7, the display panel DP includes a base layer BS, a circuit layer DP-CL provided on the base layer BS, and a display device layer DP-ED, and the display device layer DP-ED may include a light emitting device ED.

The light emitting device ED may include a first electrode EL1, a hole transport region HTR disposed on the first electrode EL1, an emission layer EML disposed on the hole transport region HTR, an electron transport region ETR disposed on the emission layer EML, and a second electrode EL2 disposed on the electron transport region ETR. The same explanations of the structures of the light emitting devices of FIG. 3 to FIG. 6 may be applied to the structure of the light emitting device ED shown in FIG. 7.

Referring to FIG. 7, the emission layer EML may be disposed in opening portions OH defined in a pixel definition layer PDL. For example, the emission layer EML which may be divided by the pixel definition layer PDL and correspondingly provided to each of luminous areas PXA-R, PXA-G. and PXA-B may emit light in a same wavelength region. In the display apparatus DD of an embodiment, the emission layer EML may emit blue light. Although not shown in the drawings, in an embodiment, the emission layer EML may be provided as a common layer for all luminous areas PXA-R, PXA-G, and PXA-B.

The light controlling layer CCL may be disposed on the display panel DP. The light controlling layer CCL may include a light converter. The light converter may include a quantum dot or a phosphor. The light converter may transform the wavelength of provided light and emit the converted light. For example, the light controlling layer CCL may be a layer including a quantum dot or a layer including a phosphor.

The light controlling layer CCL may include light controlling parts CCP1, CCP2, and CCP3. The light controlling parts CCP1, CCP2, and CCP3 may be separated from one another.

Referring to FIG. 7, a partition pattern BMP may be disposed between the light controlling parts CCP1, CCP2, and CCP3, but embodiments are not limited thereto. In FIG. 7, the partition pattern BMP is shown to not overlap with the light controlling parts CCP1, CCP2, and CCP3, but at least a portion of the edge of the light controlling parts CCP1, CCP2, and CCP3 may be overlap with the partition pattern BMP.

The light controlling layer CCL may include a first light controlling part CCP1 including a first quantum dot QD1 converting first color light provided from the light emitting device ED into second color light, a second light controlling part CCP2 including a second quantum dot QD2 converting first color light into third color light, and a third light controlling part CCP3 transmitting first color light.

In an embodiment, the first light controlling part CCP1 may provide red light which is the second color light, and the second light controlling part CCP2 may provide green light which is the third color light. The third color controlling part CCP3 may transmit and provide blue light which is the first color light provided from the light emitting device ED. For example, the first quantum dot QD1 may be a red quantum dot, and the second quantum dot QD2 may be a green quantum dot. The same description as given to the quantum dots described above may be applied to quantum dots QD1 and QD2.

The light controlling layer CCL may further include a scatterer SP. The first light controlling part CCP1 may include the first quantum dot QD1 and the scatterer SP, the second light controlling part CCP2 may include the second quantum dot QD2 and the scatterer SP, and the third light controlling part CCP3 may not include a quantum dot but include the scatterer SP.

The scatterer SP may include an inorganic particle. For example, the scatterer SP may include at least one of $TiO_2$, ZnO, $Al_2O_3$, $SiO_2$, and hollow silica. The scatterer SP may include at least one of $TiO_2$, ZnO, $Al_2O_3$, $SiO_2$, and hollow silica, or may be a mixture of two or more materials selected from $TiO_2$, ZnO, $Al_2O_3$, $SiO_2$, and hollow silica.

Each of the first light controlling part CCP1, the second light controlling part CCP2, and the third light controlling part CCP3 may include base resins BR1, BR2, and BR3 dispersing the quantum dots QD1 and QD2 and the scatterer SP. In an embodiment, the first light controlling part CCP1 may include the first quantum dot QD1 and the scatterer SP dispersed in the first base resin BR1, the second light controlling part CCP2 may include the second quantum dot QD2 and the scatterer SP dispersed in the second base resin BR2, and the third light controlling part CCP3 may include the scatterer SP dispersed in the third base resin BR3. The base resins BR1, BR2, and BR3 are mediums in which the quantum dots QD1 and QD2 and the scatterer SP are dispersed, and may be composed of various resin compositions which may be generally referred to as a binder. For example, the base resins BR1, BR2, and BR3 may include acrylic resins, urethane-based resins, silicone-based resins, epoxy-based resins, etc. The base resins BR1, BR2, and BR3 may be transparent resins. In an embodiment, the first base resin BR1, the second base resin BR2 and the third base resin BR3 may be the same as or different from each other.

The light controlling layer CCL may include a barrier layer BFL1. The barrier layer BFL1 may prevent penetration of moisture and/or oxygen (hereinafter, will be referred to as "humidity/oxygen"). The barrier layer BFL1 may be disposed on the light controlling parts CCP1, CCP2, and CCP3 to block the exposure of the light controlling parts CCP1, CCP2, and CCP3 to humidity/oxygen. The barrier layer BFL1 may cover the light controlling parts CCP1, CCP2, and CCP3. The barrier layer BFL2 may be provided between the light controlling parts CCP1, CCP2, and CCP3 and a color filter layer CFL.

The barrier layers BFL1 and BFL2 may include at least one inorganic layer. For example, the barrier layers BFL1 and BFL2 may be formed by including an inorganic material. For example, the barrier layers BFL1 and BFL2 may be formed by including silicon nitride, aluminum nitride, zirconium nitride, titanium nitride, hafnium nitride, tantalum nitride, silicon oxide, aluminum oxide, titanium oxide, tin oxide, cerium oxide and silicon oxynitride, or a metal thin film securing light transmittance. The barrier layers BFL1 and BFL2 may further include an organic layer. The barrier layers BFL1 and BFL2 may be composed of a single layer or of multiple layers.

In the display apparatus DD of an embodiment, the color filter layer CFL may be disposed on the light controlling layer CCL. For example, the color filter layer CFL may be disposed directly on the light controlling layer CCL. In an embodiment, the barrier layer BFL2 may be omitted.

The color filter layer CFL may include a light blocking part BM and filters CF1, CF2, and CF3. The color filter layer CFL may include a first filter CF1 transmitting second color light, a second filter CF2 transmitting third color light, and a third filter CF3 transmitting first color light. For example, the first filter CF1 may be a red filter, the second filter CF2 may be a green filter, and the third filter CF3 may be a blue filter. Each of the filters CF1, CF2, and CF3 may include a polymer photosensitive resin and a pigment or dye. The first filter CF1 may include a red pigment or dye, the second filter CF2 may include a green pigment or dye, and the third filter CF3 may include a blue pigment or dye. However, embodiments are not limited thereto, and the third filter CF3 may not include a pigment or dye. The third filter CF3 may include a polymer photosensitive resin and not include a pigment or dye. The third filter CF3 may be transparent. The third filter CF3 may be formed using a transparent photosensitive resin.

In an embodiment, the first filter CF1 and the second filter CF2 may be yellow filters. The first filter CF1 and the second filter CF2 may be provided in one body without distinction.

The light blocking part BM may be a black matrix. The light blocking part BM may be formed by including an organic light blocking material or an inorganic light blocking material including a black pigment or black dye. The light blocking part BM may prevent light leakage phenomenon and divide the boundaries among adjacent filters CF1, CF2, and CF3. In an embodiment, the light blocking part BM may be formed as a blue filter.

Each of the first to third filters CF1, CF2, and CF3 may be disposed corresponding to each of a red luminous area PXA-R, a green luminous area PXA-G, and a blue luminous area PXA-B.

A base substrate BL may be disposed on the color filter layer CFL. The base substrate BL may provide a base surface on which the color filter layer CFL, the light controlling layer CCL, etc. are disposed. The base substrate BL may be a glass substrate, a metal substrate, a plastic substrate, etc. However, embodiments are not limited thereto, and the base substrate BL may include an inorganic layer, an organic layer, or a composite material layer. Although not shown in the drawing, in an embodiment, the base substrate BL may be omitted.

FIG. 8 is a schematic cross-sectional view showing a portion of the display apparatus according to an embodiment. In FIG. 8, a schematic cross-sectional view of a portion corresponding to the display panel DP in FIG. 7 is shown. In a display apparatus DD-TD of an embodiment, the light emitting device ED-BT may include light emitting structures OL-B1, OL-B2, and OL-B3. The light emitting device ED-BT may include oppositely disposed first electrode EL1 and second electrode EL2, and the light emitting structures OL-B1, OL-B2, and OL-B3 stacked in order in a thickness direction and provided between the first electrode EL1 and the second electrode EL2. Each of the light emitting structures OL-B1, OL-B2, and OL-B3 may include an emission layer EML (FIG. 7), and a hole transport region HTR, and an electron transport region ETR, with the emission layer EML (FIG. 7) disposed therebetween.

The light emitting device ED-BT included in the display apparatus DD-TD of an embodiment may be a light emitting device having a tandem structure including multiple emission layers.

In an embodiment shown in FIG. 8, light emitted from the light emitting structures OL-B1, OL-B2, and OL-B3 may be all blue light. However, embodiments are not limited thereto, and the wavelength regions of light emitted from the light emitting structures OL-B1, OL-B2, and OL-B3 may be different from each other. For example, the light emitting device ED-BT including the light emitting structures OL-B1, OL-B2, and OL-B3 emitting light in different wavelength regions may emit white light.

Charge generating layers CGL1 and CGL2 may be disposed between neighboring light emitting structures OL-B1, OL-B2 and OL-B3. The charge generating layers CGL1 and CGL2 may each include a p-type charge generating layer and/or an n-type charge generating layer.

The polycyclic compound of an embodiment may be included in at least one of the light emitting structures OL-B1, OL-B2, and OL-B3 included in the display apparatus DD-TD.

The light emitting device ED according to an embodiment includes the polycyclic compound of an embodiment in at least one functional layer disposed between a first electrode EL1 and a second electrode EL2, and may show improved emission efficiency and improved life characteristics. The light emitting device ED according to an embodiment may include the polycyclic compound of an embodiment in at least one of a hole transport region HTR, an emission layer EML, and an electron transport region ETR, disposed between the first electrode EL1 and the second electrode EL2, or in a capping layer CPL.

For example, the polycyclic compound according to an embodiment may be included in the hole transport region HTR of the light emitting device ED of an embodiment, and the light emitting device of an embodiment may show excellent emission efficiency and long-life characteristics. The polycyclic compound of an embodiment includes an indolo phenoxazine skeleton or an indolo phenothiazine skeleton, and includes a crosslinked structure of 9-phenyl-9H-carbazole by an oxygen atom or a sulfur atom. By the inclusion of the oxygen atom or the sulfur atom, the compound of an embodiment may show improved hole transport capacity. By the inclusion of a heteroatom such as an oxygen atom or a sulfur atom, the molecules may be crosslinked, heat resistance and charge tolerance may be improved, and the stability of a compound and a functional layer may be improved.

Accordingly, the polycyclic compound of an embodiment may have improved stability and hole transport capacity of a material and may contribute to the improvement of the life characteristics and high efficiency properties of a light emitting device.

Hereinafter, the polycyclic compound according to an embodiment and the light emitting device of an embodiment will be explained with reference to embodiments and comparative embodiments. The embodiments below are only examples to assist the understanding of the disclosure, and the scope thereof is not limited thereto.

Examples

1. Synthesis of Polycyclic Compound

The synthesis method of a polycyclic compound according to an embodiment will be explained by illustrating the synthesis methods of Compound A1, Compound A55, Compound A66, Compound A78, Compound A113, Compound A120, Compound A132, and Compound A173 in Compound Group 1A, Compound B18, Compound B19, Compound B54, Compound B71, and Compound B145 in Compound Group 1B, Compound C15, Compound C99, Compound C117, Compound C148, and Compound C158 in Compound Group 1C, and Compound D1 in Compound Group 1D. The synthesis methods of the polycyclic compounds explained hereinafter are embodiments, and the synthesis methods for the polycyclic compound according to an embodiment are not limited to the embodiments below.

The molecular weights of the compounds synthesized by the methods below were confirmed through FAB-MS measurement using JMS-700V of JEOL Co., and the compounds were identified by measuring 1H-NMR using AVAVCE300M of Bruker Biospin K.K.

<Synthesis of Compound A1>

Compound A1 according to an embodiment may be synthesized, for example, by the steps of Reaction 1 below.

[Reaction 1]

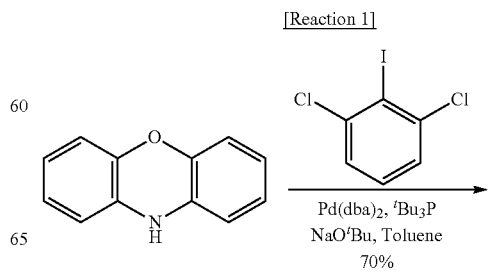

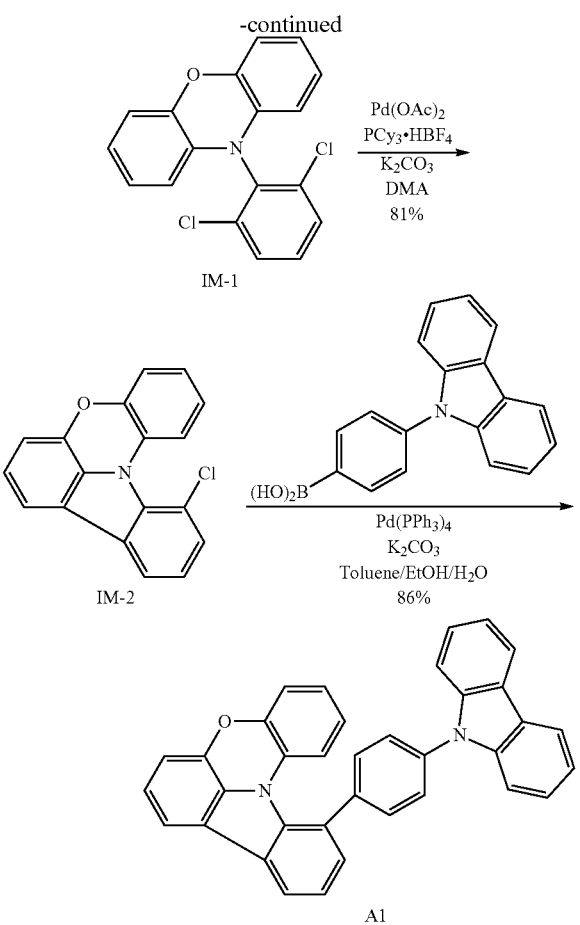

(Synthesis of Intermediate IM-1)

Under an Ar atmosphere, to a 1,000 mL, three neck flask, phenoxazine (20.00 g, 109.2 mmol), Pd(dba)$_2$ (1.88 g, 0.03 equiv, 3.3 mmol), NaO$^t$Bu (31.47 g, 3.0 equiv, 327.5 mmol), toluene (545 mL), 1,3-dichloro-2-iodobenzene (32.77 g, 1.1 equiv, 120.1 mmol) and $^t$Bu$_3$P (2.09 g, 0.1 equiv, 10.9 mmol) were added in order, and heated, refluxed and stirred. After cooling to room temperature, water was added to the reaction solution, and an organic layer was separately taken. Toluene was added to an aqueous layer, and an organic layer was further extracted. Organic layers were collected, washed with a saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-1 (25.08 g, yield 70%).

Through the measurement of FAB-MS, mass number of m/z=328 was observed as a molecular ion peak, and Intermediate IM-1 was identified.

(Synthesis of Intermediate IM-2)

Under an Ar atmosphere, to a 500 mL, three neck flask, Intermediate IM-1 (20.00 g, 60.9 mmol), Pd(OAc)$_2$ (0.82 g, 0.06 equiv, 3.7 mmol), K$_2$CO$_3$ (16.85 g, 2.0 equiv, 121.9 mmol), N,N-dimethylacetamide (DMA) (305 mL) and PCy$_3$·HBF$_4$ (2.69 g, 0.12 equiv, 7.3 mmol) were added in order, and heated, refluxed and stirred. After cooling to room temperature, water was added to the reaction solution, and an organic layer was separately taken. Toluene was added to an aqueous layer, and an organic layer was further extracted. Organic layers were collected, washed with a saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-2 (14.40 g, yield 81%).

Through the measurement of FAB-MS, mass number of m/z=291 was observed as a molecular ion peak, and Intermediate IM-2 was identified.

(Synthesis of Compound A1)

Under an Ar atmosphere, to a 300 mL, three neck flask, Intermediate IM-2 (5.00 g, 17.1 mmol), [(4-(9H-carbazol-9-yl)phenyl)boronic acid (5.41 g, 1.1 equiv, 18.9 mmol), K$_2$CO$_3$ (7.11 g, 3.0 equiv, 51.4 mmol), Pd(PPh$_3$)$_4$ (0.99 g, 0.05 eq, 0.9 mmol), and 120 mL of a mixture solution of toluene/EtOH/H$_2$O (4/2/1) were added in order, and heated to about 80° C. and stirred. After cooling to room temperature, the reaction solution was extracted with toluene. An aqueous layer was removed, and an organic layer was washed with a saturated saline solution and dried with MgSO$_4$. After filtering MgSO$_4$, an organic layer was concentrated, and the crude product thus obtained was separated by silica gel column chromatography (using a mixture solvent of hexane and toluene as a developing layer) to obtain Compound A1 (7.35 g, yield 86%).

Through the measurement of FAB-MS, mass number of m/z=498 was observed as a molecular ion peak, and Compound A1 was identified.

<Synthesis of Compound 55>

Compound A55 according to an embodiment may be synthesized, for example, by the steps of Reaction 2 below.

[Reaction 2]

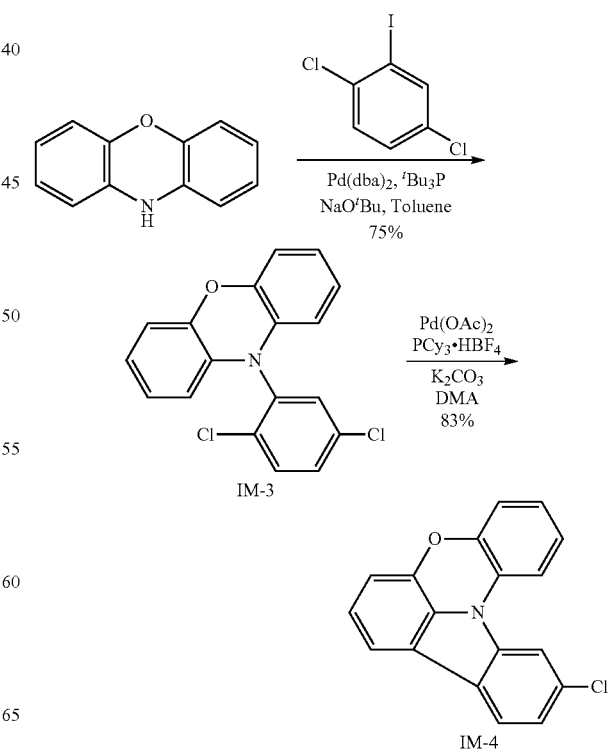

-continued

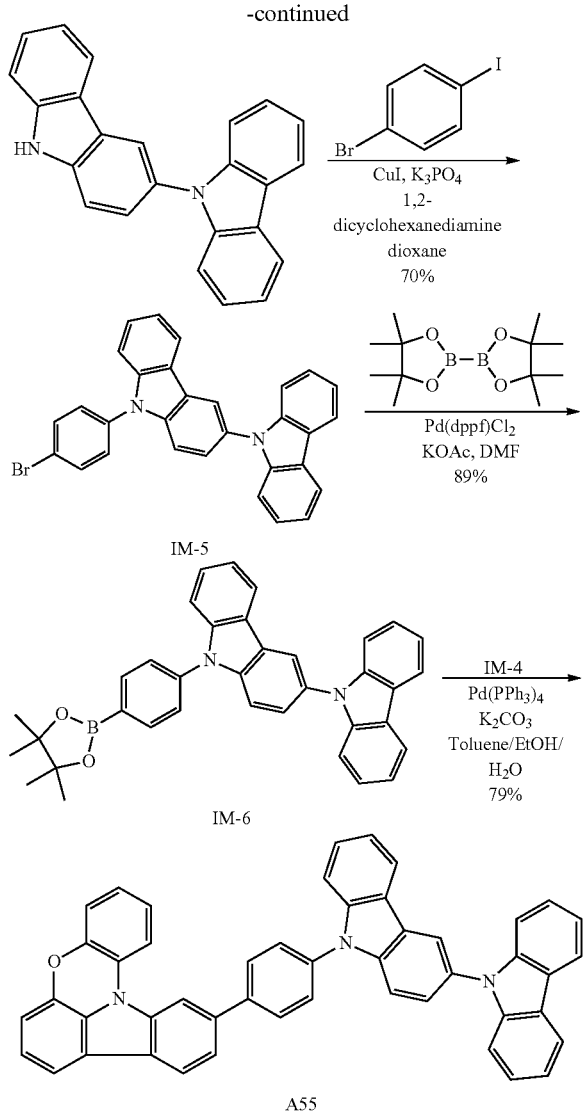

IM-5

IM-6

A55

(Synthesis of Intermediate IM-3)

Under an Ar atmosphere, to a 1,000 mL, three neck flask, phenoxazine (20.00 g, 109.2 mmol), Pd(dba)$_2$ (1.88 g, 0.03 equiv, 3.3 mmol), NaO$^t$Bu (31.47 g, 3.0 equiv, 327.5 mmol), toluene (545 mL), 1,4-dichloro-2-iodobenzene (32.77 g, 1.1 equiv, 120.1 mmol) and $^t$Bu$_3$P (2.09 g, 0.1 equiv, 10.9 mmol) were added in order, and heated, refluxed and stirred. After cooling to room temperature, water was added to the reaction solution, and an organic layer was separately taken. Toluene was added to an aqueous layer, and an organic layer was further extracted. Organic layers were collected, washed with a saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-3 (26.87 g, yield 75%).

Through the measurement of FAB-MS, mass number of m/z=328 was observed as a molecular ion peak, and Intermediate IM-3 was identified.

(Synthesis of Intermediate IM-4)

Under an Ar atmosphere, to a 500 mL, three neck flask, Intermediate IM-3 (20.00 g, 60.9 mmol), Pd(OAc)$_2$ (0.82 g, 0.06 equiv, 3.7 mmol), K$_2$CO$_3$ (16.85 g, 2.0 equiv, 121.9 mmol), N,N-dimethylacetamide (DMA) (305 mL) and PCy$_3$·HBF$_4$ (2.69 g, 0.12 equiv, 7.3 mmol) were added in order, and heated, refluxed and stirred. After cooling to room temperature, water was added to the reaction solution, and an organic layer was separately taken. Toluene was added to an aqueous layer, and an organic layer was further extracted. Organic layers were collected, washed with a saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-4 (14.76 g, yield 83%).

Through the measurement of FAB-MS, mass number of m/z=291 was observed as a molecular ion peak, and Intermediate IM-4 was identified.

(Synthesis of Intermediate IM-5)

Under an Ar atmosphere, to a 500 mL, three neck flask, 9H-3,9'-bicarbazole (20.00 g, 60.2 mmol), CuI (1.15 g, 0.1 equiv, 6.0 mmol), K$_3$PO$_4$ (38.81 g, 3.0 equiv, 180.5 mmol), 1-bromo-4-iodobenzene (85.11 g, 5.0 equiv, 300.8 mmol), 1,4-dioxane (300 mL), and 1,2-cyclohexanediamine (1.37 g, 0.2 equiv, 12.0 mmol) were added in order, and heated, refluxed and stirred. After cooling to room temperature, water was added to the reaction solution, suction filtration was performed using celite, and an organic layer was separately taken. Toluene was added to an aqueous layer, and an organic layer was further extracted. Organic layers were collected, washed with a saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-5 (21.88 g, yield 70%).

Through the measurement of FAB-MS, mass number of m/z=519 was observed as a molecular ion peak, and Intermediate IM-5 was identified.

(Synthesis of Intermediate IM-6)

Under an Ar atmosphere, to a 300 mL, three neck flask, Intermediate IM-5 (15.00 g, 28.9 mmol), Pd(dppf)Cl$_2$ (2.39 g, 0.1 equiv, 2.9 mmol), KOAc (5.67 g, 2.0 equiv, 57.7 mmol), DMF (144 mL) and bis(pinacolato)diboron (8.80 g, 1.2 equiv, 34.6 mmol) were added in order, and heated, refluxed and stirred. After cooling to room temperature, water was added to the reaction solution, and an organic layer was separately taken. Toluene was added to an aqueous layer, and an organic layer was further extracted. Organic layers were collected, washed with a saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-6 (14.56 g, yield 89%).

Through the measurement of FAB-MS, mass number of m/z=566 was observed as a molecular ion peak, and Intermediate IM-6 was identified.

(Synthesis of Compound A55)

Under an Ar atmosphere, to a 300 mL, three neck flask, Intermediate IM-4 (5.00 g, 17.1 mmol), Intermediate IM-6 (10.68 g, 1.1 equiv, 18.9 mmol), K$_2$CO$_3$ (7.11 g, 3.0 equiv, 51.4 mmol), Pd(PPh$_3$)$_4$ (0.99 g, 0.05 eq, 0.9 mmol), and 120 mL of a mixture solution of toluene/EtOH/H$_2$O (4/2/1) were added in order, and heated to about 80° C. and stirred. After cooling to room temperature, the reaction solution was extracted with toluene. An aqueous layer was removed, and an organic layer was washed with a saturated saline solution and dried with MgSO$_4$. After filtering MgSO$_4$, an organic layer was concentrated, and the crude product thus obtained was separated by silica gel column chromatography (using a mixture solvent of hexane and toluene as a developing layer) to obtain Compound A55 (8.99 g, yield 79%).

Through the measurement of FAB-MS, mass number of m/z=663 was observed as a molecular ion peak, and Compound A55 was identified.

<Synthesis of Compound A113>

Compound A113 according to an embodiment may be synthesized, for example, by the steps of Reaction 3 below.

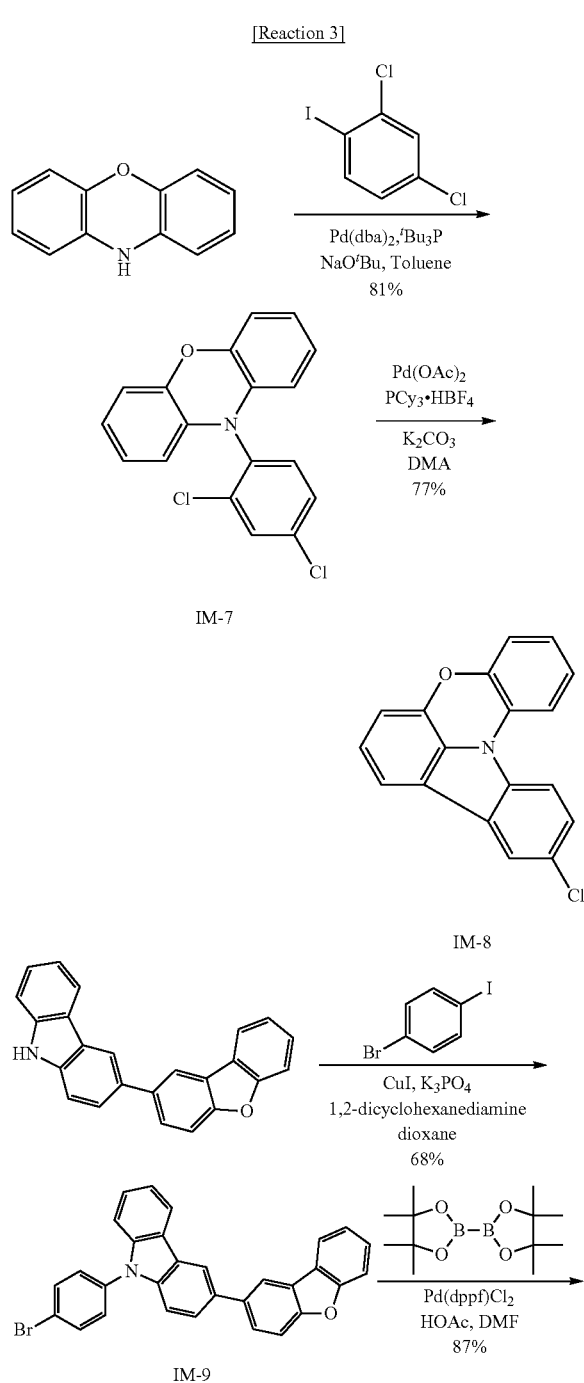

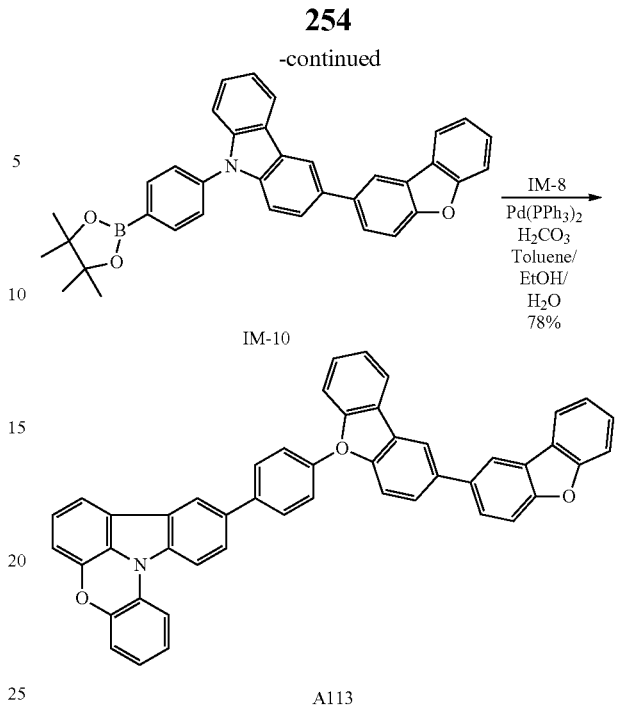

(Synthesis of Intermediate IM-7)

Under an Ar atmosphere, to a 1,000 mL, three neck flask, phenoxazine (20.00 g, 109.2 mmol), Pd(dba)$_2$ (1.88 g, 0.03 equiv, 3.3 mmol), NaO$^t$Bu (31.47 g, 3.0 equiv, 327.5 mmol), toluene (545 mL), 2,4-dichloro-1-iodobenzene (32.77 g, 1.1 equiv, 120.1 mmol) and $^t$Bu$_3$P (2.09 g, 0.1 equiv, 10.9 mmol) were added in order, and heated, refluxed and stirred. After cooling to room temperature, water was added to the reaction solution, and an organic layer was separately taken. Toluene was added to an aqueous layer, and an organic layer was further extracted. Organic layers were collected, washed with a saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-7 (29.02 g, yield 81%).

Through the measurement of FAB-MS, mass number of m/z=328 was observed as a molecular ion peak, and Intermediate IM-7 was identified.

(Synthesis of Intermediate IM-8)

Under an Ar atmosphere, to a 500 mL, three neck flask, Intermediate IM-7 (20.00 g, 60.9 mmol), Pd(OAc)$_2$ (0.82 g, 0.06 equiv, 3.7 mmol), K$_2$CO$_3$ (16.85 g, 2.0 equiv, 121.9 mmol), N,N-dimethylacetamide (DMA) (305 mL) and PCy$_3$·HBF$_4$ (2.69 g, 0.12 equiv, 7.3 mmol) were added in order, and heated, refluxed and stirred. After cooling to room temperature, water was added to the reaction solution, and an organic layer was separately taken. Toluene was added to an aqueous layer, and an organic layer was further extracted. Organic layers were collected, washed with a saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-8 (13.69 g, yield 77%).

Through the measurement of FAB-MS, mass number of m/z=291 was observed as a molecular ion peak, and Intermediate IM-8 was identified.

(Synthesis of Intermediate IM-9)

Under an Ar atmosphere, to a 500 mL, three neck flask, 3-(dibenzofuran-2-yl)-9H-carbazole (20.00 g, 60.0 mmol), CuI (1.15 g, 0.1 equiv, 6.0 mmol), K$_3$PO$_4$ (38.20 g, 3.0 equiv, 180.0 mmol), 1-bromo-4-iodobenzene (84.86 g, 5.0 equiv, 299.9 mmol), 1,4-dioxane (300 mL), and 1,2-cyclohexanediamine (1.37 g, 0.2 equiv, 12.0 mmol) were added in order, and heated, refluxed and stirred. After cooling to room temperature, water was added to the reaction solution, suction filtration was performed using celite, and an organic layer was separately taken. Toluene was added to an aqueous layer, and an organic layer was further extracted. Organic layers were collected, washed with a saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-9 (19.92 g, yield 68%).

Through the measurement of FAB-MS, mass number of m/z=488 was observed as a molecular ion peak, and Intermediate IM-9 was identified.

(Synthesis of Intermediate IM-10)

Under an Ar atmosphere, to a 300 mL, three neck flask, Intermediate IM-9 (15.00 g, 30.7 mmol), Pd(dppf)Cl$_2$ (2.50 g, 0.1 equiv, 3.1 mmol), KOAc (6.03 g, 2.0 equiv, 61.4 mmol), DMF (154 mL) and bis(pinacolato)diboron (9.36 g, 1.2 equiv, 36.9 mmol) were added in order, and heated, refluxed and stirred. After cooling to room temperature, water was added to the reaction solution, and an organic layer was separately taken. Toluene was added to an aqueous layer, and an organic layer was further extracted. Organic layers were collected, washed with a saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-10 (14.31 g, yield 87%).

Through the measurement of FAB-MS, mass number of m/z=535 was observed as a molecular ion peak, and Intermediate IM-10 was identified.

(Synthesis of Compound A113)

Under an Ar atmosphere, to a 300 mL, three neck flask, Intermediate IM-8 (5.00 g, 17.1 mmol), Intermediate IM-10 (10.09 g, 1.1 equiv, 18.9 mmol), K$_2$CO$_3$ (7.11 g, 3.0 equiv, 51.4 mmol), Pd(PPh$_3$)$_4$ (0.99 g, 0.05 eq, 0.9 mmol), and 120 mL of a mixture solution of toluene/EtOH/H$_2$O (4/2/1) were added in order, and heated to about 80° C. and stirred. After cooling to room temperature, the reaction solution was extracted with toluene. An aqueous layer was removed, and an organic layer was washed with a saturated saline solution and dried with MgSO$_4$. After filtering MgSO$_4$, an organic layer was concentrated, and the crude product thus obtained was separated by silica gel column chromatography (using a mixture solvent of hexane and toluene as a developing layer) to obtain Compound A113 (8.55 g, yield 75%).

Through the measurement of FAB-MS, mass number of m/z=664 was observed as a molecular ion peak, and Compound A113 was identified.

<Synthesis of Compound A132>

Compound A132 according to an embodiment may be synthesized, for example, by the steps of Reaction 4 below.

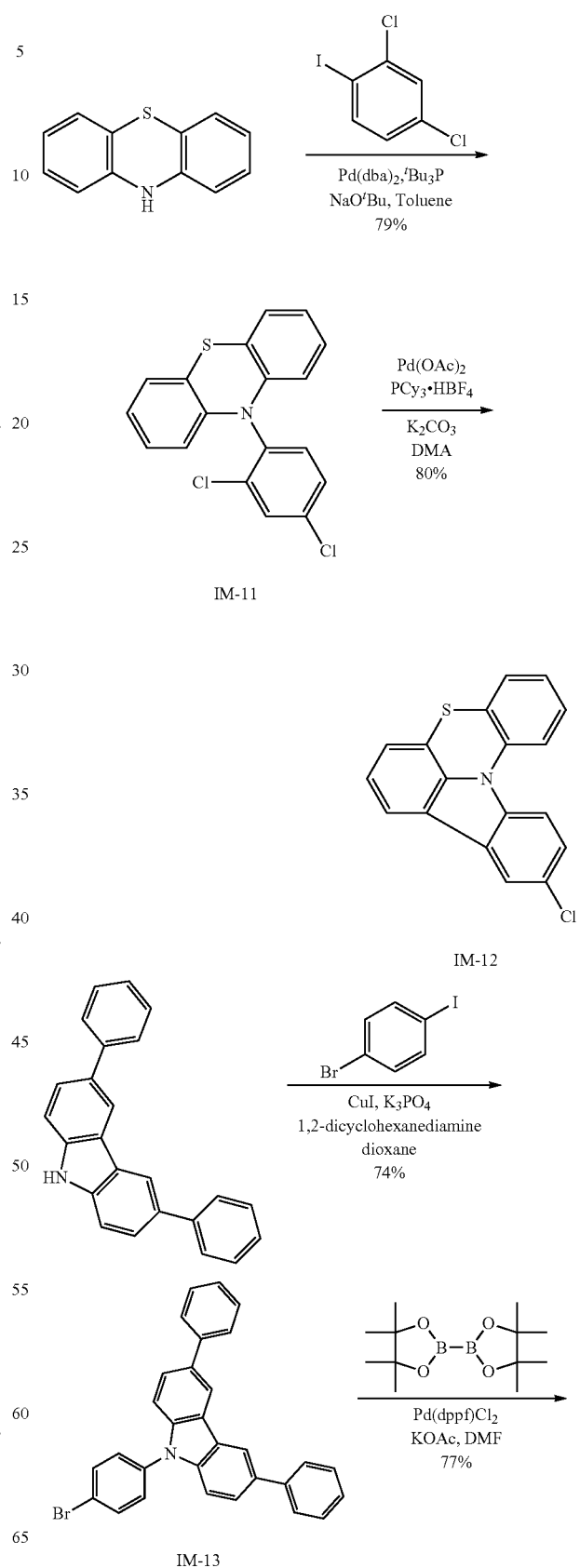

[Reaction 4]

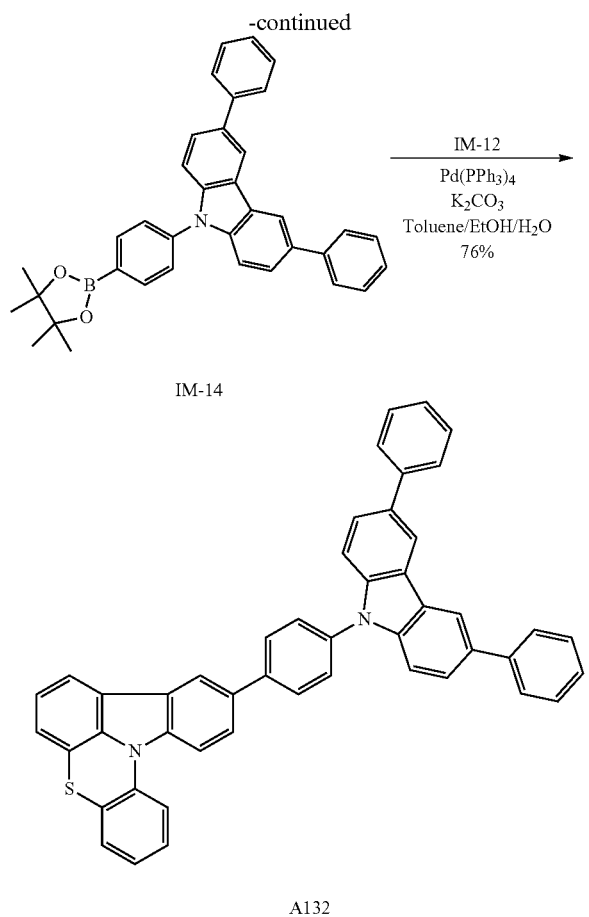

(Synthesis of Intermediate IM-11)

Under an Ar atmosphere, to a 1,000 mL, three neck flask, phenothiazine (20.00 g, 100.4 mmol), Pd(dba)$_2$ (1.73 g, 0.03 equiv, 3.0 mmol), NaO$^t$Bu (28.94 g, 3.0 equiv, 301.1 mmol), toluene (502 mL), 1,3-dichloro-4-iodobenzene (30.13 g, 1.1 equiv, 110.4 mmol) and $^t$Bu$_3$P (2.03 g, 0.1 equiv, 10.0 mmol) were added in order, and heated, refluxed and stirred. After cooling to room temperature, water was added to the reaction solution, and an organic layer was separately taken. Toluene was added to an aqueous layer, and an organic layer was further extracted. Organic layers were collected, washed with a saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-11 (27.30 g, yield 79%).

Through the measurement of FAB-MS, mass number of m/z=344 was observed as a molecular ion peak, and Intermediate IM-11 was identified.

(Synthesis of Intermediate IM-12)

Under an Ar atmosphere, to a 500 mL, three neck flask, Intermediate IM-11 (20.00 g, 58.1 mmol), Pd(OAc)$_2$ (0.78 g, 0.06 equiv, 3.4 mmol), K$_2$CO$_3$ (16.06 g, 2.0 equiv, 116.2 mmol), N,N-dimethylacetamide (DMA) (290 mL) and PCy$_3$·HBF$_4$ (2.57 g, 0.12 equiv, 7.0 mmol) were added in order, and heated, refluxed and stirred. After cooling to room temperature, water was added to the reaction solution, and an organic layer was separately taken. Toluene was added to an aqueous layer, and an organic layer was further extracted. Organic layers were collected, washed with a saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-12 (14.31 g, yield 80%).

Through the measurement of FAB-MS, mass number of m/z=307 was observed as a molecular ion peak, and Intermediate IM-12 was identified.

(Synthesis of Intermediate IM-13)

Under an Ar atmosphere, to a 500 mL, three neck flask, 3,6-diphenyl-9H-carbazole (20.00 g, 62.6 mmol), CuI (1.19 g, 0.1 equiv, 6.3 mmol), K$_3$PO$_4$ (39.87 g, 3.0 equiv, 187.8 mmol), 1-bromo-4-iodobenzene (88.57 g, 5.0 equiv, 313.1 mmol), 1,4-dioxane (313 mL), and 1,2-cyclohexanediamine (1.43 g, 0.2 equiv, 12.5 mmol) were added in order, and heated, refluxed and stirred. After cooling to room temperature, water was added to the reaction solution, suction filtration was performed using celite, and an organic layer was separately taken. Toluene was added to an aqueous layer, and an organic layer was further extracted. Organic layers were collected, washed with a saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-13 (23.47 g, yield 74%).

Through the measurement of FAB-MS, mass number of m/z=506 was observed as a molecular ion peak, and Intermediate IM-13 was identified.

(Synthesis of Intermediate IM-14)

Under an Ar atmosphere, to a 300 mL, three neck flask, Intermediate IM-13 (15.00 g, 29.6 mmol), Pd(dppf)Cl$_2$ (2.42 g, 0.1 equiv, 3.0 mmol), KOAc (5.81 g, 2.0 equiv, 59.2 mmol), DMF (148 mL) and bis(pinacolato)diboron (9.02 g, 1.2 equiv, 35.5 mmol) were added in order, and heated, refluxed and stirred. After cooling to room temperature, water was added to the reaction solution, and an organic layer was separately taken. Toluene was added to an aqueous layer, and an organic layer was further extracted. Organic layers were collected, washed with a saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-14 (12.62 g, yield 77%).

Through the measurement of FAB-MS, mass number of m/z=553 was observed as a molecular ion peak, and Intermediate IM-14 was identified.

(Synthesis of Compound A132)

Under an Ar atmosphere, to a 300 mL, three neck flask, Intermediate IM-12 (5.00 g, 16.2 mmol), Intermediate IM-14 (9.89 g, 1.1 equiv, 17.9 mmol), K$_2$CO$_3$ (6.74 g, 3.0 equiv, 48.7 mmol), Pd(PPh$_3$)$_4$ (0.94 g, 0.05 eq, 0.8 mmol), and 114 mL of a mixture solution of toluene/EtOH/H$_2$O (4/2/1) were added in order, and heated to about 80° C. and stirred. After cooling to room temperature, the reaction solution was extracted with toluene. An aqueous layer was removed, and an organic layer was washed with a saturated saline solution and dried with MgSO$_4$. After filtering MgSO$_4$, an organic layer was concentrated, and the crude product thus obtained was separated by silica gel column chromatography (using a mixture solvent of hexane and toluene as a developing layer) to obtain Compound A132 (8.23 g, yield 76%).

Through the measurement of FAB-MS, mass number of m/z=666 was observed as a molecular ion peak, and Compound A132 was identified.

<Synthesis of Compound A173>

Compound A173 according to an embodiment may be synthesized, for example, by the steps of Reaction 5 below.

[Reaction 5]

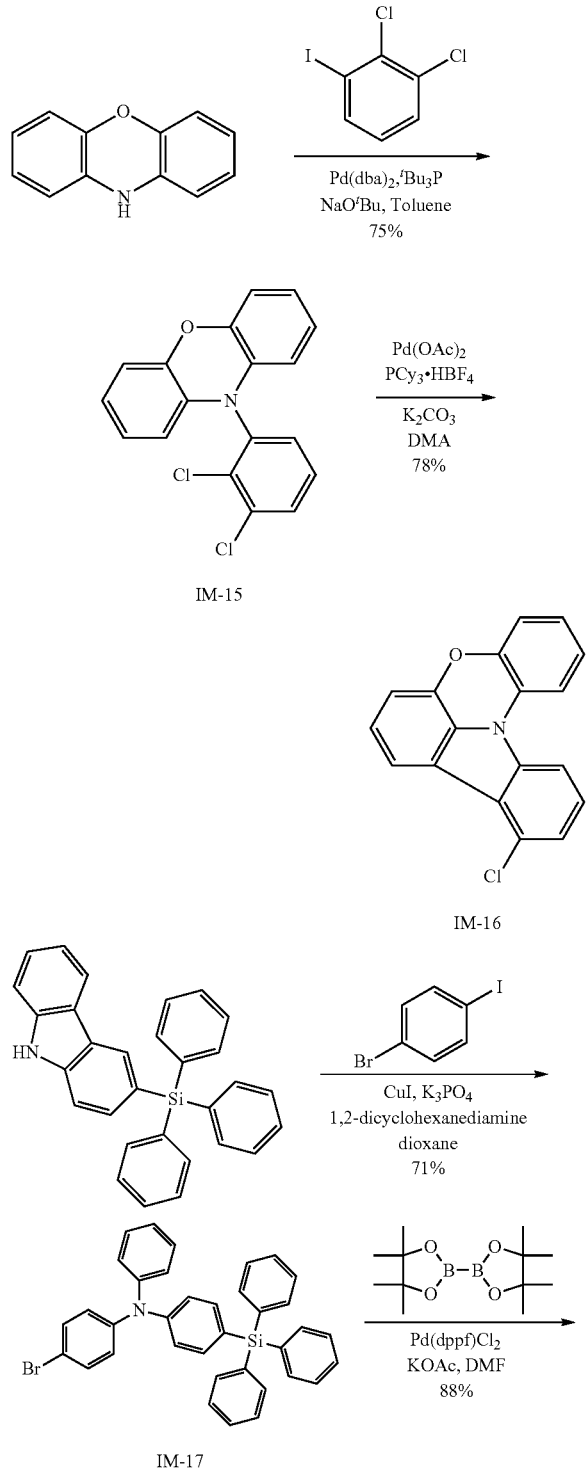

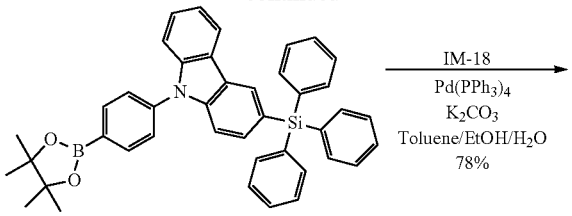

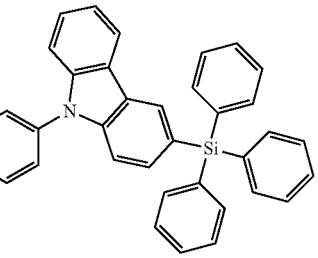

A173

(Synthesis of Intermediate IM-15)

Under an Ar atmosphere, to a 1,000 mL, three neck flask, phenoxazine (20.00 g, 109.2 mmol), Pd(dba)$_2$ (1.88 g, 0.03 equiv, 3.3 mmol), NaO$^t$Bu (31.47 g, 3.0 equiv, 327.5 mmol), toluene (545 mL), 1,2-dichloro-3-iodobenzene (32.77 g, 1.1 equiv, 120.1 mmol) and $^t$Bu$_3$P (2.09 g, 0.1 equiv, 10.9 mmol) were added in order, and heated, refluxed and stirred. After cooling to room temperature, water was added to the reaction solution, and an organic layer was separately taken. Toluene was added to an aqueous layer, and an organic layer was further extracted. Organic layers were collected, washed with a saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-15 (26.87 g, yield 75%).

Through the measurement of FAB-MS, mass number of m/z=328 was observed as a molecular ion peak, and Intermediate IM-15 was identified.

(Synthesis of Intermediate IM-16)

Under an Ar atmosphere, to a 500 mL, three neck flask, Intermediate IM-15 (20.00 g, 60.9 mmol), Pd(OAc)$_2$ (0.82 g, 0.06 equiv, 3.7 mmol), K$_2$CO$_3$ (16.85 g, 2.0 equiv, 121.9 mmol), N,N-dimethylacetamide (DMA) (305 mL) and PCy$_3$·HBF$_4$ (2.69 g, 0.12 equiv, 7.3 mmol) were added in order, and heated, refluxed and stirred. After cooling to room temperature, water was added to the reaction solution, and an organic layer was separately taken. Toluene was added to an aqueous layer, and an organic layer was further extracted. Organic layers were collected, washed with a saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-16 (13.87 g, yield 78%).

Through the measurement of FAB-MS, mass number of m/z=291 was observed as a molecular ion peak, and Intermediate IM-16 was identified.

(Synthesis of Intermediate IM-17)

Under an Ar atmosphere, to a 500 mL, three neck flask, 3-(triphenylsilyl)-9H-carbazole (20.00 g, 47.0 mmol), CuI (0.89 g, 0.1 equiv, 4.7 mmol), K$_3$PO$_4$ (29.92 g, 3.0 equiv, 140.9 mmol), 1-bromo-4-iodobenzene (66.47 g, 5.0 equiv, 235.0 mmol), 1,4-dioxane (235 mL), and 1,2-cyclohexanediamine (1.07 g, 0.2 equiv, 9.40 mmol) were added in order, and heated, refluxed and stirred. After cooling to room temperature, water was added to the reaction solution, suction filtration was performed using celite, and an organic layer was separately taken. Toluene was added to an aqueous layer, and an organic layer was further extracted. Organic layers were collected, washed with a saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-17 (19.37 g, yield 71%).

Through the measurement of FAB-MS, mass number of m/z=580 was observed as a molecular ion peak, and Intermediate IM-17 was identified.

(Synthesis of Intermediate IM-18)

Under an Ar atmosphere, to a 300 mL, three neck flask, Intermediate IM-17 (15.00 g, 25.8 mmol), Pd(dppf)Cl$_2$ (2.11 g, 0.1 equiv, 2.6 mmol), KOAc (5.07 g, 2.0 equiv, 51.7 mmol), DMF (130 mL) and bis(pinacolato)diboron (7.87 g, 1.2 equiv, 31.0 mmol) were added in order, and heated, refluxed and stirred. After cooling to room temperature, water was added to the reaction solution, and an organic layer was separately taken. Toluene was added to an aqueous layer, and an organic layer was further extracted. Organic layers were collected, washed with a saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-18 (14.27 g, yield 88%).

Through the measurement of FAB-MS, mass number of m/z=627 was observed as a molecular ion peak, and Intermediate IM-18 was identified.

(Synthesis of Compound A173)

Under an Ar atmosphere, to a 300 mL, three neck flask, Intermediate IM-6 (5.00 g, 17.1 mmol), Intermediate IM-18 (11.83 g, 1.1 equiv, 18.9 mmol), K$_2$CO$_3$ (7.11 g, 3.0 equiv, 51.4 mmol), Pd(PPh$_3$)$_4$ (0.99 g, 0.05 eq, 0.9 mmol), and 120 mL of a mixture solution of toluene/EtOH/H$_2$O (4/2/1) were added in order, and heated to about 80° C. and stirred. After cooling to room temperature, the reaction solution was extracted with toluene. An aqueous layer was removed, and an organic layer was washed with a saturated saline solution and dried with MgSO$_4$. After filtering MgSO$_4$, an organic layer was concentrated, and the crude product thus obtained was separated by silica gel column chromatography (using a mixture solvent of hexane and toluene as a developing layer) to obtain Compound A173 (10.12 g, yield 78%).

Through the measurement of FAB-MS, mass number of m/z=756 was observed as a molecular ion peak, and Compound A173 was identified.

<Synthesis of Compound B19>

Compound B19 according to an embodiment may be synthesized, for example, by the steps of Reaction 6 below.

[Reaction 6]

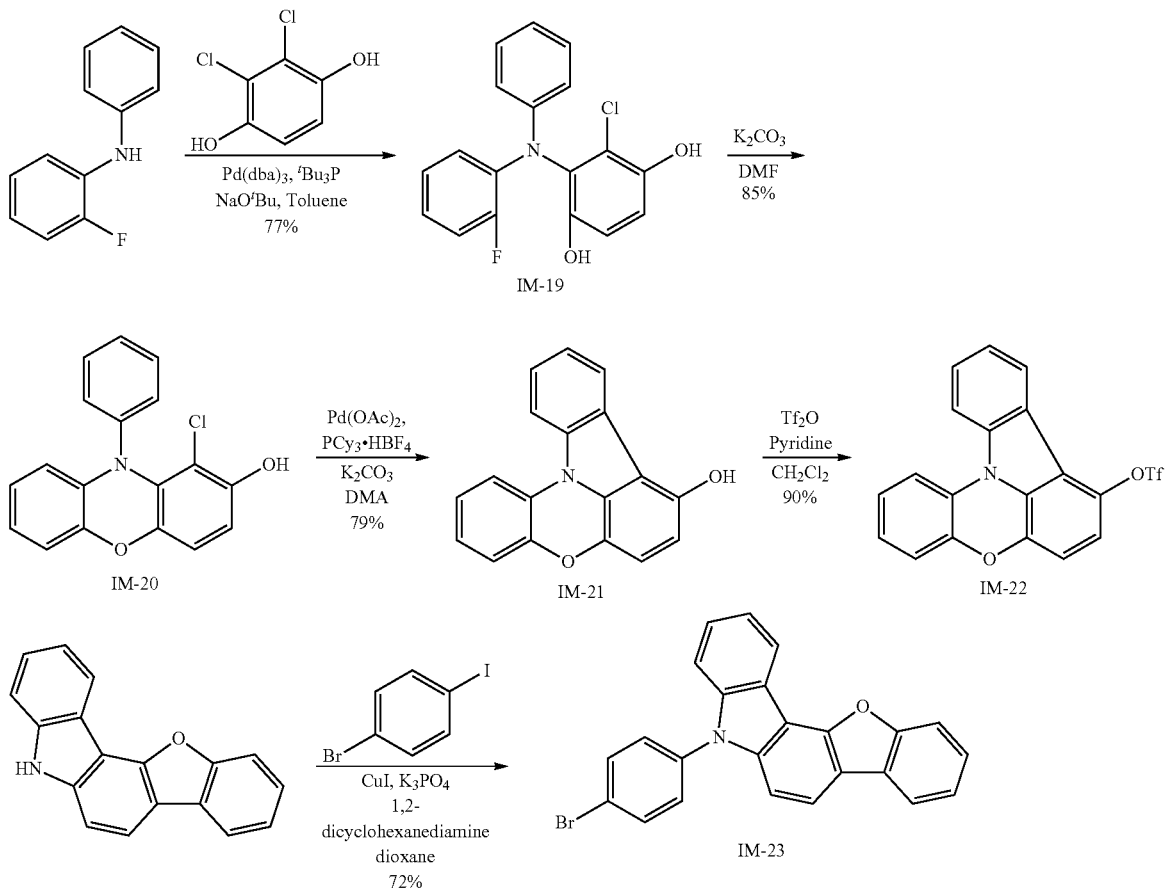

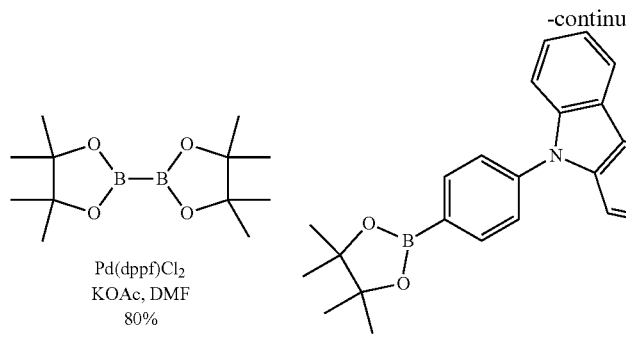
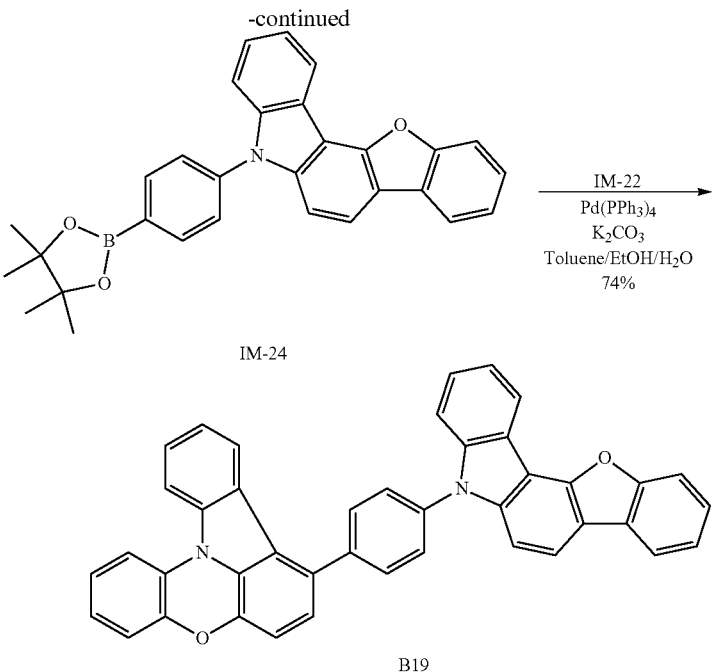

(Synthesis of Intermediate IM-19)

Under an Ar atmosphere, to a 1,000 mL, three neck flask, 2-fluoro-N-phenylaniline (20.00 g, 106.8 mmol), Pd(dba)$_2$ (1.84 g, 0.03 equiv, 3.9 mmol), NaO$^t$Bu (11.29 g, 1.1 equiv, 117.8 mmol), toluene (534 mL), p-biphenylamine (21.03 g, 1.1 equiv, 117.5 mmol) and $^t$Bu$_3$P (2.16 g, 0.1 equiv, 10.7 mmol) were added in order, and heated, refluxed and stirred. After cooling to room temperature, water was added to the reaction solution, and an organic layer was separately taken. Toluene was added to an aqueous layer, and an organic layer was further extracted. Organic layers were collected, washed with a saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-19 (27.12 g, yield 77%).

Through the measurement of FAB-MS, mass number of m/z=329 was observed as a molecular ion peak, and Intermediate IM-19 was identified.

(Synthesis of Intermediate IM-20)

Under an Ar atmosphere, to a 500 mL, three neck flask, Intermediate IM-19 (20.00 g, 60.7 mmol), DMF (303 mL), and K$_2$CO$_3$ (33.53 g, 4 equiv, 242.6 mmol) were added in order, and heated to about 140° C. and stirred. After cooling to room temperature, H$_2$O was added to the reaction solution, and an organic layer was extracted with toluene, washed with a saturated saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-20 (15.97 g, yield 85%).

Through the measurement of FAB-MS, mass number of m/z=309 was observed as a molecular ion peak, and Intermediate IM-20 was identified.

(Synthesis of Intermediate IM-21)

Under an Ar atmosphere, to a 500 mL, three neck flask, Intermediate IM-20 (15.00 g, 48.4 mmol), Pd(OAc)$_2$ (0.65 g, 0.06 equiv, 2.9 mmol), K$_2$CO$_3$ (13.39 g, 2.0 equiv, 96.9 mmol), N,N-dimethylacetamide (DMA) (242 mL) and PCy$_3$·HBF$_4$ (2.14 g, 0.12 equiv, 5.8 mmol) were added in order, and heated, refluxed and stirred. After cooling to room temperature, water was added to the reaction solution, and an organic layer was separately taken. Toluene was added to an aqueous layer, and an organic layer was further extracted. Organic layers were collected, washed with a saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-21 (10.46 g, yield 79%).

Through the measurement of FAB-MS, mass number of m/z=273 was observed as a molecular ion peak, and Intermediate IM-21 was identified.

(Synthesis of Intermediate IM-22)

Under an Ar atmosphere, to a 500 mL, three neck flask, Intermediate IM-21 (10.00 g, 36.6 mmol), pyridine (8.68 g, 3.0 equiv, 109.8 mmol), CH$_2$Cl$_2$ (282 mL) and Tf$_2$O (15.49 g, 1.5 equiv, 54.9 mmol) were added in order, and stirred at room temperature. After finishing the reaction, H$_2$O was added to the reaction solution, and an organic layer was extracted with CH$_2$Cl$_2$. The organic layer was washed with a saturated saline solution and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-22 (13.35 g, yield 90%).

Through the measurement of FAB-MS, mass number of m/z=405 was observed as a molecular ion peak, and Intermediate IM-22 was identified.

(Synthesis of Intermediate IM-23)

Under an Ar atmosphere, to a 500 mL, three neck flask, 5H-benzofuro[3,2-c]carbazole (20.00 g, 77.7 mmol), CuI (1.48 g, 0.1 equiv, 7.8 mmol), K$_3$PO$_4$ (49.50 g, 3.0 equiv, 233.2 mmol), 1-bromo-4-iodobenzene (109.96 g, 5.0 equiv, 388.7 mmol), 1,4-dioxane (388 mL), and 1,2-cyclohexanediamine (1.78 g, 0.2 equiv, 15.5 mmol) were added in order, and heated, refluxed and stirred. After cooling to room temperature, water was added to the reaction solution, suction filtration was performed using celite, and an organic layer was separately taken. Toluene was added to an aqueous layer, and an organic layer was further extracted. Organic layers were collected, washed with a saline solution, and dried with $MgSO_4$. After filtering $MgSO_4$, an organic layer was concentrated, and the crude product thus obtained was separated by silica gel column chromatography (using a mixture solvent of hexane and toluene as a developing layer) to obtain Intermediate IM-23 (24.87 g, yield 72%).

Through the measurement of FAB-MS, mass number of m/z=444 was observed as a molecular ion peak, and Intermediate IM-23 was identified.

(Synthesis of Intermediate IM-24)

Under an Ar atmosphere, to a 300 mL, three neck flask, Intermediate IM-23 (15.00 g, 33.8 mmol), Pd(dppf)$Cl_2$ (2.76 g, 0.1 equiv, 3.4 mmol), KOAc (6.63 g, 2.0 equiv, 67.5 mmol), DMF (168 mL) and bis(pinacolato)diboron (10.29 g, 1.2 equiv, 40.5 mmol) were added in order, and heated, refluxed and stirred. After cooling to room temperature, water was added to the reaction solution, and an organic layer was separately taken. Toluene was added to an aqueous layer, and an organic layer was further extracted. Organic layers were collected, washed with a saline solution, and dried with $MgSO_4$. After filtering $MgSO_4$, an organic layer was concentrated, and the crude product thus obtained was separated by silica gel column chromatography (using a mixture solvent of hexane and toluene as a developing layer) to obtain Intermediate IM-24 (13.27 g, yield 80%).

Through the measurement of FAB-MS, mass number of m/z=491 was observed as a molecular ion peak, and Intermediate IM-24 was identified.

(Synthesis of Compound B19)

Under an Ar atmosphere, to a 300 mL, three neck flask, Intermediate IM-22 (5.00 g, 12.3 mmol), Intermediate IM-18 (6.67 g, 1.1 equiv, 13.6 mmol), $K_2CO_3$ (5.11 g, 3.0 equiv, 37.0 mmol), Pd(PPh$_3$)$_4$ (0.71 g, 0.05 eq, 0.6 mmol), and 86 mL of a mixture solution of toluene/EtOH/$H_2O$ (4/2/1) were added in order, and heated to about 80° C. and stirred. After cooling to room temperature, the reaction solution was extracted with toluene. An aqueous layer was removed, and an organic layer was washed with a saturated saline solution and dried with $MgSO_4$. After filtering $MgSO_4$, an organic layer was concentrated, and the crude product thus obtained was separated by silica gel column chromatography (using a mixture solvent of hexane and toluene as a developing layer) to obtain Compound B19 (5.37 g, yield 74%).

Through the measurement of FAB-MS, mass number of m/z=588 was observed as a molecular ion peak, and Compound B19 was identified.

<Synthesis of Compound B54>

Compound B54 according to an embodiment may be synthesized, for example, by the steps of Reaction 7 below.

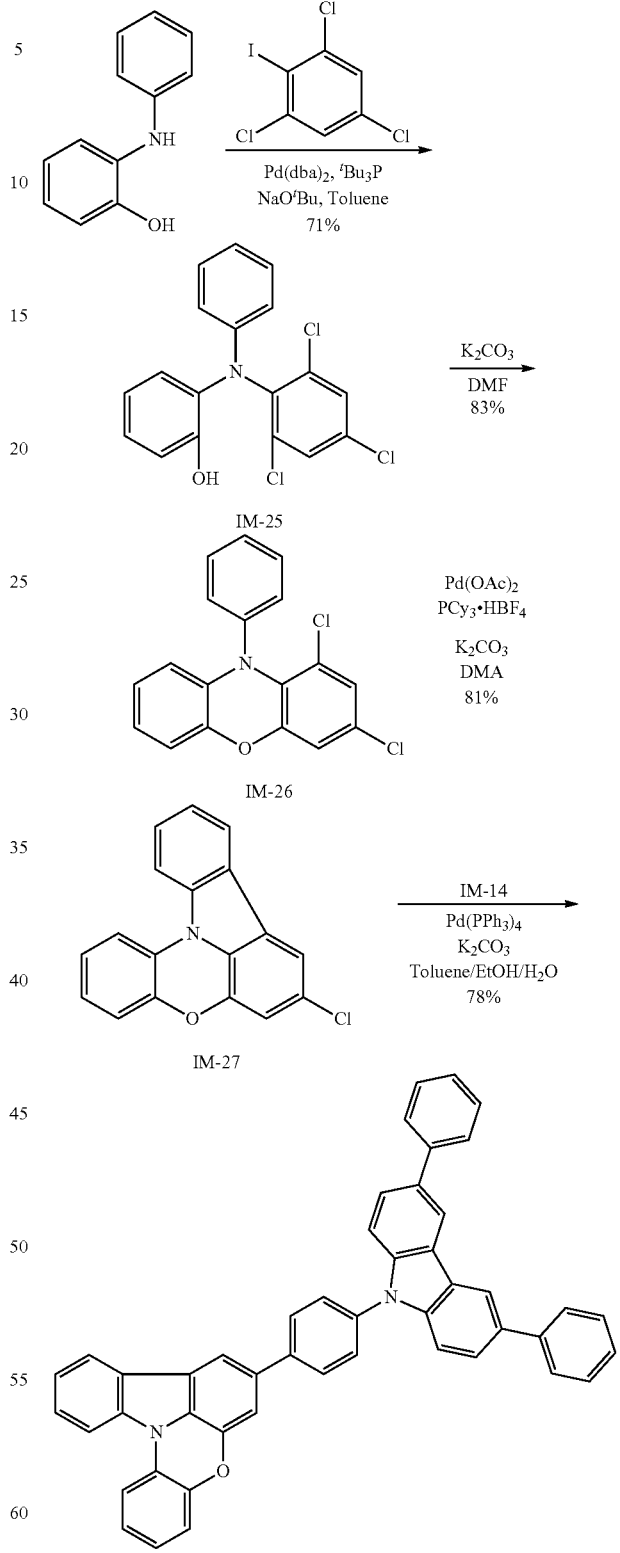

(Synthesis of Intermediate IM-25)

Under an Ar atmosphere, to a 1,000 mL, three neck flask, 2-(phenylamino)phenol (20.00 g, 108.0 mmol), Pd(dba)$_2$ (1.86 g, 0.03 equiv, 3.2 mmol), NaO$^t$Bu (11.41 g, 1.1 equiv, 118.8 mmol), toluene (540 mL), 2,4,6-trichloro-1-iodobenzene (36.50 g, 1.1 equiv, 118.8 mmol) and $^t$Bu$_3$P (2.18 g, 0.1 equiv, 10.8 mmol) were added in order, and heated, refluxed and stirred. After cooling to room temperature, water was added to the reaction solution, and an organic layer was separately taken. Toluene was added to an aqueous layer, and an organic layer was further extracted. Organic layers were collected, washed with a saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-25 (27.96 g, yield 71%).

Through the measurement of FAB-MS, mass number of m/z=364 was observed as a molecular ion peak, and Intermediate IM-25 was identified.

(Synthesis of Intermediate IM-26)

Under an Ar atmosphere, to a 500 mL, three neck flask, Intermediate IM-25 (25.00 g, 68.6 mmol), DMF (343 mL), and K$_2$CO$_3$ (37.90 g, 4 equiv, 274.2 mmol) were added in order, and heated to about 140° C. and stirred. After cooling to room temperature, H$_2$O was added to the reaction solution, and an organic layer was extracted with toluene, washed with a saturated saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-26 (18.68 g, yield 83%).

Through the measurement of FAB-MS, mass number of m/z=328 was observed as a molecular ion peak, and Intermediate IM-26 was identified.

(Synthesis of Intermediate IM-27)

Under an Ar atmosphere, to a 500 mL, three neck flask, Intermediate IM-26 (15.00 g, 45.7 mmol), Pd(OAc)$_2$ (0.62 g, 0.06 equiv, 2.7 mmol), K$_2$CO$_3$ (12.63 g, 2.0 equiv, 91.4 mmol), N,N-dimethylacetamide (DMA) (228 mL) and PCy$_3$·HBF$_4$ (2.02 g, 0.12 equiv, 5.5 mmol) were added in order, and heated, refluxed and stirred. After cooling to room temperature, water was added to the reaction solution, and an organic layer was separately taken. Toluene was added to an aqueous layer, and an organic layer was further extracted. Organic layers were collected, washed with a saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-27 (10.80 g, yield 81%).

Through the measurement of FAB-MS, mass number of m/z=291 was observed as a molecular ion peak, and Intermediate IM-27 was identified.

(Synthesis of Compound B54)

Under an Ar atmosphere, to a 300 mL, three neck flask, Intermediate IM-27 (5.00 g, 17.1 mmol), Intermediate IM-14 (10.44 g, 1.1 equiv, 18.9 mmol), K$_2$CO$_3$ (7.11 g, 3.0 equiv, 51.4 mmol), Pd(PPh$_3$)$_4$ (0.99 g, 0.05 eq, 0.9 mmol), and 120 mL of a mixture solution of toluene/EtOH/H$_2$O (4/2/1) were added in order, and heated to about 80° C. and stirred. After cooling to room temperature, the reaction solution was extracted with toluene. An aqueous layer was removed, and an organic layer was washed with a saturated saline solution and dried with MgSO$_4$. After filtering MgSO$_4$, an organic layer was concentrated, and the crude product thus obtained was separated by silica gel column chromatography (using a mixture solvent of hexane and toluene as a developing layer) to obtain Compound B54 (8.70 g, yield 78%).

Through the measurement of FAB-MS, mass number of m/z=650 was observed as a molecular ion peak, and Compound B54 was identified.

<Synthesis of Compound B145>

Compound B145 according to an embodiment may be synthesized, for example, by the steps of Reaction 8 below.

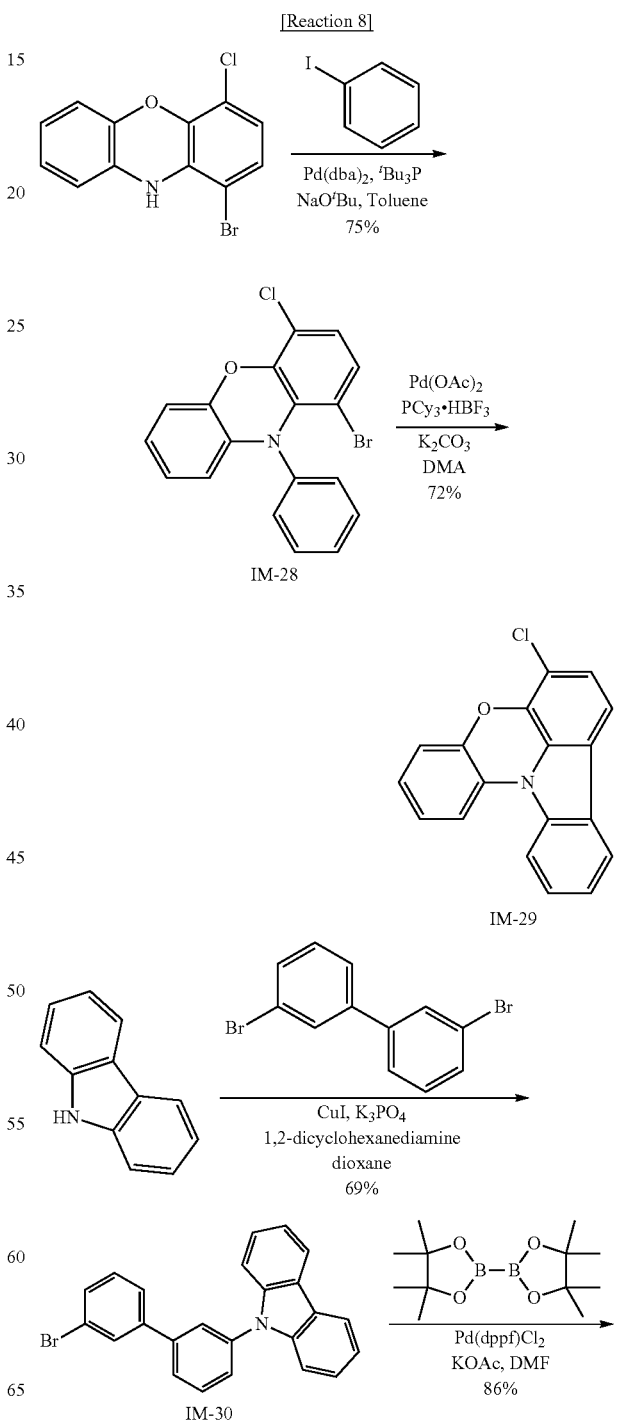

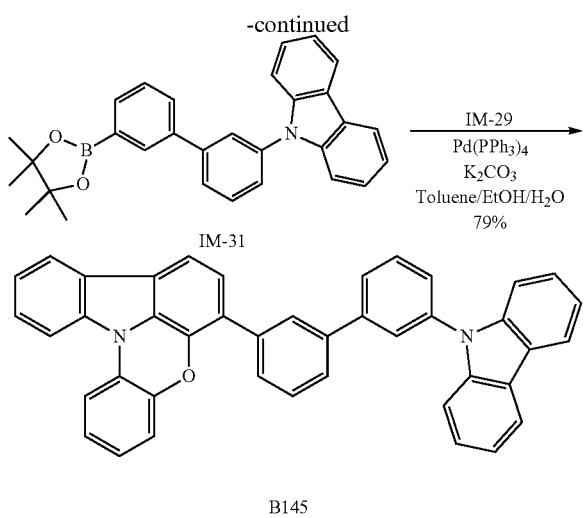

B145

(Synthesis of Intermediate IM-28)

Under an Ar atmosphere, to a 1,000 mL, three neck flask, 1-bromo-4-chloro-10H-phenoxazine (20.00 g, 67.4 mmol), Pd(dba)$_2$ (1.16 g, 0.03 equiv, 2.0 mmol), NaO$^t$Bu (7.13 g, 3.0 equiv, 74.2 mmol), toluene (337 mL), iodobenzene (15.13 g, 1.1 equiv, 74.2 mmol) and $^t$Bu$_3$P (1.36 g, 0.1 equiv, 6.7 mmol) were added in order, and heated, refluxed and stirred. After cooling to room temperature, water was added to the reaction solution, and an organic layer was separately taken. Toluene was added to an aqueous layer, and an organic layer was further extracted. Organic layers were collected, washed with a saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-28 (18.85 g, yield 75%).

Through the measurement of FAB-MS, mass number of m/z=372 was observed as a molecular ion peak, and Intermediate IM-28 was identified.

(Synthesis of Intermediate IM-29)

Under an Ar atmosphere, to a 500 mL, three neck flask, Intermediate IM-28 (15.00 g, 40.3 mmol), Pd(OAc)$_2$ (0.54 g, 0.06 equiv, 2.4 mmol), K$_2$CO$_3$ (11.13 g, 2.0 equiv, 80.5 mmol), N,N-dimethylacetamide (DMA) (201 mL) and PCy$_3$·HBF$_4$ (1.78 g, 0.12 equiv, 4.8 mmol) were added in order, and heated, refluxed and stirred. After cooling to room temperature, water was added to the reaction solution, and an organic layer was separately taken. Toluene was added to an aqueous layer, and an organic layer was further extracted. Organic layers were collected, washed with a saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-29 (8.45 g, yield 72%).

Through the measurement of FAB-MS, mass number of m/z=291 was observed as a molecular ion peak, and Intermediate IM-29 was identified.

(Synthesis of Intermediate IM-30)

Under an Ar atmosphere, to a 1,000 mL, three neck flask, 9H-carbazole (20.00 g, 119.6 mmol), CuI (2.28 g, 0.1 equiv, 11.96 mmol), K$_3$PO$_4$ (76.17 g, 3.0 equiv, 353.8 mmol), 3,3'-dibromo-1,1'-biphenyl (186.59 g, 5.0 equiv, 598.1 mmol), 1,4-dioxane (598 mL), and 1,2-cyclohexanediamine (2.73 g, 0.2 equiv, 23.9 mmol) were added in order, and heated, refluxed and stirred. After cooling to room temperature, water was added to the reaction solution, suction filtration was performed using celite, and an organic layer was separately taken. Toluene was added to an aqueous layer, and an organic layer was further extracted. Organic layers were collected, washed with a saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-30 (32.87 g, yield 69%).

Through the measurement of FAB-MS, mass number of m/z=398 was observed as a molecular ion peak, and Intermediate IM-30 was identified.

(Synthesis of Intermediate IM-31)

Under an Ar atmosphere, to a 300 mL, three neck flask, Intermediate IM-30 (15.00 g, 37.7 mmol), Pd(dppf)Cl$_2$ (3.08 g, 0.1 equiv, 3.8 mmol), KOAc (7.39 g, 2.0 equiv, 75.3 mmol), DMF (188 mL) and bis(pinacolato)diboron (11.48 g, 1.2 equiv, 45.2 mmol) were added in order, and heated, refluxed and stirred. After cooling to room temperature, water was added to the reaction solution, and an organic layer was separately taken. Toluene was added to an aqueous layer, and an organic layer was further extracted. Organic layers were collected, washed with a saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-31 (14.42 g, yield 86%).

Through the measurement of FAB-MS, mass number of m/z=445 was observed as a molecular ion peak, and Intermediate IM-31 was identified.

(Synthesis of Compound B145)

Under an Ar atmosphere, to a 300 mL, three neck flask, Intermediate IM-29 (5.00 g, 17.1 mmol), Intermediate IM-31 (8.40 g, 1.1 equiv, 18.9 mmol), K$_2$CO$_3$ (7.11 g, 3.0 equiv, 51.4 mmol), Pd(PPh$_3$)$_4$ (0.99 g, 0.05 eq, 0.9 mmol), and 120 mL of a mixture solution of toluene/EtOH/H$_2$O (4/2/1) were added in order, and heated to about 80° C. and stirred. After cooling to room temperature, the reaction solution was extracted with toluene. An aqueous layer was removed, and an organic layer was washed with a saturated saline solution and dried with MgSO$_4$. After filtering MgSO$_4$, an organic layer was concentrated, and the crude product thus obtained was separated by silica gel column chromatography (using a mixture solvent of hexane and toluene as a developing layer) to obtain Compound B145 (7.78 g, yield 79%).

Through the measurement of FAB-MS, mass number of m/z=574 was observed as a molecular ion peak, and Compound B145 was identified.

<Synthesis of Compound C15>

Compound C15 according to an embodiment may be synthesized, for example, by the steps of Reaction 9 below.

[Reaction 9]

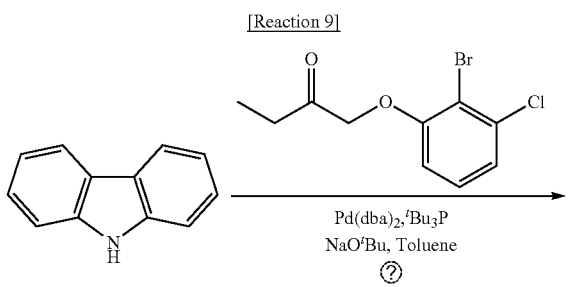

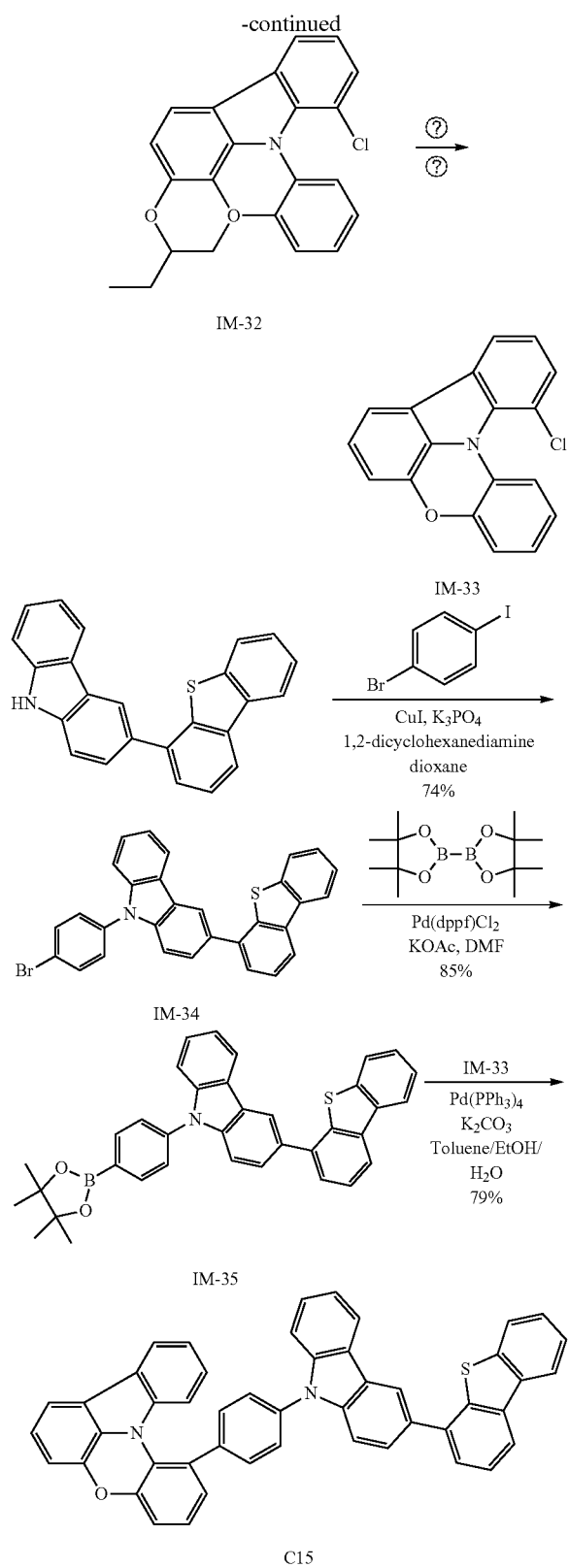

(Synthesis of Intermediate IM-32)

Under an Ar atmosphere, to a 1,000 mL, three neck flask, 9H-carbazole (20.00 g, 119.6 mmol), Pd(dba)$_2$ (2.06 g, 0.03 equiv, 3.6 mmol), NaO$^t$Bu (12.6 g, 1.1 equiv, 131.6 mmol), toluene (590 mL), 1-(2-bromo-3-chlorophenoxy)butan-2-one (36.52 g, 1.1 equiv, 131.6 mmol) and $^t$Bu$_3$P (2.42 g, 0.1 equiv, 12.0 mmol) were added in order, and heated, refluxed and stirred. After cooling to room temperature, water was added to the reaction solution, and an organic layer was separately taken. Toluene was added to an aqueous layer, and an organic layer was further extracted. Organic layers were collected, washed with a saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-32 (30.03 g, yield 69%).

Through the measurement of FAB-MS, mass number of m/z=363 was observed as a molecular ion peak, and Intermediate IM-32 was identified.

(Synthesis of Intermediate IM-33)

Under an Ar atmosphere, to a 500 mL, three neck flask, Intermediate IM-32 (15.00 g, 41.2 mmol), and TfOH (61.87 g, 10.0 equiv, 412.3 mmol) were added in order, and stirred at room temperature. After finishing the reaction, a mixture solution of pyridine (206 mL, 0.2 M), and H$_2$O (41 mL, 1 M) were slowly added to the reaction solution and stirred for about 1 hour. CH$_2$Cl$_2$ was added to the reaction solution, and an organic layer was separately taken. CH$_2$C12 was added to an aqueous layer and an organic layer was further extracted. Organic layers were collected, washed with a saturated saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-33 (9.74 g, yield 81%).

Through the measurement of FAB-MS, mass number of m/z=291 was observed as a molecular ion peak, and Intermediate IM-33 was identified.

(Synthesis of Intermediate IM-34)

Under an Ar atmosphere, to a 500 mL, three neck flask, 3-(dibenzothiophen-4-yl)-9H-carbazole (20.00 g, 57.2 mmol), CuI (1.09 g, 0.1 equiv, 5.72 mmol), K$_3$PO$_4$ (36.45 g, 3.0 equiv, 171.7 mmol), 1-bromo-4-iodobenzene (80.96 g, 5.0 equiv, 286.2 mmol), 1,4-dioxane (286 mL), and 1,2-cyclohexanediamine (1.31 g, 0.2 equiv, 11.4 mmol) were added in order, and heated, refluxed and stirred. After cooling to room temperature, water was added to the reaction solution, suction filtration was performed using celite, and an organic layer was separately taken. Toluene was added to an aqueous layer, and an organic layer was further extracted. Organic layers were collected, washed with a saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-34 (21.36 g, yield 74%).

Through the measurement of FAB-MS, mass number of m/z=504 was observed as a molecular ion peak, and Intermediate IM-34 was identified.

(Synthesis of Intermediate IM-35)

Under an Ar atmosphere, to a 300 mL, three neck flask, Intermediate IM-34 (15.00 g, 29.7 mmol), Pd(dppf)Cl$_2$ (2.43 g, 0.1 equiv, 3.0 mmol), KOAc (5.84 g, 2.0 equiv, 59.5 mmol), DMF (148 mL) and bis(pinacolato)diboron (9.06 g, 1.2 equiv, 35.7 mmol) were added in order, and heated, refluxed and stirred. After cooling to room temperature, water was added to the reaction solution, and an organic layer was separately taken. Toluene was added to an aqueous layer, and an organic layer was further extracted. Organic layers were collected, washed with a saline solution, and dried with MgSO₄. After filtering MgSO₄, an organic layer was concentrated, and the crude product thus obtained was separated by silica gel column chromatography (using a mixture solvent of hexane and toluene as a developing layer) to obtain Intermediate IM-35 (13.94 g, yield 85%).

Through the measurement of FAB-MS, mass number of m/z=551 was observed as a molecular ion peak, and Intermediate IM-35 was identified.

(Synthesis of Compound C15)

Under an Ar atmosphere, to a 300 mL, three neck flask, Intermediate IM-33 (5.00 g, 17.1 mmol), Intermediate IM-35 (10.40 g, 1.1 equiv, 18.9 mmol), K₂CO₃ (7.11 g, 3.0 equiv, 51.4 mmol), Pd(PPh₃)₄ (0.99 g, 0.05 eq, 0.9 mmol), and 120 mL of a mixture solution of toluene/EtOH/H₂O (4/2/1) were added in order, and heated to about 80° C. and stirred. After cooling to room temperature, the reaction solution was extracted with toluene. An aqueous layer was removed, and an organic layer was washed with a saturated saline solution and dried with MgSO₄. After filtering MgSO₄, an organic layer was concentrated, and the crude product thus obtained was separated by silica gel column chromatography (using a mixture solvent of hexane and toluene as a developing layer) to obtain Compound C15 (9.22 g, yield 79%).

Through the measurement of FAB-MS, mass number of m/z=680 was observed as a molecular ion peak, and Compound C15 was identified.

<Synthesis of Compound C99>

Compound C99 according to an embodiment may be synthesized, for example, by the steps of Reaction 10 below.

[Reaction 10]

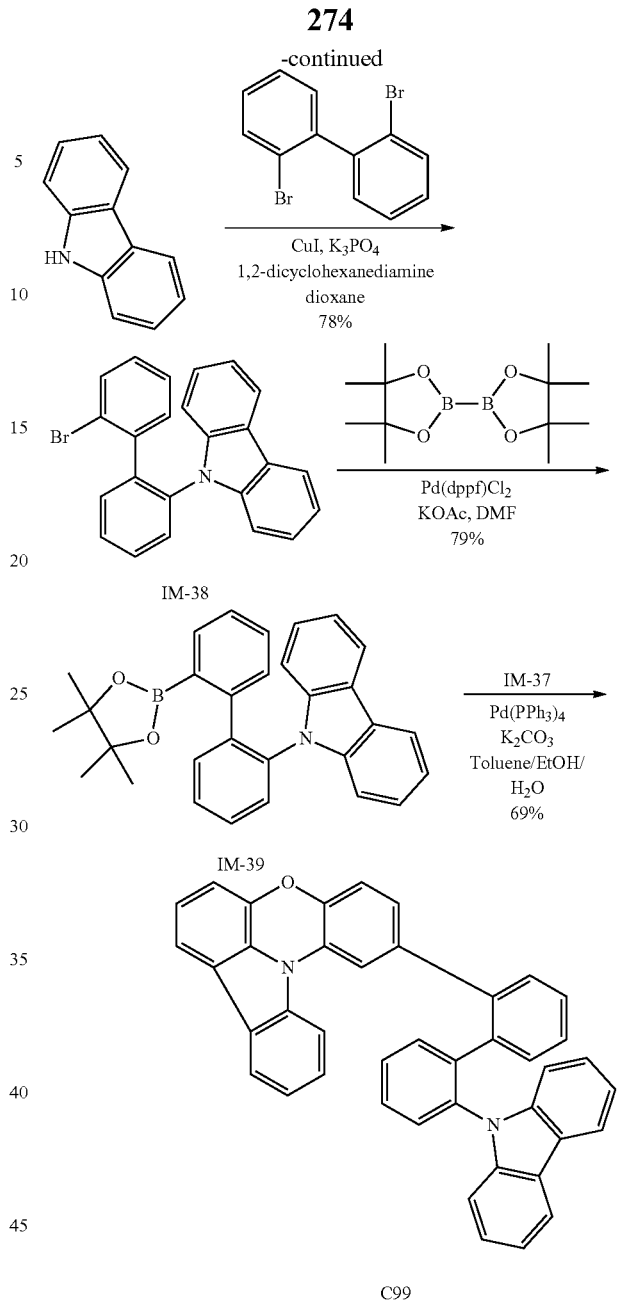

C99

(Synthesis of Intermediate IM-36)

Under an Ar atmosphere, to a 1,000 mL, three neck flask, 9H-carbazole (20.00 g, 119.6 mmol), Pd(dba)₂ (2.06 g, 0.03 equiv, 3.6 mmol), NaOᵗBu (12.6 g, 1.1 equiv, 131.6 mmol), toluene (590 mL), 1-(2-bromo-3-chlorophenoxy)butan-2-one (36.52 g, 1.1 equiv, 131.6 mmol) and ᵗBu₃P (2.42 g, 0.1 equiv, 12.0 mmol) were added in order, and heated, refluxed and stirred. After cooling to room temperature, water was added to the reaction solution, and an organic layer was separately taken. Toluene was added to an aqueous layer, and an organic layer was further extracted. Organic layers were collected, washed with a saline solution, and dried with MgSO₄. After filtering MgSO₄, an organic layer was concentrated, and the crude product thus obtained was separated by silica gel column chromatography (using a mixture solvent of hexane and toluene as a developing layer) to obtain Intermediate IM-36 (31.77 g, yield 73%).

Through the measurement of FAB-MS, mass number of m/z=363 was observed as a molecular ion peak, and Intermediate IM-36 was identified.

(Synthesis of Intermediate IM-37)

Under an Ar atmosphere, to a 500 mL, three neck flask, Intermediate IM-36 (15.00 g, 41.2 mmol), and TfOH (61.87 g, 10.0 equiv, 412.3 mmol) were added in order, and stirred at room temperature. After finishing the reaction, a mixture solution of pyridine (206 mL, 0.2 M), and H$_2$O (41 mL, 1 M) were slowly added to the reaction solution and stirred for about 1 hour. CH$_2$Cl$_2$ was added to the reaction solution, and an organic layer was separately taken. CH$_2$C12 was added to an aqueous layer and an organic layer was further extracted. Organic layers were collected, washed with a saturated saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-37 (10.22 g, yield 85%).

Through the measurement of FAB-MS, mass number of m/z=291 was observed as a molecular ion peak, and Intermediate IM-37 was identified.

(Synthesis of Intermediate IM-38)

Under an Ar atmosphere, to a 1,000 mL, three neck flask, 9H-carbazole (20.00 g, 119.6 mmol), CuI (2.28 g, 0.1 equiv, 11.96 mmol), K$_3$PO$_4$ (76.17 g, 3.0 equiv, 358.8 mmol), 2,2'-dibromo-1,1'-biphenyl (186.59 g, 5.0 equiv, 598.1 mmol), 1,4-dioxane (598 mL), and 1,2-cyclohexanediamine (2.73 g, 0.2 equiv, 23.9 mmol) were added in order, and heated, refluxed and stirred. After cooling to room temperature, water was added to the reaction solution, suction filtration was performed using celite, and an organic layer was separately taken. Toluene was added to an aqueous layer, and an organic layer was further extracted. Organic layers were collected, washed with a saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-38 (33.35 g, yield 70%).

Through the measurement of FAB-MS, mass number of m/z=398 was observed as a molecular ion peak, and Intermediate IM-38 was identified.

(Synthesis of Intermediate IM-39)

Under an Ar atmosphere, to a 300 mL, three neck flask, Intermediate IM-38 (15.00 g, 37.7 mmol), Pd(dppf)Cl$_2$ (3.08 g, 0.1 equiv, 3.8 mmol), KOAc (7.39 g, 2.0 equiv, 75.3 mmol), DMF (188 mL) and bis(pinacolato)diboron (11.48 g, 1.2 equiv, 45.2 mmol) were added in order, and heated, refluxed and stirred. After cooling to room temperature, water was added to the reaction solution, and an organic layer was separately taken. Toluene was added to an aqueous layer, and an organic layer was further extracted. Organic layers were collected, washed with a saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-39 (13.25 g, yield 79%).

Through the measurement of FAB-MS, mass number of m/z=445 was observed as a molecular ion peak, and Intermediate IM-39 was identified.

(Synthesis of Compound C99)

Under an Ar atmosphere, to a 300 mL, three neck flask, Intermediate IM-37 (5.00 g, 17.1 mmol), Intermediate IM-39 (8.40 g, 1.1 equiv, 18.9 mmol), K$_2$CO$_3$ (7.11 g, 3.0 equiv, 51.4 mmol), Pd(PPh$_3$)$_4$ (0.99 g, 0.05 eq, 0.9 mmol), and 120 mL of a mixture solution of toluene/EtOH/H$_2$O (4/2/1) were added in order, and heated to about 80° C. and stirred. After cooling to room temperature, the reaction solution was extracted with toluene. An aqueous layer was removed, and an organic layer was washed with a saturated saline solution and dried with MgSO$_4$. After filtering MgSO$_4$, an organic layer was concentrated, and the crude product thus obtained was separated by silica gel column chromatography (using a mixture solvent of hexane and toluene as a developing layer) to obtain Compound C99 (6.80 g, yield 69%).

Through the measurement of FAB-MS, mass number of m/z=574 was observed as a molecular ion peak, and Compound C99 was identified.

<Synthesis of Compound C148>

Compound C148 according to an embodiment may be synthesized, for example, by the steps of Reaction 11 below.

[Reaction 11]

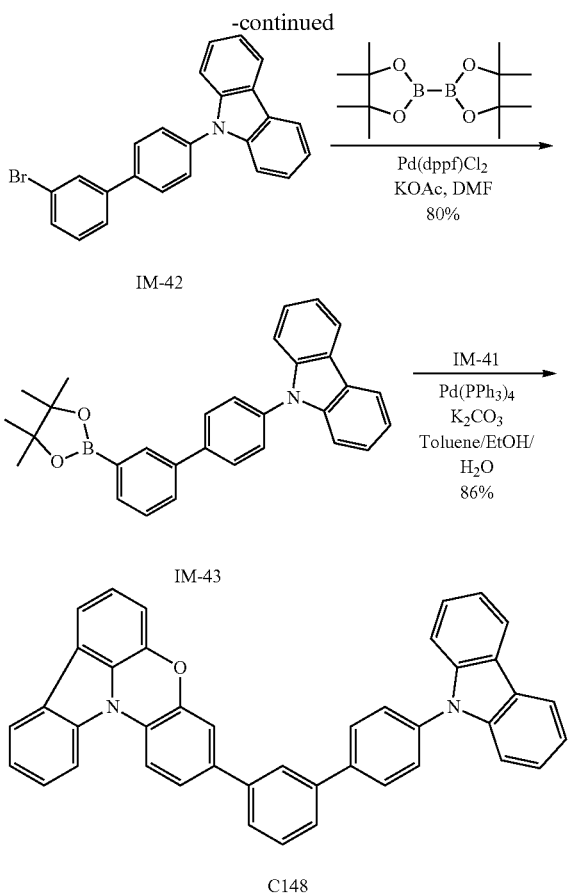

(Synthesis of Intermediate IM-40)

Under an Ar atmosphere, to a 1,000 mL, three neck flask, 9H-carbazole (20.00 g, 119.6 mmol), Pd(dba)$_2$ (2.06 g, 0.03 equiv, 3.6 mmol), NaO$^t$Bu (12.6 g, 1.1 equiv, 131.6 mmol), toluene (590 mL), 1-(5-bromo-2-iodophenoxy)butan-2-one (48.55 g, 1.1 equiv, 131.6 mmol) and $^t$Bu$_3$P (2.42 g, 0.1 equiv, 12.0 mmol) were added in order, and heated, refluxed and stirred. After cooling to room temperature, water was added to the reaction solution, and an organic layer was separately taken. Toluene was added to an aqueous layer, and an organic layer was further extracted. Organic layers were collected, washed with a saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-40 (39.57 g, yield 81%).

Through the measurement of FAB-MS, mass number of m/z=408 was observed as a molecular ion peak, and Intermediate IM-40 was identified.

(Synthesis of Intermediate IM-41)

Under an Ar atmosphere, to a 500 mL, three neck flask, Intermediate IM-40 (20.00 g, 49.0 mmol), and TfOH (73.51 g, 10.0 equiv, 489.8 mmol) were added in order, and stirred at room temperature. After finishing the reaction, a mixture solution of pyridine (245 mL, 0.2 M), and H$_2$O (49 mL, 1 M) were slowly added to the reaction solution and stirred for about 1 hour. CH$_2$Cl$_2$ was added to the reaction solution, and an organic layer was separately taken. CH$_2$Cl2 was added to an aqueous layer and an organic layer was further extracted. Organic layers were collected, washed with a saturated saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-41 (13.17 g, yield 80%).

Through the measurement of FAB-MS, mass number of m/z=336 was observed as a molecular ion peak, and Intermediate IM-41 was identified.

(Synthesis of Intermediate IM-42)

Under an Ar atmosphere, to a 1,000 mL, three neck flask, 9H-carbazole (20.00 g, 119.6 mmol), CuI (2.28 g, 0.1 equiv, 11.96 mmol), K$_3$PO$_4$ (76.17 g, 3.0 equiv, 358.8 mmol), 3-bromo-4'-iodo-1,1'-biphenyl (214.70 g, 5.0 equiv, 598.1 mmol), 1,4-dioxane (598 mL), and 1,2-cyclohexanediamine (2.73 g, 0.2 equiv, 23.9 mmol) were added in order, and heated, refluxed and stirred. After cooling to room temperature, water was added to the reaction solution, suction filtration was performed using celite, and an organic layer was separately taken. Toluene was added to an aqueous layer, and an organic layer was further extracted. Organic layers were collected, washed with a saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-42 (34.30 g, yield 72%).

Through the measurement of FAB-MS, mass number of m/z=398 was observed as a molecular ion peak, and Intermediate IM-42 was identified.

(Synthesis of Intermediate IM-43)

Under an Ar atmosphere, to a 500 mL, three neck flask, Intermediate IM-42 (15.00 g, 37.7 mmol), Pd(dppf)Cl$_2$ (3.08 g, 0.1 equiv, 3.8 mmol), KOAc (7.39 g, 2.0 equiv, 75.3 mmol), DMF (188 mL) and bis(pinacolato)diboron (11.48 g, 1.2 equiv, 45.2 mmol) were added in order, and heated, refluxed and stirred. After cooling to room temperature, water was added to the reaction solution, and an organic layer was separately taken. Toluene was added to an aqueous layer, and an organic layer was further extracted. Organic layers were collected, washed with a saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-43 (13.42 g, yield 80%).

Through the measurement of FAB-MS, mass number of m/z=445 was observed as a molecular ion peak, and Intermediate IM-43 was identified.

(Synthesis of Compound C148)

Under an Ar atmosphere, to a 300 mL, three neck flask, Intermediate IM-41 (5.00 g, 14.9 mmol), Intermediate IM-43 (7.29 g, 1.1 equiv, 16.4 mmol), K$_2$CO$_3$ (6.17 g, 3.0 equiv, 44.6 mmol), Pd(PPh$_3$)$_4$ (0.86 g, 0.05 eq, 0.7 mmol), and 104 mL of a mixture solution of toluene/EtOH/H$_2$O (4/2/1) were added in order, and heated to about 80° C. and stirred. After cooling to room temperature, the reaction solution was extracted with toluene. An aqueous layer was removed, and an organic layer was washed with a saturated saline solution and dried with MgSO$_4$. After filtering MgSO$_4$, an organic layer was concentrated, and the crude product thus obtained was separated by silica gel column chromatography (using a mixture solvent of hexane and toluene as a developing layer) to obtain Compound C148 (7.35 g, yield 86%).

Through the measurement of FAB-MS, mass number of m/z=574 was observed as a molecular ion peak, and Compound C148 was identified.

<Synthesis of Compound C158>
Compound C158 according to an embodiment may be synthesized, for example, by the steps of Reaction 12 below.
[Reaction 12]
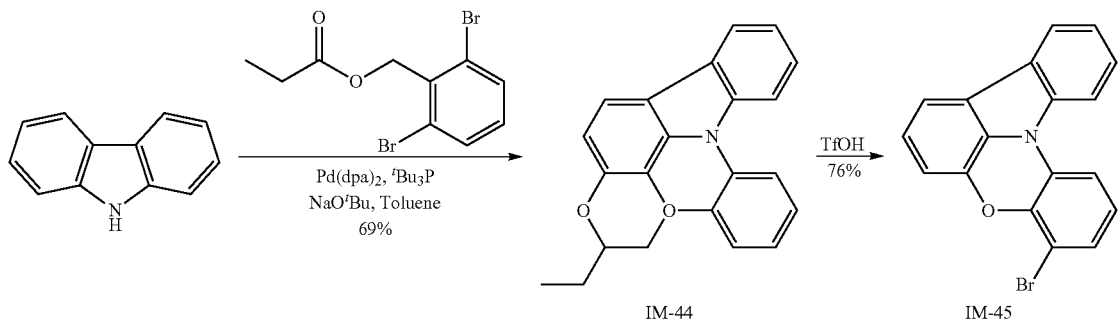
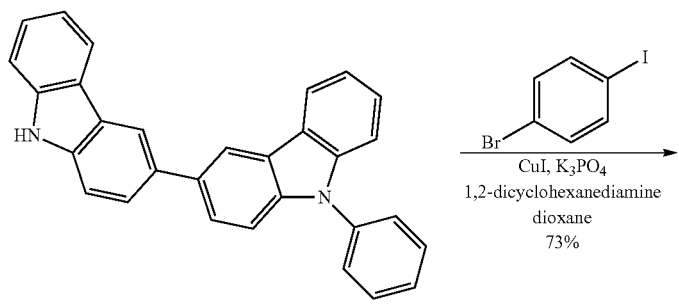
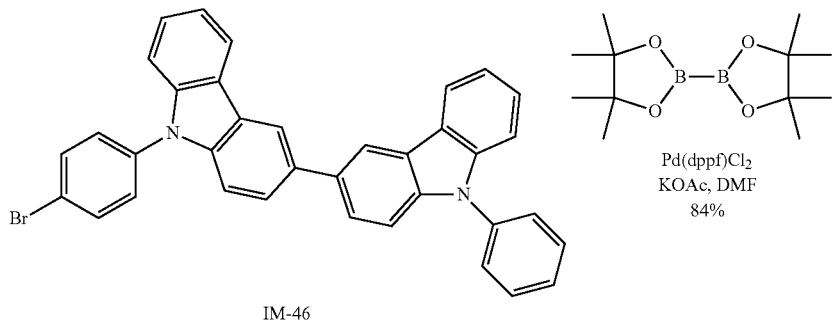
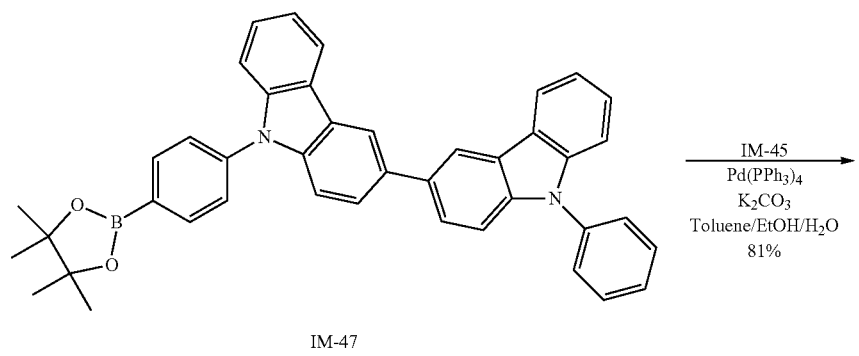

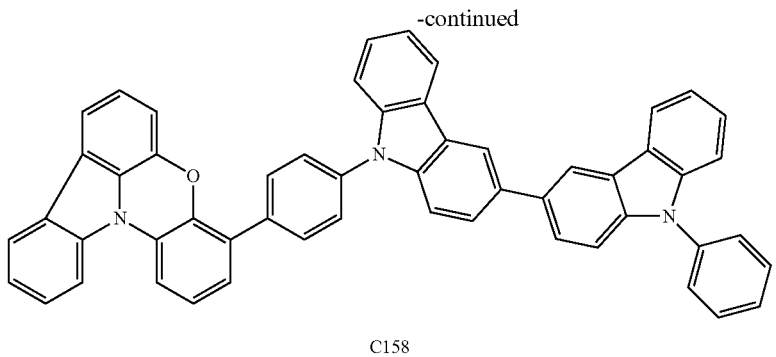

C158

(Synthesis of Intermediate IM-44)

Under an Ar atmosphere, to a 1,000 mL, three neck flask, carbazole (20.00 g, 119.6 mmol), Pd(dba)$_2$ (2.06 g, 0.03 equiv, 3.6 mmol), NaO$^t$Bu (12.6 g, 1.1 equiv, 131.6 mmol), toluene (590 mL), 1-(2,6-dibromophenoxy)butan-2-one (42.37 g, 1.1 equiv, 131.6 mmol) and $^t$Bu$_3$P (2.42 g, 0.1 equiv, 12.0 mmol) were added in order, and heated, refluxed and stirred. After cooling to room temperature, water was added to the reaction solution, and an organic layer was separately taken. Toluene was added to an aqueous layer, and an organic layer was further extracted. Organic layers were collected, washed with a saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-44 (33.70 g, yield 69%).

Through the measurement of FAB-MS, mass number of m/z=408 was observed as a molecular ion peak, and Intermediate IM-44 was identified.

(Synthesis of Intermediate IM-45)

Under an Ar atmosphere, to a 500 mL, three neck flask, Intermediate IM-44 (15.00 g, 36.7 mmol), and TfOH (55.13 g, 10.0 equiv, 367.4 mmol) were added in order, and stirred at room temperature. After finishing the reaction, a mixture solution of pyridine (184 mL, 0.2 M), and H$_2$O (36 mL, 1 M) were slowly added to the reaction solution and stirred for about 1 hour. CH$_2$Cl$_2$ was added to the reaction solution, and an organic layer was separately taken. CH$_2$C12 was added to an aqueous layer and an organic layer was further extracted. Organic layers were collected, washed with a saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-45 (9.64 g, yield 78%).

Through the measurement of FAB-MS, mass number of m/z=336 was observed as a molecular ion peak, and Intermediate IM-45 was identified.

(Synthesis of Intermediate IM-46)

Under an Ar atmosphere, to a 500 mL, three neck flask, 9-phenyl-9H,9'H-3,3'-bicarbazole (20.00 g, 49.0 mmol), CuI (0.93 g, 0.1 equiv, 4.9 mmol), K$_3$PO$_4$ (31.18 g, 3.0 equiv, 146.9 mmol), 1-bromo-4-iodobenzene (69.26 g, 5.0 equiv, 244.8 mmol), 1,4-dioxane (244 mL), and 1,2-cyclohexanediamine (1.12 g, 0.2 equiv, 9.8 mmol) were added in order, and heated, refluxed and stirred. After cooling to room temperature, water was added to the reaction solution, suction filtration was performed using celite, and an organic layer was separately taken. Toluene was added to an aqueous layer, and an organic layer was further extracted. Organic layers were collected, washed with a saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-46 (20.14 g, yield 73%).

Through the measurement of FAB-MS, mass number of m/z=519 was observed as a molecular ion peak, and Intermediate IM-46 was identified.

(Synthesis of Intermediate IM-47)

Under an Ar atmosphere, to a 300 mL, three neck flask, Intermediate IM-46 (15.00 g, 26.6 mmol), Pd(dppf)Cl$_2$ (2.17 g, 0.1 equiv, 2.7 mmol), KOAc (5.22 g, 2.0 equiv, 53.2 mmol), DMF (144 mL) and bis(pinacolato)diboron (8.11 g, 1.2 equiv, 31.9 mmol) were added in order, and heated, refluxed and stirred. After cooling to room temperature, water was added to the reaction solution, and an organic layer was separately taken. Toluene was added to an aqueous layer, and an organic layer was further extracted. Organic layers were collected, washed with a saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-47 (13.65 g, yield 84%).

Through the measurement of FAB-MS, mass number of m/z=610 was observed as a molecular ion peak, and Intermediate IM-47 was identified.

(Synthesis of Compound C158)

Under an Ar atmosphere, to a 300 mL, three neck flask, Intermediate IM-45 (5.00 g, 14.9 mmol), Intermediate IM-47 (9.99 g, 1.1 equiv, 16.4 mmol), K$_2$CO$_3$ (6.17 g, 3.0 equiv, 44.6 mmol), Pd(PPh$_3$)$_4$ (0.86 g, 0.05 eq, 0.7 mmol), and 104 mL of a mixture solution of toluene/EtOH/H$_2$O (4/2/1) were added in order, and heated to about 80° C. and stirred. After cooling to room temperature, the reaction solution was extracted with toluene. An aqueous layer was removed, and an organic layer was washed with a saturated saline solution and dried with MgSO$_4$. After filtering MgSO$_4$, an organic layer was concentrated, and the crude product thus obtained was separated by silica gel column chromatography (using a mixture solvent of hexane and toluene as a developing layer) to obtain Compound C158 (8.91 g, yield 81%).

Through the measurement of FAB-MS, mass number of m/z=739 was observed as a molecular ion peak, and Compound C158 was identified.

<Synthesis of Compound D1>

Compound D1 according to an embodiment may be synthesized, for example, by the steps of Reaction 13 below.

[Reaction 13]

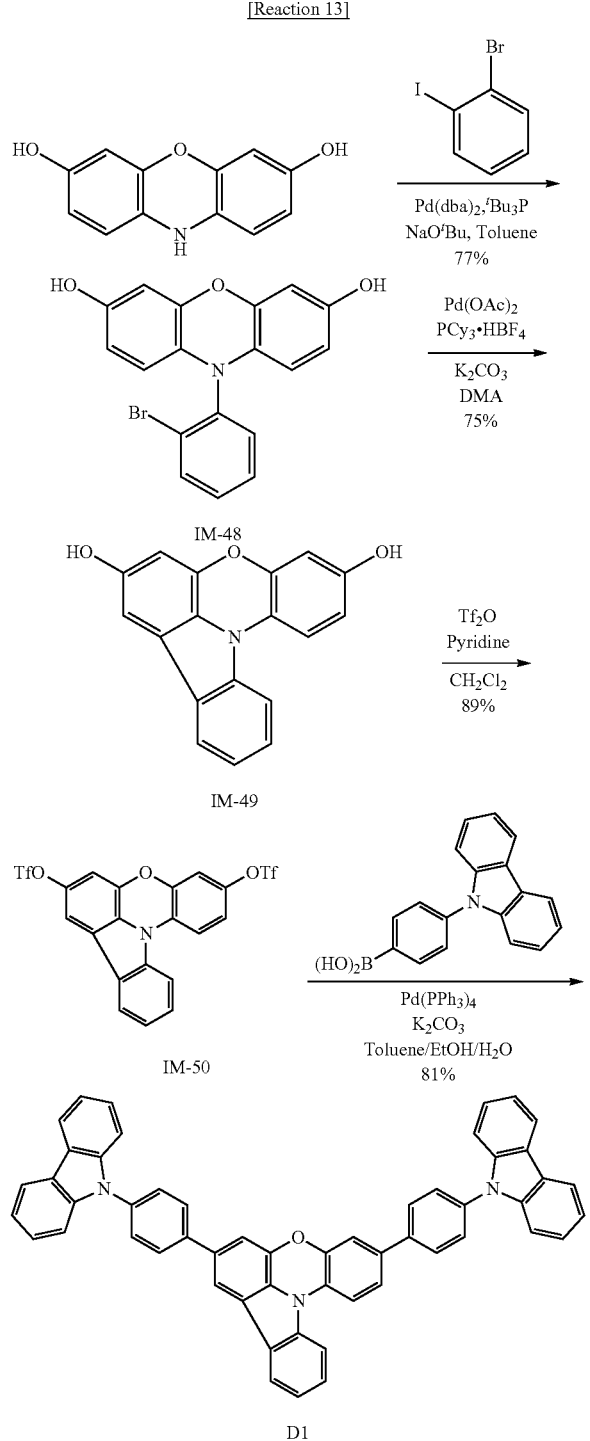

(Synthesis of Intermediate IM-48)

Under an Ar atmosphere, to a 1,000 mL, three neck flask, 10H-phenoxazine-3,7-diol (20.00 g, 92.9 mmol), Pd(dba)$_2$ (1.60 g, 0.03 equiv, 2.8 mmol), NaO$^t$Bu (26.79 g, 3.0 equiv, 278.8 mmol), toluene (464 mL), 1-bromo-2-iodobenzene (28.92 g, 1.1 equiv, 102.2 mmol) and $^t$Bu$_3$P (1.88 g, 0.1 equiv, 9.3 mmol) were added in order, and heated, refluxed and stirred. After cooling to room temperature, water was added to the reaction solution, and an organic layer was separately taken. Toluene was added to an aqueous layer, and an organic layer was further extracted. Organic layers were collected, washed with a saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-48 (26.49 g, yield 77%).

Through the measurement of FAB-MS, mass number of m/z=370 was observed as a molecular ion peak, and Intermediate IM-48 was identified.

(Synthesis of Intermediate IM-49)

Under an Ar atmosphere, to a 500 mL, three neck flask, Intermediate IM-48 (20.00 g, 54.0 mmol), Pd(OAc)$_2$ (0.73 g, 0.06 equiv, 3.2 mmol), K$_2$CO$_3$ (14.93 g, 2.0 equiv, 108.0 mmol), N,N-dimethylacetamide (DMA) (270 mL) and PCy$_3$·HBF$_4$ (2.39 g, 0.12 equiv, 6.5 mmol) were added in order, and heated, refluxed and stirred. After cooling to room temperature, water was added to the reaction solution, and an organic layer was separately taken. Toluene was added to an aqueous layer, and an organic layer was further extracted. Organic layers were collected, washed with a saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-49 (11.72 g, yield 75%).

Through the measurement of FAB-MS, mass number of m/z=289 was observed as a molecular ion peak, and Intermediate IM-49 was identified.

(Synthesis of Intermediate IM-50)

Under an Ar atmosphere, to a 500 mL, three neck flask, Intermediate IM-49 (10.00 g, 34.6 mmol), pyridine (16.41 g, 6.0 equiv, 207.4 mmol), CH$_2$Cl$_2$ (282 mL) and Tf$_2$O (29.26 g, 3.0 equiv, 103.7 mmol) were added in order, and stirred at room temperature. After finishing the reaction, H$_2$O was added to the reaction solution and extracted with CH$_2$Cl$_2$. An organic layer was washed with a saturated saline solution and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-50 (17.03 g, yield 89%).

Through the measurement of FAB-MS, mass number of m/z=553 was observed as a molecular ion peak, and Intermediate IM-50 was identified.

(Synthesis of Compound D1)

Under an Ar atmosphere, to a 300 mL, three neck flask, Intermediate IM-50 (10.00 g, 18.1 mmol), [(4-(9H-carbazol-9-yl)phenyl)boronic acid (11.41 g, 2.2 equiv, 39.8 mmol), K$_2$CO$_3$ (14.98 g, 3.0 equiv, 108.4 mmol), Pd(PPh$_3$)$_4$ (2.09 g, 0.1 eq, 1.8 mmol), and 126 mL of a mixture solution of toluene/EtOH/H$_2$O (4/2/1) were added in order, and heated to about 80° C. and stirred. After cooling to room temperature, the reaction solution was extracted with toluene. An aqueous layer was removed, and an organic layer was washed with a saturated saline solution and dried with MgSO$_4$. After filtering MgSO$_4$, an organic layer was concentrated, and the crude product thus obtained was separated by silica gel column chromatography (using a mixture solvent of hexane and toluene as a developing layer) to obtain Compound D1 (10.83 g, yield 81%).

Through the measurement of FAB-MS, mass number of m/z=739 was observed as a molecular ion peak, and Compound D1 was identified.

<Synthesis of Compound A66>

Compound A66 according to an embodiment may be synthesized, for example, by the steps of Reaction 14 below.

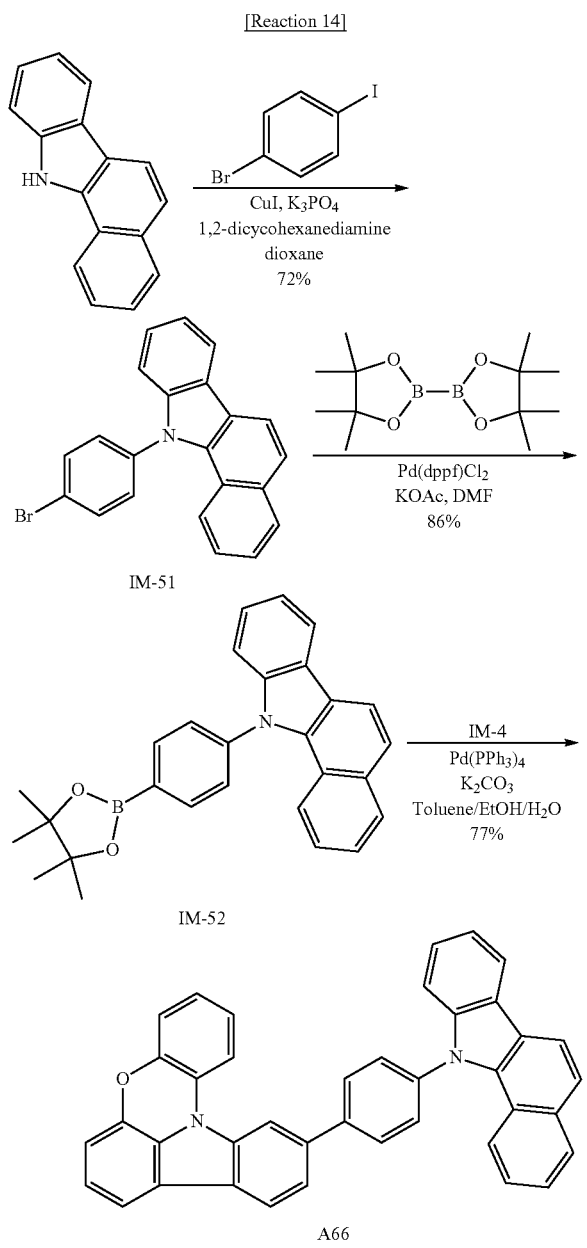

IM-51

IM-52

A66

(Synthesis of Intermediate IM-51)

Under an Ar atmosphere, to a 1,000 mL, three neck flask, 11H-benzo[a]carbazole (20.00 g, 92.1 mmol), CuI (1.75 g, 0.1 equiv, 9.2 mmol), $K_3PO_4$ (58.62 g, 3.0 equiv, 276.2 mmol), 1-bromo-4-iodobenzene (130.21 g, 5.0 equiv, 460.3 mmol), 1,4-dioxane (460 mL), and 1,2-cyclohexanediamine (2.10 g, 0.2 equiv, 18.4 mmol) were added in order, and heated, refluxed and stirred. After cooling to room temperature, water was added to the reaction solution, suction filtration was performed using celite, and an organic layer was separately taken. Toluene was added to an aqueous layer, and an organic layer was further extracted. Organic layers were collected, washed with a saline solution, and dried with $MgSO_4$. After filtering $MgSO_4$, an organic layer was concentrated, and the crude product thus obtained was separated by silica gel column chromatography (using a mixture solvent of hexane and toluene as a developing layer) to obtain Intermediate IM-51 (24.67 g, yield 72%).

Through the measurement of FAB-MS, mass number of m/z=372 was observed as a molecular ion peak, and Intermediate IM-51 was identified.

(Synthesis of Intermediate IM-52)

Under an Ar atmosphere, to a 500 mL, three neck flask, Intermediate IM-51 (15.00 g, 40.3 mmol), $Pd(dppf)Cl_2$ (3.29 g, 0.1 equiv, 4.0 mmol), KOAc (7.91 g, 2.0 equiv, 80.6 mmol), DMF (201 mL) and bis(pinacolato)diboron (12.28 g, 1.2 equiv, 48.4 mmol) were added in order, and heated, refluxed and stirred. After cooling to room temperature, water was added to the reaction solution, and an organic layer was separately taken. Toluene was added to an aqueous layer, and an organic layer was further extracted. Organic layers were collected, washed with a saline solution, and dried with $MgSO_4$. After filtering $MgSO_4$, an organic layer was concentrated, and the crude product thus obtained was separated by silica gel column chromatography (using a mixture solvent of hexane and toluene as a developing layer) to obtain Intermediate IM-52 (15.64 g, yield 86%).

Through the measurement of FAB-MS, mass number of m/z=451 was observed as a molecular ion peak, and Intermediate IM-52 was identified.

(Synthesis of Compound A66)

Under an Ar atmosphere, to a 300 mL, three neck flask, Intermediate IM-4 (5.00 g, 17.1 mmol), Intermediate IM-52 (8.51 g, 1.1 equiv, 18.9 mmol), $K_2CO_3$ (7.11 g, 3.0 equiv, 51.4 mmol), $Pd(PPh_3)_4$ (0.99 g, 0.05 eq, 0.9 mmol), and 120 mL of a mixture solution of toluene/EtOH/$H_2O$ (4/2/1) were added in order, and heated to about 80° C. and stirred. After cooling to room temperature, the reaction solution was extracted with toluene. An aqueous layer was removed, and an organic layer was washed with a saturated saline solution and dried with $MgSO_4$. After filtering $MgSO_4$, an organic layer was concentrated, and the crude product thus obtained was separated by silica gel column chromatography (using a mixture solvent of hexane and toluene as a developing layer) to obtain Compound A66 (7.24 g, yield 77%).

Through the measurement of FAB-MS, mass number of m/z=548 was observed as a molecular ion peak, and Compound A66 was identified.

<Synthesis of Compound A78>

Compound A78 according to an embodiment may be synthesized, for example, by the steps of Reaction 15 below.

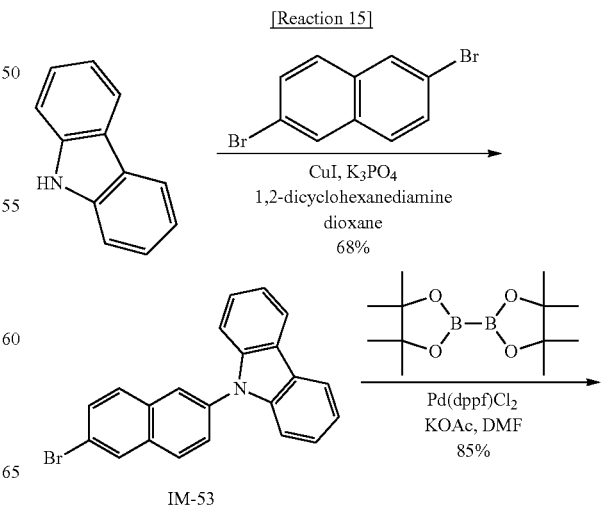

IM-53

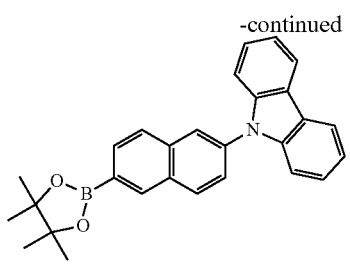

IM-54

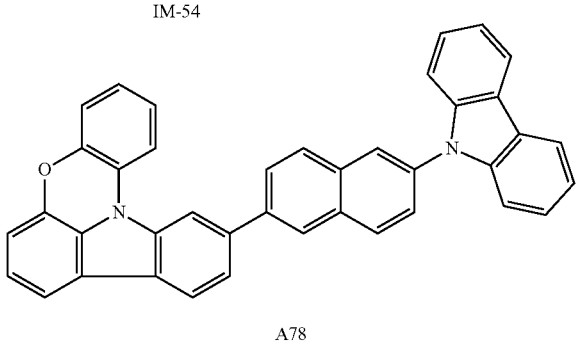

A78

(Synthesis of Intermediate IM-53)

Under an Ar atmosphere, to a 1,000 mL, three neck flask, 9H-carbazole (20.00 g, 119.6 mmol), CuI (2.28 g, 0.1 equiv, 12.0 mmol), $K_3PO_4$ (76.17 g, 3.0 equiv, 358.8 mmol), 2,6-dibromonaphthalene (171.02 g, 5.0 equiv, 598.1 mmol), 1,4-dioxane (598 mL), and 1,2-cyclohexanediamine (2.73 g, 0.2 equiv, 23.9 mmol) were added in order, and heated, refluxed and stirred. After cooling to room temperature, water was added to the reaction solution, suction filtration was performed using celite, and an organic layer was separately taken. Toluene was added to an aqueous layer, and an organic layer was further extracted. Organic layers were collected, washed with a saline solution, and dried with $MgSO_4$. After filtering $MgSO_4$, an organic layer was concentrated, and the crude product thus obtained was separated by silica gel column chromatography (using a mixture solvent of hexane and toluene as a developing layer) to obtain Intermediate IM-53 (30.28 g, yield 68%).

Through the measurement of FAB-MS, mass number of m/z=372 was observed as a molecular ion peak, and Intermediate IM-53 was identified.

(Synthesis of Intermediate IM-54)

Under an Ar atmosphere, to a 500 mL, three neck flask, Intermediate IM-53 (15.00 g, 40.3 mmol), Pd(dppf)Cl$_2$ (3.29 g, 0.1 equiv, 4.0 mmol), KOAc (7.91 g, 2.0 equiv, 80.6 mmol), DMF (201 mL) and bis(pinacolato)diboron (12.28 g, 1.2 equiv, 48.4 mmol) were added in order, and heated, refluxed and stirred. After cooling to room temperature, water was added to the reaction solution, and an organic layer was separately taken. Toluene was added to an aqueous layer, and an organic layer was further extracted. Organic layers were collected, washed with a saline solution, and dried with $MgSO_4$. After filtering $MgSO_4$, an organic layer was concentrated, and the crude product thus obtained was separated by silica gel column chromatography (using a mixture solvent of hexane and toluene as a developing layer) to obtain Intermediate IM-54 (15.46 g, yield 85%).

Through the measurement of FAB-MS, mass number of m/z=451 was observed as a molecular ion peak, and Intermediate IM-54 was identified.

(Synthesis of Compound A78)

Under an Ar atmosphere, to a 300 mL, three neck flask, Intermediate IM-4 (5.00 g, 17.1 mmol), Intermediate IM-54 (8.51 g, 1.1 equiv, 18.9 mmol), $K_2CO_3$ (7.11 g, 3.0 equiv, 51.4 mmol), Pd(PPh$_3$)$_4$ (0.99 g, 0.05 eq, 0.9 mmol), and 120 mL of a mixture solution of toluene/EtOH/H$_2$O (4/2/1) were added in order, and heated to about 80° C. and stirred. After cooling to room temperature, the reaction solution was extracted with toluene. An aqueous layer was removed, and an organic layer was washed with a saturated saline solution and dried with $MgSO_4$. After filtering $MgSO_4$, an organic layer was concentrated, and the crude product thus obtained was separated by silica gel column chromatography (using a mixture solvent of hexane and toluene as a developing layer) to obtain Compound A78 (7.33 g, yield 78%).

Through the measurement of FAB-MS, mass number of m/z=548 was observed as a molecular ion peak, and Compound A78 was identified.

<Synthesis of Compound A120>

Compound A120 according to an embodiment may be synthesized, for example, by the steps of Reaction 16 below.

[Reaction 16]

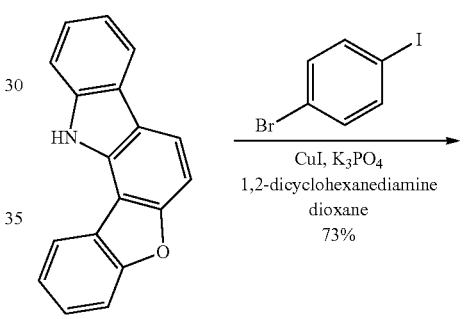

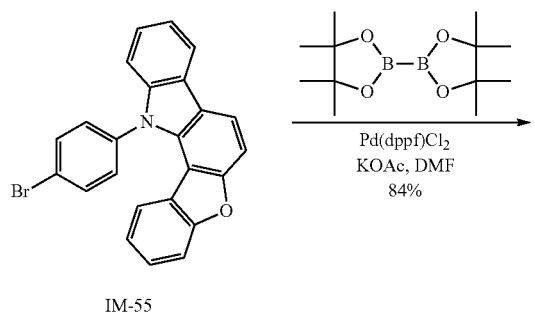

IM-55

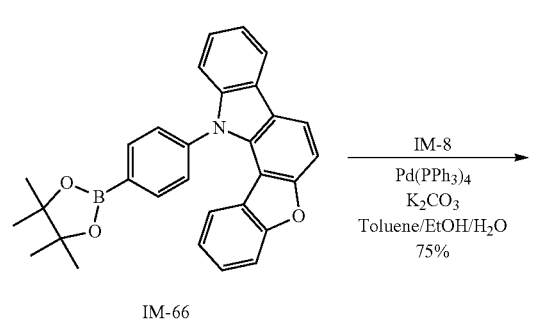

IM-66

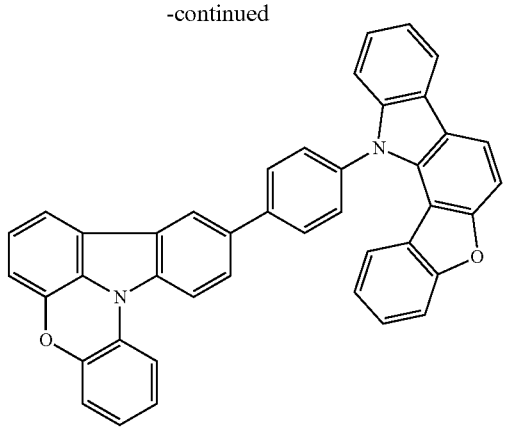

A120

(Synthesis of Intermediate IM-55)

Under an Ar atmosphere, to a 1,000 mL, three neck flask, 12H-benzofuro[3,2-a]carbazole (20.00 g, 77.7 mmol), CuI (1.48 g, 0.1 equiv, 7.8 mmol), $K_3PO_4$ (49.50 g, 3.0 equiv, 233.2 mmol), 1-bromo-4-iodobenzene (110.0 g, 5.0 equiv, 388.7 mmol), 1,4-dioxane (388 mL), and 1,2-cyclohexanediamine (1.78 g, 0.2 equiv, 15.5 mmol) were added in order, and heated, refluxed and stirred. After cooling to room temperature, water was added to the reaction solution, suction filtration was performed using celite, and an organic layer was separately taken. Toluene was added to an aqueous layer, and an organic layer was further extracted. Organic layers were collected, washed with a saline solution, and dried with $MgSO_4$. After filtering $MgSO_4$, an organic layer was concentrated, and the crude product thus obtained was separated by silica gel column chromatography (using a mixture solvent of hexane and toluene as a developing layer) to obtain Intermediate IM-55 (23.40 g, yield 73%).

Through the measurement of FAB-MS, mass number of m/z=412 was observed as a molecular ion peak, and Intermediate IM-55 was identified.

(Synthesis of Intermediate IM-56)

Under an Ar atmosphere, to a 500 mL, three neck flask, Intermediate IM-55 (15.00 g, 36.4 mmol), Pd(dppf)Cl$_2$ (2.97 g, 0.1 equiv, 3.6 mmol), KOAc (7.14 g, 2.0 equiv, 72.7 mmol), DMF (182 mL) and bis(pinacolato)diboron (11.09 g, 1.2 equiv, 43.7 mmol) were added in order, and heated, refluxed and stirred. After cooling to room temperature, water was added to the reaction solution, and an organic layer was separately taken. Toluene was added to an aqueous layer, and an organic layer was further extracted. Organic layers were collected, washed with a saline solution, and dried with $MgSO_4$. After filtering $MgSO_4$, an organic layer was concentrated, and the crude product thus obtained was separated by silica gel column chromatography (using a mixture solvent of hexane and toluene as a developing layer) to obtain Intermediate IM-56 (15.02 g, yield 84%).

Through the measurement of FAB-MS, mass number of m/z=491 was observed as a molecular ion peak, and Intermediate IM-56 was identified.

(Synthesis of Compound A120)

Under an Ar atmosphere, to a 300 mL, three neck flask, Intermediate IM-8 (5.00 g, 17.1 mmol), Intermediate IM-56 (9.27 g, 1.1 equiv, 18.9 mmol), $K_2CO_3$ (7.11 g, 3.0 equiv, 51.4 mmol), Pd(PPh$_3$)$_4$ (0.99 g, 0.05 eq, 0.9 mmol), and 120 mL of a mixture solution of toluene/EtOH/H$_2$O (4/2/1) were added in order, and heated to about 80° C. and stirred. After cooling to room temperature, the reaction solution was extracted with toluene. An aqueous layer was removed, and an organic layer was washed with a saturated saline solution and dried with $MgSO_4$. After filtering $MgSO_4$, an organic layer was concentrated, and the crude product thus obtained was separated by silica gel column chromatography (using a mixture solvent of hexane and toluene as a developing layer) to obtain Compound A120 (7.57 g, yield 75%).

Through the measurement of FAB-MS, mass number of m/z=588 was observed as a molecular ion peak, and Compound A120 was identified.

<Synthesis of Compound B18>

Compound B18 according to an embodiment may be synthesized, for example, by the steps of Reaction 17 below.

[Reaction 17]

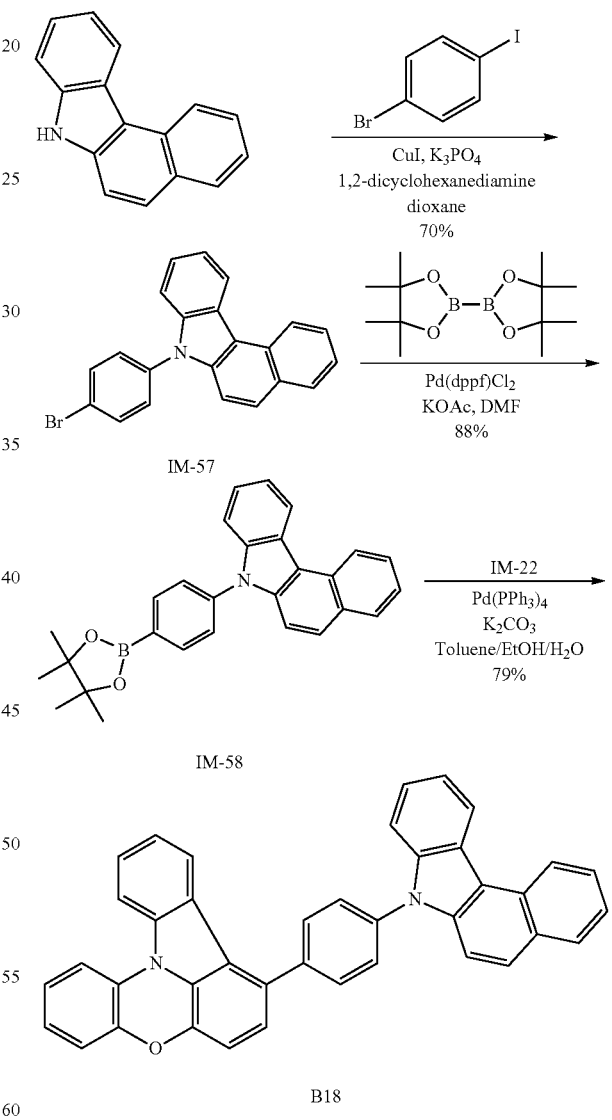

(Synthesis of Intermediate IM-57)

Under an Ar atmosphere, to a 1,000 mL, three neck flask, 7H-benzo[c]carbazole (20.00 g, 92.1 mmol), CuI (1.75 g, 0.1 equiv, 9.2 mmol), $K_3PO_4$ (58.62 g, 3.0 equiv, 276.2 mmol), 1-bromo-4-iodobenzene (130.21 g, 5.0 equiv, 460.3 mmol), 1,4-dioxane (460 mL), and 1,2-cyclohexanediamine (2.10 g, 0.2 equiv, 18.4 mmol) were added in order, and heated, refluxed and stirred. After cooling to room temperature, water was added to the reaction solution, suction filtration was performed using celite, and an organic layer was separately taken. Toluene was added to an aqueous layer, and an organic layer was further extracted. Organic layers were collected, washed with a saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-57 (23.99 g, yield 70%).

Through the measurement of FAB-MS, mass number of m/z=372 was observed as a molecular ion peak, and Intermediate IM-57 was identified.

(Synthesis of Intermediate IM-58)

Under an Ar atmosphere, to a 500 mL, three neck flask, Intermediate IM-57 (15.00 g, 40.3 mmol), Pd(dppf)Cl$_2$ (3.29 g, 0.1 equiv, 4.0 mmol), KOAc (7.91 g, 2.0 equiv, 80.6 mmol), DMF (201 mL) and bis(pinacolato)diboron (12.28 g, 1.2 equiv, 48.4 mmol) were added in order, and heated, refluxed and stirred. After cooling to room temperature, water was added to the reaction solution, and an organic layer was separately taken. Toluene was added to an aqueous layer, and an organic layer was further extracted. Organic layers were collected, washed with a saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-58 (16.01 g, yield 88%).

Through the measurement of FAB-MS, mass number of m/z=451 was observed as a molecular ion peak, and Intermediate IM-58 was identified.

(Synthesis of Compound B180)

Under an Ar atmosphere, to a 300 mL, three neck flask, Intermediate IM-22 (5.00 g, 12.3 mmol), Intermediate IM-58 (6.13 g, 1.1 equiv, 13.6 mmol), K$_2$CO$_3$ (5.11 g, 3.0 equiv, 37.0 mmol), Pd(PPh$_3$)$_4$ (0.71 g, 0.05 eq, 0.6 mmol), and 86 mL of a mixture solution of toluene/EtOH/H$_2$O (4/2/1) were added in order, and heated to about 80° C. and stirred. After cooling to room temperature, the reaction solution was extracted with toluene. An aqueous layer was removed, and an organic layer was washed with a saturated saline solution and dried with MgSO$_4$. After filtering MgSO$_4$, an organic layer was concentrated, and the crude product thus obtained was separated by silica gel column chromatography (using a mixture solvent of hexane and toluene as a developing layer) to obtain Compound B18 (5.35 g, yield 79%).

Through the measurement of FAB-MS, mass number of m/z=548 was observed as a molecular ion peak, and Compound B18 was identified.

<Synthesis of Compound B71>

Compound B71 according to an embodiment may be synthesized, for example, by the steps of Reaction 18 below.

[Reaction 18]

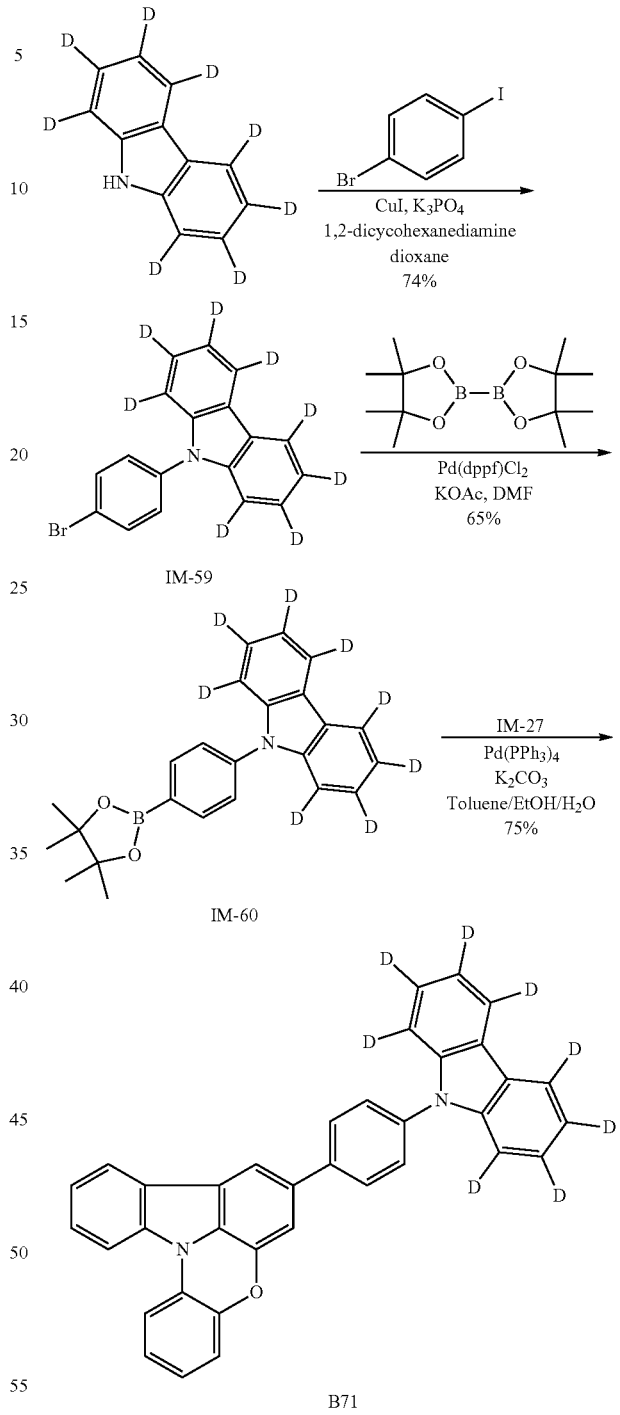

(Synthesis of Intermediate IM-59)

Under an Ar atmosphere, to a 1,000 mL, three neck flask, 9H-1,2,3,4,5,6,7,8-d8 (20.00 g, 114.1 mmol), CuI (2.17 g, 0.1 equiv, 11.4 mmol), K$_3$PO$_4$ (72.7 g, 3.0 equiv, 342.3 mmol), 1-bromo-4-iodobenzene (161.42 g, 5.0 equiv, 570.6 mmol), 1,4-dioxane (570 mL), and 1,2-cyclohexanediamine (2.61 g, 0.2 equiv, 22.8 mmol) were added in order, and heated, refluxed and stirred. After cooling to room temperature, water was added to the reaction solution, suction filtration was performed using celite, and an organic layer was separately taken. Toluene was added to an aqueous layer, and an organic layer was further extracted. Organic layers were collected, washed with a saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-59 (27.89 g, yield 74%).

Through the measurement of FAB-MS, mass number of m/z=330 was observed as a molecular ion peak, and Intermediate IM-59 was identified.

(Synthesis of Intermediate IM-60)

Under an Ar atmosphere, to a 500 mL, three neck flask, Intermediate IM-59 (15.00 g, 45.4 mmol), Pd(dppf)Cl$_2$ (3.71 g, 0.1 equiv, 4.5 mmol), KOAc (8.92 g, 2.0 equiv, 90.8 mmol), DMF (227 mL) and bis(pinacolato)diboron (13.84 g, 1.2 equiv, 54.5 mmol) were added in order, and heated, refluxed and stirred. After cooling to room temperature, water was added to the reaction solution, and an organic layer was separately taken. Toluene was added to an aqueous layer, and an organic layer was further extracted. Organic layers were collected, washed with a saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-60 (15.81 g, yield 85%).

Through the measurement of FAB-MS, mass number of m/z=409 was observed as a molecular ion peak, and Intermediate IM-60 was identified.

(Synthesis of Compound B71)

Under an Ar atmosphere, to a 300 mL, three neck flask, Intermediate IM-27 (5.00 g, 17.1 mmol), Intermediate IM-60 (7.72 g, 1.1 equiv, 18.9 mmol), K$_2$CO$_3$ (7.11 g, 3.0 equiv, 51.4 mmol), Pd(PPh$_3$)$_4$ (0.99 g, 0.05 eq, 0.9 mmol), and 120 mL of a mixture solution of toluene/EtOH/H$_2$O (4/2/1) were added in order, and heated to about 80° C. and stirred. After cooling to room temperature, the reaction solution was extracted with toluene. An aqueous layer was removed, and an organic layer was washed with a saturated saline solution and dried with MgSO$_4$. After filtering MgSO$_4$, an organic layer was concentrated, and the crude product thus obtained was separated by silica gel column chromatography (using a mixture solvent of hexane and toluene as a developing layer) to obtain Compound B71 (6.51 g, yield 75%).

Through the measurement of FAB-MS, mass number of m/z=506 was observed as a molecular ion peak, and Compound B71 was identified.

<Synthesis of Compound C117>

Compound C117 according to an embodiment may be synthesized, for example, by the steps of Reaction 19 below.

[Reaction 19]

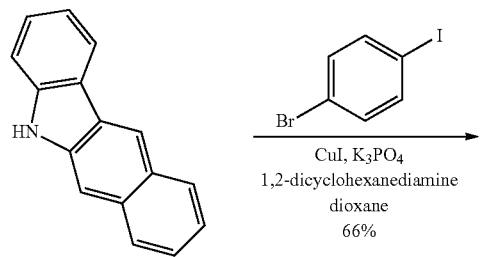

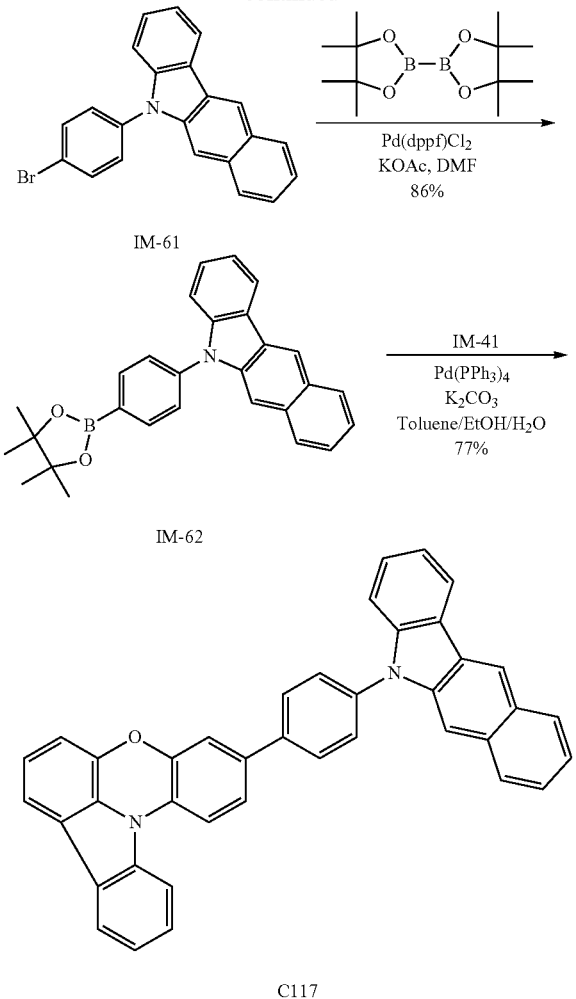

(Synthesis of Intermediate IM-61)

Under an Ar atmosphere, to a 1,000 mL, three neck flask, 5H-benzo[c]carbazole (20.00 g, 92.1 mmol), CuI (1.75 g, 0.1 equiv, 9.2 mmol), K$_3$PO$_4$ (58.62 g, 3.0 equiv, 276.2 mmol), 1-bromo-4-iodobenzene (130.21 g, 5.0 equiv, 460.3 mmol), 1,4-dioxane (460 mL), and 1,2-cyclohexanediamine (2.10 g, 0.2 equiv, 18.4 mmol) were added in order, and heated, refluxed and stirred. After cooling to room temperature, water was added to the reaction solution, suction filtration was performed using celite, and an organic layer was separately taken. Toluene was added to an aqueous layer, and an organic layer was further extracted. Organic layers were collected, washed with a saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-61 (22.62 g, yield 66%).

Through the measurement of FAB-MS, mass number of m/z=372 was observed as a molecular ion peak, and Intermediate IM-61 was identified.

(Synthesis of Intermediate IM-62)

Under an Ar atmosphere, to a 500 mL, three neck flask, Intermediate IM-61 (15.00 g, 40.3 mmol), Pd(dppf)Cl$_2$ (3.29 g, 0.1 equiv, 4.0 mmol), KOAc (7.91 g, 2.0 equiv, 80.6 mmol), DMF (201 mL) and bis(pinacolato)diboron (12.28 g, 1.2 equiv, 48.4 mmol) were added in order, and heated, refluxed and stirred. After cooling to room temperature, water was added to the reaction solution, and an organic layer was separately taken. Toluene was added to an aqueous layer, and an organic layer was further extracted. Organic layers were collected, washed with a saline solution, and dried with MgSO$_4$. After filtering MgSO$_4$, an organic layer was concentrated, and the crude product thus obtained was separated by silica gel column chromatography (using a mixture solvent of hexane and toluene as a developing layer) to obtain Intermediate IM-62 (15.46 g, yield 85%).

Through the measurement of FAB-MS, mass number of m/z=451 was observed as a molecular ion peak, and Intermediate IM-62 was identified.

(Synthesis of Compound C117)

Under an Ar atmosphere, to a 300 mL, three neck flask, Intermediate IM-41 (5.00 g, 14.9 mmol), Intermediate IM-62 (7.39 g, 1.1 equiv, 16.4 mmol), K$_2$CO$_3$ (6.16 g, 3.0 equiv, 44.6 mmol), Pd(PPh$_3$)$_4$ (0.86 g, 0.05 eq, 0.7 mmol), and 105 mL of a mixture solution of toluene/EtOH/H$_2$O (4/2/1) were added in order, and heated to about 80° C. and stirred. After cooling to room temperature, the reaction solution was extracted with toluene. An aqueous layer was removed, and an organic layer was washed with a saturated saline solution and dried with MgSO$_4$. After filtering MgSO$_4$, an organic layer was concentrated, and the crude product thus obtained was separated by silica gel column chromatography (using a mixture solvent of hexane and toluene as a developing layer) to obtain Compound C117 (6.28 g, yield 77%).

Through the measurement of FAB-MS, mass number of m/z=548 was observed as a molecular ion peak, and Compound C117 was identified.

2. Manufacture and Evaluation of Light Emitting Device

Light emitting devices of Examples 1 and 13 including Compound A1, Compound A55, Compound A66, Compound A78, Compound A113, Compound A120, Compound A132, Compound A173, Compound B18, Compound B19, Compound B54, Compound B71, Compound B145, Compound C15, Compound C99, Compound C148, Compound C158, Compound C117, and Compound D1 in a functional layer were manufactured.

(Example Compounds Used for Manufacturing Devices)

A1

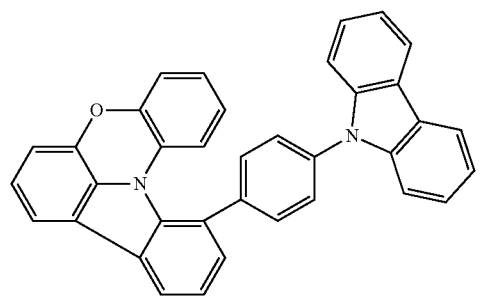

A55

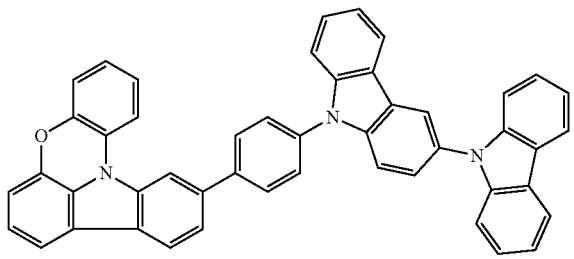

A113

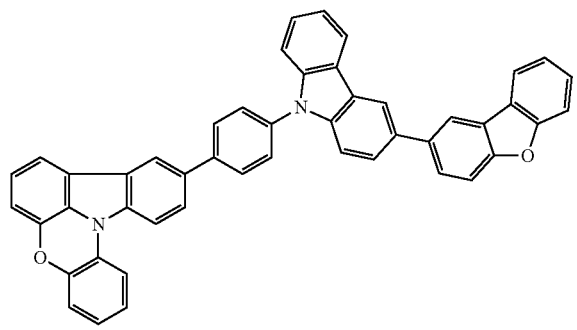

A132

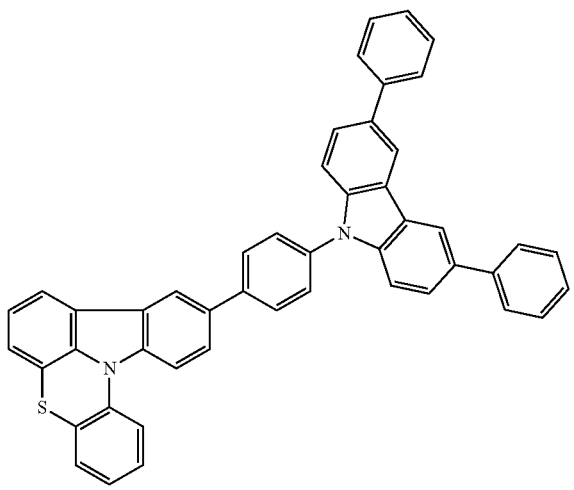

-continued
A173
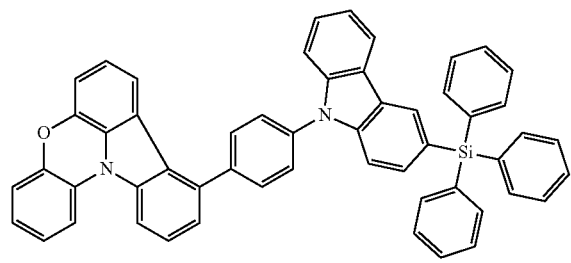
B19
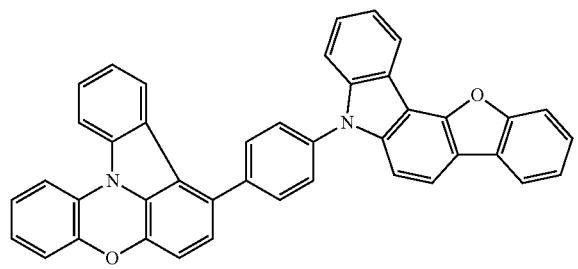
B54
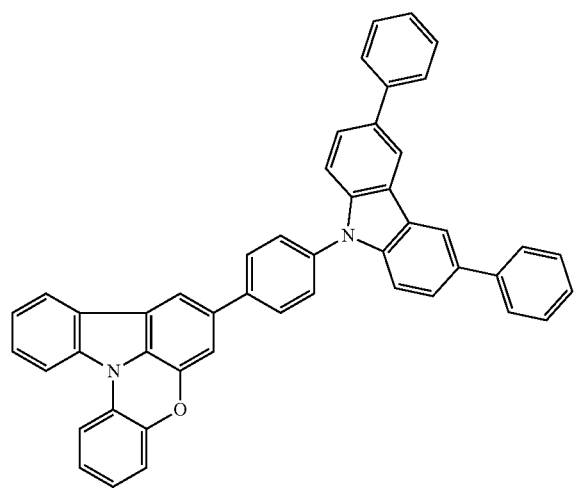
B145
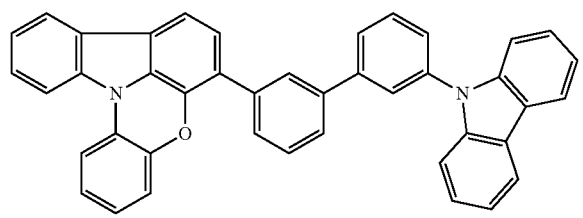
C15
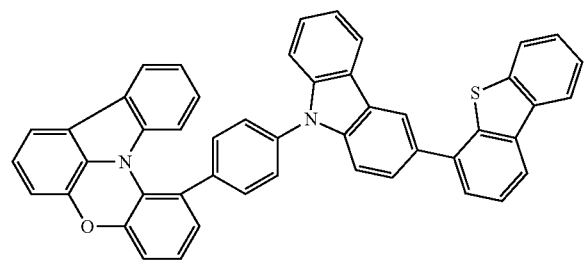
C58
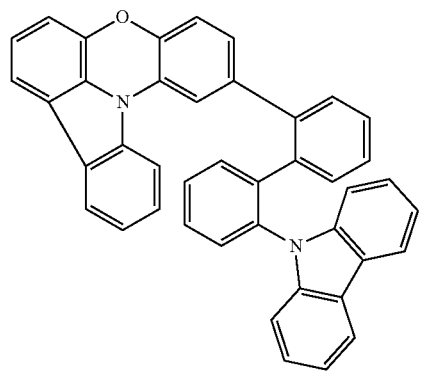
C148
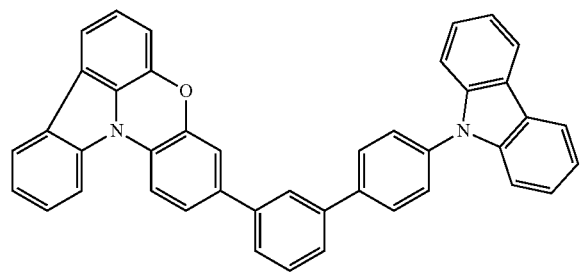
C158
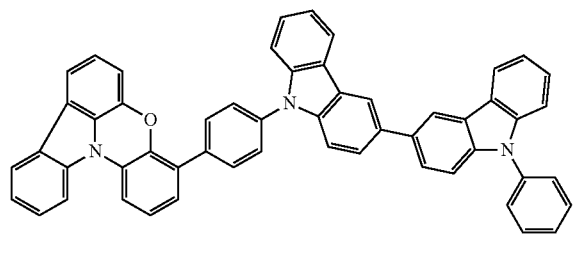

-continued
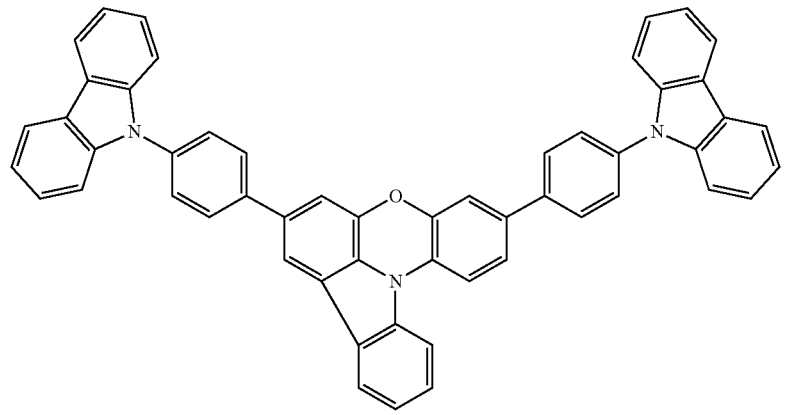
D1
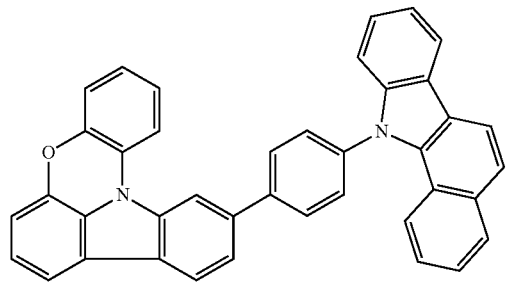
A66
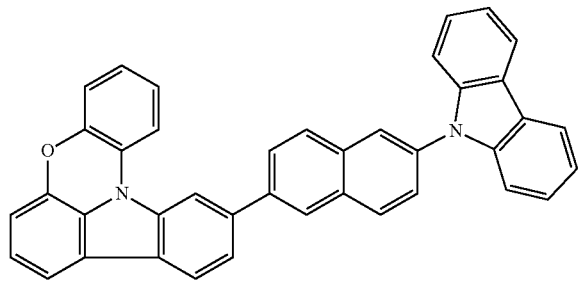
A78
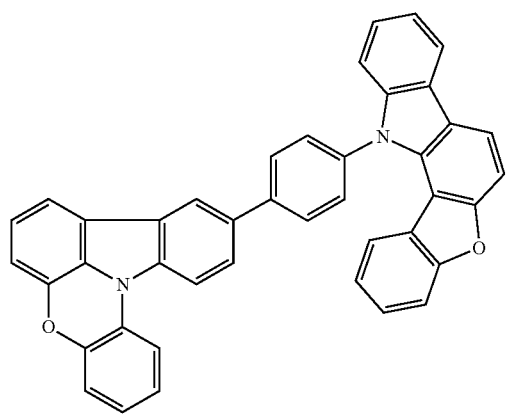
A120
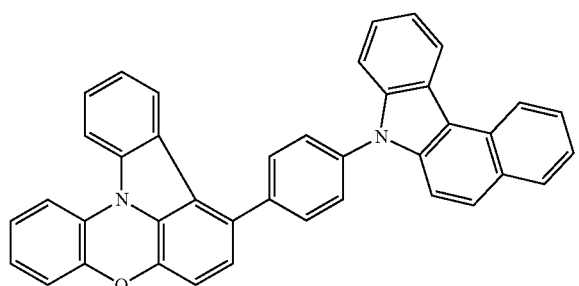
B18
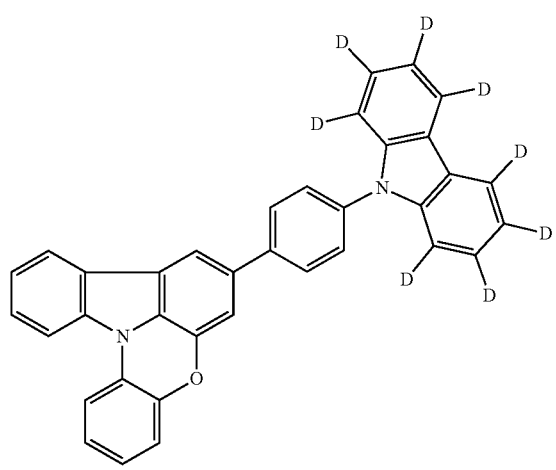
B71
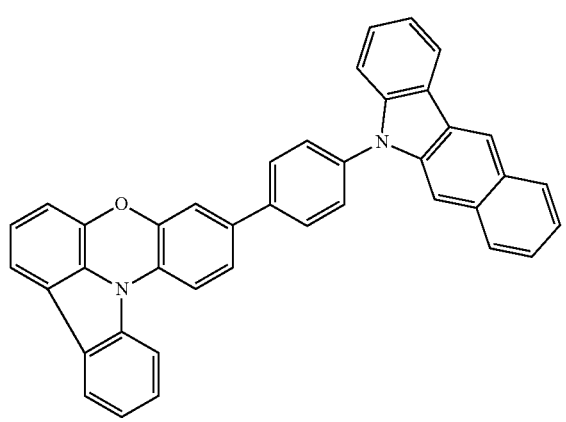
C117

301
(Comparative Compounds Used for Manufacturing Devices)
R1
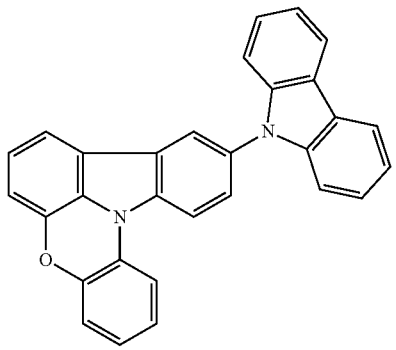
R2
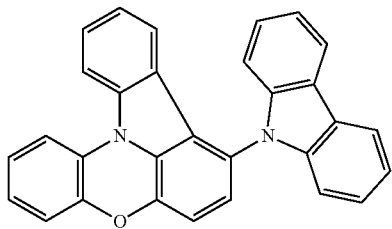
R3
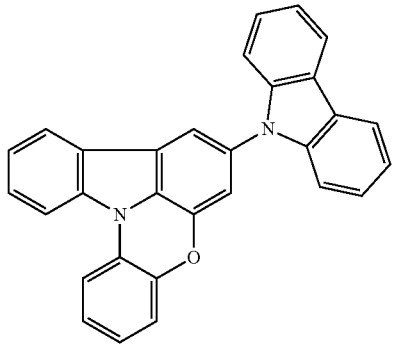
R4
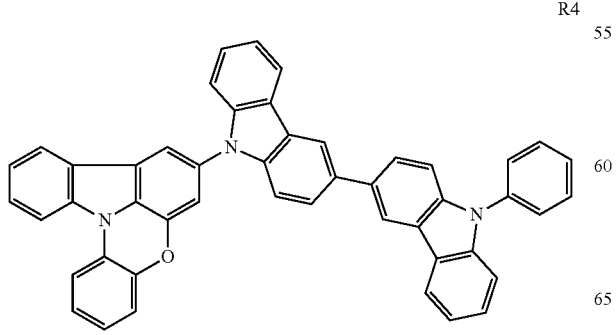
302
-continued
R5
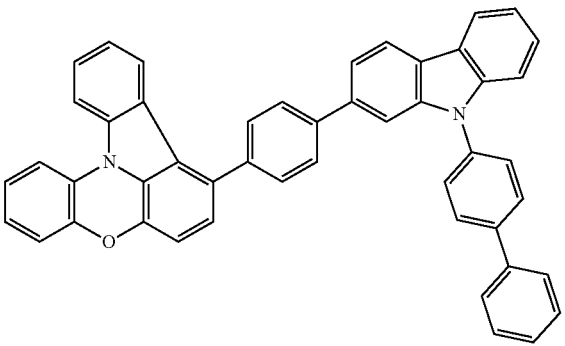
R6
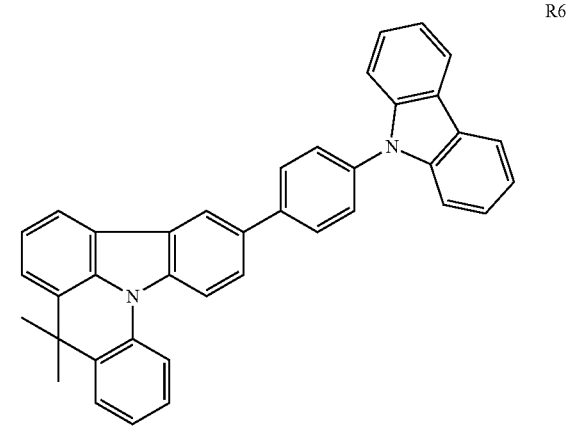
R7
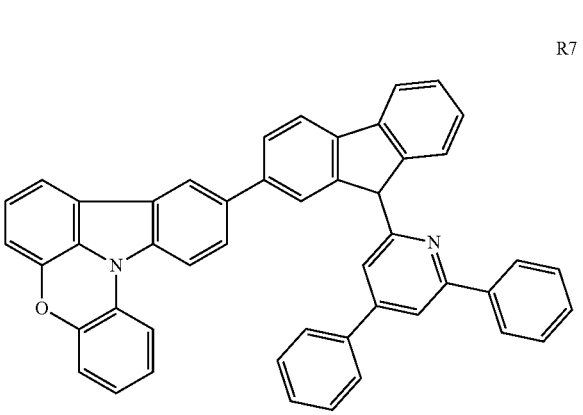
R8
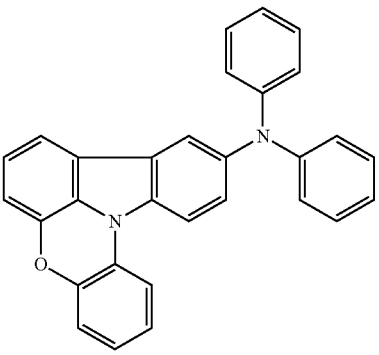

-continued

R9
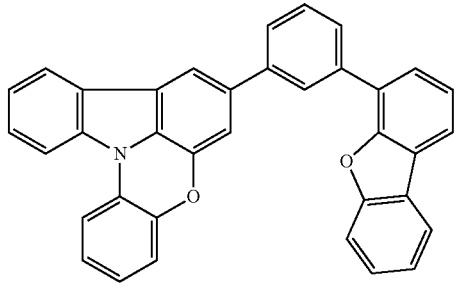

R10
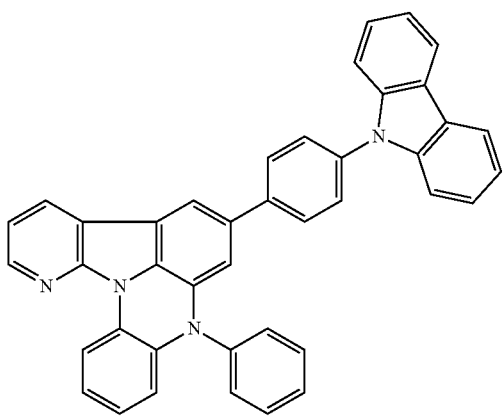

R11
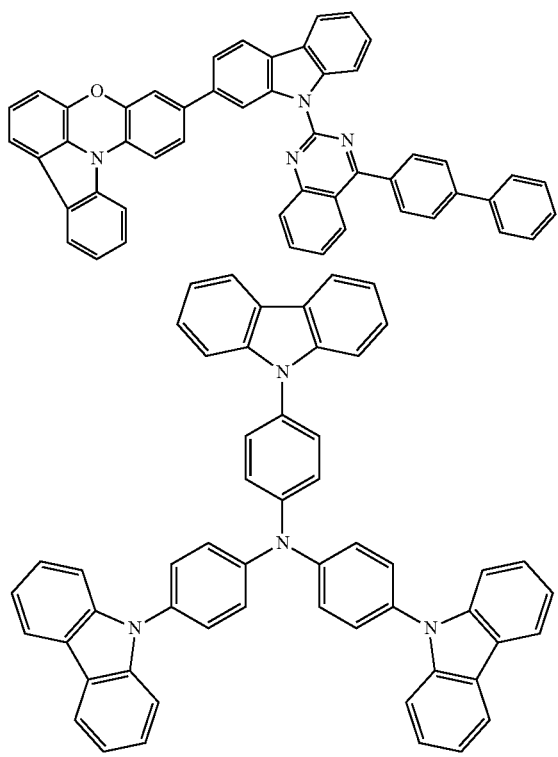

TCTA

-continued

5
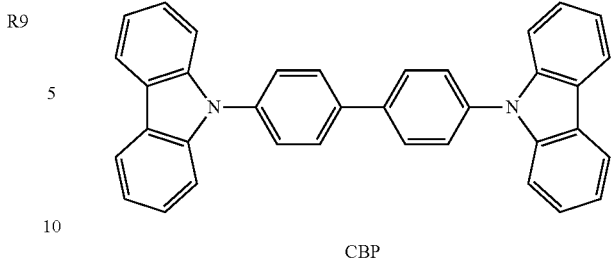

10
CBP (Manufacture of Light Emitting Device 1)

A light emitting device of an embodiment, including the polycyclic compound of an embodiment or the Comparative Compound in a hole transport layer and a fluorescence emitting material in an emission layer was manufactured by a method below.

On a glass substrate, ITO with a thickness of about 1,500 Å was patterned, and washed with ultrapure water and treated with UV and ozone for about 10 minutes. 2-TNATA was deposited to a thickness of about 600 Å to form a hole injection layer. The Example Compound or Comparative Compound was deposited to a thickness of about 300 Å to form a hole transport layer. Light emitting devices were manufactured using Compound A1, Compound A55, Compound A113, Compound A132, Compound A173, Compound B19, Compound B54, Compound B145, Compound C15, Compound C99, Compound C148, Compound C158, Compound D1, Compound A66, Compound A78, Compound A120, Compound B18, Compound B71, and Compound C117 as hole transport layer materials in Example 1-1 to Example 19, respectively. In Comparative Examples 1-1 to 1-11, light emitting devices were manufactured using Comparative Compounds R1 to R11 as hole transport layer materials, respectively.

An emission layer of ADN doped with 3% TBP was formed to a thickness of about 250 Å. $Alq_3$ was deposited to a thickness of about 250 Å to form an electron transport layer, and LiF was deposited to a thickness of about 10 Å to form an electron injection layer.

Al was provided to a thickness of about 1,000 Å to form a second electrode.

In the Examples, the hole injection layer, the hole transport layer, the emission layer, the electron transport layer, the electron injection layer and the second electrode were formed using a vacuum deposition apparatus.

(Evaluation of Properties of Light Emitting Device 1)

In Table 1, the evaluation results of the light emitting devices of Example 1-1 to Example 1-19, and Comparative Example 1-1 to Comparative Example 1-11 are shown. In Table 1, the emission efficiency and device life of the light emitting devices manufactured are compared. In the evaluation results on the properties of the Examples and Comparative Examples shown in Table 1, the emission efficiency shows an efficiency value at a current density of about 10 $mA/cm^2$, and the device life (LT50) shows luminance half life at about 1.0 $mA/cm^2$.

The current density, voltage and emission efficiency of the light emitting devices of the Examples and the Comparative Examples were measured using 2400 series Source Meter of Keithley Instrument Co., Color Luminance Meter CS-200 of Konica Minolta Co. and PC Program LabVIEW 2.0 for measurement of Japanese National Instrument Co. in a dark room.

TABLE 1

| Device manufacturing example | Hole transport layer material | Emission efficiency (cd/A) | Device life LT50 (h) |
|---|---|---|---|
| Example 1-1 | Example Compound A1 | 127% | 141% |
| Example 1-2 | Example Compound A55 | 123% | 144% |
| Example 1-3 | Example Compound A113 | 124% | 152% |
| Example 1-4 | Example Compound A132 | 129% | 155% |
| Example 1-5 | Example Compound A173 | 134% | 149% |
| Example 1-6 | Example Compound B19 | 131% | 147% |
| Example 1-7 | Example Compound B54 | 126% | 155% |
| Example 1-8 | Example Compound B145 | 140% | 150% |
| Example 1-9 | Example Compound C15 | 129% | 148% |
| Example 1-10 | Example Compound C99 | 132% | 146% |
| Example 1-11 | Example Compound C148 | 127% | 145% |
| Example 1-12 | Example Compound C158 | 133% | 144% |
| Example 1-13 | Example Compound D1 | 130% | 150% |
| Example 1-14 | Example Compound A66 | 126% | 144% |
| Example 1-15 | Example Compound A78 | 123% | 148% |
| Example 1-16 | Example Compound A120 | 129% | 143% |
| Example 1-17 | Example Compound B18 | 132% | 145% |
| Example 1-18 | Example Compound B71 | 130% | 148% |
| Example 1-19 | Example Compound C117 | 128% | 143% |
| Comparative Example 1-1 | Comparative Compound R1 | 100% | 100% |
| Comparative Example 1-2 | Comparative Compound R2 | 104% | 95% |
| Comparative Example 1-3 | Comparative Compound R3 | 103% | 92% |
| Comparative Example 1-4 | Comparative Compound R4 | 94% | 90% |
| Comparative Example 1-5 | Comparative Compound R5 | 105% | 105% |
| Comparative Example 1-6 | Comparative Compound R6 | 93% | 60% |
| Comparative Example 1-7 | Comparative Compound R7 | 86% | 45% |
| Comparative Example 1-8 | Comparative Compound R8 | 103% | 96% |
| Comparative Example 1-9 | Comparative Compound R9 | 86% | 55% |
| Comparative Example 1-10 | Comparative Compound R10 | 82% | 53% |
| Comparative Example 1-11 | Comparative Compound R11 | 84% | 49% |

The emission efficiency and device-life characteristics shown in Table 1 are relative values based on Comparative Example 1-1. The emission efficiency and device life correspond to relative ratios in case where the emission efficiency and device life of Comparative Example 1-1 are set to 10000. Referring to the results of Table 1, it could be found that the Examples of the light emitting devices using the polycyclic compounds of embodiments as hole transport layer materials showed excellent device efficiency and improved device-life characteristics. Referring to Table 1, it could be confirmed that the devices of Example 1-1 to Example 1-19 showed longer life and higher efficiency when compared with the devices of Comparative Example 1-1 to Comparative Example 1-11.

(Manufacture of Light Emitting Device 2)

A light emitting device of an embodiment including the polycyclic compound of an embodiment or the Comparative Compound in a hole transport layer and a phosphorescence emitting material in an emission layer was manufactured by a method below.

On a glass substrate, ITO with a thickness of about 1,200 Å was patterned, and washed with ultrapure water and treated with UV and ozone for about 10 minutes. NPB was deposited to a thickness of about 400 Å to form a hole injection layer. The Example Compound or Comparative Compound was deposited to a thickness of about 100 Å to form a hole transport layer. Light emitting devices were manufactured using Compound A1, Compound A55, Compound A113, Compound A132, Compound A173, Compound B19, Compound B54, Compound B145, Compound C15, Compound C99, Compound C148, Compound C158, Compound A66, Compound A78, Compound A120, Compound B18, Compound B71, and Compound C117 as hole transport layer materials in Example 2-1 to Example 2-18, respectively. In Comparative Examples 2-1 to 1-8, and 2-10 to 2-12, light emitting devices were manufactured using Comparative Compounds R1 to R11 as hole transport layer materials, respectively. In Comparative Example 2-9, TCTA was used as a hole transport layer material.

An emission layer of CBP doped with 5% Ir(ppy)$_3$ was formed to a thickness of about 300 Å. BPhen was deposited to a thickness of about 500 Å to form an electron transport layer, and LiF was deposited to a thickness of about 10 Å to form an electron injection layer.

Al was provided to a thickness of about 1,100 Å to form a second electrode.

In the Examples, the hole injection layer, the hole transport layer, the emission layer, the electron transport layer, the electron injection layer and the second electrode were formed using a vacuum deposition apparatus.

(Evaluation of Properties of Light Emitting Device 2)

In Table 2, the evaluation results of the light emitting devices of Example 2-1 to Example 2-18, and Comparative Example 2-1 to Comparative Example 2-12 are shown. In Table 2, the emission efficiency and device life of the light emitting devices manufactured are compared. In the evaluation results on the properties of the Examples and Comparative Examples shown in Table 2, the emission efficiency shows an efficiency value at a current density of about 10 mA/cm$^2$, and the device life (LT50) shows luminance half life at about 1.0 mA/cm$^2$.

The current density, voltage and emission efficiency of the light emitting devices of the Examples and the Comparative Examples were measured using 2400 series Source Meter of Keithley Instrument Co., Color Luminance Meter C1-200 of Konica Minolta Co. and PC Program LabVIEW 2.0 for measurement of Japanese National Instrument Co. in a dark room.

TABLE 2

| Device manufacturing example | Hole transport layer material | Emission efficiency (cd/A) | Device life LT50 (h) |
|---|---|---|---|
| Example 2-1 | Example Compound A1 | 124% | 144% |
| Example 2-2 | Example Compound A55 | 122% | 142% |
| Example 2-3 | Example Compound A113 | 127% | 152% |
| Example 2-4 | Example Compound A132 | 129% | 155% |
| Example 2-5 | Example Compound A173 | 131% | 141% |
| Example 2-6 | Example Compound B19 | 130% | 160% |
| Example 2-7 | Example Compound B54 | 128% | 165% |
| Example 2-8 | Example Compound B145 | 132% | 144% |
| Example 2-9 | Example Compound C15 | 130% | 148% |
| Example 2-10 | Example Compound C99 | 136% | 147% |
| Example 2-11 | Example Compound C148 | 130% | 141% |
| Example 2-12 | Example Compound C158 | 128% | 148% |
| Example 2-13 | Example Compound A66 | 123% | 144% |
| Example 2-14 | Example Compound A78 | 126% | 152% |
| Example 2-15 | Example Compound A120 | 130% | 156% |
| Example 2-16 | Example Compound B18 | 132% | 149% |
| Example 2-17 | Example Compound B71 | 129% | 152% |
| Example 2-18 | Example Compound C117 | 129% | 148% |
| Comparative Example 2-1 | Comparative Compound R1 | 100% | 100% |
| Comparative Example 2-2 | Comparative Compound R2 | 103% | 94% |

TABLE 2-continued

| Device manufacturing example | Hole transport layer material | Emission efficiency (cd/A) | Device life LT50 (h) |
|---|---|---|---|
| Comparative Example 2-3 | Comparative Compound R3 | 101% | 90% |
| Comparative Example 2-4 | Comparative Compound R4 | 91% | 87% |
| Comparative Example 2-5 | Comparative Compound R5 | 102% | 104% |
| Comparative Example 2-6 | Comparative Compound R6 | 90% | 62% |
| Comparative Example 2-7 | Comparative Compound R7 | 84% | 46% |
| Comparative Example 2-8 | Comparative Compound R8 | 101% | 92% |
| Comparative Example 2-9 | TCTA | 93% | 86% |
| Comparative Example 2-10 | Comparative Compound R9 | 80% | 58% |
| Comparative Example 2-11 | Comparative Compound R10 | 77% | 45% |
| Comparative Example 2-12 | Comparative Compound R11 | 81% | 47% |

The emission efficiency and device-life characteristics shown in Table 2 are relative values based on Comparative Example 2-1. The emission efficiency and device life correspond to relative ratios in case where the emission efficiency and device life of Comparative Example 2-1 are set to 100%. Referring to the results of Table 2, it could be found that the Examples of the light emitting devices using the polycyclic compounds of embodiments as hole transport layer materials showed excellent device efficiency and improved device-life characteristics. Referring to Table 2, it could be confirmed that the devices of Example 2-1 to Example 2-18 showed longer life and higher efficiency when compared with the devices of Comparative Example 2-1 to Comparative Example 2-12.

(Manufacture of Light Emitting Device 3)

A light emitting device of an embodiment including the polycyclic compound of an embodiment or the Comparative Compound in a hole transport layer and a phosphorescence emitting material in an emission layer was manufactured by a method below.

On a glass substrate, ITO with a thickness of about 1,200 Å was patterned, and washed with ultrapure water and treated with UV and ozone for about 10 minutes. NPB was deposited to a thickness of about 400 Å to form a hole injection layer. TCTA was deposited to a thickness of about 100 Å to form a hole transport layer.

An emission layer of the Example Compound or Comparative Compound doped with 5% Ir(ppy)$_3$ was formed to a thickness of about 300 Å. Light emitting devices were manufactured using Compound A1, Compound A55, Compound A113, Compound A132, Compound A173, Compound B19, Compound B54, Compound B145, Compound C15, Compound C99, Compound C148, Compound C158, Compound A66, Compound A78, Compound A120, Compound B18, Compound B71, and Compound C117 as emission layer materials in Example 3-1 to Example 3-18, respectively. In Comparative Examples 3-1 to 3-8, and 3-10 to 3-12, light emitting devices were manufactured using Comparative Compounds R1 to R11 as emission layer materials, respectively. In Comparative Example 3-9, CBP was used as an emission layer material.

BPhen was deposited to a thickness of about 500 Å to form an electron transport layer, and LiF was deposited to a thickness of about 10 Å to form an electron injection layer. Al was provided to a thickness of about 1,100 Å to form a second electrode.

In the Examples, the hole injection layer, the hole transport layer, the emission layer, the electron transport layer, the electron injection layer and the second electrode were formed using a vacuum deposition apparatus.

(Evaluation of Properties of Light Emitting Device 3)

In Table 3, the evaluation results of the light emitting devices of Example 3-1 to Example 3-18, and Comparative Example 3-1 to Comparative Example 3-12 are shown. In Table 3, the emission efficiency and device life of the light emitting devices manufactured are compared. In the evaluation results on the properties of the Examples and Comparative Examples shown in Table 3, the emission efficiency shows an efficiency value at a current density of about 10 mA/cm$^2$, and the device life (LT50) shows luminance half life at about 1.0 mA/cm$^2$.

The current density, voltage and emission efficiency of the light emitting devices of the Examples and the Comparative Examples were measured using 2400 series Source Meter of Keithley Instrument Co., Color Luminance Meter CS-200 of Konica Minolta Co. and PC Program LabVIEW 2.0 for measurement of Japanese National Instrument Co. in a dark room.

TABLE 3

| Device manufacturing example | Emission layer material | Emission efficiency (cd/A) | Device life LT50 (h) |
|---|---|---|---|
| Example 3-1 | Example Compound A1 | 129% | 135% |
| Example 3-2 | Example Compound A55 | 127% | 139% |
| Example 3-3 | Example Compound A113 | 130% | 141% |
| Example 3-4 | Example Compound A132 | 134% | 143% |
| Example 3-5 | Example Compound A173 | 139% | 131% |
| Example 3-6 | Example Compound B19 | 140% | 135% |
| Example 3-7 | Example Compound B54 | 131% | 140% |
| Example 3-8 | Example Compound B145 | 129% | 135% |
| Example 3-9 | Example Compound C15 | 132% | 142% |
| Example 3-10 | Example Compound C99 | 130% | 129% |
| Example 3-11 | Example Compound C148 | 131% | 132% |
| Example 3-12 | Example Compound C158 | 132% | 140% |
| Example 3-13 | Example Compound A66 | 135% | 141% |
| Example 3-14 | Example Compound A78 | 133% | 145% |
| Example 3-15 | Example Compound A120 | 138% | 137% |
| Example 3-16 | Example Compound B18 | 134% | 139% |
| Example 3-17 | Example Compound B71 | 130% | 140% |
| Example 3-18 | Example Compound C117 | 131% | 138% |
| Comparative Example 3-1 | Comparative Compound R1 | 100% | 100% |
| Comparative Example 3-2 | Comparative Compound R2 | 103% | 95% |
| Comparative Example 3-3 | Comparative Compound R3 | 100% | 92% |
| Comparative Example 3-4 | Comparative Compound R4 | 96% | 90% |
| Comparative Example 3-5 | Comparative Compound R5 | 102% | 105% |
| Comparative Example 3-6 | Comparative Compound R6 | 96% | 60% |
| Comparative Example 3-7 | Comparative Compound R7 | 89% | 45% |
| Comparative Example 3-8 | Comparative Compound R8 | 105% | 96% |
| Comparative Example 3-9 | CBP | 91% | 90% |
| Comparative Example 3-10 | Comparative Compound R9 | 88% | 75% |
| Comparative Example 3-11 | Comparative Compound R10 | 79% | 79% |
| Comparative Example 3-12 | Comparative Compound R11 | 75% | 81% |

The emission efficiency an device-life characteristics shown in Table are relative values based on Comparative Example 3-1. The emission efficiency and device life correspond to relative ratios in case where the emission efficiency and device life of Comparative Example 3-1 are set to 100%. Referring to the results of Table 3, it could be found that the Examples of the light emitting devices using the polycyclic compounds of embodiments as emission layer materials showed excellent device efficiency and improved device-life characteristics. Referring to Table 3, it could be confirmed that the devices of Example 3-1 to Example 3-18 showed longer life and higher efficiency when compared with the devices of Comparative Example 3-1 to Comparative Example 3-12.

The Example Compounds used in Table 1 to Table 3 include a structure in which a carbazole group is bonded to an indolo phenoxazine skeleton, and achieved high efficiency and long life.

Comparative Compound R1 to Comparative Compound R4 have a structure in which a carbazole group is directly bonded to an indolo phenoxazine skeleton without a separate linker, and since there is no linker, the conjugation length of a nitrogen atom is short. Accordingly, Comparative Compound R1 to Comparative Compound R4 could insufficiently stabilize radicals and radical cations to deteriorate materials during driving light emitting devices. When compared with the light emitting devices of the Examples, all the light emitting devices of Comparative Examples 1 to 4 showed degraded results of emission efficiency and device life.

In Comparative Compound R5, a carbon atom at position 2 of a carbazole group is bonded to an indolo phenoxazine skeleton via a linker. The position bonded of a carbazole group to indolo phenoxazine is different from the Example Compounds, and accordingly, charge distribution and electron donating properties by the carbazole group were changed, and degraded results of both device efficiency and life were shown when compared with the Examples.

Comparative Compound R6 has a fused structure of a carbazole group like in embodiments of the disclosure, but a $sp^3$ hybrid carbon atom moiety is included in the fused structure to be thermally unstable when compared embodiments of the disclosure which include a heteroatom. Accordingly, device life was degraded when compared with the Examples.

Comparative Compound R7 and Comparative Compound R11 include an electron withdrawing heterocycle as a substituent, and Comparative Compound R10 includes an electron withdrawing pyridine ring in an indolo phenoxazine skeleton. Comparative Compound R7, Comparative Compound R10, and Comparative Compound R11 include an electron withdrawing heterocycle, and have a reduced highest occupied molecular orbital (HOMO) level. Accordingly, hole transport properties were markedly reduced, and device efficiency was deteriorated when compared with the Examples.

Comparative Compound R8 includes an amine group, and carrier balance was collapsed when compared with the Example Compounds. Accordingly, degraded results of both device efficiency and life were shown when compared with the Examples.

Comparative Compound R9 does not include a carbazole group, and hole transport capacity is degraded. Accordingly, degraded results of both device efficiency and life were shown when compared with the Examples.

Comparative Compound TCTA used in Comparative Example 2-9 and Comparative Compound CBP used in Comparative Example 3-9 include a carbazole group but do not include an indolo phenoxazine skeleton when compared with the Example Compounds. Accordingly, the hole transport capacity and stability of a molecule were deteriorated, and degraded results of both device efficiency and life were shown when compared with the Examples.

The polycyclic compound of an embodiment may include an indolo phenoxazine skeleton or an indolo phenothiazine skeleton, a substituted or unsubstituted carbazole group, and a linker. When the polycyclic compound of an embodiment it applied to a light emitting device, emission efficiency and device life may each be improved. The indolo phenoxazine skeleton and the indolo phenothiazine skeleton are strongly crosslinked forms of 9-phenyl-9H-carbazole by the incorporation of heteroatoms, and hole transport capacity, heat resistance, and charge tolerance may be improved. A structure in which a carbazole group is bonded to an indolo phenoxazine or an indolo phenothiazine skeleton via a linker is included, and the hole transport capacity of a molecule may be improved.

Accordingly, if applied to a light emitting device, the Example Compounds may improve emission efficiency and device life when compared with the Comparative Compounds.

The light emitting device of an embodiment includes a polycyclic compound of an embodiment in a hole transport region and may show high efficiency and long-life characteristics.

The polycyclic compound of an embodiment may improve the emission efficiency and device life of a light emitting device.

Embodiments have been disclosed herein, and although terms are employed, they are used and are to be interpreted in a generic and descriptive sense only and not for purpose of limitation. In some instances, as would be apparent by one of ordinary skill in the art, features, characteristics, and/or elements described in connection with an embodiment may be used singly or in combination with features, characteristics, and/or elements described in connection with other embodiments unless otherwise specifically indicated. Accordingly, it will be understood by those of ordinary skill in the art that various changes in form and details may be made without departing from the spirit and scope of the disclosure as set forth in the following claims.

What is claimed is:

1. A light emitting device, comprising:
   a first electrode;
   a second electrode disposed on the first electrode; and
   at least one functional layer disposed between the first electrode and the second electrode, and comprising a polycyclic compound represented by Formula 1:

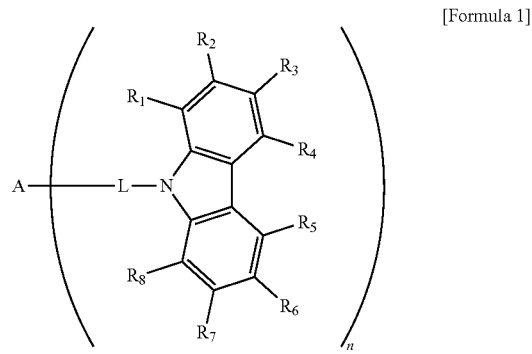

[Formula 1]

wherein in Formula 1,

L is a substituted or unsubstituted arylene group of 6 to 30 ring-forming carbon atoms, $R_1$ to $R_8$ are each independently a hydrogen atom, a deuterium atom, a halogen atom, a substituted or unsubstituted silyl group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or are combined with an adjacent group to form a ring, n is 1 or 2, and A is a group represented by Formula 2:

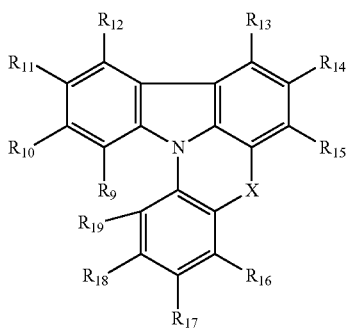

[Formula 2]

wherein in Formula 2,

X is O or S, $R_9$ to $R_{19}$ are each independently a hydrogen atom, a deuterium atom, a halogen atom, a substituted or unsubstituted alkyl group of 1 to 20 carbon atoms, or are combined with an adjacent group to form a ring, and at least one of $R_9$ to $R_{19}$ is bonded to L of Formula 1.

2. The light emitting device of claim 1, wherein
the at least one functional layer comprises:
an emission layer;
a hole transport region disposed between the first electrode and the emission layer; and
an electron transport region disposed between the emission layer and the second electrode, and
the hole transport region comprises the polycyclic compound.

3. The light emitting device of claim 2, wherein
the hole transport region comprises at least one of a hole injection layer, a hole transport layer, and an electron blocking layer, and
at least one of the hole injection layer, the hole transport layer, and the electron blocking layer comprises the polycyclic compound.

4. The light emitting device of claim 1, wherein
the at least one functional layer comprises:
an emission layer;
a hole transport region disposed between the first electrode and the emission layer; and
an electron transport region disposed between the emission layer and the second electrode, and
the emission layer comprises the polycyclic compound.

5. The light emitting device of claim 1, wherein L is a substituted or unsubstituted phenylene group, a substituted or unsubstituted divalent biphenyl group, a substituted or unsubstituted divalent naphthyl group, a substituted or unsubstituted divalent fluorenyl group, or a substituted or unsubstituted divalent phenanthryl group.

6. The light emitting device of claim 1, wherein L is a group selected from Compound Group L-1:

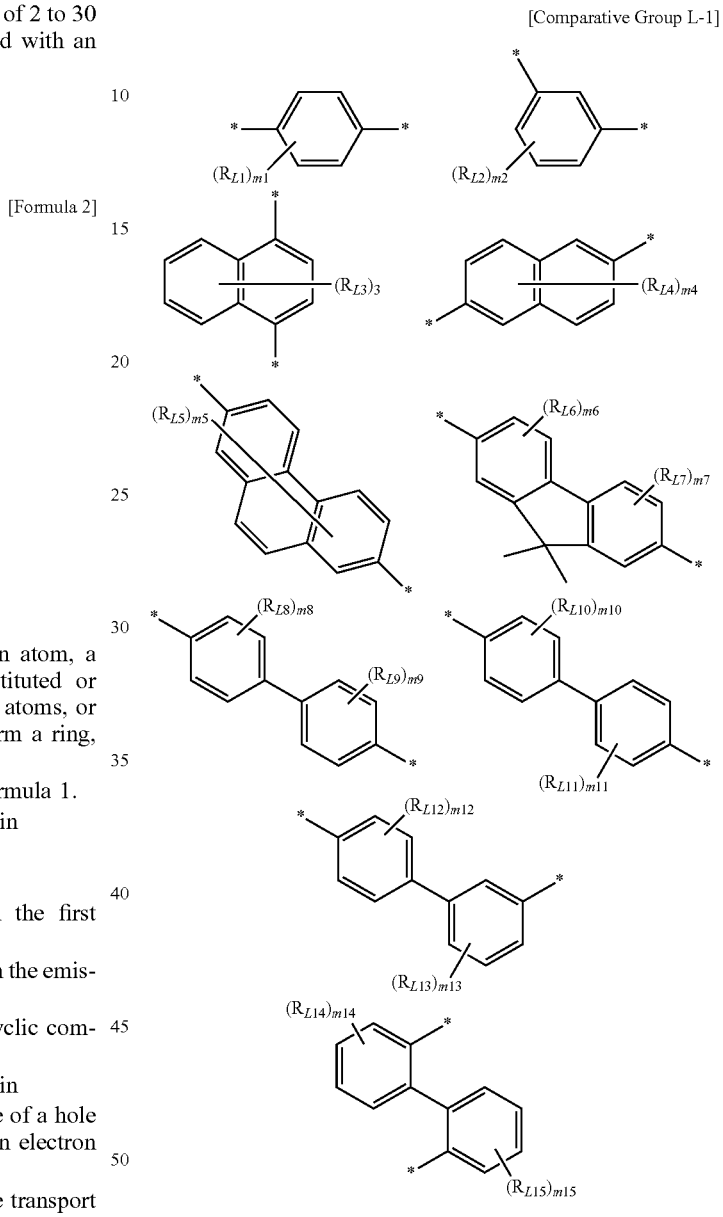

[Comparative Group L-1]

wherein in Compound Group L-1, $R_{L1}$ to $R_{L15}$ are each independently a hydrogen atom, a deuterium atom, a halogen atom, a substituted or unsubstituted silyl group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or are combined with an adjacent group to form a ring, m1 and m2 are each independently an integer from 0 to 4, m3 and m4 are each independently an integer from 0 to 6, m5 is an integer from 0 to 8, m6 and m7 are each independently an integer from 0 to 3, m8 to m15 are each independently an integer from 0 to 4, and -* represents a position bonded to A or N in Formula 1.

7. The light emitting device of claim 1, wherein $R_1$ to $R_8$ are each independently a hydrogen atom, a deuterium atom, a halogen atom, a methyl group, a t-butyl group, a substituted or unsubstituted amine group, a substituted or unsubstituted silyl group, a substituted or unsubstituted phenyl group, a substituted or unsubstituted carbazole group, a substituted or unsubstituted dibenzofuran group, a substituted or unsubstituted dibenzothiophene group, a substituted or unsubstituted phenoxazine group, or a substituted or unsubstituted acridyl group.

8. The light emitting device of claim 1, wherein the polycyclic compound represented by Formula 1 is represented by Formula 1-1 or Formula 1-2:

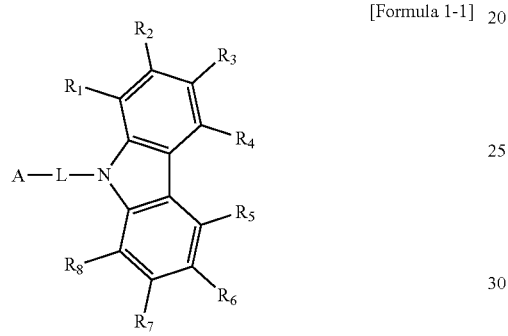

[Formula 1-1]

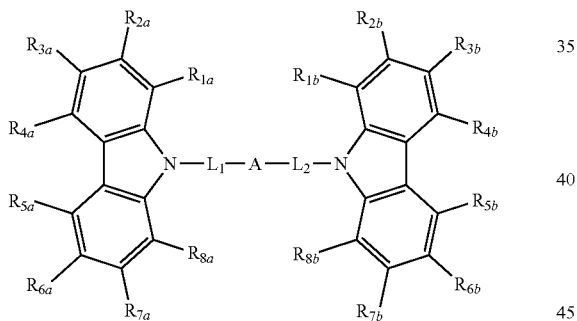

[Formula 1-2]

wherein in Formula 1-1 and Formula 1-2, $L_1$ and $L_2$ are each independently a substituted or unsubstituted arylene group of 6 to 30 ring-forming carbon atoms, $R_{1a}$ to $R_{8a}$, and $R_{1b}$ to $R_{8b}$ are each independently a hydrogen atom, a deuterium atom, a halogen atom, a substituted or unsubstituted silyl group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or are combined with an adjacent group to form a ring, and A, L, and $R_1$ to $R_8$ are the same as defined in connection with Formula 1.

9. The light emitting device of claim 1, wherein the polycyclic compound represented by Formula 1 is represented by one of Formula 3-1 to Formula 3-6:

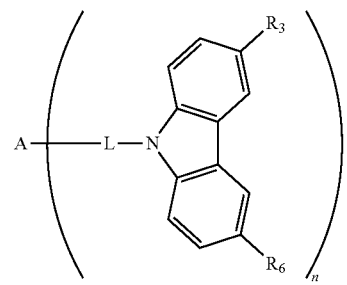

[Formula 3-1]

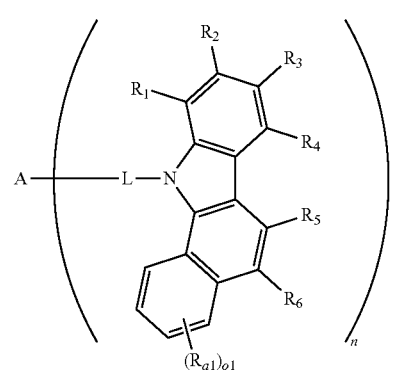

[Formula 3-2]

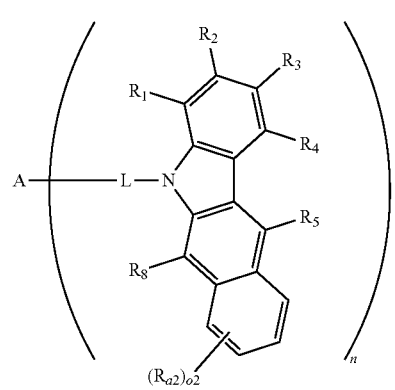

[Formula 3-3]

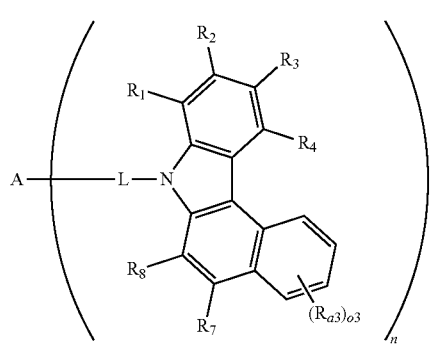

[Formula 3-4]

[Formula 3-5]

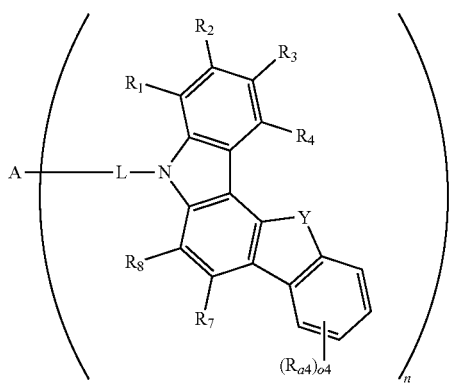

[Formula 4-1]

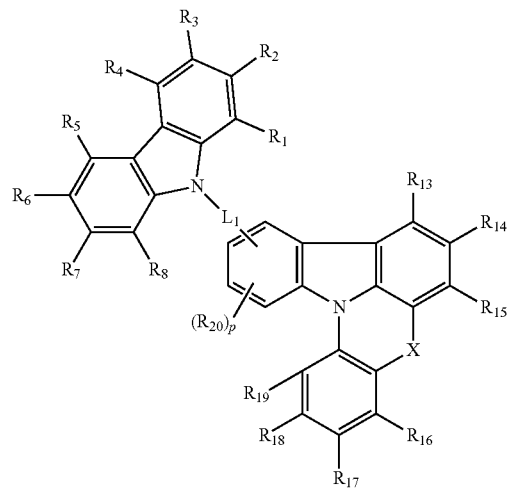

[Formula 3-6]

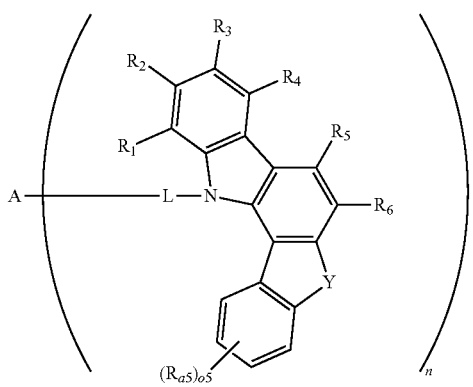

[Formula 4-2]

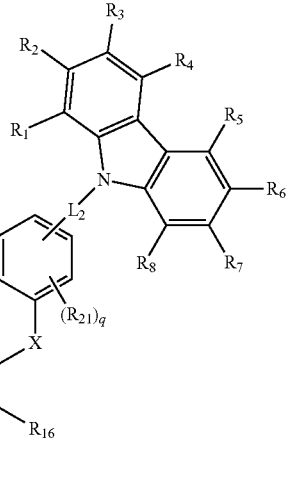

wherein in Formula 3-1 to Formula 3-6,

Y is O or S, $R_{a1}$ to $R_{a5}$ are each independently a hydrogen atom, a deuterium atom, a halogen atom, a substituted or unsubstituted silyl group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or are combined with an adjacent group to form a ring, o1 to o5 are each independently an integer from 0 to 4, and A, L, n, and $R_1$ to $R_8$ are the same as defined in connection with Formula 1.

10. The light emitting device of claim 1, wherein the polycyclic compound represented by Formula 1 is represented by one of Formula 4-1 to Formula 4-6:

[Formula 4-3]

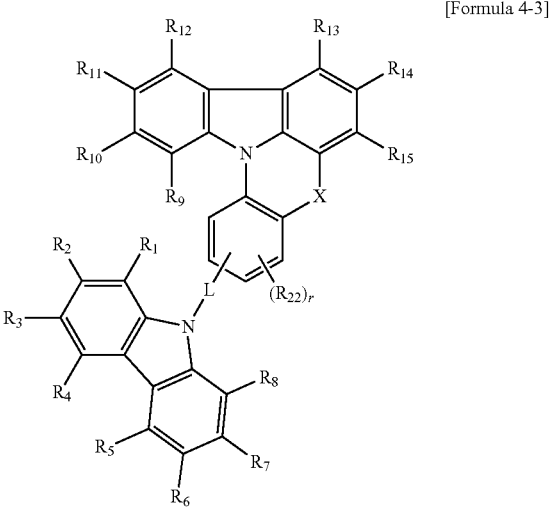

-continued

[Formula 4-4]

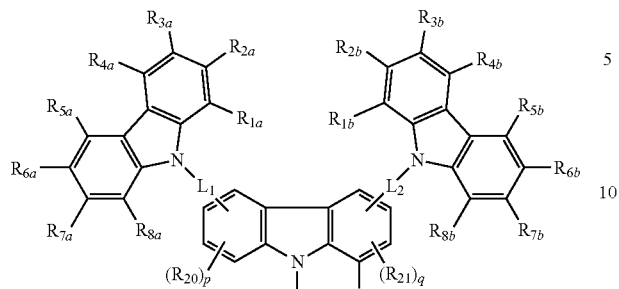

[Formula 4-5]

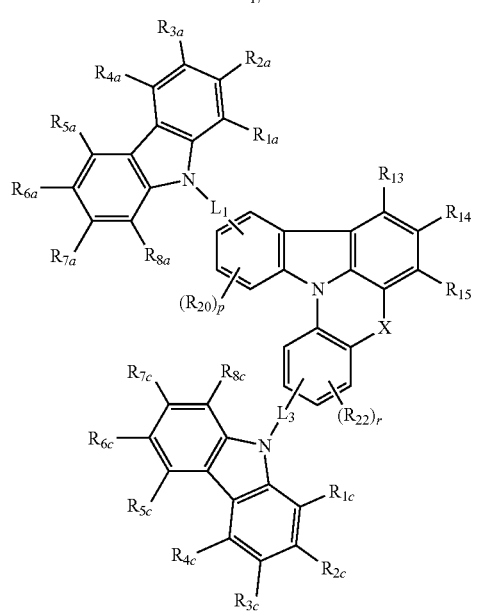

[Formula 4-6]

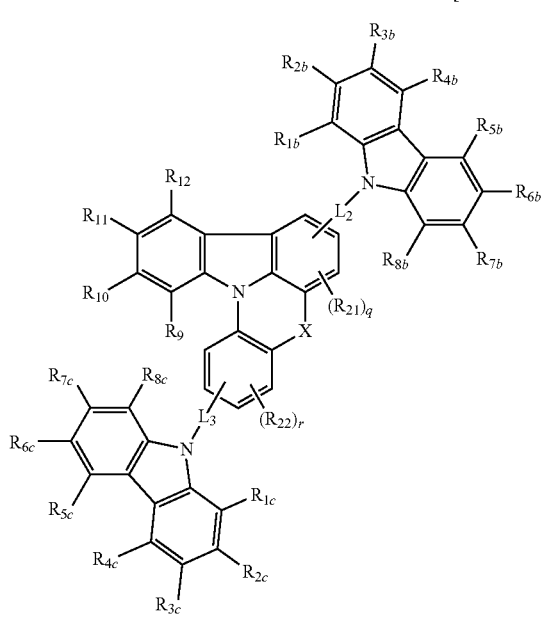

wherein in Formula 4-1 to Formula 4-6, $R_{20}$, $R_{21}$, and $R_{22}$ are each independently a hydrogen atom, a deuterium atom, a halogen atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or are combined with an adjacent group to form a ring, p is an integer from 0 to 3, q is an integer from 0 to 2, r is an integer from 0 to 3, $L_1$ to $L_3$ are each independently a substituted or unsubstituted arylene group of 6 to 30 ring-forming carbon atoms, $R_{1a}$ to $R_{8a}$, $R_{1b}$ to $R_{8b}$, and $R_{1c}$ to $R_{8c}$ are each independently a hydrogen atom, a deuterium atom, a halogen atom, a substituted or unsubstituted silyl group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or are combined with an adjacent group to form a ring, and L, X, and $R_1$ to $R_{19}$ are the same as defined in connection with Formula 1 and Formula 2.

11. The light emitting device of claim 1, wherein the polycyclic compound comprised in the at least one functional layer is one selected from Compound Group 1A to Compound Group 1D:

[Compound Group 1A]

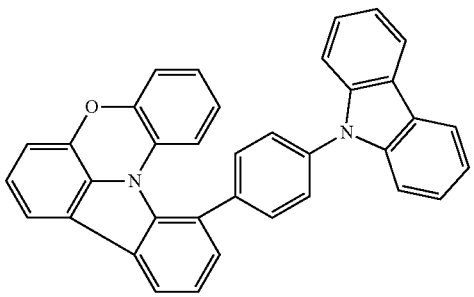

A1

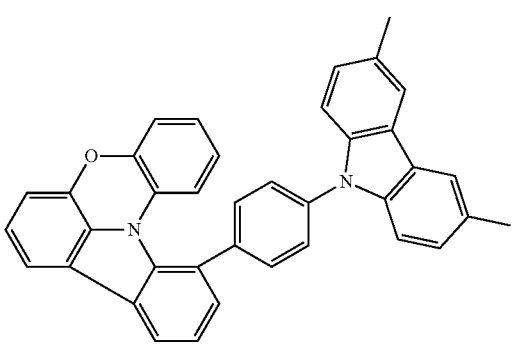

A2

-continued
A3
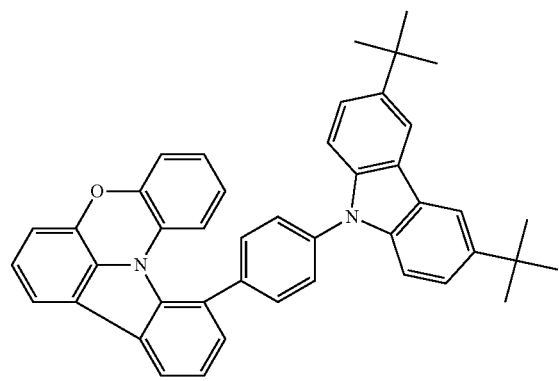
A4
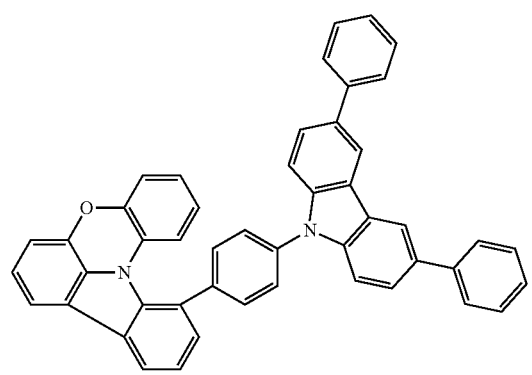
A5
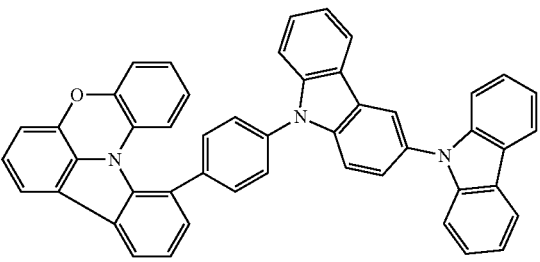
A6
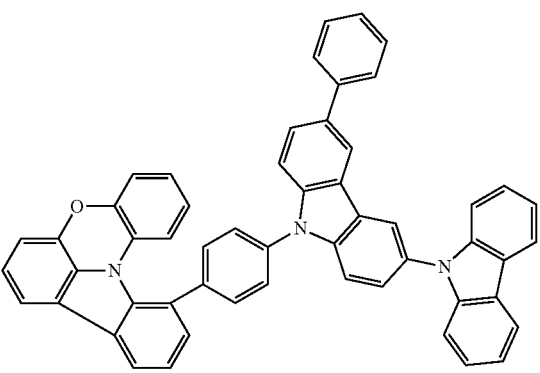
-continued
A7
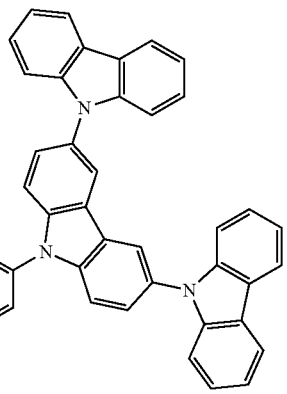
A8
A9
A10
A11
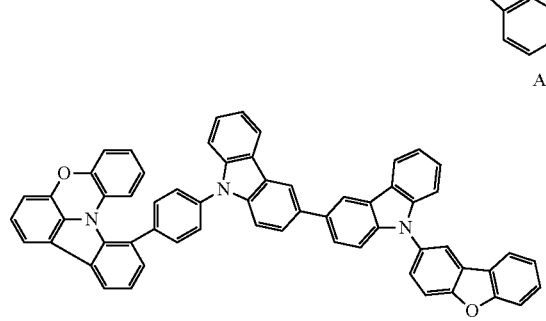

A12
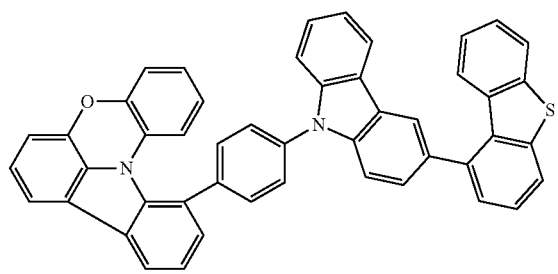
A13
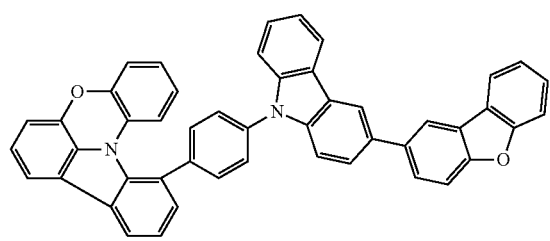
A14
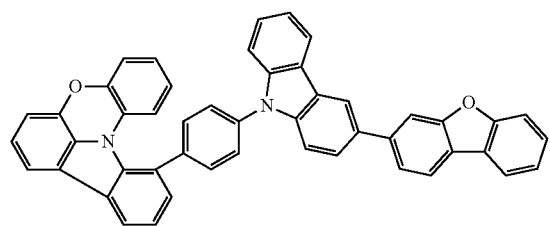
A15
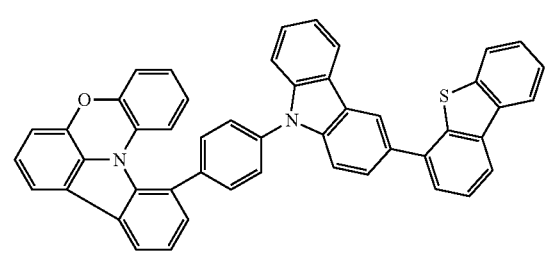
A16
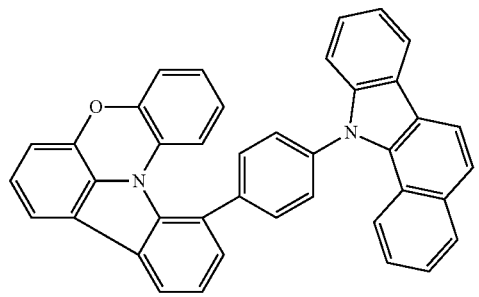
A17
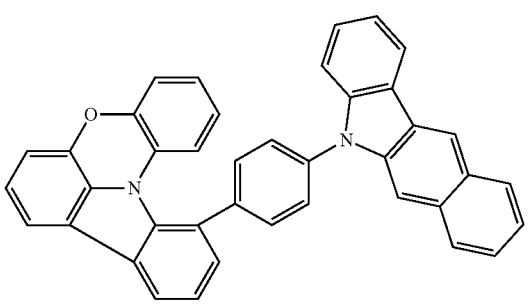
A18
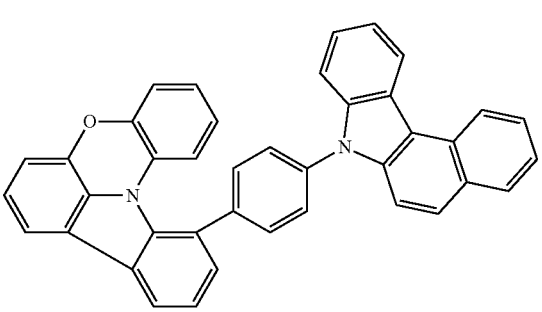
A19
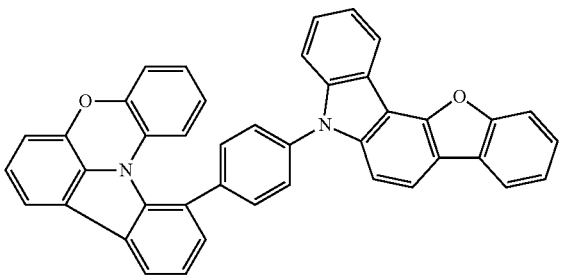
A20
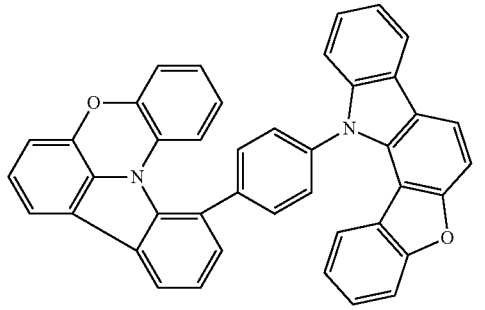
A21
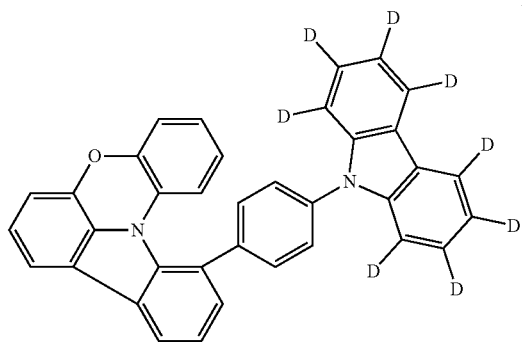

-continued
A22
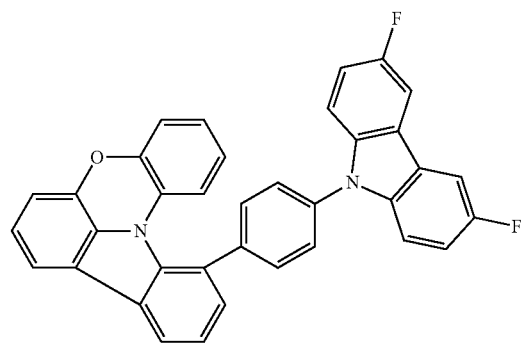
A23
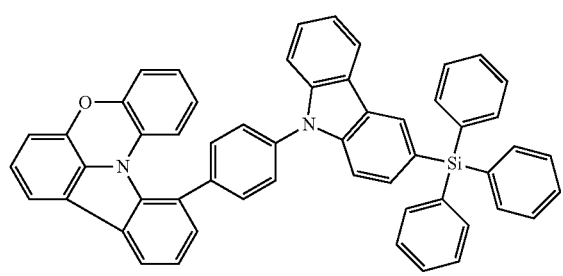
A24
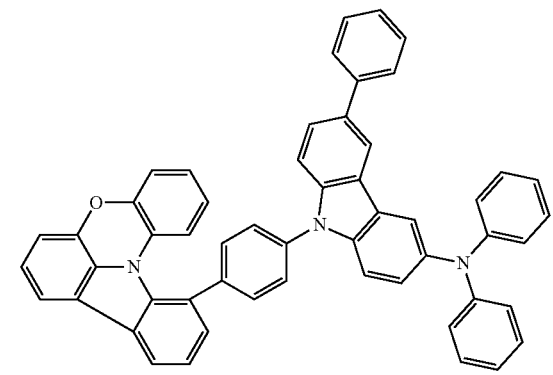
A25
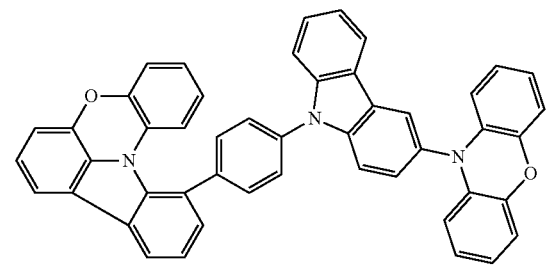
A26
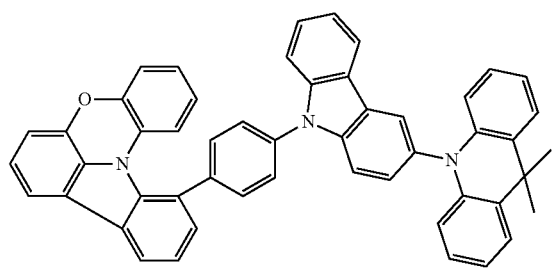
-continued
A27
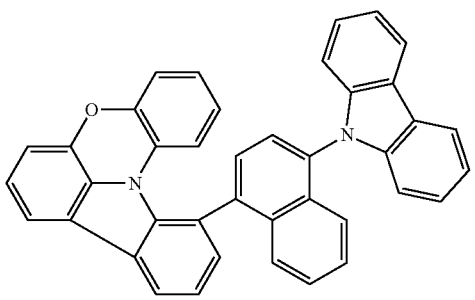
A28
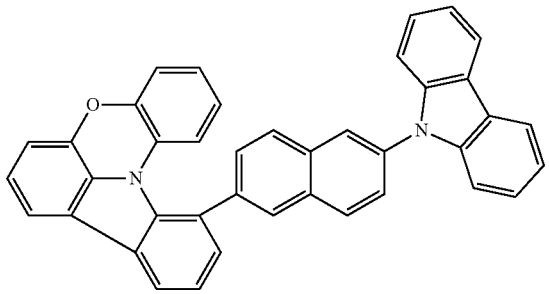
A29
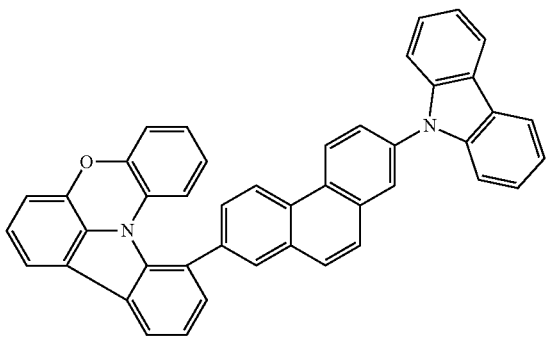
A30
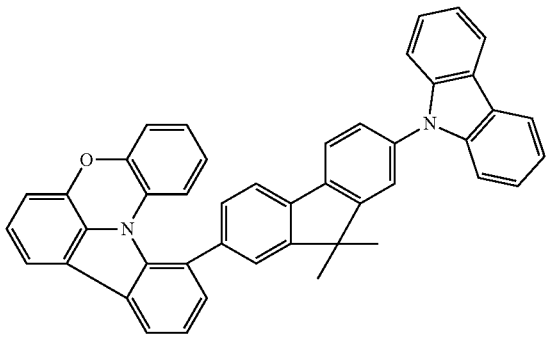
A31
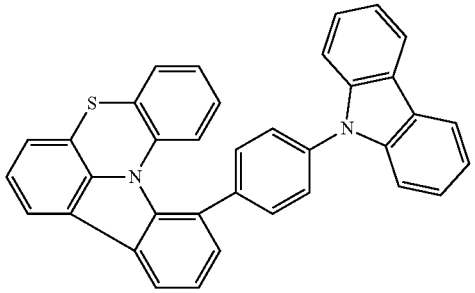

A32
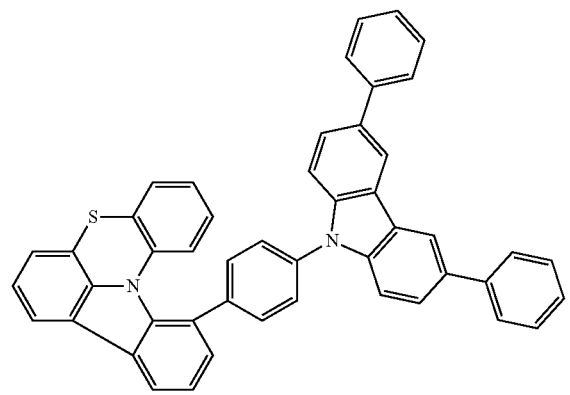
A33
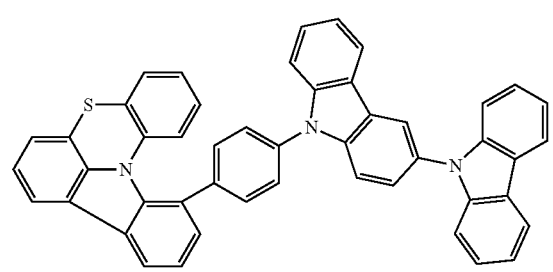
A34
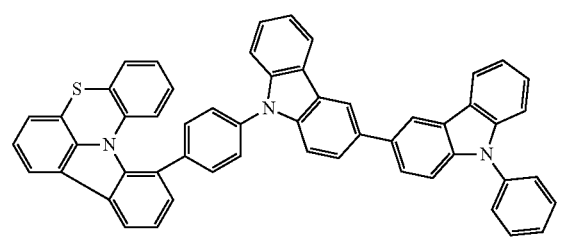
A35
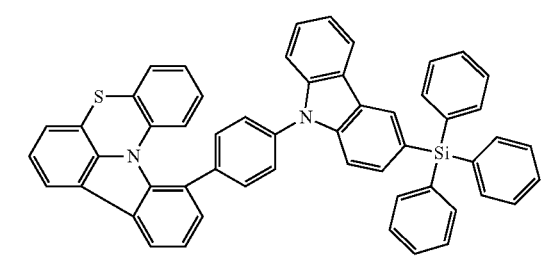
A36
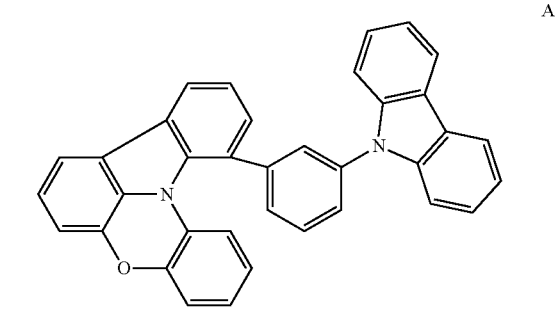
A37
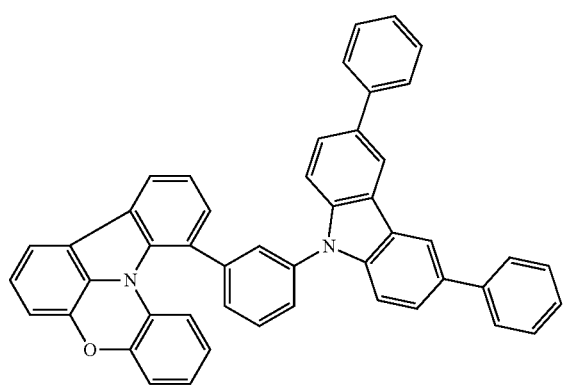
A38
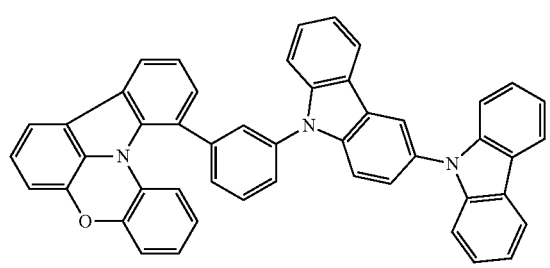
A39
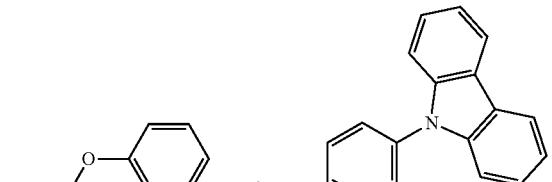
A40
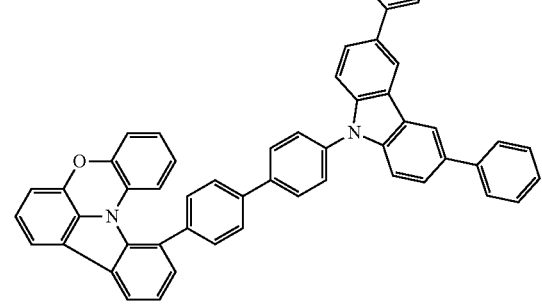

A41
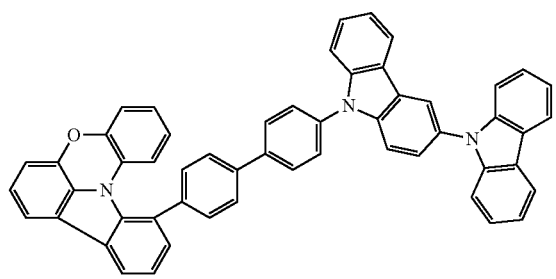
A42
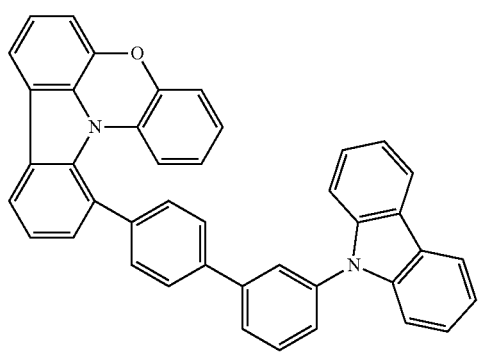
A43
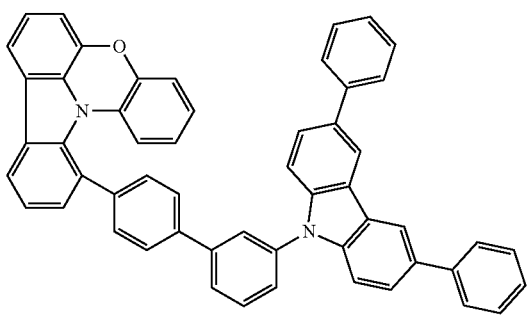
A44
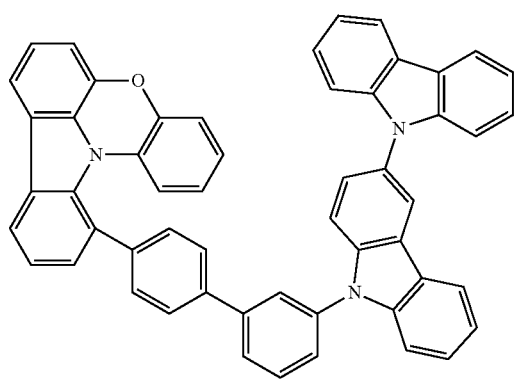
A45
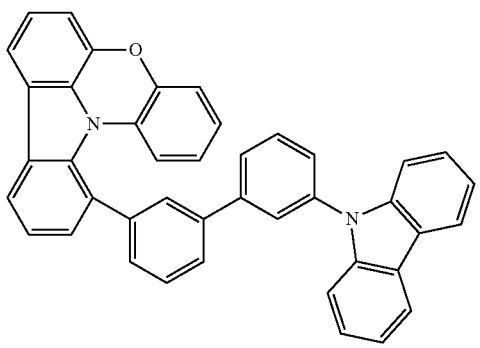
A46
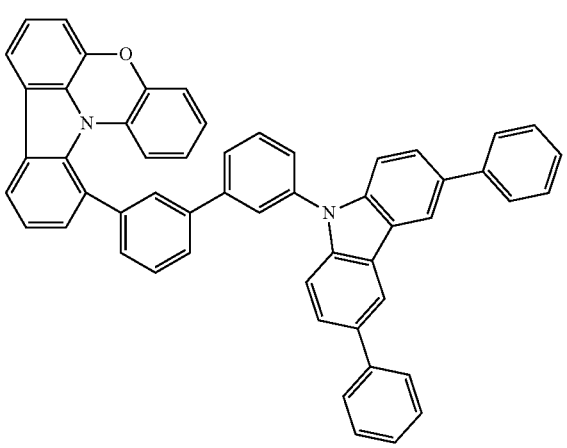
A47
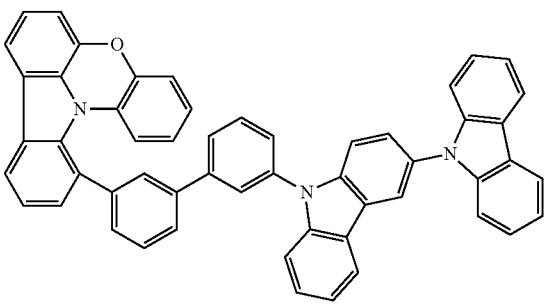
A48

A49 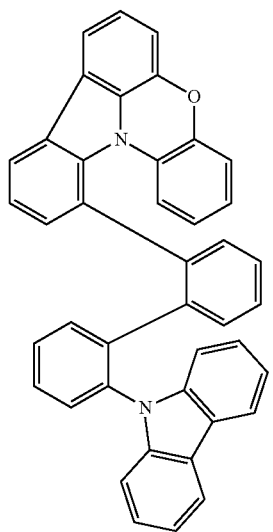
A50 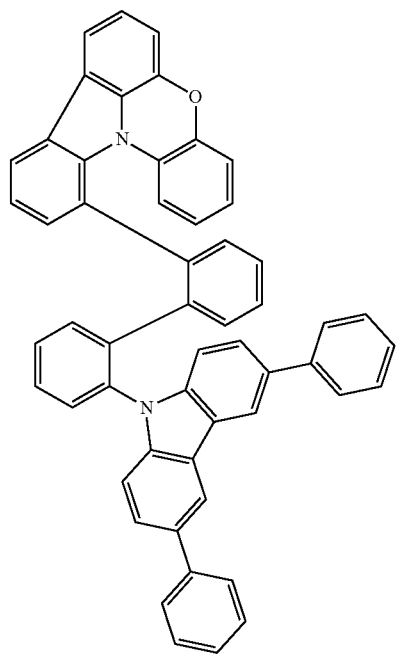
A51 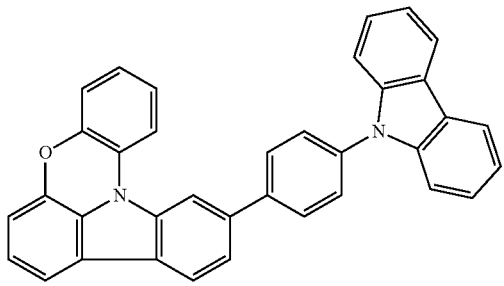
A52 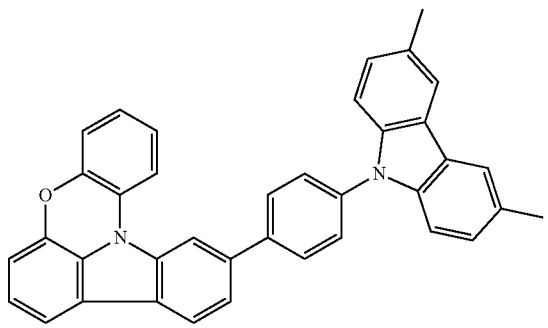
A53 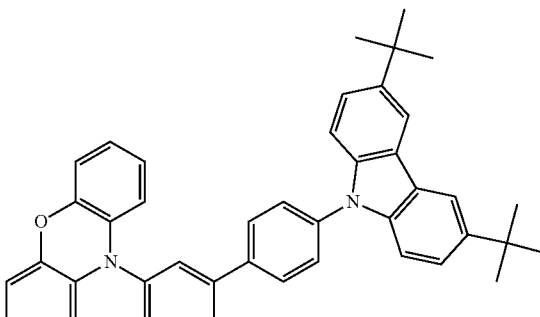
A54 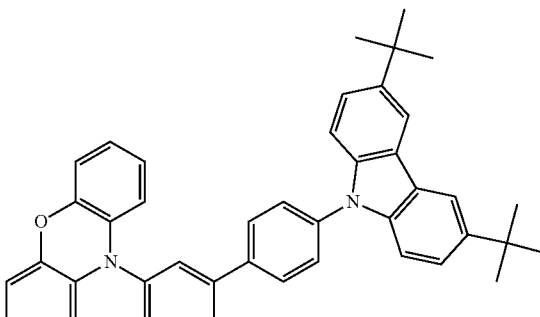
A55 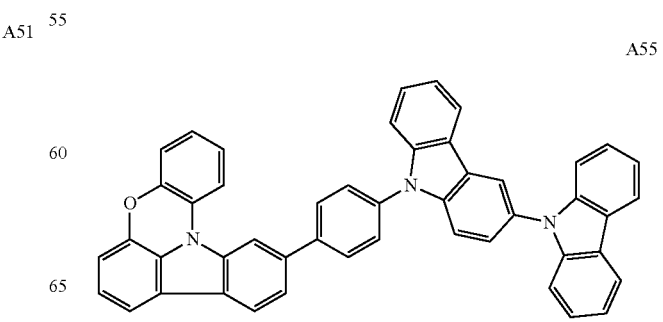

-continued
A56
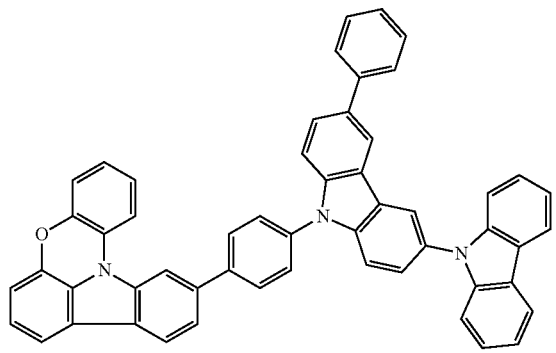
A57
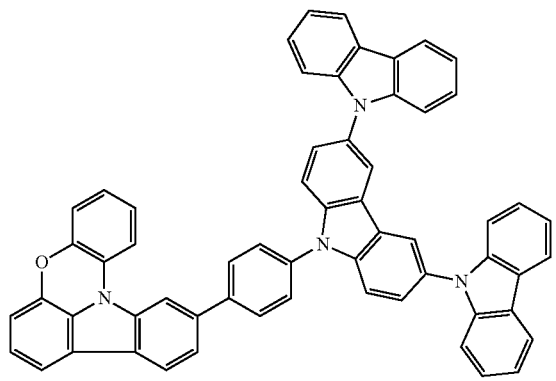
-continued
A61
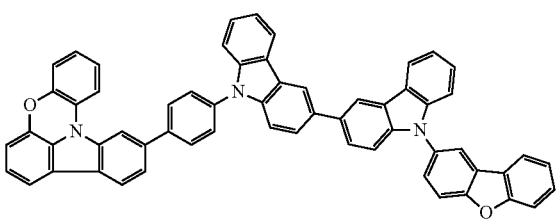
A62
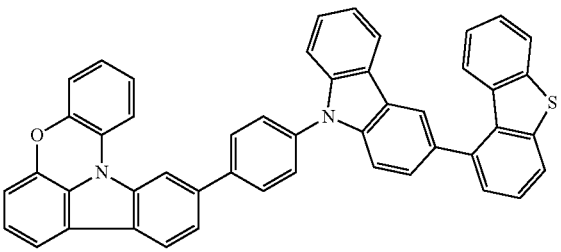
A63
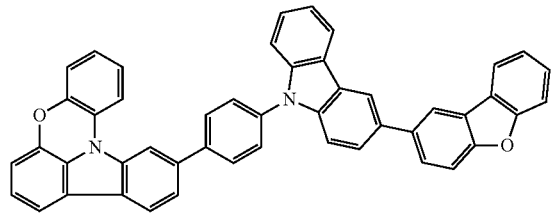
A64
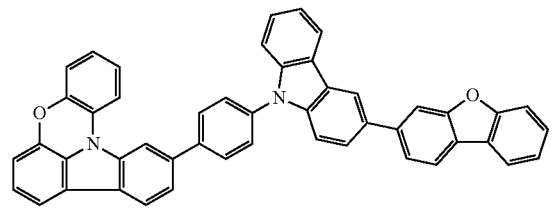
A65
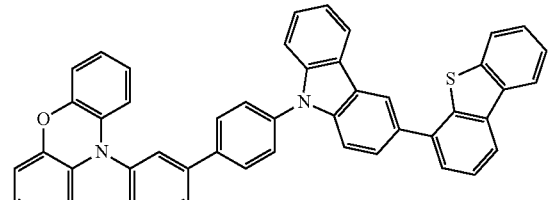
A66
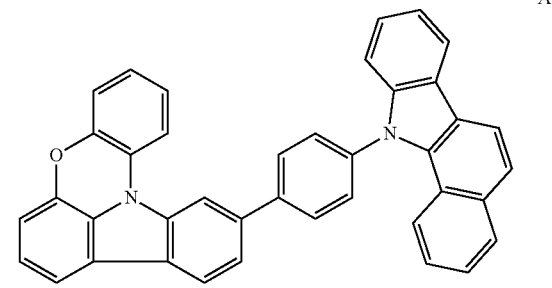

A67
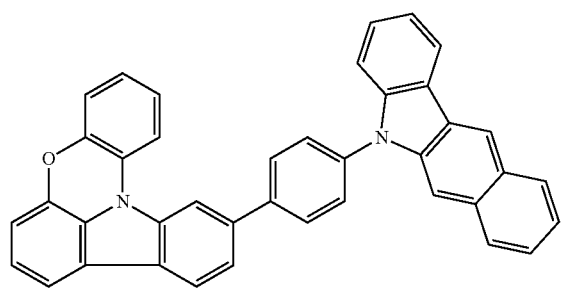
A68
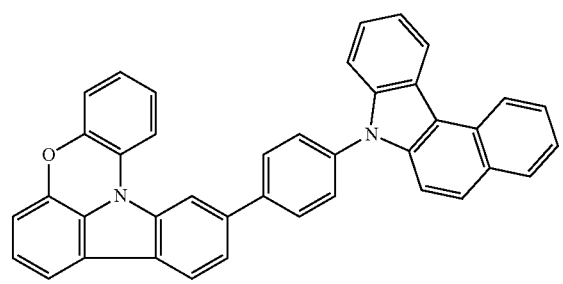
A69
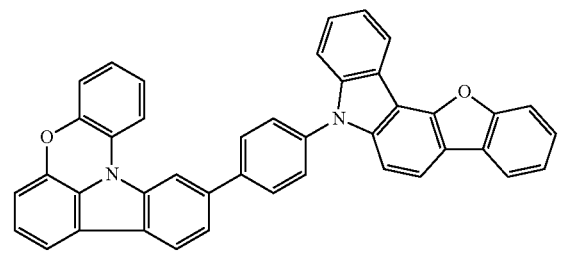
A70
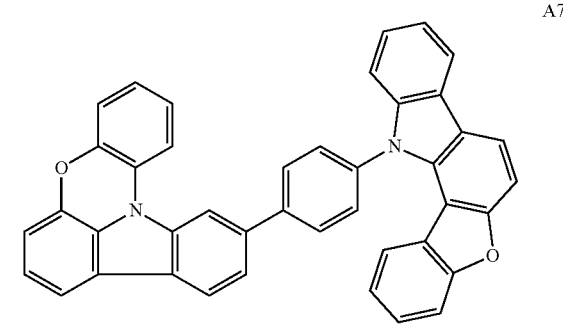
A71
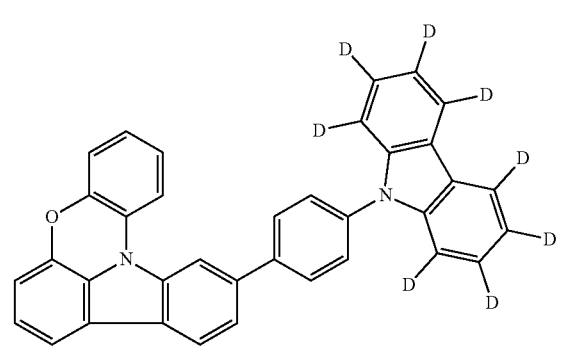
A72
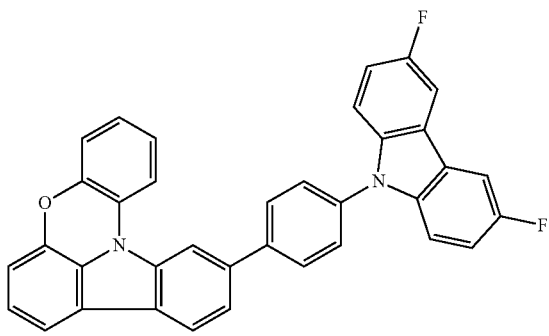
A73
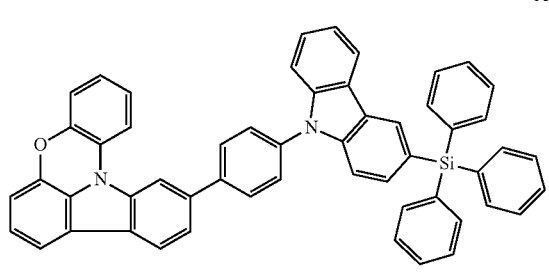
A74
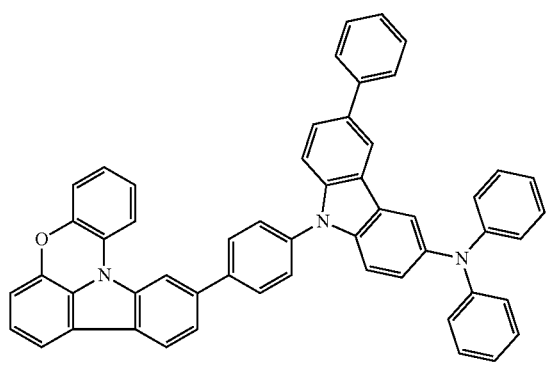
A75
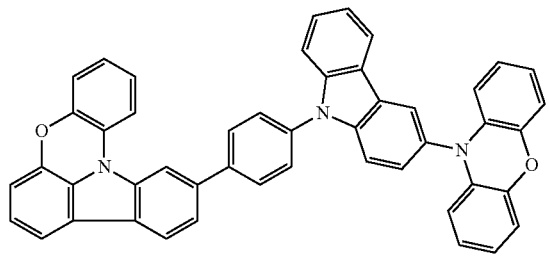
A76
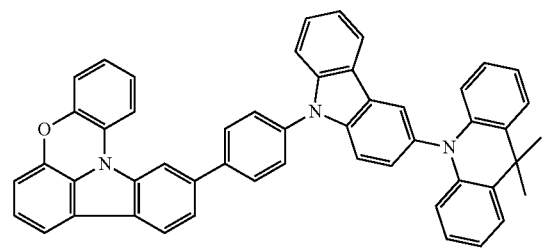

-continued
A77
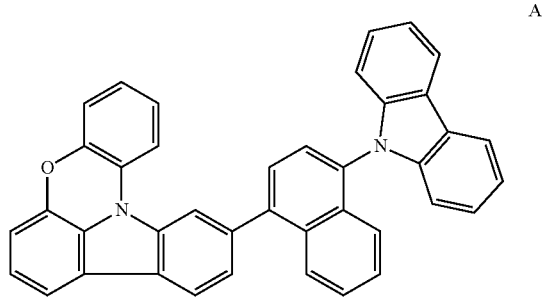
A78
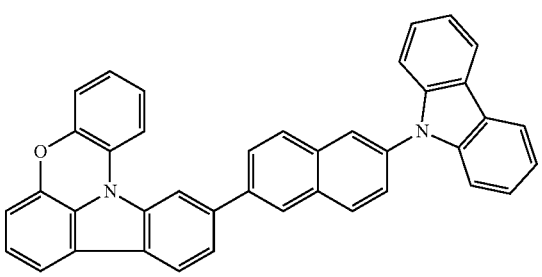
A79
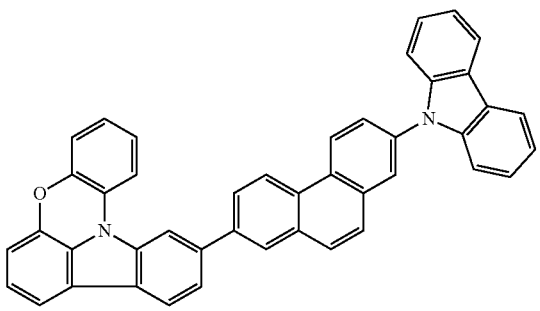
A80
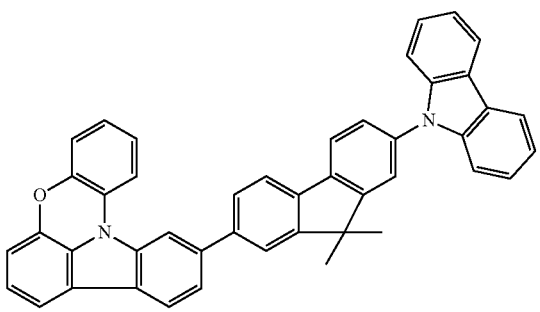
A81
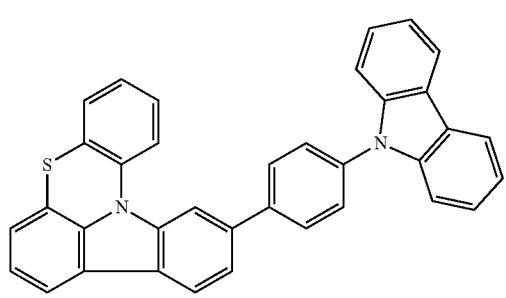
-continued
A82
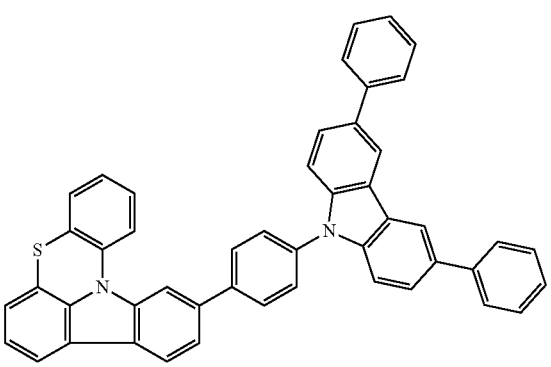
A83
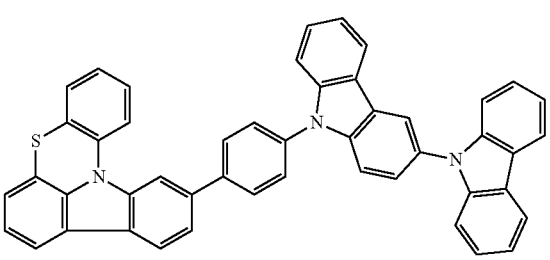
A84
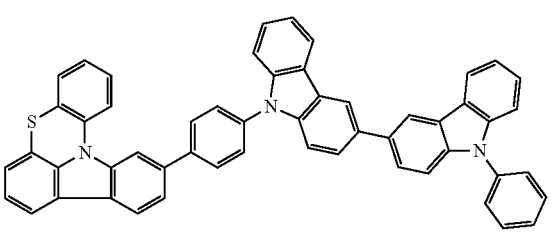
A85
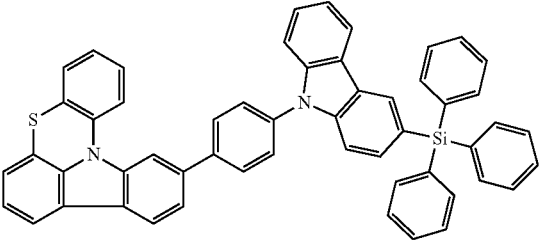
A86
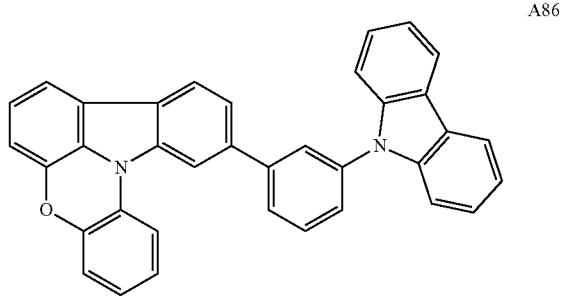

A87
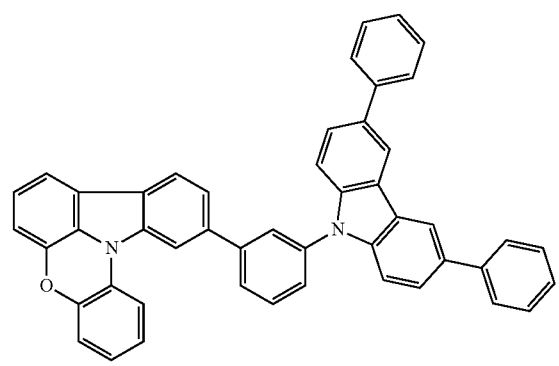
A88
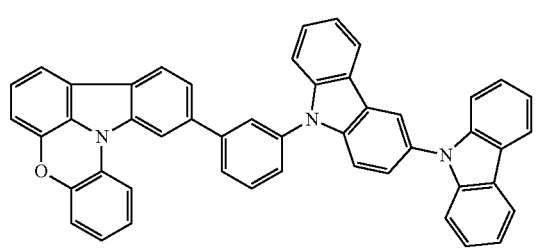
A89
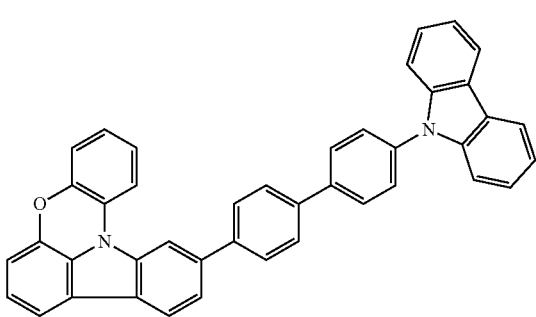
A90
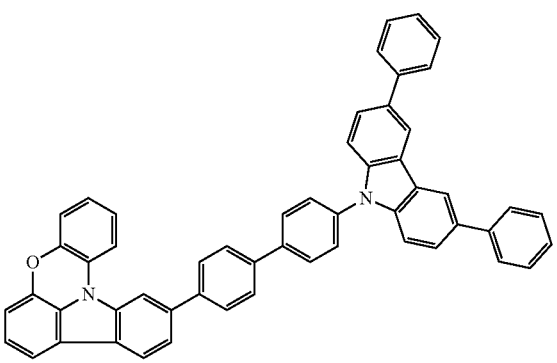
A91
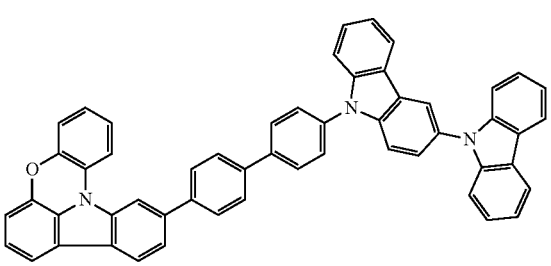
A92
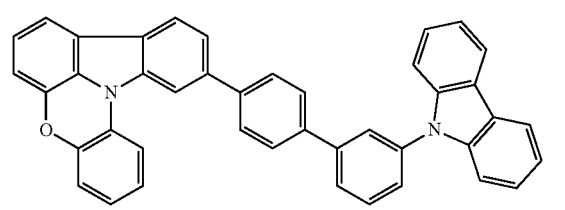
A93
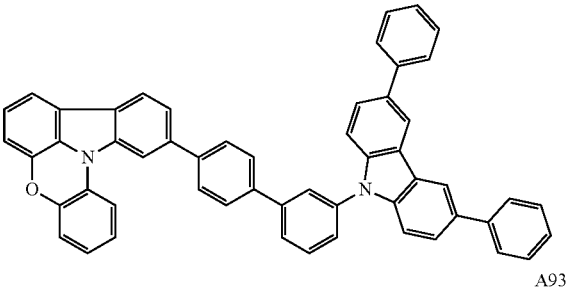
A93
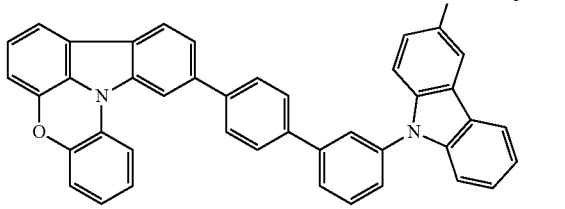
A95
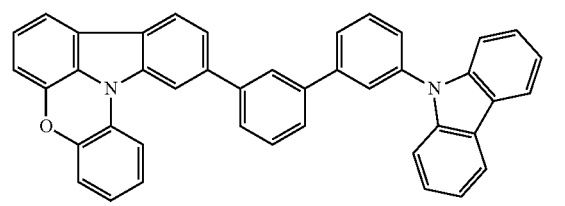
A96
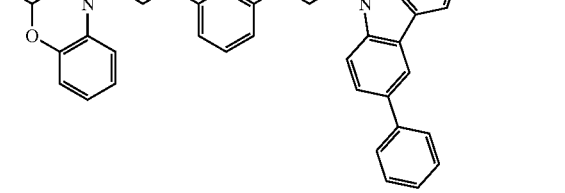
A97
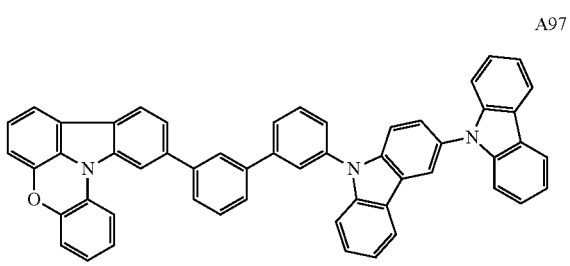

-continued
A98
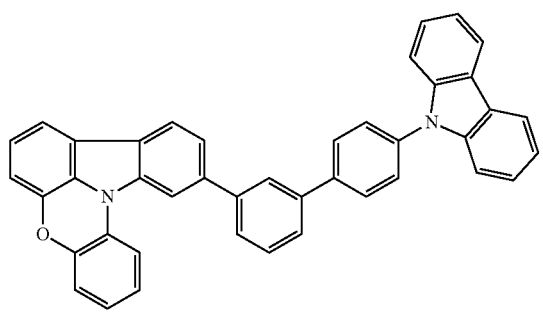
A99
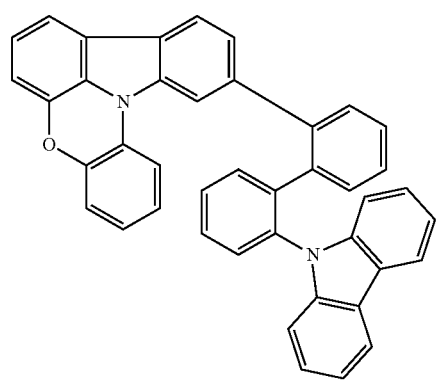
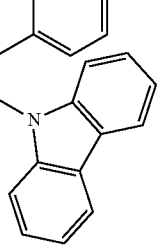
A100
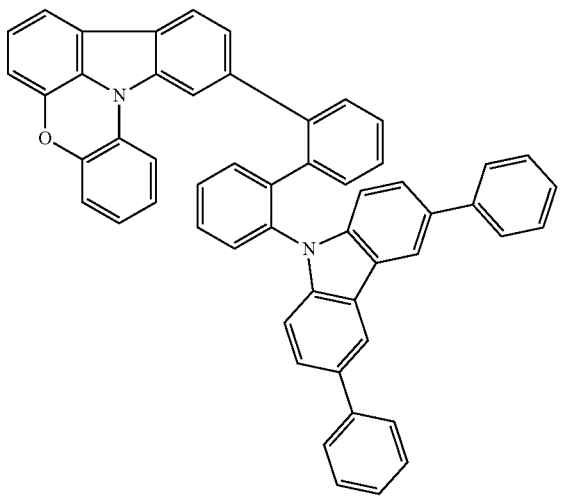
A101
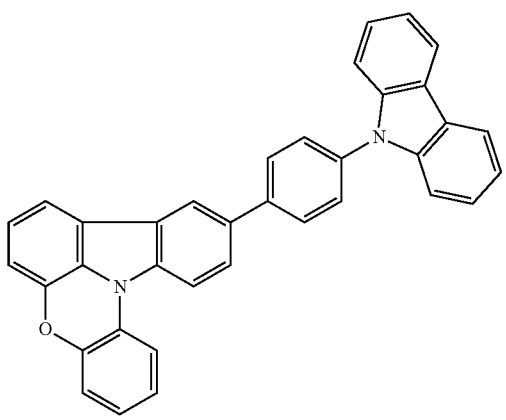
-continued
A102
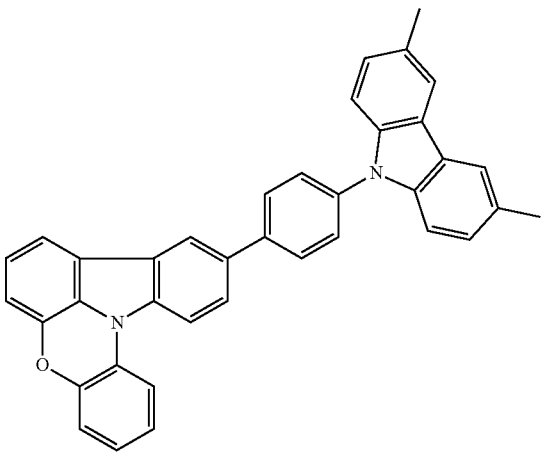
A103
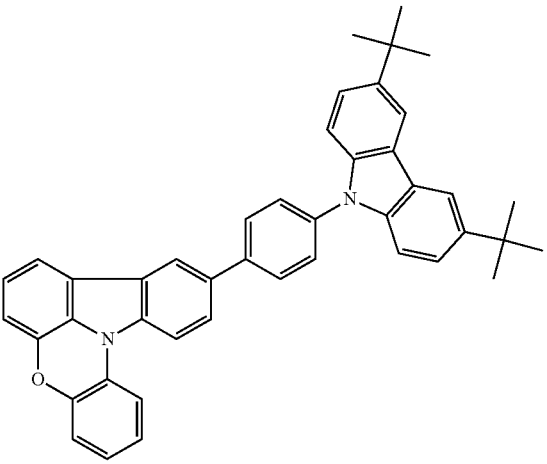
A104
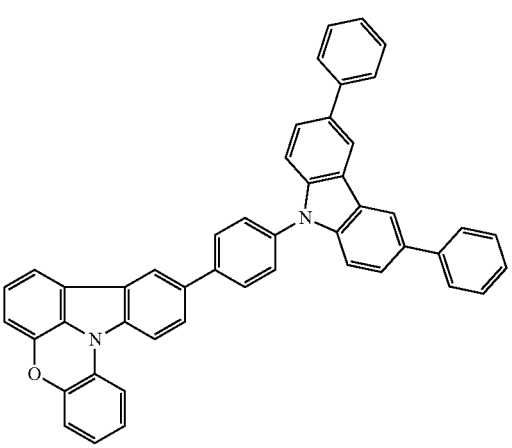

A105
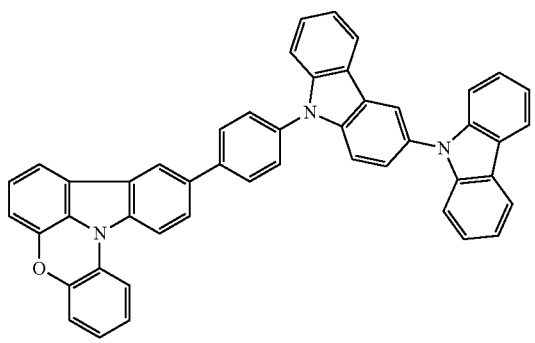
A106
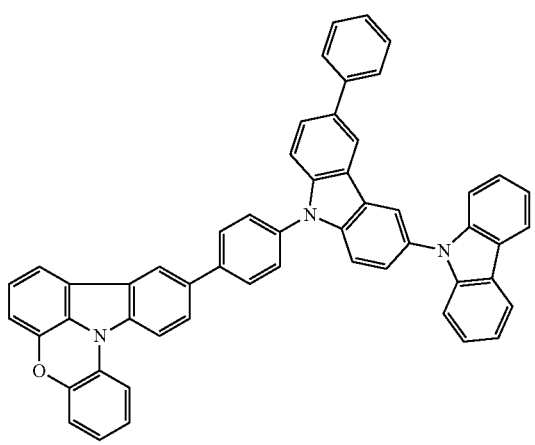
A107
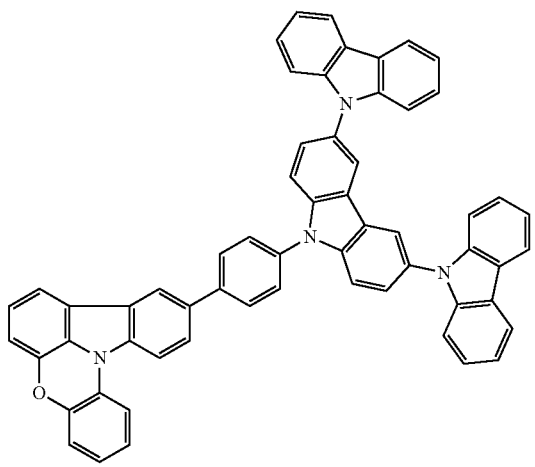
A108
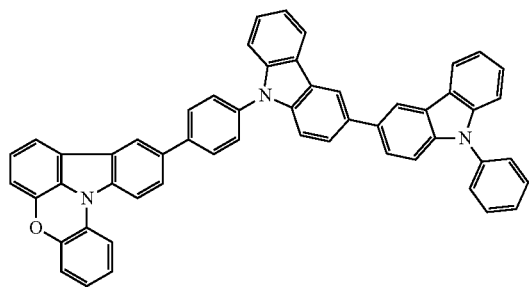
A109
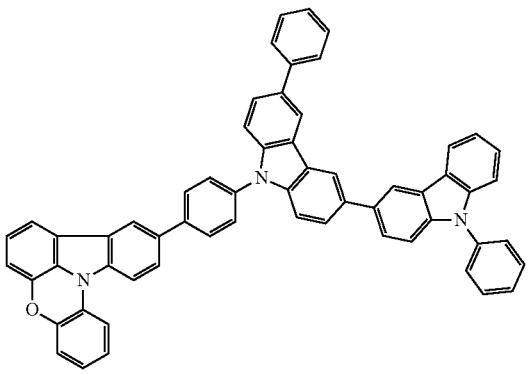
A110
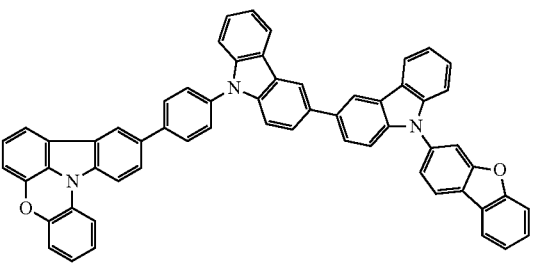
A111
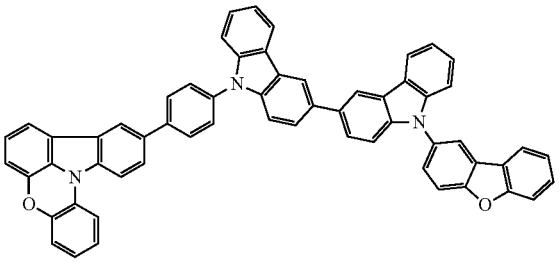
A112
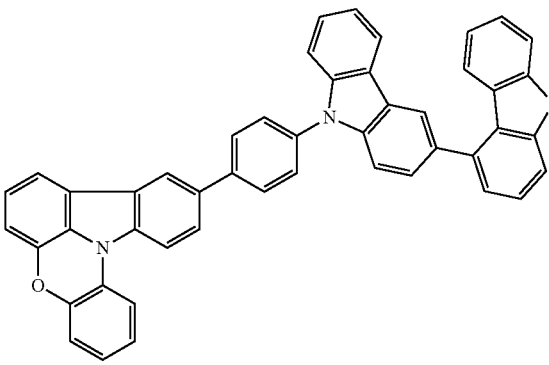

A113
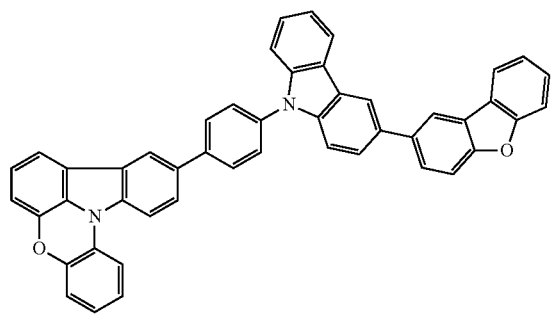
A114
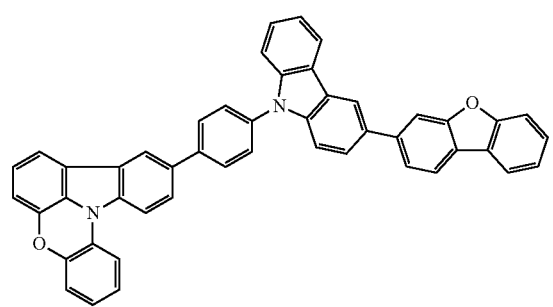
A115
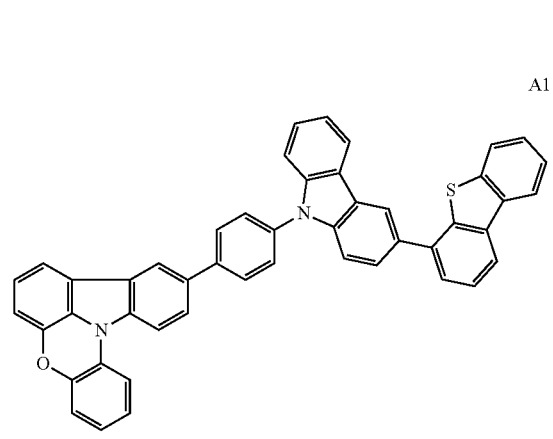
A116
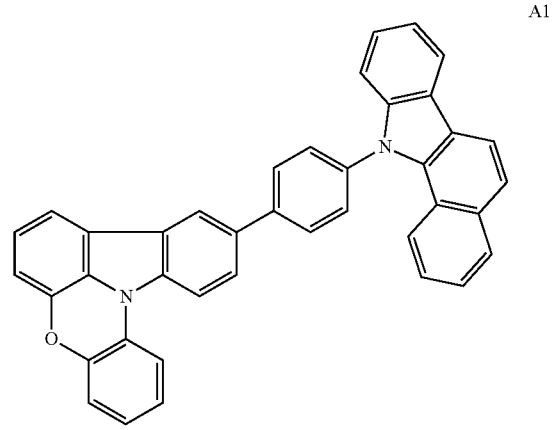
A117
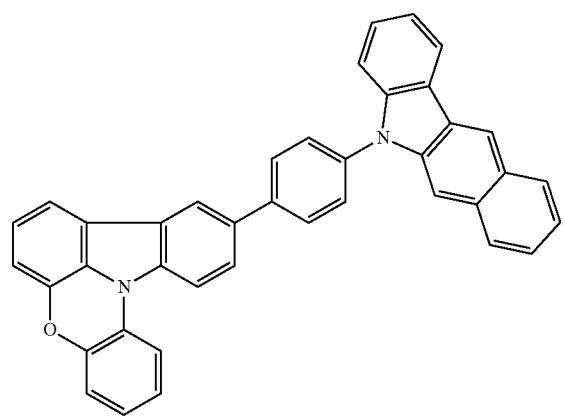
A118
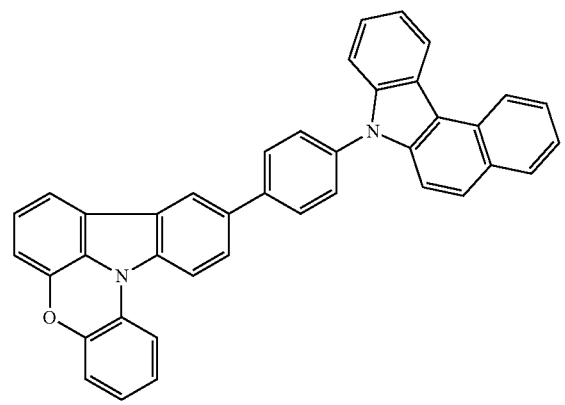
A119

A120
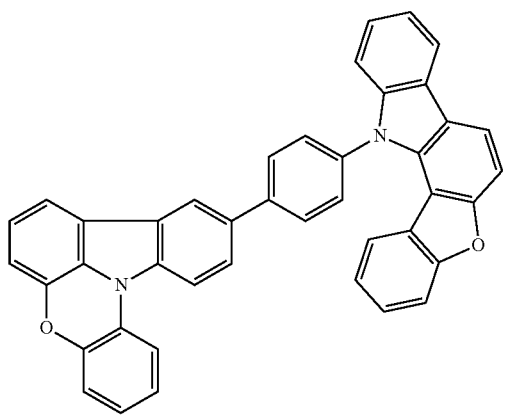
A121
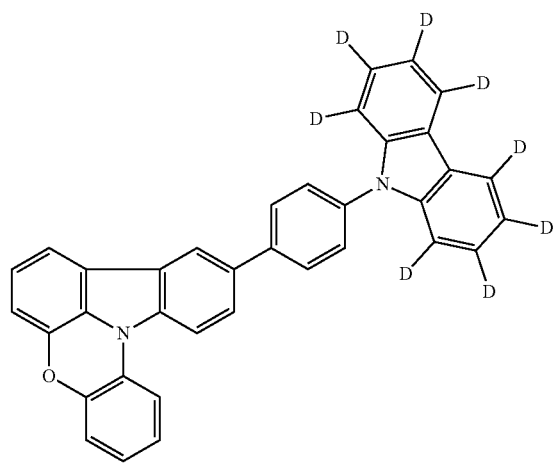
A122
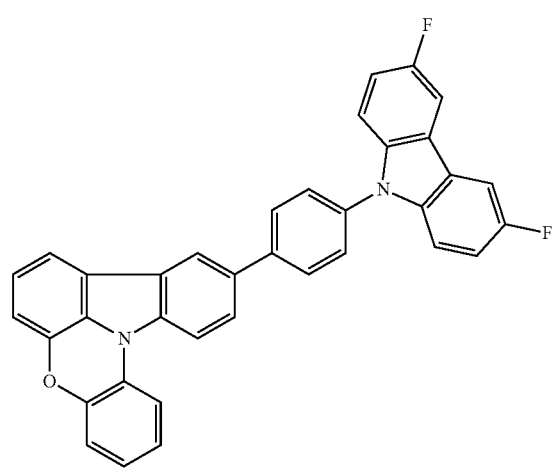
A123
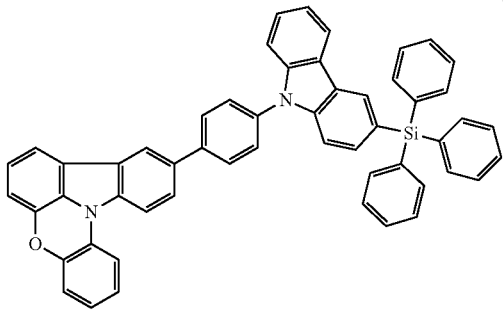
A124
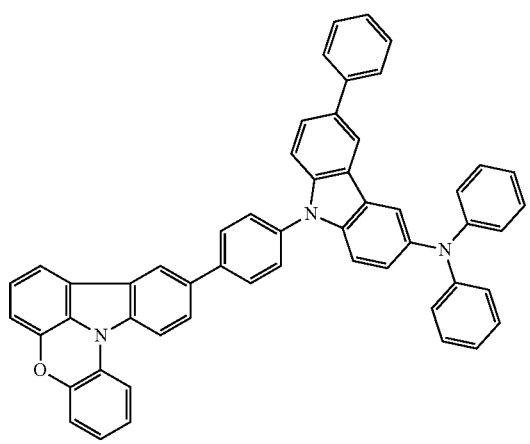
A125
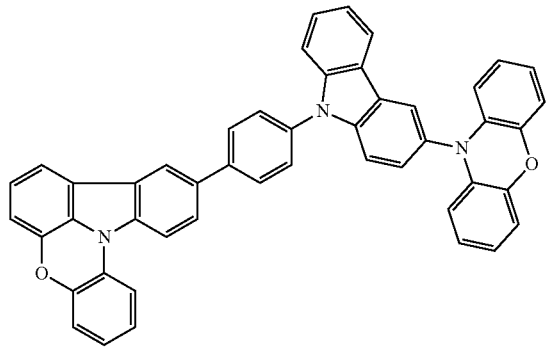
A126
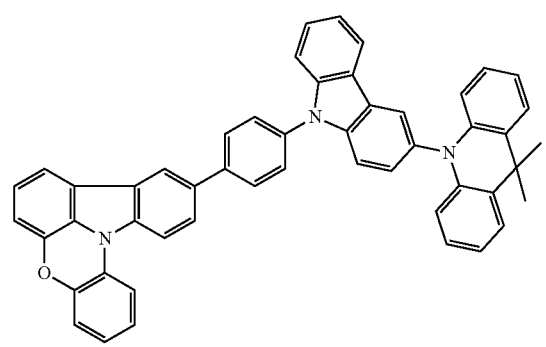

A127
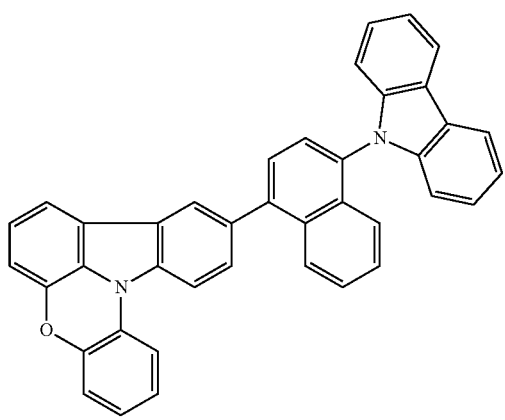
A130
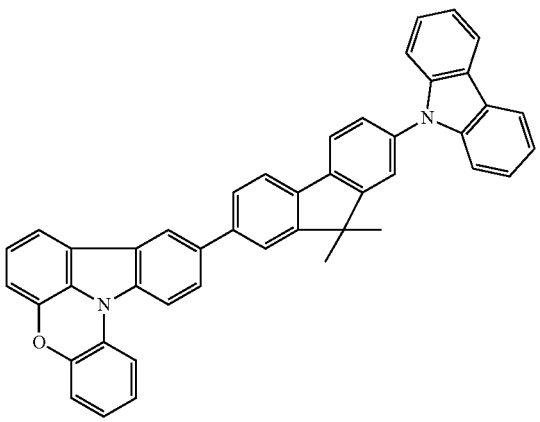
A128
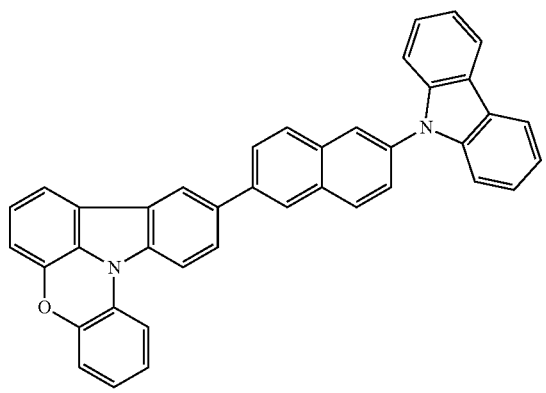
A131
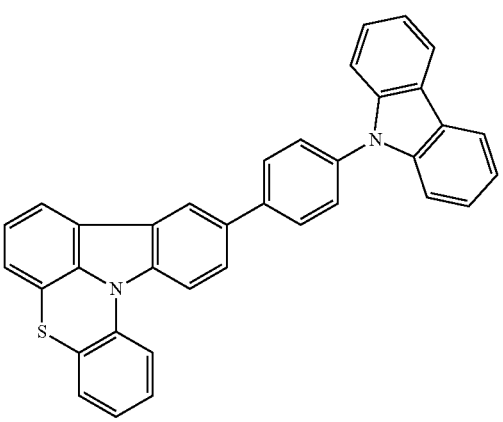
A129
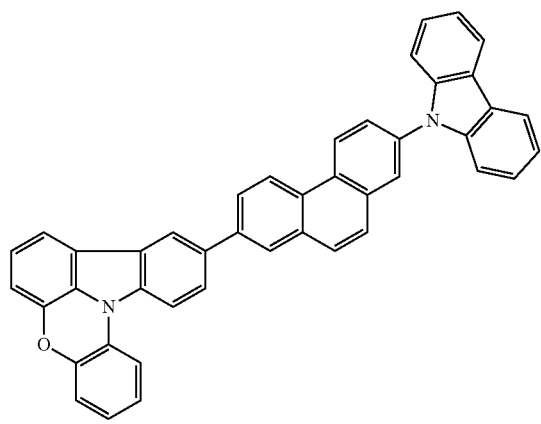
A132
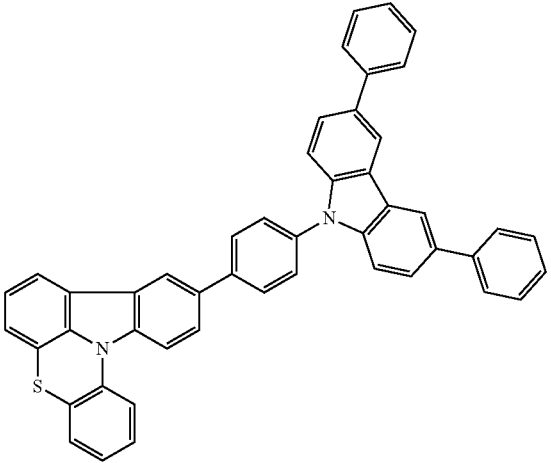

A133
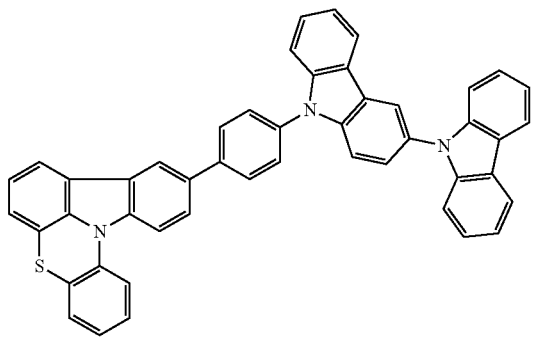
A134
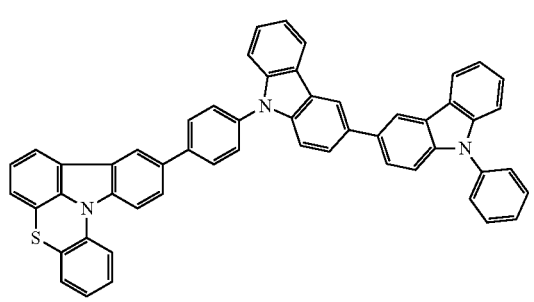
A135
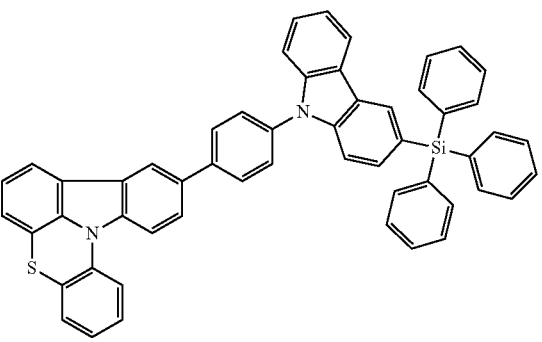
A136
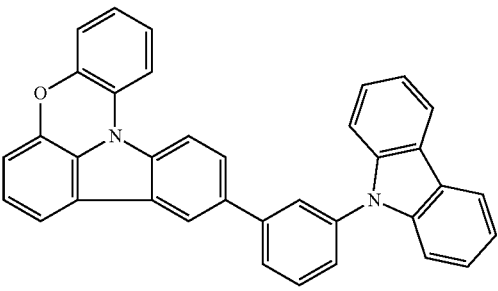
A137
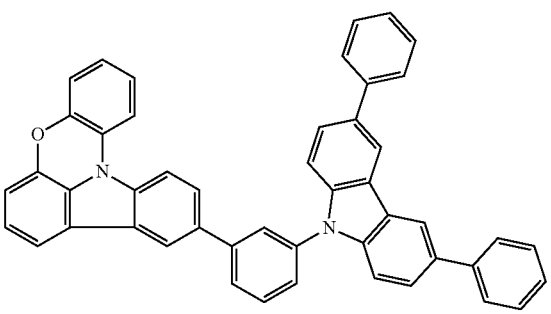
A138
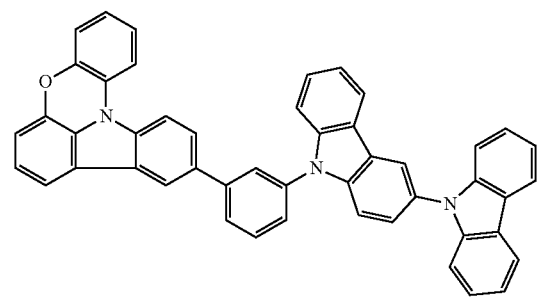
A139
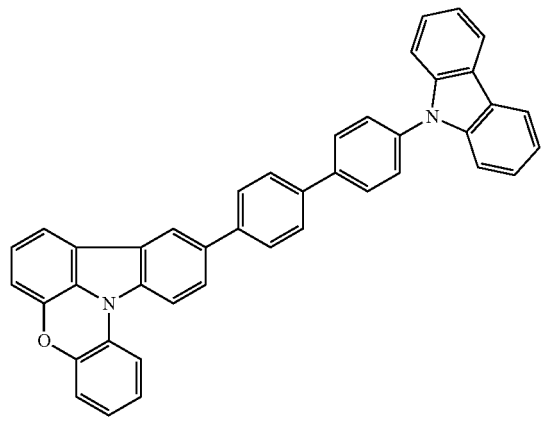
A140
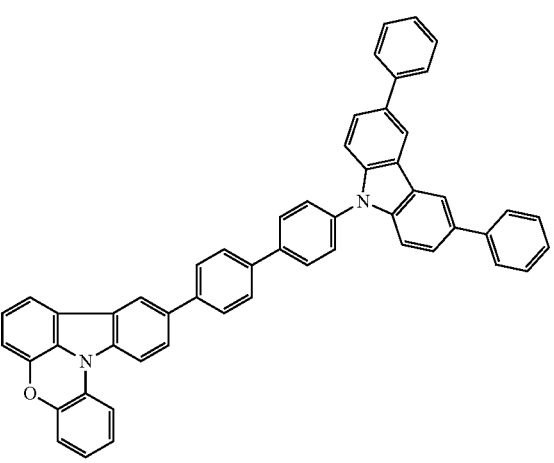

-continued
A141
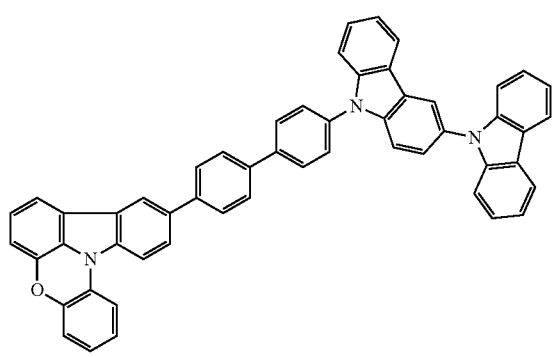
A142
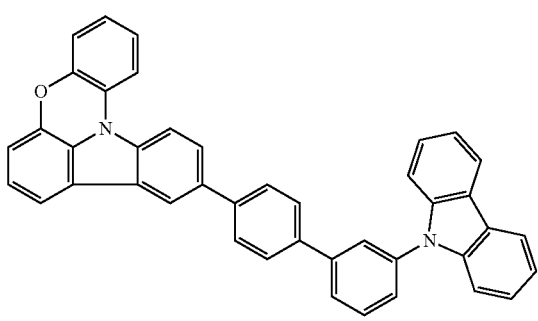
A143
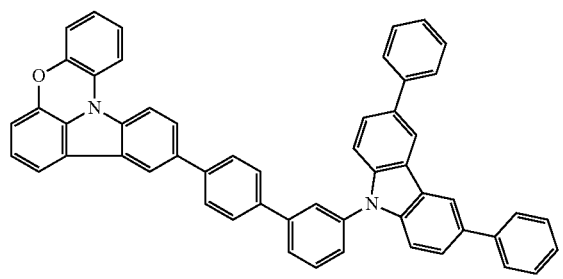
A144
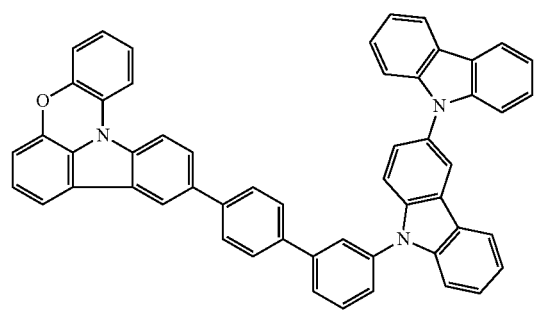
A145
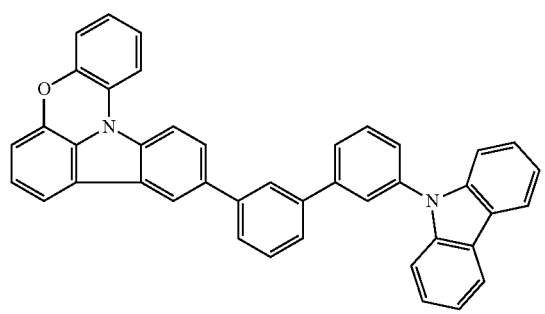
A146
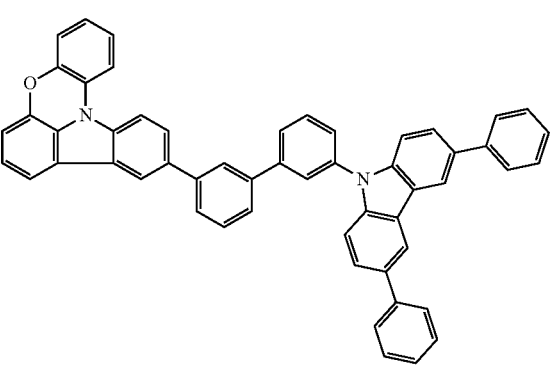
A147
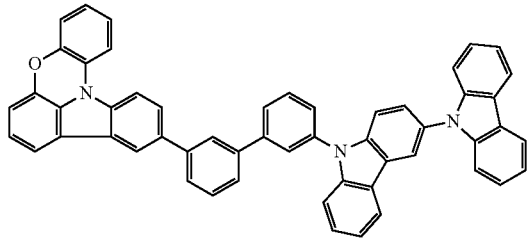
A148
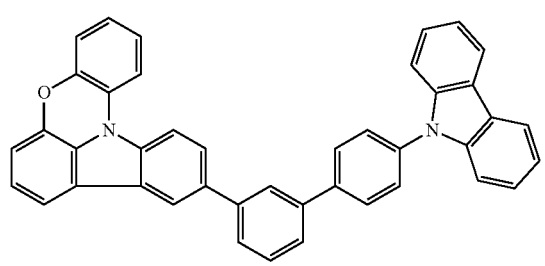

A149
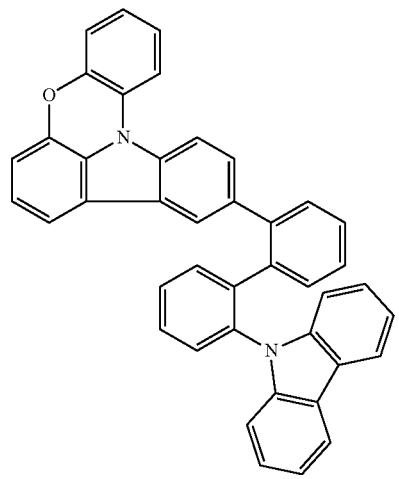
A152
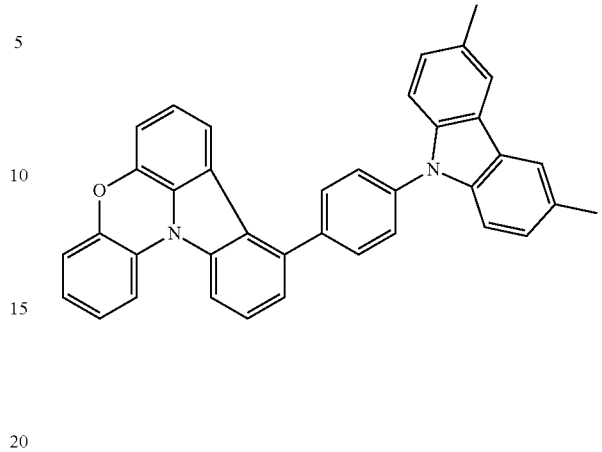
A150
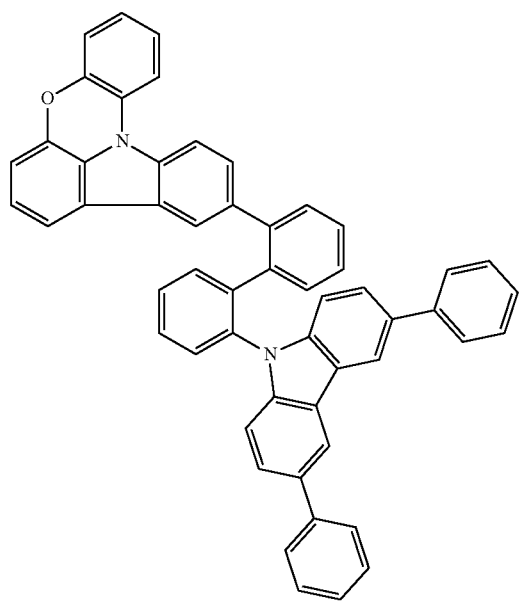
A153
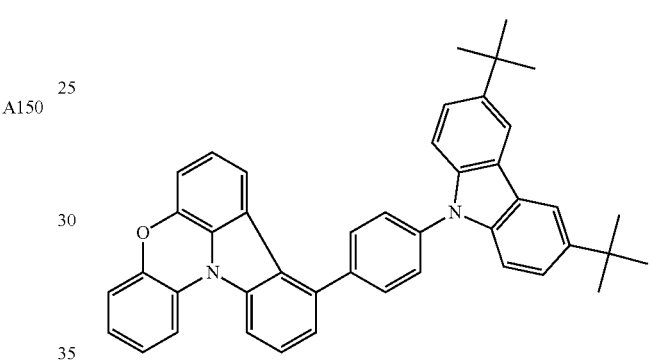
A154
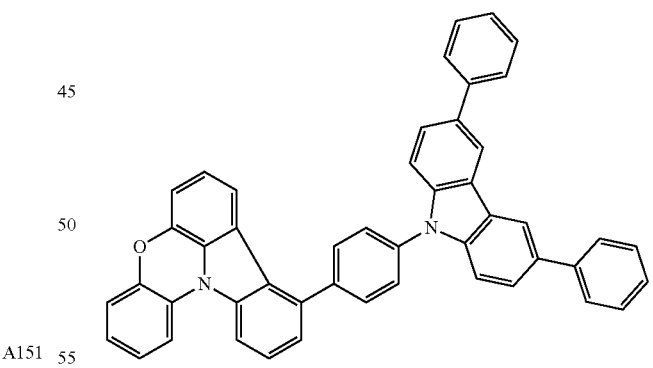
A151
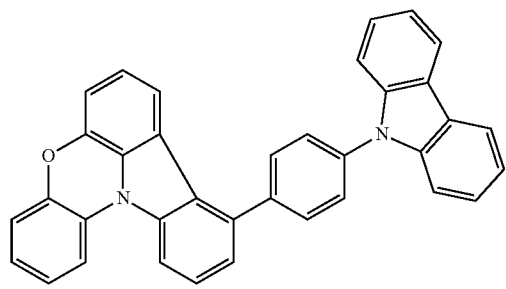
A155
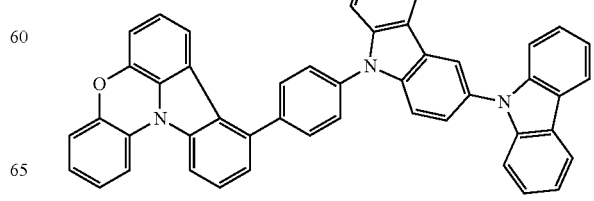

A156
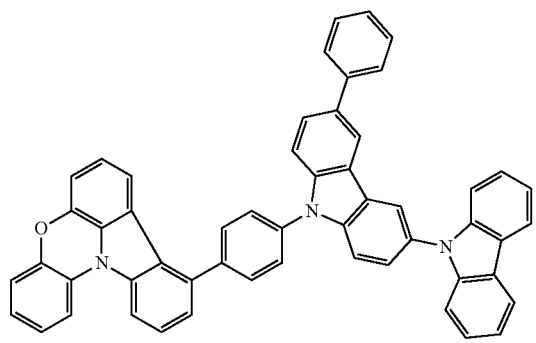
A157
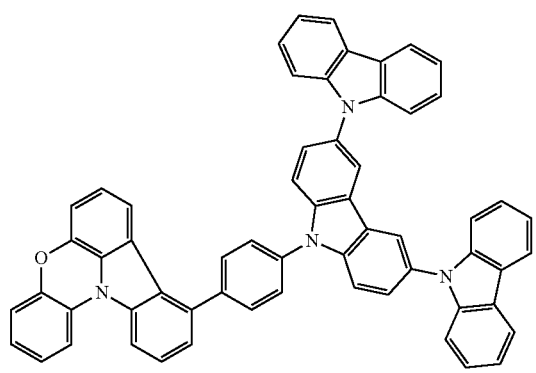
A158
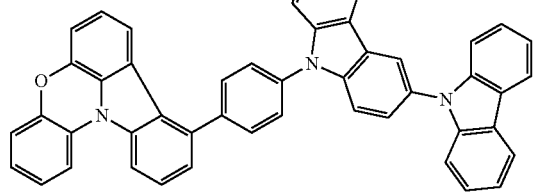
A159
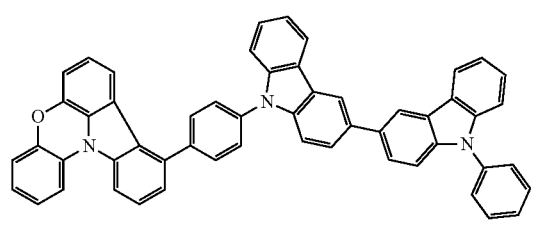
A160
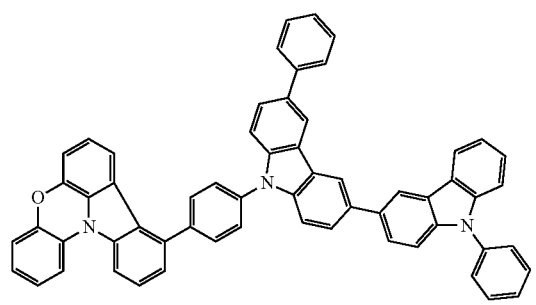
A161
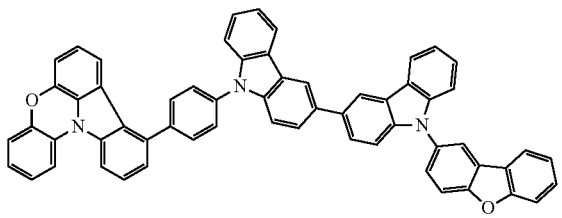
A162
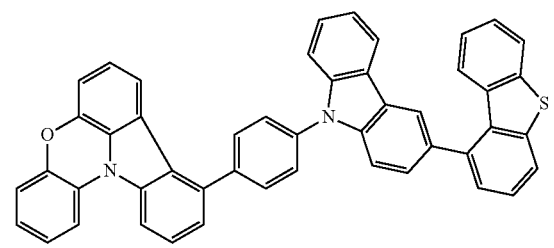
A163
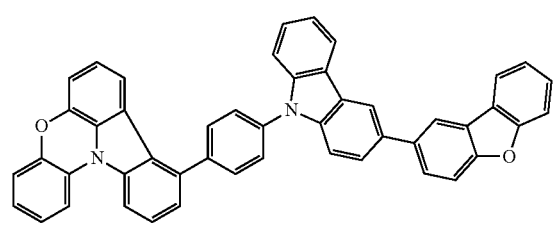
A164
A165
A166
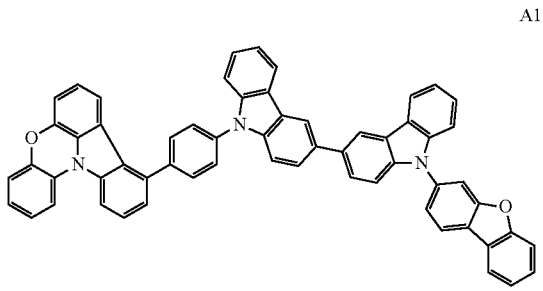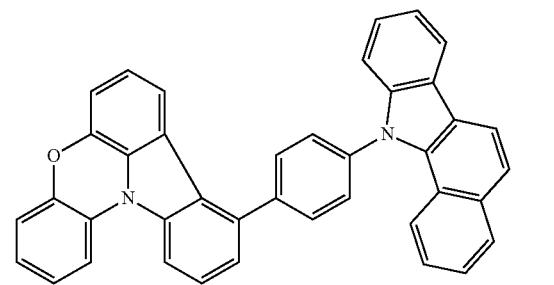

A167
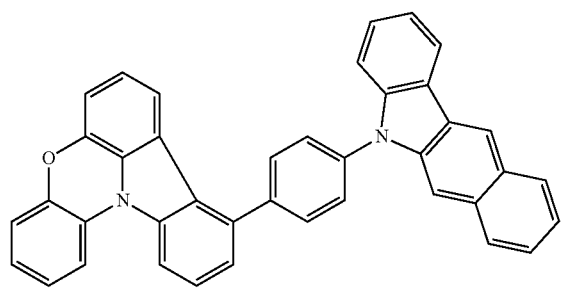
A168
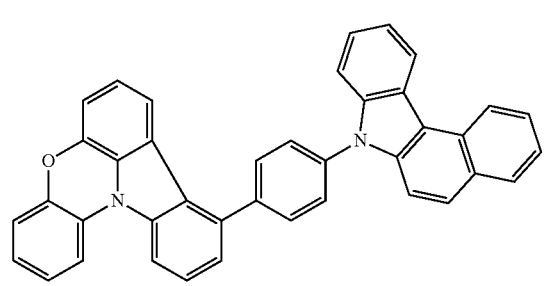
A169
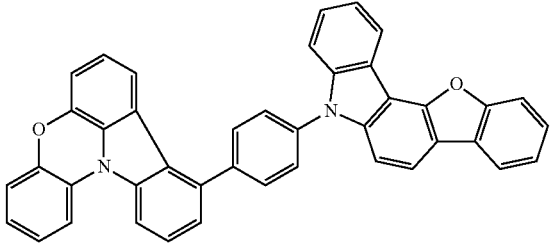
A170
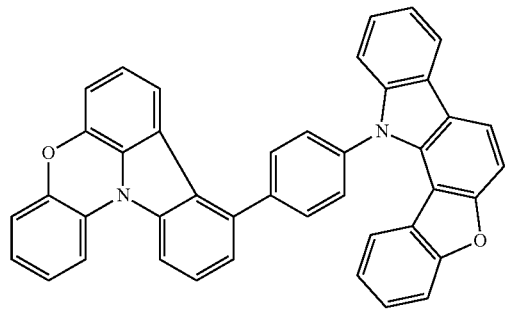
A171
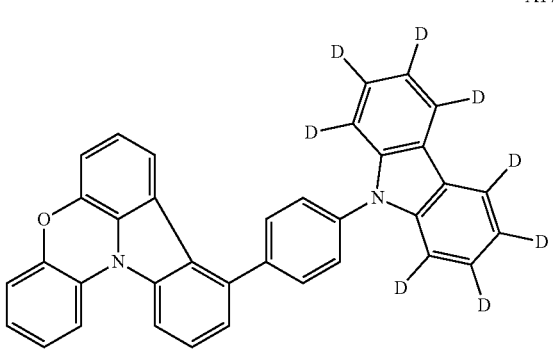
A172
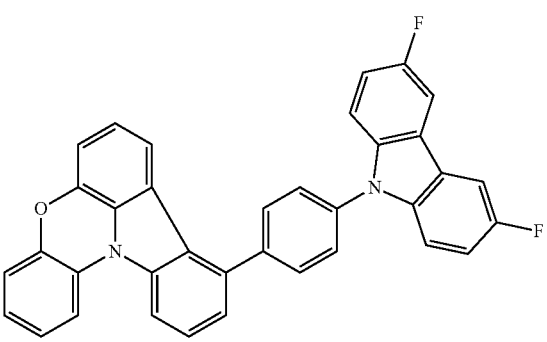
A173
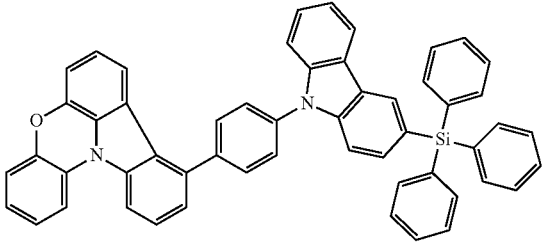
A174
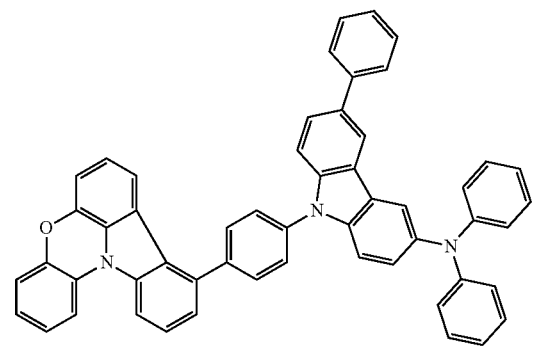
A175
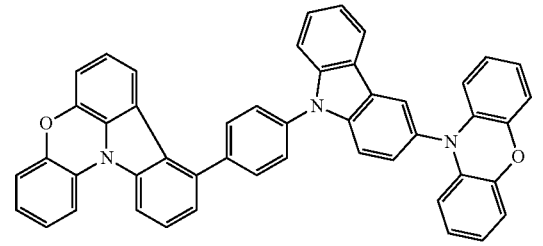
A176
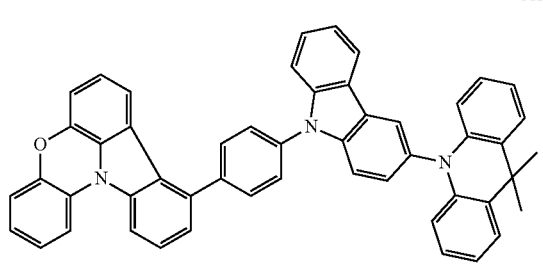

A177
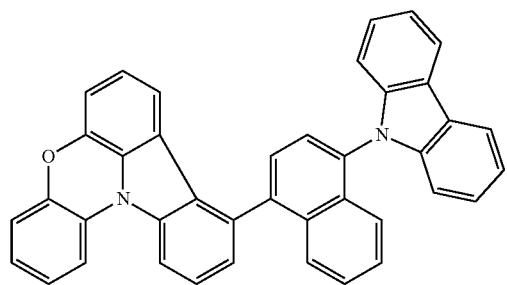
A178
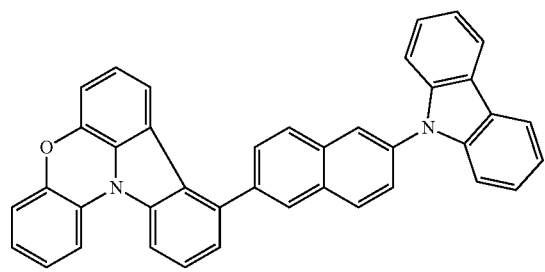
A179
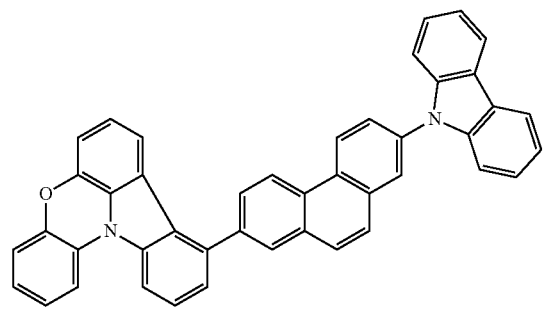
A180
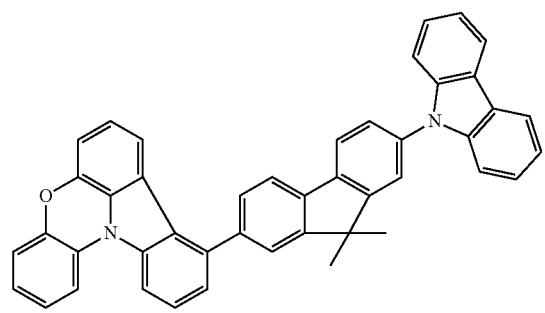
A181
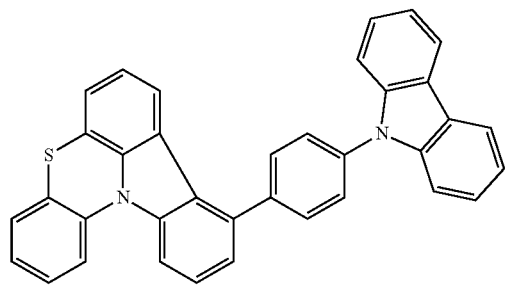
A182
A183
A184
A185
A186

A187
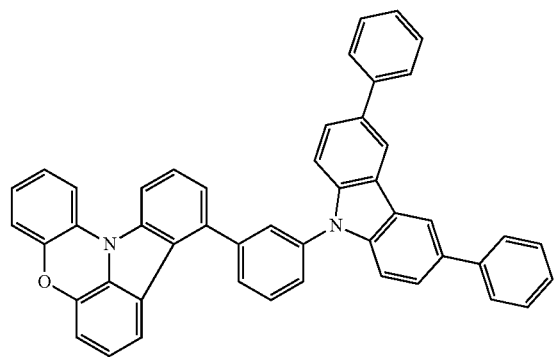
A190
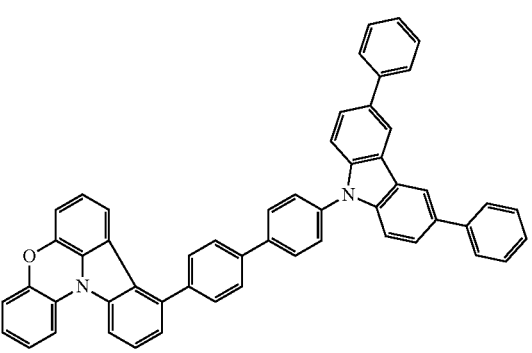
A188
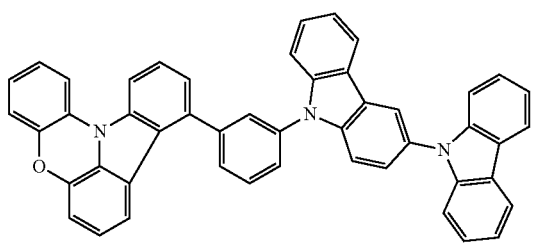
A191
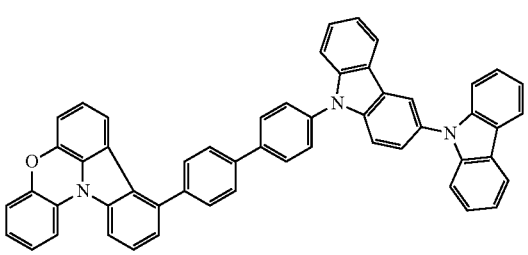
A189
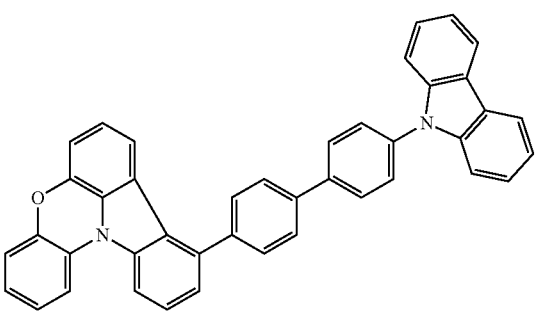
A192
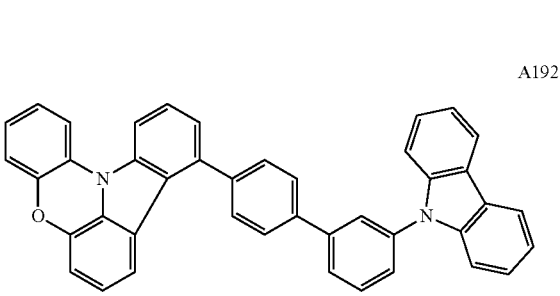
A193
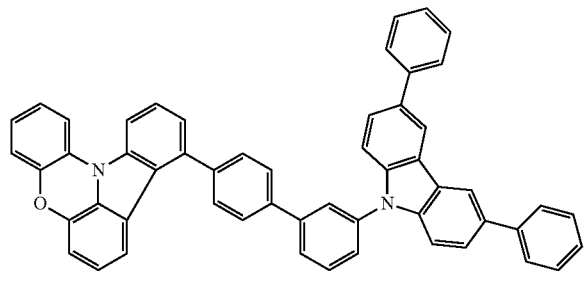
A194
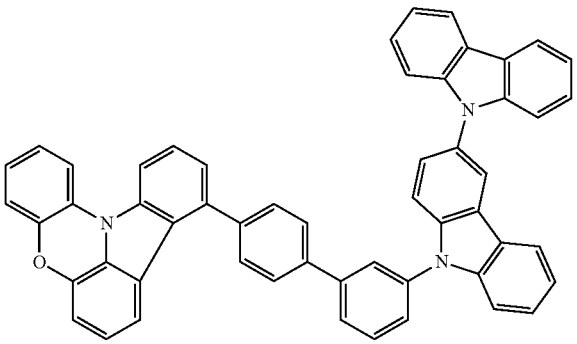

-continued
A195
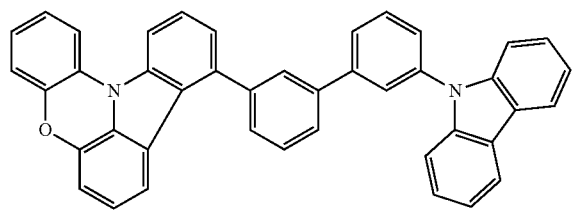
A196
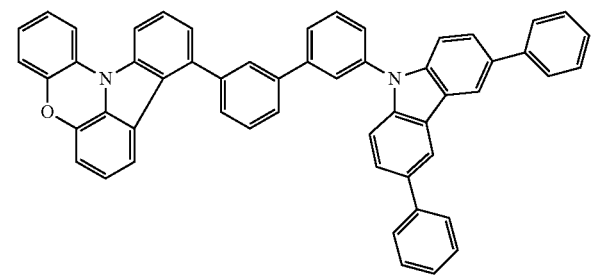
A197
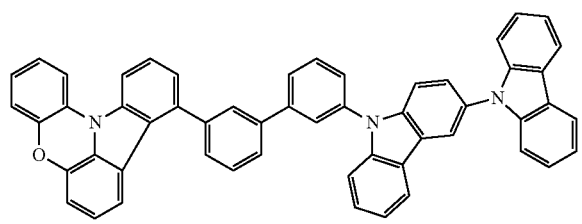
A198
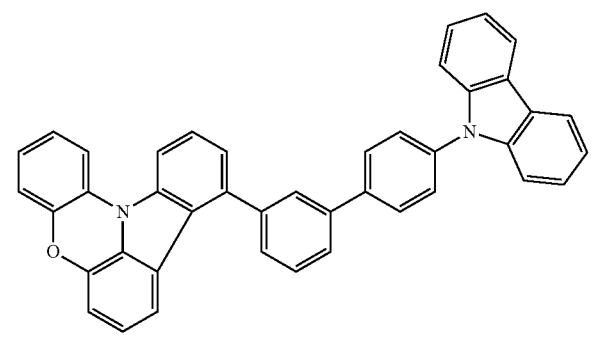
A199
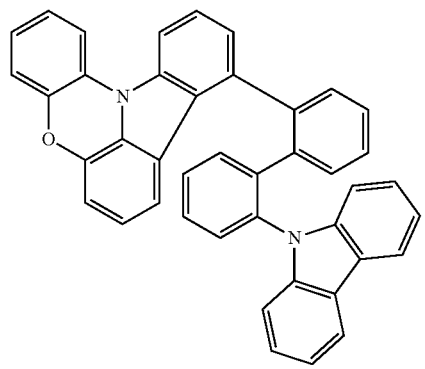
A200
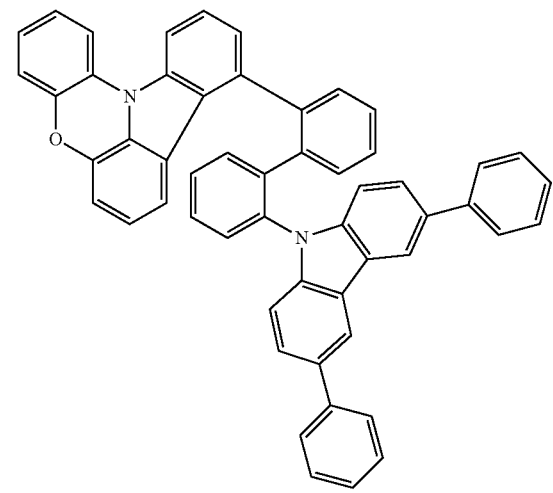
[Compound Group 1B]
B1
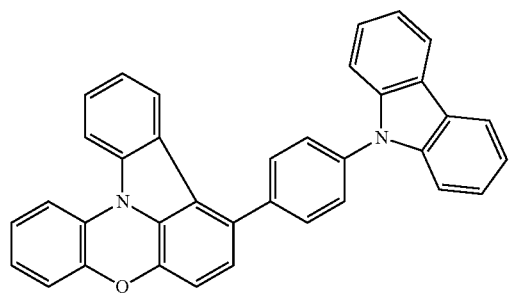
B2
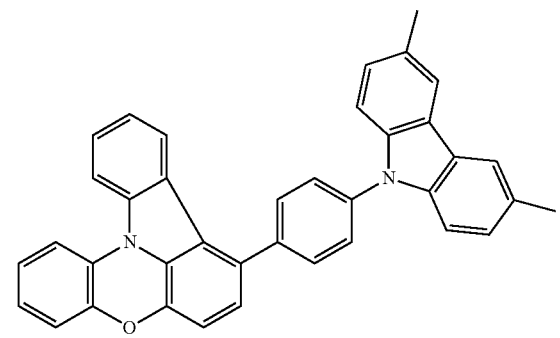

-continued
B3
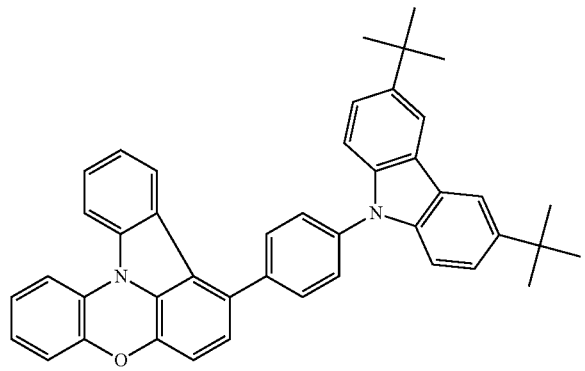
B4
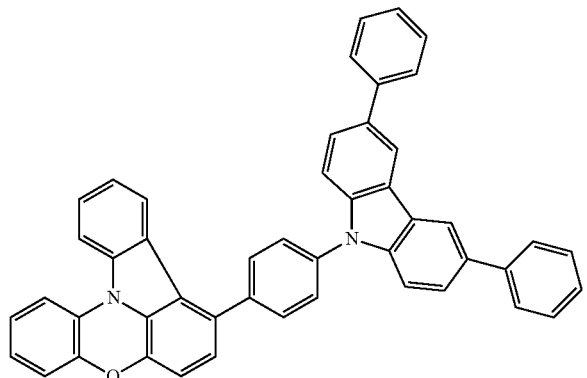
B5
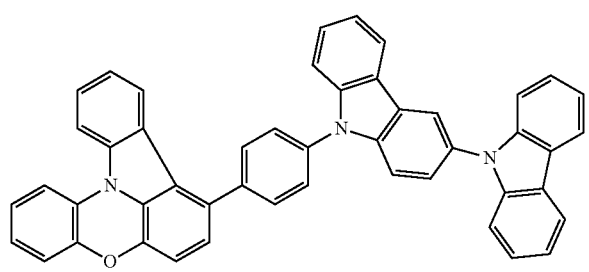
B6
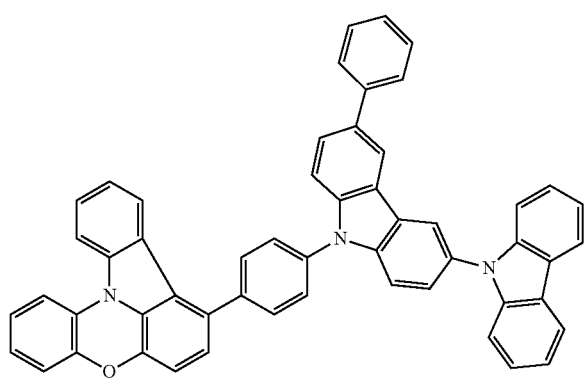
B7
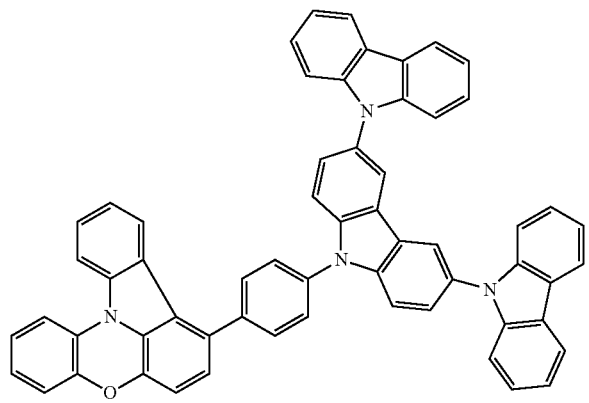
B8
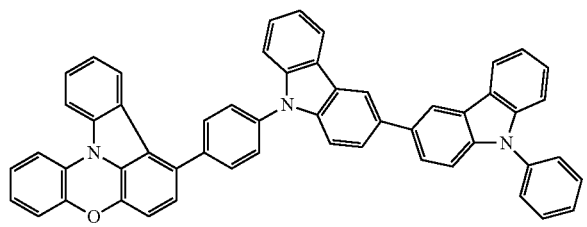
B9
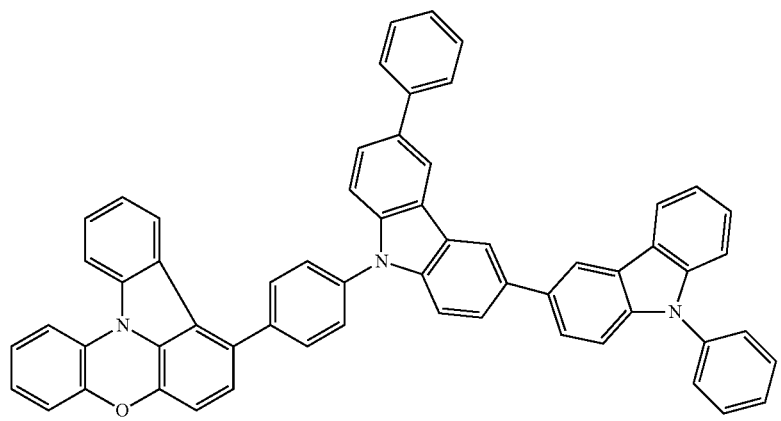

-continued
B10
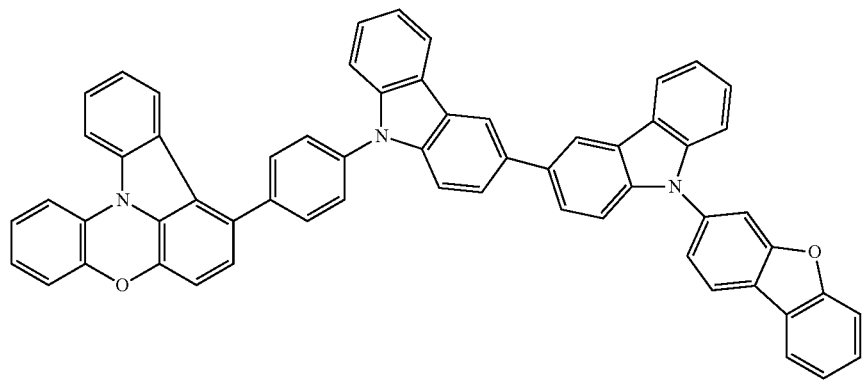
B11
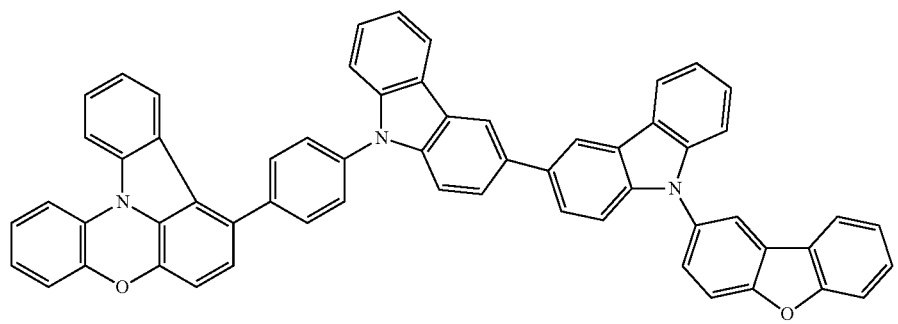
B12
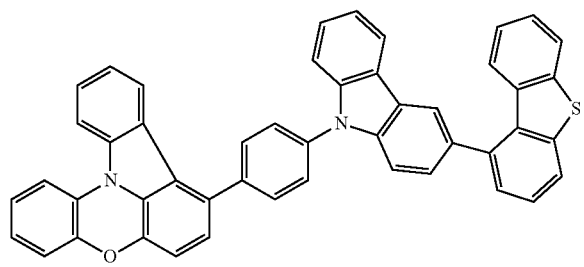
B13
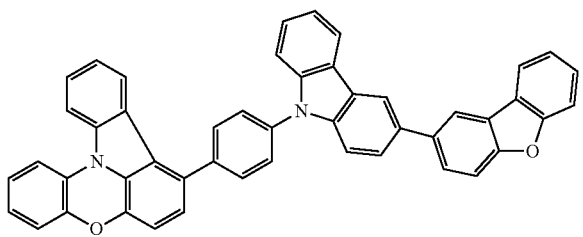
B14
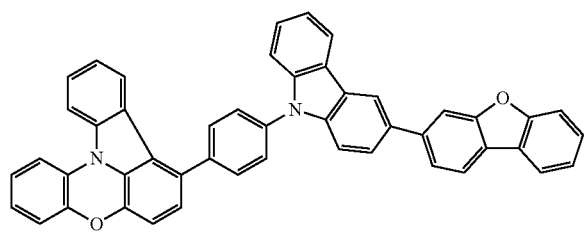
B15
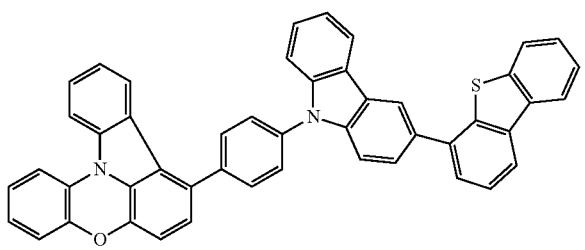
B16
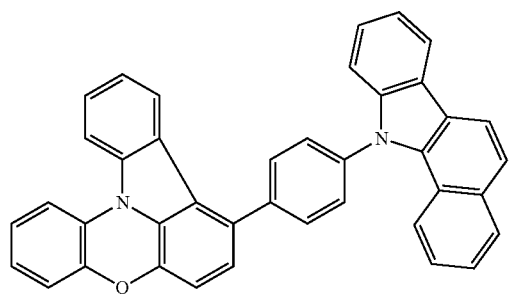
B17
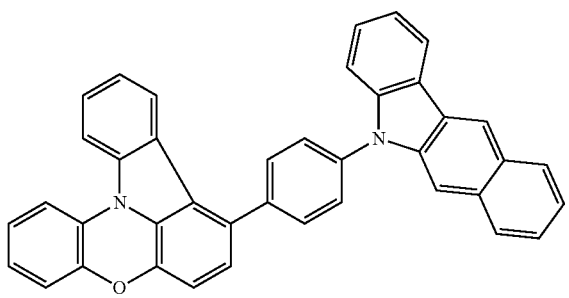

-continued
B18
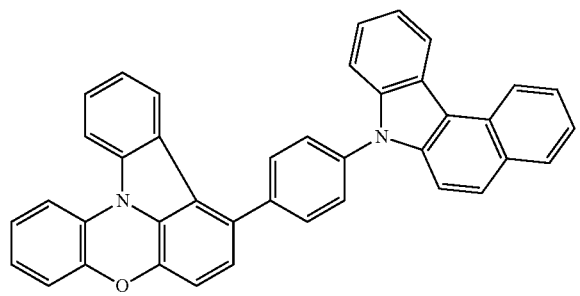
B19
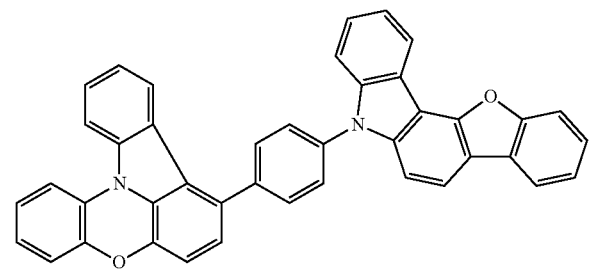
B20
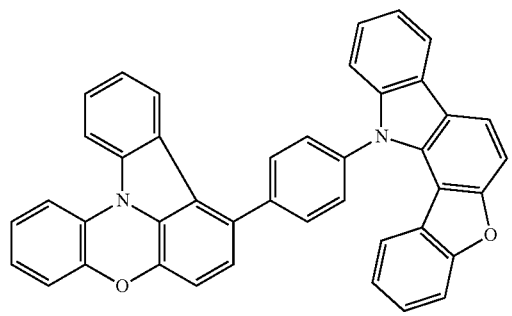
B21
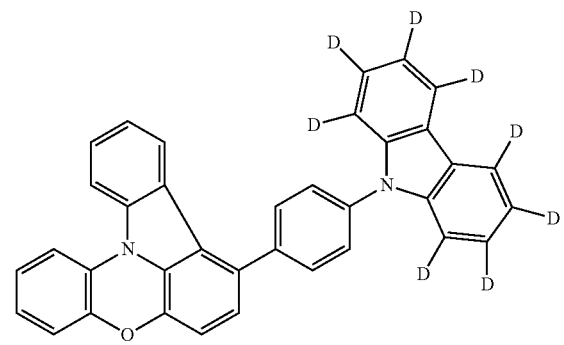
B22
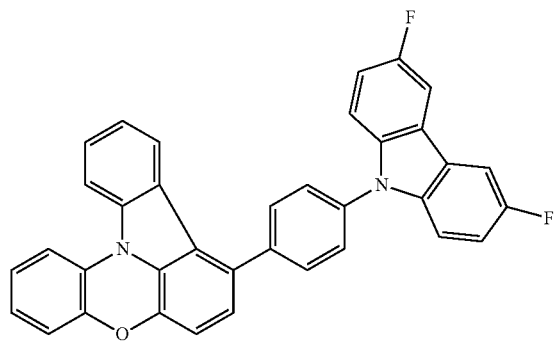
B23
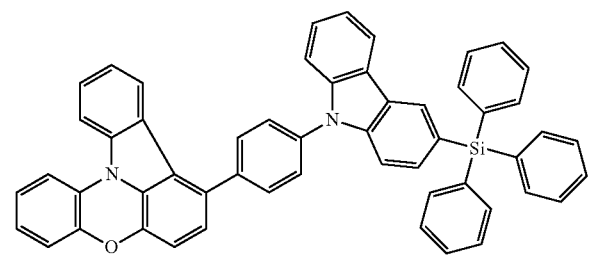
B24
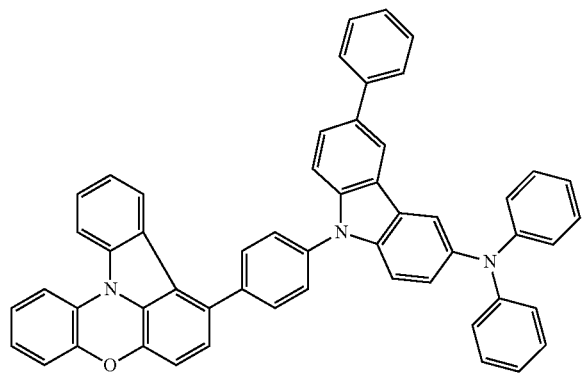
B25
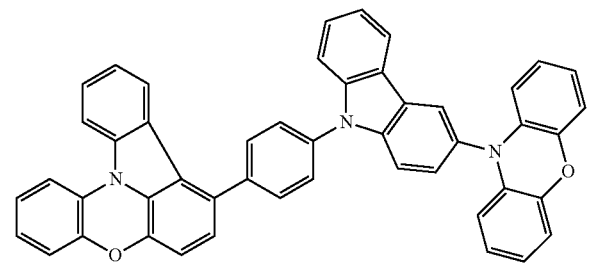

-continued
B26
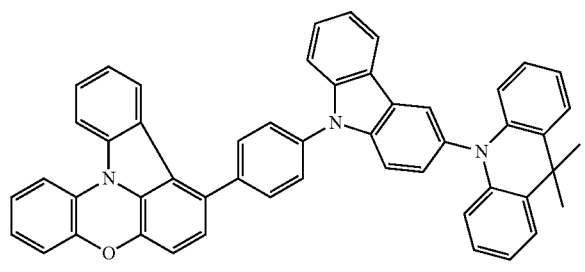
B27
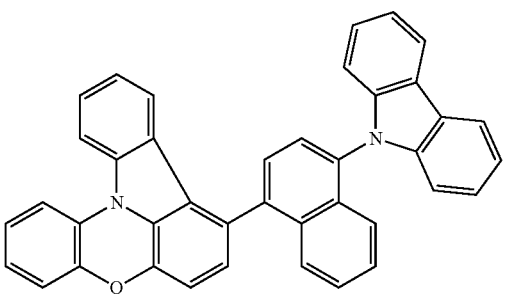
B28
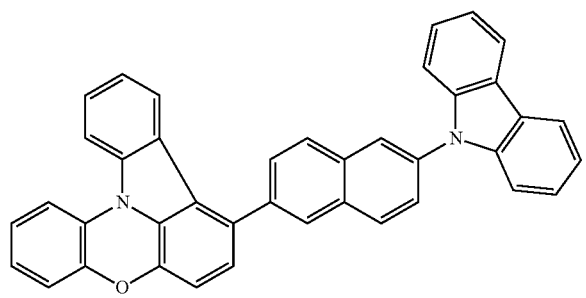
B29
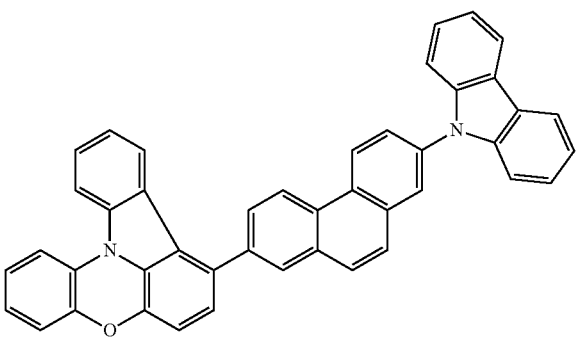
B30
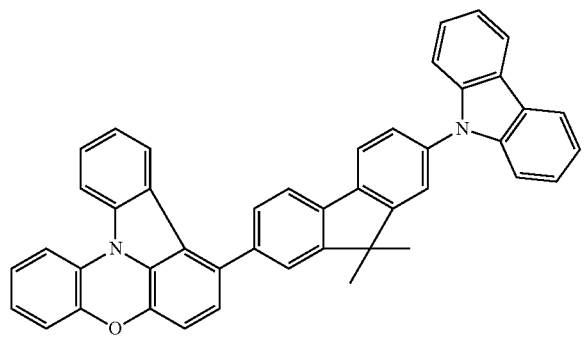
B31
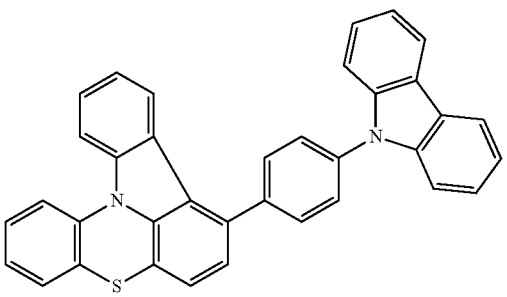
B32
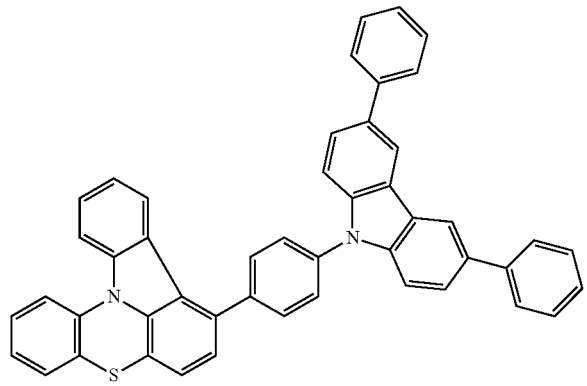
B33
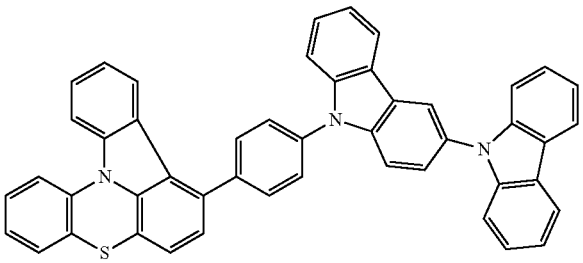

B34
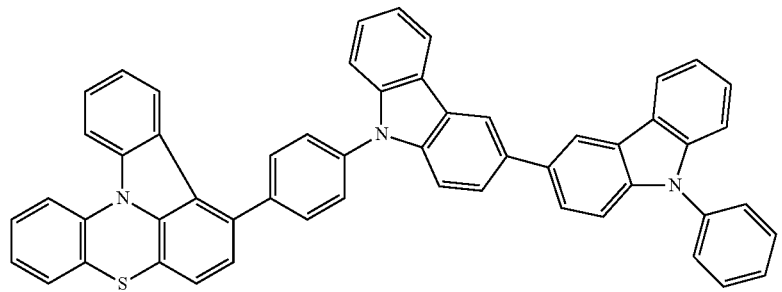
B35
B36
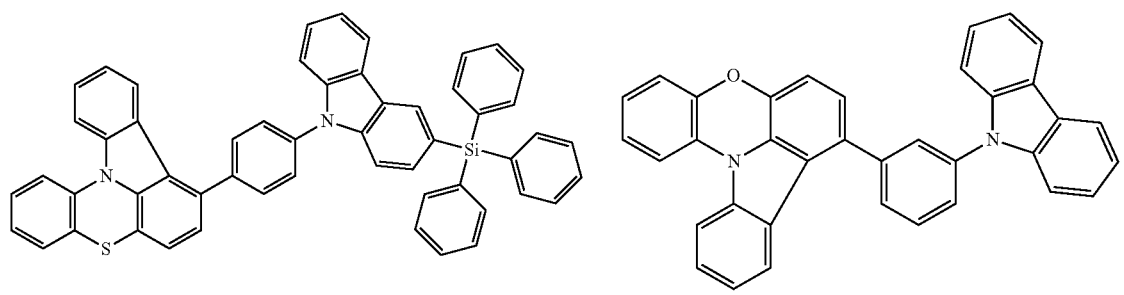
B37
B38
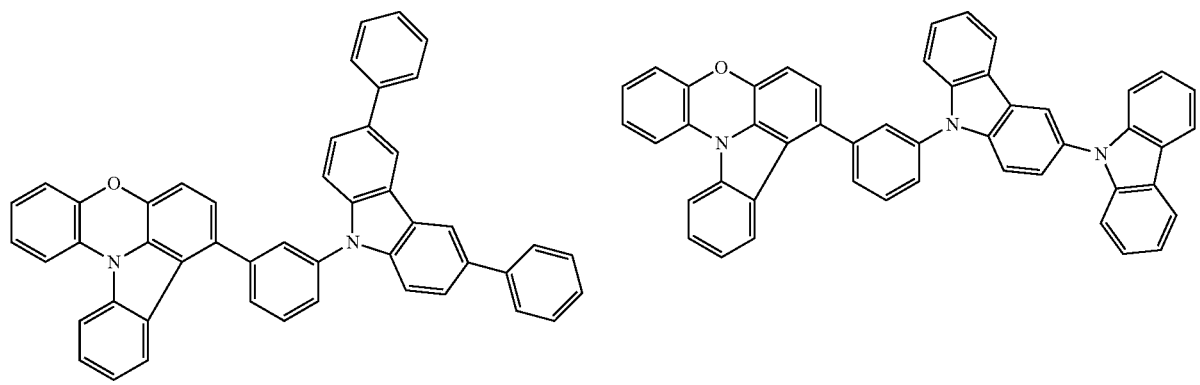
B39
B40
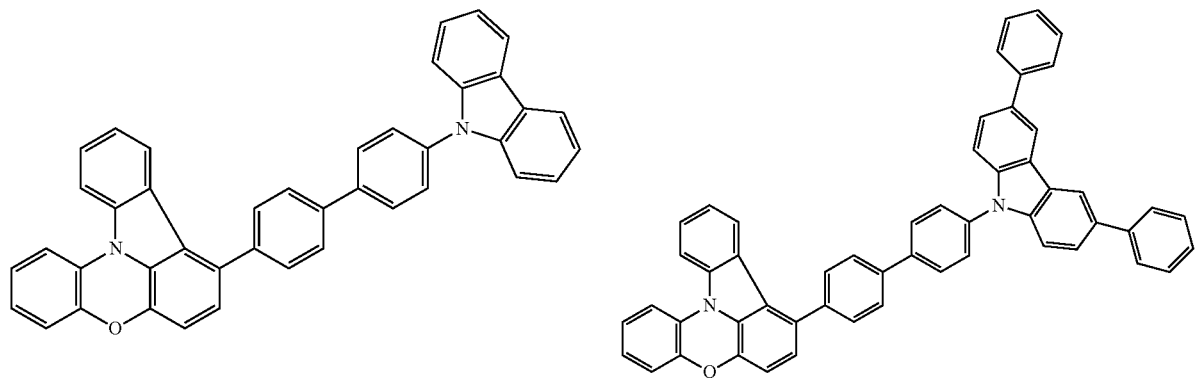

-continued
B41
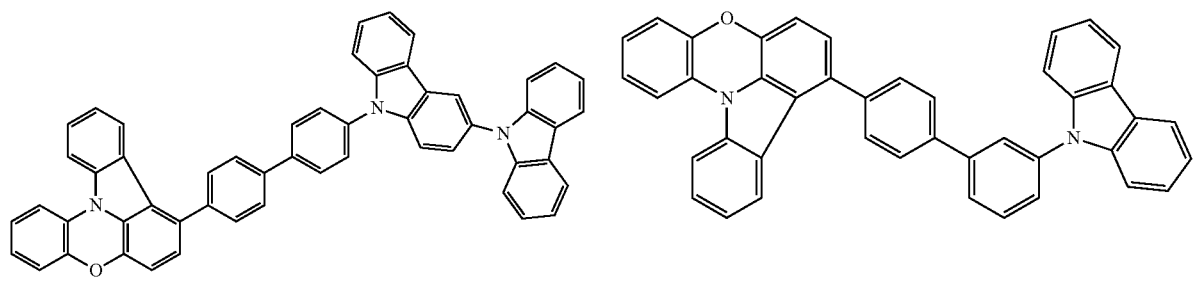
B42
B43
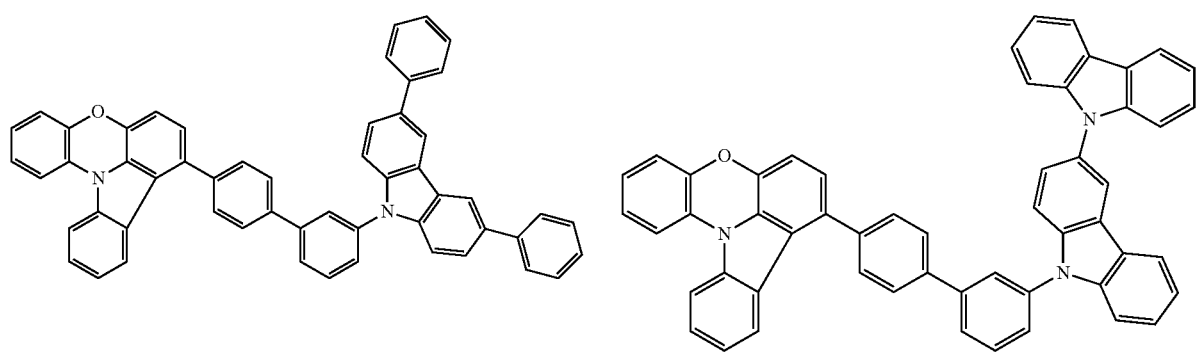
B44
B45
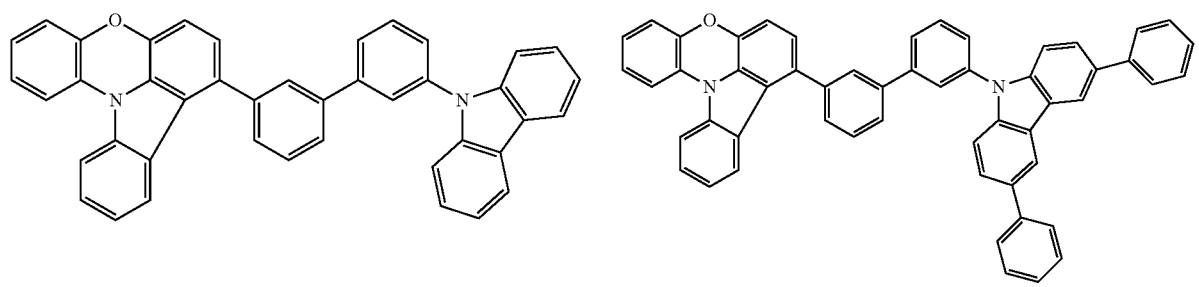
B46
B47
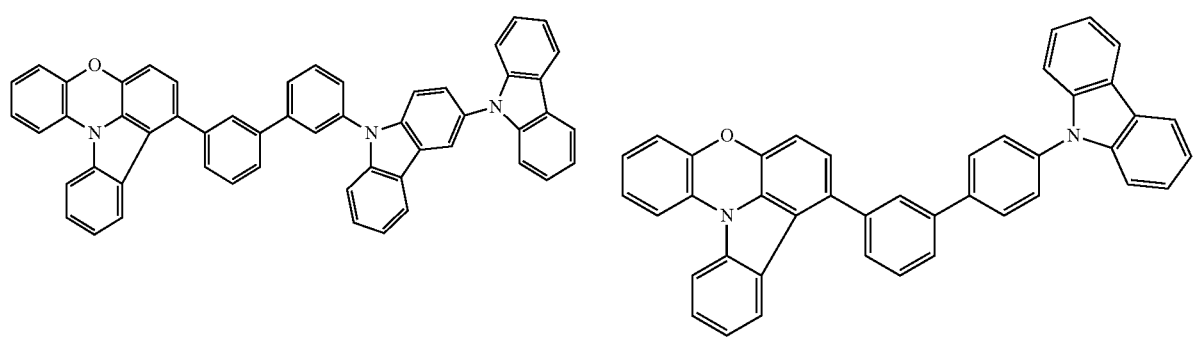
B48

B49
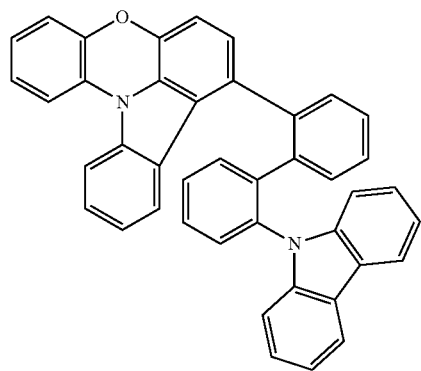
B50
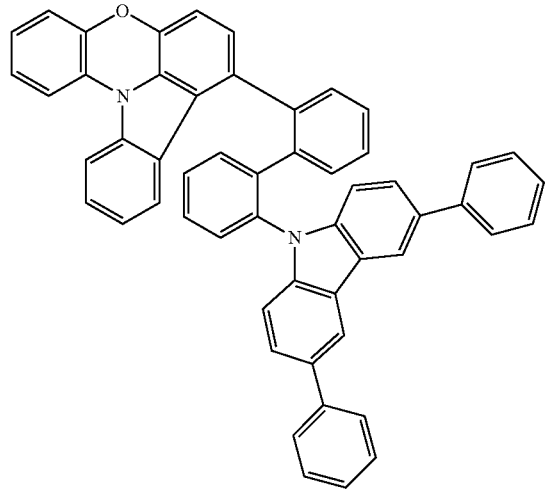
B51
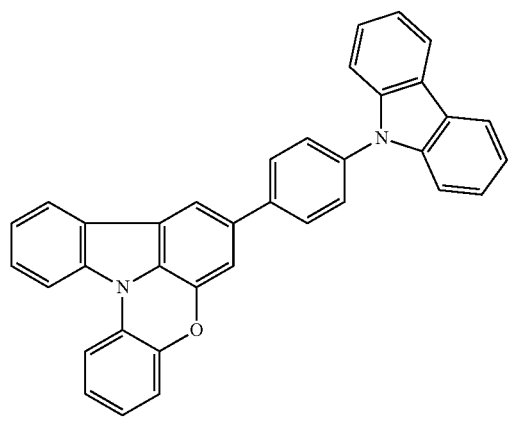
B52
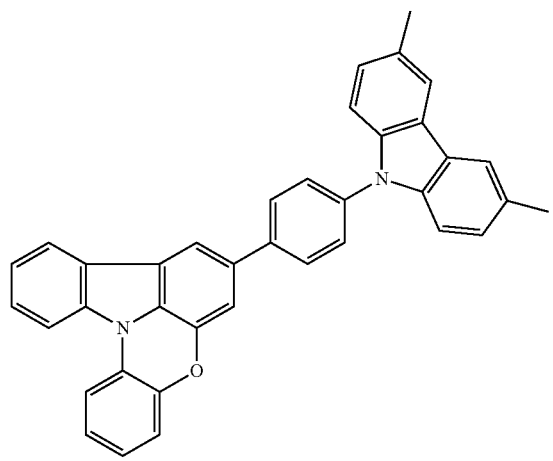
B53
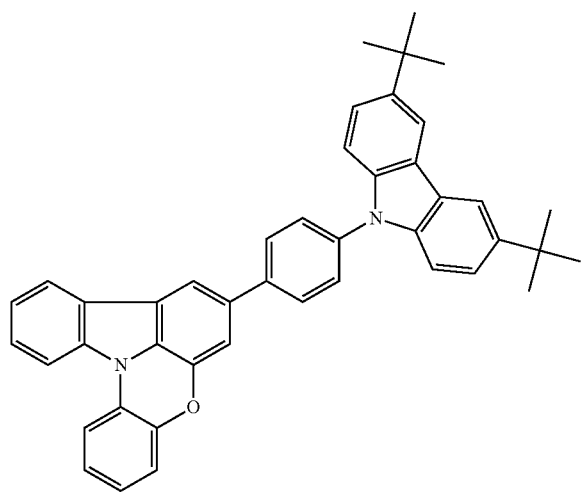
B54
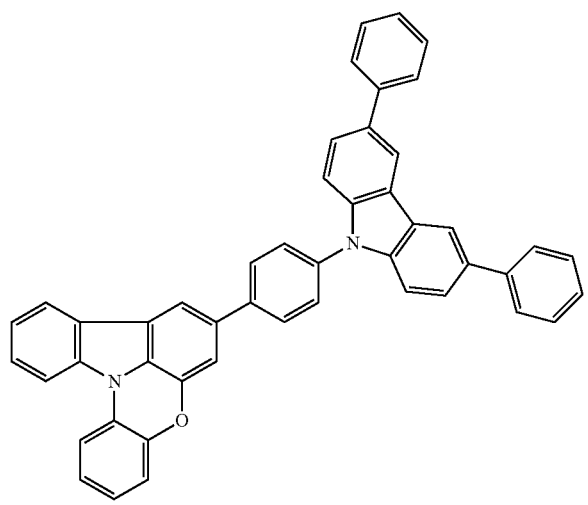

-continued
B55
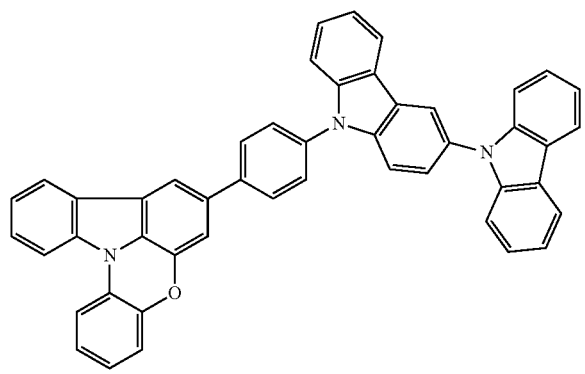
B56
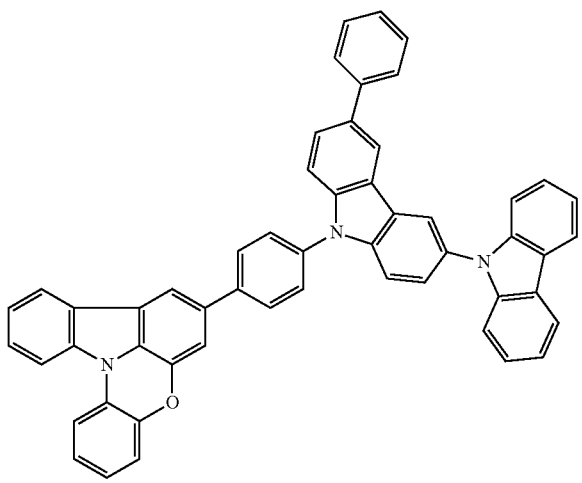
B57
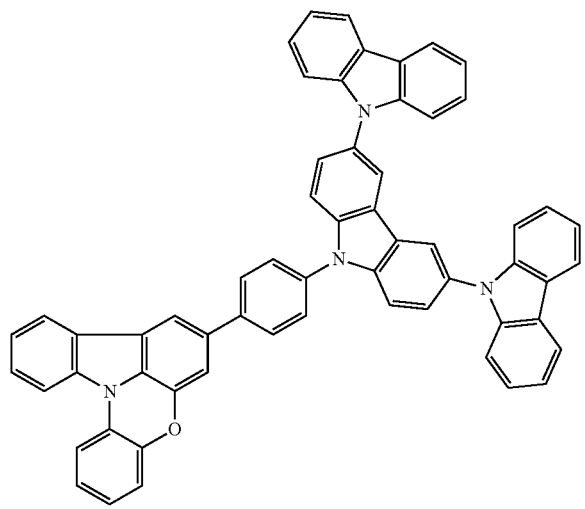
B58
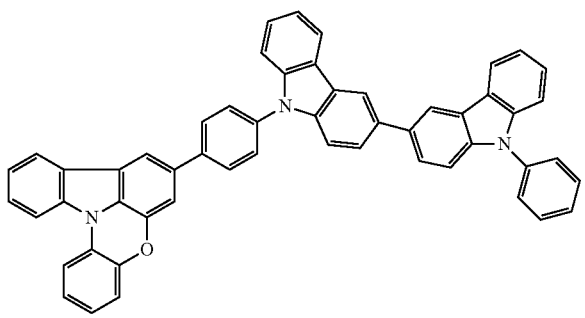
B59
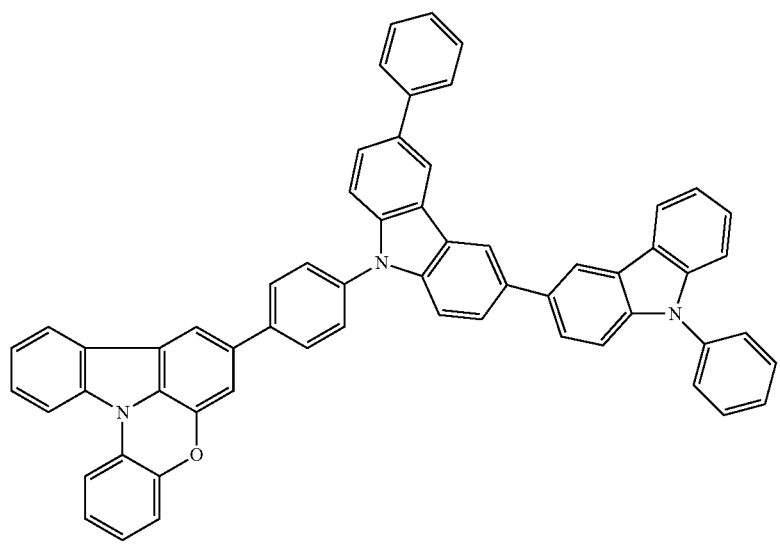

-continued
B60
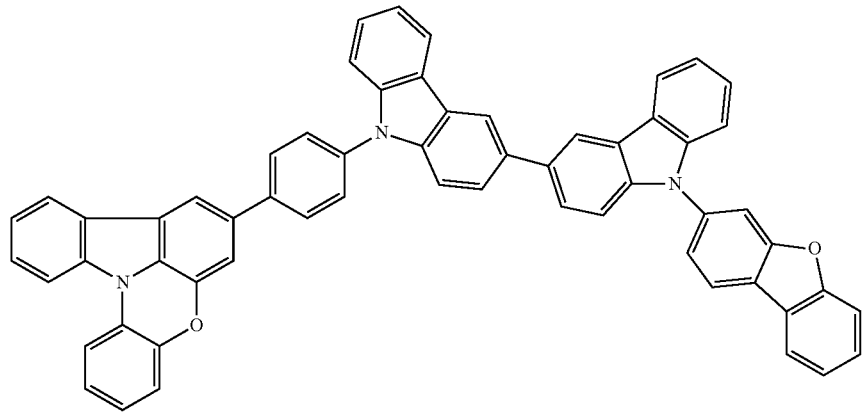
B61
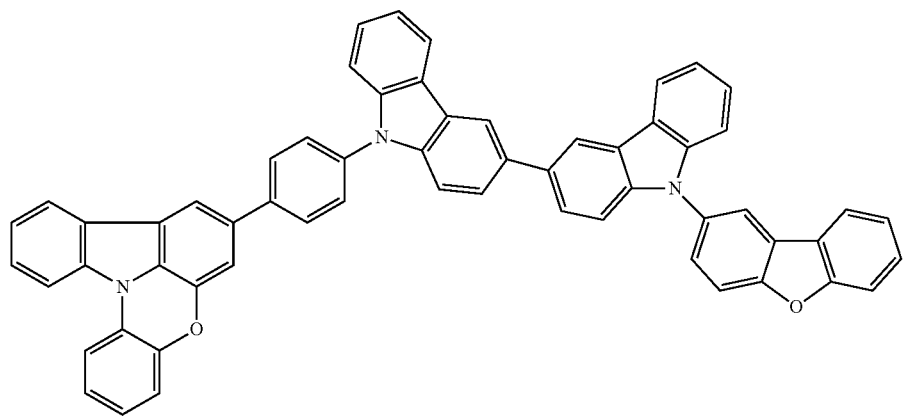
B62
B63
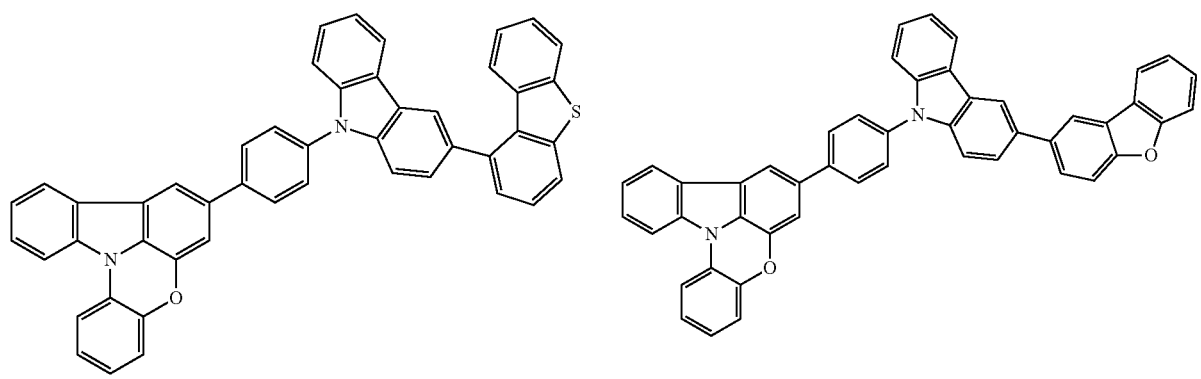
B64
B65
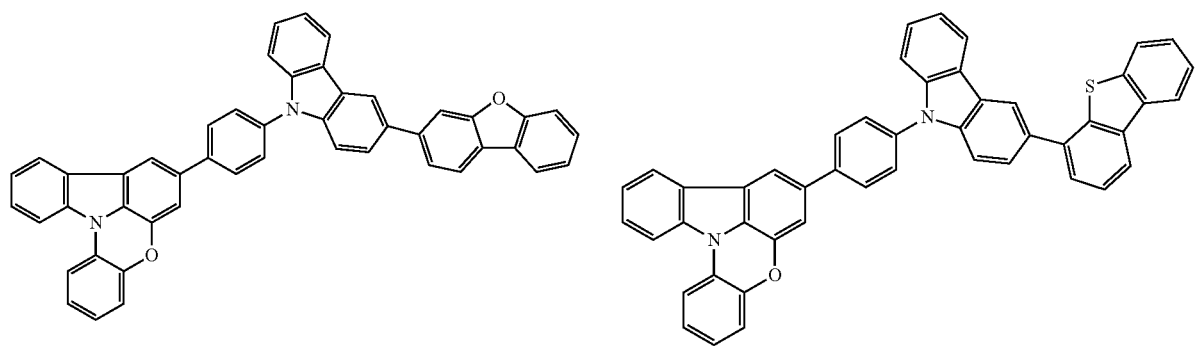

-continued
B66
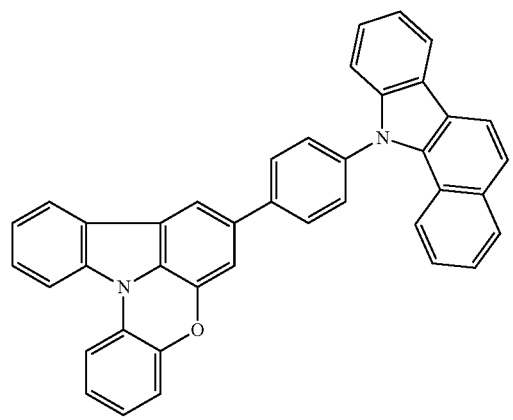
B67
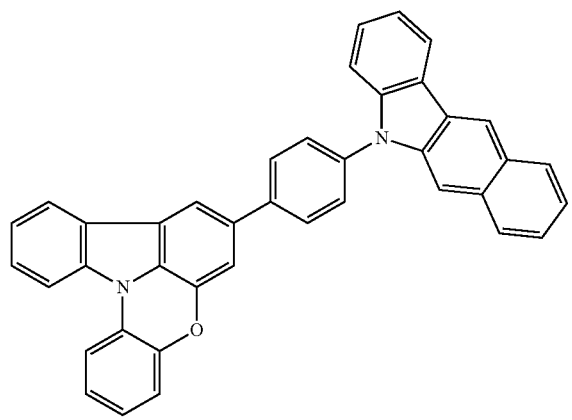
B68
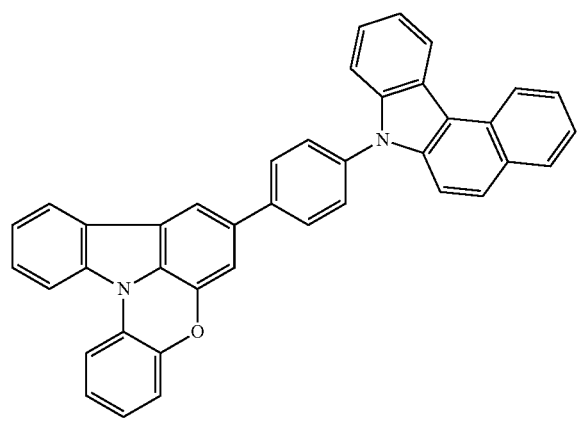
B69
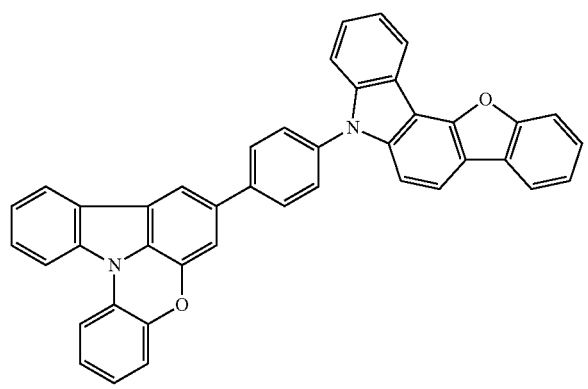
B71
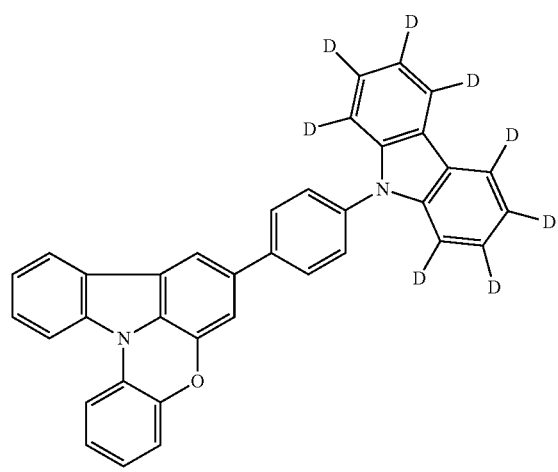
B72
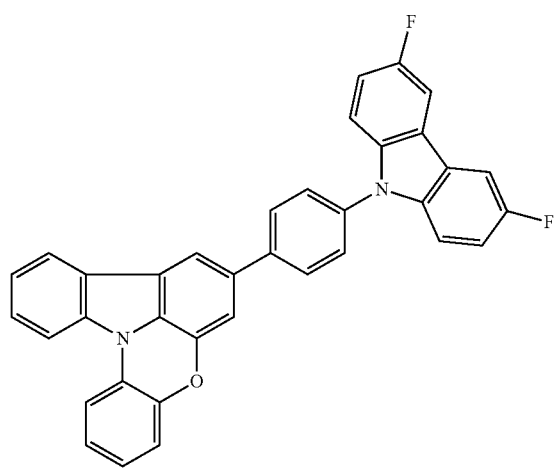

-continued
B70
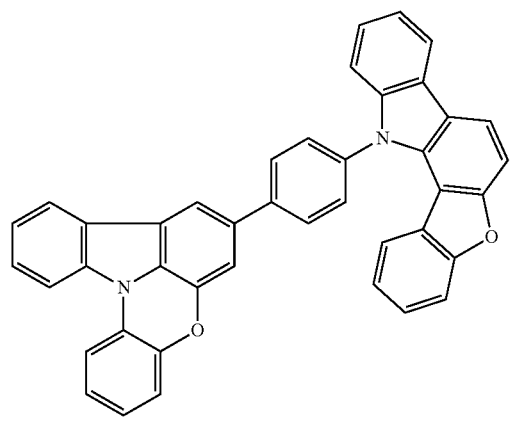
B73
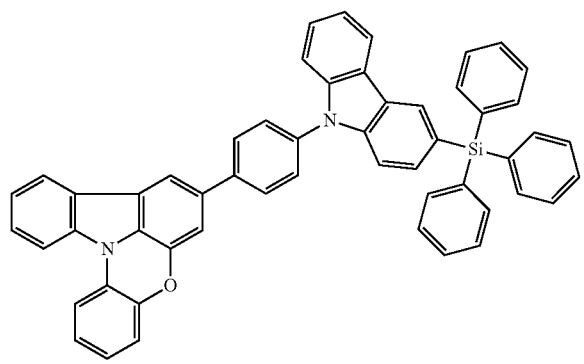
B74
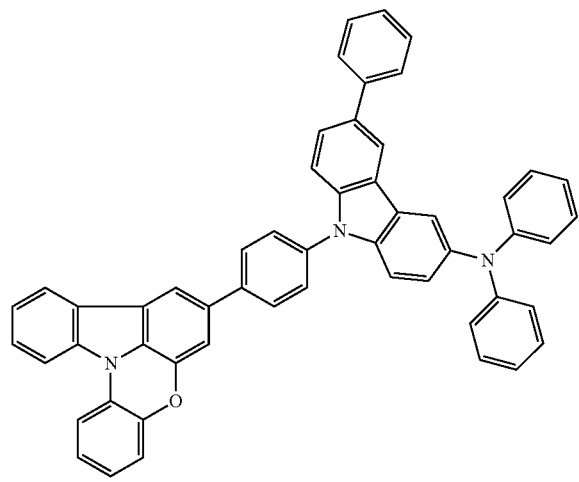
B75
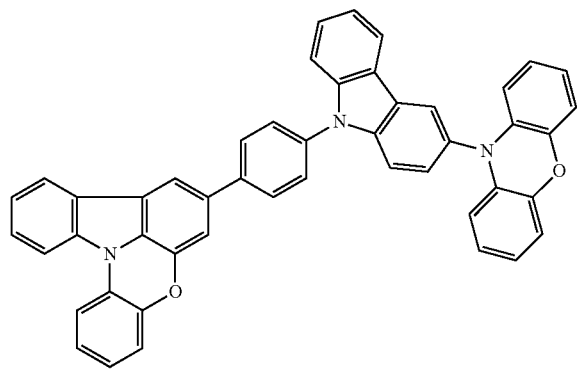
B76
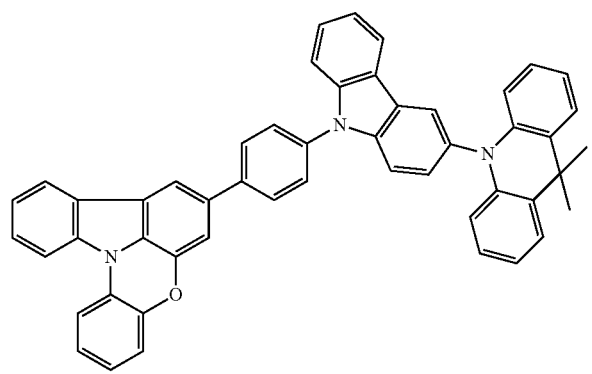
B77
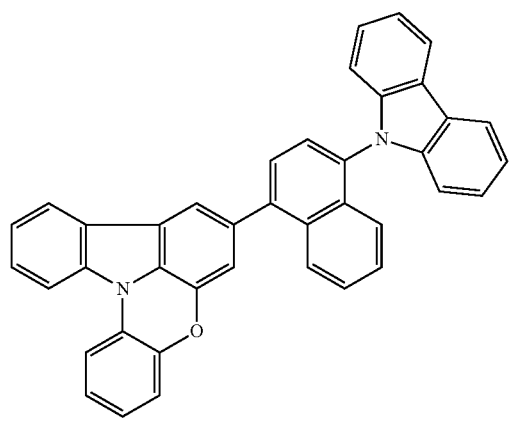

-continued
B78
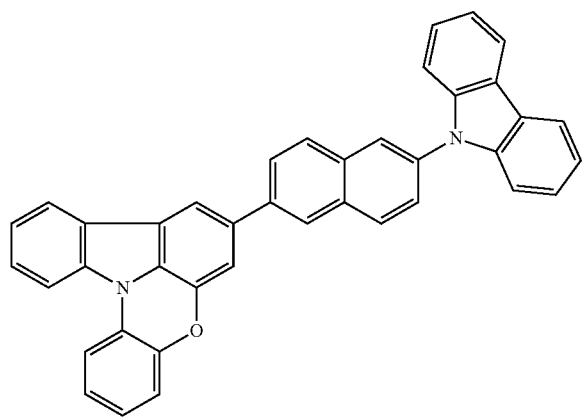
B79
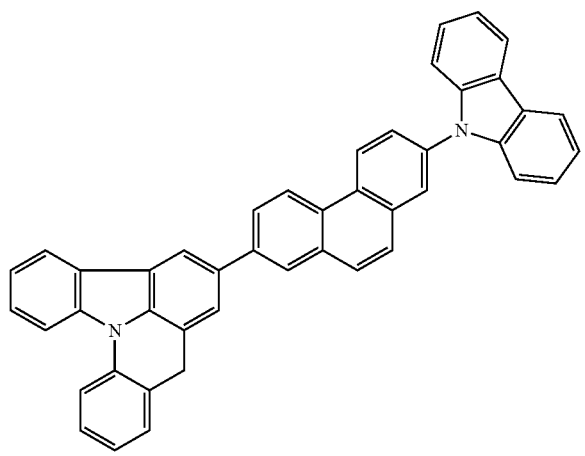
B80
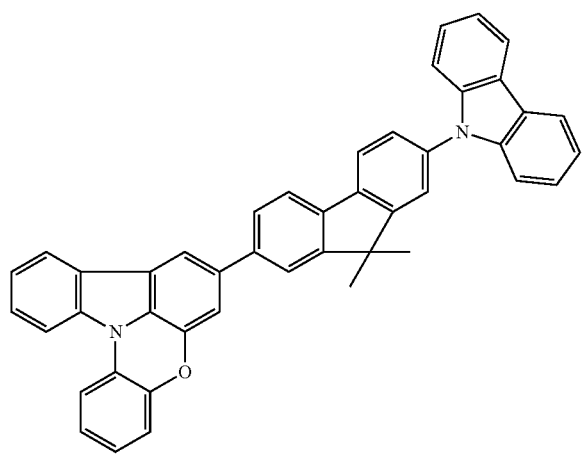
B81
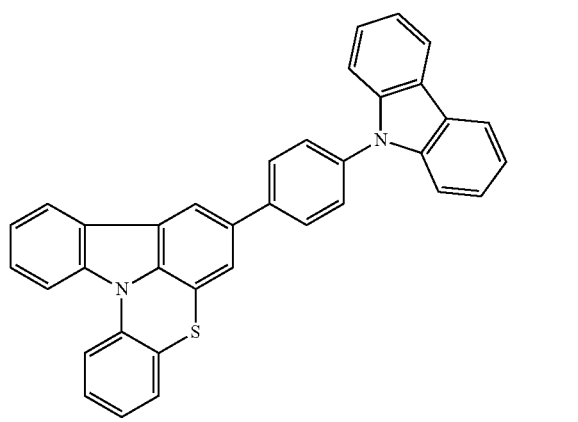
B82
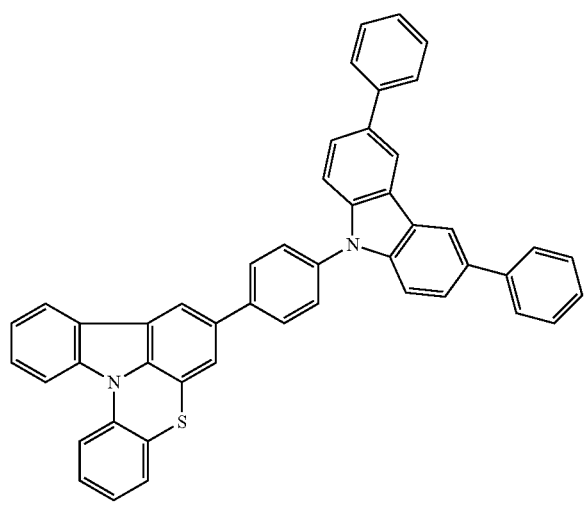
B83
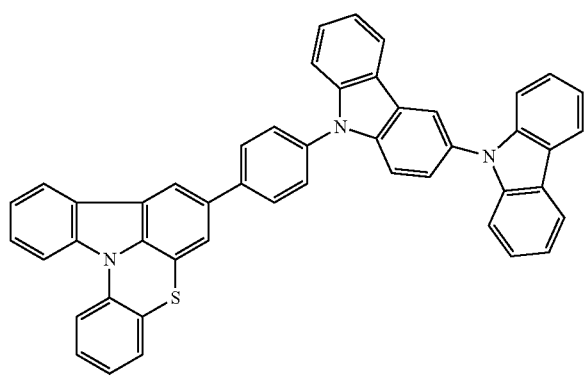

-continued
B84
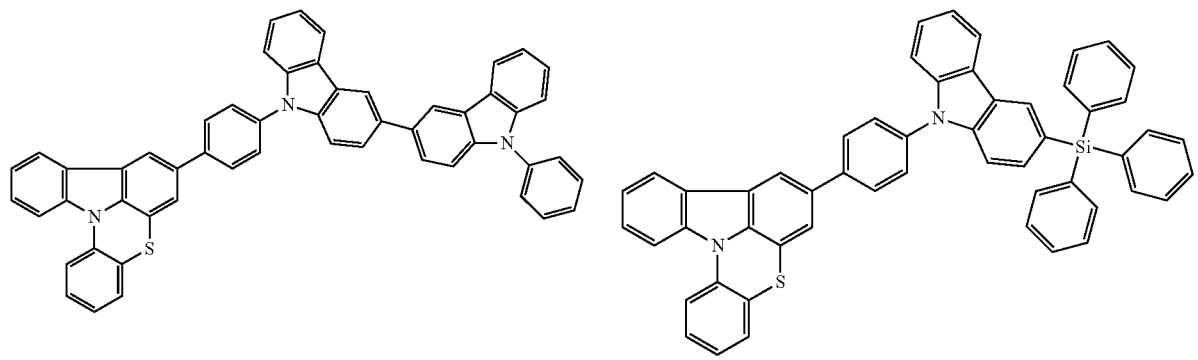
B85
B86
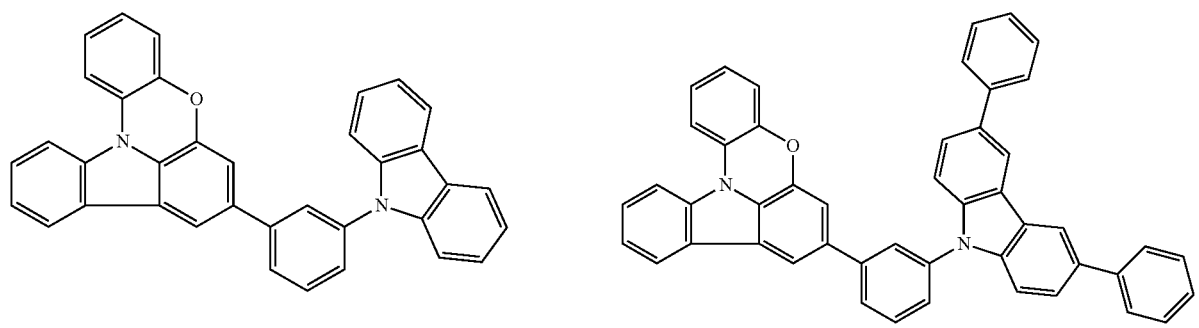
B87
B88
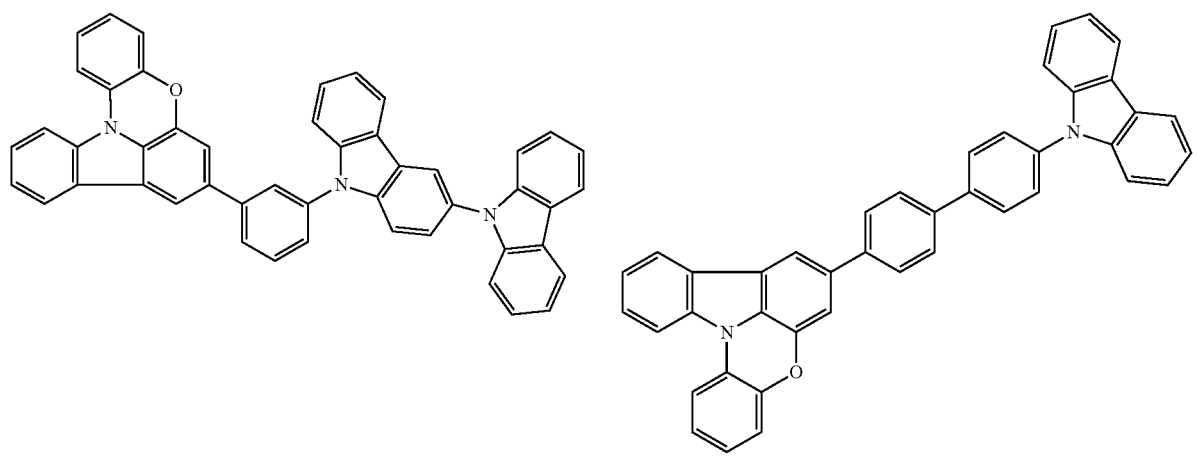
B89

-continued
B90
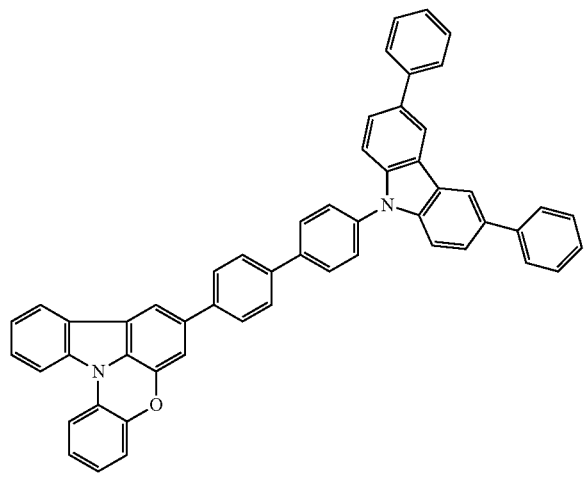
B91
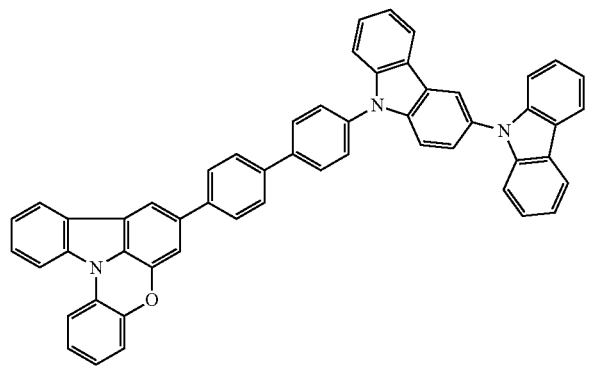
B92
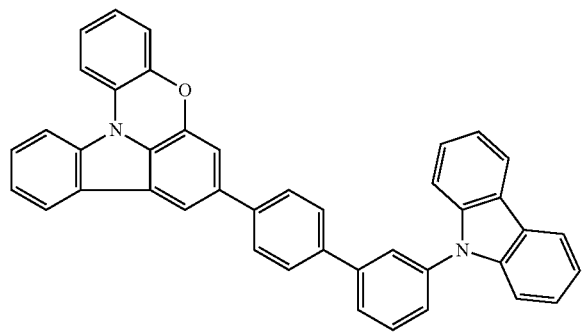
B93
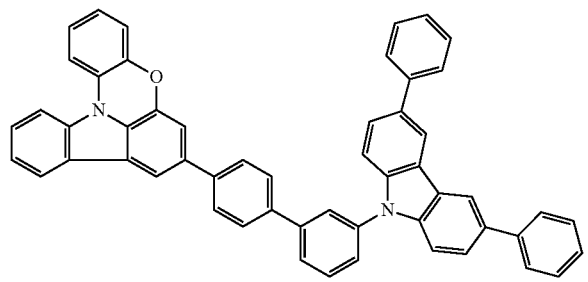
B94
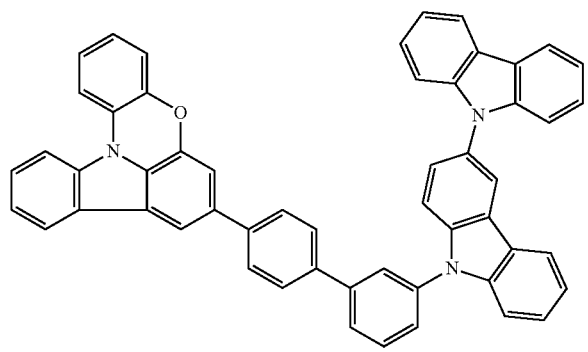
B95
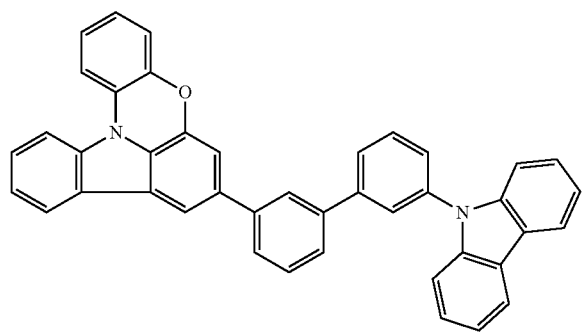
B96
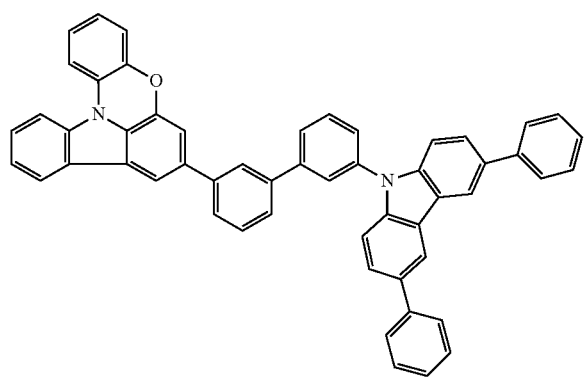
B97
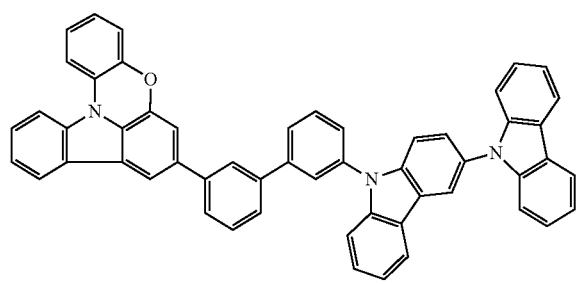

-continued
B98
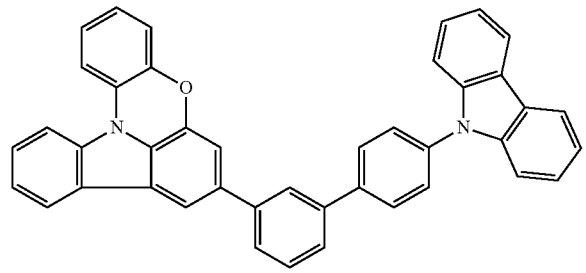
B99
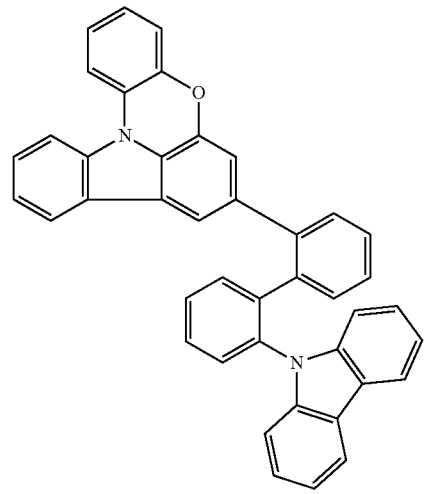
B100
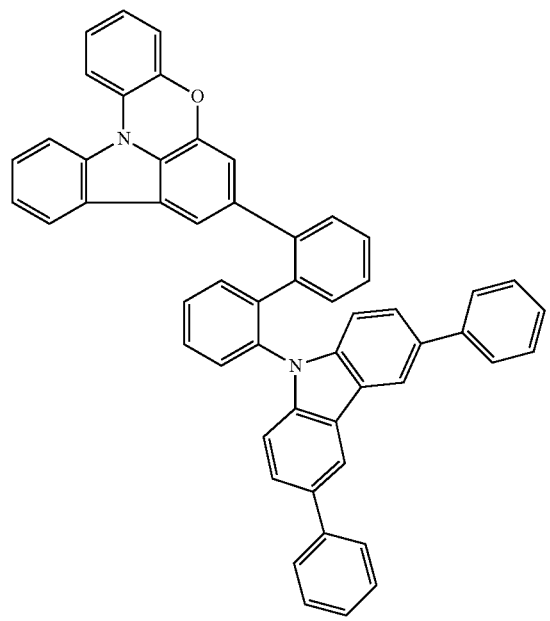
B101
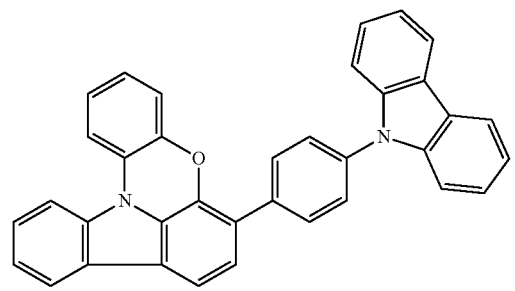
B102
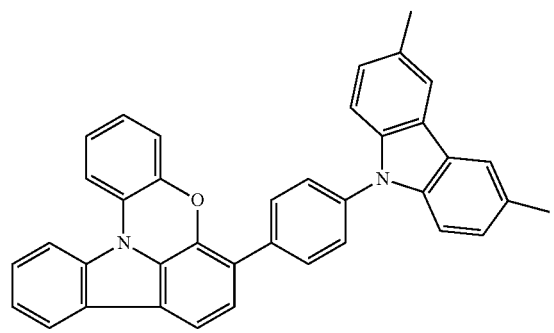
B103
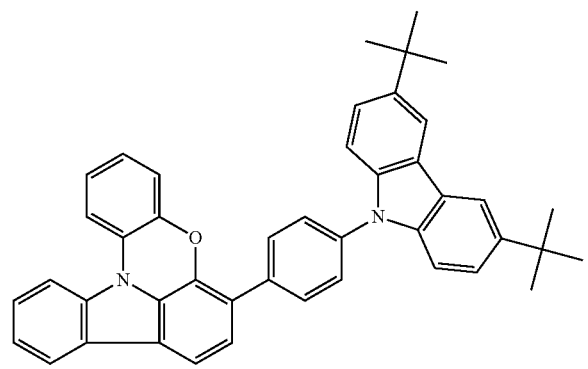

-continued
B104
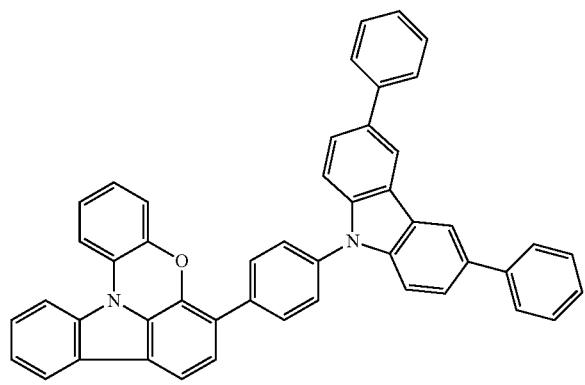
B105
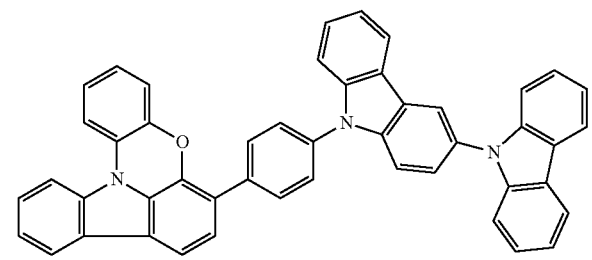
B106
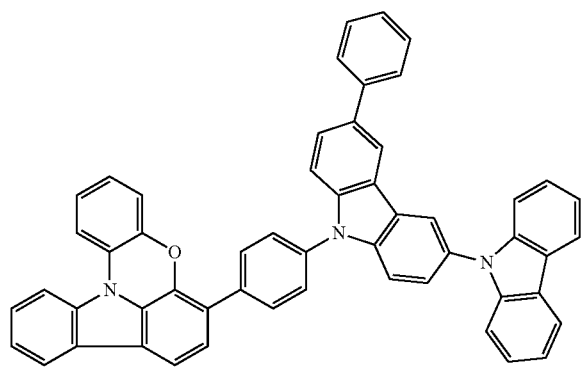
B107
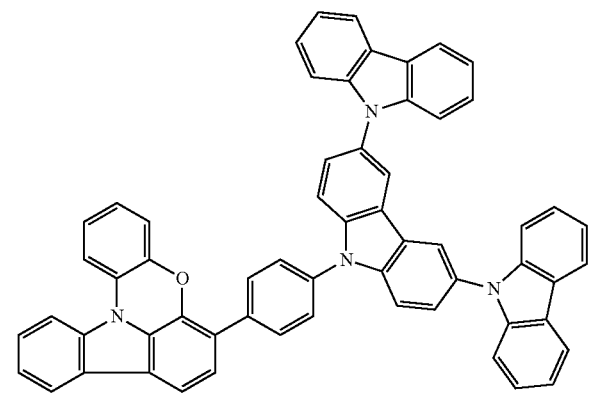
B108
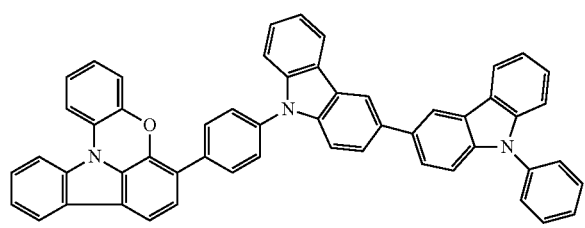
B109
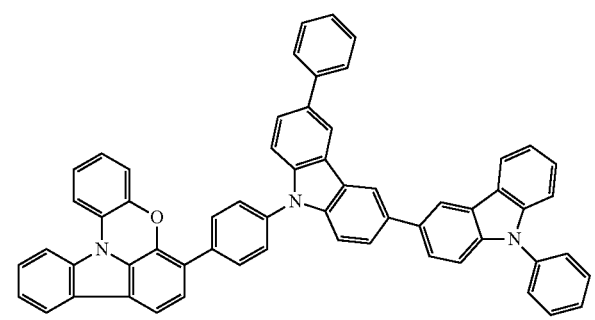
B110
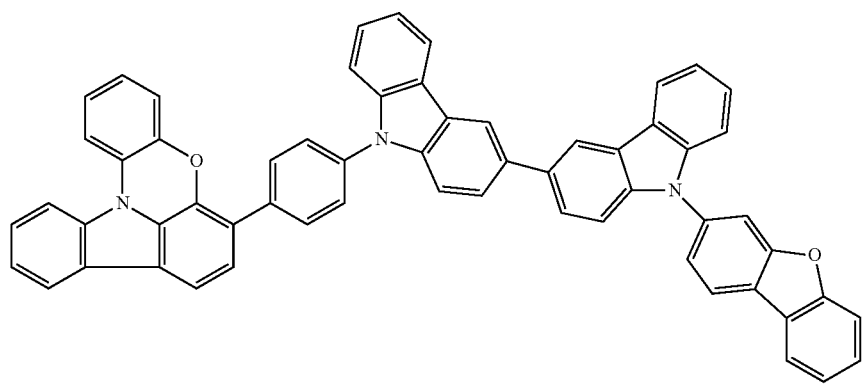

-continued
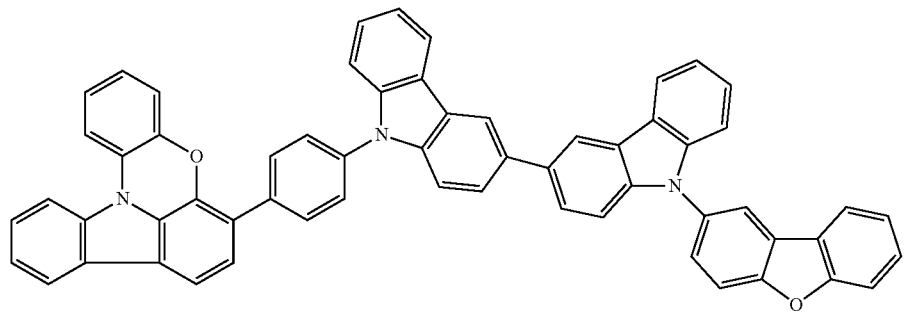
B111
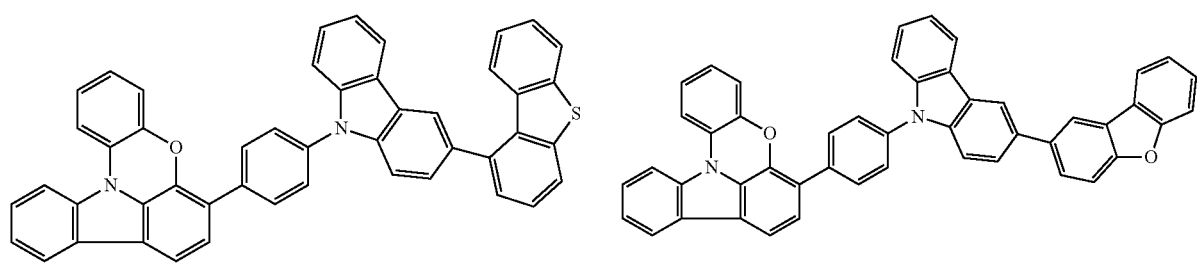
B112  B113
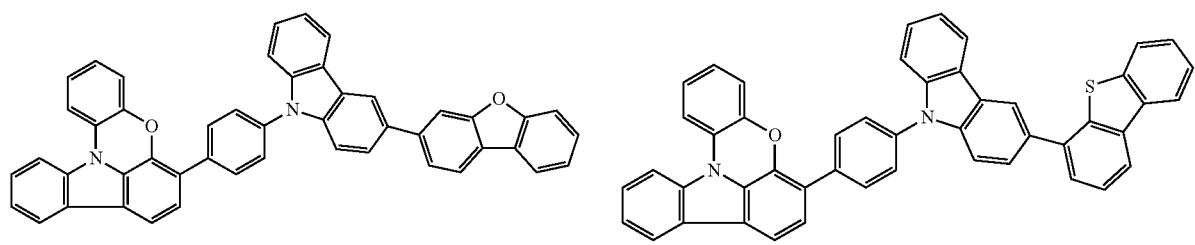
B114  B115
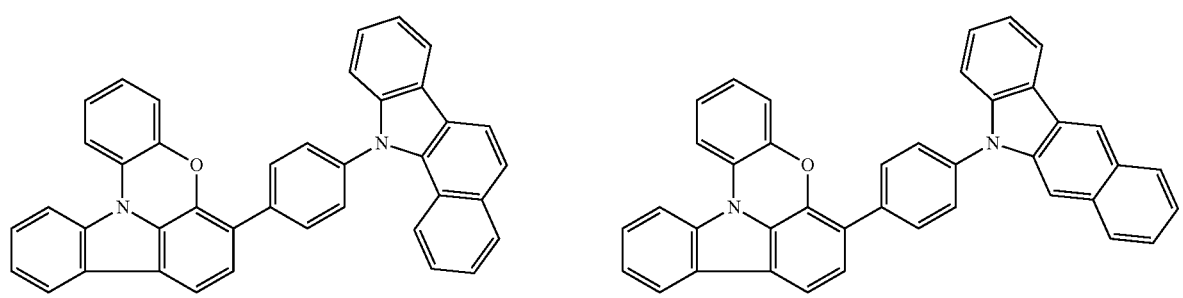
B116  B117
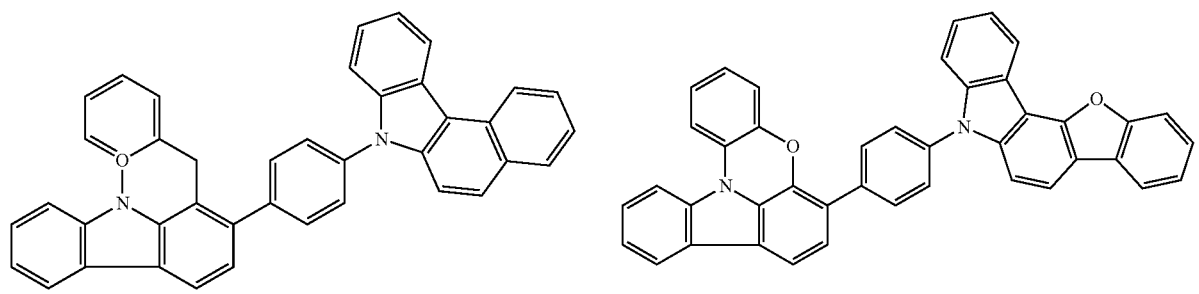
B118  B119

-continued
B120
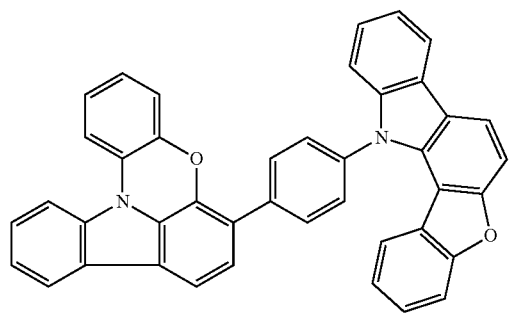
B121
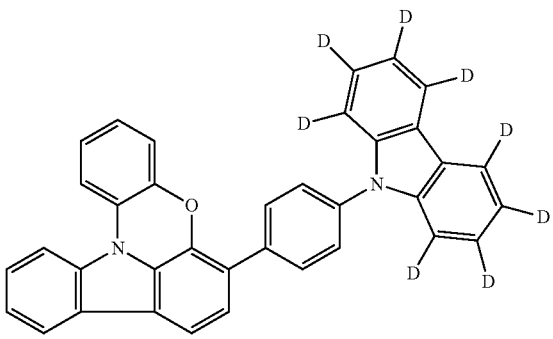
B122
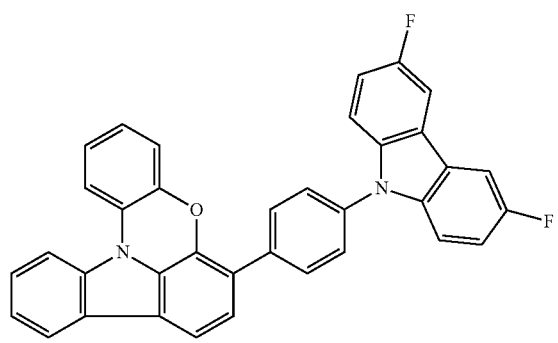
B123
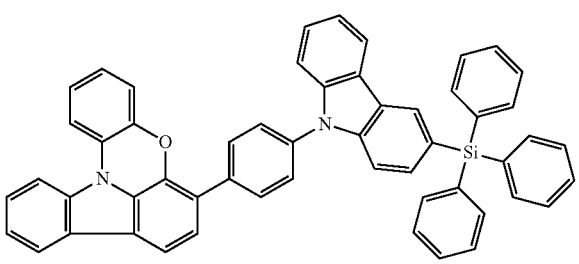
B124
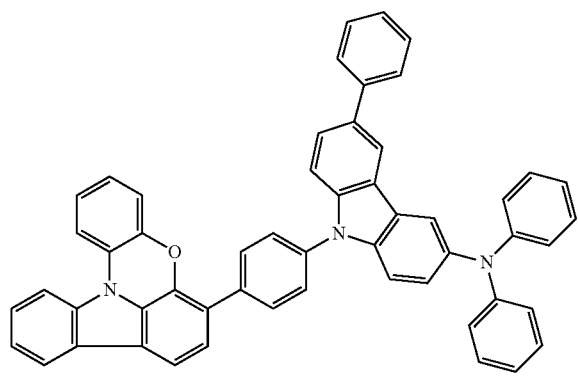
B125
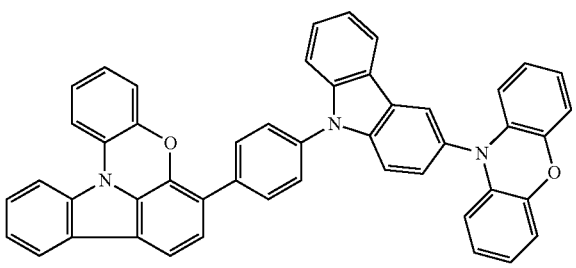
B126
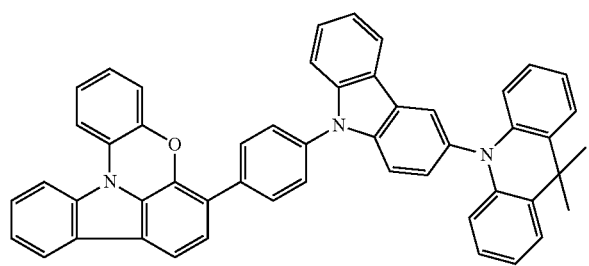
B127
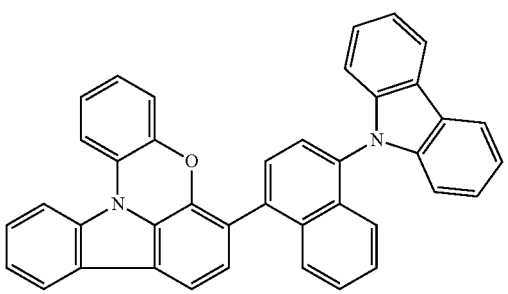

-continued
B128
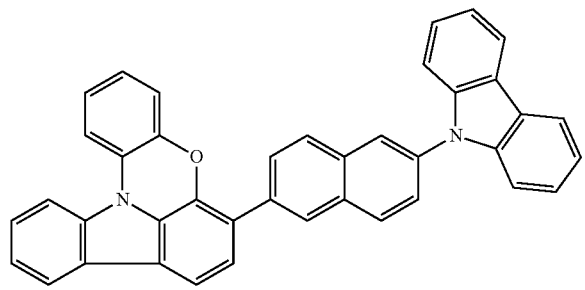
B129
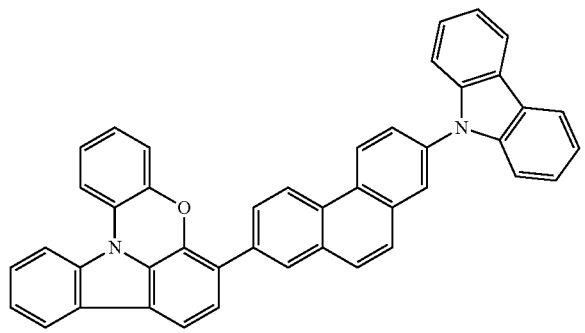
B130
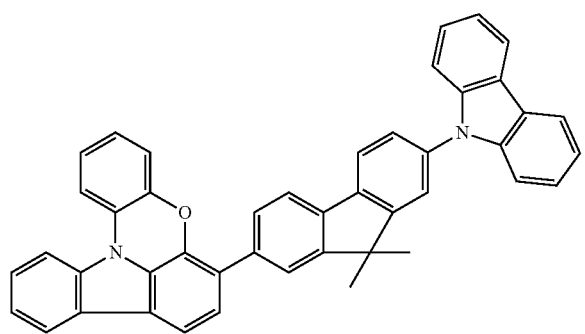
B131
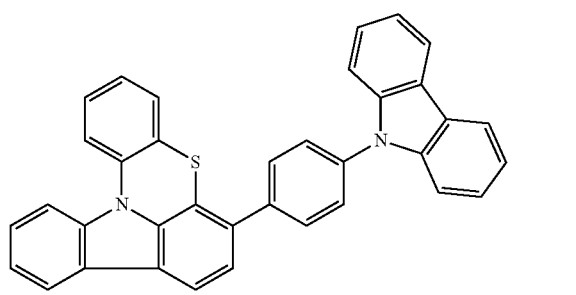
B132
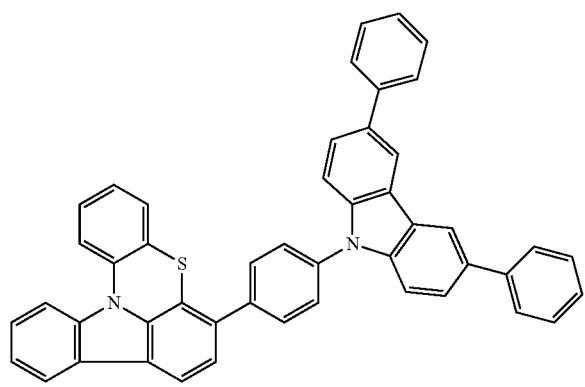
B133
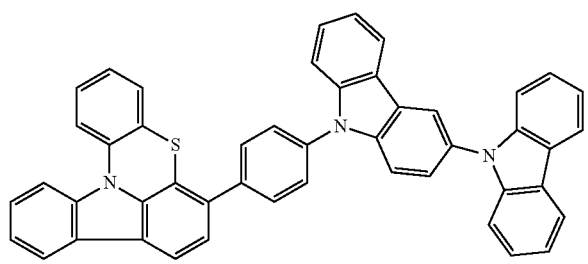
B134
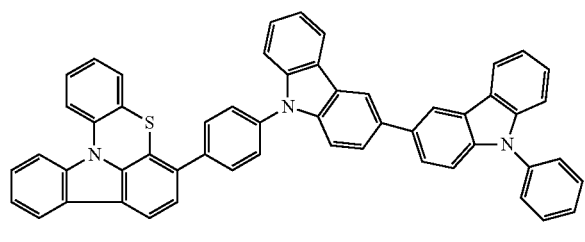
B135
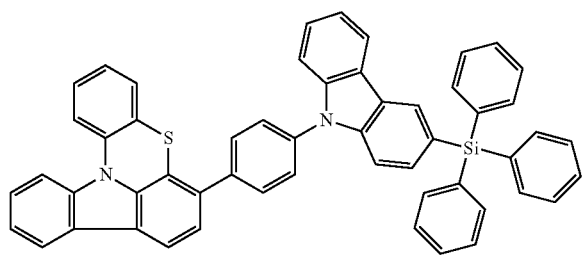

-continued
B136
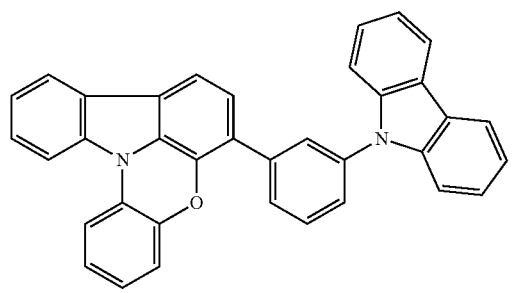
B137
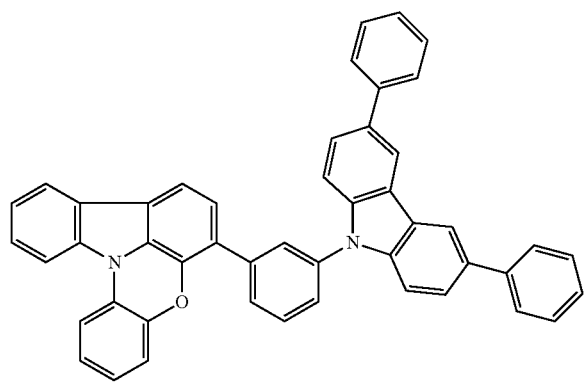
B138
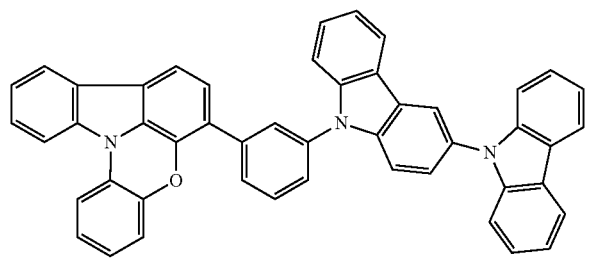
B139
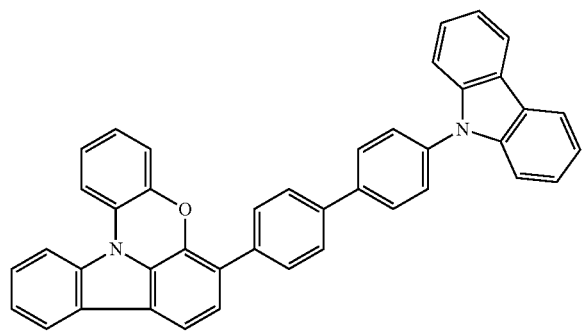
B140
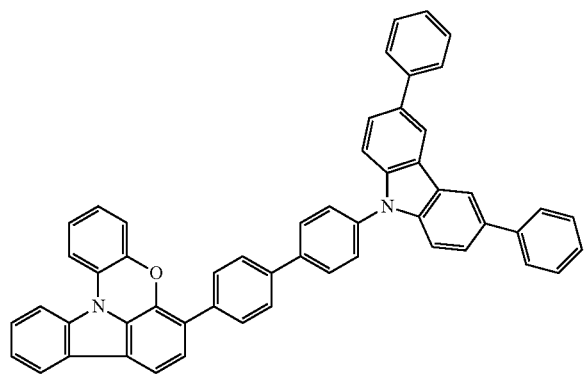
B141
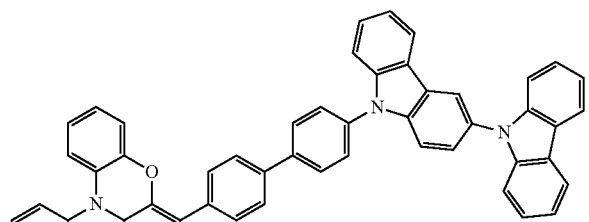
B142
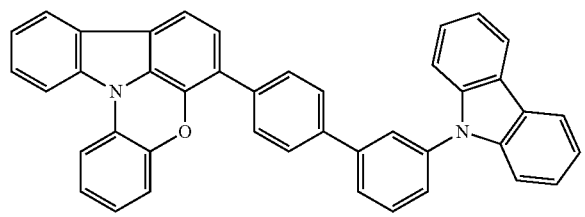
B143
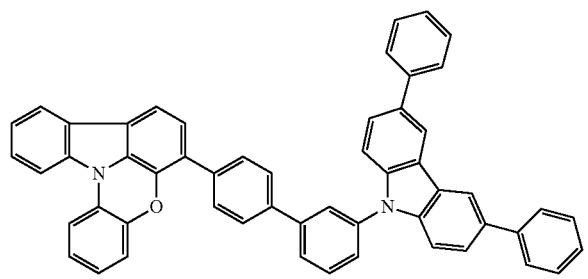

-continued
B144 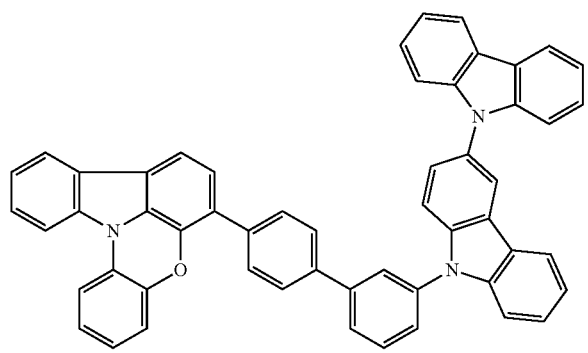
B145 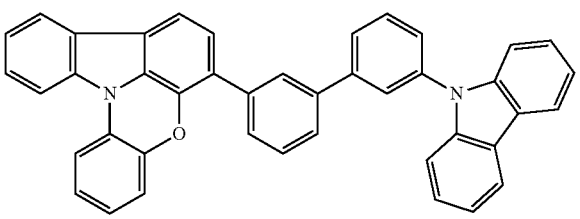
B146 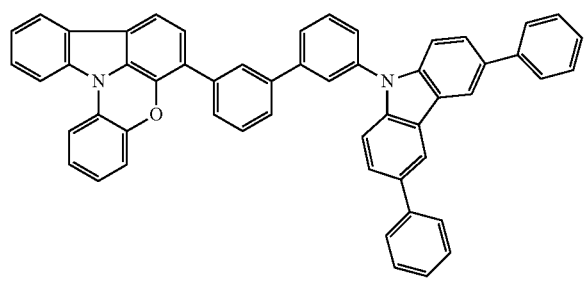
B147 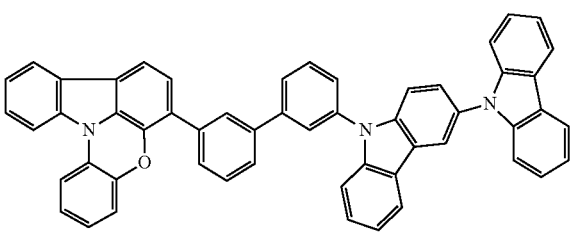
B148 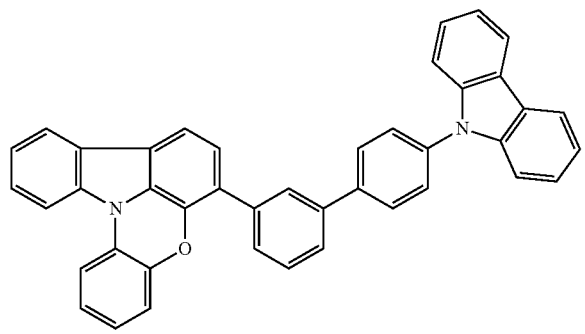
B149 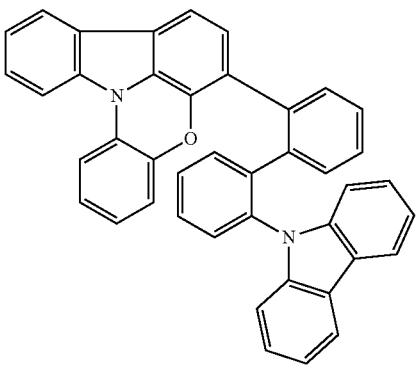
B150 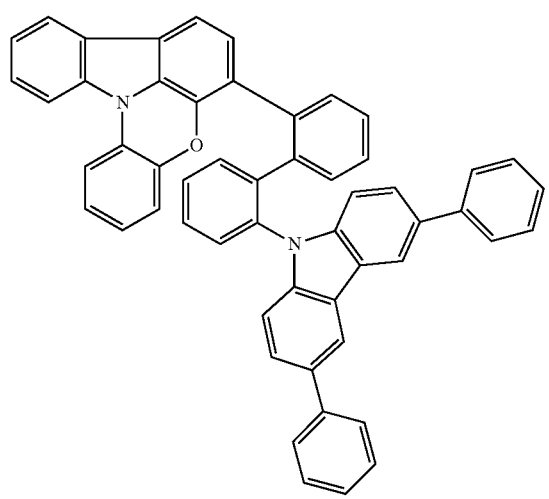

-continued
[Compound Group 1C]
C1
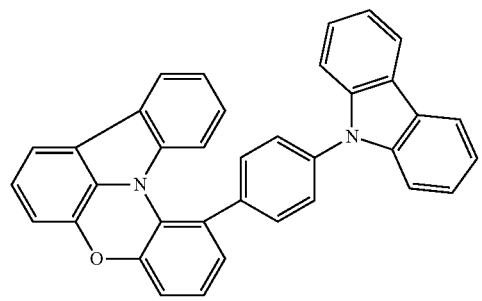
C2
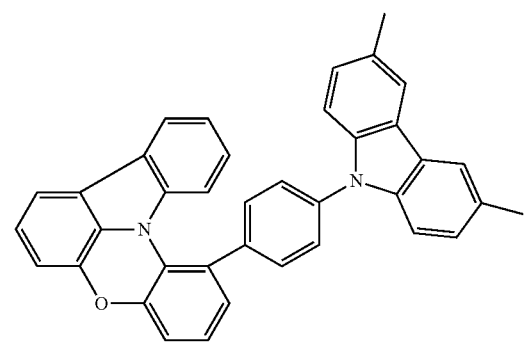
C3
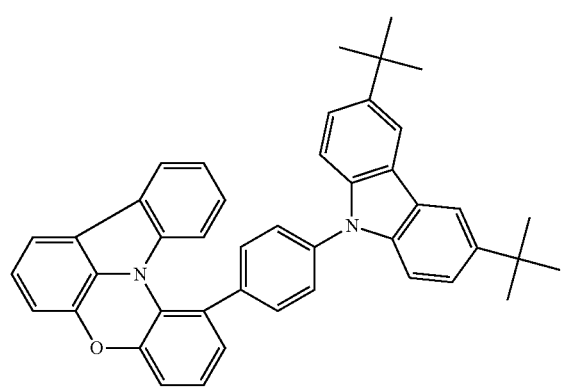
C4
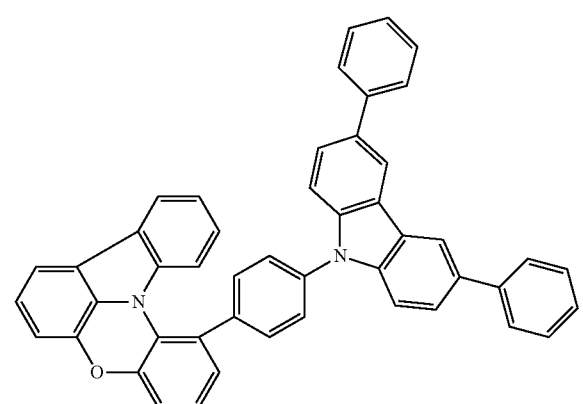
C5
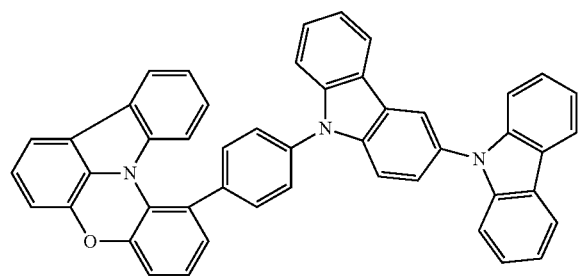
C6
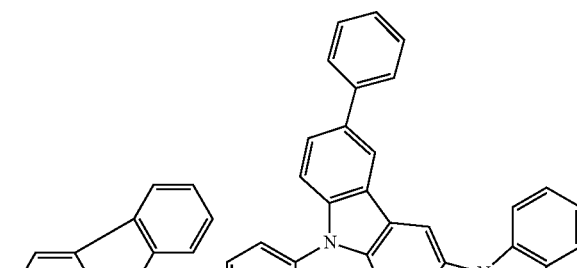
C7
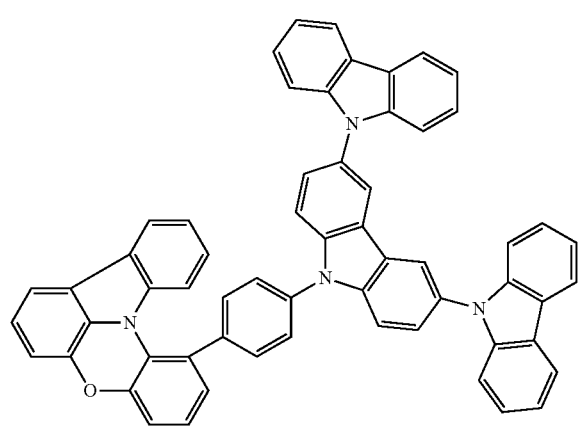
C8
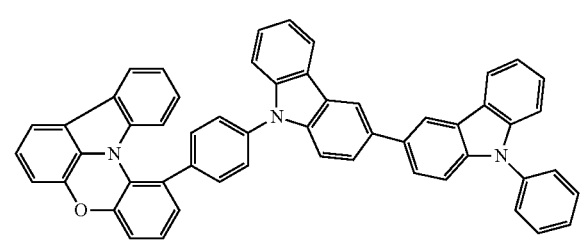

C9
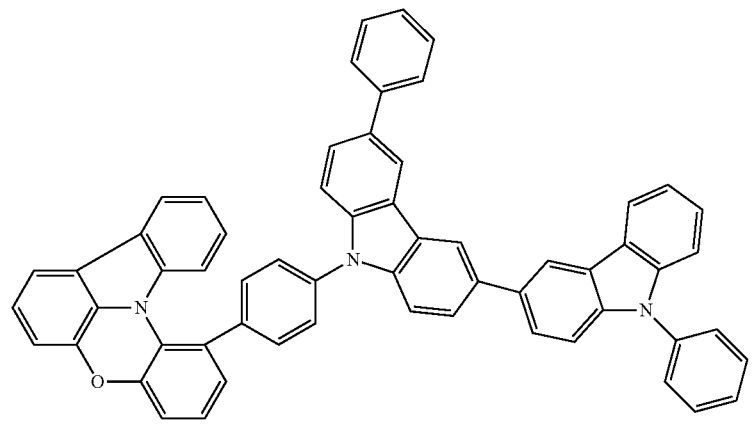
C10
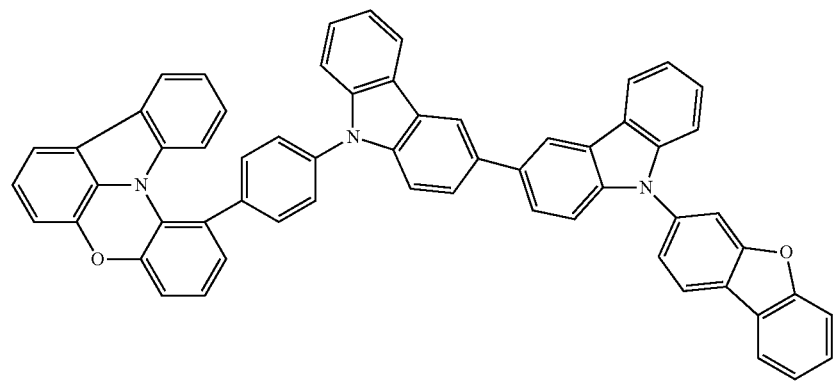
C11
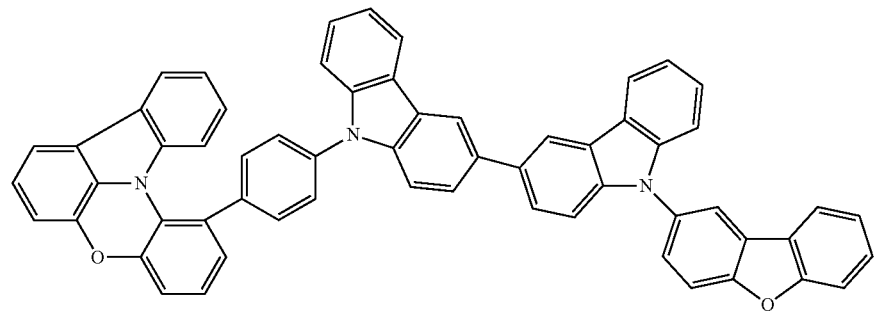
C12
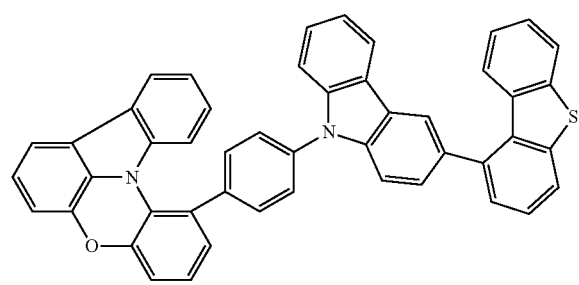
C13
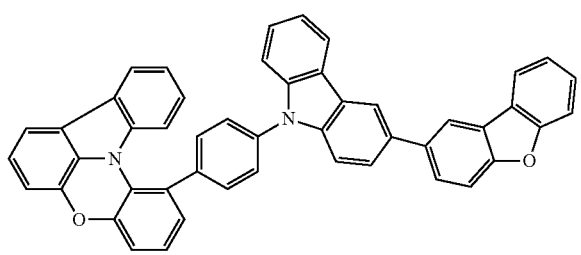

-continued
| 411 | 412 |
|---|---|
| C14 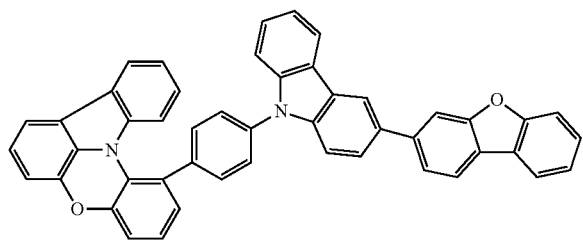 | C15 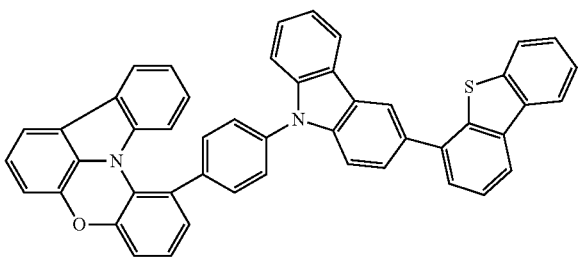 |
| C16 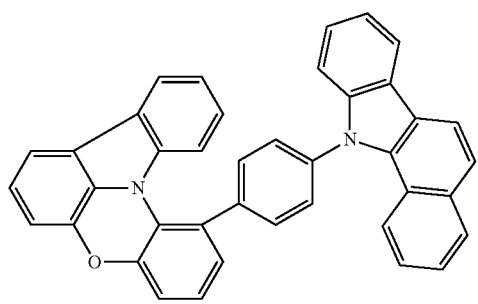 | C17 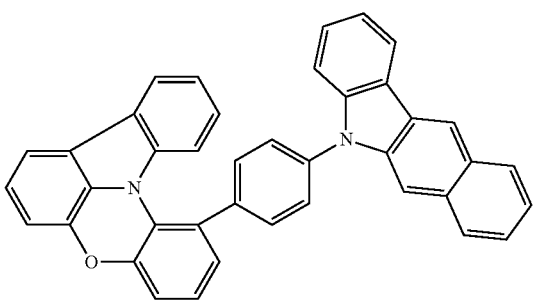 |
| C18 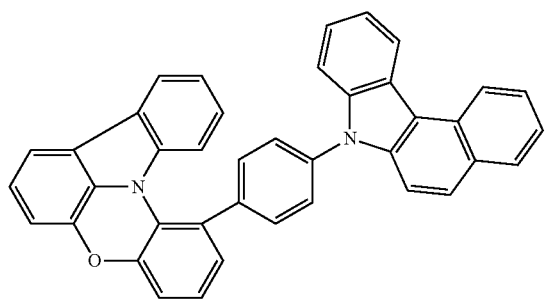 | C19 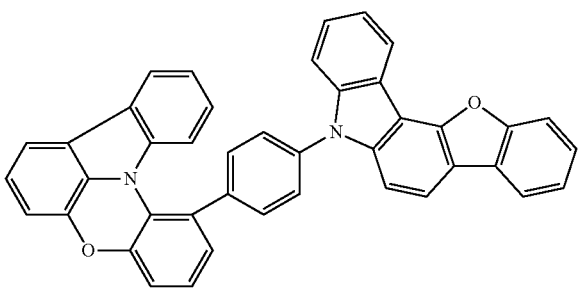 |
| C20 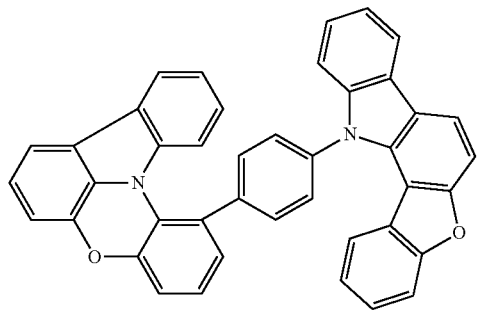 | C21 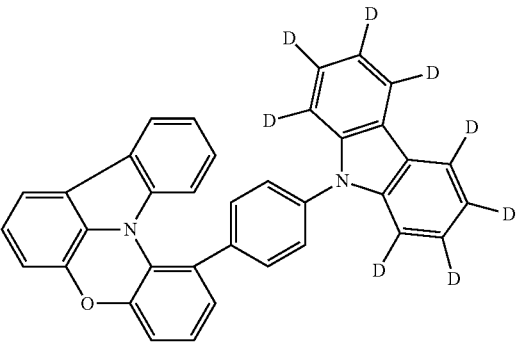 |
| C22 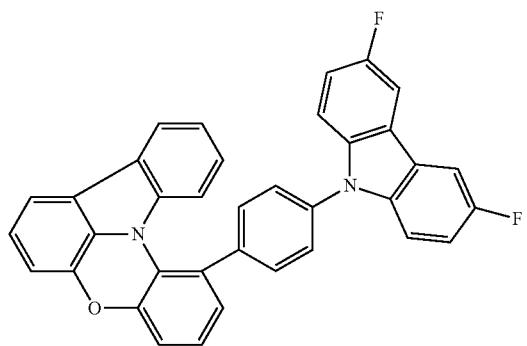 | C23 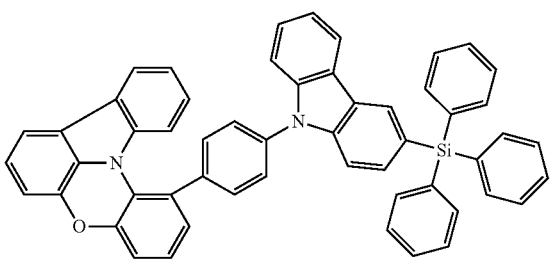 |

C24
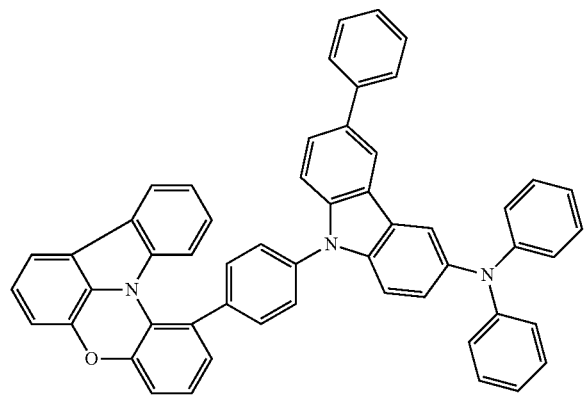
C25
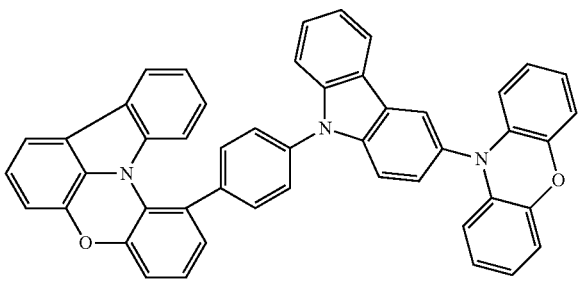
C26
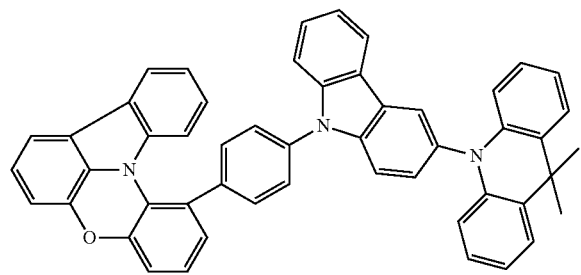
C27
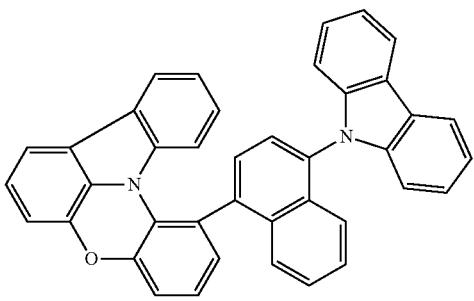
C28
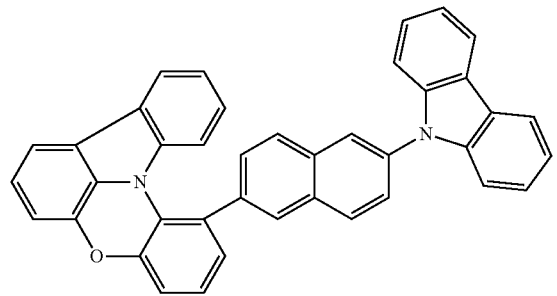
C29
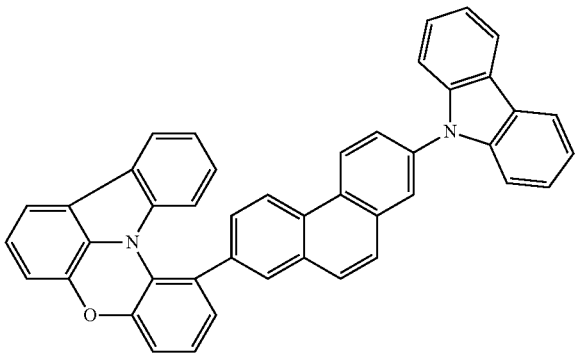
C30
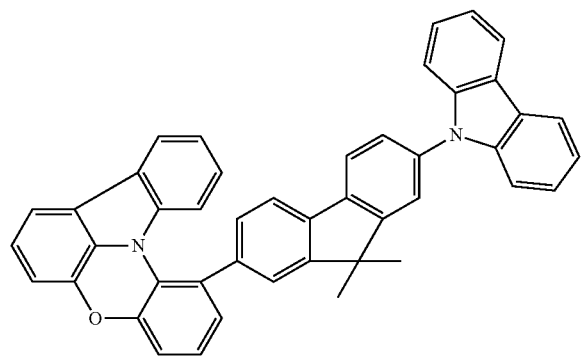
C31
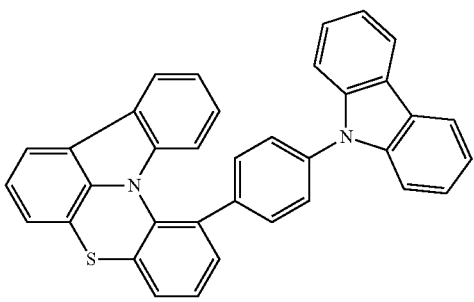

-continued
C32
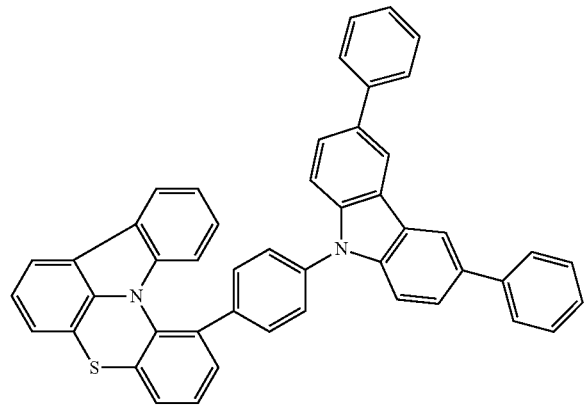
C33
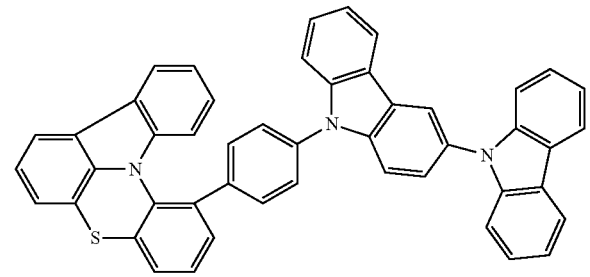
C34
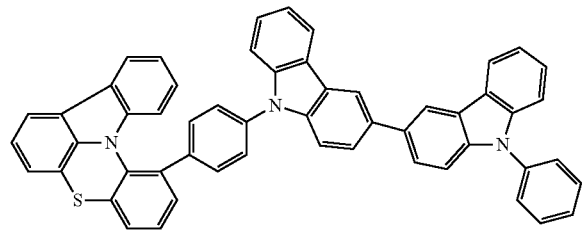
C35
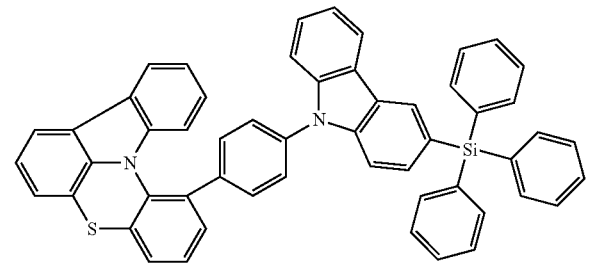
C36
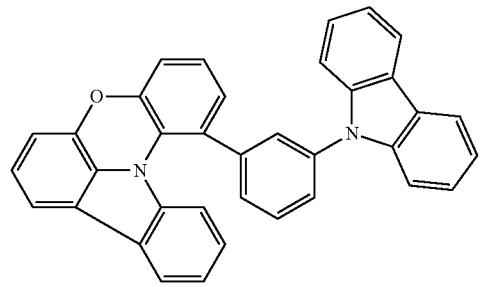
C37
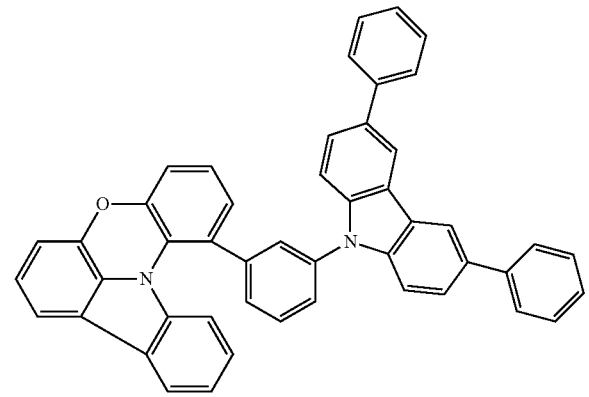
C38
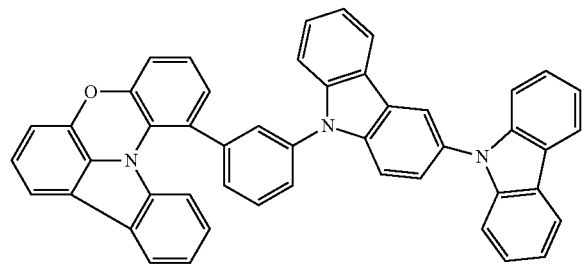
C39
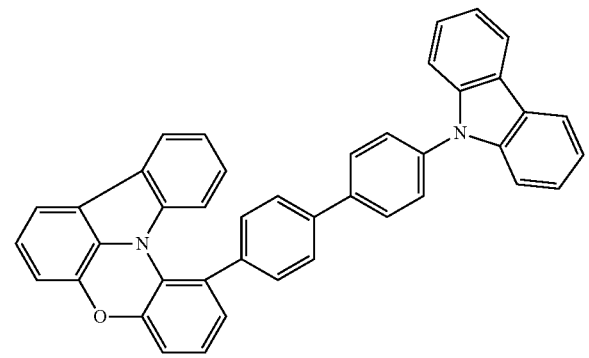

-continued
C40
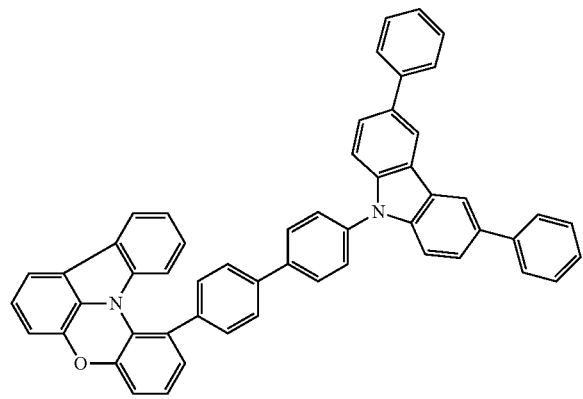
417
C41
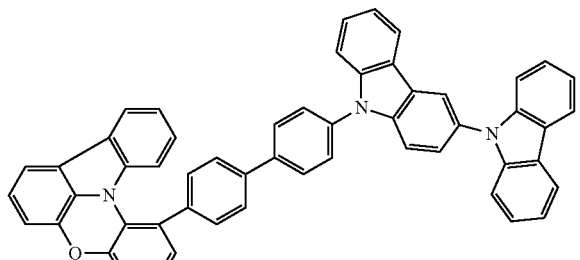
418
C42
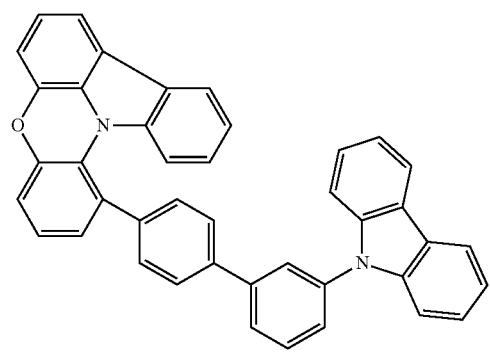
C43
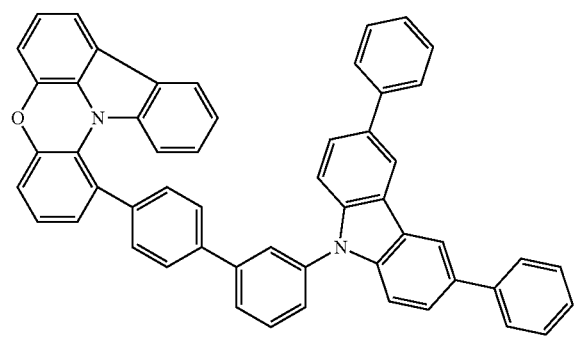
C44
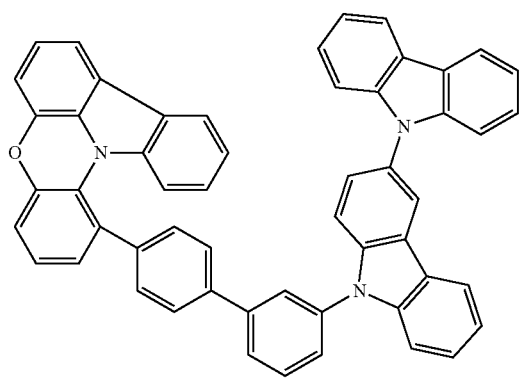

-continued
C45
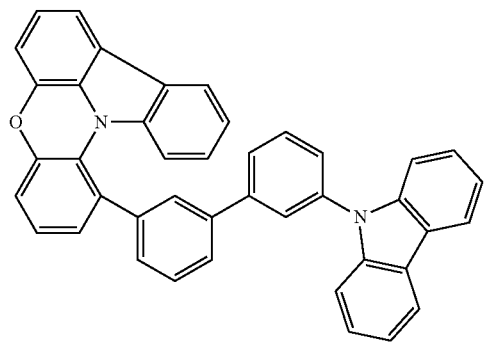
C46
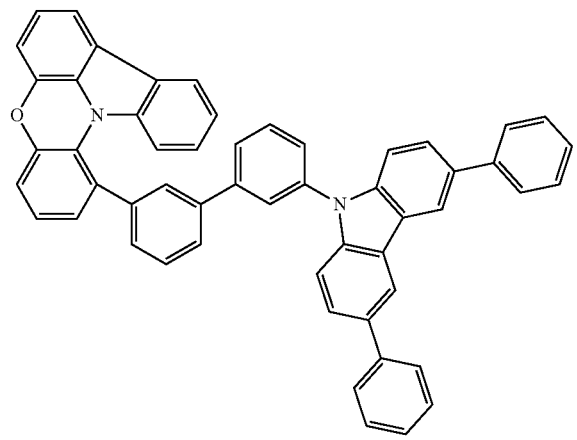
C47
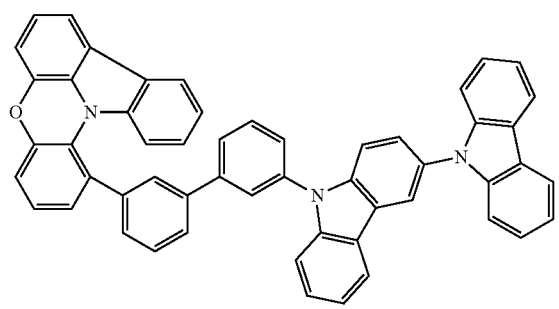
C48
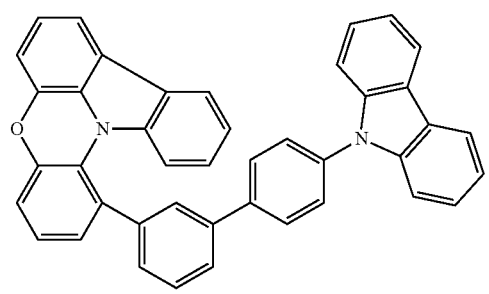
C49
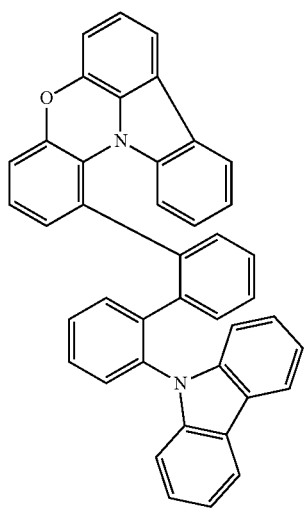
C50
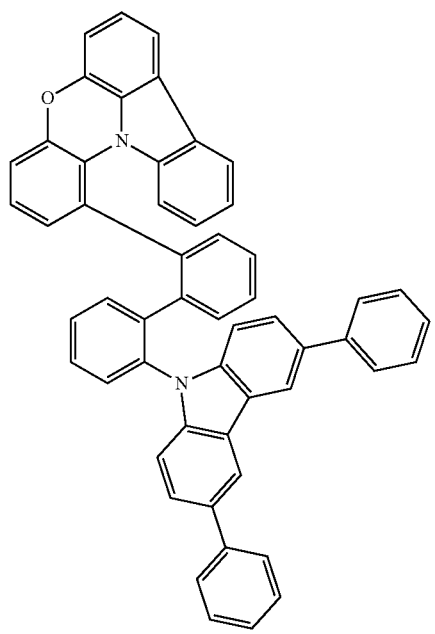

-continued
C51
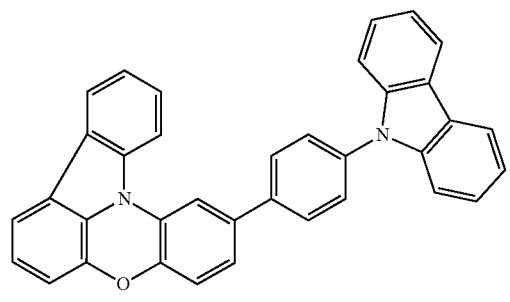
C52
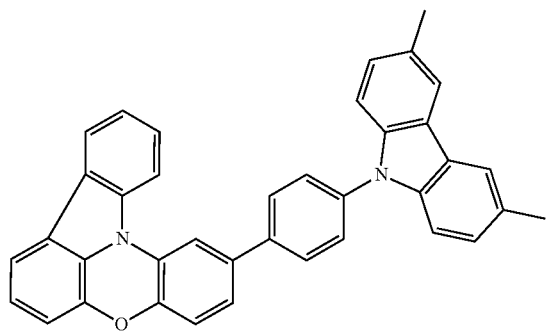
C53
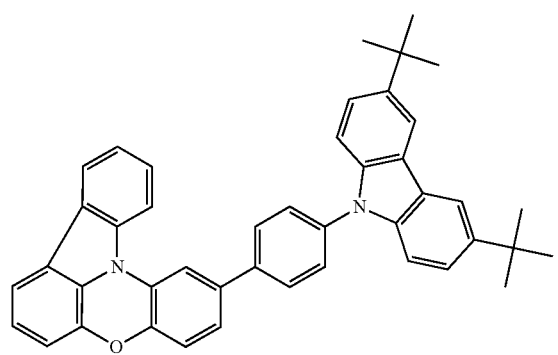
C54
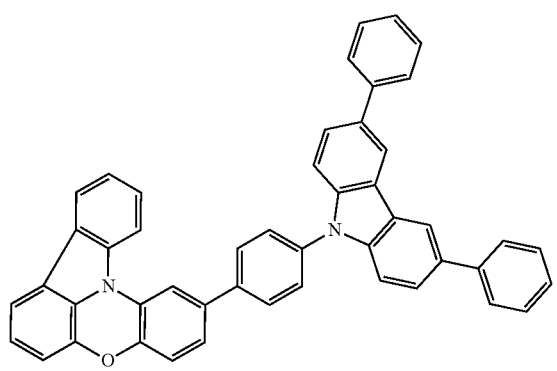
C55
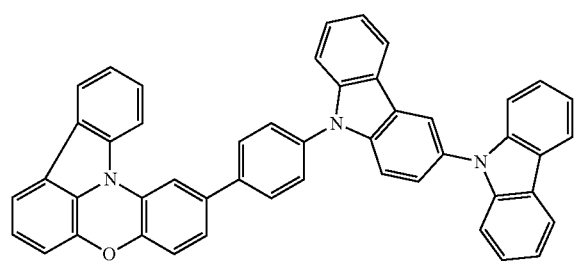
C56
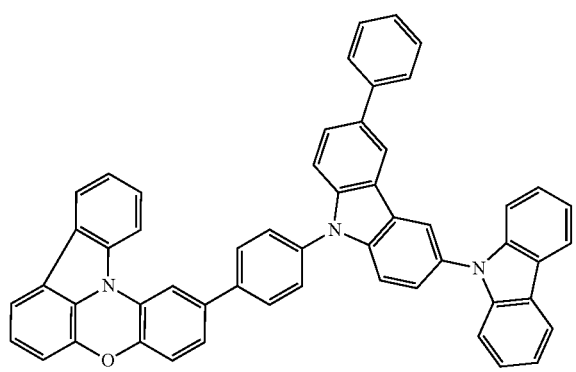
C57
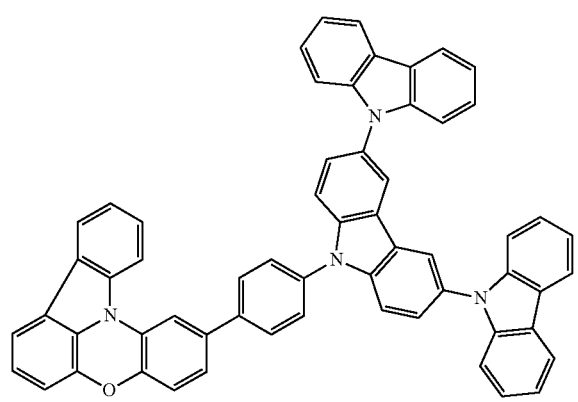
C58
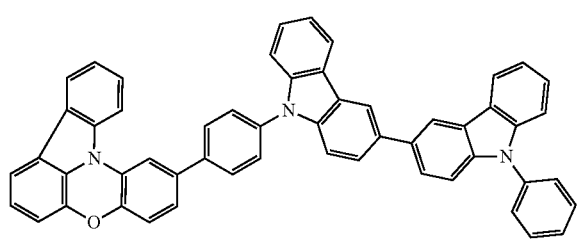

-continued
C59
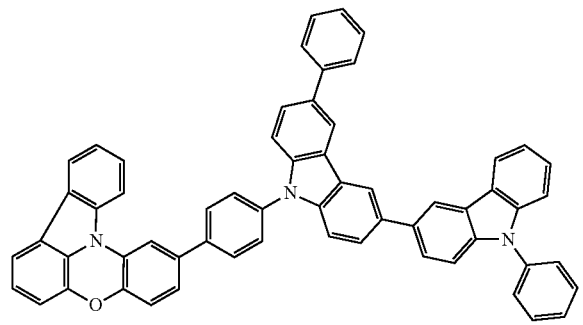
C60
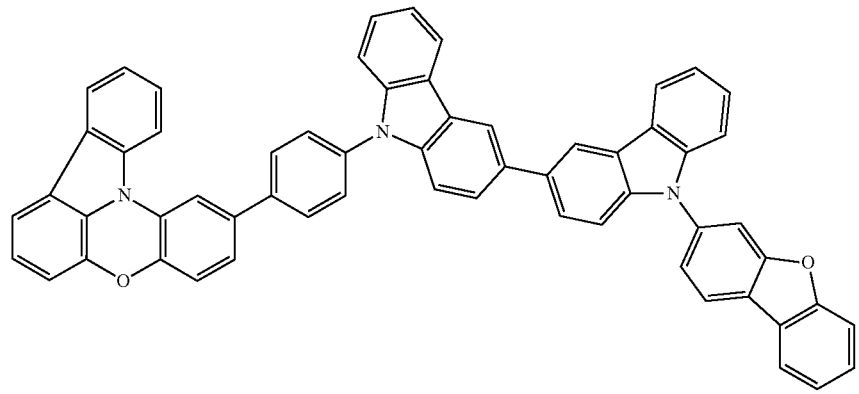
C61
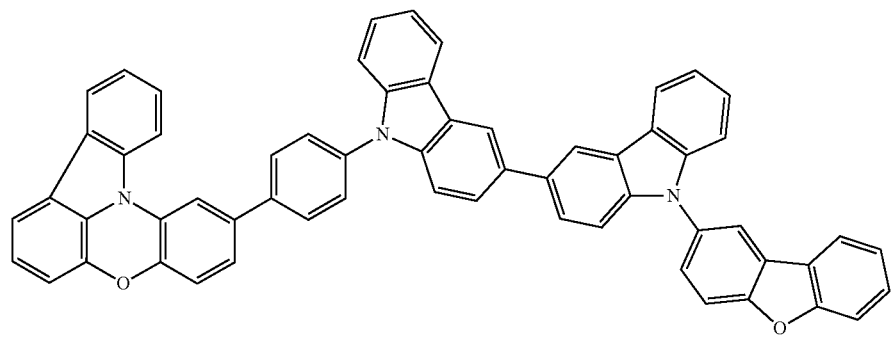
C62
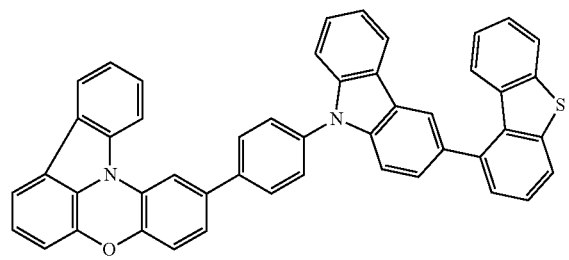
C63
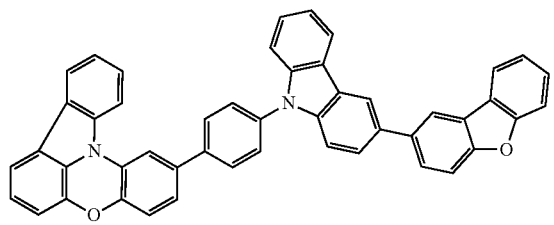
C64
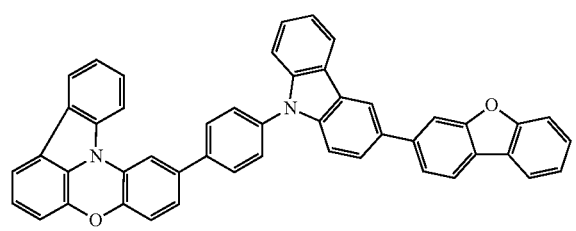
C65
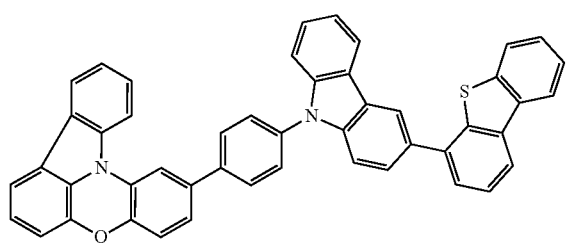

-continued
C66
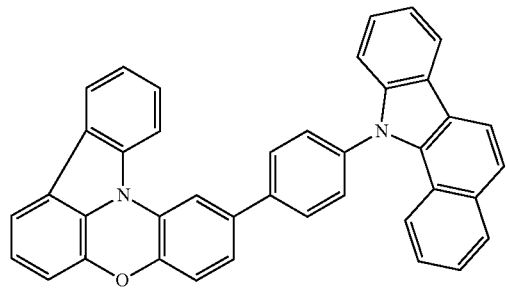
C64
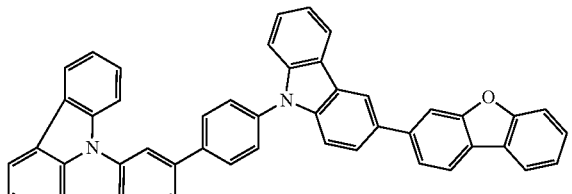
C65
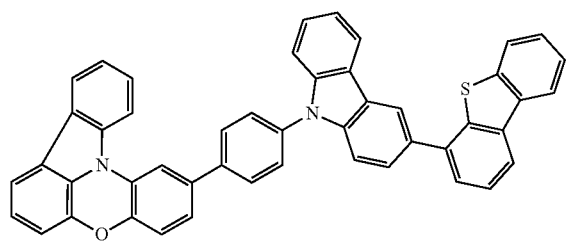
C66
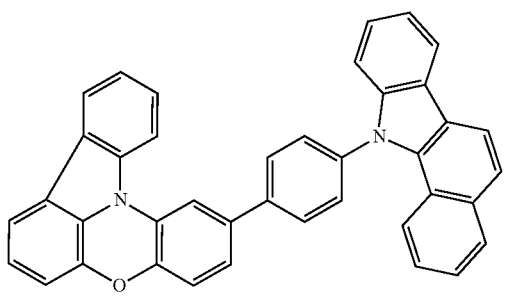
C67
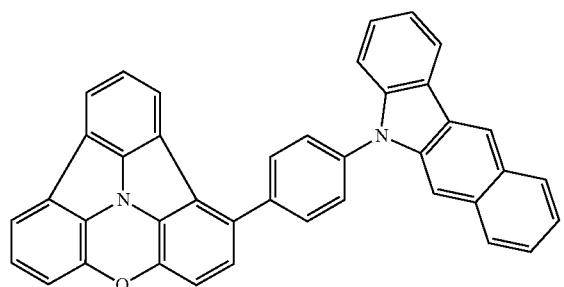
C68
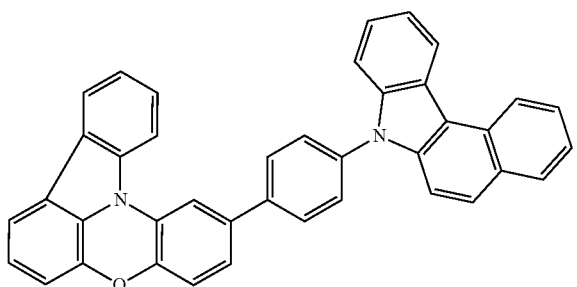
C69
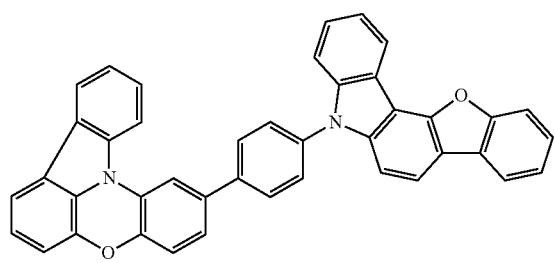
C70
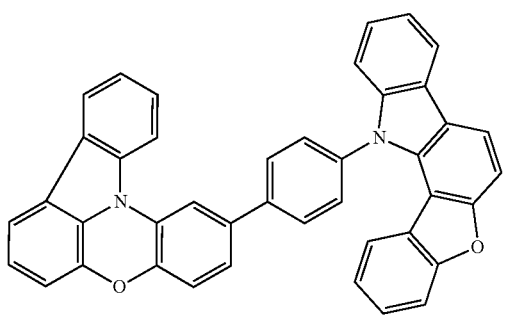
C71
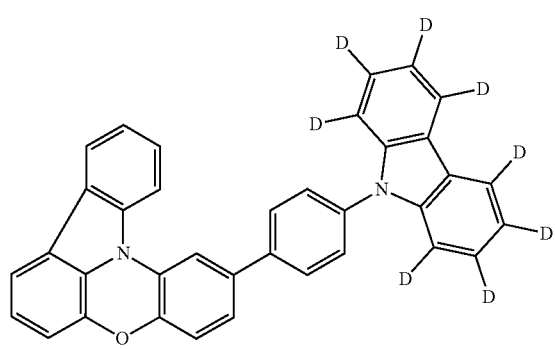
C72
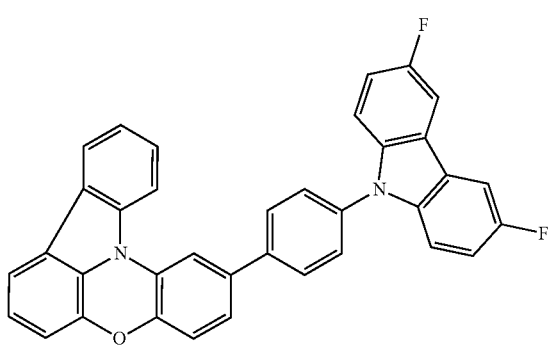

-continued
C73
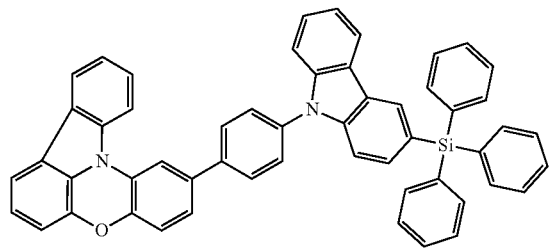
C74
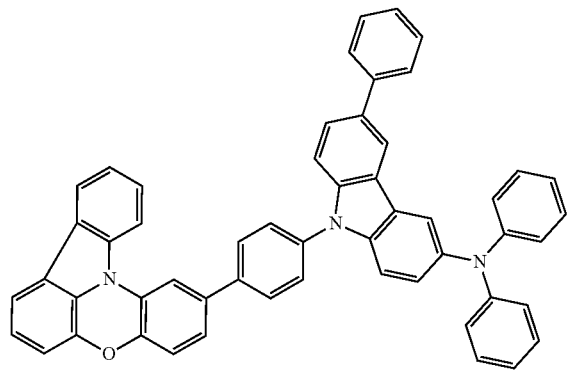
C75
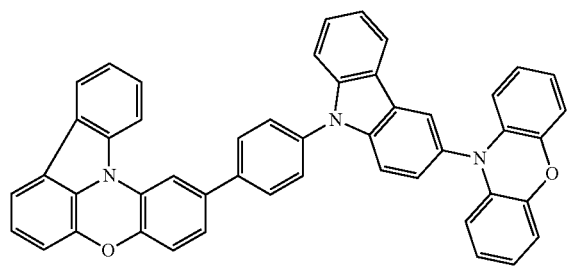
C76
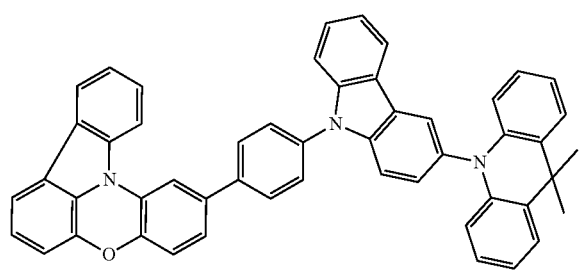
C77
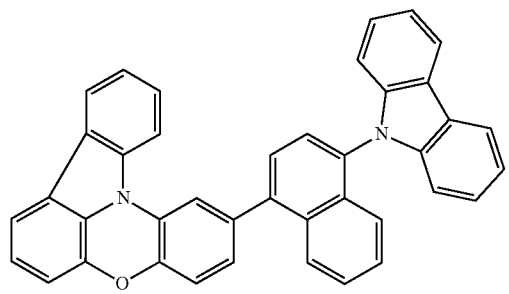
C78
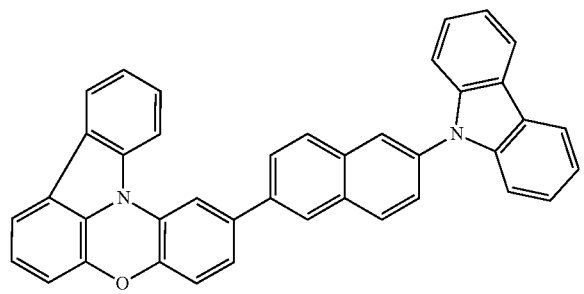
C79
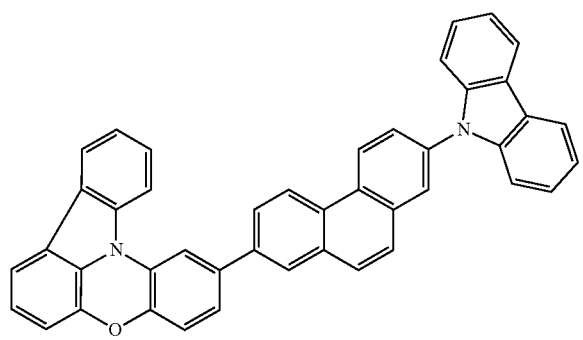
C80
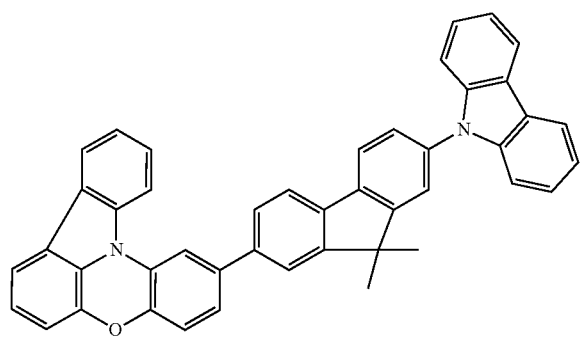

-continued
C81
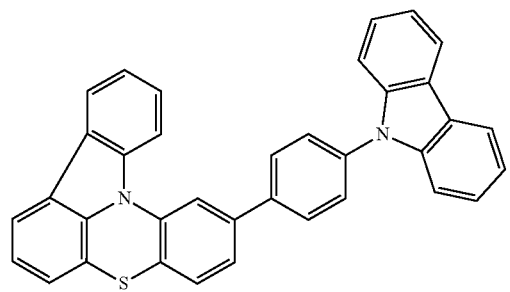
C82
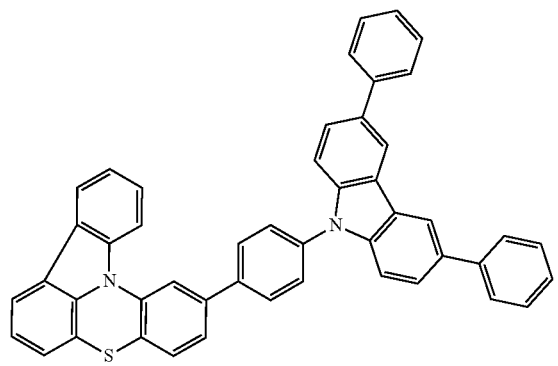
C83
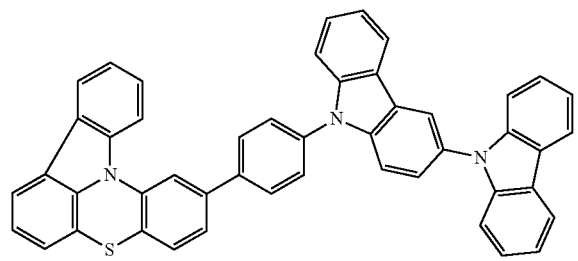
C84
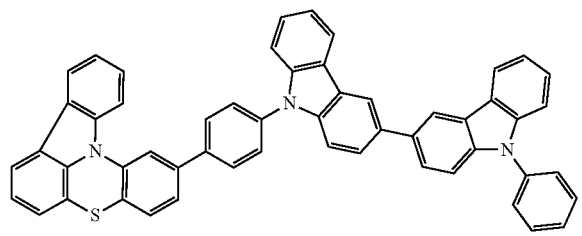
C85
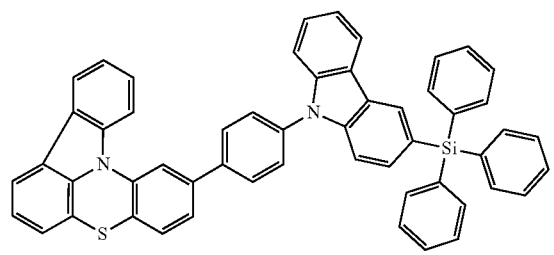
C86
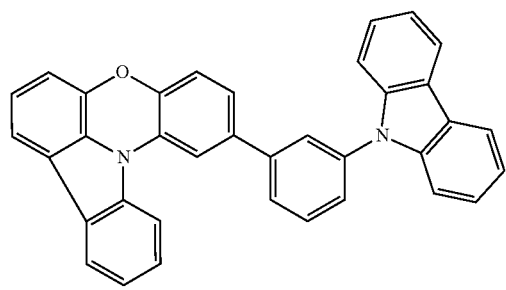
C87
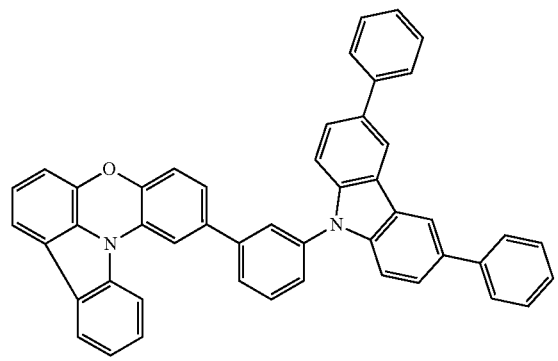
C88
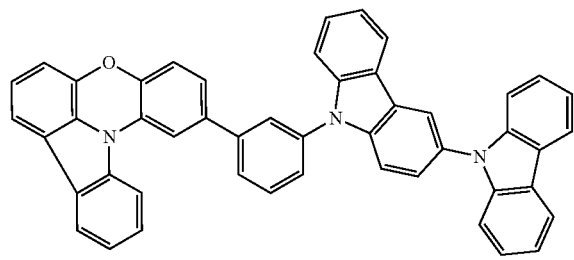

-continued
C89
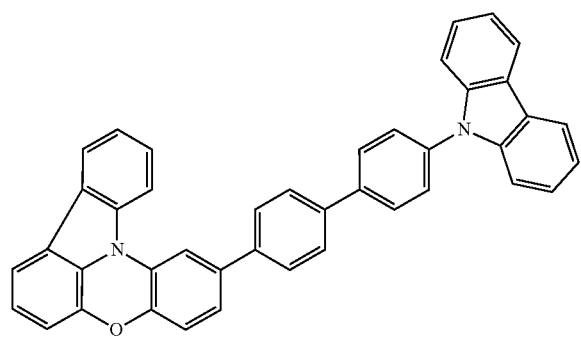
C90
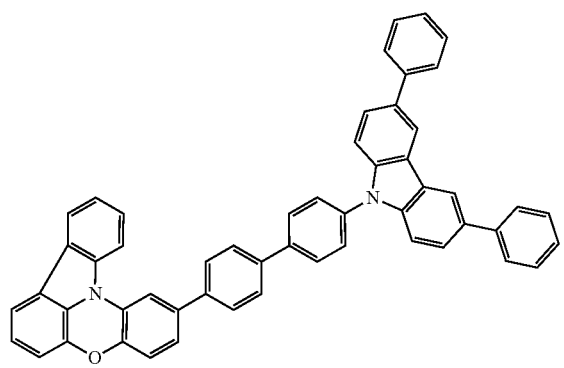
C91
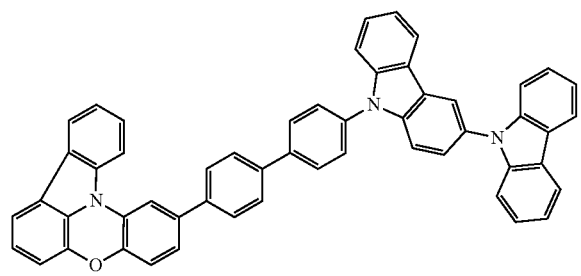
C92
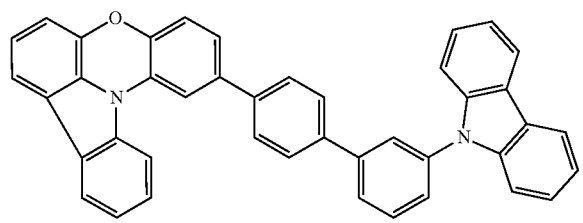
C93
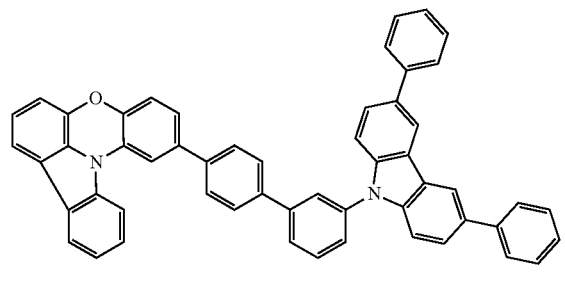
C94
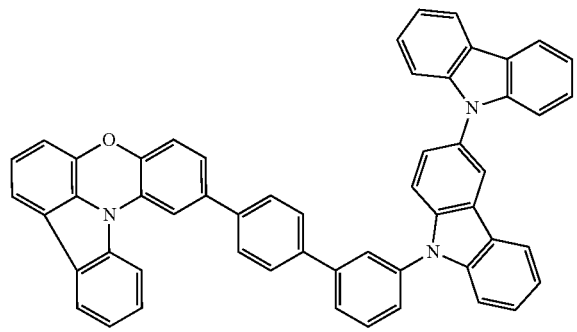
C95
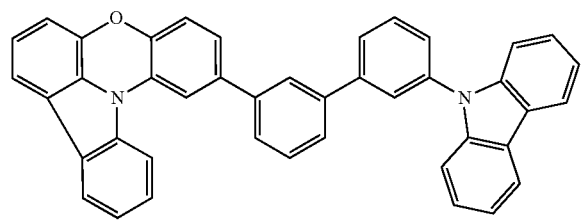
C96
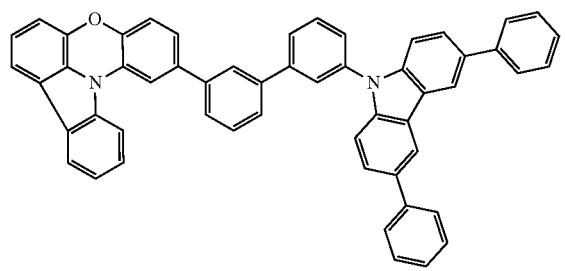

-continued
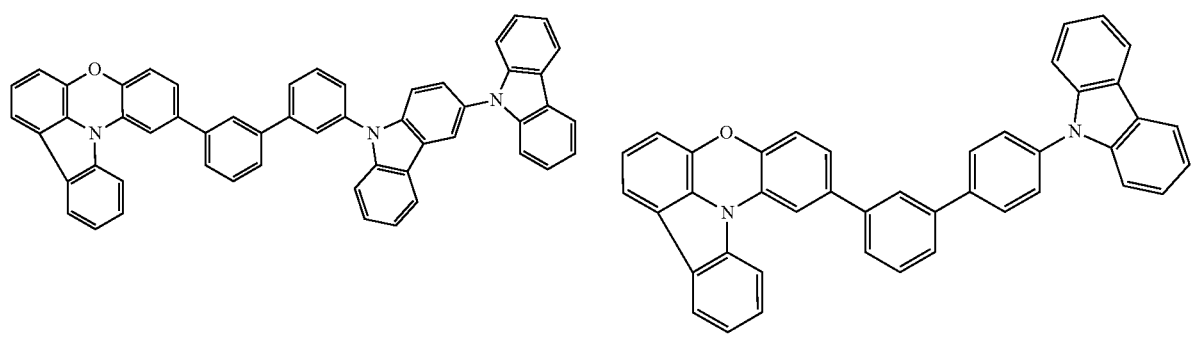
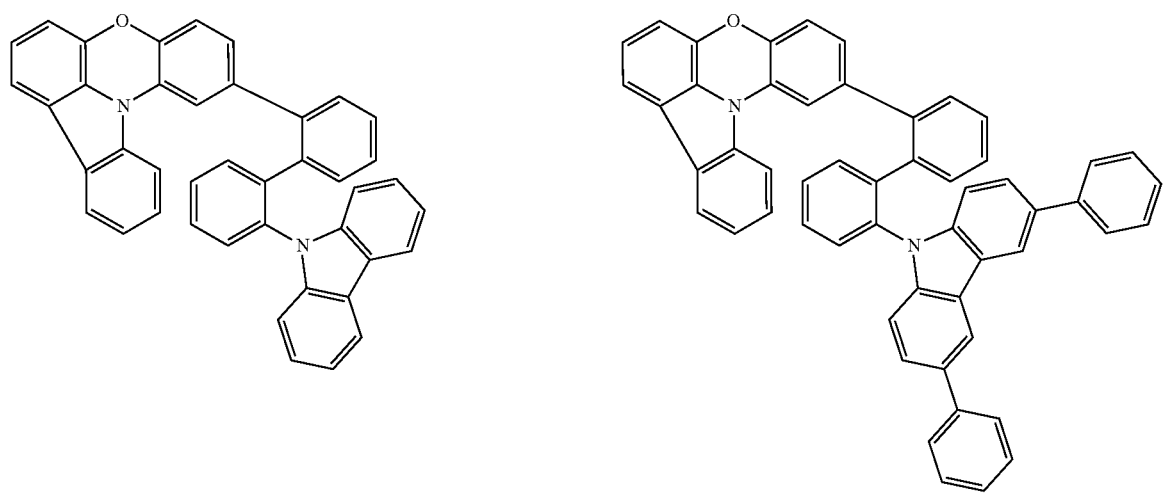
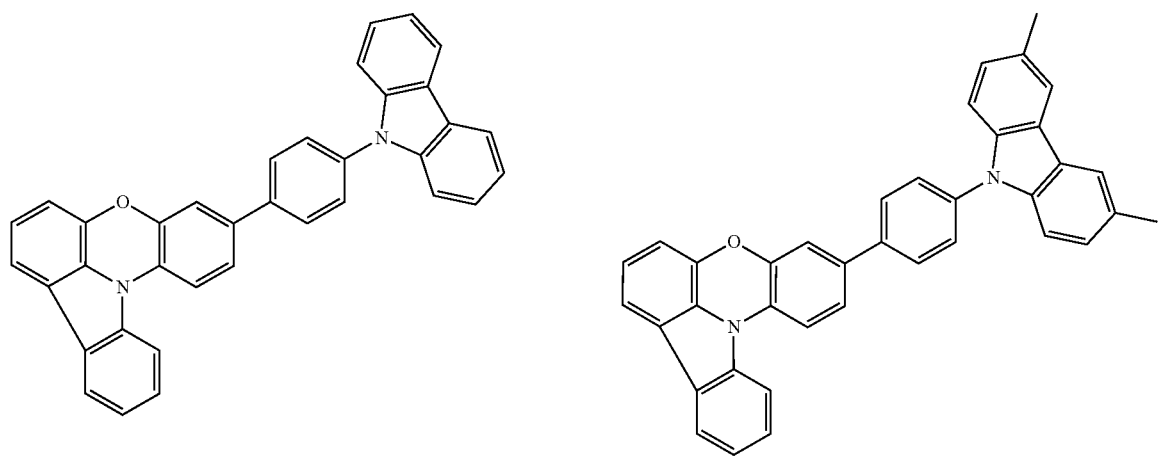

-continued
C103
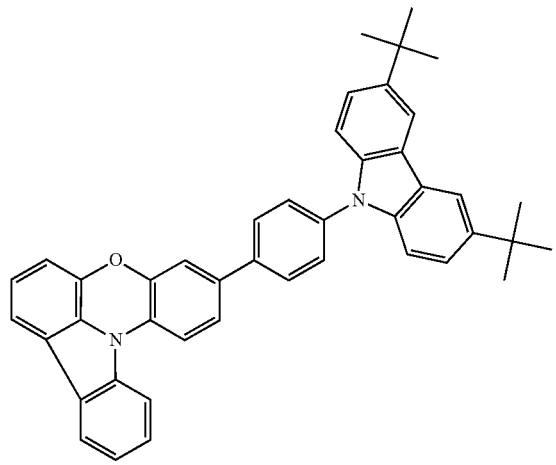
C104
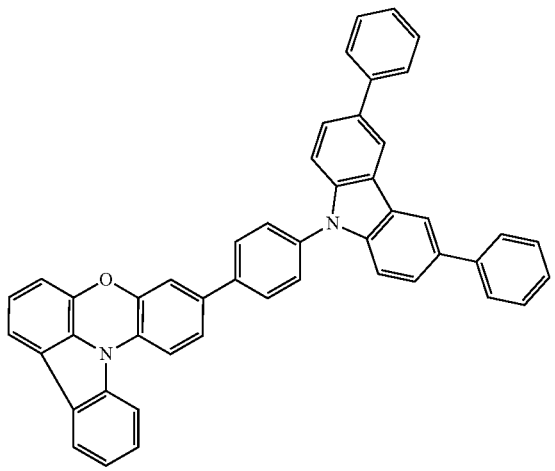
C105
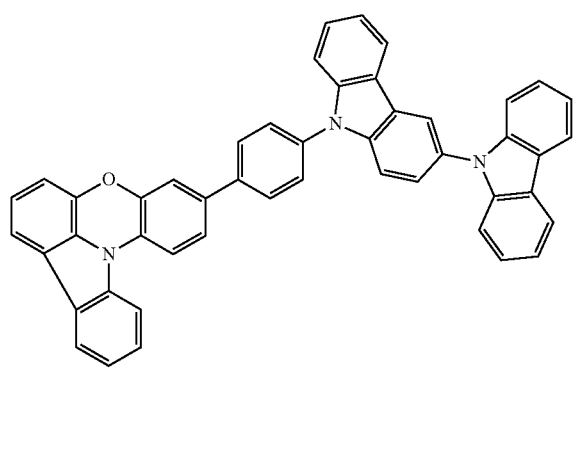
C106
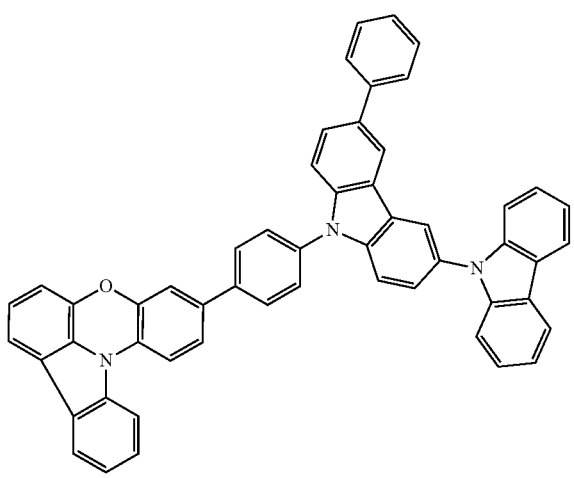
C107
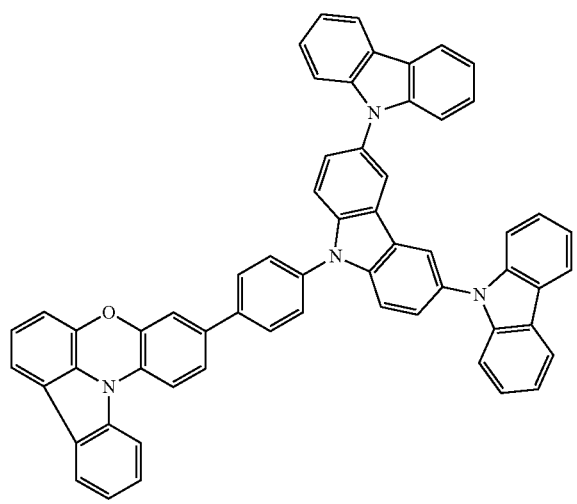
C108
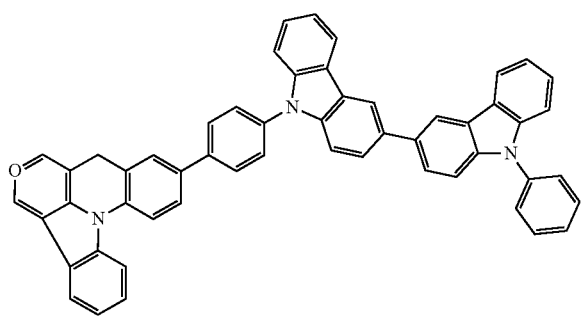

-continued
C109
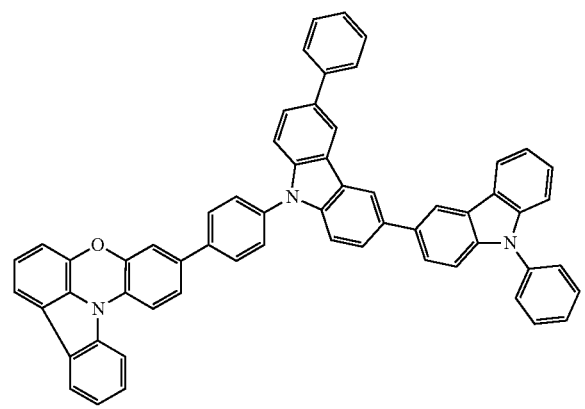
C110
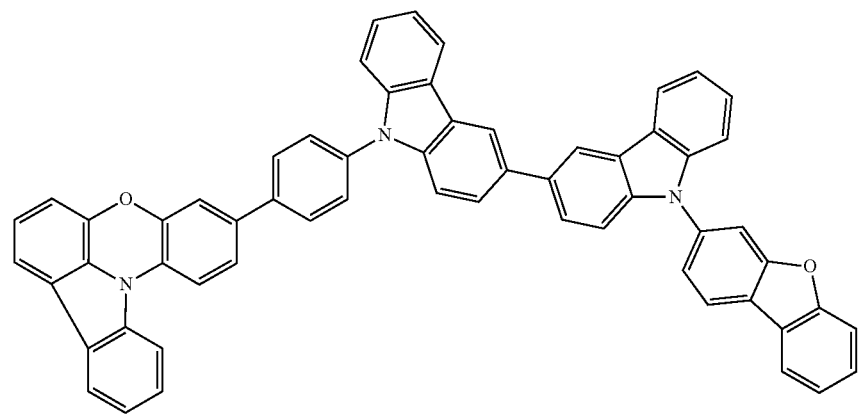
C111
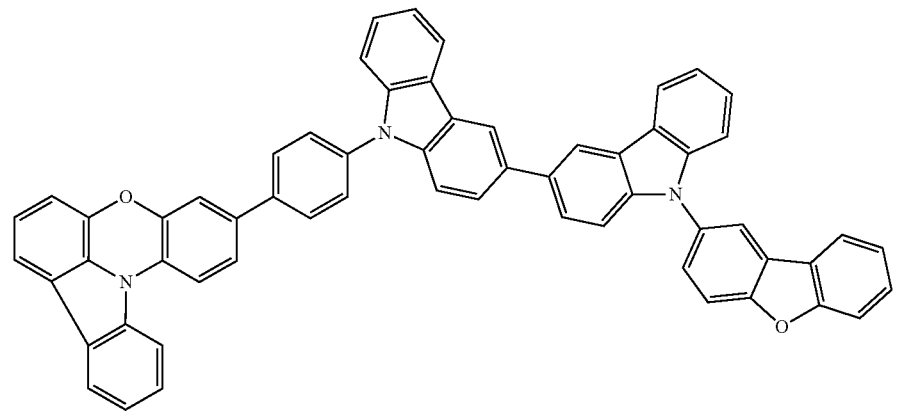
C112 C113
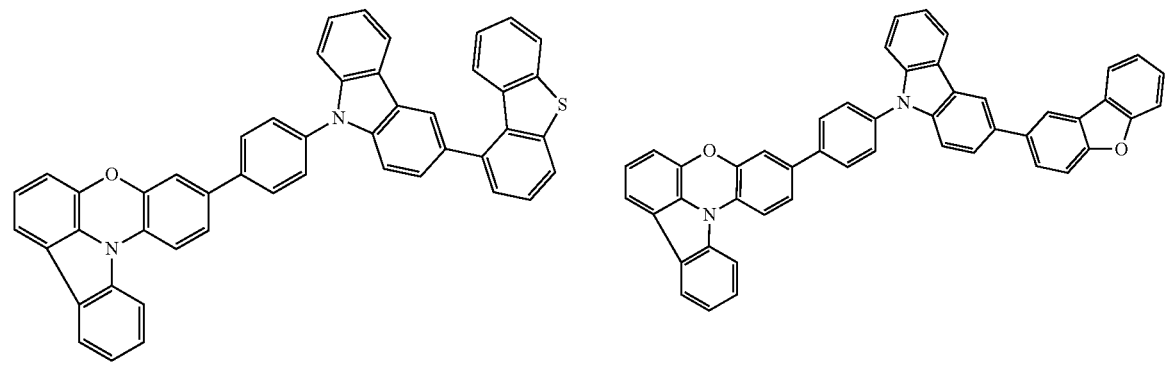

-continued
C114
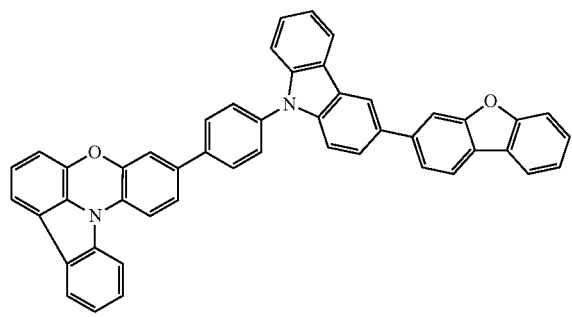
C115
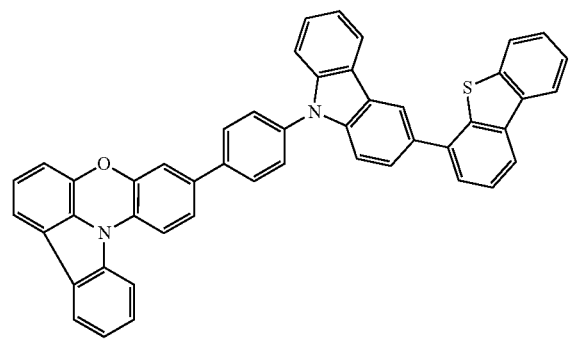
C116
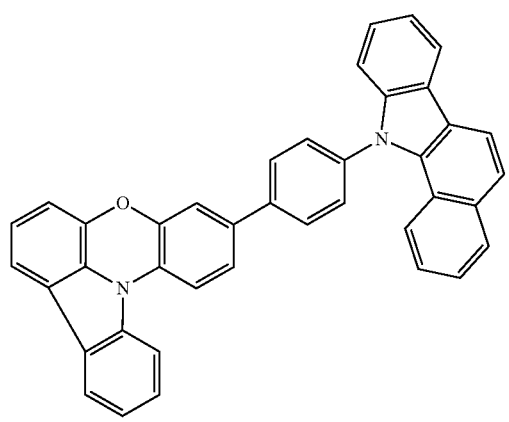
C117
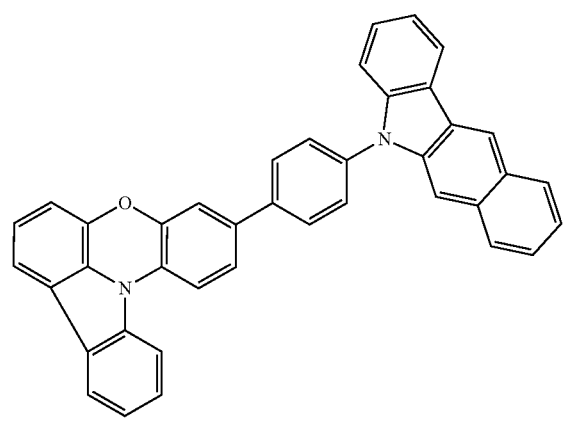
C118
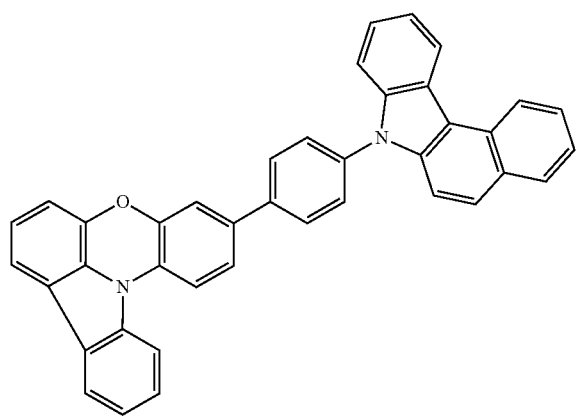
C119
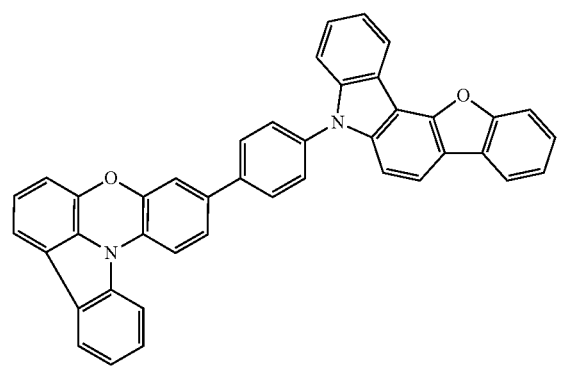

-continued
441 442
C120
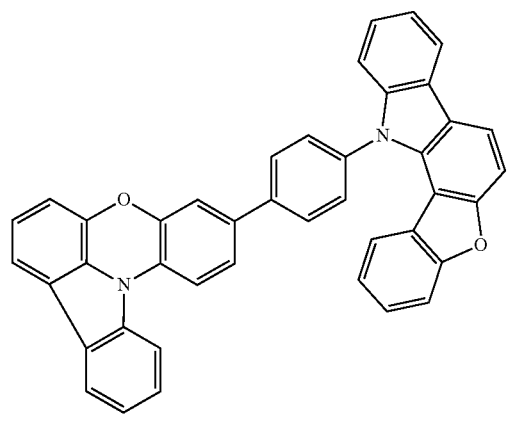
C121
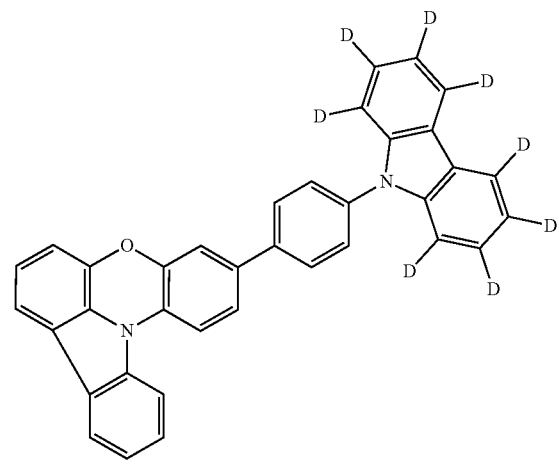
C122
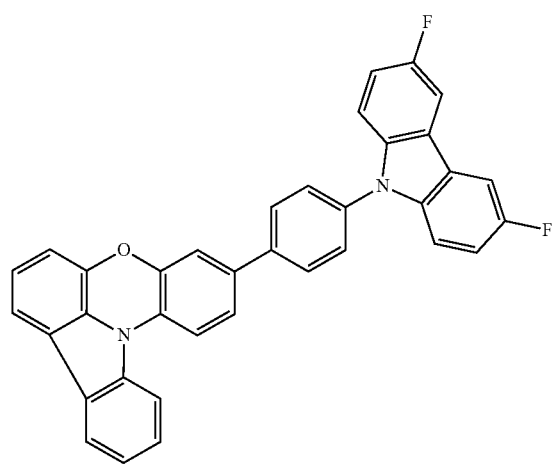
C123
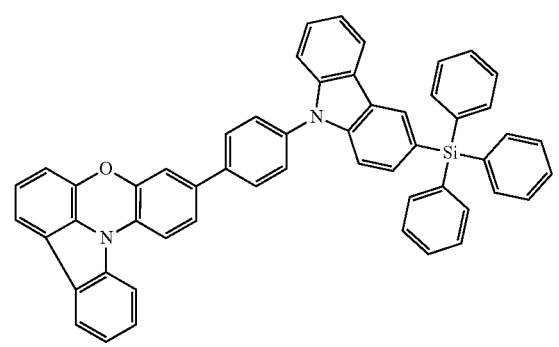
C124
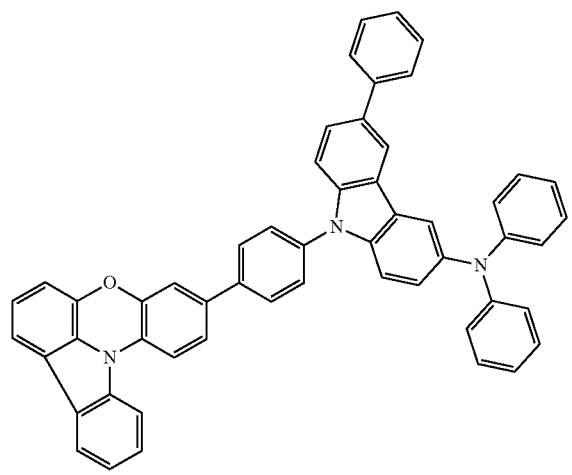
C125
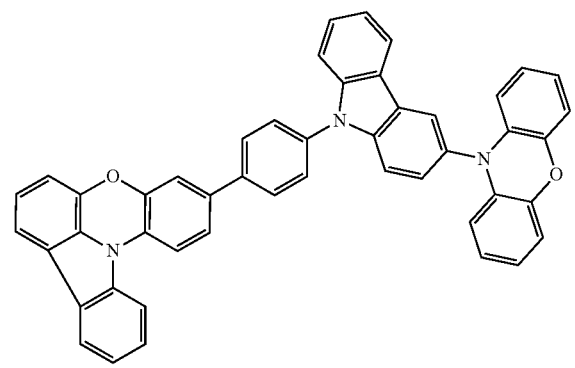

-continued
C126
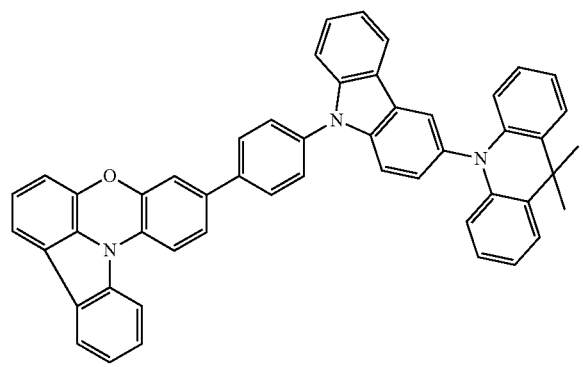
C127
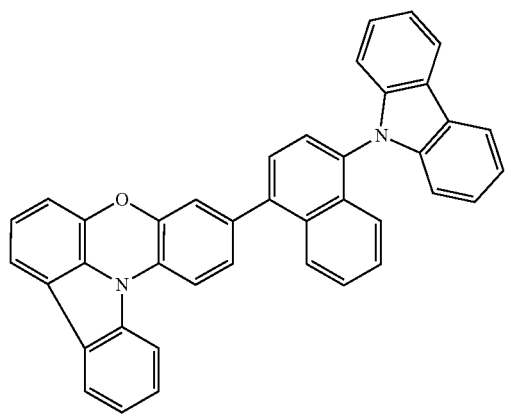
C128
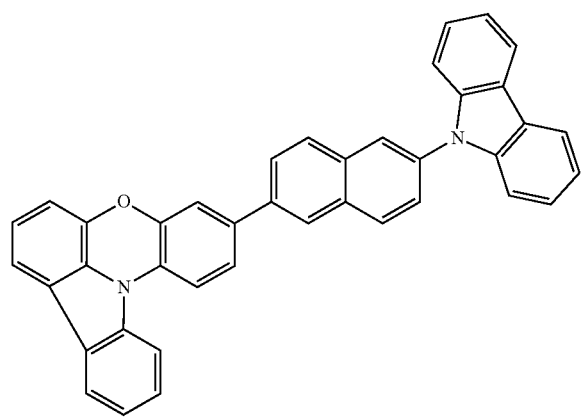
C129
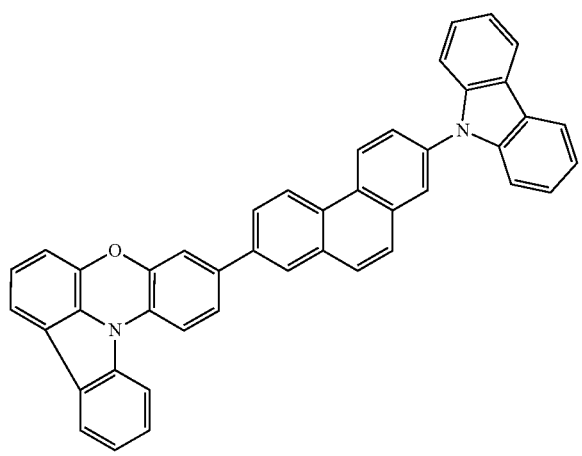
C130
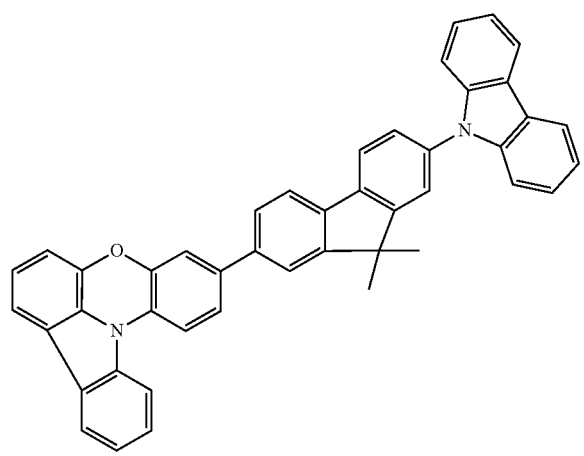
C131
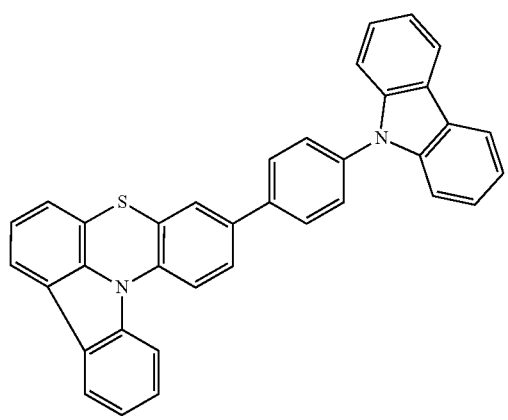

-continued
C132
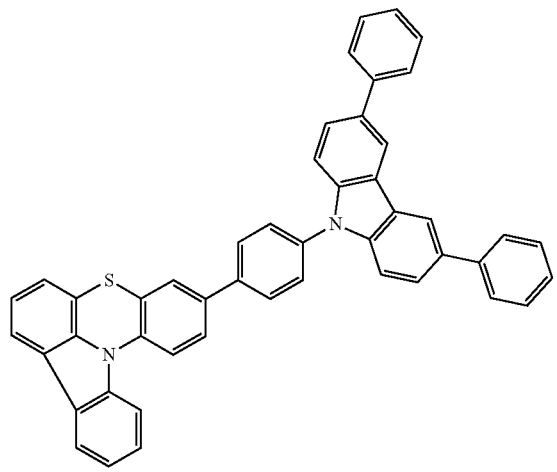
C133
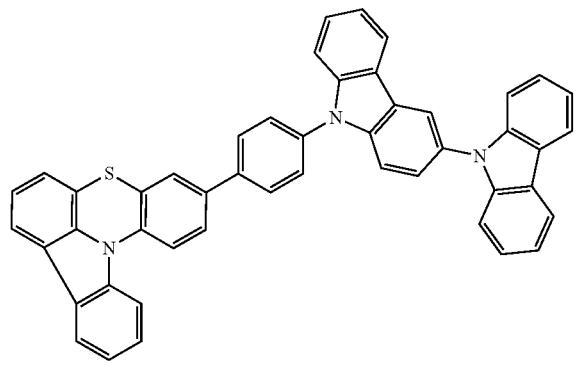
C134
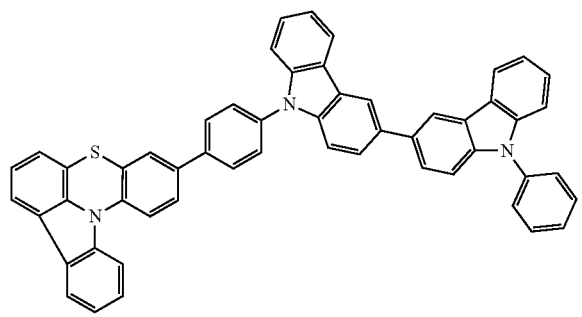
C135
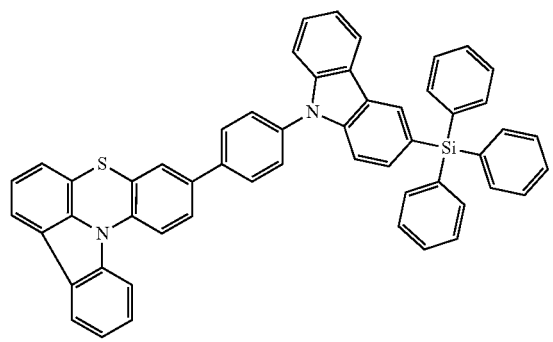
C136
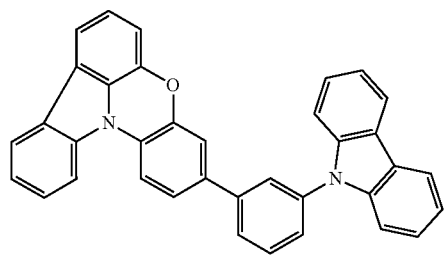
C137
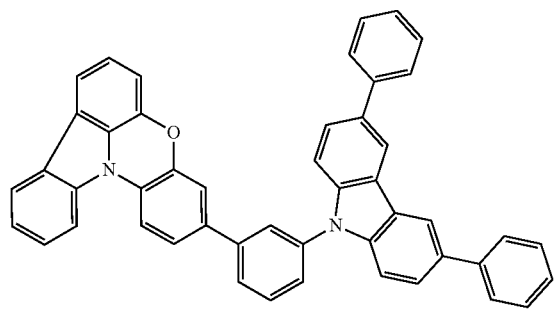
C138
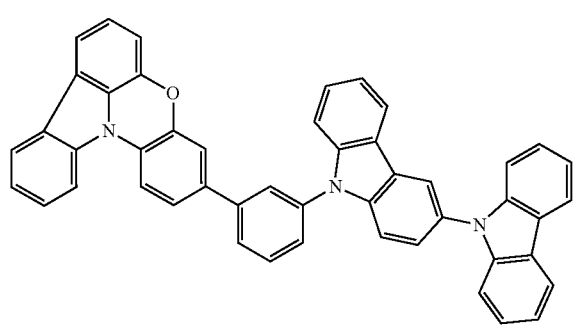
C139
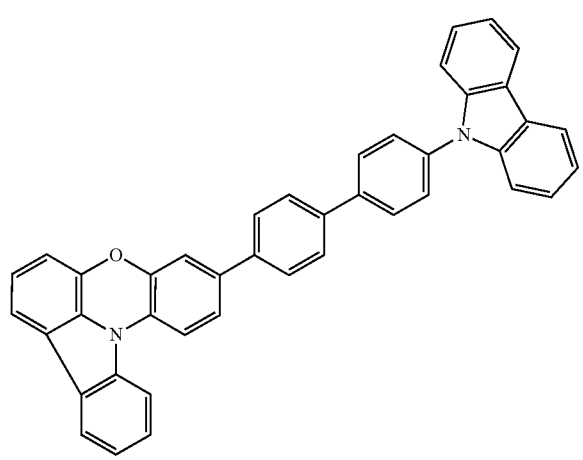

-continued
C140
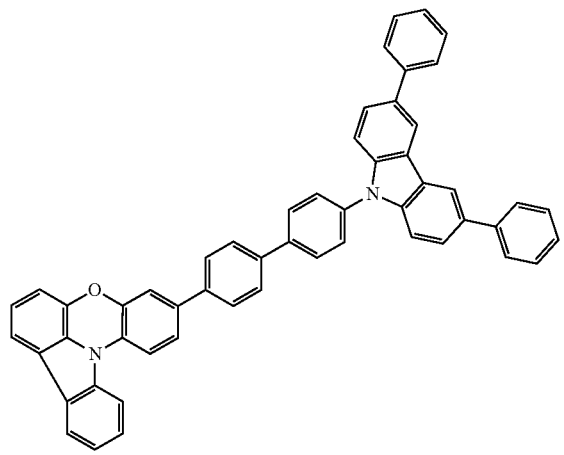
C141
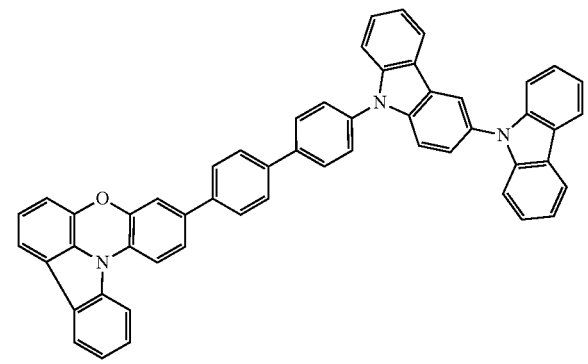
C142
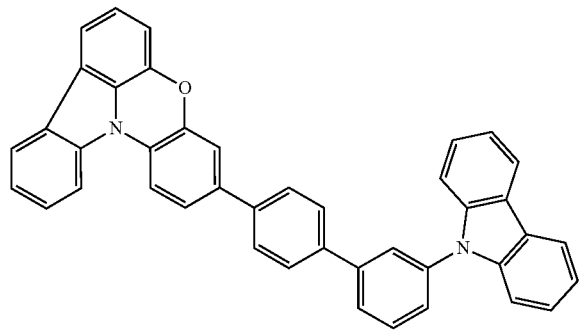
C143
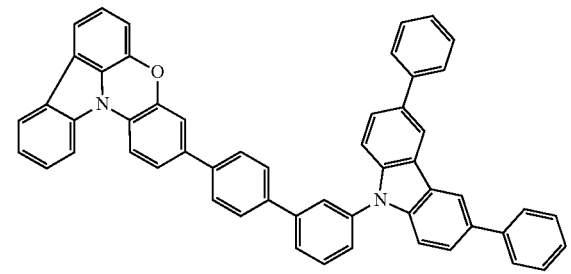
C144
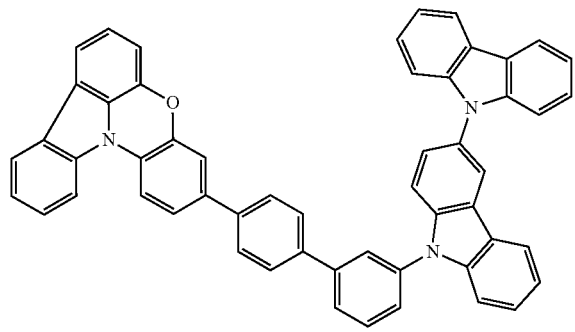
C145
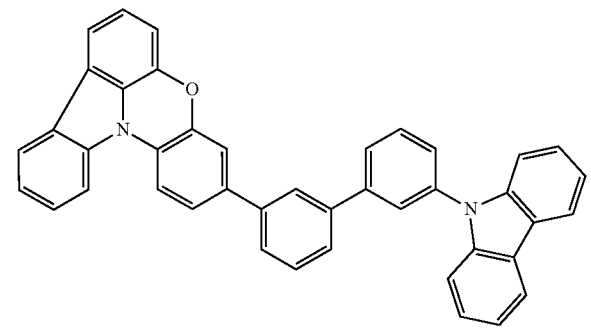
C146
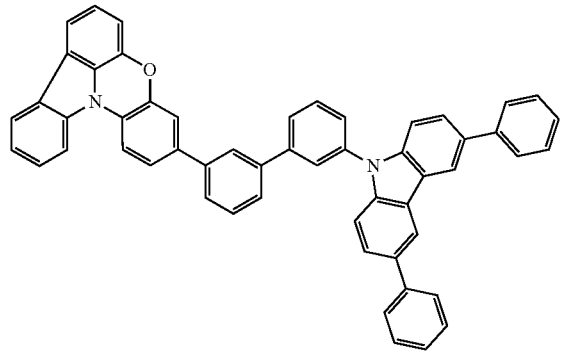
C147
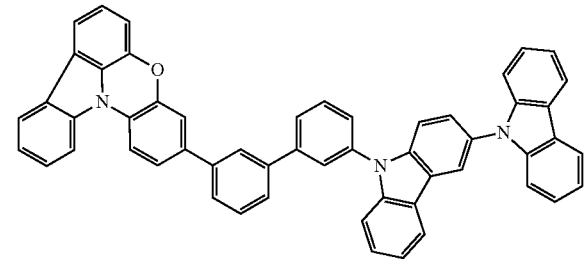

-continued
C148
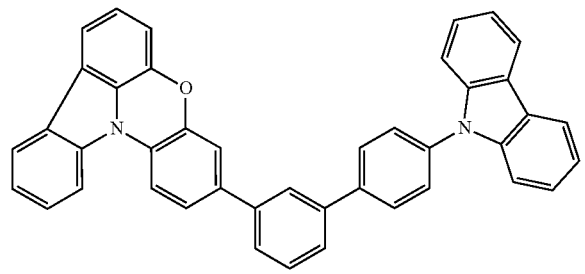
C149
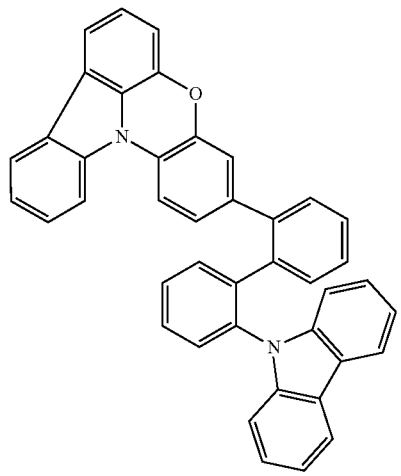
C150
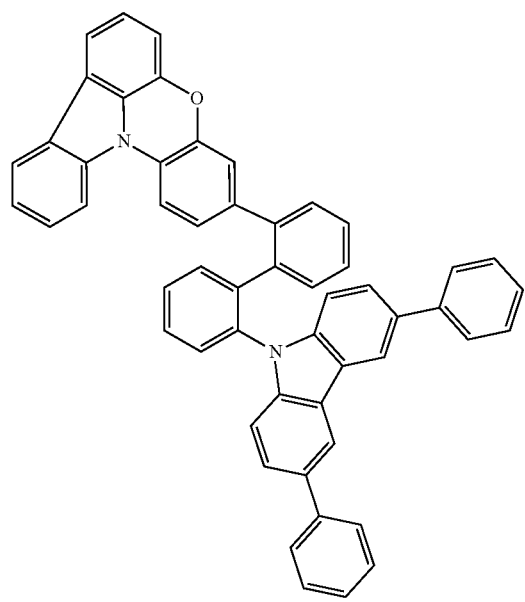
C151
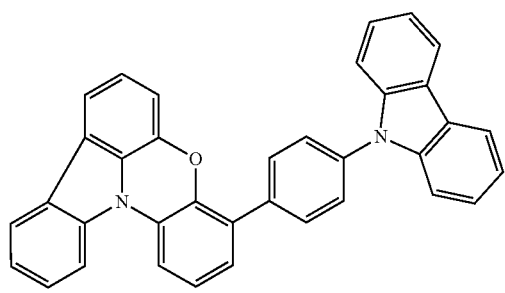
C152
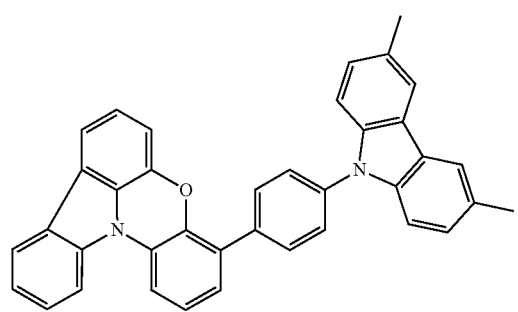
C153
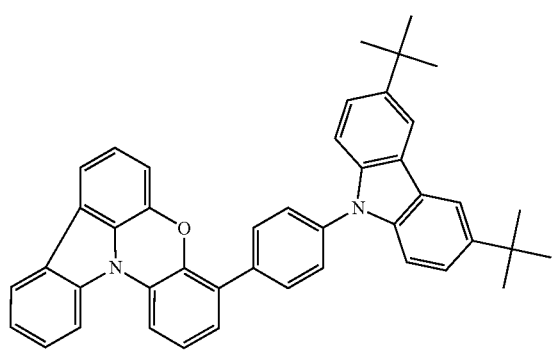

-continued
C154
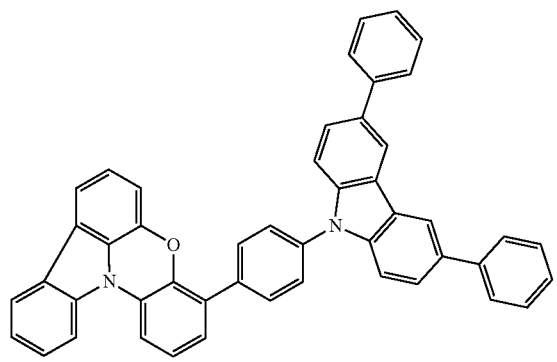
C155
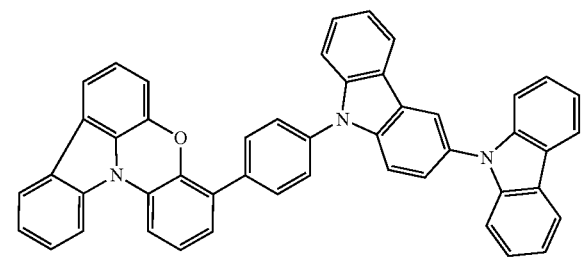
C156
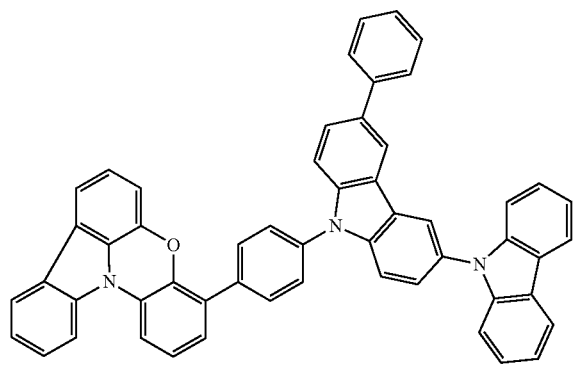
C157
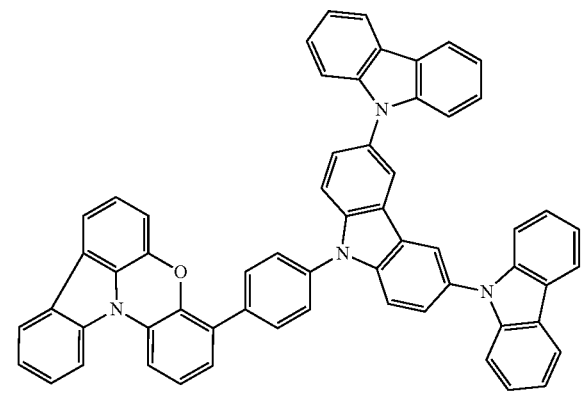
C158
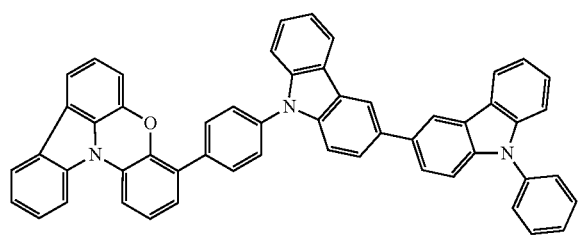
C159
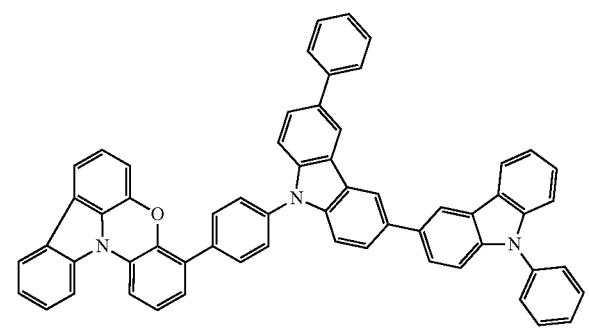
C160
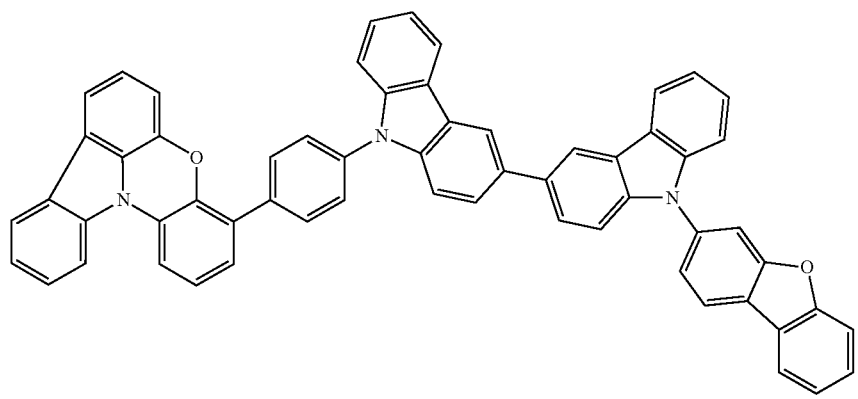

-continued
C161
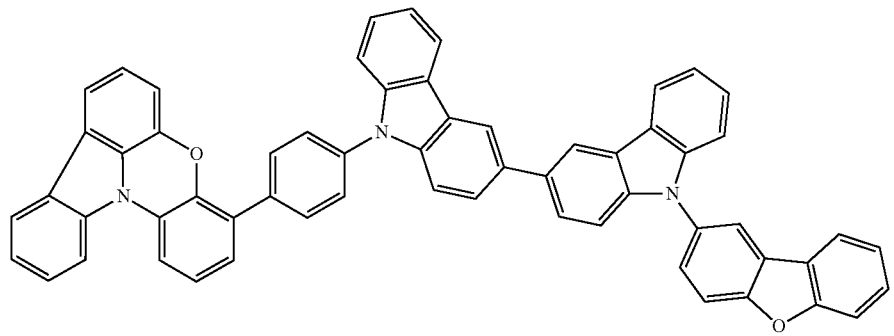
C162  C163
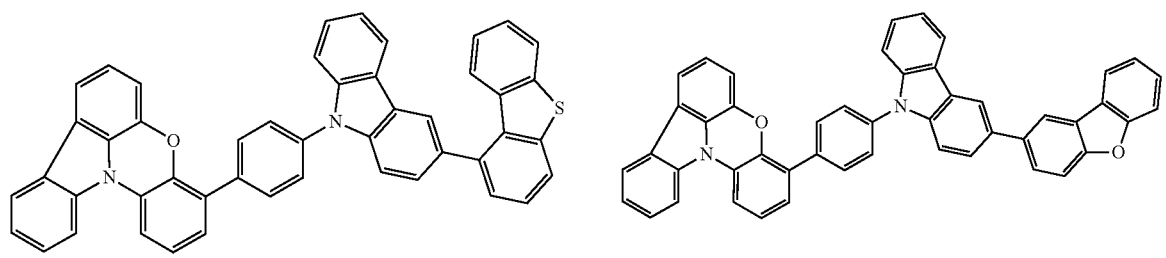
C164  C165
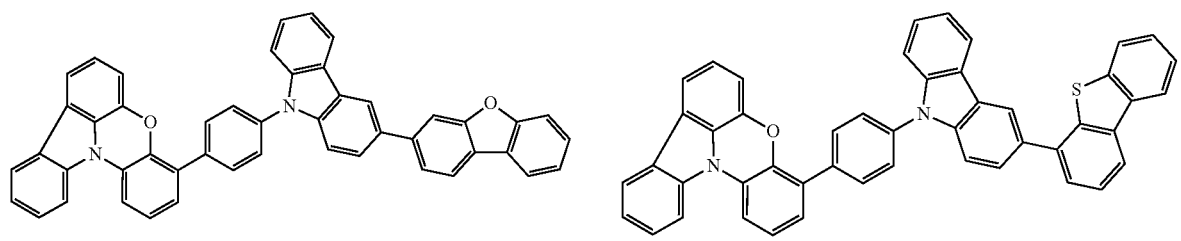
C166  C167
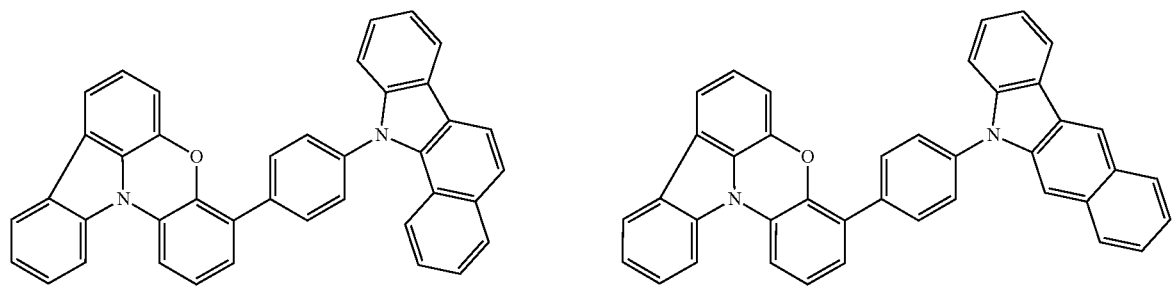
C168  C169
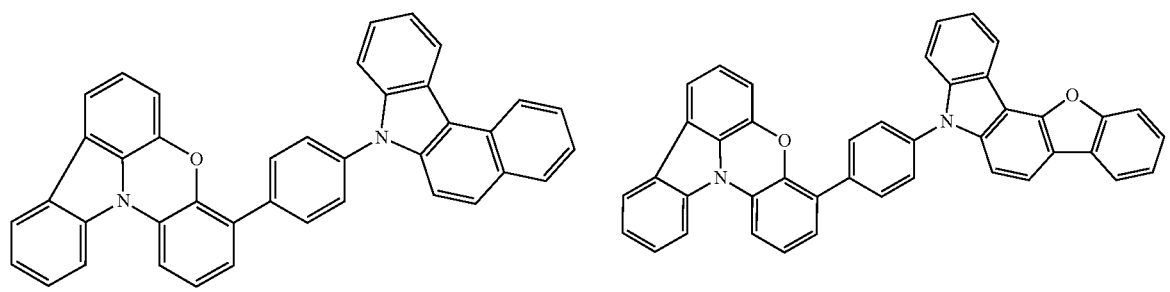

-continued
C170
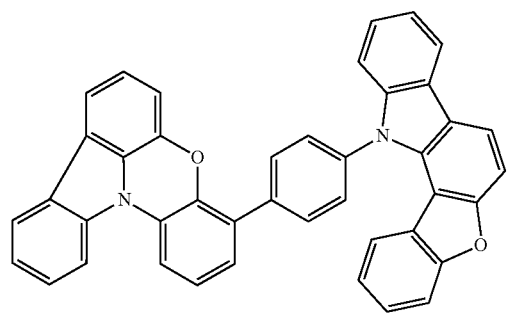
C171
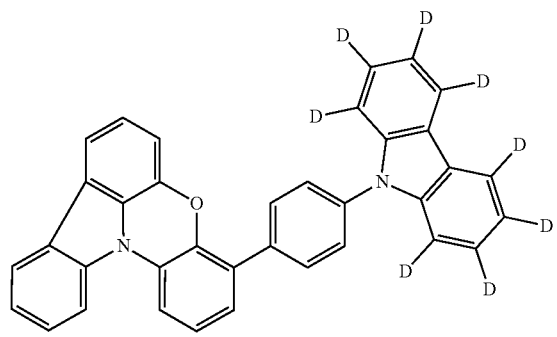
C172
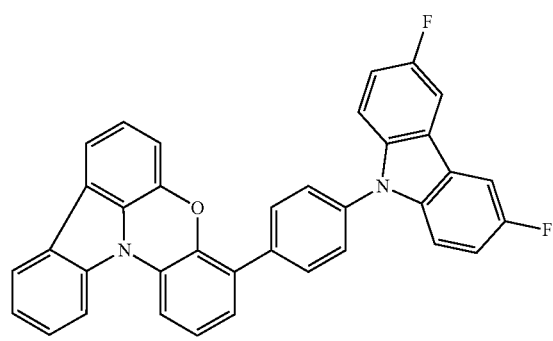
C173
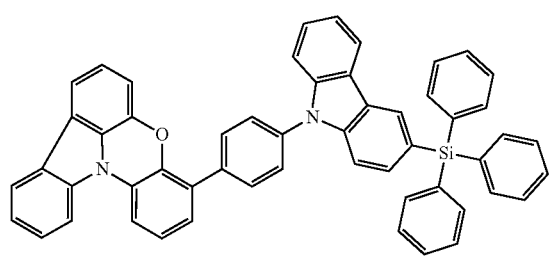
C174
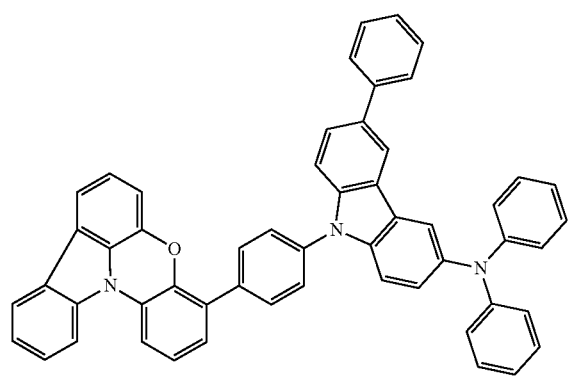
C175
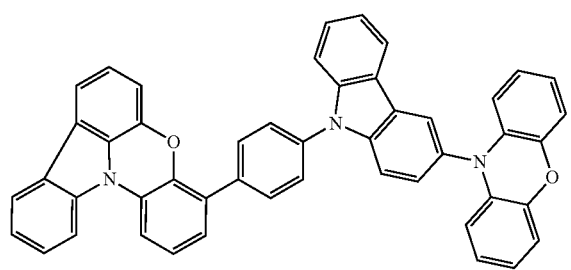
C176
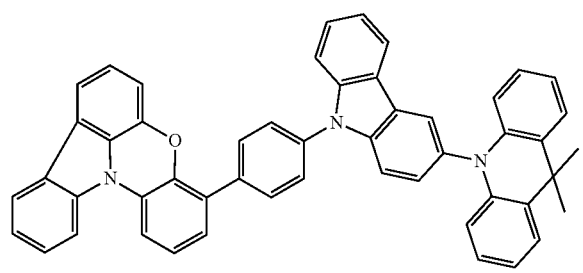
C177
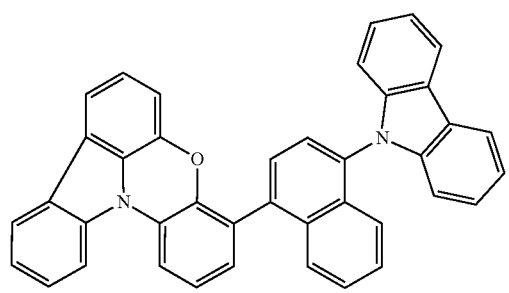

-continued
C178
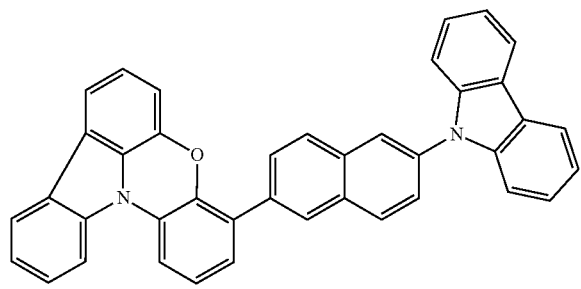
C179
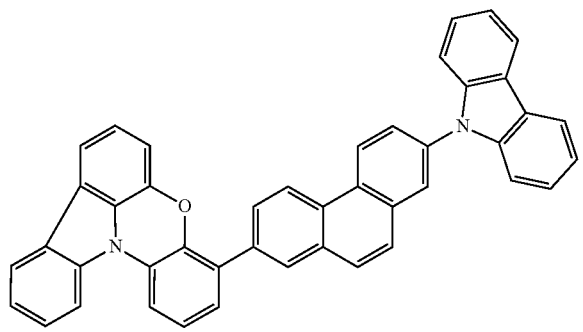
C180
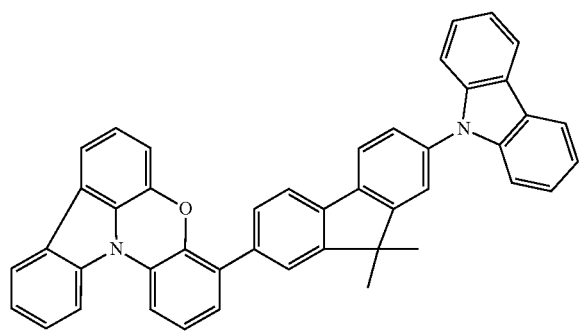
C181
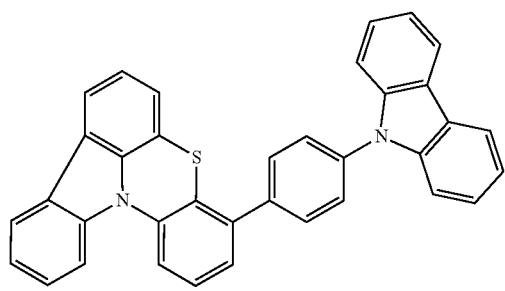
C182
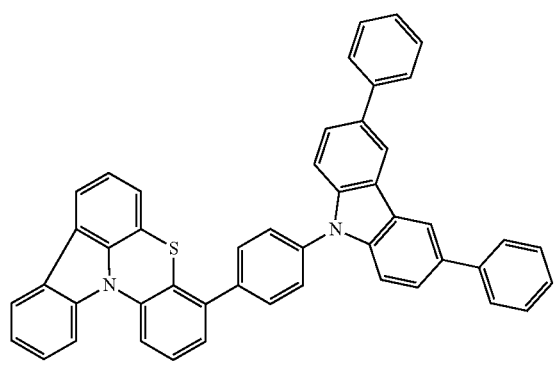
C183
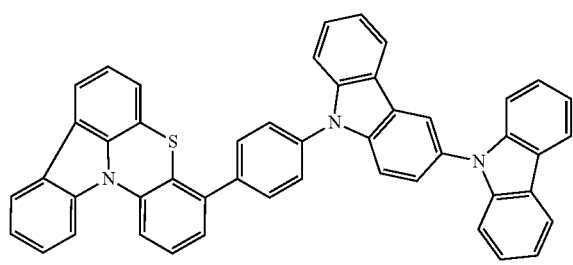
C184
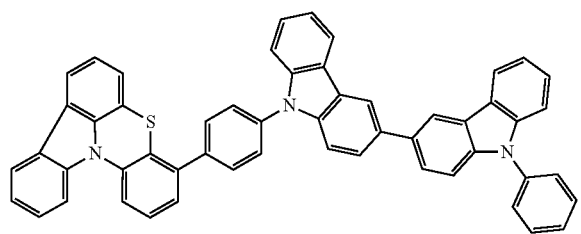
C185
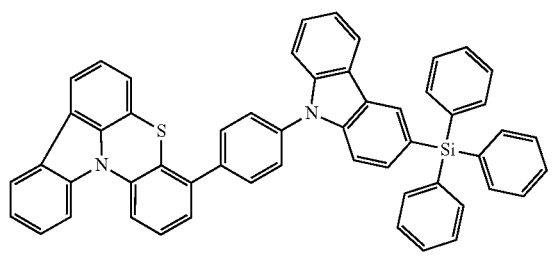

-continued
C186
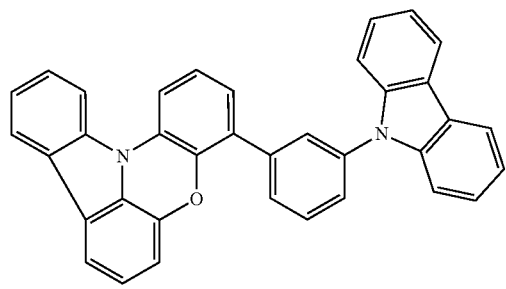
C187
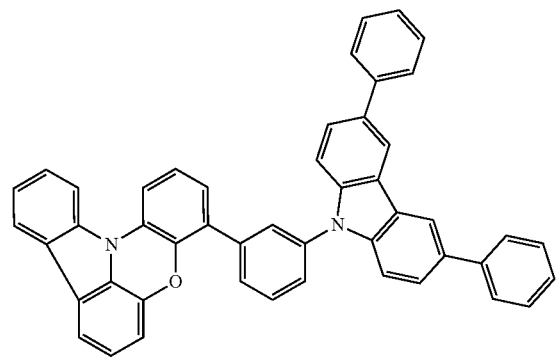
C188
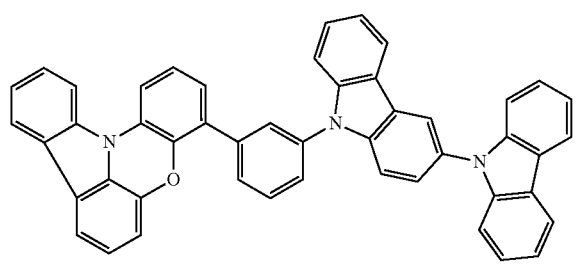
C189
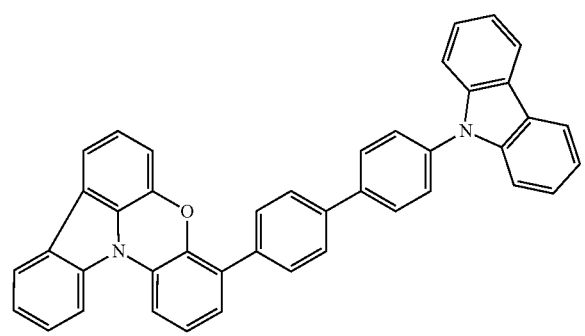
C190
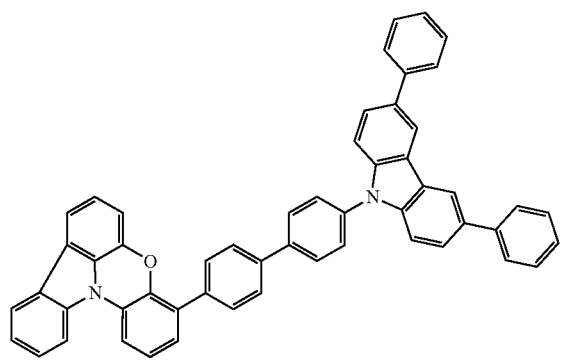
C191
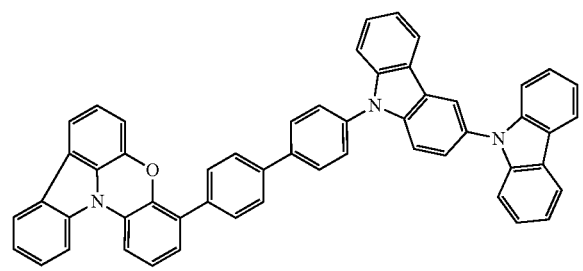
C192
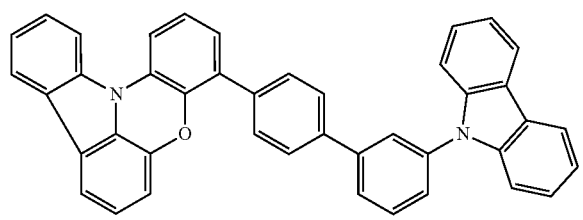
C193
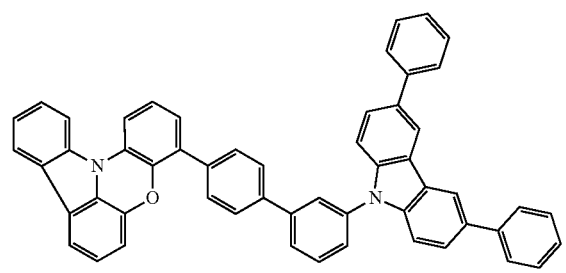

-continued
C194
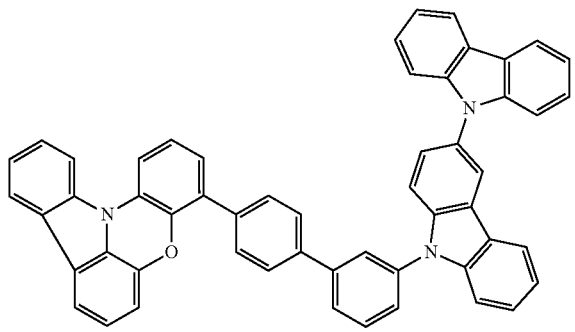
C195
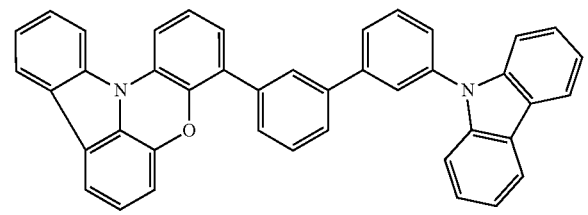
C196
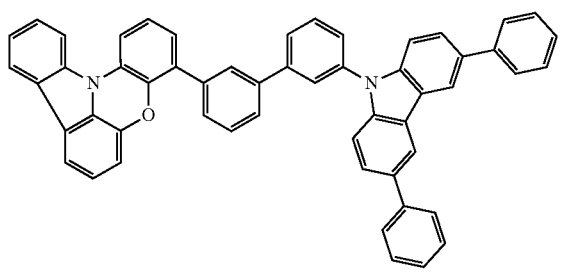
C197
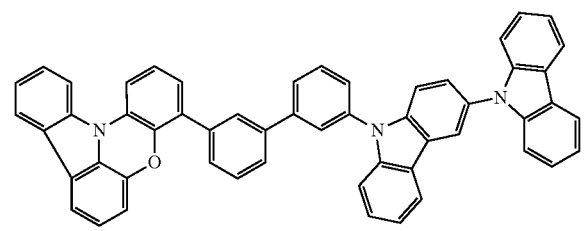
C198
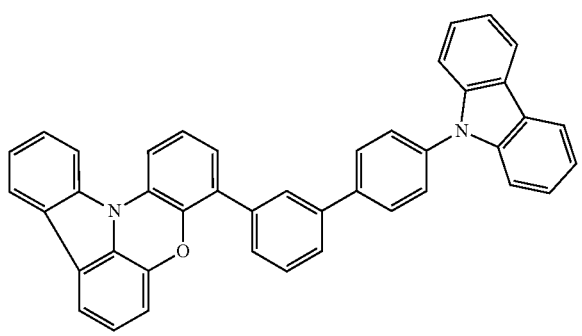
C199
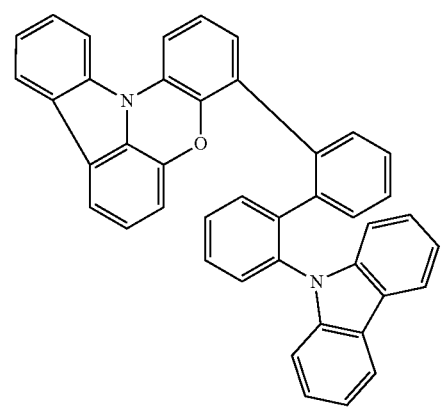
C200
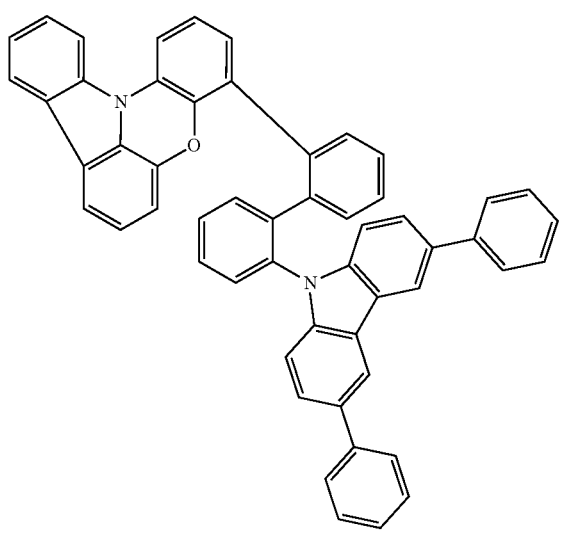

[Compound Group 1D]
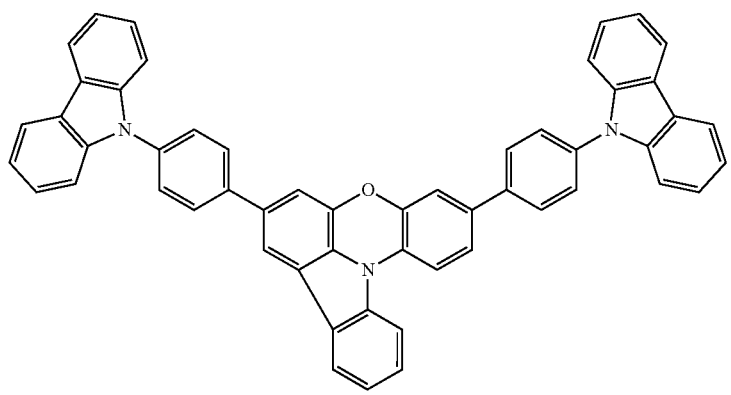
D1
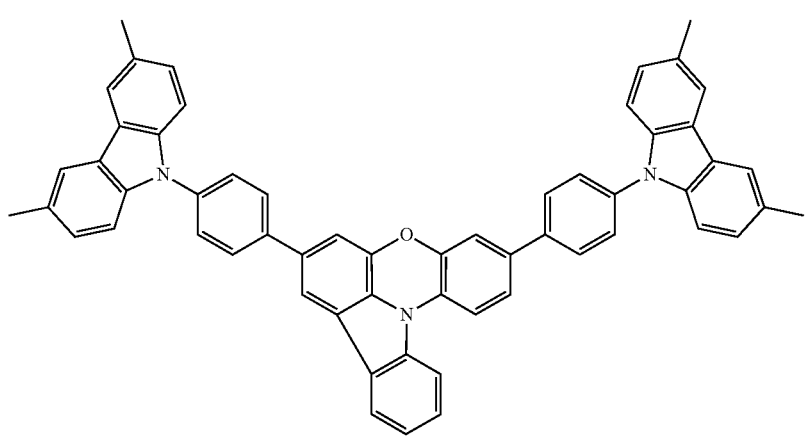
D2
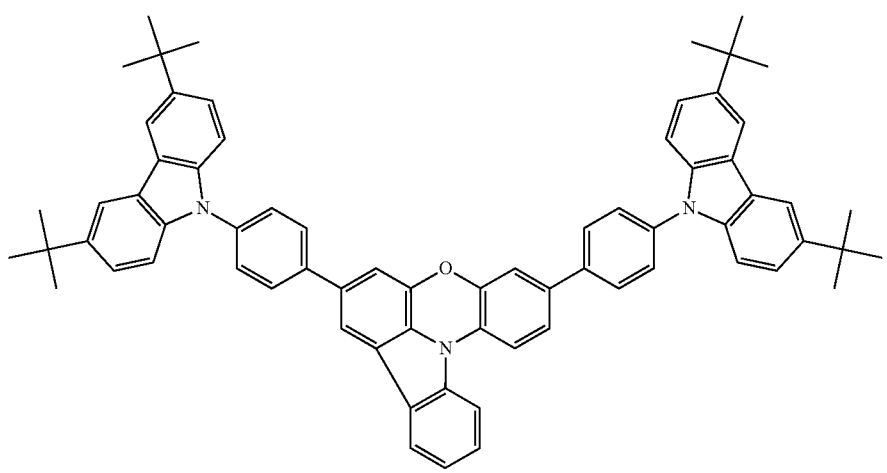
D3

-continued
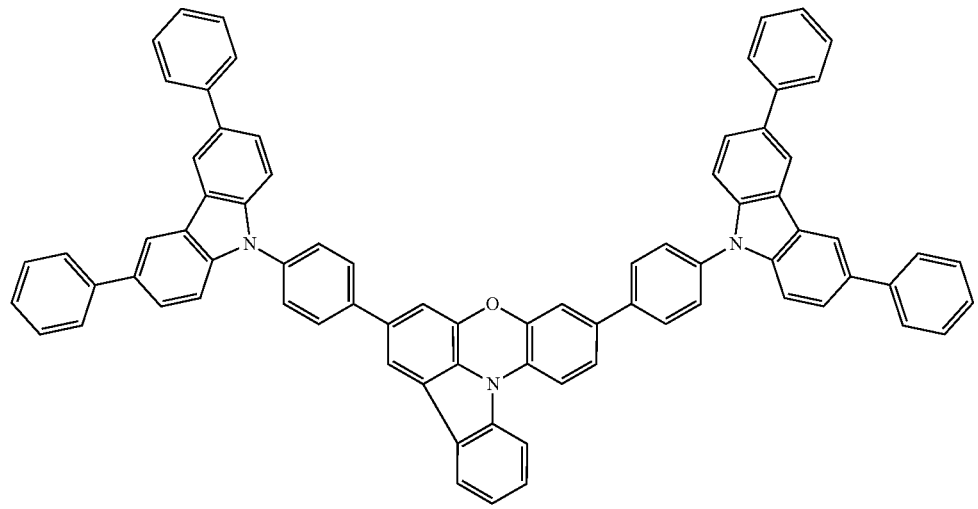
D4
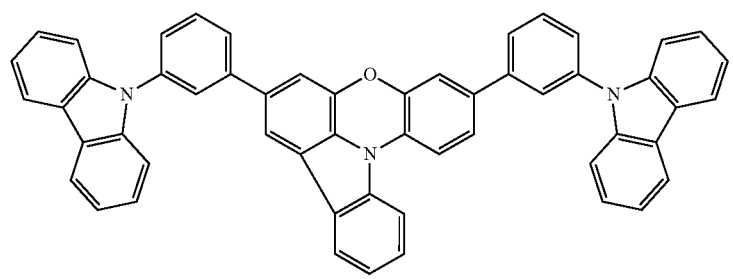
D5
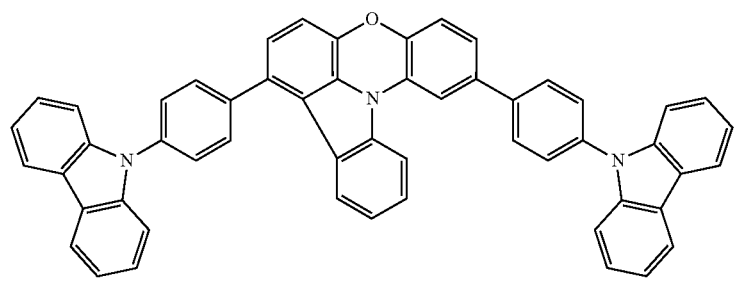
D6
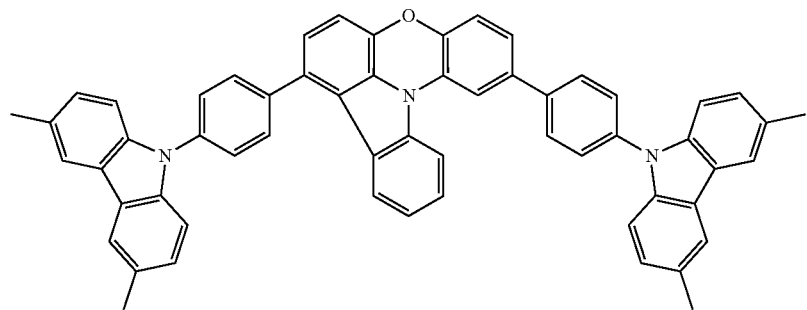
D7

-continued
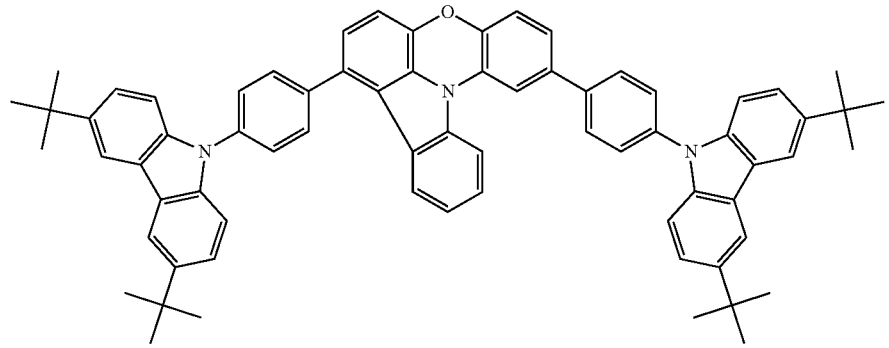
D8
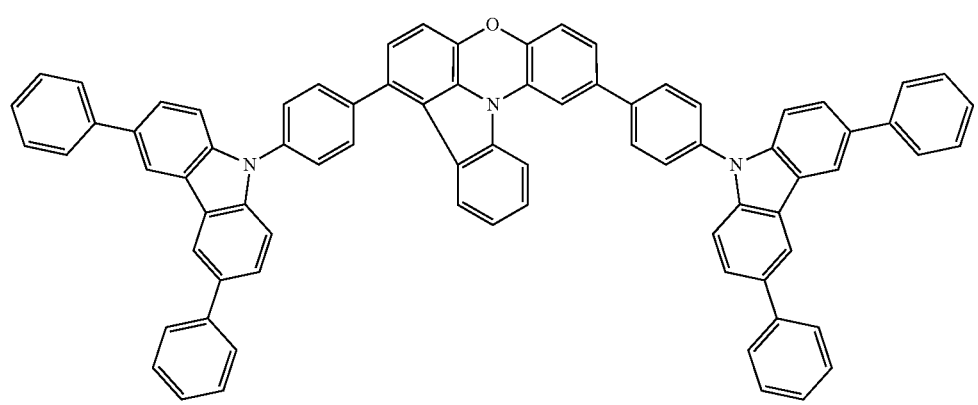
D9
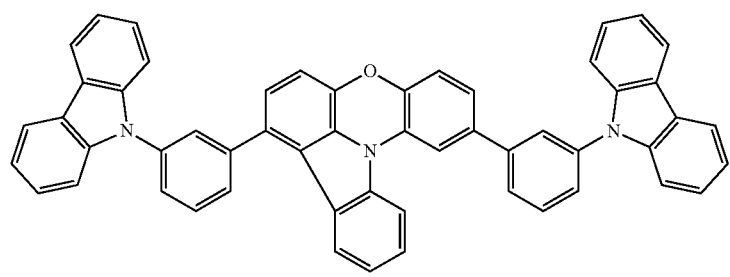
D10
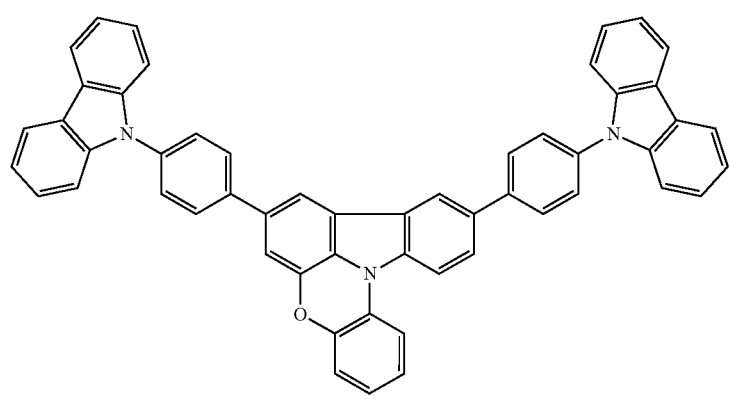
D11

-continued
D12
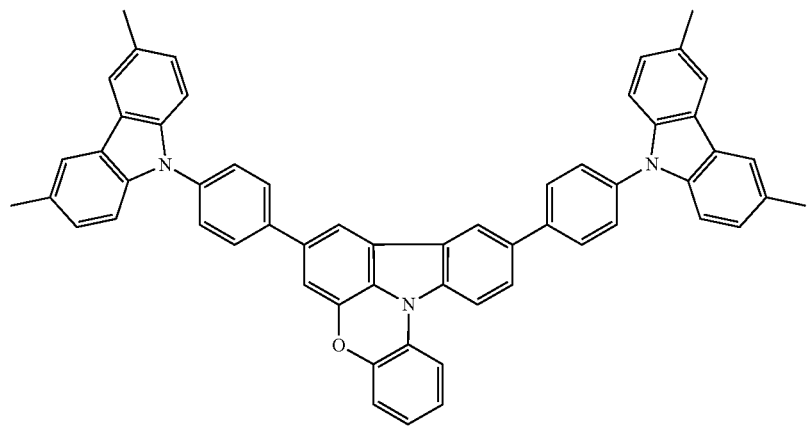
D13
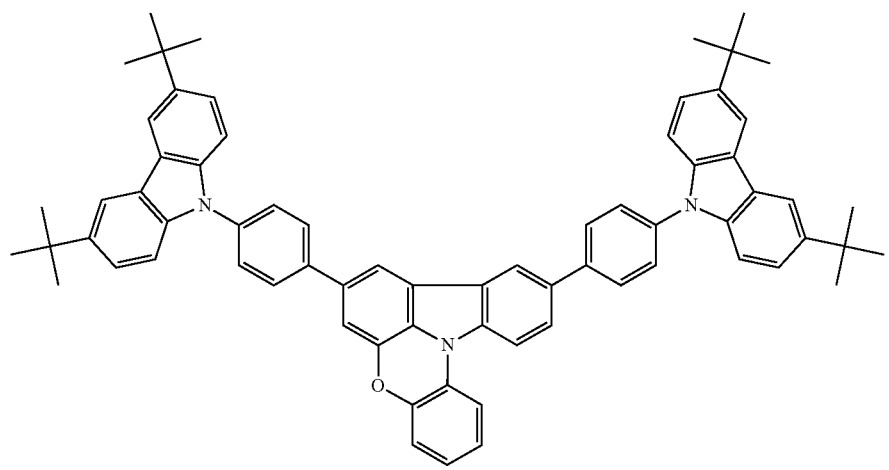
D14
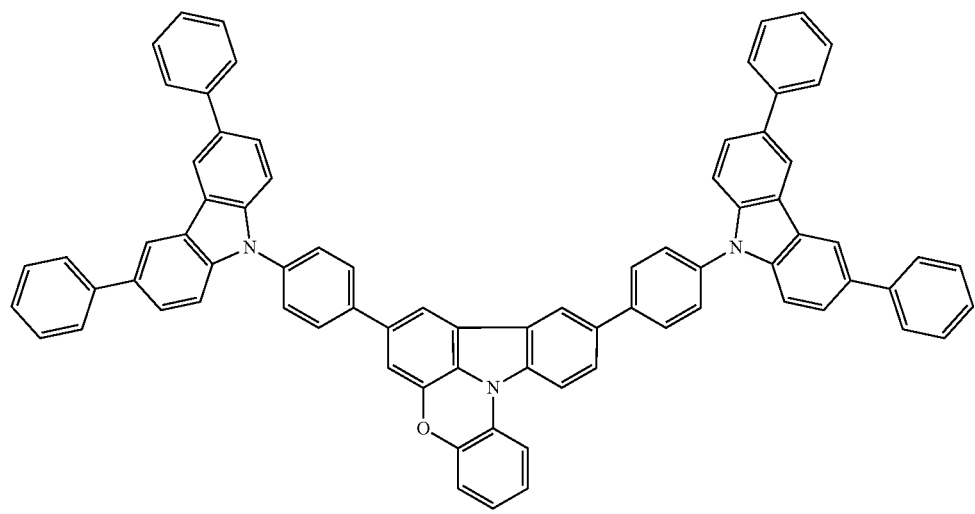

-continued
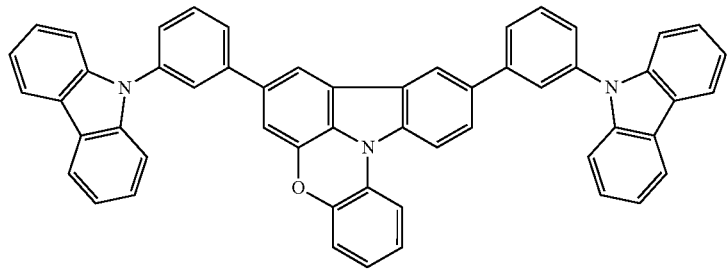
D15
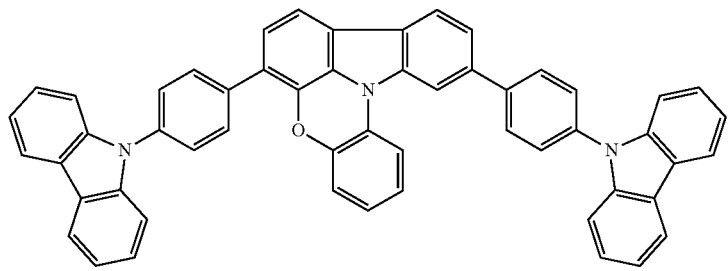
D16
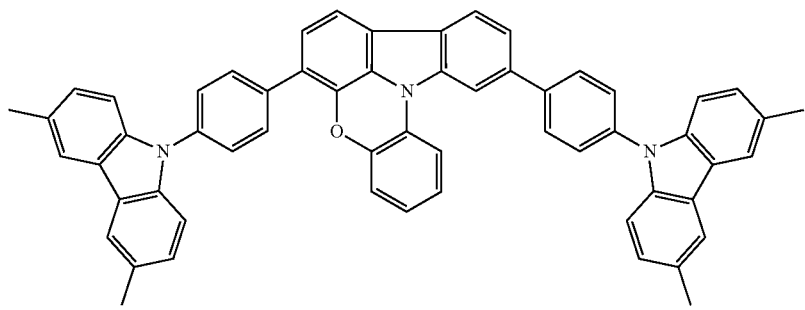
D17
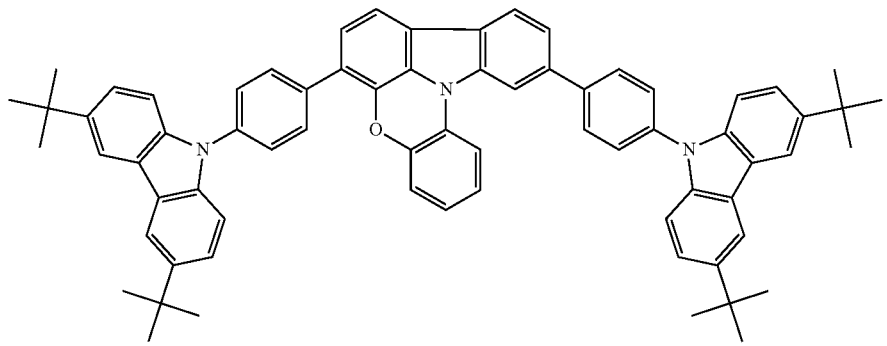
D18
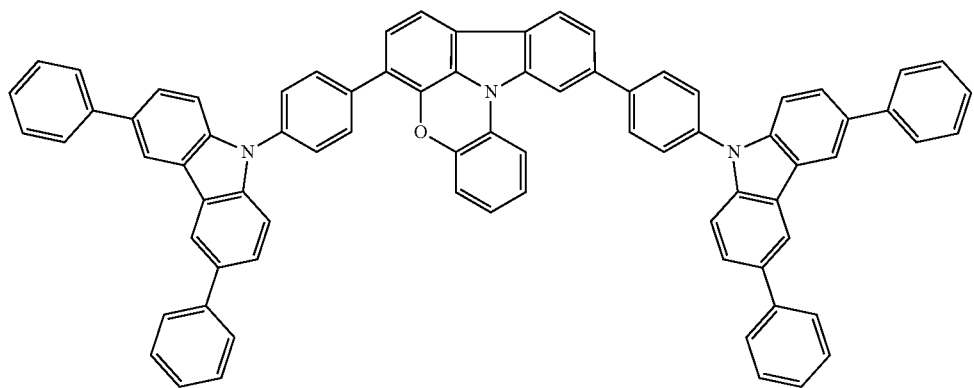
D19

-continued
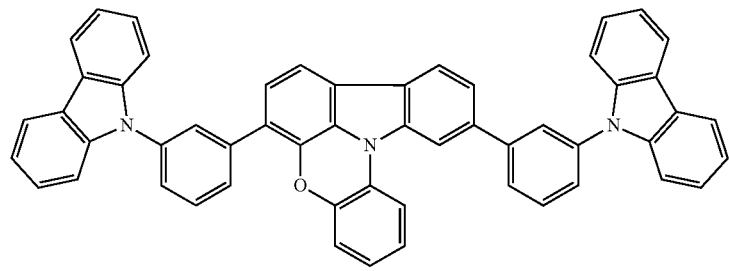
D20
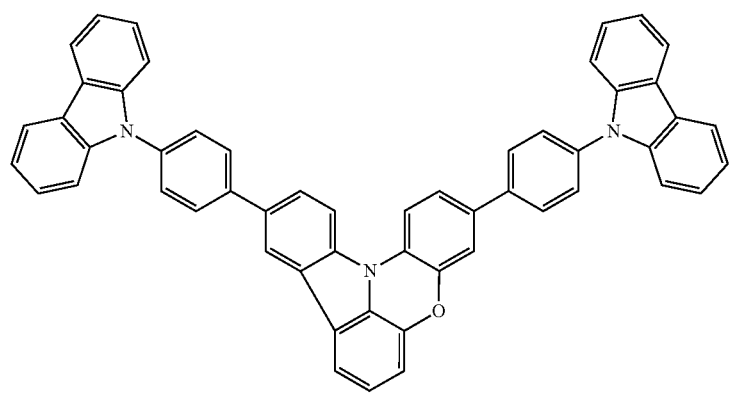
D21
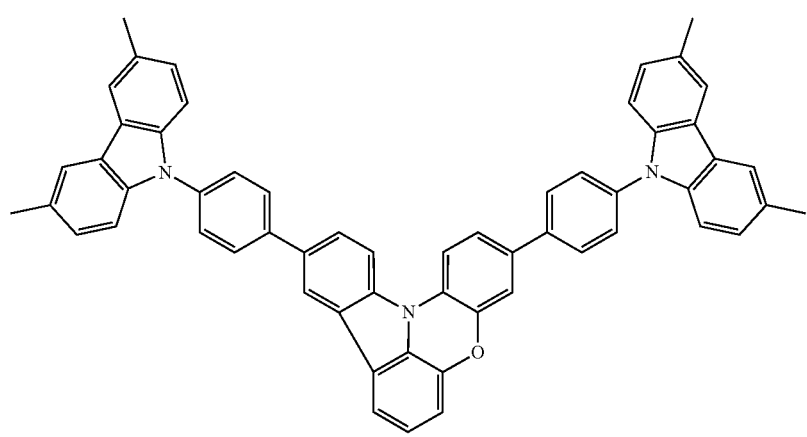
D22
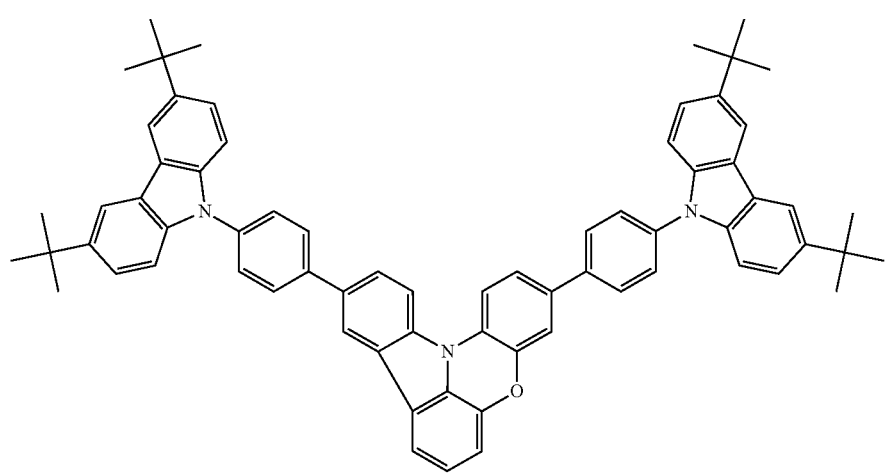
D23

-continued
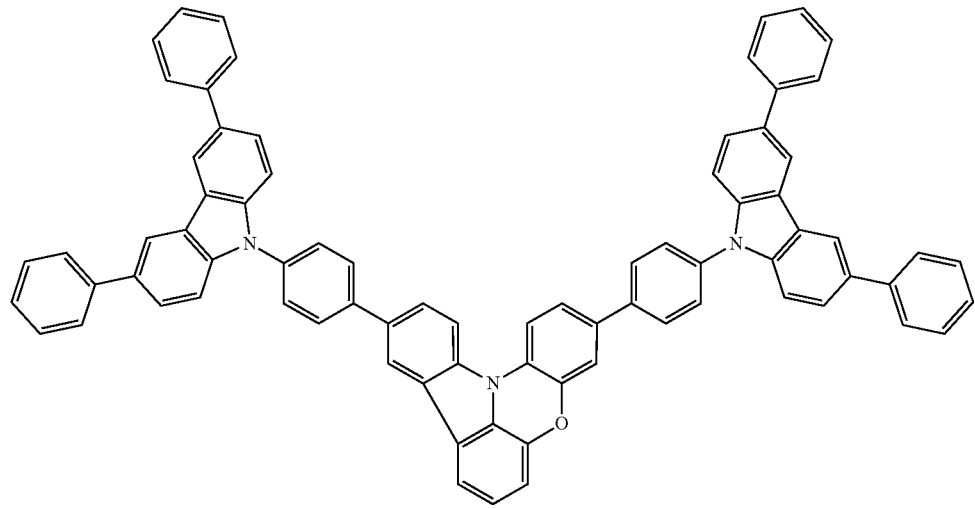
D24
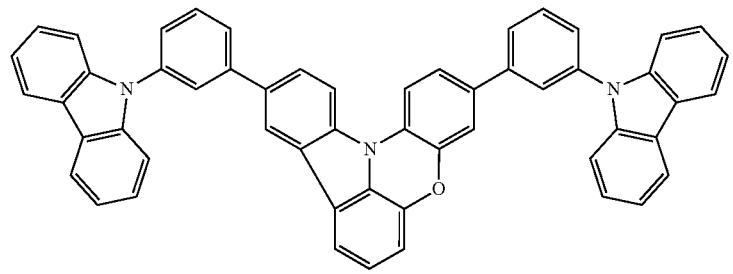
D25
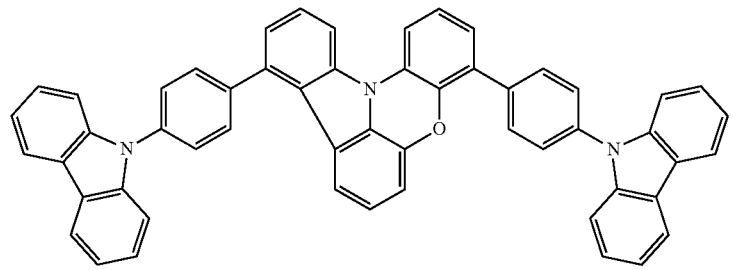
D26
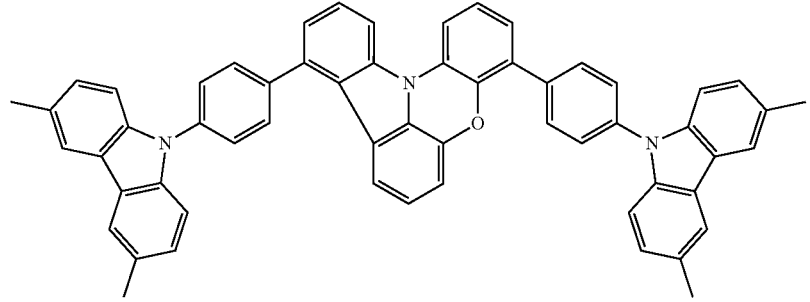
D27

-continued

D28

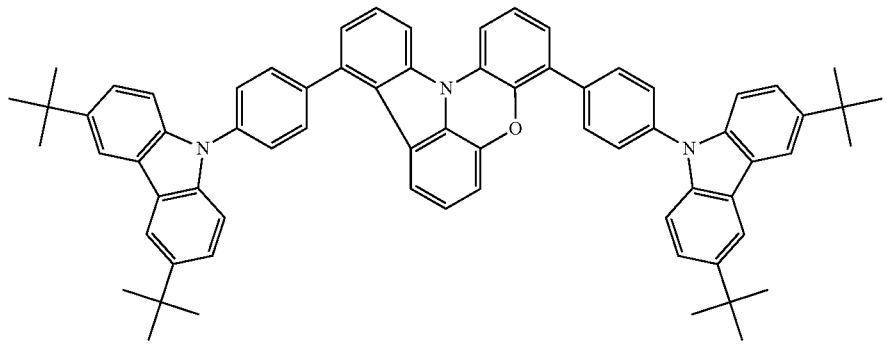

D29

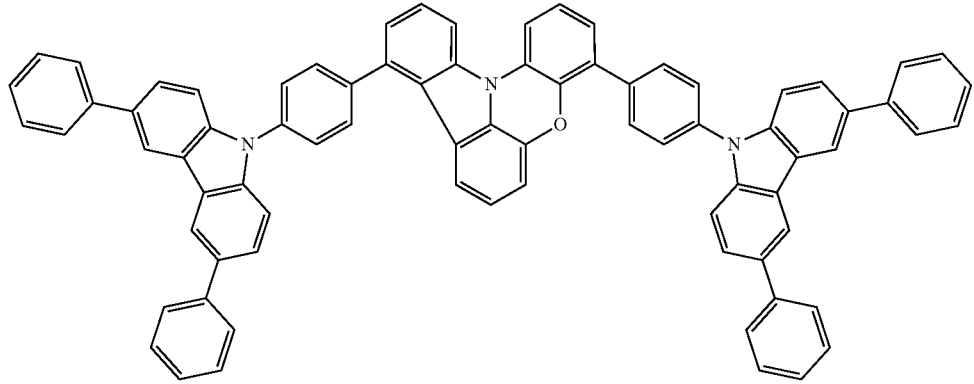

D30

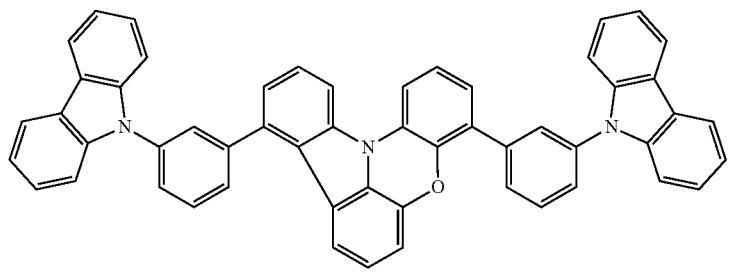

12. A polycyclic compound represented by Formula 1:

[Formula 1]

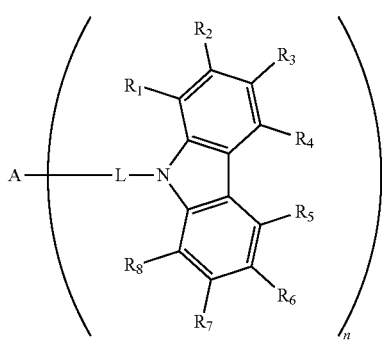

wherein in Formula 1,
L is a substituted or unsubstituted arylene group of 6 to 30 ring-forming carbon atoms,
$R_1$ to $R_8$ are each independently a hydrogen atom, a deuterium atom, a halogen atom, a substituted or unsubstituted silyl group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or are combined with an adjacent group to form a ring,
n is 1 or 2, and
A is a group represented by Formula 2:

[Formula 2]

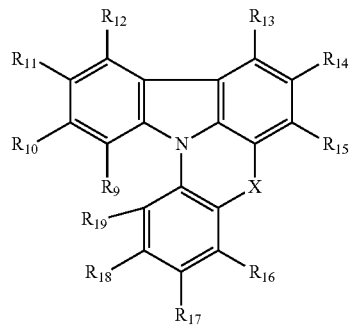

wherein in Formula 2,

X is O or S, $R_9$ to $R_{19}$ are each independently a hydrogen atom, a deuterium atom, a halogen atom, a substituted or unsubstituted alkyl group of 1 to 20 carbon atoms, or are combined with an adjacent group to form a ring, and at least one of $R_9$ to $R_{19}$ is bonded to L of Formula 1.

13. The polycyclic compound of claim 12, wherein L is a substituted or unsubstituted phenylene group, a substituted or unsubstituted divalent biphenyl group, a substituted or unsubstituted divalent naphthyl group, a substituted or unsubstituted divalent fluorenyl group, or a substituted or unsubstituted divalent phenanthryl group.

14. The polycyclic compound of claim 12, wherein L is a group selected from Compound Group L-1:

[Compound Group L-1]

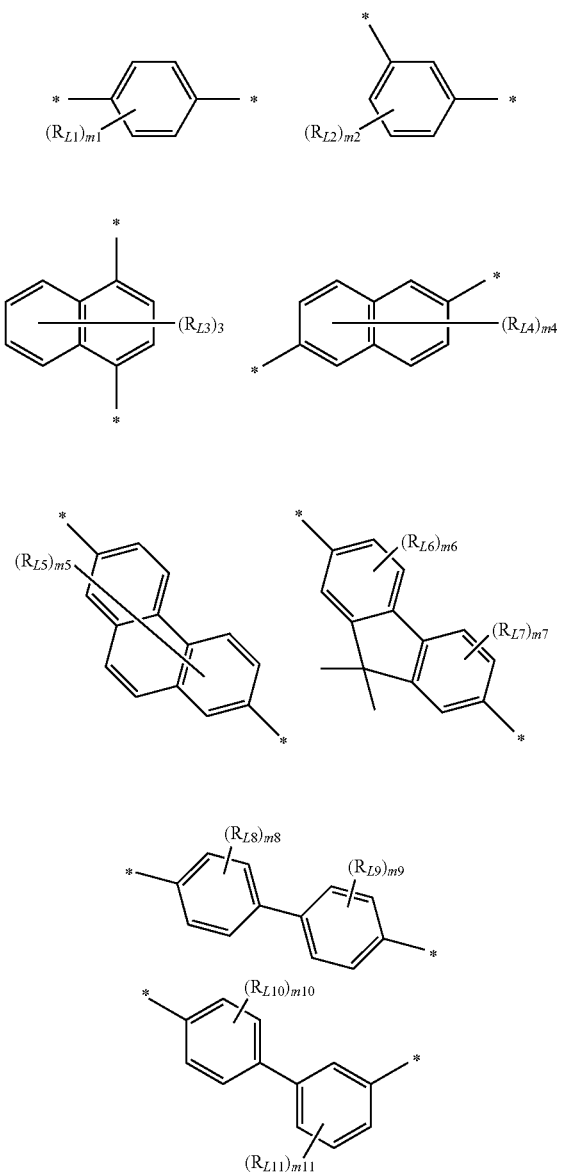

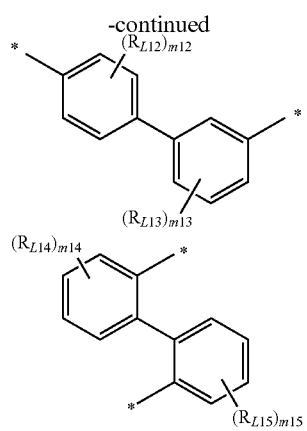

wherein in Compound Group L-1, $R_{L1}$ to $R_{L15}$ are each independently a hydrogen atom, a deuterium atom, a halogen atom, a substituted or unsubstituted silyl group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or are combined with an adjacent group to form a ring, m1 and m2 are each independently an integer from 0 to 4, m3 and m4 are each independently an integer from 0 to 6, m5 is an integer from 0 to 8, m6 and m7 are each independently an integer from 0 to 3, m8 to m15 are each independently an integer from 0 to 4, and -* represents a position bonded to A or N in Formula 1.

15. The polycyclic compound of claim 12, wherein $R_1$ to $R_8$ are each independently a hydrogen atom, a deuterium atom, a halogen atom, a methyl group, a t-butyl group, a substituted or unsubstituted amine group, a substituted or unsubstituted silyl group, a substituted or unsubstituted phenyl group, a substituted or unsubstituted carbazole group, a substituted or unsubstituted dibenzofuran group, a substituted or unsubstituted dibenzothiophene group, a substituted or unsubstituted phenoxazine group, or a substituted or unsubstituted acridyl group.

16. The polycyclic compound of claim 12, wherein the polycyclic compound represented by Formula 1 is represented by Formula 1-1 or Formula 1-2:

[Formula 1-1]

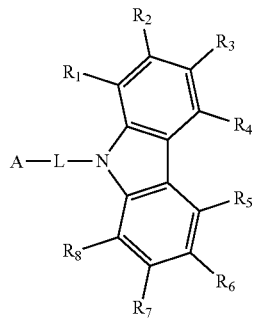

[Formula 1-2]

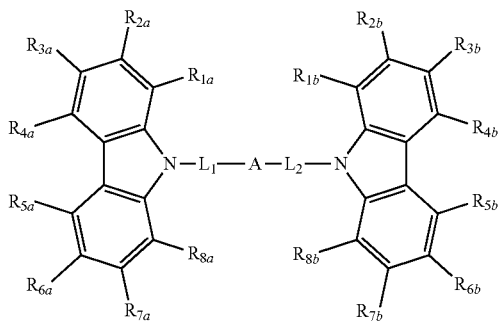

wherein in Formula 1-1 and Formula 1-2, $L_1$ and $L_2$ are each independently a substituted or unsubstituted arylene group of 6 to 30 ring-forming carbon atoms, $R_{1a}$ to $R_{8a}$, and $R_{1b}$ to $R_{8b}$ are each independently a hydrogen atom, a deuterium atom, a halogen atom, a substituted or unsubstituted silyl group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or are combined with an adjacent group to form a ring, and A, L, and $R_1$ to $R_8$ are the same as defined in connection with Formula 1.

17. The polycyclic compound of claim 12, wherein the polycyclic compound represented by Formula 1 is represented by one of Formula 3-1 to Formula 3-6:

[Formula 3-1]

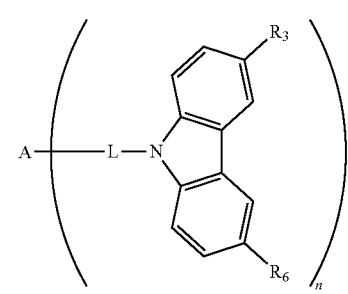

[Formula 3-2]

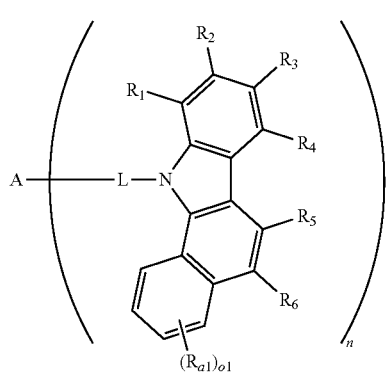

[Formula 3-3]

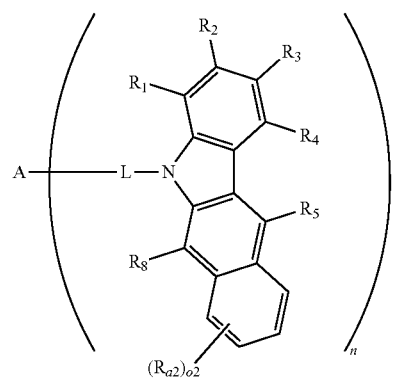

[Formula 3-4]

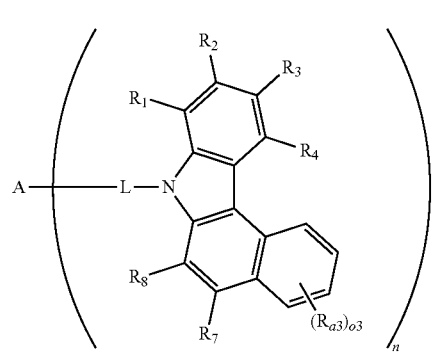

[Formula 3-5]

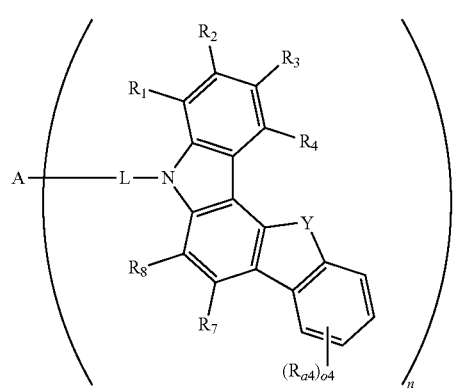

[Formula 3-6]

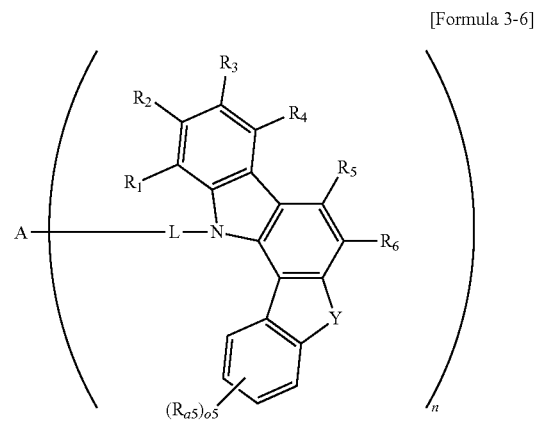

wherein in Formula 3-1 to Formula 3-6,

Y is O or S, $R_{a1}$ to $R_{a5}$ are each independently a hydrogen atom, a deuterium atom, a halogen atom, a substituted or unsubstituted silyl group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or are combined with an adjacent group to form a ring, o1 to o5 are each independently an integer from 0 to 4, and A, L, n, and $R_1$ to $R_8$ are the same as defined in connection with Formula 1.

18. The polycyclic compound of claim 12, wherein the polycyclic compound represented by Formula 1 is represented by one of Formula 4-1 to Formula 4-6:

[Formula 4-1]

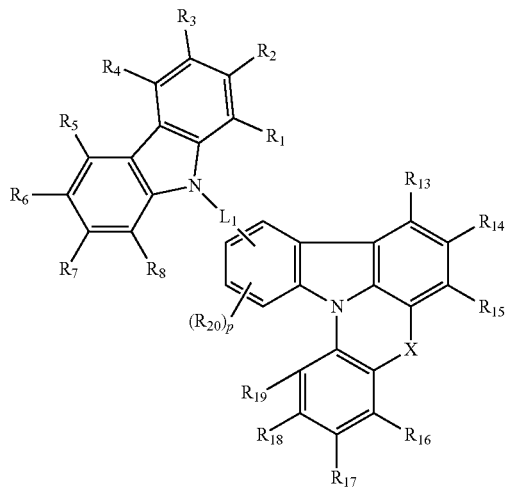

[Formula 4-2]

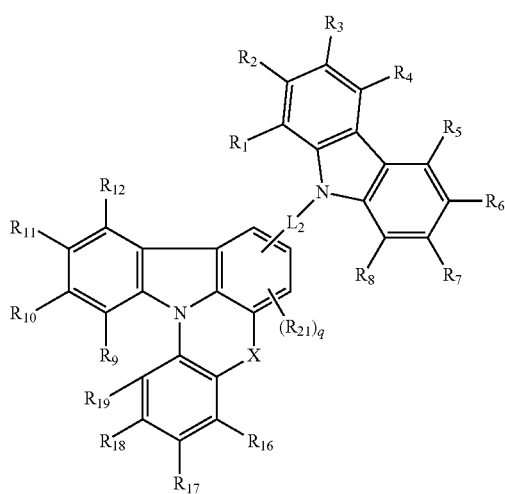

[Formula 4-3]

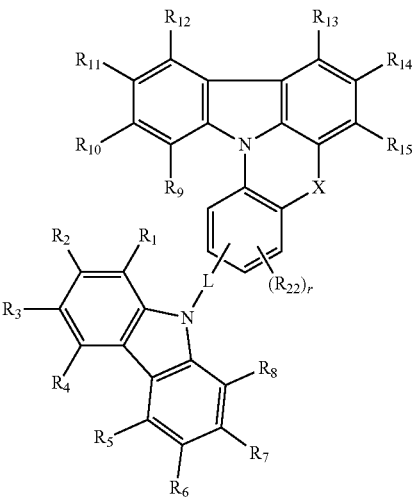

[Formula 4-4]

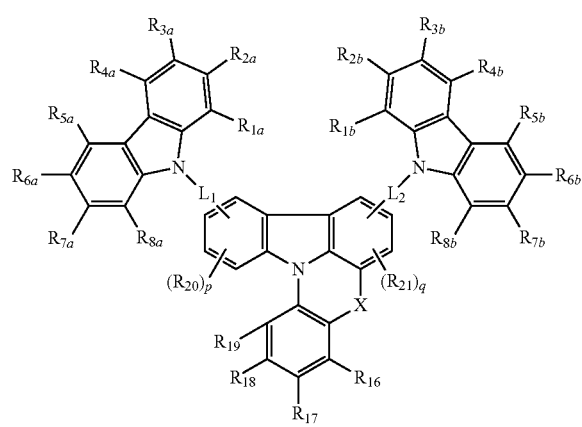

[Formula 4-5]

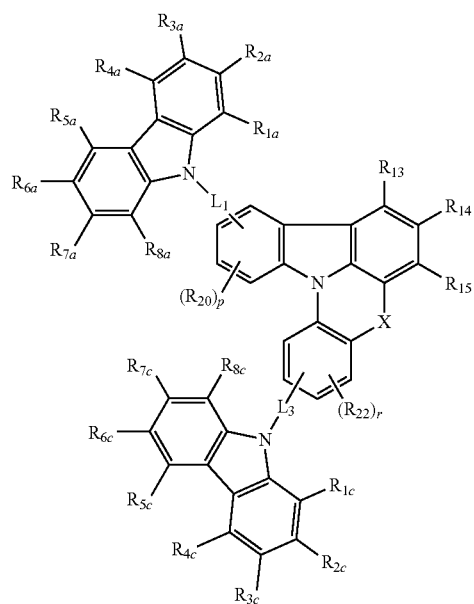

-continued

[Formula 4-6]

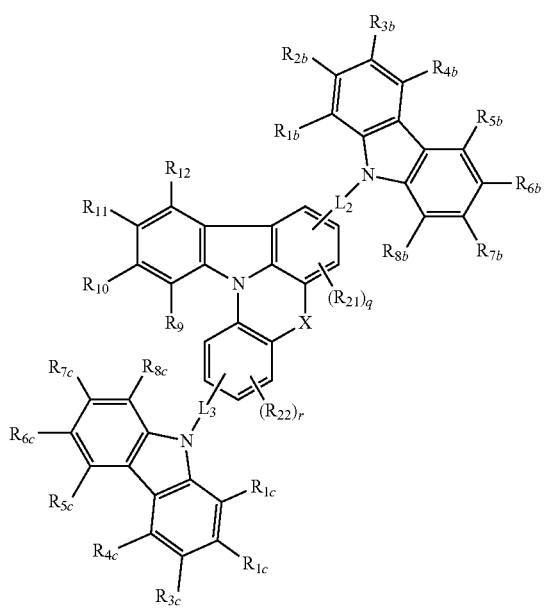

wherein in Formula 4-1 to Formula 4-6, $R_{20}$, $R_{21}$, and $R_{22}$ are each independently a hydrogen atom, a deuterium atom, a halogen atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or are combined with an adjacent group to form a ring, p is an integer from 0 to 3, q is an integer from 0 to 2, r is an integer from 0 to 3, $L_1$ to $L_3$ are each independently a substituted or unsubstituted arylene group of 6 to 30 ring-forming carbon atoms, $R_{1a}$ to $R_a$, $R_{1b}$ to $R_{8b}$, and $R_{1c}$ to $R_{8c}$ are each independently a hydrogen atom, a deuterium atom, a halogen atom, a substituted or unsubstituted silyl group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or are combined with an adjacent group to form a ring, and L, X, and $R_1$ to $R_{19}$ are the same as defined in connection with Formula 1 and Formula 2.

* * * * *